US011427800B2

(12) United States Patent
Gabant

(10) Patent No.: US 11,427,800 B2
(45) Date of Patent: Aug. 30, 2022

(54) CONTROLLED GROWTH OF MICROORGANISMS

(71) Applicant: Syngulon SA, Seraing (BE)

(72) Inventor: Philippe Gabant, Ottignies Louvain-la-Neuve (BE)

(73) Assignee: Syngulon SA, Seraing (BE)

( * ) Notice: Subject to any disclaimer, the term of this patent is extended or adjusted under 35 U.S.C. 154(b) by 764 days.

(21) Appl. No.: 16/227,371

(22) Filed: Dec. 20, 2018

(65) Prior Publication Data
US 2019/0191709 A1 Jun. 27, 2019

Related U.S. Application Data

(60) Continuation of application No. 15/087,706, filed on Mar. 31, 2016, now Pat. No. 10,188,114, which is a division of application No. 14/459,810, filed on Aug. 14, 2014, now Pat. No. 9,333,227.

(60) Provisional application No. 61/867,510, filed on Aug. 19, 2013.

(51) Int. Cl.
C12N 1/12 (2006.01)
A61K 36/06 (2006.01)
A61K 35/74 (2015.01)
A61K 36/02 (2006.01)
C12N 1/16 (2006.01)
C12N 1/20 (2006.01)
C07K 14/195 (2006.01)
C12N 1/38 (2006.01)
A01N 63/50 (2020.01)

(52) U.S. Cl.
CPC ............. C12N 1/12 (2013.01); A01N 63/50 (2020.01); A61K 35/74 (2013.01); A61K 36/02 (2013.01); A61K 36/06 (2013.01); C07K 14/195 (2013.01); C12N 1/16 (2013.01); C12N 1/20 (2013.01); C12N 1/38 (2013.01)

(58) Field of Classification Search
CPC ........ A01N 63/50; A01N 63/20; A01N 63/22; A61K 35/74; A61K 36/02; A61K 36/06; C07K 14/195; C12N 1/12; C12N 1/16; C12N 1/20; C12N 1/38
See application file for complete search history.

(56) References Cited

U.S. PATENT DOCUMENTS

| 5,300,431 A | 4/1994 | Pierce et al. |
| 5,549,895 A | 8/1996 | Lyon et al. |
| 5,631,153 A | 5/1997 | Capecchi et al. |
| 5,670,370 A | 9/1997 | Molin et al. |
| 5,855,732 A | 1/1999 | Yoshida |
| 5,888,732 A | 3/1999 | Hartley et al. |
| 5,910,438 A | 6/1999 | Bernard et al. |
| 5,922,583 A | 7/1999 | Morsey |
| 6,143,557 A | 11/2000 | Hartley et al. |
| 6,171,861 B1 | 1/2001 | Hartley et al. |
| 6,180,407 B1 | 1/2001 | Bernard et al. |
| 6,270,969 B1 | 8/2001 | Hartley et al. |
| 6,271,359 B1 | 8/2001 | Norris et al. |
| 6,528,285 B1 | 3/2003 | Biet et al. |
| 7,176,029 B2 | 2/2007 | Bernard et al. |
| 7,183,097 B1 | 2/2007 | Gerdes et al. |
| 7,595,185 B2 | 9/2009 | Gerdes et al. |
| 7,595,186 B2 | 9/2009 | Gerdes et al. |
| 8,318,497 B2 | 11/2012 | Szpirer et al. |
| 8,470,580 B2 | 6/2013 | Gabant et al. |
| 8,476,048 B2 | 7/2013 | Caimi et al. |
| 8,697,426 B2 | 4/2014 | Leana et al. |
| 8,877,504 B2 | 11/2014 | Gabant et al. |
| 9,333,227 B2 * | 5/2016 | Gabant ............... C12N 1/38 |
| 10,188,114 B2 | 1/2019 | Gabant |
| 2004/0115811 A1 | 6/2004 | Gabant |
| 2005/0130308 A1 | 6/2005 | Bernard |
| 2005/0260585 A1 | 11/2005 | Szpirer |
| 2010/0330041 A1 | 12/2010 | Bayrock |
| 2013/0115658 A1 | 5/2013 | Szpirer et al. |
| 2013/0280810 A1 | 10/2013 | Gabant et al. |
| 2014/0148379 A1 | 5/2014 | Liu et al. |
| 2014/0178956 A1 | 6/2014 | Leana et al. |
| 2015/0050253 A1 | 2/2015 | Gabant |
| 2021/0070812 A1 | 3/2021 | Gabant et al. |

FOREIGN PATENT DOCUMENTS

| DE | 10038573 | 2/2002 |
| EP | 1 111 061 | 6/2001 |
| EP | 2 543 255 | 1/2013 |
| WO | WO 94/03616 | 2/1994 |

(Continued)

OTHER PUBLICATIONS (1992) Journal of Cellular Biochemistry, Keystone Symposia on Molecular & Cellular Biology, 104.
Abremski, et al. (1984) Bacteriophage P1'Site-specific Recombination. J. Bio. I. Chem. 259(3):1509-1514.
Acuna, et al., FEBS Open Bio, 2: 12-19, 2012.
Adetunji and Olaoye, Malaysian Journal of Microbiology 9: 130-13, 2013.
Aizenman, et al. (1996) An *Escherichia coli* chromosomal "addiction module" regulated by 3', 5'-bispyroohosohate: A modayk for programmed bacterial cell death. Proc. Nail. Acad. Sci. 93:6059-6063.

(Continued)

Primary Examiner — Blaine Lankford
(74) Attorney, Agent, or Firm — Knobbe, Martens, Olson & Bear, LLP

(57) ABSTRACT

It can be useful to regulate the growth of microbial cells. Some embodiments herein provide genetically engineered microbial cells that can produce bacteriocins to control the growth of microbial cells. In some embodiments, microbial cells are contained within a desired environment. In some embodiments, contaminating microbial cells are neutralized. In some embodiments, a first microbial cell type regulates the growth of a second microbial cell type so as to maintain a desired ratio of the two cell types.

18 Claims, 8 Drawing Sheets
Specification includes a Sequence Listing.

(56) References Cited

FOREIGN PATENT DOCUMENTS

| WO | WO 97/13401 | 4/1997 |
|---|---|---|
| WO | WO 97/14805 | 4/1997 |
| WO | WO 99/02555 | 1/1999 |
| WO | WO 99/21977 | 5/1999 |
| WO | WO 99/58652 | 11/1999 |
| WO | WO 01/31039 | 5/2001 |
| WO | WO 01/42509 | 6/2001 |
| WO | WO 01/46444 | 6/2001 |
| WO | WO 02/12474 | 2/2002 |
| WO | WO 02/66657 | 8/2002 |
| WO | WO 2004/022745 | 3/2004 |
| WO | WO 2010/060057 | 5/2010 |
| WO | WO 2019/121983 A1 | 6/2019 |

OTHER PUBLICATIONS

Allison et al., "Functional Analysis of the Gene Encoding Immunity to Lactacin F, laf, and Its Use as a Lactobacillus-Specific, Food-Grade Genetic Marker", Applied and Environmental Microbiology, vol. 62, No. 12, pp. 4450-4460, Dec. 1996.
Altschul, S.F., et al., "Basic local alignment search tool", J. Mol. Biol. 215:403-410, 1990.
Backman, et al., (1983), "Tetracycline Resistance Determined by pBR322 is Mediated by one Polypeptide." Gene 26. pp. 197-203.
Bacteriocin, Wikipedia, http://en.wikpedia.org/wiki/Bacteriocin Printed on Oct. 3, 2014.
Bahassi, et al. (1995) F plasmid CcdB killer protein: ccd8 gene mutants coding for non-cy1otoxic proteins which retain their regulatory functions. Molecular Microbiology 15(6\:1031 -1037.
Baum, "Tn5401, a New Class II Transposable Element from Bacillus thuringiensis," Journal of Bacteriology, vol. 176. No. 10, May 1994, pp. 2835-2845.
Baunonis, et al. (1993) Genomic Targeting with Purified Cre Recombinase. Nucleic Acids Research 21 (9):2025-2029.
Bech et al., "Sequence of the reLB transcription unit from *Escherichia coli* and Identification of the reLB gene," The EMBO Journal, vol. 4, No. 4 00.1059-1066 1985.
Bernard (1996) Positive Selection of Recombinant DNA by CcdB. BioTechniques 21(2)320-323.
Bernard et al., 1992 "Cell killing, by the F plasmid CcdB protein involves poisoning of DNA-topoisomerase II complexes," J. Mol. Biol. 226:735-745.
Bernard, et al. (1991) The 41 carboxy-terminal residues of the miniF plasmid CcdA protein are sufficient to antagonize the killer activity of the CcdB protein. Mol. Gen Genet 226:297-304.
Bernard, P., et al. (1994) Positive-Selection Vectors Using the F Plasmid cedB Killer Gene. Gene 148, pp. 71-74.
Bex, et al. (1983) Mini-F encoded proteins: identification of a new 10.5 kilodalton species. The EMBO Journal,2(11):1853-1861.
Biswas, et al. (1993) High-Efficiency Gene Inactivation and Replacement System for Gram-Positive Bacteria. J. Bacteriology 175(11):3628-3635.
Bochner, et al. (1980) Positive Selection for loss of Tetracycline Resistance. J. Bacteriology 143(2):923-933.
Boyd (1993) Turbo Cloning: A Fast, Efficient Method for Cloning PCR Products and Other Blunt-Ended DNA Fragments into Plasmids. Nucleic Acids Research 21(4):817-821.
Bravo, et al. (1988) Killing of *Escherichia coli* cells modulated by components of the stability system ParD of plasmid R1. Mol. Gen. Genet. 215:146-151.
Bubeck, et al. (1993) Rapid Cloning by Homologous Recombination in vivo. Nucleic Acids Research 21(15):3601-3602.
Bult, "Complete Genome Sequence of the Methanogenic Archaeon, Methanococcus Jannaschii," SCIENCE, vol. 273 Aug. 23, 1996.00.1058-1073.
Burns, et al. (1984) Positive Selection Vectors: A Small Plasmid Vector Useful for the Direct Selection of Sau2A-aenerated overlapping DNA Fragments. Gene 27:323-325.

Campelo et al., "A bacteriocin gene cluster able to enhance plasmid maintenance in *Lactococcus lactis*", Microbial Cell Factories 2014, 13:77. Accessible on the world wide web at www.microbialcellfactories.com/content/13/1/77. 9 pages.
Cole et al., "Deciphering the Biology of Mycobacterium Tuberculosis from the Complete Genome Sequence," Nature vol. 393, Jun. 11, 1998 Do.537-544.
Communication under Rule 164(2)(a) EPC dated Oct. 17, 2018 in European Application No. 14758511.1.
Cotter, P. D. et al., "Bacteriocins-a viable alternative to antibiotics", Nature Reviews Microbiology 11:95-105.
Couturier, et al. (1998) Bacterial death by DNA gyrase poisoning. Trends in Microbiology 6(7):269-275.
Craine, (1982) Novel Selection for Tetracycline-or Chloramphenicol—Sensitive *Escherichia coli*. J. Bacteriology 151(1):487-490.
Cui et al., "Class IIa Bacteriocins: Diversity and New Developments", Int. J. Mol. Sci., vol. 13, pp. 16668-16707, 2012.
D'Souza, S.F., "Microbial biosensors", Biosensors & Bioelectronics, vol. 16, 2001, pp. 337-353.
Daw et al., "Bacteriocins: Nature, Function and Structure", Micron, vol. 27, No. 6, pp. 467-479, 1996.
Ebert et al. "A Moloney MLV-Rat Somatotropin Fusion Gene Produces Biologically Active Somatotropin in a transgenic pig." Molecular Endocrinology. 2:277-283, 1988.
File History of U.S. Appl. No. 13/919,952.
File History of U.S. Appl. No. 10/468,536.
File History of U.S. Appl. No. 10/526,525.
File History of U.S. Appl. No. 13/660,907.
File History of U.S. Appl. No. 09/700,130.
File History of U.S. Appl. No. 11/558,856.
File History of U.S. Appl. No. 11/837,456.
Fleischmann et al., "Whole-Genome Random Sequencing and Assembly of Haemophilus Influenza Rd," Science, vol. 269. 00.496-512 Jul. 28, 1995.
Gabant et al., 1997 "Bifunctional lacZ a-ccdB genes for selective cloning of PCR products," Biotechniques 23:938-941.
Gabant et al., 1998 "Direct selection cloning vectors adapted to the genetic analysis of gram-negative bacteria and their plasmids," Gene 207:87-92.
Gabant et al., 2000 "New positive selection system based on the parD (kislkid) system of the R1 plasmid," Biotechniques 28:784-788.
Gabant et al., 2001 "Use of poison/antidote systems for selective cloning," in Plasmid Biology 2000: International, Symposium on Molecular Bioloy of Bacterial Plasmids, Meeting Abstracts, 00.135-170, Plasmid 45:160-161.
Gajic et al., "Novel Mechanism of Bacteriocin Secretion and Immunity Carried Out by Lactococcal Multidrug Resistance Proteins*", The Journal of Biological Chemistry, Sep. 5, 2003, vol. 278, No. 36, pp. 34291-34298.
Gerard et al., "Bactericidal Activity of Colicin V Is Mediated by an Inner Membrane Protein, SdaC, of *Escherichia coli*", Journal of Bacteriology, vol. 187, No. 6, pp. 1945-1950, Mar. 2005.
Gerdes (2000) Toxin-Antitoxin modules may regulate synthesis of macromolecules during nutritional stress. Journal of Bacteriology 182:561-572.
Gerdes, et al. "RNA antitoxins." (2007) Current Opinion in Microbiology, vol. 10, p. 117-124.
Gibson et al, "Creation of a Bacterial Cell Controlled by a Chemically Synthesized Genome", Science, vol. 329, pp. 52-56, 2010.
Goni-Moreno, et al., "Multicellular Computing Using Conjugation for Wiring", PLoS ONE 8(6): e65986, 2013.
Gossen, J. A., et al. (1992) Application of Galactose-Sensitive *E.coli* Strains as Selective Hosts for LacZ Plasmids. Nucleic Acids Res. 20.0.3254.
Gotfredsen, et al., "The *Escherichia coli* relBE genes belong to a new toxin-antitoxin gene family" Molecular Microbiology (1998) 29(4): 1065-1076.
Green and Sambrook, "Molecular Cloning: a Laboratory Manual", Cold Spring Harbor Laboratory Press; 4th edition, 2012.
Gronenborn (1978) Methylation of single-stranded DNA in vitro introduces new restriction endonuclease cleavage sites. Nature, 272:375-377.

(56) References Cited

OTHER PUBLICATIONS

Gronlund et al., "Toxin-Antitoxin Systems Homologous with relBE of *Escherichia coli* Plasmid P307 are Ubiquitous in Prokaryotes," Journal of Molecular Biology, vol. 285, No. 4, Jan. 29, 1999, pp. 1401-1415.
Guilfoyle, R.A., and I.M. Smith (1994) "A Direct Selection Strategy for Stotgun Cloning and Sequencing in the Bacteriophage M13." Nucleic Acids Res.22, pp. 100-107.
Guzman et al. 1995 "Tight regulation, modulation, and high-level expression by vectors containing the arabinose PBAO promoter," J. Bacteriol. 177:4121-4130.
Hammer et al. "Genetic Engineering of Mammalian Embryos." J. Anim. Sci. 63:269-278, 1986.
Hartley et al., DNA cloning using in vitro site-specific recombination: Genome Res. 10:1788-1795, 2000.
Hasan et al., Gene, vol. 56, pp. 145, 1987.
Hebsgaard, S.M., et al. (1996) "Splice Site Prediction in Arabidopsis Thaliana Pre-mRNA by Combining Local and Global Sequence information." Nucleic Acids Research, 24(17) 3439-3452.
Henrich et al. 1986 "Use of the lysis gene of bacteriophage X174 for the construction of a positive selection vector," Gene 42:345-349.
Herrero, M., et al., (1990) "Transposon Vectors Containing Non-Antibiotic Resistance Selection markers for Cloning and Stable Chromosomal Insertion of Foreign Genes in Gram-Negative Bacteria." J. Bact. 172,11, pp. 6557-6567.
Holt, et al. (1993) A Novel Phage A Replacement Cre-lox Vector that has Automatic Subcloning Capabilities, Gene 133:95-97.
Inglis, et al., "The Role of Bacteriocins as Selfish Genetic Elements". Biology Letters, Issue 9, vol. 3 Jun. 2013. Published Apr. 24, 2013, DOI: 10.1098/rsbl.2012.1173. 6 pages.
International Search Report and Written Opinion dated Feb. 5, 2015 in PCT Application No. PCT/EP2014/067418.
International Search Report from PCT/BE02/00151, dated May 22, 2001.
International Search Report from PCT/BE02/00021, dated Jul. 12, 2002.
International Preliminary Examination Report from PCT/BE02/00021, dated Feb. 19, 2003.
International Preliminary Examination Report from PCT/BE03/00045, dated Feb. 24, 2004.
Ioannou, et al. (1994) A new bacteriophage P1-derived vector for the propagation of large human DNA fragments, Nature Genetics 6:84-89.
Jaramillo, A., "Synthetic Biology—Engineered stable ecosystems", Nature Microbiology, vol. 2, No. 17119, pp. 1-2, Jul. 25, 2017.
Jensen et al., 1995 "Comparison of ccd of F, parDE of RP4, and parD of R1 using a novel conditional replication control system of plasmid R1," Molecular Microbiology 17:211-220.
Jensen et al., 1995 "Programmed cell death in bacteria: protect plasmid stabilization systems," Molecular Microbiology 17:205-210.
Kaneko et al., "Sequence Analysis of the Genome of the Unicellular Cyanobacterium Synechocystis sp. Strain PCC6803. II. Sequence Determination of the Entire Genome and Assignment of Potential Protein-Coding Regions " DNA Research, vol. 3, 00.109-136.1996.
Karoui, et al. (1983) Ham22, a mini-F mutation which is lethal to host cell and promotes recA-dependent induction of lambdoid prophage. The EMBO Journal. 2(11): 1863-1868.
Kristoffersen et al. "Bacterial Toxin-Antitoxin Gene Systems as Containment Control in Yeast Cells" Applied and Environmental Microbiology, vol. 66 No. 12, Dec. 2000, p. 5524-5526.
Kuhn et al. 1986 "Positive-selection vectors utilizing lethality of the EcoRI endonuclease," Gene 44:253-263.
Landy, Arthur, 1989 Dynamic, structural, and regulatory aspects of A site-specific recombination: Annu. Rev. Biochem 58:913-949.
Lehnherr, et al. (1993) Plasmid Addiction Genes of Bacteriophage P1: doc, which cause cell death on curing of prophage, and phd, which prevents host death when prophage is retained. J. Mol. Biol. 233:414-428.

Liu (1989) DNA Topoisomerase poisons as antitumor drugs. Annu. Rev. Biochem. 58:351-375.
Maki, et al (1992) Modulation of DNA Supercoiling Activity of *Escherichia coli* DNA Gyrase by F Plasmid Proteins, The Journal of Biological Chemistry vol. 267(17): 12244-12251.
Maloy, et al. (1981) Selection for Loss of Tetracycline Resistance by *Escherichia coli*, Journal of Bacteriology, 145(2):1110-1112.
Manning, P.A., "Nucleotide Sequence encoding the Mannose-fucose-resistant Hemagglutinin of Vibrio Cholerae 01 and Construction of a Mutant," EMBL Sequence Database, Aug. 7, 1993. pp. 1-7.
Maxwell, et al. (1986) Mechanistic aspects of DNA Topoisomerases. Advan. Protein Chem. 38:69-107.
McAuliffe et al., "Identification and overexpression of ltnI, a novel gene which confers immunity to the two-component lantibiotic lacticin 3147", Microbiology, 2000, vol. 146, pp. 129-138.
McBride, et al., "Contamination management in Low Cost Open Algae Ponds for Biofuels Production", Industrial Biotechnology, vol. 10, pp. 221-227, 2014.
Messing, et al. (1977) Filamentous coliphage M13 as a cloning vehicle: Insertion of a HindII Fragment of the lac regulatory region in M13 replicative form in vitro. Proc Nail. Acad. Sci. 74(9):3642-3646.
Miki, et al. (1984) Control of Cell Division by Sex Factor F in *Escherichia coli*. J. Mol. Bioi. 174:627-646.
Miki, et al. (1984) Control of Cell Division by Sex Factor F in *Escherichia coli*. J. Mol. Biol. 174:605-625.
Moreadith et al. "Gene Targeting in Embryonic Stem Cells: The new Physiology and metabolism." J. Mol. Med. 75:208-216 1997.
Mori, Hirotada, et al., "Prophage λ Induction Caused by Mini-F Plasmid Genes." (1984) Mol Gen Genet 196:185-193.
Mullins et al. "Perspective Series: Molecular Medicine in Genetically-Engineered Animals." J. Clin. Invest. 98 (Suppl.): 837-S40, 1996.
Murphy, et al. (1991), pλZd39: A New Type of cDNA Expression Vector for Low Background, High Efficiency Directional Cloning. Nucleic Acids Research 19(12):3403-3408.
Muyrers et al. 2001 "Techniques: recombinogenic engineering—new 'options for cloning and manipulating DNA," Trends in Biochem. Sci. 26:325-331.
Nilsson, et al. (1983) An Improved Positive Selection Plasmid Vector Constructed by Oligonucleotide Mediated Mutagenesis. Nucleic Acids Research 11 (22):8019-8029.
Nomura M., "Colicins and Related Bacteriocins", Annual Review of Microbiology, vol. 21, pp. 257-284, Oct. 1967.
Norrander, et al. (1983) Construction of improved M13 vectors using oligodeoxynucleotide-directed mutagenesis. Gene 26:101-106.
Notice of Allowability from U.S. Appl. No. 08/379,614, dated Mar. 3, 1998.
Notice of Allowance dated Feb. 11, 2016 in U.S. Appl. No. 14/459,810.
Office Action dated Sep. 29, 2006 in U.S. Appl. No. 10/468,536.
Office Action dated Jun. 19, 2007 in U.S, U.S. Appl. No. 10/468,536.
Office Action dated Mar. 25, 2008 in U.S. Appl. No. 10/468,536.
Office Action dated Jan. 29, 2009 in U.S. Appl. No. 10/468,536.
Office Action dated Nov. 16, 2009 in U.S. Appl. No. 10/468,536.
Office Action dated Jul. 27, 2012 in U.S. Appl. No. 10/468,536.
Office Action dated Apr. 20, 2009 in U.S. Appl. No. 10/526,525.
Office Action dated Jun. 14, 2010 in U.S. Appl. No. 10/526,525.
Office Action dated Mar. 2, 2011 in U.S. Appl. No. 10/526,525.
Office Action dated Sep. 9, 2011 in U.S. Appl. No. 10/526,525.
Office Action dated Feb. 10, 2012 in U.S. Appl. No. 10/526,525.
Office Action dated Jun. 14, 2005 in U.S. Appl. No. 09/700,130.
Office Action dated Jan. 5, 2006 in U.S. Appl. No. 09/700,130.
Office Action from U.S. Appl. No. 08/379,614, dated Aug. 27, 1996.
Office Action from U.S. Appl. No. 08/379,614, dated Aug. 4, 1997.
Office Action from U.S. Appl. No. 09/225,152, dated Sep. 13, 1999.
Office Action from U.S. Appl. No. 09/634 039, dated Dec. 20, 2001.
Office Action from U.S. Appl. No. 09/634,039, dated Jan. 15, 2003.
Office Action from U.S. Appl. No. 09/634,039, dated Sep. 24, 2003.
Office Action from U.S. Appl. No. 09/634,039, dated Dec. 16, 2004.
Office Action from U.S. Appl. No. 09/634,039, dated Jun. 29, 2005.
Office Action dated Oct. 25, 2013 in U.S. Appl. No. 13/919,952.
Office Action dated May 5, 2014 in U.S. Appl. No. 13/919,952.

(56) References Cited

OTHER PUBLICATIONS

Office Action dated Aug. 28, 2015 in U.S. Appl. No. 14/459,810.
Office Action dated Nov. 30, 2017 in Chinese Application No. 201480057387.2 with English translation.
Office Action dated Nov. 5, 2018 in Chinese Patent Application No. 201480057387.2; 4 pages.
Ogura, et al. (1983) Mini-F plasmid genes that couple host cell division to plasmid proliferation. Proc. Natl. Acad. Sci. USA 80:4734-4788.
Opinion of the Scientific Panel on Food Additives, Flavourings, Processing Aids and Materials in Contact with Food on a Request from the Commission Related to the use of Nisin (E 234) as a food additive. Question No. EFSA-Q-2005-031. Adopted on Jan. 26, 2006. The EFSA Journal (2006) 314, pp. 1-16.
Pag et al., "Molecular Analysis of Expression of the Lantibiotic Pep5 Immunity Phenotype", Applied and Environmental Microbiology, Feb. 1999, vol. 65, No. 2, pp. 591-598.
Partial International Search Report dated Jan. 13, 2015 in Application No. PCT/EP2014/067418.
Peakman, et al. (1992) Highly Efficient Generation of Recombinant Baculoviruses by Enzymatically Mediated Site-Specific in vitro Recombination. Nucleic Acids Research 20(3):495-500.
Pecota, et al. "Combining the hok/sok, parDE, and pnd Postsegregational Killer Loci to Enhance Plasmid Stability." (1997) Applied and Environmental Microbiology, vol. 63, p. 1917-1924.
pGT-N28 Vector DNA (catalog #N3728) New England Biolabs Online Catalog, Jun. 2, 1999, p. 1, www.neb.comlneb/products/nucleicJ307-28.html the whole document.
Pierce et al. 1992 "A positive selection vector for cloning high molecular weight DNA by the bacteriophage P1 system: improved cloning efficacy," PNAS USA 89:2056-2060.
pKO Scrambler Series Gene Targeting Vectors for Knockout Mice. Stratagene Online Catalog, Jan. 1998, pp. 1-3; www.stratagene.com/cellbio/toxicology/pko.htm, the whole document.
Pomares et al., "Potential Applicability of Chymotrypsin-Susceptible Microcin J25 Derivatives to Food Preservation", Applied and Environmental Microbiology, vol. 75, No. 17, pp. 5734-5738, Sep. 2009.
Pre-Interview Communication dated Jan. 28, 2015 in U.S. Appl. No. 14/459,810.
Reeves et al., "Engineering *Escherichia coli* into a Protein Delivery System for Mammalian Cells", ACS Synth. Biol., vol. 4, pp. 644-654, 2015.
Riley et al., "BACTERIOCINS: Evolution, Ecology, and Application", Annu. Rev. Microbiol., 2002, vol. 56, pp. 117-137.
Roberts, et al. (1994) The parDE operon of the broad-host-range plasmid RK2 specifies growth inhibition associated with plasmid loss. J. Mol. Biol. 18; 237 (1): 35-51.
Roberts, et al. (1992) Definition of a Minimal Plasmid Stabilization System from the Broad-Host-Range Plasmid RK2. Journal of Bacteriology Dec. 1992:8119-8132.
Roca, et al. (1992) A Hit-and-Run System for Targeted Genetic Manipulations in Yeast. Nucleic Acid Research 20(17):4671-4672.
Ruiz-Echevarria et al. (1991) Structural and functional comparison between the stability systems ParD of plasmid R1 and Ccd of plasmid. F. Mol. Gen. Genet 225:355-362.
Ruiz-Echevarria et al. 1995 A mutation that decreases the efficiency of plasmid R1 replication leads to the activation of parD, a killer stability system of the plasmid: FEMS Microb. Letters 130: 129-136.
Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.
Sadler, et al. (1980) Plasmids containing many tandem copies of a synthetic lactose operator. Gene 8:279-300.
Salmon et al., "The Antidote and Autoregulatory Functions of the F Plasmid CcdA Protein: a Genetic and biochemical Survey" Molecular and General Genetics vol. 244, pp. 530-538. 1994.
Sambrook, et al. (1989) Molecular Cloning: A Laboratory Manual. Cold Spring Harbor Laboratory Press, Cold Spring Harbor, NY, pp. xi-xxxviii.
Sambrook, et al. (1989) Molecular Cloning: A Laboratory Manual. Cold Spring Harbor Laboratory Press, Cold Spring Harbor, NY, pp. 4.12 A.9-A.13.
Saul, et al., "Nucleotide Sequence and Replication Characteristics of RepFIB, a Basic Replicon of IncF Plasmids," Journal of Bacteriology. vol. 171 No.5 00.2697-2707, May 1989.
Schlieper et al. 1998 "A positive selection vector for cloning of long polymerase chain reaction fragments based on a lethal mutant of the crp gene of *Escherichia coli*," Anal. Biochem. 257:203-209.
Seamark R.F. "Progress and Emerging Problems in Livestock Transgenesis: a Summary perspective." Repod. Fert. Dev. 6:653-657, 1994.
Shalani and Srivastava (2008) The Internet Journal of Microbiology. vol. 5 No. 2. DOI: 10.5580127dd—accessible on the worldwide web at archive.ispub.comljournallthe-internet-journal-of-microbiology/volume-5-number-2/screening-for-antifungal-activity-of-pseudomonas-fluorescens-against-phytopathogenic-fungi.html#sthash.dOYs03UO.1DKuT1US.dpuf.
Shekh and Roy, BMC Microbiology 12: 132, 2012.
Shenin et al., "Characteristics of Alirin B1, the major component of a fungicidal substance produced by Bacillus subtilis 10-VIZR". Antibiot Khimioter 1995 vol. 50: pp. 3-7.
Sierra et al. 1998 "Functional interactions between chpB and parD, two homologous conditional killer systems found in the *Escherichia coli* chromosome and in plasmid R1," FEMS Microb. Letters 168:51-58.
Simons, R. W., et al. (1987) "Improved Single and Multicopy Lac-Based Cloning Vectors for Protein and Operon Fusions." Gene 53 Do.85-96.
Smith, et al. (1985) Modification and Selection of Human Interleukin 2 Produced in Insect Cells by Baculovirus Expression Vector. Nalt Acad. Sci. 82:8404-8408.
Smith, et al. (1997) The poison-antidote stability system of the broad-host-range Thiobacilus ferroxidans plasmid pTF-FC2. Molecular Microbioloav 26(5):961-970.
Thisted, et al., "Mechanism of Post-segregational Killing by the hok/sok System of Plasmid R1; Sok Antisense RNA Regulates hok Gene Expression Indirectly Through the Overlapping mok Gene." (1992) J. Mol. Biol., vol. 223, p. 41-54.
Tomb et al., "The Complete Genome Sequence of the Gastric Pathogen Helicobacter Pylori," Nature. vol. 388 Aug. 7, 1997 pp. 539-547.
Trudel et al., (1996), pGATA: a positive selection vector based on the toxicity of the transcription factor GATA-1 to bacteria: BioTechniques 20:684-693.
Tsuchimoto et al. (1988) Two Genes, pelK and peml, responsible for stable maintenance of resistance plasmid R100. J. of Bateriol., 170(4):1461-1466.
Tsuchimoto et al.,"The Stable Maintenance System pern of Plasmid R100: Degradation of Peml Protein May Allow PemK Protein To Inhibit Cell Growth." Journal of Bacteriology, vol. 174, No. 13, pp. 4205-4211 Jul. 1992.
Tsuchimoto, et al. (1993) Autoregulation by cooperative binding of the Peml and PemK proteins to the promoter region of the pern operon. 237:81-88.
Union Nationale des Groupements de Distillateurs D'Alcool, "Kamoran", 2005.
U.S. Appl. No. 09/634,039, filed Aug. 8, 2000 by Bernard, et al.
Van Melderen, et al., "Bacterial Toxin-Antitoxin Systems: More Than Selfish Entities?", PLoS Genetics, vol. 5, No. 3, Mar. 2009, pp. 1-6.
Van Reeth, T., et al. (1998) "Positive Selection Vectors to Generate Fused Genes for the Expression of His-Tagged Proteins." BioTechniques. 25(5):898-904.
Vernet, T., et al. (1985) "A Direct-Selection Vector Derived from pColE3-CA38 and adapted for Foreign Gene Expression." Gene 34:87-93.
Wang, (1985), DNA Topoisomerases. Ann. Rev. Biochem. 54:665-697.

(56) References Cited

OTHER PUBLICATIONS

Wang et al., Genome Mining Demonstrates the Widespread Occurrence of Gene Clusters Encoding Bacteriocins in Cyanobacteria. PLoS ONE 6(7): e22384, 2011.
Wright et al., "Building-in biosafety for synthetic biology", Microbiology, vol. 159, pp. 1221-1235, 2013.
Yanisch-Perron, et al. (1985) Improved M13 phage closing vectors and host strains: Nucleotide sequence of the M13mp18 and DUC19 vectors. Gen, 33:103-119.
Yarmolinsky (1995) Programmed cell death in bacterial populations. Science, 267:836-837.
Yu et al. 2000 "An efficient recombination system for chromosome engineering in *Escherichia coli*," PNAS USA 97:5978-5983.
Zuber, P et al., "Peptide Antibiotics", in Sonenshein ed, "Bacillus subtilis and Other Gram-Positive Bacteria", 1993 American Society for Microbiology, Washington D.C. pp. 897-916.
Office Action dated Apr. 28, 2017 in U.S. Appl. No. 15/087,706.
Office Action dated Sep. 14, 2017 in U.S. Appl. No. 15/087,706.
Office Action dated Apr. 5, 2018 in U.S. Appl. No. 15/087,706.
Notice of Allowance dated Sep. 12, 2018 in U.S. Appl. No. 15/087,706.
Borrero et al., "Cloning, Production, and Functional Expressing of the Bacteriocin Enterocin A, Produced by *Enterococcus faecium* T136, by the Yeasts *Pichia pastoris, Kluyveromyces lactis, Hansenula polymorpha, and Arxula adeninivorans*", Applied and Environmental Microbiology, vol. 78, No. 16, pp. 5956-5961, Aug. 2012.
Basanta et al., "Development of Bacteriocinogenic Strains of *Saccharomyces cerevisiae* Heterologously Expressing and Secreting the Leaderless Enterocin L50 Peptides L50A and L50B from Enterococcus faecium L50", Applied and Environmental Microbiology, vol. 75, No. 8, pp. 2382-2392, Apr. 2009.
Bondaryk et al., "Natural Antimicrobial Peptides as Inspiration for Design of a New Generation Antifungal Compounds", J. Fungi, vol. 3, No. 46, pp. 1-36, 2017.
Communication pursuant to Article 94(3) EPC in European Application No. 14 758 511.1.
Lum et al., "Activity of Novel Synthetic Peptides against Candida albicans", Scientific Reports, vol. 5, No. 9657, pp. 1-12, 2015.
Office Action dated Aug. 15, 2019 in Brazilian Application No. BR 11 2016 003533 0 with English Translation.
Schoeman et al., "The Development of Bactericidal Yeast Strains by Expressing the *Pediococcus acidilactici* Pediocin Gene (ped A) in *Saccharomyces cerevisiae*", Yeast, vol. 15, pp. 647-656, 1999.
Office Action dated Mar. 12, 2021 in Indian Patent Application No. 201617008769 with English translation.
Office Action dated Apr. 20, 2021 in Brazilian Application No. BR 11 2016 003533 0 with English Translation.
Office Action dated Sep. 10, 2020 in European Application No. 14758511.1.
Communication pursuant to Rule 45 EPC dated Aug. 9, 2021 in European Application No. 21178464.0.
Communication pursuant to Article 94(3) EPC in European Application No. 14 758 511.1 dated Feb. 5, 2020.
European Search Report dated Mar. 8, 2022, in European Patent Application No. 21178464.0 in 12 pages.
Sanchez, J. et al., Cloning and Heterologous Production of Hiracin JM79, a Sec-Dependent Bacteriocin Produced by Enterococcus Hirae DCI-I5, in Lactic Acid Bacteria and Pichia Pastoris, Applied And Environmental Microbiology, vol. 74, No. 8, pp. 2471-2479, 2008.
Borrero, J. et al., Protein Expression Vector And Secretion Signal Peptide Optinlization To Drive The Production, Secretion, And Functional Expression Of The Bacteriocin Enterocin A In Lactic Acid Bacteria, Journal of Biotechnology, vol. 156, pp. 76-86, 2011.
Office Action with English Translation dated Apr. 21, 2022 in Chinese Patent Application No. 201910882176.7 in 8 pages.

* cited by examiner

SEQUENCE LISTING

```
<160> NUMBER OF SEQ ID NOS: 698

<210> SEQ ID NO 1
<211> LENGTH: 40
<212> TYPE: PRT
<213> ORGANISM: Enterococcus faecalis

<400> SEQUENCE: 1

Trp Leu Pro Pro Ala Gly Leu Leu Gly Arg Cys Gly Arg Trp Phe Arg
1               5                   10                  15

Pro Trp Leu Leu Trp Leu Gln Ser Gly Ala Gln Tyr Lys Trp Leu Gly
            20                  25                  30

Asn Leu Phe Gly Leu Gly Pro Lys
```

35                  40

<210> SEQ ID NO 2
<211> LENGTH: 5
<212> TYPE: PRT
<213> ORGANISM: Artificial Sequence
<220> FEATURE:
<223> OTHER INFORMATION: N-terminal motif of class terminal IIa
<220> FEATURE:
<221> NAME/KEY: VARIANT
<222> LOCATION: 3
<223> OTHER INFORMATION: Xaa = any amino acid

<400> SEQUENCE: 2

Tyr Gly Xaa Gly Val
1               5

<210> SEQ ID NO 3
<211> LENGTH: 135
<212> TYPE: PRT
<213> ORGANISM: Artificial Sequence
<220> FEATURE:
<223> OTHER INFORMATION: Hybrid bacteriocin Ent35-MccV

<400> SEQUENCE: 3

Gly Lys Tyr Tyr Gly Asn Gly Val Ser Cys Asn Lys Gly Cys Ser
1               5                   10                  15

Val Asp Trp Gly Arg Ala Ile Gly Ile Ile Gly Asn Asn Ser Ala Ala
            20                  25                  30

Asn Leu Ala Thr Gly Gly Ala Ala Gly Trp Lys Ser Gly Gly Ala
            35                  40                  45

Ser Gly Arg Asp Ile Ala Met Ala Ile Gly Thr Leu Ser Gly Gln Phe
    50                  55                  60

Val Ala Gly Gly Ile Gly Ala Ala Ala Gly Val Ala Gly Gly Ala
65                  70                  75                  80

Ile Tyr Asp Tyr Ala Ser Thr His Lys Pro Asn Pro Ala Met Ser Pro
                85                  90                  95

Ser Gly Leu Gly Gly Thr Ile Lys Gln Lys Pro Glu Gly Ile Pro Ser
            100                 105                 110

Glu Ala Trp Asn Tyr Ala Ala Gly Arg Leu Cys Asn Trp Ser Pro Asn
            115                 120                 125

Asn Leu Ser Asp Val Cys Leu
        130                 135

<210> SEQ ID NO 4
<211> LENGTH: 46
<212> TYPE: PRT
<213> ORGANISM: Lactobacillus acidophilus

<400> SEQUENCE: 4

Met Ile Ser Ser His Gln Lys Thr Leu Thr Asp Lys Glu Leu Ala Leu
1               5                   10                  15

Ile Ser Gly Gly Lys Thr His Tyr Pro Thr Asn Ala Trp Lys Ser Leu
            20                  25                  30

Trp Lys Gly Phe Trp Glu Ser Leu Arg Tyr Thr Asp Gly Phe
            35                  40                  45

<210> SEQ ID NO 5
<211> LENGTH: 141
<212> TYPE: DNA
<213> ORGANISM: Lactobacillus acidophilus

<400> SEQUENCE: 5

```
atgatttcat ctcatcaaaa aacgttaact gataaagaat tagcattaat ttctgggggg      60
aaaacgcact acccgactaa tgcatggaaa agtctttgga aaggtttctg ggaaagcctt     120
cgttatactg acggttttta g                                               141
```

<210> SEQ ID NO 6
<211> LENGTH: 81
<212> TYPE: PRT
<213> ORGANISM: Lactobacillus acidophilus

<400> SEQUENCE: 6

```
Met Ile Ser Met Ile Ser Ser His Gln Lys Thr Leu Thr Asp Lys Glu
1               5                   10                  15
Leu Ala Leu Ile Ser Gly Gly Lys Thr Tyr Tyr Gly Thr Asn Gly Val
            20                  25                  30
His Cys Thr Lys Lys Ser Leu Trp Gly Lys Val Arg Leu Lys Asn Val
        35                  40                  45
Ile Pro Gly Thr Leu Cys Arg Lys Gln Ser Leu Pro Ile Lys Gln Asp
    50                  55                  60
Leu Lys Ile Leu Leu Gly Trp Ala Thr Gly Ala Phe Gly Lys Thr Phe
65                  70                  75                  80
His
```

<210> SEQ ID NO 7
<211> LENGTH: 246
<212> TYPE: DNA
<213> ORGANISM: Lactobacillus acidophilus

<400> SEQUENCE: 7

```
atgatttcaa tgatttcatc tcatcaaaaa acgttaactg ataaagaatt agcattaatt      60
tctggggga aaacgtacta tggtactaat ggtgtgcatt gtactaaaaa gagtctttgg     120
ggtaaagtac gcttaaaaaa cgtgattcct ggaactcttt gtcgtaagca atcgttgccg     180
atcaaacagg atttaaaaat tttactgggc tgggctacag gtgcttttgg caagacattt     240
cattaa                                                                246
```

<210> SEQ ID NO 8
<211> LENGTH: 60
<212> TYPE: PRT
<213> ORGANISM: Lactobacillus acidophilus

<400> SEQUENCE: 8

```
Met Asp Lys Lys Thr Lys Ile Leu Phe Glu Val Leu Tyr Ile Ile Cys
1               5                   10                  15
Ile Ile Gly Pro Gln Phe Ile Leu Phe Val Thr Ala Lys Asn Asn Met
            20                  25                  30
Tyr Gln Leu Val Gly Ser Phe Val Gly Ile Val Trp Phe Ser Tyr Ile
        35                  40                  45
Phe Trp Tyr Ile Phe Phe Lys Gln His Lys Lys Met
    50                  55                  60
```

<210> SEQ ID NO 9
<211> LENGTH: 183
<212> TYPE: DNA
<213> ORGANISM: Lactobacillus acidophilus

<400> SEQUENCE: 9

```
atggataaga aaacaaaaat attatttgaa gtattataca tcatctgtat aataggccct      60
caatttatat tatttgtgac tgcaaaaaac aatatgtatc agttggtggg ttcgtttgtt     120
ggaatagtat ggttttcgta tattttttgg tatattttt tcaaacaaca taaaaaaatg     180
tag                                                                  183
```

<210> SEQ ID NO 10
<211> LENGTH: 65
<212> TYPE: PRT
<213> ORGANISM: Lactobacillus gasseri

<400> SEQUENCE: 10

Met Ala Leu Lys Thr Leu Glu Lys His Glu Leu Arg Asn Val Met Gly
1               5                   10                  15

Gly Asn Lys Trp Gly Asn Ala Val Ile Gly Ala Ala Thr Gly Ala Thr
            20                  25                  30

Arg Gly Val Ser Trp Cys Arg Gly Phe Gly Pro Trp Gly Met Thr Ala
        35                  40                  45

Cys Ala Leu Gly Gly Ala Ala Ile Gly Gly Tyr Leu Gly Tyr Lys Ser
    50                  55                  60

Asn
65

<210> SEQ ID NO 11
<211> LENGTH: 198
<212> TYPE: DNA
<213> ORGANISM: Lactobacillus gasseri

<400> SEQUENCE: 11

```
atggcttaa aaacattaga aaacatgaa ttaagaaatg taatgggtgg aaacaagtgg      60
gggaatgctg taataggagc tgctacggga gctactcgcg gagtaagttg gtgcagagga     120
ttcggaccat ggggaatgac tgcctgtgcg ttaggaggtg ctgcaattgg aggatatctg     180
ggatataaga gtaattaa                                                  198
```

<210> SEQ ID NO 12
<211> LENGTH: 51
<212> TYPE: PRT
<213> ORGANISM: Staphylococcus aureus

<400> SEQUENCE: 12

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50

<210> SEQ ID NO 13
<211> LENGTH: 156
<212> TYPE: DNA
<213> ORGANISM: Staphylococcus aureus

<400> SEQUENCE: 13

```
atgagttggt taaattttt aaatacatc gctaaatatg gcaaaaaagc ggtatctgct       60
gcttggaagt acaaaggtaa agtattagaa tggcttaatg ttggtcctac tcttgaatgg    120
```
gtatggcaaa aattaaagaa aattgctgga ttataa    156

<210> SEQ ID NO 14
<211> LENGTH: 61
<212> TYPE: PRT
<213> ORGANISM: Enterococcus avium

<400> SEQUENCE: 14

Met Thr Arg Ser Lys Lys Leu Asn Leu Arg Glu Met Lys Asn Val Val
1               5                   10                  15

Gly Gly Thr Tyr Tyr Gly Asn Gly Val Ser Cys Asn Lys Lys Gly Cys
            20                  25                  30

Ser Val Asp Trp Gly Lys Ala Ile Ser Ile Ile Gly Asn Asn Ser Ala
        35                  40                  45

Ala Asn Leu Ala Thr Gly Gly Ala Ala Gly Trp Lys Ser
    50                  55                  60

<210> SEQ ID NO 15
<211> LENGTH: 186
<212> TYPE: DNA
<213> ORGANISM: Enterococcus avium

<400> SEQUENCE: 15
atgacaagat caaaaaaatt aaatttacgc gaaatgaaga atgttgttgg tggtacctac    60
tatggaaatg gtgtatcttg taacaagaaa ggctgttcag ttgactgggg caaagccatc    120
agtattatag gaaataattc cgcagcaaac ttagcaactg gtggtgctgc tggttggaag    180
tcataa    186

<210> SEQ ID NO 16
<211> LENGTH: 67
<212> TYPE: PRT
<213> ORGANISM: Enterococcus faecalis

<400> SEQUENCE: 16

Met Lys Lys Lys Leu Val Ile Cys Gly Ile Ile Gly Ile Gly Phe Thr
1               5                   10                  15

Ala Leu Gly Thr Asn Val Glu Ala Ala Thr Tyr Tyr Gly Asn Gly Leu
            20                  25                  30

Tyr Cys Asn Lys Gln Lys Cys Trp Val Asp Trp Asn Lys Ala Ser Arg
        35                  40                  45

Glu Ile Gly Lys Ile Ile Val Asn Gly Trp Val Gln His Gly Pro Trp
    50                  55                  60

Ala Pro Arg
65

<210> SEQ ID NO 17
<211> LENGTH: 204
<212> TYPE: DNA
<213> ORGANISM: Enterococcus faecalis

<400> SEQUENCE: 17
atgaaaaaga aattagttat ttgtggcatt attgggattg gttttacagc attaggaaca    60
aatgtagaag ctgctacgta ttacggaaat ggtttatatt gtaataagca aaaatgttgg    120
gtagactgga ataaagcttc aagggaaatt ggaaaaatta ttgttaatgg ttgggtacaa    180
catggccctt gggctcctag atag    204

<210> SEQ ID NO 18

<211> LENGTH: 51
<212> TYPE: PRT
<213> ORGANISM: Lactococcus lactis

<400> SEQUENCE: 18

Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Val Ile Tyr Asn Ser Trp Asn Phe Val Phe Thr
        35                  40                  45

Cys Cys Ser
    50

<210> SEQ ID NO 19
<211> LENGTH: 156
<212> TYPE: DNA
<213> ORGANISM: Lactococcus lactis

<400> SEQUENCE: 19
atgaaagaac aaaactcttt taatcttctt caagaagtga cagaaagtga attggacctt      60
attttaggtg caaaaggcgg cagtggagtt attcatacaa tttctcatga agtaatatat     120
aatagctgga actttgtatt tacttgctgc tcttaa                               156

<210> SEQ ID NO 20
<211> LENGTH: 74
<212> TYPE: PRT
<213> ORGANISM: Enterococcus faecium

<400> SEQUENCE: 20

Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
            20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70

<210> SEQ ID NO 21
<211> LENGTH: 225
<212> TYPE: DNA
<213> ORGANISM: Enterococcus faecium

<400> SEQUENCE: 21
atgaaaaaga agtattaaa acattgtgtt attctaggaa tattaggaac ttgtctagct       60
ggcatcggta caggaataaa agttgatgca gctacttact atggaaatgg tctttattgt     120
aacaaagaaa aatgtgggt agattggaat caagctaaag gagaaattgg aaaaattatt     180
gttaatggtt gggttaatca tggtccatgg gcacctagaa ggtag                     225

<210> SEQ ID NO 22
<211> LENGTH: 50
<212> TYPE: PRT
<213> ORGANISM: Clostridium botulinum

<400> SEQUENCE: 22

```
Met Gln Lys Pro Glu Ile Ile Ser Ala Asp Leu Gly Leu Cys Ala Val
1               5                   10                  15

Asn Glu Phe Val Ala Leu Ala Ala Ile Pro Gly Gly Ala Ala Thr Phe
            20                  25                  30

Ala Val Cys Gln Met Pro Asn Leu Asp Glu Ile Val Ser Asn Ala Ala
        35                  40                  45

Tyr Val
    50

<210> SEQ ID NO 23
<211> LENGTH: 153
<212> TYPE: DNA
<213> ORGANISM: Clostridium botulinum

<400> SEQUENCE: 23
atgcaaaaac cagaaattat tagtgctgat ttagggcttt gtgcagttaa tgaatttgta      60
gctcttgctg ccattcctgg tggtgctgct acatttgcag tatgccaaat gccaaacttg     120
gatgagattg ttagtaatgc agcatatgtt taa                                  153

<210> SEQ ID NO 24
<211> LENGTH: 58
<212> TYPE: PRT
<213> ORGANISM: Streptococcus equinus

<400> SEQUENCE: 24

Met Met Asn Ala Thr Glu Asn Gln Ile Phe Val Glu Thr Val Ser Asp
1               5                   10                  15

Gln Glu Leu Glu Met Leu Ile Gly Gly Ala Asp Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55

<210> SEQ ID NO 25
<211> LENGTH: 177
<212> TYPE: DNA
<213> ORGANISM: Streptococcus equinus

<400> SEQUENCE: 25
atgatgaatg ctactgaaaa ccaaattttt gttgagactg tgagtgacca agaattagaa      60
atgttaattg gtggtgcaga tcgtggatgg attaagactt taacaaaaga ttgtccaaat     120
gtaatttctt caatttgtgc aggtacaatt attacagctt gtaaaaattg tgcttaa       177

<210> SEQ ID NO 26
<211> LENGTH: 77
<212> TYPE: PRT
<213> ORGANISM: Brochothrix campestris

<400> SEQUENCE: 26

Met His Lys Val Lys Lys Leu Asn Asn Gln Glu Leu Gln Gln Ile Val
1               5                   10                  15

Gly Gly Tyr Ser Ser Lys Asp Cys Leu Lys Asp Ile Gly Lys Gly Ile
            20                  25                  30

Gly Ala Gly Thr Val Ala Gly Ala Ala Gly Gly Leu Ala Ala Gly
        35                  40                  45

Leu Gly Ala Ile Pro Gly Ala Phe Val Gly Ala His Phe Gly Val Ile
    50                  55                  60
```

Gly Gly Ser Ala Ala Cys Ile Gly Gly Leu Leu Gly Asn
65                  70                  75

<210> SEQ ID NO 27
<211> LENGTH: 234
<212> TYPE: DNA
<213> ORGANISM: Brochothrix campestris

<400> SEQUENCE: 27
atgcacaagg taaaaaaatt aaacaatcaa gagttacaac agatcgtggg aggttacagt       60
tcaaaagatt gtctaaaaga tattggtaaa ggaattggtg ctggtacagt agctggggca      120
gccggcggtg gcctagctgc aggattaggt gctatcccag gagcattcgt tggagcacat      180
tttggagtaa tcggcggatc tgccgcatgc attggtggat tattaggtaa ctag            234

<210> SEQ ID NO 28
<211> LENGTH: 80
<212> TYPE: PRT
<213> ORGANISM: Butyrivibrio fibrisolvens

<400> SEQUENCE: 28

Met Ser Lys Lys Gln Ile Met Ser Asn Cys Ile Ser Ile Ala Leu Leu
1               5                   10                  15

Ile Ala Leu Ile Pro Asn Ile Tyr Phe Ile Ala Asp Lys Met Gly Ile
                20                  25                  30

Gln Leu Ala Pro Ala Trp Tyr Gln Asp Ile Val Asn Trp Val Ser Ala
            35                  40                  45

Gly Gly Thr Leu Thr Thr Gly Phe Ala Ile Ile Val Gly Val Thr Val
        50                  55                  60

Pro Ala Trp Ile Ala Glu Ala Ala Ala Ala Phe Gly Ile Ala Ser Ala
65                  70                  75                  80

<210> SEQ ID NO 29
<211> LENGTH: 243
<212> TYPE: DNA
<213> ORGANISM: Butyrivibrio fibrisolvens

<400> SEQUENCE: 29
atgagtaaaa aacaaattat gagtaactgt atatcaattg cattattaat agcactaatt       60
cctaatatct attttattgc agataaaatg gaattcagt tagcacctgc ttggtatcaa      120
gatattgtga attgggtatc tgctggtgga acacttacta ctggttttgc gattattgta      180
ggagttacag taccggcatg gatagcagaa gcagctgcag cttttggtat agcttcagca      240
tga                                                                    243

<210> SEQ ID NO 30
<211> LENGTH: 48
<212> TYPE: PRT
<213> ORGANISM: Butyrivibrio fibrisolvens

<400> SEQUENCE: 30

Met Asn Lys Glu Leu Asn Ala Leu Thr Asn Pro Ile Asp Glu Lys Glu
1               5                   10                  15

Leu Glu Gln Ile Leu Gly Gly Gly Asn Gly Val Ile Lys Thr Ile Ser
                20                  25                  30

His Glu Cys His Met Asn Thr Trp Gln Phe Ile Phe Thr Cys Cys Ser
            35                  40                  45

<210> SEQ ID NO 31
<211> LENGTH: 147
<212> TYPE: DNA
<213> ORGANISM: Butyrivibrio fibrisolvens

<400> SEQUENCE: 31
atgaacaaag aacttaatgc acttacaaat cctattgacg agaaggagct tgagcagatc    60
ctcggtggtg gcaatggtgt catcaagaca atcagccacg agtgccacat gaacacatgg   120
cagttcattt tcacatgttg ctcttaa                                       147

<210> SEQ ID NO 32
<211> LENGTH: 66
<212> TYPE: PRT
<213> ORGANISM: Carnobacterium maltaromaticum

<400> SEQUENCE: 32

Met Asn Ser Val Lys Glu Leu Asn Val Lys Glu Met Lys Gln Leu His
1               5                   10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
    50                  55                  60

Arg Pro
65

<210> SEQ ID NO 33
<211> LENGTH: 201
<212> TYPE: DNA
<213> ORGANISM: Carnobacterium maltaromaticum

<400> SEQUENCE: 33
atgaatagcg taaaagaatt aaacgtgaaa gaaatgaaac aattacacgg tggagtaaat    60
tatggtaatg gtgtttcttg cagtaaaaca aaatgttcag ttaactgggg acaagccttt   120
caagaaagat acacagctgg aattaactca tttgtaagtg gagtcgcttc tggggcagga   180
tccattggta ggagaccgta a                                             201

<210> SEQ ID NO 34
<211> LENGTH: 61
<212> TYPE: PRT
<213> ORGANISM: Carnobacterium maltaromaticum

<400> SEQUENCE: 34

Met Lys Ser Val Lys Glu Leu Asn Lys Lys Glu Met Gln Gln Ile Asn
1               5                   10                  15

Gly Gly Ala Ile Ser Tyr Gly Asn Gly Val Tyr Cys Asn Lys Glu Lys
            20                  25                  30

Cys Trp Val Asn Lys Ala Glu Asn Lys Gln Ala Ile Thr Gly Ile Val
        35                  40                  45

Ile Gly Gly Trp Ala Ser Ser Leu Ala Gly Met Gly His
    50                  55                  60

<210> SEQ ID NO 35
<211> LENGTH: 186
<212> TYPE: DNA
<213> ORGANISM: Carnobacterium maltaromaticum

<400> SEQUENCE: 35

```
atgaaaagcg ttaaagaact aaataaaaaa gaaatgcaac aaattaatgg tggagctatc    60
tcttatggca atggtgttta ttgtaacaaa gagaaatgtt gggtaaacaa ggcagaaaac   120
aaacaagcta ttactggaat agttatcggt ggatgggctt ctagtttagc aggaatggga   180
cattaa                                                              186
```

<210> SEQ ID NO 36
<211> LENGTH: 71
<212> TYPE: PRT
<213> ORGANISM: Carnobacterium maltaromaticum

<400> SEQUENCE: 36

```
Met Asn Asn Val Lys Glu Leu Ser Ile Lys Glu Met Gln Gln Val Thr
1               5                   10                  15

Gly Gly Asp Gln Met Ser Asp Gly Val Asn Tyr Gly Lys Gly Ser Ser
            20                  25                  30

Leu Ser Lys Gly Gly Ala Lys Cys Gly Leu Gly Ile Val Gly Gly Leu
        35                  40                  45

Ala Thr Ile Pro Ser Gly Pro Leu Gly Trp Leu Ala Gly Ala Ala Gly
    50                  55                  60

Val Ile Asn Ser Cys Met Lys
65                  70
```

<210> SEQ ID NO 37
<211> LENGTH: 216
<212> TYPE: DNA
<213> ORGANISM: Carnobacterium maltaromaticum

<400> SEQUENCE: 37

```
atgaataatg taaagagtt aagtattaaa gaaatgcaac aagttactgg tggagaccaa    60
atgtcagatg gtgtaaatta tggaaaaggc tctagcttat caaaggtgg tgccaaatgt   120 ggtttaggga tcgtcggcgg attagctact atcccttcag gtcctttagg ctggttagcc   180
ggagcagcag gtgtaattaa tagctgtatg aaataa                             216
```

<210> SEQ ID NO 38
<211> LENGTH: 64
<212> TYPE: PRT
<213> ORGANISM: Carnobacterium maltaromaticum

<400> SEQUENCE: 38

```
Met Leu Tyr Glu Leu Val Ala Tyr Gly Ile Ala Gln Gly Thr Ala Glu
1               5                   10                  15

Lys Val Val Ser Leu Ile Asn Ala Gly Leu Thr Val Gly Ser Ile Ile
            20                  25                  30

Ser Ile Leu Gly Gly Val Thr Val Gly Leu Ser Gly Val Phe Thr Ala
        35                  40                  45

Val Lys Ala Ala Ile Ala Lys Gln Gly Ile Lys Lys Ala Ile Gln Leu
    50                  55                  60
```

<210> SEQ ID NO 39
<211> LENGTH: 195
<212> TYPE: DNA
<213> ORGANISM: Carnobacterium maltaromaticum

<400> SEQUENCE: 39

```
atgttatatg aattagttgc atatggtatc gcacaaggta cagctgaaaa ggttgtaagt    60
ctaattaacg caggtttaac agtagggtct attatttcaa ttttgggtgg ggtcacagtc   120
```

```
ggtttatcag gtgtcttcac agcagttaaa gcagcaattg ctaaacaagg aataaaaaaa      180
gcaattcaat tataa                                                       195

<210> SEQ ID NO 40
<211> LENGTH: 836
<212> TYPE: PRT
<213> ORGANISM: Pectobacterium carotovorum subsp. carotovorum

<400> SEQUENCE: 40

Met Ile Lys Tyr Arg Leu Tyr Ala Pro Asn Asp Gly Asp Thr Met Thr
1               5                   10                  15

Val Ser Gly Gly Gly Trp Val Ser Asn Asp Arg Lys Gly Gly
            20                  25                  30

Asn Asp Arg Asp Asn Gly Lys Gly Ser Ala Val Asp Phe Ser Lys
        35                  40                  45

Asn Pro Glu Lys Gln Ala Ile Val Asn Pro Tyr Leu Ala Ile Ala Ile
    50                  55                  60

Pro Met Pro Val Tyr Pro Leu Tyr Gly Lys Leu Gly Phe Thr Ile Asn
65                  70                  75                  80

Thr Thr Ala Ile Glu Thr Glu Leu Ala Asn Val Arg Ala Ala Ile Asn
                85                  90                  95

Thr Lys Leu Ala Thr Leu Ser Ala Val Ile Gly Arg Ser Leu Pro Val
            100                 105                 110

Val Gly Arg Val Phe Gly Val Thr Ala Ala Gly Met Trp Pro Ser Ser
        115                 120                 125

Thr Ala Pro Ser Ser Leu Asp Ser Ile Tyr Asn Gln Ala His Gln Gln
    130                 135                 140

Ala Leu Ala Gln Leu Ala Ala Gln Gln Gly Val Leu Asn Lys Gly Tyr
145                 150                 155                 160

Asn Val Thr Ala Met Pro Ala Gly Phe Val Ser Ser Leu Pro Val Ser
                165                 170                 175

Glu Ile Lys Ser Leu Pro Thr Ala Pro Ala Ser Leu Leu Ala Gln Ser
            180                 185                 190

Val Ile Asn Thr Glu Leu Ser Gln Arg Gln Leu Ala Leu Thr Gln Pro
        195                 200                 205

Thr Thr Asn Ala Pro Val Ala Asn Ile Pro Val Val Lys Ala Glu Lys
    210                 215                 220

Thr Ala Met Pro Gly Val Tyr Ser Ala Lys Ile Ile Ala Gly Glu Pro
225                 230                 235                 240

Ala Phe Gln Ile Lys Val Asp Asn Thr Lys Pro Ala Leu Ala Gln Asn
                245                 250                 255

Pro Pro Lys Val Lys Asp Asp Ile Gln Val Ser Ser Phe Leu Ser Ser
            260                 265                 270

Pro Val Ala Asp Thr His His Ala Phe Ile Asp Phe Gly Ser Asp His
        275                 280                 285

Glu Pro Val Tyr Val Ser Leu Ser Lys Ile Val Thr Ala Glu Glu Glu
    290                 295                 300

Lys Lys Gln Val Glu Glu Ala Lys Arg Arg Glu Gln Glu Trp Leu Leu
305                 310                 315                 320

Arg His Pro Ile Thr Ala Ala Glu Arg Lys Leu Thr Glu Ile Arg Gln
                325                 330                 335

Val Ile Ser Phe Ala Gln Gln Leu Lys Glu Ser Ser Val Ala Thr Ile
            340                 345                 350
```

```
Ser Glu Lys Thr Lys Thr Val Ala Val Tyr Gln Glu Gln Val Asn Thr
            355                 360                 365

Ala Ala Lys Asn Arg Asp Asn Phe Tyr Asn Gln Asn Arg Gly Leu Leu
        370                 375                 380

Ser Ala Gly Ile Thr Gly Gly Pro Gly Tyr Pro Ile Tyr Leu Ala Leu
385                 390                 395                 400

Trp Gln Thr Met Asn Asn Phe His Gln Ala Tyr Phe Arg Ala Asn Asn
                405                 410                 415

Ala Leu Glu Gln Glu Ser His Val Leu Asn Leu Ala Arg Ser Asp Leu
            420                 425                 430

Ala Lys Ala Glu Gln Leu Leu Ala Glu Asn Asn Arg Leu Gln Val Glu
        435                 440                 445

Thr Glu Arg Thr Leu Ala Glu Glu Lys Glu Ile Lys Arg Asn Arg Val
450                 455                 460

Asn Val Ser Thr Phe Gly Thr Val Gln Thr Gln Leu Ser Lys Leu Leu
465                 470                 475                 480

Ser Asp Phe Tyr Ala Val Thr Ser Leu Ser Gln Ser Val Pro Ser Gly
                485                 490                 495

Ala Leu Ala Ser Phe Ser Tyr Asn Pro Gln Gly Met Ile Gly Ser Gly
            500                 505                 510

Lys Ile Val Gly Lys Asp Val Asp Val Leu Phe Ser Ile Pro Val Lys
        515                 520                 525

Asp Ile Pro Gly Tyr Lys Ser Pro Ile Asn Leu Asp Asp Leu Ala Lys
        530                 535                 540

Lys Asn Gly Ser Leu Asp Leu Pro Ile Arg Leu Ala Phe Ser Asp Glu
545                 550                 555                 560

Asn Gly Glu Arg Val Leu Arg Ala Phe Lys Ala Asp Ser Leu Arg Ile
                565                 570                 575

Pro Ser Ser Val Arg Gly Val Ala Gly Ser Tyr Asp Lys Asn Thr Gly
                580                 585                 590

Ile Phe Ser Ala Glu Ile Asp Gly Val Ser Ser Arg Leu Val Leu Glu
                595                 600                 605

Asn Pro Ala Phe Pro Pro Thr Gly Asn Val Gly Asn Thr Gly Asn Thr
610                 615                 620

Ala Pro Asp Tyr Lys Ala Leu Leu Asn Thr Gly Val Asp Val Lys Pro
625                 630                 635                 640

Val Asp Lys Ile Thr Val Thr Val Thr Pro Val Ala Asp Pro Val Asp
                645                 650                 655

Ile Asp Asp Tyr Ile Ile Trp Leu Pro Thr Ala Ser Gly Ser Gly Val
                660                 665                 670

Glu Pro Ile Tyr Val Val Phe Asn Ser Asn Pro Tyr Gly Gly Thr Glu
            675                 680                 685

Lys Gly Lys Tyr Ser Lys Arg Tyr Tyr Asn Pro Asp Lys Ala Gly Gly
            690                 695                 700

Pro Ile Leu Glu Leu Asp Trp Lys Asn Val Lys Ile Asp His Ala Gly
705                 710                 715                 720

Val Asp Asn Val Lys Leu His Thr Gly Arg Phe Lys Ala Ser Val Glu
                725                 730                 735

Asn Lys Val Met Ile Glu Arg Leu Glu Asn Ile Leu Asn Gly Gln Ile
                740                 745                 750

Thr Ala Thr Asp Thr Asp Lys Arg Phe Tyr Thr His Glu Leu Arg Glu
            755                 760                 765

Leu Asn Arg Tyr Arg Asn Leu Gly Ile Lys Asp Gly Glu Val Pro Ser
```

```
                    770                 775                 780
Ser Ile Gln Glu Glu Ser Ala Val Trp Asn Asp Thr His Thr Ala Thr
785                 790                 795                 800

Leu Glu Asp Tyr Lys Ile Asn Glu Lys Glu Gln Pro Leu Tyr Thr Asp
                805                 810                 815

Ala Ala Leu Gln Ala Ala Tyr Glu Gln Glu Leu Lys Asp Ala Leu Gly
            820                 825                 830

Gly Lys His Gly
        835

<210> SEQ ID NO 41
<211> LENGTH: 2511
<212> TYPE: DNA
<213> ORGANISM: Pectobacterium carotovorum subsp. carotovorum

<400> SEQUENCE: 41
```

| | | | | | |
|---|---|---|---|---|---|
| atgattaaat | accgtttata | tgctccaaat | gatggagaca | ccatgacagt | gagtggtggt | 60 |
| ggtggttggg | tttcaaacga | tgatcgcaaa | ggtggtaatg | acaggacaa | tgcaaaggt | 120 |
| ggttctgccg | ttgattttag | taaaaatcca | gaaaagcagg | ctatcgttaa | tccctatttg | 180 |
| gcaatcgcga | taccgatgcc | ggtctaccct | ctttatggaa | agctagggtt | cacaataaat | 240 |
| acgacggcaa | ttgagactga | actcgcaaat | gtcagagcag | caattaacac | taaacttgca | 300 |
| acactcagtg | cagtgattgg | cagatcactt | ccggtcgttg | ggcgggtatt | tggtgttact | 360 |
| gccgccggaa | tgtggccttc | tagtaccgct | cccagtagtc | tcgattctat | atacaatcaa | 420 |
| gcacatcagc | aggctttagc | ccagttagct | gctcaacagg | gagtattaaa | taagggtat | 480 |
| aacgttacag | caatgcctgc | aggtttcgtc | agcagtttgc | ctgttagtga | aatcaaatca | 540 |
| ttgccaacag | ctcccgccag | tttactggca | caaagtgtga | ttaataccga | actttcccag | 600 |
| cgtcaactgg | ctcttactca | gcccacgacg | aatgcaccag | tcgcgaatat | tcccgtagtt | 660 |
| aaaagcagaga | aaacagcaat | gccaggtgtg | tattcagcga | aaattattgc | tggtgagcct | 720 |
| gcattccaaa | tcaaggtcga | taataccaaa | cctgctttgg | cacagaatcc | gccgaaagta | 780 |
| aaagatgata | ttcaggtatc | ttctttcctt | tcctcgccag | tagctgatac | gcaccatgca | 840 |
| tttattgatt | ttggcagcga | tcatgaaccg | gtatacgtgt | ctcttttcaaa | gatcgtgaca | 900 |
| gccgaggagg | agaaaaaaca | ggttgaagag | gccaagcgcc | gtgagcagga | gtggttgttg | 960 |
| cgtcatccaa | ttacagctgc | ggagcgaaaa | ttaactgaaa | tccgccaagt | gatctctttt | 1020 |
| gctcaacagc | taaagaaag | ctctgtcgca | accatttcag | aaaaaactaa | aactgttgcg | 1080 |
| gtttaccaag | aacaggtgaa | taccgctgca | aaaaatcgcg | acaatttta | taatcaaaat | 1140 |
| agaggtctgt | taagtgcggg | tataactggg | ggaccgggat | atcctatta | tcttgcttta | 1200 |
| tggcaaacga | tgaataactt | tcatcaggct | tatttcagag | caataatgc | attggaacaa | 1260 |
| gagagtcatg | ttctgaacct | ggctcgttct | gatctggcta | aggctgagca | attgcttgct | 1320 |
| gagaataatc | gacttcaggt | tgaaacggag | cgaacgcttg | ccgaagaaaa | agagataaaa | 1380 |
| cgcaacaggg | ttaatgtatc | aacatttggc | acagtgcaaa | ctcaacttag | taaattgctg | 1440 |
| tcagatttt | atgctgttac | atcactttcc | caaagtgttc | cttcggggc | attagcctct | 1500 |
| ttttcatata | atccacaagg | gatgattggc | agcggtaaga | ttgttgggaa | ggatgtcgat | 1560 |
| gtttatttt | ccatcccagt | aaaagatatt | ccgggatata | atctcctat | taacttggac | 1620 |
| gatttagcca | agaaaaatgg | aagtctggat | cttcccattc | gtctggcatt | ttctgatgag | 1680 |
| aatggagaaa | gggttcttcg | ggcattcaaa | gcggatagtc | tgcgaatccc | ttcgagtgtc | 1740 |

```
agaggtgtag cgggcagtta tgacaaaaat acgggtattt ttagtgcaga aattgatggt 1800
gtttcatctc gccttgtact ggaaaaccca gcgtttcctc cgaccggaaa tgtcggtaat 1860
acgggtaata ctgcacctga ctataaagca ttactgaata ctggtgttga tgttaaacct 1920
gttgataaaa tcacagttac ggtaacacca gttgctgatc cagtggatat tgatgactat 1980
ataatctggt tgccaactgc gtctggttct ggcgtggaac ccatttatgt cgtgtttaac 2040
agtaatccgt atggtgggac ggaaaaagga aaatatagca aacgttatta taatccagat 2100
aaggcaggcg gtccgatctt ggagctggat tggaaaaacg ttaagattga ccatgcaggt 2160
gtggacaatg ttaaattaca cacagggcgt ttcaaagcgt cggttgaaaa caaagtgatg 2220
attgaacgtt tggaaaacat actgaatggt caaatcacgg ccacggatac tgacaagcga 2280
ttctatacgc atgaattaag agagttaaac cgctacagaa atttaggcat caaagacggt 2340
gaagtgccta gtagcattca agaagaaagc gctgtttgga acgacacaca cacagcgacg 2400
cttgaagact acaaaattaa tgagaaagag caaccgttgt acactgatgc tgctttgcag 2460
gcagcctacg aacaggaact caaagacgca ttaggaggga aacatggcta a 2511
```

<210> SEQ ID NO 42
<211> LENGTH: 74
<212> TYPE: PRT
<213> ORGANISM: Bacillus cereus

<400> SEQUENCE: 42

```
Met Glu Asn Leu Gln Met Leu Thr Glu Glu Glu Leu Met Glu Ile Glu
1 5 10 15

Gly Gly Gly Trp Trp Asn Ser Trp Gly Lys Cys Val Ala Gly Thr Ile
20 25 30

Gly Gly Ala Gly Thr Gly Gly Leu Gly Gly Ala Ala Ala Gly Ser Ala
35 40 45

Val Pro Val Ile Gly Thr Gly Ile Gly Gly Ala Ile Gly Gly Val Ser
50 55 60

Gly Gly Leu Thr Gly Ala Ala Thr Phe Cys
65 70

<210> SEQ ID NO 43
<211> LENGTH: 225
<212> TYPE: DNA
<213> ORGANISM: Bacillus cereus
<400> SEQUENCE: 43
atggaaaact tacaaatgtt aactgaagaa gaattaatgg aaattgaagg tggaggctgg 60
tggaatagct ggggtaaatg tgttgctgga actatcggtg gagctggaac tggtggttta 120
ggtggagctg ctgcaggttc agctgttccg gttattggta ctggtattgg tggcgctatt 180
ggtggagtta gcggtggcct tacaggtgca gctacttttt gctaa 225

<210> SEQ ID NO 44
<211> LENGTH: 78
<212> TYPE: PRT
<213> ORGANISM: Streptoverticillium griseoverticillatum

<400> SEQUENCE: 44

Met Thr Ala Ser Ile Leu Gln Gln Ser Val Val Asp Ala Asp Phe Arg
1 5 10 15

Ala Ala Leu Leu Glu Asn Pro Ala Ala Phe Gly Ala Ser Ala Ala Ala
20 25 30
```

```
Leu Pro Thr Pro Val Glu Ala Gln Asp Gln Ala Ser Leu Asp Phe Trp
        35                  40                  45

Thr Lys Asp Ile Ala Ala Thr Glu Ala Phe Ala Cys Arg Gln Ser Cys
    50                  55                  60

Ser Phe Gly Pro Phe Thr Phe Val Cys Asp Gly Asn Thr Lys
65                  70                  75

<210> SEQ ID NO 45
<211> LENGTH: 237
<212> TYPE: DNA
<213> ORGANISM: Streptoverticillium griseoverticillatum

<400> SEQUENCE: 45
atgaccgctt ccattcttca gcagtccgtc gtggacgccg acttccgcgc ggcgctgctt      60
gagaaccccg ccgccttcgg cgcttccgcc gcggccctgc ccacgcccgt cgaggcccag     120
gaccaggcgt cccttgactt ctggaccaag gacatcgccg ccacggaagc cttcgcctgc     180
cgccagagct gcagcttcgg cccgttcacc ttcgtgtgcg acggcaacac caagtaa        237

<210> SEQ ID NO 46
<211> LENGTH: 76
<212> TYPE: PRT
<213> ORGANISM: Geobacillus kaustophilus

<400> SEQUENCE: 46

Met Ser Leu Leu Ala Leu Val Ala Gly Thr Leu Gly Val Ser Gln Ser
1               5                   10                  15

Ile Ala Thr Thr Val Val Ser Ile Val Leu Thr Gly Ser Thr Leu Ile
            20                  25                  30

Ser Ile Ile Leu Gly Ile Thr Ala Ile Leu Ser Gly Gly Val Asp Ala
        35                  40                  45

Ile Leu Glu Ile Gly Trp Ser Ala Phe Val Ala Thr Val Lys Lys Ile
    50                  55                  60

Val Ala Glu Arg Gly Lys Ala Ala Ala Ile Ala Trp
65                  70                  75

<210> SEQ ID NO 47
<211> LENGTH: 231
<212> TYPE: DNA
<213> ORGANISM: Geobacillus kaustophilus

<400> SEQUENCE: 47
atgagtttgc tggcgcttgt tgccgggacg ctcggcgtgt cacagtcaat cgcgacgacg      60
gttgtttcga ttgtgttgac cggctccact ctcatttcta ttattcttgg gatcaccgct     120
attttgtcag gtggagtcga cgccattttg gaaattgggt ggtcagcttt tgtcgcgacg     180
gtgaaaaaaa tagtggcgga acgaggaaaa gcggcagcga ttgcatggta a              231

<210> SEQ ID NO 48
<211> LENGTH: 309
<212> TYPE: PRT
<213> ORGANISM: Clostridium tyrobutyricum

<400> SEQUENCE: 48

Met Arg Lys Val Phe Leu Arg Ser Ile Ile Ser Thr Leu Val Met Cys
1               5                   10                  15

Ala Phe Val Ser Ser Ser Phe Ser Val Asn Ala Asp Glu Ser Lys Pro
            20                  25                  30
```

```
Asn Asp Glu Lys Ile Ile Asn Asn Ile Glu Asn Val Thr Thr Thr Lys
             35                  40                  45
Asp Ile Val Lys Ser Asn Lys Asn Asn Ile Val Tyr Leu Asp Glu Gly
 50                  55                  60
Val Met Ser Ile Pro Leu Ser Gly Arg Lys Pro Ile Ala Ile Lys Asp
 65                  70                  75                  80
Asp Asn Asn Lys Glu Asp Leu Thr Val Thr Leu Pro Ile Lys Asn Thr
                 85                  90                  95
Gly Asp Ile Ser Lys Ile Ser Ser Asn Gly Thr Ile Leu Tyr Lys Asn
            100                 105                 110
Asn Ser Ser Asn Ser Ser Asn Ile Ala Leu Gln Pro Lys Asn Asp Gly
        115                 120                 125
Phe Lys Ala Leu Ile Asn Ile Asn Asp Lys Leu Ala Asn Lys Glu Tyr
130                 135                 140
Glu Phe Thr Phe Asn Leu Pro Lys Asn Ser Lys Leu Ile Ser Ala Ala
145                 150                 155                 160
Thr Tyr Leu Gly Lys Glu Tyr Asp Thr Lys Glu Val Phe Val Val Asp
                165                 170                 175
Lys Asn Asn Ile Ile Thr Ser Ile Ile Ser Pro Ala Trp Ala Lys Asp
            180                 185                 190
Ala Asn Gly His Asn Val Ser Thr Tyr Tyr Lys Ile Val Ser Asn Asn
        195                 200                 205
Lys Leu Val Gln Val Glu Phe Thr Glu Asn Thr Ala Phe Pro Val
210                 215                 220
Val Ala Asp Pro Asn Trp Thr Lys Ile Gly Lys Cys Ala Gly Ser Ile
225                 230                 235                 240
Ala Trp Ala Ile Gly Ser Gly Leu Phe Gly Gly Ala Lys Leu Ile Lys
                245                 250                 255
Ile Lys Lys Tyr Ile Ala Glu Leu Gly Gly Leu Gln Lys Ala Ala Lys
            260                 265                 270
Leu Leu Val Gly Ala Thr Thr Trp Glu Glu Lys Leu His Ala Gly Gly
        275                 280                 285
Tyr Ala Leu Ile Asn Leu Ala Ala Glu Leu Thr Gly Val Ala Gly Ile
290                 295                 300
Gln Ala Asn Cys Phe
305

<210> SEQ ID NO 49
<211> LENGTH: 930
<212> TYPE: DNA
<213> ORGANISM: Clostridium tyrobutyricum

<400> SEQUENCE: 49
ttgagaaaag tattttaag atcaataatt tcaacattag ttatgtgtgc atttgtttca      60
agcagctttt cagtaaatgc ggatgaaagc aaaccaaatg atgaaaaaat aattaataac     120
atagaaaacg ttactactac taagatatt gtaaaaagta ataaaaataa tattgtatat     180
ttagatgaag gtgtaatgag tattccattg tctgggagaa aacccattgc tattaaagat     240
gataataata aagaagattt aactgttaca ttacctatta gaatactgg agatatatct     300
aaaattagta gtaatggtac tattctgtat aaaaataata gtagtaattc atctaatata     360
gctttacaac ctaaaaatga tggatttaag gctttaataa atattaatga taagttagct     420
aataaagaat atgaatttac atttaattta cccaaaaaca gtaaattaat tagtgctgcc     480
acatatttgg gtaaagaata tgatacaaaa gaagtatttg tagtagacaa aaataatata     540
```

```
attacgagta ttattagtcc agcttgggct aaagatgcaa atggacataa tgtttctact    600
tattataaga tagtatcgaa aataaaatta gtacaagttg ttgaattcac agaaaatact    660
gcattcccgg tggtagctga tcctaattgg actaaaattg ggaaatgcgc tgggtcaata    720
gcatgggcta taggttctgg cctttttggt ggagcaaagc taattaaaat aaaaaaatat    780
atagcagagc ttggaggact tcaaaaagca gctaaattat tagttggtgc aaccacttgg    840
gaagaaaaat tacacgcagg cggttatgca ttaattaact tagctgctga gctaacaggt    900
gtagcaggta tacaagcaaa ttgtttttaa                                     930

<210> SEQ ID NO 50
<211> LENGTH: 62
<212> TYPE: PRT
<213> ORGANISM: Bacillus coagulans

<400> SEQUENCE: 50

Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Thr His Lys Cys
    50                  55                  60

<210> SEQ ID NO 51
<211> LENGTH: 189
<212> TYPE: DNA
<213> ORGANISM: Bacillus coagulans

<400> SEQUENCE: 51
atgaaaaaaa ttgaaaaatt aactgaaaaa gaaatggcca atatcattgg tggtaaatac    60
tacggtaatg gggttacttg tggcaaacat tcctgctctg ttgactgggg taaggctacc    120
acctgcataa tcaataatgg agctatggca tgggctactg gtggacatca aggtactcat    180
aaatgctag                                                            189

<210> SEQ ID NO 52
<211> LENGTH: 490
<212> TYPE: PRT
<213> ORGANISM: Escherichia coli

<400> SEQUENCE: 52

Met Asp Lys Val Thr Asp Asn Ser Pro Asp Val Glu Ser Thr Glu Ser
1               5                   10                  15

Thr Glu Gly Ser Phe Pro Thr Val Gly Val Asp Thr Gly Asp Thr Ile
            20                  25                  30

Thr Ala Thr Leu Ala Thr Gly Thr Glu Asn Val Gly Gly Gly Gly
        35                  40                  45

Ala Phe Gly Gly Ala Ser Glu Ser Ser Ala Ala Ile His Ala Thr Ala
    50                  55                  60

Lys Trp Ser Thr Ala Gln Leu Lys Lys His Gln Ala Glu Gln Ala Ala
65                  70                  75                  80

Arg Ala Ala Ala Ala Glu Ala Ala Leu Ala Lys Ala Lys Ser Gln Arg
                85                  90                  95

Asp Ala Leu Thr Gln Arg Leu Lys Asp Ile Val Asn Asp Ala Leu Arg
            100                 105                 110
```

```
Ala Asn Ala Ala Arg Ser Pro Ser Val Thr Asp Leu Ala His Ala Asn
            115                 120                 125

Asn Met Ala Met Gln Ala Glu Ala Glu Arg Leu Arg Leu Ala Lys Ala
        130                 135                 140

Glu Gln Lys Ala Arg Glu Ala Glu Ala Ala Glu Lys Ala Leu Arg
145                 150                 155                 160

Glu Ala Glu Arg Gln Arg Asp Glu Ile Ala Arg Gln Ala Glu Thr
                165                 170                 175

Ala His Leu Leu Ala Met Ala Glu Ala Glu Ala Glu Lys Asn Arg
            180                 185                 190

Gln Asp Ser Leu Asp Glu Glu His Arg Ala Val Glu Val Ala Glu Lys
                195                 200                 205

Lys Leu Ala Glu Ala Lys Ala Glu Leu Ala Lys Ala Glu Ser Asp Val
210                 215                 220

Gln Ser Lys Gln Ala Ile Val Ser Arg Val Ala Gly Glu Leu Glu Asn
225                 230                 235                 240

Ala Gln Lys Ser Val Asp Val Lys Val Thr Gly Phe Pro Gly Trp Arg
                245                 250                 255

Asp Val Gln Lys Lys Leu Glu Arg Gln Leu Gln Asp Lys Lys Asn Glu
                260                 265                 270

Tyr Ser Ser Val Thr Asn Ala Leu Asn Ser Ala Val Ser Ile Arg Asp
        275                 280                 285

Ala Lys Lys Thr Glu Val Gln Asn Ala Glu Ile Lys Leu Lys Glu Ala
        290                 295                 300

Lys Asp Ala Leu Glu Lys Ser Gln Val Lys Asp Ser Val Asp Thr Met
305                 310                 315                 320

Val Gly Phe Tyr Gln Tyr Ile Thr Glu Gln Tyr Gly Glu Lys Tyr Ser
                325                 330                 335

Arg Ile Ala Gln Asp Leu Ala Glu Lys Ala Lys Gly Ser Lys Phe Asn
                340                 345                 350

Ser Val Asp Glu Ala Leu Ala Ala Phe Glu Lys Tyr Lys Asn Val Leu
        355                 360                 365

Asp Lys Lys Phe Ser Lys Val Asp Arg Asp Ile Phe Asn Ala Leu
        370                 375                 380

Glu Ser Ile Thr Tyr Asp Glu Trp Ala Lys His Leu Glu Lys Ile Ser
385                 390                 395                 400

Arg Ala Leu Lys Val Thr Gly Tyr Leu Ser Phe Gly Tyr Asp Val Trp
                405                 410                 415

Asp Gly Thr Leu Lys Gly Leu Lys Thr Gly Asp Trp Lys Pro Leu Phe
                420                 425                 430

Val Thr Leu Glu Lys Ser Ala Val Asp Phe Gly Val Ala Lys Ile Val
        435                 440                 445

Ala Leu Met Phe Ser Phe Ile Val Gly Ala Pro Leu Gly Phe Trp Gly
        450                 455                 460

Ile Ala Ile Ile Thr Gly Ile Val Ser Ser Tyr Ile Gly Asp Asp Glu
465                 470                 475                 480

Leu Asn Lys Leu Asn Glu Leu Leu Gly Ile
                485                 490

<210> SEQ ID NO 53
<211> LENGTH: 1473
<212> TYPE: DNA
<213> ORGANISM: Escherichia coli
```

<400> SEQUENCE: 53

```
atggataaag tcactgataa ttctccagat gtggagagca cagaatctac tgagggtca      60
ttcccaactg ttggggttga tactggcgat acgattacag cgacgcttgc aactggaact    120
gaaaatgttg gtgaggcgg tggagcattt ggtggggcca gtgaaagttc tgctgcgata     180
catgcaaccg ctaaatggtc taccgcgcag ttgaaaaaac atcaggctga acaggctgcc    240
cgtgctgctg cggctgaggc agcattggca aaagcgaaat ctcagcgtga tgccctgact    300
caacgtctca aggatattgt taatgacgct ttacgtgcta atgccgctcg tagtccatca    360
gtaactgacc ttgctcatgc caataatatg gcaatgcagg cagaggctga gcgtttgcgc    420
cttgcgaagg cagagcaaaa agcccgtgaa gaagctgaag cagcagaaaa agcgctccgg    480
gaagcagaac gccaacgtga tgagattgcc cgccaacagg ctgaaaccgc gcatttgtta    540
gcaatggcgg aggcagcaga ggctgagaaa atcgacagg attctcttga tgaagagcat     600
cgggctgtgg aagtggcaga gaagaagctg gctgaggcta aagctgaact ggcgaaggcc    660
gaaagcgatg tacagagtaa gcaagcgatt gtttccagag ttgcagggga gcttgaaaac    720
gctcaaaaaa gtgttgatgt gaaggttacc ggatttcctg gatggcgtga tgttcagaaa    780
aaactggaga gacaattgca ggataagaag aatgaatatt cgtcagtgac gaatgctctt    840
aattctgctg ttagcattag agatgctaaa aaacagaag ttcagaatgc tgagataaaa     900
ttaaaagaag ctaaggatgc tcttgagaag agtcaggtaa aagactctgt tgatactatg    960
gttgggtttt atcaatatat aaccgaacaa tatggggaaa atattccag aatagctcag     1020
gatttagctg aaaaggcgaa gggtagtaaa tttaatagtg ttgatgaagc acttgctgca    1080
tttgaaaagt ataaaaatgt actggataag aaattcagta aggttgatag ggatgatatt    1140
tttaatgctt tagagtctat tacttatgat gagtgggcca agcatctaga aaagatctct    1200
agggctctta aggttactgg atatttgtct ttcgggtatg atgtatggga tggtacccta    1260
aagggattaa aaacaggaga ctggaagcct ttatttgtca ctctggagaa gagcgcggta    1320
gatttcggcg tggcaaaaat tgtggcatta atgtttagtt ttattgttgg tgcgcctctt    1380
ggcttctggg gaattgcaat tatcacaggt attgtttctt cttacatagg ggatgatgag    1440
ttgaacaagc ttaatgaatt actaggtatt taa                                 1473
```

<210> SEQ ID NO 54
<211> LENGTH: 522
<212> TYPE: PRT
<213> ORGANISM: Escherichia coli

<400> SEQUENCE: 54

```
Met Glu Thr Ala Val Ala Tyr Tyr Lys Asp Gly Val Pro Tyr Asp Asp
1               5                   10                  15

Lys Gly Gln Val Ile Ile Thr Leu Leu Asn Gly Thr Pro Asp Gly Ser
            20                  25                  30

Gly Ser Gly Gly Gly Gly Gly Lys Gly Gly Ser Lys Ser Glu Ser Ser
        35                  40                  45

Ala Ala Ile His Ala Thr Ala Lys Trp Ser Thr Ala Gln Leu Lys Lys
    50                  55                  60

Thr Gln Ala Glu Gln Ala Ala Arg Ala Lys Ala Ala Glu Ala Gln
65                  70                  75                  80

Ala Lys Ala Lys Ala Asn Arg Asp Ala Leu Thr Gln Arg Leu Lys Asp
                85                  90                  95

Ile Val Asn Glu Ala Leu Arg His Asn Ala Ser Arg Thr Pro Ser Ala
```

```
                100              105                110
Thr Glu Leu Ala His Ala Asn Asn Ala Ala Met Gln Ala Glu Asp Glu
            115                 120                 125

Arg Leu Arg Leu Ala Lys Ala Glu Lys Ala Arg Lys Glu Ala Glu
        130                 135             140

Ala Ala Glu Lys Ala Phe Gln Glu Ala Glu Gln Arg Arg Lys Glu Ile
145                 150                 155                 160

Glu Arg Glu Lys Ala Glu Thr Glu Arg Gln Leu Lys Leu Ala Glu Ala
                165                 170                 175

Glu Glu Lys Arg Leu Ala Ala Leu Ser Glu Glu Ala Lys Ala Val Glu
            180                 185                 190

Ile Ala Gln Lys Lys Leu Ser Ala Ala Gln Ser Glu Val Val Lys Met
        195                 200                 205

Asp Gly Glu Ile Lys Thr Leu Asn Ser Arg Leu Ser Ser Ile His
    210                 215                 220

Ala Arg Asp Ala Glu Met Lys Thr Leu Ala Gly Lys Arg Asn Glu Leu
225                 230                 235                 240

Ala Gln Ala Ser Ala Lys Tyr Lys Glu Leu Asp Glu Leu Val Lys Lys
                245                 250                 255

Leu Ser Pro Arg Ala Asn Asp Pro Leu Gln Asn Arg Pro Phe Phe Glu
            260                 265                 270

Ala Thr Arg Arg Val Gly Ala Gly Lys Ile Arg Glu Glu Lys Gln
        275                 280                 285

Lys Gln Val Thr Ala Ser Glu Thr Arg Ile Asn Arg Ile Asn Ala Asp
        290                 295                 300

Ile Thr Gln Ile Gln Lys Ala Ile Ser Gln Val Ser Asn Asn Arg Asn
305                 310                 315                 320

Ala Gly Ile Ala Arg Val His Glu Ala Glu Asn Leu Lys Lys Ala
            325                 330                 335

Gln Asn Asn Leu Leu Asn Ser Gln Ile Lys Asp Ala Val Asp Ala Thr
            340                 345                 350

Val Ser Phe Tyr Gln Thr Leu Thr Glu Lys Tyr Gly Glu Lys Tyr Ser
            355                 360                 365

Lys Met Ala Gln Glu Leu Ala Asp Lys Ser Lys Gly Lys Lys Ile Gly
        370                 375                 380

Asn Val Asn Glu Ala Leu Ala Ala Phe Glu Lys Tyr Lys Asp Val Leu
385                 390                 395                 400

Asn Lys Lys Phe Ser Lys Ala Asp Arg Asp Ala Ile Phe Asn Ala Leu
                405                 410                 415

Ala Ser Val Lys Tyr Asp Asp Trp Ala Lys His Leu Asp Gln Phe Ala
                420                 425                 430

Lys Tyr Leu Lys Ile Thr Gly His Val Ser Phe Gly Tyr Asp Val Val
            435                 440                 445

Ser Asp Ile Leu Lys Ile Lys Asp Thr Gly Asp Trp Lys Pro Leu Phe
    450                 455                 460

Leu Thr Leu Glu Lys Lys Ala Ala Asp Ala Gly Val Ser Tyr Val Val
465                 470                 475                 480

Ala Leu Leu Phe Ser Leu Leu Ala Gly Thr Thr Leu Gly Ile Trp Gly
                485                 490                 495

Ile Ala Ile Val Thr Gly Ile Leu Cys Ser Tyr Ile Asp Lys Asn Lys
            500                 505                 510

Leu Asn Thr Ile Asn Glu Val Leu Gly Ile
            515                 520
```

<210> SEQ ID NO 55
<211> LENGTH: 1569
<212> TYPE: DNA
<213> ORGANISM: Escherichia coli

<400> SEQUENCE: 55

```
atggaaaccg cggtagcgta ctataaagat ggtgttcctt atgatgataa gggacaggta      60
attattactc ttttgaatgg tactcctgac gggagtggct ctggcggcgg aggtggaaaa     120
ggaggcagta aaagtgaaag ttctgcagct attcatgcaa ctgctaaatg gtctactgct     180
caattaaaga aaacacaggc agagcaggct gcccgggcaa aagctgcagc ggaagcacag     240
gcgaaagcaa aggcaaacag ggatgcgctg actcagcgcc tgaaggatat cgtgaatgag     300
gctcttcgtc acaatgcctc acgtacgcct tcagcaacag agcttgctca tgctaataat     360
gcagctatgc aggcggaaga cgagcgtttg cgccttgcga aagcagaaga aaaagcccgt     420
aaagaagcgg aagcagcaga aaaggctttt caggaagcag aacaacgacg taaagagatt     480
gaacgggaga aggctgaaac agaacgccag ttgaaactgg ctgaagctga gagaaacga     540
ctggctgcat tgagtgaaga agctaaagct gttgagatcg cccaaaaaaa actttctgct     600
gcacaatctg aagtggtgaa atggatgga gagattaaga ctctcaattc tcgtttaagc     660
tccagtatcc atgcccgtga tgcagaaatg aaaacgctcg ctggaaaacg aaatgaactg     720
gctcaggcat ccgctaaata taagaactg gatgagctgg tcaaaaaact atcaccaaga     780
gccaatgatc cgcttcagaa ccgtcctttt tttgaagcaa ccagacgacg ggttggggcc     840
ggtaagatta gagaagaaaa acaaaaacag gtaacagcat cagaaacacg tattaaccgg     900
ataaatgctg atataactca gatccagaag gctatttctc aggtcagtaa taatcgtaat     960
gccggtatcg ctcgtgttca tgaagctgaa gaaaatttga aaaagcaca gaataatctc    1020
cttaattcac agattaagga tgctgttgat gcaacagtta gctttatca aacgctgact    1080
gaaaaatatg gtgaaaaata ttcgaaaatg gcacaggaac ttgctgataa gtctaaaggt    1140
aagaaaatcg gcaatgtgaa tgaagctctc gctgcttttg aaaaatacaa ggatgtttta    1200
aataagaaat tcagcaaagc cgatcgtgat gctattttta atgcgttggc atcggtgaag    1260
tatgatgact gggctaaaca tttagatcag tttgccaagt acttgaagat tacggggcat    1320
gtttctttg gatatgatgt ggtatctgat atcctaaaaa ttaaggatac aggtgactgg    1380
aagccactat ttcttacatt agagaagaaa gctgcagatg caggggtgag ttatgttgtt    1440
gctttacttt ttagcttgct tgctggaact acattaggta tttggggtat gctattgtt    1500
acaggaattc tatgctccta tattgataag aataaactta atactataaa tgaggtgtta    1560
gggatttaa                                                           1569
```

<210> SEQ ID NO 56
<211> LENGTH: 626
<212> TYPE: PRT
<213> ORGANISM: Escherichia coli

<400> SEQUENCE: 56

```
Met Ser Asp Pro Val Arg Ile Thr Asn Pro Gly Ala Glu Ser Leu Gly
 1               5                  10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Ala Trp Ser Ser
        35                  40                  45
```

```
Phe Gly Asn Lys Thr Ile Trp Gly Asn Glu Trp Val Asp Asp Ser
     50                  55                  60
Pro Thr Arg Ser Asp Ile Glu Lys Arg Asp Lys Glu Ile Thr Ala Tyr
 65                  70                  75                  80
Lys Asn Thr Leu Ser Ala Gln Gln Lys Glu Asn Glu Asn Lys Arg Thr
                 85                  90                  95
Glu Ala Gly Lys Arg Leu Ser Ala Ala Ile Ala Ala Arg Glu Lys Asp
                100                 105                 110
Glu Asn Thr Leu Lys Thr Leu Arg Ala Gly Asn Ala Asp Ala Ala Asp
            115                 120                 125
Ile Thr Arg Gln Glu Phe Arg Leu Leu Gln Ala Glu Leu Arg Glu Tyr
            130                 135                 140
Gly Phe Arg Thr Glu Ile Ala Gly Tyr Asp Ala Leu Arg Leu His Thr
145                 150                 155                 160
Glu Ser Arg Met Leu Phe Ala Asp Ala Asp Ser Leu Arg Ile Ser Pro
                165                 170                 175
Arg Glu Ala Arg Ser Leu Ile Glu Gln Ala Glu Lys Arg Gln Lys Asp
                180                 185                 190
Ala Gln Asn Ala Asp Lys Lys Ala Ala Asp Met Leu Ala Glu Tyr Glu
            195                 200                 205
Arg Arg Lys Gly Ile Leu Asp Thr Arg Leu Ser Glu Leu Glu Lys Asn
            210                 215                 220
Gly Gly Ala Ala Leu Ala Val Leu Asp Ala Gln Gln Ala Arg Leu Leu
225                 230                 235                 240
Gly Gln Gln Thr Arg Asn Asp Arg Ala Ile Ser Glu Ala Arg Asn Lys
                245                 250                 255
Leu Ser Ser Val Thr Glu Ser Leu Asn Thr Ala Arg Asn Ala Leu Thr
                260                 265                 270
Arg Ala Glu Gln Gln Leu Thr Gln Gln Lys Asn Thr Pro Asp Gly Lys
            275                 280                 285
Thr Ile Val Ser Pro Glu Lys Phe Pro Gly Arg Ser Ser Thr Asn His
            290                 295                 300
Ser Ile Val Val Ser Gly Asp Pro Arg Phe Ala Gly Thr Ile Lys Ile
305                 310                 315                 320
Thr Thr Ser Ala Val Ile Asp Asn Arg Ala Asn Leu Asn Tyr Leu Leu
                325                 330                 335
Ser His Ser Gly Leu Asp Tyr Lys Arg Asn Ile Leu Asn Asp Arg Asn
            340                 345                 350
Pro Val Val Thr Glu Asp Val Glu Gly Asp Lys Lys Ile Tyr Asn Ala
            355                 360                 365
Glu Val Ala Glu Trp Asp Lys Leu Arg Gln Arg Leu Leu Asp Ala Arg
            370                 375                 380
Asn Lys Ile Thr Ser Ala Glu Ser Ala Val Asn Ser Ala Arg Asn Asn
385                 390                 395                 400
Leu Ser Ala Arg Thr Asn Glu Gln Lys His Ala Asn Asp Ala Leu Asn
                405                 410                 415
Ala Leu Leu Lys Glu Lys Glu Asn Ile Arg Asn Gln Leu Ser Gly Ile
            420                 425                 430
Asn Gln Lys Ile Ala Glu Glu Lys Arg Lys Gln Asp Glu Leu Lys Ala
            435                 440                 445
Thr Lys Asp Ala Ile Asn Phe Thr Thr Glu Phe Leu Lys Ser Val Ser
450                 455                 460
```

| | | | | | | | | | | | | |
|---|---|---|---|---|---|---|---|---|---|---|---|---|
| Glu | Lys | Tyr | Gly | Ala | Lys | Ala | Glu | Gln | Leu | Ala | Arg | Glu | Met | Ala | Gly |
| 465 | | | | 470 | | | | 475 | | | | 480 |

```
Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
                580                 585                 590

Gly Ser Ala Leu Gly Ile Ile Gly Tyr Gly Leu Leu Met Ala Val Thr
                595                 600                 605

Gly Ala Leu Ile Asp Glu Ser Leu Val Glu Lys Ala Asn Lys Phe Trp
610                 615                 620

Gly Ile
625
```

<210> SEQ ID NO 57
<211> LENGTH: 1881
<212> TYPE: DNA
<213> ORGANISM: Escherichia coli

<400> SEQUENCE: 57

| | |
|---|---|
| atgtctgacc ctgtacgtat tacaaatccc ggtgcagaat cgctggggta tgattcagat | 60 |
| ggccatgaaa ttatggccgt tgatatttat gtaaaccctc cacgtgtcga tgtctttcat | 120 |
| ggtaccccgc ctgcatggag ttccttcggg aacaaaacca tctggggcgg aaacgagtgg | 180 |
| gttgatgatt ccccaacccg aagtgatatc gaaaaaaggg acaaggaaat cacagcgtac | 240 |
| aaaaacacgc tcagcgcgca gcagaaagag aatgagaata gcgtactga agccggaaaa | 300 |
| cgcctctctg cggcgattgc tgcaagggaa aaagatgaaa acacactgaa aacactccgt | 360 |
| gccggaaacg cagatgccgc tgatattaca cgacaggagt tcagactcct gcaggcagag | 420 |
| ctgagagaat acggattccg tactgaaatc gccggatatg acgccctccg gctgcataca | 480 |
| gagagccgga tgctgtttgc tgatgctgat tctcttcgta tatctccccg ggaggccagg | 540 |
| tcgttaatcg aacaggctga aaaacggcag aaggatgcgc agaacgcaga caagaaggcc | 600 |
| gctgatatgc ttgctgaata cgagcgcaga aaggtattc tggacacccg gttgtcagag | 660 |
| ctggaaaaaa atggcggggc agcccttgcc gttcttgatg cacaacaggc ccgtctgctc | 720 |
| gggcagcaga cacggaatga cagggccatt tcagaggccc ggaataaact cagttcagtg | 780 |
| acggaatcgc ttaacacggc ccgtaatgca ttaaccagag ctgaacaaca gctgacgcaa | 840 |
| cagaaaaaca cgcctgacgg caaaacgata gtttcccctg aaaaattccc ggggcgttca | 900 |
| tcaacaaatg attctattgt tgtgagcggt gatccgagat tgccggtac gataaaaatc | 960 |
| acaaccagcg cagtcatcga taaccgtgca aacctgaatt atcttctgag ccattccggt | 1020 |
| ctggactata aacgcaatat tctgaatgac cggaatccgg tggtgacaga ggatgtggaa | 1080 |
| ggtgacaaga aaatttataa tgctgaagtt gctgaatggg ataagttacg gcaaagattg | 1140 |

```
cttgatgcca gaaataaaat cacctctgct gaatctgcgg taaattcggc gagaaataac    1200
ctcagtgcca gaacaaatga gcaaaagcat gcaaatgacg ctcttaatgc cctgttgaag    1260
gaaaaagaga atatccgtaa ccagctttcc ggcatcaatc agaagatagc ggaagagaaa    1320
agaaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aaagatcgtg cagcgattgc cgcagcccett    1560 gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtattta a                                              1881

<210> SEQ ID NO 58
<211> LENGTH: 626
<212> TYPE: PRT
<213> ORGANISM: Escherichia coli

<400> SEQUENCE: 58

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240
```

```
Gly Gln Gln Thr Arg Asn Asp Arg Ala Ile Ser Glu Ala Arg Asn Lys
                245                 250                 255

Leu Ser Ser Val Thr Glu Ser Leu Lys Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Thr His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Ile Asn Ser Ala Arg Asn Asn
385                 390                 395                 400

Val Ser Ala Arg Thr Asn Glu Gln Lys His Ala Asn Asp Ala Leu Asn
                405                 410                 415

Ala Leu Leu Lys Glu Lys Glu Asn Ile Arg Ser Gln Leu Ala Asp Ile
            420                 425                 430

Asn Gln Lys Ile Ala Glu Glu Lys Arg Lys Arg Asp Glu Ile Asn Met
        435                 440                 445

Val Lys Asp Ala Ile Lys Leu Thr Ser Asp Phe Tyr Arg Thr Ile Tyr
    450                 455                 460

Asp Glu Phe Gly Lys Gln Ala Ser Glu Leu Ala Lys Glu Leu Ala Ser
465                 470                 475                 480

Val Ser Gln Gly Lys Gln Ile Lys Ser Val Asp Ala Leu Asn Ala
                485                 490                 495

Phe Asp Lys Phe Arg Asn Asn Leu Asn Lys Lys Tyr Asn Ile Gln Asp
            500                 505                 510

Arg Met Ala Ile Ser Lys Ala Leu Glu Ala Ile Asn Gln Val His Met
        515                 520                 525

Ala Glu Asn Phe Lys Leu Phe Ser Lys Ala Phe Gly Phe Thr Gly Lys
    530                 535                 540

Val Ile Glu Arg Tyr Asp Val Ala Val Glu Leu Gln Lys Ala Val Lys
545                 550                 555                 560

Thr Asp Asn Trp Arg Pro Phe Phe Val Lys Leu Glu Ser Leu Ala Ala
                565                 570                 575

Gly Arg Ala Ala Ser Ala Val Thr Ala Trp Ala Phe Ser Val Met Leu
            580                 585                 590

Gly Thr Pro Val Gly Ile Leu Gly Phe Ala Ile Ile Met Ala Ala Val
        595                 600                 605

Ser Ala Leu Val Asn Asp Lys Phe Ile Glu Gln Val Asn Lys Leu Ile
    610                 615                 620

Gly Ile
625

<210> SEQ ID NO 59
<211> LENGTH: 1881
<212> TYPE: DNA
```

<213> ORGANISM: Escherichia coli

<400> SEQUENCE: 59

```
atgtctgacc ctgtacgtat tacaaatccc ggtgcagaat cgctgggata tgattcagat        60
ggccatgaaa ttatggccgt tgatatttat gtaaaccctc cacgtgtcga tgtctttcat       120
ggtaccccgc ctgcatggag ttccttcggg aacaaaacca tctggggtgg aaacgagtgg       180
gtcgatgatt ccccaacccg aagtgatatc gaaaaaggg acaaggaaat cacagcgtac        240
aaaaacacgc tcagcgcgca gcagaaagag aatgagaata agcgtactga agctggaaaa       300
cgcctttctg cggcaattgc tgcaaggaa aagatgaaa acacactgaa acactccgt         360
gccggaaacg cagatgccgc tgatattaca cgacaggagt tcagactcct gcaggcagag       420
ctgagagaat acggattccg tactgaaatc gccggatatg atgccctccg gctgcataca       480
gagagccgga tgctgtttgc tgatgctgat tctcttcgta tatctccccg cgaggccagg       540
tcgttaatcg aacaggctga aaacggcag aaggatgcgc agaacgcaga caagaaggcc        600
gctgatatgc ttgctgaata cgagcgcaga aaggtattc tggacacgcg gttgtcagag        660
ctggaaaaaa atggcgggc agcccttgcc gttcttgatg cacaacaggc ccgtctgctc        720
gggcagcaga cacggaatga cagggccatt tcagaggccc ggaataaaact cagttcggtg      780
acggaatcgc ttaagacgg ccgtaatgca ttaaccagag ctgaacaaca gctgacgcaa        840
cagaaaaaca cgcctgacgg caaaacgata gtttcccctg aaaaattccc ggggcgttca      900
tcaacaaatc attctattgt tgtgagtggt gatccgaggt ttgccggtac gataaaaatc      960
acaaccagcg cggtcatcga taaccgtgca aacctgaatt atcttctgac ccattccggt     1020
ctggactata aacgcaatat tctgaatgac cggaatccgg tggtgacaga ggatgtggaa     1080
ggtgacaaga aaatttataa tgctgaagtt gctgaatggg ataagttacg caacgattg       1140
cttgatgcca gaaataaaat cacctctgct gaatctgcga taaattcggc gagaaataac      1200
gtcagtgcca gaacaaatga acaaaagcat gcaaatgacg ctcttaatgc cctgttgaag     1260
gaaaagagaa atatccgtag ccagcttgct gacatcaatc agaaaatagc tgaagagaaa      1320
agaaaagggg atgaaataaa tatggtaaag gatgccataa aactcacctc tgatttctac     1380
agaacgatat atgatgagtt cggtaaacaa gcatccgaac ttgctaagga gctggcttct    1440
gtatctcaag ggaaacagat taagagtgtg gatgatgcac tgaacgcttt tgataaattc      1500
cgtaataatc tgaacaagaa atataacata caagatcgca tggccatttc taaagccctg      1560
gaagctatta atcaggtcca tatggcggag aatttttaagc tgttcagtaa ggcatttggt    1620
tttaccggaa aagttattga acgttatgat gttgctgtgg agttacaaaa ggctgtaaaa      1680
acggacaact ggcgtccatt ttttgtaaaa cttgaatcac tggcagcagg aagagctgct    1740
tcagcagtta cagcatgggc gttttccgtc atgctgggaa cccctgtagg tattctgggt     1800
tttgcaatta ttatggcggc tgtgagtgcg cttgttaatg ataagtttat tgagcaggtc      1860
aataaactta ttggtatctg a                                               1881
```

<210> SEQ ID NO 60
<211> LENGTH: 271
<212> TYPE: PRT
<213> ORGANISM: Escherichia coli

<400> SEQUENCE: 60

```
Met Glu Thr Leu Thr Val His Ala Pro Ser Pro Ser Thr Asn Leu Pro
1               5                   10                  15
```

Ser Tyr Gly Asn Gly Ala Phe Ser Leu Ser Ala Pro His Val Pro Gly
                20                  25                  30

Ala Gly Pro Leu Leu Val Gln Val Val Tyr Ser Phe Phe Gln Ser Pro
            35                  40                  45

Asn Met Cys Leu Gln Ala Leu Thr Gln Leu Glu Asp Tyr Ile Lys Lys
        50                  55                  60

His Gly Ala Ser Asn Pro Leu Thr Leu Gln Ile Ile Ser Thr Asn Ile
 65                  70                  75                  80

Gly Tyr Phe Cys Asn Ala Asp Arg Asn Leu Val Leu His Pro Gly Ile
                85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
        115                 120                 125

Pro Ile Val Ala Leu Ala His Tyr Leu Trp Gly Asn Gly Ala Glu Arg
    130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
        195                 200                 205

Ile Ser Ala Asn Gly Ser Trp Thr Tyr Asn Gly Val Val Arg Ser Tyr
    210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
                245                 250                 255

Ile Leu Leu Pro Gly Glu Ile His Ile Lys Glu Ser Gly Lys Arg
            260                 265                 270

<210> SEQ ID NO 61
<211> LENGTH: 816
<212> TYPE: DNA
<213> ORGANISM: Escherichia coli

<400> SEQUENCE: 61
atggaaacct taactgttca tgcaccatca ccatcaacta acttaccaag ttatggcaat      60
ggtgcatttt ctctttcagc accacatgtg cctggtgctg gccctctttt agtccaggtt     120
gtttatagtt ttttccagag tccaaacatg tgtcttcagg cttttaactca acttgaggat    180 tacatcaaaa aacatggggc cagcaaccct ctcacattgc agatcatatc gacaaatatt     240
ggttacttct gtaacgccga ccgaaatctg gttcttcacc ctggaataag cgtttatgac     300
gcttaccact cgcaaaaacc agcgccaagt caatatgact atcgctcaat gaatatgaaa     360
caaatgagcg gtaatgtcac tacaccaatt gtggcgcttg ctcactattt atggggtaat     420
ggcgctgaaa ggagcgttaa tatcgccaac attggtctta aatttcccc tatgaaaatt      480 aatcagataa aagacattat aaaatctggt gtagtaggca cattccctgt ttctacaaag     540
ttcacacatg ccactggtga ttataatgtt attaccggtg catatcttgg taatatcaca     600
ctgaaaacag aaggtacttt aactatctct gccaatggct cctggactta caatggcgtt     660
gttcgttcat atgatgataa atacgatttt aacgccagca ctcaccgtgg cattatcgga     720

```
gagtcgctca caaggctcgg ggcgatgttt tctggtaaag agtaccagat actgcttcct    780
ggtgaaattc acattaaaga aagtggtaag cgataa                              816
```

<210> SEQ ID NO 62
<211> LENGTH: 387
<212> TYPE: PRT
<213> ORGANISM: Escherichia coli

<400> SEQUENCE: 62

```
Met Gly Ser Asn Gly Ala Asp Asn Ala His Asn Asn Ala Phe Gly Gly
1               5                   10                  15

Gly Lys Asn Pro Gly Ile Gly Asn Thr Ser Gly Ala Gly Ser Asn Gly
                20                  25                  30

Ser Ala Ser Ser Asn Arg Gly Asn Ser Asn Gly Trp Ser Trp Ser Asn
            35                  40                  45

Lys Pro His Lys Asn Asp Gly Phe His Ser Asp Gly Ser Tyr His Ile
        50                  55                  60

Thr Phe His Gly Asp Asn Asn Ser Lys Pro Lys Pro Gly Gly Asn Ser
65                  70                  75                  80

Gly Asn Arg Gly Asn Asn Gly Asp Gly Ala Ser Ala Lys Val Gly Glu
                85                  90                  95

Ile Thr Ile Thr Pro Asp Asn Ser Lys Pro Gly Arg Tyr Ile Ser Ser
                100                 105                 110

Asn Pro Glu Tyr Ser Leu Leu Ala Lys Leu Ile Asp Ala Glu Ser Ile
            115                 120                 125

Lys Gly Thr Glu Val Tyr Thr Phe His Thr Arg Lys Gly Gln Tyr Val
        130                 135                 140

Lys Val Thr Val Pro Asp Ser Asn Ile Asp Lys Met Arg Val Asp Tyr
145                 150                 155                 160

Val Asn Trp Lys Gly Pro Lys Tyr Asn Asn Lys Leu Val Lys Arg Phe
                165                 170                 175

Val Ser Gln Phe Leu Leu Phe Arg Lys Glu Lys Glu Lys Asn Glu
            180                 185                 190

Lys Glu Ala Leu Leu Lys Ala Ser Glu Leu Val Ser Gly Met Gly Asp
        195                 200                 205

Lys Leu Gly Glu Tyr Leu Gly Val Lys Tyr Lys Asn Val Ala Lys Glu
    210                 215                 220

Val Ala Asn Asp Ile Lys Asn Phe His Gly Arg Asn Ile Arg Ser Tyr
225                 230                 235                 240

Asn Glu Ala Met Ala Ser Leu Asn Lys Val Leu Ala Asn Pro Lys Met
                245                 250                 255

Lys Val Asn Lys Ser Asp Lys Asp Ala Ile Val Asn Ala Trp Lys Gln
            260                 265                 270

Val Asn Ala Lys Asp Met Ala Asn Lys Ile Gly Asn Leu Gly Lys Ala
        275                 280                 285

Phe Lys Val Ala Asp Leu Ala Ile Lys Val Glu Lys Ile Arg Glu Lys
    290                 295                 300

Ser Ile Glu Gly Tyr Asn Thr Gly Asn Trp Gly Pro Leu Leu Leu Glu
305                 310                 315                 320

Val Glu Ser Trp Ile Ile Gly Gly Val Val Ala Gly Val Ala Ile Ser
                325                 330                 335

Leu Phe Gly Ala Val Leu Ser Phe Leu Pro Ile Ser Gly Leu Ala Val
            340                 345                 350
```

Thr Ala Leu Gly Val Ile Gly Ile Met Thr Ile Ser Tyr Leu Ser Ser
            355                 360                 365

Phe Ile Asp Ala Asn Arg Val Ser Asn Ile Asn Asn Ile Ile Ser Ser
        370                 375                 380

Val Ile Arg
385

<210> SEQ ID NO 63
<211> LENGTH: 51
<212> TYPE: DNA
<213> ORGANISM: Escherichia coli

<400> SEQUENCE: 63
gcaaatcgag tttcgaatat aaataacatt atatctagtg ttattcgatg a          51

<210> SEQ ID NO 64
<211> LENGTH: 103
<212> TYPE: PRT
<213> ORGANISM: Escherichia coli

<400> SEQUENCE: 64

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Gly Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100

<210> SEQ ID NO 65
<211> LENGTH: 312
<212> TYPE: DNA
<213> ORGANISM: Escherichia coli

<400> SEQUENCE: 65
atgagaactc tgactctaaa tgaattagat tctgtttctg gtggtgcttc agggcgtgat     60
attgcgatgg ctataggaac actatccgga caatttgttg caggaggaat tggagcagct    120
gctgggggtg tggctggagg tgcaatatat gactatgcat ccactcacaa acctaatcct    180
gcaatgtctc catccggttt aggaggaaca attaagcaaa acccgaagg gataccttca    240 gaagcatgga actatgctgc gggaagattg tgtaattgga gtccaaataa tcttagtgat    300
gtttgtttat aa                                                       312

<210> SEQ ID NO 66
<211> LENGTH: 58
<212> TYPE: PRT
<213> ORGANISM: Enterococcus columbae

<400> SEQUENCE: 66

Met Met Asn Ala Thr Glu Asn Gln Ile Phe Val Glu Thr Val Ser Asp
1               5                   10                  15

```
Gln Glu Leu Glu Met Leu Ile Gly Gly Ala Gly Arg Gly Trp Ile Lys
             20                  25                  30

Thr Leu Thr Lys Asp Cys Pro Asn Val Ile Ser Ser Ile Cys Ala Gly
         35                  40                  45

Thr Ile Ile Thr Ala Cys Lys Asn Cys Ala
     50                  55

<210> SEQ ID NO 67
<211> LENGTH: 177
<212> TYPE: DNA
<213> ORGANISM: Enterococcus columbae

<400> SEQUENCE: 67
atgatgaatg ctactgaaaa ccaaattttt gttgagactg tgagtgacca agaattagaa      60
atgttaattg gtggtgcagg tcgtggatgg attaagactt taacaaaaga ttgtccaaat     120
gtgatttctt caatttgtgc aggtacaatt attacagctt gtaaaaattg tgcttaa        177

<210> SEQ ID NO 68
<211> LENGTH: 59
<212> TYPE: PRT
<213> ORGANISM: Lactobacillus curvatus

<400> SEQUENCE: 68

Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
             20                  25                  30

Cys Trp Val Asn Arg Gly Glu Ala Thr Gln Ser Ile Ile Gly Gly Met
         35                  40                  45

Ile Ser Gly Trp Ala Ser Gly Leu Ala Gly Met
     50                  55

<210> SEQ ID NO 69
<211> LENGTH: 180
<212> TYPE: DNA
<213> ORGANISM: Lactobacillus curvatus

<400> SEQUENCE: 69
atgaataatg taaagaatt aagtatgaca gaattacaaa caattaccgg cggtgctaga      60
tcatatggca acggtgttta ctgtaataat aaaaaatgtt gggtaaatcg gggtgaagca    120
acgcaaagta ttattggtgg tatgattagc ggctgggcta gtggtttagc tggaatgtaa    180

<210> SEQ ID NO 70
<211> LENGTH: 64
<212> TYPE: PRT
<213> ORGANISM: Streptomyces sp.

<400> SEQUENCE: 70

Met Arg Ser Glu Met Thr Leu Thr Ser Thr Asn Ser Ala Glu Ala Leu
1               5                   10                  15

Ala Ala Gln Asp Phe Ala Asn Thr Val Leu Ser Ala Ala Pro Gly
             20                  25                  30

Phe His Ala Asp Cys Glu Thr Pro Ala Met Ala Thr Pro Ala Thr Pro
         35                  40                  45

Thr Val Ala Gln Phe Val Ile Gln Gly Ser Thr Ile Cys Leu Val Cys
     50                  55                  60

<210> SEQ ID NO 71
```

<211> LENGTH: 195
<212> TYPE: DNA
<213> ORGANISM: Streptomyces sp.

<400> SEQUENCE: 71

```
gtgcgatctg agatgactct tacgagcacg aattccgctg aggctctggc ggcgcaggac      60
tttgcgaaca ccgttctcag cgcggcggcc ccgggcttcc acgcggactg cgagacgccg     120
gccatggcca ccccggccac gccgaccgtc gcccagttcg tgatccaggg cagcacgatc     180
tgcctggtct gctga                                                      195
```

<210> SEQ ID NO 72
<211> LENGTH: 65
<212> TYPE: PRT
<213> ORGANISM: Bacillus halodurans

<400> SEQUENCE: 72

```
Met Val Asn Ser Lys Asp Leu Arg Asn Pro Glu Phe Arg Lys Ala Gln
1               5                   10                  15

Gly Leu Gln Phe Val Asp Glu Val Asn Glu Lys Glu Leu Ser Ser Leu
            20                  25                  30

Ala Gly Ser Gly Asp Val His Ala Gln Thr Thr Trp Pro Cys Ala Thr
        35                  40                  45

Val Gly Val Ser Val Ala Leu Cys Pro Thr Thr Lys Cys Thr Ser Gln
    50                  55                  60

Cys
65
```

<210> SEQ ID NO 73
<211> LENGTH: 198
<212> TYPE: DNA
<213> ORGANISM: Bacillus halodurans

<400> SEQUENCE: 73

```
atggtaaatt caaaagattt gcgtaatcct gaattccgca aagcccaagg tctacaattc      60
gttgacgagg tgaacgagaa ggaactttcg tctctagctg gttcaggaga tgtgcatgca     120
caaacaactt ggccttgcgc tacagttggt gtctccgtag ccttgtgccc aactacaaag     180
tgtacaagcc agtgctaa                                                   198
```

<210> SEQ ID NO 74
<211> LENGTH: 66
<212> TYPE: PRT
<213> ORGANISM: Carnobacterium divergens

<400> SEQUENCE: 74

```
Met Lys Asn Leu Lys Glu Gly Ser Tyr Thr Ala Val Asn Thr Asp Glu
1               5                   10                  15

Leu Lys Ser Ile Asn Gly Gly Thr Lys Tyr Tyr Gly Asn Gly Val Tyr
            20                  25                  30

Cys Asn Ser Lys Lys Cys Trp Val Asp Trp Gly Gln Ala Ser Gly Cys
        35                  40                  45

Ile Gly Gln Thr Val Val Gly Gly Trp Leu Gly Gly Ala Ile Pro Gly
    50                  55                  60

Lys Cys
65
```

<210> SEQ ID NO 75
<211> LENGTH: 201

```
<212> TYPE: DNA
<213> ORGANISM: Carnobacterium divergens

<400> SEQUENCE: 75
atgaaaaact taaaagaagg ttcatacact gctgttaata ctgatgaatt aaaaagtatc    60
aatggtggaa caaatatta tgggaatggc gtttattgca attctaaaaa atgttgggta   120
gattggggac aagcttcagg ttgtatcggt caaactgttg ttggcggatg ctaggcgga    180 gctataccag gtaaatgcta a                                             201

<210> SEQ ID NO 76
<211> LENGTH: 63
<212> TYPE: PRT
<213> ORGANISM: Carnobacterium divergens

<400> SEQUENCE: 76

Met Ile Lys Arg Glu Lys Asn Arg Thr Ile Ser Ser Leu Gly Tyr Glu
1               5                   10                  15

Glu Ile Ser Asn His Lys Leu Gln Glu Ile Gln Gly Gly Lys Gly Ile
            20                  25                  30

Leu Gly Lys Leu Gly Val Val Gln Ala Gly Val Asp Phe Val Ser Gly
        35                  40                  45

Val Trp Ala Gly Ile Lys Gln Ser Ala Lys Asp His Pro Asn Ala
    50                  55                  60

<210> SEQ ID NO 77
<211> LENGTH: 192
<212> TYPE: DNA
<213> ORGANISM: Carnobacterium divergens

<400> SEQUENCE: 77
atgattaaaa gagaaaagaa cagaacaatt tcttcccttg gttatgaaga aatttctaat    60
cataaattgc aagaaataca aggtggaaaa ggaattcttg gtaaactagg agtagtacag   120
gcaggagtgg atttttgtatc aggagtgtgg gctggaataa aacagtctgc caaagatcat   180
cctaatgcgt aa                                                        192

<210> SEQ ID NO 78
<211> LENGTH: 75
<212> TYPE: PRT
<213> ORGANISM: Carnobacterium divergens

<400> SEQUENCE: 78

Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Ala Ala Pro
            20                  25                  30

Lys Ile Thr Gln Lys Gln Lys Asn Cys Val Asn Gly Gln Leu Gly Gly
        35                  40                  45

Met Leu Ala Gly Ala Leu Gly Gly Pro Gly Gly Val Val Leu Gly Gly
    50                  55                  60

Ile Gly Gly Ala Ile Ala Gly Gly Cys Phe Asn
65                  70                  75

<210> SEQ ID NO 79
<211> LENGTH: 228
<212> TYPE: DNA
<213> ORGANISM: Carnobacterium divergens

<400> SEQUENCE: 79
```

```
atgaaaaaac aaattttaaa agggttggtt atagttgttt gtttatctgg ggcaacattt    60
ttctcaacac cacaacaagc ttctgctgct gcaccgaaaa ttactcaaaa acaaaaaaat   120
tgtgttaatg acaattaggt ggaatgcttt gctggagctt ggggtggacc tggcggagtt   180
gtgttaggtg gtataggtgg tgcaatagca ggaggttgtt ttaattaa                228
```

<210> SEQ ID NO 80
<211> LENGTH: 72
<212> TYPE: PRT
<213> ORGANISM: Enterococcus durans

<400> SEQUENCE: 80

```
Met Gln Thr Ile Lys Glu Leu Asn Thr Met Glu Leu Gln Glu Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Pro Gly Gly Phe Ile Ser Ala Gly
    50                  55                  60

Ile Ser Ala Val Leu Gly Cys Met
65                  70
```

<210> SEQ ID NO 81
<211> LENGTH: 219
<212> TYPE: DNA
<213> ORGANISM: Enterococcus durans

<400> SEQUENCE: 81

```
atgcaaacga tcaaagaatt gaacacgatg gaattacaag aaataattgg aggtgaaaat    60
gaccatcgga tgccttacga attgaaccgt ccaaataatt tatccaaagg tggggctaag   120
tgtgctgctg gaatacttgg cgctggacta ggcgcagtag gcggtggacc tggcggattt   180
attagtgccg gaatcagtgc tgttcttggt tgtatgtaa                          219
```

<210> SEQ ID NO 82
<211> LENGTH: 72
<212> TYPE: PRT
<213> ORGANISM: Enterococcus durans

<400> SEQUENCE: 82

```
Met Gln Thr Ile Lys Glu Leu Asn Thr Met Glu Leu Gln Lys Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Pro Gly Gly Phe Ile Ser Ala Gly
    50                  55                  60

Ile Ser Ala Val Leu Gly Cys Met
65                  70
```

<210> SEQ ID NO 83
<211> LENGTH: 219
<212> TYPE: DNA
<213> ORGANISM: Enterococcus durans

<400> SEQUENCE: 83

-continued

```
atgcaaacga tcaaagaatt gaacacgatg gaattacaaa aaataattgg aggtgaaaat    60
gaccatcgga tgccttacga attgaaccgt ccaaataatt tatccaaagg tggagctaag   120
tgcgctgccg gaatacttgg tgctggatta ggcgcagtag gcggtggacc tggcggattt   180
attagtgccg gaatcagtgc tgttcttggt tgtatgtaa                          219
```

<210> SEQ ID NO 84
<211> LENGTH: 220
<212> TYPE: PRT
<213> ORGANISM: Streptococcus dysgalactiae subsp. equisimilis

<400> SEQUENCE: 84

```
Met Lys Lys Leu Lys Arg Leu Val Ile Ser Leu Val Thr Ser Leu Leu
1               5                   10                  15

Val Ile Ser Ser Thr Val Pro Ala Leu Val Tyr Ala Asn Glu Thr Asn
            20                  25                  30

Asn Phe Ala Glu Thr Gln Lys Glu Ile Thr Thr Asn Ser Glu Ala Thr
        35                  40                  45

Leu Thr Asn Glu Asp Tyr Thr Lys Leu Thr Ser Glu Val Lys Thr Ile
    50                  55                  60

Tyr Thr Asn Leu Ile Gln Tyr Asp Gln Thr Lys Asn Lys Phe Tyr Val
65                  70                  75                  80

Asp Glu Asp Lys Thr Glu Gln Tyr Tyr Asn Tyr Asp Glu Ser Ile
                85                  90                  95

Lys Gly Val Tyr Leu Met Lys Asp Ser Leu Asn Asp Glu Leu Asn Asn
            100                 105                 110

Asn Asn Ser Ser Asn Tyr Ser Glu Ile Ile Asn Gln Lys Ile Ser Glu
        115                 120                 125

Ile Asp Tyr Val Leu Gln Gly Asn Asp Ile Asn Asn Leu Ile Pro Ser
    130                 135                 140

Asn Thr Arg Val Lys Arg Ser Ala Asp Phe Ser Trp Ile Gln Arg Cys
145                 150                 155                 160

Leu Glu Glu Ala Trp Gly Tyr Ala Ile Ser Leu Val Thr Leu Lys Gly
                165                 170                 175

Ile Ile Asn Leu Phe Lys Ala Gly Lys Phe Glu Ala Ala Ala Ala Lys
            180                 185                 190

Leu Ala Ser Ala Thr Ala Gly Arg Ile Ala Gly Met Ala Ala Leu Phe
        195                 200                 205

Ala Phe Val Ala Thr Cys Gly Ala Thr Thr Val Ser
    210                 215                 220
```

<210> SEQ ID NO 85
<211> LENGTH: 663
<212> TYPE: DNA
<213> ORGANISM: Streptococcus dysgalactiae subsp. equisimilis

<400> SEQUENCE: 85

```
atgaaaaaat taaacgtct tgttatctct cttgttactt cattactagt aatttcaagt    60
acagttccag cacttgttta cgctaatgaa acaaataact ttgcagaaac tcaaaaagaa   120
attacaacaa attcagaagc aacattaacc aatgaagact acactaaatt aacttccgaa   180
gtaaaaacaa tttatacaaa tctgattcaa tacgaccaaa caaaaaacaa attttacgtc   240
gatgaagaca aaactgaaca atattataac tacgatgatg aagtatataa aggggtttat   300
ctcatgaaag atagtttgaa cgatgagtta acaataata actcttcaaa ctattctgaa   360
ataattaatc aaaaaatctc tgaaattgac tatgtccttc aaggaaacga tataaataat   420
```

```
ttaattccta gcaataccag agtaaaaaga tcagcagatt tttcttggat tcaaagatgt      480
ctagaagaag catggggata tgctattagt ctagttactc taaaaggaat aatcaatcta      540
tttaaagcag gaaaatttga agctgctgct gctaaattag cttctgctac agcaggtaga      600
atcgctggaa tggctgcctt atttgctttc gtagcaactt gcggtgcgac aactgtatca      660
taa                                                                    663
```

<210> SEQ ID NO 86
<211> LENGTH: 57
<212> TYPE: PRT
<213> ORGANISM: Enterococcus faecalis

<400> SEQUENCE: 86

```
Met Lys Gln Tyr Lys Val Leu Asn Glu Lys Glu Met Lys Lys Pro Ile
1               5                   10                  15

Gly Gly Glu Ser Val Phe Ser Lys Ile Gly Asn Ala Val Gly Pro Ala
            20                  25                  30

Ala Tyr Trp Ile Leu Lys Gly Leu Gly Asn Met Ser Asp Val Asn Gln
        35                  40                  45

Ala Asp Arg Ile Asn Arg Lys Lys His
    50                  55
```

<210> SEQ ID NO 87
<211> LENGTH: 174
<212> TYPE: DNA
<213> ORGANISM: Enterococcus faecalis

<400> SEQUENCE: 87

```
atgaagcaat ataaagtatt gaatgaaaaa gaaatgaaaa aacctattgg gggagagtcg      60
gtttttagta aataggtaa tgctgtaggt ccagctgctt attggatttt aaaaggatta      120
ggtaatatga gtgatgtaaa ccaagctgat agaattaata gaaagaaaca ttaa            174
```

<210> SEQ ID NO 88
<211> LENGTH: 44
<212> TYPE: PRT
<213> ORGANISM: Enterococcus faecalis

<400> SEQUENCE: 88

```
Met Gly Ala Ile Ala Lys Leu Val Ala Lys Phe Gly Trp Pro Ile Val
1               5                   10                  15

Lys Lys Tyr Tyr Lys Gln Ile Met Gln Phe Ile Gly Glu Gly Trp Ala
            20                  25                  30

Ile Asn Lys Ile Ile Asp Trp Ile Lys Lys His Ile
        35                  40
```

<210> SEQ ID NO 89
<211> LENGTH: 135
<212> TYPE: DNA
<213> ORGANISM: Enterococcus faecalis

<400> SEQUENCE: 89

```
atgggagcaa tcgcaaaatt agtagcaaag tttggatggc caattgttaa aaagtattac      60
aaacaaatta tgcaatttat tggagaagga tgggcaatta caaaaattat tgattggatc      120
aaaaaacata tttaa                                                      135
```

<210> SEQ ID NO 90
<211> LENGTH: 43

```
<212> TYPE: PRT
<213> ORGANISM: Enterococcus faecalis

<400> SEQUENCE: 90

Met Gly Ala Ile Ala Lys Leu Val Ala Lys Phe Gly Trp Pro Phe Ile
1               5                   10                  15

Lys Lys Phe Tyr Lys Gln Ile Met Gln Phe Ile Gly Gln Gly Trp Thr
                20                  25                  30

Ile Asp Gln Ile Glu Lys Trp Leu Lys Arg His
            35                  40

<210> SEQ ID NO 91
<211> LENGTH: 132
<212> TYPE: DNA
<213> ORGANISM: Enterococcus faecalis

<400> SEQUENCE: 91
atgggagcaa tcgcaaaatt agtagcaaag tttggatggc catttattaa aaaattctac      60
aaacaaatta tgcagtttat cggacaagga tggacaatag atcaaattga aaatggtta     120 aaaagacatt ga                                                        132

<210> SEQ ID NO 92
<211> LENGTH: 74
<212> TYPE: PRT
<213> ORGANISM: Enterococcus faecalis

<400> SEQUENCE: 92

Met Leu Asn Lys Lys Leu Leu Glu Asn Gly Val Val Asn Ala Val Thr
1               5                   10                  15

Ile Asp Glu Leu Asp Ala Gln Phe Gly Gly Met Ser Lys Arg Asp Cys
                20                  25                  30

Asn Leu Met Lys Ala Cys Cys Ala Gly Gln Ala Val Thr Tyr Ala Ile
            35                  40                  45

His Ser Leu Leu Asn Arg Leu Gly Gly Asp Ser Ser Asp Pro Ala Gly
        50                  55                  60

Cys Asn Asp Ile Val Arg Lys Tyr Cys Lys
65                  70

<210> SEQ ID NO 93
<211> LENGTH: 225
<212> TYPE: DNA
<213> ORGANISM: Enterococcus faecalis

<400> SEQUENCE: 93
atgttaaata aaaaattatt agaaaatggt gtagtaaatg ctgtaacaat tgatgaactt      60
gatgctcaat ttggtggaat gagcaaacgt gattgtaact tgatgaaggc gtgttgtgct    120
ggacaagcag taacatatgc tattcatagt cttttaaatc gattaggtgg agactctagt    180
gatccagctg gttgtaatga tattgtaaga aaatattgta aataa                    225

<210> SEQ ID NO 94
<211> LENGTH: 65
<212> TYPE: PRT
<213> ORGANISM: Enterococcus faecium

<400> SEQUENCE: 94

Met Lys His Leu Lys Ile Leu Ser Ile Lys Glu Thr Gln Leu Ile Tyr
1               5                   10                  15

Gly Gly Thr Thr His Ser Gly Lys Tyr Tyr Gly Asn Gly Val Tyr Cys
```

```
            20                  25                  30
Thr Lys Asn Lys Cys Thr Val Asp Trp Ala Lys Ala Thr Thr Cys Ile
        35                  40                  45

Ala Gly Met Ser Ile Gly Gly Phe Leu Gly Gly Ala Ile Pro Gly Lys
    50                  55                  60

Cys
65

<210> SEQ ID NO 95
<211> LENGTH: 195
<212> TYPE: DNA
<213> ORGANISM: Enterococcus faecium

<400> SEQUENCE: 95
atgaaacatt taaaattttt gtctattaaa gagacacaac ttatctatgg gggtaccact     60
catagtggaa aatattatgg aaatggagtg tattgcacta aaaataaatg tacggtcgat    120
tgggccaagg caactacttg tattgcagga atgtctatag gtggttttt aggtggagca     180 attccaggga agtgc                                                     195

<210> SEQ ID NO 96
<211> LENGTH: 105
<212> TYPE: PRT
<213> ORGANISM: Enterococcus faecalis

<400> SEQUENCE: 96

Met Val Lys Glu Asn Lys Phe Ser Lys Ile Phe Ile Leu Met Ala Leu
1               5                   10                  15

Ser Phe Leu Gly Leu Ala Leu Phe Ser Ala Ser Leu Gln Phe Leu Pro
            20                  25                  30

Ile Ala His Met Ala Lys Glu Phe Gly Ile Pro Ala Ala Val Ala Gly
        35                  40                  45

Thr Val Leu Asn Val Val Glu Ala Gly Gly Trp Val Thr Thr Ile Val
    50                  55                  60

Ser Ile Leu Thr Ala Val Gly Ser Gly Gly Leu Ser Leu Leu Ala Ala
65                  70                  75                  80

Ala Gly Arg Glu Ser Ile Lys Ala Tyr Leu Lys Lys Glu Ile Lys Lys
                85                  90                  95

Lys Gly Lys Arg Ala Val Ile Ala Trp
            100                 105

<210> SEQ ID NO 97
<211> LENGTH: 318
<212> TYPE: DNA
<213> ORGANISM: Enterococcus faecalis

<400> SEQUENCE: 97
atggttaaag aaaataaatt ttctaagatt tttattttaa tggctttgag ttttttgggg     60
ttagccttgt ttagtgcaag tcttcagttt tgcccattg cacatatggc taaagagttc    120
ggtataccag cagcagttgc aggaactgtg cttaatgtag ttgaagctgg tggatgggtc    180
actactattg tatcaattct tactgctgta ggtagcggag tcttttcttt actcgctgca    240
gcaggaagag agtcaattaa agcatacctt aagaagaaa ttaagaaaaa aggaaaaaga    300
gcagttattg cttggtaa                                                 318

<210> SEQ ID NO 98
<211> LENGTH: 71
```

```
<212> TYPE: PRT
<213> ORGANISM: Enterococcus faecium

<400> SEQUENCE: 98

Met Gln Asn Val Lys Glu Leu Ser Thr Lys Glu Met Lys Gln Ile Ile
1               5                   10                  15

Gly Gly Glu Asn Asp His Arg Met Pro Asn Glu Leu Asn Arg Pro Asn
            20                  25                  30

Asn Leu Ser Lys Gly Gly Ala Lys Cys Gly Ala Ala Ile Ala Gly Gly
        35                  40                  45

Leu Phe Gly Ile Pro Lys Gly Pro Leu Ala Trp Ala Ala Gly Leu Ala
    50                  55                  60

Asn Val Tyr Ser Lys Cys Asn
65                  70

<210> SEQ ID NO 99
<211> LENGTH: 216
<212> TYPE: DNA
<213> ORGANISM: Enterococcus faecium

<400> SEQUENCE: 99
atgcaaaatg taaagaatt aagtacgaaa gagatgaaac aaattatcgg tggagaaaat      60
gatcacagaa tgcctaatga gttaaataga cctaacaact tatctaaagg tggagcaaaa    120
tgtggtgctg caattgctgg ggattattt ggaatcccaa aaggaccact agcatgggct     180
gctgggttag caaatgtata ctctaaatgc aactaa                               216

<210> SEQ ID NO 100
<211> LENGTH: 58
<212> TYPE: PRT
<213> ORGANISM: Enterococcus mundtii

<400> SEQUENCE: 100

Met Lys Lys Leu Thr Ser Lys Glu Met Ala Gln Val Val Gly Gly Lys
1               5                   10                  15

Tyr Tyr Gly Asn Gly Val Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55

<210> SEQ ID NO 101
<211> LENGTH: 177
<212> TYPE: DNA
<213> ORGANISM: Enterococcus mundtii

<400> SEQUENCE: 101
ttgaagaaat taacatcaaa agaaatggca caagtagtag gtggaaaata ctacggtaat      60
ggagtctcat gtaataaaaa agggtgcagt gttgattggg gaaaagctat tggcattatt   120
ggaaataatt ctgctgcgaa tttagctact ggtggagcag ctggttggaa aagttaa       177

<210> SEQ ID NO 102
<211> LENGTH: 44
<212> TYPE: PRT
<213> ORGANISM: Enterococcus faecalis

<400> SEQUENCE: 102

Met Leu Ala Lys Ile Lys Ala Met Ile Lys Lys Phe Pro Asn Pro Tyr
```

```
1               5                   10                  15
Thr Leu Ala Ala Lys Leu Thr Thr Tyr Glu Ile Asn Trp Tyr Lys Gln
            20                  25                  30

Gln Tyr Gly Arg Tyr Pro Trp Glu Arg Pro Val Ala
            35                  40
```

<210> SEQ ID NO 103
<211> LENGTH: 135
<212> TYPE: DNA
<213> ORGANISM: Enterococcus faecalis

<400> SEQUENCE: 103

```
atgttagcaa aaattaaagc gatgattaag aagtttccga acccttatac tttagcagct    60
aagctaacga cttacgaaat taattggtat aaacaacaat acggtcgtta tccttgggag   120
cgccctgtag cataa                                                    135
```

<210> SEQ ID NO 104
<211> LENGTH: 71
<212> TYPE: PRT
<213> ORGANISM: Enterococcus faecium

<400> SEQUENCE: 104

```
Met Arg Lys Lys Leu Phe Ser Leu Ala Leu Ile Gly Ile Phe Gly Leu
1               5                   10                  15

Val Val Thr Asn Phe Gly Thr Lys Val Asp Ala Ala Thr Arg Ser Tyr
            20                  25                  30

Gly Asn Gly Val Tyr Cys Asn Asn Ser Lys Cys Trp Val Asn Trp Gly
        35                  40                  45

Glu Ala Lys Glu Asn Ile Ala Gly Ile Val Ile Ser Gly Trp Ala Ser
    50                  55                  60

Gly Leu Ala Gly Met Gly His
65                  70
```

<210> SEQ ID NO 105
<211> LENGTH: 216
<212> TYPE: DNA
<213> ORGANISM: Enterococcus faecium

<400> SEQUENCE: 105

```
atgagaaaaa aattatttag tttagctctt attggaatat ttgggttagt tgtgacaaat    60
tttggtacaa aagttgatgc agctacgcgt tcatatggta atggtgttta ttgtaataat   120
agtaaatgct gggttaactg gggagaagct aaagagaata ttgcaggaat cgttattagt   180
ggctgggctt ctggtttggc aggtatggga cattaa                             216
```

<210> SEQ ID NO 106
<211> LENGTH: 34
<212> TYPE: PRT
<213> ORGANISM: Enterococcus faecium

<400> SEQUENCE: 106

```
Met Asn Phe Leu Lys Asn Gly Ile Ala Lys Trp Met Thr Gly Ala Glu
1               5                   10                  15

Leu Gln Ala Tyr Lys Lys Lys Tyr Gly Cys Leu Pro Trp Glu Lys Ile
            20                  25                  30

Ser Cys
```

<210> SEQ ID NO 107

```
<211> LENGTH: 105
<212> TYPE: DNA
<213> ORGANISM: Enterococcus faecium

<400> SEQUENCE: 107
atgaattttc ttaaaaatgg tatcgcaaaa tggatgaccg gtgctgaatt gcaagcgtat    60
aaaaagaaat atggatgctt gccatgggaa aaaatttctt gttaa                  105

<210> SEQ ID NO 108
<211> LENGTH: 76
<212> TYPE: PRT
<213> ORGANISM: Enterococcus faecalis

<400> SEQUENCE: 108

Met Lys Lys Lys Leu Val Lys Gly Leu Val Ile Cys Gly Met Ile Gly
1               5                   10                  15

Ile Gly Phe Thr Ala Leu Gly Thr Asn Val Glu Ala Ala Thr Tyr Tyr
            20                  25                  30

Gly Asn Gly Val Tyr Cys Asn Lys Gln Lys Cys Trp Val Asp Trp Ser
        35                  40                  45

Arg Ala Arg Ser Glu Ile Ile Asp Arg Gly Val Lys Ala Tyr Val Asn
    50                  55                  60

Gly Phe Thr Lys Val Leu Gly Gly Ile Gly Gly Arg
65                  70                  75

<210> SEQ ID NO 109
<211> LENGTH: 231
<212> TYPE: DNA
<213> ORGANISM: Enterococcus faecalis

<400> SEQUENCE: 109
atgaaaaaga aattagttaa aggcttagtt atttgtggca tgattgggat tggttttaca    60
gcattaggaa caaatgtaga agccgccacg tattacggaa atggtgtcta ttgcaataag   120
caaaaatgtt gggtagattg gagtagagca cgttctgaaa ttatagacag aggcgtaaaa   180
gcatacgtca atggatttac gaaagtgtta ggtggtatag gtggaagata a            231

<210> SEQ ID NO 110
<211> LENGTH: 60
<212> TYPE: PRT
<213> ORGANISM: Enterococcus faecalis

<400> SEQUENCE: 110

Met Lys Lys Glu Glu Leu Val Gly Met Ala Lys Glu Asp Phe Leu Asn
1               5                   10                  15

Val Ile Cys Glu Asn Asp Asn Lys Leu Glu Asn Ser Gly Ala Lys Cys
            20                  25                  30

Pro Trp Trp Asn Leu Ser Cys His Leu Gly Asn Asp Gly Lys Ile Cys
        35                  40                  45

Thr Tyr Ser His Glu Cys Thr Ala Gly Cys Asn Ala
    50                  55                  60

<210> SEQ ID NO 111
<211> LENGTH: 183
<212> TYPE: DNA
<213> ORGANISM: Enterococcus faecalis

<400> SEQUENCE: 111
atgaaaaaag aagaattagt aggaatggct aaggaagact ttttaaatgt tatttgtgaa    60
```

```
aatgacaaca aactagaaaa tagtggagca aaatgtcctt ggtggaatct ttcttgtcat    120
ttaggcaatg atggtaaaat ttgcacttat tcacatgaat gtaccgcagg ttgtaatgca    180
taa                                                                  183
```

<210> SEQ ID NO 112
<211> LENGTH: 61
<212> TYPE: PRT
<213> ORGANISM: Enterococcus faecalis

<400> SEQUENCE: 112

```
Met Thr Glu Leu Asn Lys Arg Leu Gln Leu Lys Arg Asp Val Ser Thr
1               5                   10                  15

Glu Asn Ser Leu Lys Lys Ile Ser Asn Thr Asp Glu Thr His Gly Gly
            20                  25                  30

Val Thr Thr Ser Ile Pro Cys Thr Val Met Val Ser Ala Ala Val Cys
        35                  40                  45

Pro Thr Leu Val Cys Ser Asn Lys Cys Gly Gly Arg Gly
    50                  55                  60
```

<210> SEQ ID NO 113
<211> LENGTH: 186
<212> TYPE: DNA
<213> ORGANISM: Enterococcus faecalis

<400> SEQUENCE: 113

```
atgactgaac ttaacaaaag attacaatta aaaagagatg tttcaacaga aaatagtttg     60
aaaaaaattt ctaatactga tgaaacacat ggggagtta ctacatcaat tccatgtaca    120
gtaatggtta gtgcggcagt atgtcctacc cttgtttgct cgaataaatg tggcggtaga   180
ggctag                                                              186
```

<210> SEQ ID NO 114
<211> LENGTH: 58
<212> TYPE: PRT
<213> ORGANISM: Enterococcus faecium

<400> SEQUENCE: 114

```
Met Gln Asn Val Lys Glu Val Ser Val Lys Glu Met Lys Gln Ile Ile
1               5                   10                  15

Gly Gly Ser Asn Asp Ser Leu Trp Tyr Gly Val Gly Gln Phe Met Gly
            20                  25                  30

Lys Gln Ala Asn Cys Ile Thr Asn His Pro Val Lys His Met Ile Ile
        35                  40                  45

Pro Gly Tyr Cys Leu Ser Lys Ile Leu Gly
    50                  55
```

<210> SEQ ID NO 115
<211> LENGTH: 177
<212> TYPE: DNA
<213> ORGANISM: Enterococcus faecium

<400> SEQUENCE: 115

```
atgcaaaatg taaagaagt ttctgtaaaa gagatgaaac aaattatcgg tggttctaat     60
gatagtcttt ggtatggtgt aggacaattt atgggtaaac aagcaaactg tataacaaac   120
catcctgtta aacacatgat aattcctgga tattgtttat cgaaaatttt agggtaa      177
```

<210> SEQ ID NO 116
<211> LENGTH: 55

```
<212> TYPE: PRT
<213> ORGANISM: Enterococcus faecium

<400> SEQUENCE: 116

Met Lys Lys Tyr Asn Glu Leu Ser Lys Lys Glu Leu Leu Gln Ile Gln
1               5                   10                  15

Gly Gly Ile Ala Pro Ile Ile Val Ala Gly Leu Gly Tyr Leu Val Lys
            20                  25                  30

Asp Ala Trp Asp His Ser Asp Gln Ile Ile Ser Gly Phe Lys Lys Gly
        35                  40                  45

Trp Asn Gly Gly Arg Lys
        50                  55

<210> SEQ ID NO 117
<211> LENGTH: 168
<212> TYPE: DNA
<213> ORGANISM: Enterococcus faecium

<400> SEQUENCE: 117
atgaaaaaat ataatgagtt atctaaaaaa gaacttctac agattcaagg aggaatagca      60
cctattatag ttgctggcct tggctattta gtaaaagatg catgggatca ctcagatcaa     120
ataatctcag gatttaaaaa aggttggaat ggtggacgta gaaaataa                   168

<210> SEQ ID NO 118
<211> LENGTH: 343
<212> TYPE: PRT
<213> ORGANISM: Enterococcus faecalis

<400> SEQUENCE: 118

Met Lys Asn Ile Leu Leu Ser Ile Leu Gly Val Leu Ser Ile Val Val
1               5                   10                  15

Ser Leu Ala Phe Ser Ser Tyr Ser Val Asn Ala Ala Ser Asn Glu Trp
            20                  25                  30

Ser Trp Pro Leu Gly Lys Pro Tyr Ala Gly Arg Tyr Glu Glu Gly Gln
        35                  40                  45

Gln Phe Gly Asn Thr Ala Phe Asn Arg Gly Gly Thr Tyr Phe His Asp
    50                  55                  60

Gly Phe Asp Phe Gly Ser Ala Ile Tyr Gly Asn Gly Ser Val Tyr Ala
65                  70                  75                  80

Val His Asp Gly Lys Ile Leu Tyr Ala Gly Trp Asp Pro Val Gly Gly
                85                  90                  95

Gly Ser Leu Gly Ala Phe Ile Val Leu Gln Ala Gly Asn Thr Asn Val
            100                 105                 110

Ile Tyr Gln Glu Phe Ser Arg Asn Val Gly Asp Ile Lys Val Ser Thr
        115                 120                 125

Gly Gln Thr Val Lys Lys Gly Gln Leu Ile Gly Lys Phe Thr Ser Ser
    130                 135                 140

His Leu His Leu Gly Met Thr Lys Lys Glu Trp Arg Ser Ala His Ser
145                 150                 155                 160

Ser Trp Asn Lys Asp Asp Gly Thr Trp Phe Asn Pro Ile Pro Ile Leu
                165                 170                 175

Gln Gly Gly Ser Thr Pro Thr Pro Pro Asn Pro Gly Pro Lys Asn Phe
            180                 185                 190

Thr Thr Asn Val Arg Tyr Gly Leu Arg Val Leu Gly Ser Trp Leu
        195                 200                 205

Pro Glu Val Thr Asn Phe Asn Asn Thr Asn Asp Gly Phe Ala Gly Tyr
```

Pro Asn Arg Gln His Asp Met Leu Tyr Ile Lys Val Asp Lys Gly Gln
225                 230                 235                 240

Met Lys Tyr Arg Val His Thr Ala Gln Ser Gly Trp Leu Pro Trp Val
            245                 250                 255

Ser Lys Gly Asp Lys Ser Asp Thr Val Asn Gly Ala Ala Gly Met Pro
        260                 265                 270

Gly Gln Ala Ile Asp Gly Val Gln Leu Asn Tyr Ile Thr Pro Lys Gly
    275                 280                 285

Glu Lys Leu Ser Gln Ala Tyr Tyr Arg Ser Gln Thr Thr Lys Arg Ser
290                 295                 300

Gly Trp Leu Lys Val Ser Ala Asp Asn Gly Ser Ile Pro Gly Leu Asp
305                 310                 315                 320

Ser Tyr Ala Gly Ile Phe Gly Glu Pro Leu Asp Arg Leu Gln Ile Gly
                325                 330                 335

Ile Ser Gln Ser Asn Pro Phe
            340

<210> SEQ ID NO 119
<211> LENGTH: 1032
<212> TYPE: DNA
<213> ORGANISM: Enterococcus faecalis

<400> SEQUENCE: 119
atgaaaaata ttttactttc tattctaggg gtattatcta tcgttgtttc tttggcgttt        60
tcttcttatt ctgtcaacgc agcttctaat gagtggtcgt ggccactggg caaaccatat       120
gcgggaagat atgaagaagg acaacaattc gggaacactg catttaaccg aggaggtact       180
tatttccatg atgggtttga ctttggttct gctatttatg aaatggcag tgtgtatgct       240 gtgcatgatg gtaaaatttt atatgctggt tgggatcctg taggtggagg ctcattaggt       300
gcatttattg tactacaagc gggaaacaca aatgtgattt atcaagaatt agccgaaat       360 gttggagata ttaaagttag cactggacaa actgttaaaa aaggacagct gataggaaag       420
tttacttcta gtcatttaca tttaggaatg acaaaaaaag aatggcgttc tgctcattct       480
tcttggaata agatgatgg cacttggttt aacccaattc ctatacttca aggaggatct       540
acgcctacgc ctccaaatcc aggaccaaaa aatttcacaa caatgttcg ttacggattg       600 cgggtcctcg gaggttcatg gttaccagaa gtaaccaact ttaacaatac caatgatggt       660
ttcgcaggtt accctaatcg tcaacatgat atgctttata taaaggtaga taaagggcaa       720
atgaaatatc gtgttcacac ggctcaaagt ggatggttgc cttgggtaag taaaggggat       780
aagagcgata cagtaaatgg agcggcaggt atgcctggac aagcaattga tggtgttcag       840
ctaaactata taactcctaa gggagaaaaa ttatcacagg cttactatcg ttcacaaact       900
acgaaacgat caggctggtt aaaagtaagt gcagataatg gttctattcc tggactagac       960
agttatgcag gaatctttgg agaaccgttg gatcgcttgc aaataggtat ttcacagtca      1020
aatccatttt aa                                                         1032

<210> SEQ ID NO 120
<211> LENGTH: 56
<212> TYPE: PRT
<213> ORGANISM: Staphylococcus epidermidis

<400> SEQUENCE: 120

Met Glu Asn Lys Lys Asp Leu Phe Asp Leu Glu Ile Lys Lys Asp Asn

```
1               5                   10                  15
Met Glu Asn Asn Asn Glu Leu Glu Ala Gln Ser Leu Gly Pro Ala Ile
            20                  25                  30
Lys Ala Thr Arg Gln Val Cys Pro Lys Ala Thr Arg Phe Val Thr Val
            35                  40                  45
Ser Cys Lys Lys Ser Asp Cys Gln
        50                  55
```

<210> SEQ ID NO 121
<211> LENGTH: 171
<212> TYPE: DNA
<213> ORGANISM: Staphylococcus epidermidis

<400> SEQUENCE: 121
atggaaaaca aaaagattt atttgattta gaaatcaaaa aagataatat ggaaaataat    60
aatgaattag aagctcaatc tcttggtcct gcaattaagg caactagaca ggtatgtcct   120
aaagcaacac gttttgttac agtttcttgt aaaaaaagtg attgtcaata g            171

<210> SEQ ID NO 122
<211> LENGTH: 51
<212> TYPE: PRT
<213> ORGANISM: Staphylococcus epidermidis

<400> SEQUENCE: 122

```
Met Ala Ala Phe Met Lys Leu Ile Gln Phe Leu Ala Thr Lys Gly Gln
1               5                   10                  15
Lys Tyr Val Ser Leu Ala Trp Lys His Lys Gly Thr Ile Leu Lys Trp
            20                  25                  30
Ile Asn Ala Gly Gln Ser Phe Glu Trp Ile Tyr Lys Gln Ile Lys Lys
            35                  40                  45
Leu Trp Ala
        50
```

<210> SEQ ID NO 123
<211> LENGTH: 156
<212> TYPE: DNA
<213> ORGANISM: Staphylococcus epidermidis

<400> SEQUENCE: 123
atggcagcat ttatgaagtt aattcagttc ttagcaacta aaggtcaaaa gtatgtttca    60
cttgcatgga acataaagg tactatttta aaatggatta acgccggtca aagttttgaa   120
tggatttata acaaatcaa aaaattatgg gcataa                              156

<210> SEQ ID NO 124
<211> LENGTH: 52
<212> TYPE: PRT
<213> ORGANISM: Staphylococcus epidermidis

<400> SEQUENCE: 124

```
Met Glu Ala Val Lys Glu Lys Asn Asp Leu Phe Asn Leu Asp Val Lys
1               5                   10                  15
Val Asn Ala Lys Glu Ser Asn Asp Ser Gly Ala Glu Pro Arg Ile Ala
            20                  25                  30
Ser Lys Phe Ile Cys Thr Pro Gly Cys Ala Lys Thr Gly Ser Phe Asn
            35                  40                  45
Ser Tyr Cys Cys
        50
```

<210> SEQ ID NO 125
<211> LENGTH: 159
<212> TYPE: DNA
<213> ORGANISM: Staphylococcus epidermidis

<400> SEQUENCE: 125
atggaagcag taaaagaaaa aaatgatctt tttaatcttg atgttaaagt taatgcaaaa      60
gaatctaacg attcaggagc tgaaccaaga attgctagta aatttatatg tactcctgga     120
tgtgcaaaaa caggtagttt taacagttat tgttgttaa                            159

<210> SEQ ID NO 126
<211> LENGTH: 55
<212> TYPE: PRT
<213> ORGANISM: Staphylococcus epidermidis

<400> SEQUENCE: 126

Met Asn Asn Ser Leu Phe Asp Leu Asn Leu Asn Lys Gly Val Glu Thr
1               5                   10                  15

Gln Lys Ser Asp Leu Ser Pro Gln Ser Ala Ser Val Leu Lys Thr Ser
            20                  25                  30

Ile Lys Val Ser Lys Lys Tyr Cys Lys Gly Val Thr Leu Thr Cys Gly
        35                  40                  45

Cys Asn Ile Thr Gly Gly Lys
    50                  55

<210> SEQ ID NO 127
<211> LENGTH: 168
<212> TYPE: DNA
<213> ORGANISM: Staphylococcus epidermidis

<400> SEQUENCE: 127
atgaataact cattattcga tttaaaccta aacaaaggtg tagaaactca aaagagtgat      60
ttaagtccgc aatctgctag tgtcttgaag acttctatta agtatctaa aaaatattgt     120 aaaggtgtta ctttaacatg cggttgcaat attactggtg gtaaataa                 168

<210> SEQ ID NO 128
<211> LENGTH: 52
<212> TYPE: PRT
<213> ORGANISM: Staphylococcus gallinarum

<400> SEQUENCE: 128

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
        35                  40                  45

Ser Tyr Cys Cys
    50

<210> SEQ ID NO 129
<211> LENGTH: 159
<212> TYPE: DNA
<213> ORGANISM: Staphylococcus gallinarum

<400> SEQUENCE: 129
atggaagcag taaaagagaa aaatgaactt tttgatcttg acgttaaagt aaatgcaaaa      60
gagtctaatg attcaggcgc agaaccacga attgctagta aatttttatg tactcctgga     120

-continued tgtgccaaaa caggtagctt caatagctac tgttgttaa    159

<210> SEQ ID NO 130
<211> LENGTH: 63
<212> TYPE: PRT
<213> ORGANISM: Lactococcus garvieae

<400> SEQUENCE: 130

Met Glu Asn Asn Asn Tyr Thr Val Leu Ser Asp Glu Glu Leu Gln Lys
1               5                   10                  15

Ile Asp Gly Gly Ile Gly Gly Ala Leu Gly Asn Ala Leu Asn Gly Leu
            20                  25                  30

Gly Thr Trp Ala Asn Met Met Asn Gly Gly Phe Val Asn Gln Trp
        35                  40                  45

Gln Val Tyr Ala Asn Lys Gly Lys Ile Asn Gln Tyr Arg Pro Tyr
    50                  55                  60

<210> SEQ ID NO 131
<211> LENGTH: 192
<212> TYPE: DNA
<213> ORGANISM: Lactococcus garvieae

<400> SEQUENCE: 131
atggaaaaca acaattacac agtactttca gatgaagaac tacaaaaaat tgatggtgga    60
atcggcgggg ctcttggtaa tgctctcaac ggattaggta cctgggcaaa catgatgaac    120
ggtggaggat tgttaatca gtggcaagtt tatgctaata aggaaaaat aaatcaatac    180 cgtccgtatt aa    192

<210> SEQ ID NO 132
<211> LENGTH: 63
<212> TYPE: PRT
<213> ORGANISM: Lactococcus garvieae

<400> SEQUENCE: 132

Met Phe Asp Leu Val Ala Thr Gly Met Ala Ala Gly Val Ala Lys Thr
1               5                   10                  15

Ile Val Asn Ala Val Ser Ala Gly Met Asp Ile Ala Thr Ala Leu Ser
            20                  25                  30

Leu Phe Ser Gly Ala Phe Thr Ala Ala Gly Gly Ile Met Ala Leu Ile
        35                  40                  45

Lys Lys Tyr Ala Gln Lys Lys Leu Trp Lys Gln Leu Ile Ala Ala
    50                  55                  60

<210> SEQ ID NO 133
<211> LENGTH: 192
<212> TYPE: DNA
<213> ORGANISM: Lactococcus garvieae

<400> SEQUENCE: 133
atgtttgatt tagtcgcgac tggaatggct gcaggtgtag caaaaactat tgttaatgcc    60
gttagtgctg gtatggatat tgccactgct ttatcattgt tctcaggagc ttttactgca    120 gctggggaa ttatggcact cattaaaaaa tatgctcaaa agaaattatg gaaacagctt    180
attgctgcat aa    192

<210> SEQ ID NO 134
<211> LENGTH: 91
<212> TYPE: PRT

<213> ORGANISM: Lactobacillus gasseri

<400> SEQUENCE: 134

```
Met Val Thr Lys Tyr Gly Arg Asn Leu Gly Leu Asn Lys Val Glu Leu
1               5                   10                  15
Phe Ala Ile Trp Ala Val Leu Val Ala Leu Leu Thr Thr Ala
            20                  25                  30
Asn Ile Tyr Trp Ile Ala Asp Gln Phe Gly Ile His Leu Ala Thr Gly
            35                  40                  45
Thr Ala Arg Lys Leu Leu Asp Ala Met Ala Ser Gly Ala Ser Leu Gly
50                  55                  60
Thr Ala Phe Ala Ala Ile Leu Gly Val Thr Leu Pro Ala Trp Ala Leu
65                  70                  75                  80
Ala Ala Ala Gly Ala Leu Gly Ala Thr Ala Ala
                85                  90
```

<210> SEQ ID NO 135
<211> LENGTH: 276
<212> TYPE: DNA
<213> ORGANISM: Lactobacillus gasseri

<400> SEQUENCE: 135

```
atggttacta agtacggacg taatttaggt ttgaacaagg tagagttgtt tgcaatttgg     60
gcggttttag tagttgctct tttattgacc acagcgaaca tttattggat tgctgatcaa    120
ttcgggattc atttagcgac tggaacagcc cgtaagttat tagatgcaat ggcttctggt    180
gcctcattgg gaactgcctt tgctgctatt ttgggcgtga cattacctgc atgggctttg    240
gcagctgcag gagcattggg agcgactgca gcctag                             276
```

<210> SEQ ID NO 136
<211> LENGTH: 75
<212> TYPE: PRT
<213> ORGANISM: Lactobacillus gasseri

<400> SEQUENCE: 136

```
Met Lys Asn Phe Asn Thr Leu Ser Phe Glu Thr Leu Ala Asn Ile Val
1               5                   10                  15
Gly Gly Arg Asn Asn Trp Ala Ala Asn Ile Gly Gly Val Gly Gly Ala
            20                  25                  30
Thr Val Ala Gly Trp Ala Leu Gly Asn Ala Val Cys Gly Pro Ala Cys
            35                  40                  45
Gly Phe Val Gly Ala His Tyr Val Pro Ile Ala Trp Ala Gly Val Thr
50                  55                  60
Ala Ala Thr Gly Gly Phe Gly Lys Ile Arg Lys
65                  70                  75
```

<210> SEQ ID NO 137
<211> LENGTH: 228
<212> TYPE: DNA
<213> ORGANISM: Lactobacillus gasseri

<400> SEQUENCE: 137

```
atgaaaaatt ttaatacatt atcatttgaa acattggcta acatagttgg tggagaaaat     60
aattgggctg ctaatatagg tggagtaggt ggagcgacag tcgctggatg ggctcttgga    120
aatgcagttt gcggtcctgc ttgtggcttt gttggagcac actatgttcc aatagcatgg    180
gctggcgtaa cggcagctac tggtggattc ggaaagataa gaaagtag                228
```

<210> SEQ ID NO 138
<211> LENGTH: 64
<212> TYPE: PRT
<213> ORGANISM: Lactobacillus plantarum

<400> SEQUENCE: 138

Met Ser Lys Leu Val Lys Thr Leu Thr Ile Ser Glu Ile Ser Lys Ala
1               5                   10                  15

Gln Asn Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Ile Lys His His Ser Ser Gly Ser Ser Ser Tyr His Cys
    50                  55                  60

<210> SEQ ID NO 139
<211> LENGTH: 195
<212> TYPE: DNA
<213> ORGANISM: Lactobacillus plantarum

<400> SEQUENCE: 139
atgagtaaat tggttaagac acttactata agtgaaattt ctaaggctca aaacaacggt      60
ggaaaacctg catggtgttg gtatacttta gcaatgtgtg gtgctggtta tgattcggga     120
acctgtgatt atatgtattc gcattgtttt ggtataaagc atcatagtag tggtagtagc     180
agttatcatt gttag                                                      195

<210> SEQ ID NO 140
<211> LENGTH: 359
<212> TYPE: PRT
<213> ORGANISM: Haloferax mediterranei

<400> SEQUENCE: 140

Met Ser Lys Asp Arg Asp Gly Arg Arg Thr Ser Arg Arg Gly Thr Leu
1               5                   10                  15

Lys Lys Ile Gly Gly Phe Ser Leu Gly Ala Leu Ser Phe Gly Ala Val
            20                  25                  30

Gly Arg Thr Gln Ala Ala Thr Gly Ser Ser Val Thr Thr Ala Asp Ile
        35                  40                  45

Ala Pro Pro Gly Pro Asn Gly Asp Pro Lys Ser Val Gln Ile Asp Asp
    50                  55                  60

Lys Tyr Thr Gly Ala Glu Met Tyr Gly Glu Gly Asp Phe Arg Val Gly
65                  70                  75                  80

Leu Gly Thr Asp Leu Thr Met Tyr Pro Pro Val Tyr Arg Glu Ser Leu
                85                  90                  95

Gly Asn Gly Ser Gly Gly Trp Glu Phe Asp Phe Thr Val Cys Gly Ser
            100                 105                 110

Thr Ala Cys Arg Phe Val Asp Ser Asn Gly Asp Val Lys Glu Asp Asp
        115                 120                 125

Lys Ala Lys Glu Met Trp Trp Gln Glu Ile Asn Phe Asn Asp Ile Asn
    130                 135                 140

Gln Asp Leu Tyr Ser Arg Asn Asp Ser Asp Trp Val Gly Ser Thr Pro
145                 150                 155                 160

Ala Asp Thr Gln Pro Glu Phe Asp Tyr Thr Glu Phe Ala Leu Ala Arg
                165                 170                 175

Asp Gly Val Thr Leu Ala Leu Thr Ala Leu Asn Pro Ala Met Gly Ser
            180                 185                 190

```
Leu Ala Leu Gly Ala Thr Tyr Phe Leu Ser Asp Met Val Asn Trp Ile
        195                 200                 205

Ala Ser Gln His Glu Asp Asp Ser Ser Leu Lys Arg Lys Trp Asp Tyr
        210                 215                 220

Asp Gly Leu Ser Gly Pro Leu Tyr Ala Asp Ser Ser Thr Tyr Leu Leu
225                 230                 235                 240

Ala Arg Asp Glu Met Thr Ser Asn Ser Tyr Glu Ser Phe Thr Ile Asp
                245                 250                 255

Asn Ile Ala Val Ala Phe Pro Glu Phe Pro Val Arg Thr Lys Tyr Tyr
                260                 265                 270

Val Thr Phe Thr Ala Pro Asp Asp Pro Ser Thr Gln Ser Ile Ser Thr
                275                 280                 285

Leu Glu Glu Gly Ile Tyr Arg Val Pro Ala Thr Glu Val Ala Ala
        290                 295                 300

Ala Arg Pro Pro Gly Ser Arg Arg Ser Lys Ser Ala Ala Asp Glu Met
305                 310                 315                 320

Val Tyr Val Ala Asp Pro Lys Lys Phe Ile Glu Val Glu Pro Val Lys
                325                 330                 335

Asn Pro Ser Ile Pro Asp Arg Ile Tyr Glu Glu Ile Glu Gln Lys Lys
                340                 345                 350

Lys Gln Arg Ser Arg Lys Gln
        355

<210> SEQ ID NO 141
<211> LENGTH: 1080
<212> TYPE: DNA
<213> ORGANISM: Haloferax mediterranei

<400> SEQUENCE: 141
atgtcgaaag acagagatgg gagaaggaca agtcggcgag gcacgttaaa gaaaatcggc      60
ggtttcagtc tcggagcgct tagtttcggg gcagtcggac gaactcaagc ggcgaccggc     120
tcatcggtta cgaccgctga tatcgcacct cccggaccga acggagaccc gaagagtgtt     180
cagatagatg ataaatacac cggagccgag atgtacggcg agggtgactt cagagtcggt     240
ctcggaactg acctgacgat gtatccgccc gtgtaccgtg agagtcttgg aaatggaagc     300
gggggttggg aattcgactt caccgttgt gggtccactg cctgtcgatt tgtggacagt      360
aacggtgacg tcaaagagga cgacaaggcg aaagaaatgt ggtggcagga aattaacttc     420
aacgacataa atcaggattt atacagtcgg aacgattccg actgggtcgg tcgacccct      480
gccgataccc aaccggagtt cgattacacc gactttgcgc tcgctcggga cggagtgacg     540
ctcgctctca cggcactcaa ccccgcaatg gggagtcttg cactcggtgc acgtacttc      600
ctcagcgaca tggtgaactg gattgcgagc cagcacgaag acgacagttc gctcaagaga     660
aaatgggatt acgacgggct aagtgggccg ttgtacgccg attcgtcgac gtacctactg     720
gcacgcgacg agatgacttc gaactcgtac gaatcattca cgatcgataa catcgccgtt     780
gccttcccag agttccccgt ccggaccaag tactacgtca cattcactgc gccggatgac     840
ccgtcaacgc agtcgatatc tacgctcgaa gaggagggaa tctaccgagt gcccgctacg     900
gaagtggctg cggccagacc accggggtcc cgacgttcca atcggcagc cgacgagatg     960
gtgtacgttg ccgatccgaa gaagttcata gaggtcgagc cggtgaagaa cccaagtatc    1020
ccggaccgaa tctacgagga gatagagcaa aaaaagaaac aacggagtag gaaacagtag    1080
```

<210> SEQ ID NO 142
<211> LENGTH: 311
<212> TYPE: PRT
<213> ORGANISM: Haloarchaeon S8a

<400> SEQUENCE: 142

```
Met Ser Asp Lys Asp Ser Ile Asn Arg Arg Asn Val Leu Arg Lys Ile
1               5                   10                  15

Gly Gly Ile Gly Val Ala Ser Ala Val Gly Phe Ser Gly Leu Ala Ser
            20                  25                  30

Gly Glu Ser Leu Ser Asp Asp Glu Lys Gln Asp Val Ile Asp Thr Ile
        35                  40                  45

Tyr Lys Ser Gln Arg Val Glu Gln Ile Lys Lys Phe Gly Gly Val
    50                  55                  60

Asn Ile Glu Pro Lys Lys Val Gln Ser Val Thr Thr Asn Gln Ser Gly
65                  70                  75                  80

Asp Leu Val Thr Ala Lys Leu Ser Val Ser Asp Gly Asp Leu Val Tyr
                85                  90                  95

Ser Ser Val Lys Asp Thr Thr Val Ile Val Gln Phe Asp Arg Ser Ala
            100                 105                 110

Ser Glu Ile Gly Glu Ser Trp Pro Lys Asn Thr Glu Ala Phe Ile Lys
        115                 120                 125

Ser Thr Ser Ser Gly Val Asp Leu Leu Arg Thr Ala Thr Asp Glu Glu
    130                 135                 140

Ile Lys Asp Val Thr Glu Gly Val Asn Thr Ser Glu Ile Glu Ser Ala
145                 150                 155                 160

Asp Ala Val Asn Ile Phe Ile Asp Pro Glu Ser Gln Thr Tyr Tyr Met
                165                 170                 175

Glu Lys Tyr Asp Phe Asn Asn Lys Val Leu Glu Met Phe Glu Leu Ala
            180                 185                 190

Thr Gly Gly Thr Ser Ser Gly Lys Ile Ser Pro Thr Arg Glu Asp Gln
        195                 200                 205

Asn His Glu Tyr Asn Val Arg Glu His Lys Val Phe Asn Ser Glu Lys
    210                 215                 220

Gln Asn Ile Gln Leu Gln Ser Asp Cys Asn Ile Asn Ser Asn Thr Ala
225                 230                 235                 240

Ala Asp Val Ile Leu Cys Phe Asn Gln Val Gly Ser Cys Ala Leu Cys
                245                 250                 255

Ser Pro Thr Leu Val Gly Gly Pro Val Pro Thr Val Ala Cys Leu Leu
            260                 265                 270

Val Val Cys Phe Gly Thr Pro Asn Ala Val Ser Ala Ile Leu Glu Glu
        275                 280                 285

Val Asp Asn Ser Cys Phe Asn Leu Ile Lys Asp Val Ile Ser Cys Trp
    290                 295                 300

Asp Glu Trp Thr Ser Phe Trp
305                 310
```

<210> SEQ ID NO 143
<211> LENGTH: 936
<212> TYPE: DNA
<213> ORGANISM: Haloarchaeon S8a

<400> SEQUENCE: 143

| | |
|---|---|
| atgtcggata aagacagcat taacagaaga aatgtattaa gaaaaattgg cggtatcggt | 60 |
| gtggcttcag ctgtcggatt ttctggtttg gcaagcgggg aaagtcttag cgatgatgag | 120 |

```
aaacaagatg ttattgacac aatttacaaa tcacaaagag ttgaacagat aaagaaaaag    180
ttcggaggag tgaatattga gccgaaaaag gttcaatctg taacgaccaa tcagagcgga    240
gatcttgtta cggcgaagct gtcggttagt gatggggatt tggtatattc gagtgtcaaa    300
gatacaactg taatagttca gttcgataga tcggcttctg aaattggtga agttggccc    360 aagaatactg aggcattcat caaatcgacg tcctctgggg tcgatcttct acgtacagca    420
actgatgaag aaataaagga cgttactgag ggagtcaaca catctgaaat tgaatctgcg    480
gatgctgtta acatatttat tgatcctgaa tcacagacat actatatgga gaaatatgac    540
tttaataata aggtacttga gatgtttgaa ttagcgacag gtgggacaag tagtggtaaa    600
atctccccca cacgtgaaga ccagaatcac gaatataatg ttagggaaca taaagtattt    660
aactcagaaa aacagaatat acaacttcag agtgactgta atataaacag taacaccgct    720
gctgatgtta ttctatgctt caaccaggtt ggttcttgtg cactctgctc cccgactta    780 gtcggaggtc cagtccctac agttgcatgt ctcttagtcg tctgtttcgg cactccaaat    840
gctgtgtccg cgatacttga agaagtcgat aattcttgct ttaacttgat caaggatgta    900
atttcgtgtt gggatgaatg gactagcttc tggtga                             936
```

<210> SEQ ID NO 144
<211> LENGTH: 333
<212> TYPE: PRT
<213> ORGANISM: Lactobacillus helveticus

<400> SEQUENCE: 144

```
Met Lys His Leu Asn Glu Thr Thr Asn Val Arg Ile Leu Ser Gln Phe
1               5                   10                  15

Asp Met Asp Thr Gly Tyr Gln Ala Val Val Gln Lys Gly Asn Val Gly
            20                  25                  30

Ser Lys Tyr Val Tyr Gly Leu Gln Leu Arg Lys Gly Ala Thr Thr Ile
        35                  40                  45

Leu Arg Gly Tyr Arg Gly Ser Lys Ile Asn Asn Pro Ile Leu Glu Leu
    50                  55                  60

Ser Gly Gln Ala Gly Gly His Thr Gln Thr Trp Glu Phe Ala Gly Asp
65                  70                  75                  80

Arg Lys Asp Ile Asn Gly Glu Glu Arg Ala Gly Gln Trp Phe Ile Gly
                85                  90                  95

Val Lys Pro Ser Lys Ile Glu Gly Ser Lys Ile Ile Trp Ala Lys Gln
            100                 105                 110

Ile Ala Arg Val Asp Leu Arg Asn Gln Met Gly Pro His Tyr Ser Asn
        115                 120                 125

Thr Asp Phe Pro Arg Leu Ser Tyr Leu Asn Arg Ala Gly Ser Asn Pro
    130                 135                 140

Phe Ala Gly Asn Lys Met Thr His Ala Glu Ala Val Ser Pro Asp
145                 150                 155                 160

Tyr Thr Lys Phe Leu Ile Ala Thr Val Glu Asn Cys Ile Gly His
                165                 170                 175

Phe Thr Ile Tyr Asn Leu Asp Thr Ile Asn Glu Lys Leu Asp Glu Lys
            180                 185                 190

Gly Asn Ser Glu Asp Val Asn Leu Glu Thr Val Lys Tyr Glu Asp Ser
        195                 200                 205

Phe Ile Ile Asp Asn Leu Tyr Gly Asp Asp Asn Ser Ile Val Asn
    210                 215                 220

Ser Ile Gln Gly Tyr Asp Leu Asp Asn Asp Gly Asn Ile Tyr Ile Ser
```

```
                225                 230                 235                 240

Ser Gln Lys Ala Pro Asp Phe Asp Gly Ser Tyr Tyr Ala His His Lys
                245                 250                 255

Gln Ile Val Lys Ile Pro Tyr Tyr Ala Arg Ser Lys Glu Ser Glu Asp
                260                 265                 270

Gln Trp Arg Ala Val Asn Leu Ser Glu Phe Gly Gly Leu Asp Ile Pro
                275                 280                 285

Gly Lys His Ser Glu Val Glu Ser Ile Gln Ile Gly Glu Asn His
                290                 295                 300

Cys Tyr Leu Thr Val Ala Tyr His Ser Lys Asn Lys Ala Gly Glu Asn
305                 310                 315                 320

Lys Thr Thr Leu Asn Glu Ile Tyr Glu Leu Ser Trp Asn
                325                 330

<210> SEQ ID NO 145
<211> LENGTH: 1002
<212> TYPE: DNA
<213> ORGANISM: Lactobacillus helveticus

<400> SEQUENCE: 145
```

| | | |
|---|---|---|
| atgaagcatt taaatgaaac aactaatgtt agaattttaa gtcaatttga tatggatact | 60 |
| ggctatcaag cagtagttca aaaaggcaat gtaggttcaa aatatgtata tggattacaa | 120 |
| cttcgcaaag tgctactac tatcttgcgt ggttaccgtg aagtaaaat taataaccct | 180 |
| attcttgaat tatctggtca agcaggtggt cacacacaga catgggaatt tgctggtgat | 240 |
| cgtaaagaca ttaatggtga agaaagagca ggtcaatggt ttataggtgt taaaccatcg | 300 |
| aaaattgaag gaagcaaaat tatttgggca agcaaattg caagagttga tcttagaaat | 360 |
| caaatgggac ctcattattc aaatactgac tttcctcgat tatcctactt gaatcgcgcc | 420 |
| ggttctaatc catttgctgg taataagatg acgcatgccg aagccgcagt atcacctgat | 480 |
| tatactaagt ttttaattgc tactgttgaa ataactgta ttggtcattt tactatatac | 540 |
| aatttagata caattaatga aaacttgat gaaagggaa atagtgaaga tgttaatctc | 600 |
| gaaactgtta aatacgaaga tagttttatc attgataatt tatatggtga tgataataat | 660 |
| tctattgtaa attcaattca agggtatgat ttggataatg atggaaatat ttatatttcc | 720 |
| agtcaaaaag cgccagattt tgatggctct tattatgcac atcataagca gattgttaag | 780 |
| attccatatt atgctcggtc taaagaaagc gaagaccaat ggagagctgt aaatttaagc | 840 |
| gaattcggtg gcttggatat tccaggtaaa catagtgaag ttgaaagcat ccaaattatt | 900 |
| ggtgagaatc attgttactt aactgttgca tatcattcta aaaataaagc gggtgaaaat | 960 |
| aaaactactt tgaatgagat ttatgaatta tcttggaatt ag | 1002 |

```
<210> SEQ ID NO 146
<211> LENGTH: 74
<212> TYPE: PRT
<213> ORGANISM: Enterococcus hirae

<400> SEQUENCE: 146

Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
                20                  25                  30

Tyr Tyr Gly Asn Gly Leu Tyr Cys Asn Lys Glu Lys Cys Trp Val Asp
                35                  40                  45
```

Trp Asn Gln Ala Lys Gly Glu Ile Gly Lys Ile Ile Val Asn Gly Trp
            50                  55                  60

Val Asn His Gly Pro Trp Ala Pro Arg Arg
 65                  70

<210> SEQ ID NO 147
<211> LENGTH: 225
<212> TYPE: DNA
<213> ORGANISM: Enterococcus hirae

<400> SEQUENCE: 147
atgaaaaaga aagtattaaa acattgtgtt attctaggaa tattaggaac ttgtctagct    60
ggcatcggta caggaataaa agttgatgca gctacttact atggaaatgg tctttattgt   120
aacaaagaaa aatgttgggt agattggaat caagctaaag gagaaattgg aaaaattatt   180
gttaatggtt gggttaatca tggtccatgg gcacctagaa ggtag                   225

<210> SEQ ID NO 148
<211> LENGTH: 75
<212> TYPE: PRT
<213> ORGANISM: Lactobacillus johnsonii

<400> SEQUENCE: 148

Met Lys Gln Phe Asn Tyr Leu Ser His Lys Asp Leu Ala Val Val Val
 1               5                  10                  15

Gly Gly Arg Asn Asn Trp Gln Thr Asn Val Gly Gly Ala Val Gly Ser
            20                  25                  30

Ala Met Ile Gly Ala Thr Val Gly Gly Thr Ile Cys Gly Pro Ala Cys
        35                  40                  45

Ala Val Ala Gly Ala His Tyr Leu Pro Ile Leu Trp Thr Ala Val Thr
    50                  55                  60

Ala Ala Thr Gly Gly Phe Gly Lys Ile Arg Lys
 65                  70                  75

<210> SEQ ID NO 149
<211> LENGTH: 228
<212> TYPE: DNA
<213> ORGANISM: Lactobacillus johnsonii

<400> SEQUENCE: 149
atgaaacaat ttaattattt atcacataaa gatttagcag tcgttgttgg tggaagaaat    60
aattggcaaa caaatgtggg aggagcagtg ggatcagcta tgattggggc tacagttggt   120
ggtacaattt gtggacctgc atgtgctgta gctggtgccc attatcttcc tattttatgg   180
acagcggtta cagctgcaac aggtggtttt ggcaagataa gaaagtag                228

<210> SEQ ID NO 150
<211> LENGTH: 62
<212> TYPE: PRT
<213> ORGANISM: Lactobacillus johnsonii

<400> SEQUENCE: 150

Met Lys Leu Asn Asp Lys Glu Leu Ser Lys Ile Val Gly Gly Asn Arg
 1               5                  10                  15

Trp Gly Asp Thr Val Leu Ser Ala Ala Ser Gly Ala Thr Gly Ile
            20                  25                  30

Lys Ala Cys Lys Ser Phe Gly Pro Trp Gly Met Ala Ile Cys Gly Val
        35                  40                  45

Gly Gly Ala Ala Ile Gly Gly Tyr Phe Gly Tyr Thr His Asn

<210> SEQ ID NO 151
<211> LENGTH: 189
<212> TYPE: DNA
<213> ORGANISM: Lactobacillus johnsonii

<400> SEQUENCE: 151
atgaaattaa atgacaaaga attatcaaag attgttggtg gaaatcgatg gggagatact      60
gttttatcag ctgctagtgg cgcaggaact ggtattaaag catgtaaaag ttttggccca     120
tggggaatgg caatttgtgg tgtaggaggt gcagcaatag gaggttattt tggctatact     180
cataattaa                                                            189

<210> SEQ ID NO 152
<211> LENGTH: 59
<212> TYPE: PRT
<213> ORGANISM: Lactococcus lactis subsp. lactis

<400> SEQUENCE: 152

Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala Cys Ser Thr
            20                  25                  30

Asn Thr Phe Ser Leu Ser Asp Tyr Trp Gly Asn Asn Gly Ala Trp Cys
        35                  40                  45

Thr Leu Thr His Glu Cys Met Ala Trp Cys Lys
    50                  55

<210> SEQ ID NO 153
<211> LENGTH: 180
<212> TYPE: DNA
<213> ORGANISM: Lactococcus lactis subsp. lactis

<400> SEQUENCE: 153
atgaacaaaa atgaaattga aacacaacca gttacatggt tggaagaagt atctgatcaa      60
aattttgatg aagatgtatt tggtgcgtgt agtactaaca cattctcgct cagtgattac     120
tggggaaata acggggcttg gtgtacactc actcatgaat gtatggcttg gtgtaaataa     180

<210> SEQ ID NO 154
<211> LENGTH: 65
<212> TYPE: PRT
<213> ORGANISM: Lactococcus lactis subsp. lactis

<400> SEQUENCE: 154

Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly Thr Thr Pro Ala Thr Pro Ala Ile Ser Ile Leu Ser
        35                  40                  45

Ala Tyr Ile Ser Thr Asn Thr Cys Pro Thr Lys Cys Thr Arg Ala
    50                  55                  60

Cys
65

<210> SEQ ID NO 155
<211> LENGTH: 198
<212> TYPE: DNA

<213> ORGANISM: Lactococcus lactis subsp. lactis

<400> SEQUENCE: 155

```
atgaaagaaa aaaatatgaa aaagaatgac actattgaat tacaattggg aaaataccct     60
gaagatgata tgattgaatt agctgaaggg gatgagtctc atggaggaac acaccagca    120
actcctgcaa tctctattct cagtgcatat attagtacca atacttgtcc aacaacaaaa   180
tgtacacgtg cttgttaa                                                 198
```

<210> SEQ ID NO 156
<211> LENGTH: 51
<212> TYPE: PRT
<213> ORGANISM: Lactococcus lactis subsp. lactis

<400> SEQUENCE: 156

```
Met Lys Glu Gln Asn Ser Phe Asn Leu Leu Gln Glu Val Thr Glu Ser
1               5                  10                  15
Glu Leu Asp Leu Ile Leu Gly Ala Lys Gly Gly Ser Gly Val Ile His
            20                  25                  30
Thr Ile Ser His Glu Cys Asn Met Asn Ser Trp Gln Phe Val Phe Thr
        35                  40                  45
Cys Cys Ser
    50
```

<210> SEQ ID NO 157
<211> LENGTH: 156
<212> TYPE: DNA
<213> ORGANISM: Lactococcus lactis subsp. lactis

<400> SEQUENCE: 157

```
atgaaagaac aaaactcttt taatcttctt caagaagtga cagaaagtga attggacctt     60
attttaggtg caaaaggcgg cagtggagtt attcatacaa tttctcatga atgtaatatg    120
aatagctggc aatttgtatt tacttgctgc tcttaa                              156
```

<210> SEQ ID NO 158
<211> LENGTH: 53
<212> TYPE: PRT
<213> ORGANISM: Lactococcus lactis

<400> SEQUENCE: 158

```
Met Ala Gly Phe Leu Lys Val Val Gln Leu Leu Ala Lys Tyr Gly Ser
1               5                  10                  15
Lys Ala Val Gln Trp Ala Trp Ala Asn Lys Gly Lys Ile Leu Asp Trp
            20                  25                  30
Leu Asn Ala Gly Gln Ala Ile Asp Trp Val Val Ser Lys Ile Lys Gln
        35                  40                  45
Ile Leu Gly Ile Lys
    50
```

<210> SEQ ID NO 159
<211> LENGTH: 162
<212> TYPE: DNA
<213> ORGANISM: Lactococcus lactis

<400> SEQUENCE: 159

```
atggcagggt tttaaaagt agttcaatta ctagctaaat atggttctaa agctgtacaa      60
tgggcttggg caaacaaggg taagatttta gattggctta atgcaggtca ggctattgat    120
tgggtagttt cgaaaattaa gcaaatttta ggtattaagt aa                       162
```

<210> SEQ ID NO 160
<211> LENGTH: 53
<212> TYPE: PRT
<213> ORGANISM: Lactococcus lactis

<400> SEQUENCE: 160

Met Ala Gly Phe Leu Lys Val Val Gln Ile Leu Ala Lys Tyr Gly Ser
1               5                   10                  15

Lys Ala Val Gln Trp Ala Trp Ala Asn Lys Gly Lys Ile Leu Asp Trp
            20                  25                  30

Ile Asn Ala Gly Gln Ala Ile Asp Trp Val Val Glu Lys Ile Lys Gln
        35                  40                  45

Ile Leu Gly Ile Lys
    50

<210> SEQ ID NO 161
<211> LENGTH: 162
<212> TYPE: DNA
<213> ORGANISM: Lactococcus lactis

<400> SEQUENCE: 161
atggcagggt tttaaaagt agtccaaatt ttggctaagt atggttctaa agccgtacaa        60
tgggcatggg caaataaagg aaaaatctta gattggatta atgcaggtca agctattgac       120
tgggtagttg aaaagattaa gcaaattttg ggtattaaat aa                         162

<210> SEQ ID NO 162
<211> LENGTH: 65
<212> TYPE: PRT
<213> ORGANISM: Lactobacillus amylovorus

<400> SEQUENCE: 162

Met Lys Gln Leu Asn Ser Glu Gln Leu Gln Asn Ile Ile Gly Gly Asn
1               5                   10                  15

Arg Trp Thr Asn Ala Tyr Ser Ala Ala Leu Gly Cys Ala Val Pro Gly
            20                  25                  30

Val Lys Tyr Gly Lys Lys Leu Gly Gly Val Trp Gly Ala Val Ile Gly
        35                  40                  45

Gly Val Gly Gly Ala Ala Val Cys Gly Leu Ala Gly Tyr Val Arg Lys
    50                  55                  60

Gly
65

<210> SEQ ID NO 163
<211> LENGTH: 198
<212> TYPE: DNA
<213> ORGANISM: Lactobacillus amylovorus

<400> SEQUENCE: 163
atgaaacaat tgaattcaga acaattacaa atattatcg gtggaaatag atggactaat        60
gcatacagcg cagctttggg atgcgctgtc cctggagtta aatatggaaa aaaacttggt       120
ggcgtatggg gtgctgtaat tggtggcgta ggcggtgcag cagtctgtgg cttggcgggt       180
tatgttcgta aaggctaa                                                    198

<210> SEQ ID NO 164
<211> LENGTH: 68
<212> TYPE: PRT
<213> ORGANISM: Lactobacillus sakei L45

<400> SEQUENCE: 164

Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp Ser
            20                  25                  30

Thr Pro Val Leu Ala Ser Val Ala Val Ser Met Glu Leu Leu Pro Thr
        35                  40                  45

Ala Ser Val Leu Tyr Ser Asp Val Ala Gly Cys Phe Lys Tyr Ser Ala
    50                  55                  60

Lys His His Cys
65

<210> SEQ ID NO 165
<211> LENGTH: 207
<212> TYPE: DNA
<213> ORGANISM: Lactobacillus sakei L45

<400> SEQUENCE: 165
atgaaaacag aaaaaaaggt tttagatgaa ctgagcttac acgcttctgc aaaaatggga      60
gcacgtgatg ttgaatccag catgaatgca gactcaacac cagttttagc atcagtcgct     120
gtatccatgg aattattgcc aactgcgtct gttctttatt cggatgttgc aggttgcttc     180
aaatattctg caaacatca ttgttag                                          207

<210> SEQ ID NO 166
<211> LENGTH: 91
<212> TYPE: PRT
<213> ORGANISM: Lactococcus lactis subsp. lactis

<400> SEQUENCE: 166

Met Lys Thr Lys Ser Leu Val Leu Ala Leu Ser Ala Val Thr Leu Phe
1               5                   10                  15

Ser Ala Gly Gly Ile Val Ala Gln Ala Glu Gly Thr Trp Gln His Gly
            20                  25                  30

Tyr Gly Val Ser Ser Ala Tyr Ser Asn Tyr His His Gly Ser Lys Thr
        35                  40                  45

His Ser Ala Thr Val Val Asn Asn Asn Thr Gly Arg Gln Gly Lys Asp
    50                  55                  60

Thr Gln Arg Ala Gly Val Trp Ala Lys Ala Thr Val Gly Arg Asn Leu
65                  70                  75                  80

Thr Glu Lys Ala Ser Phe Tyr Tyr Asn Phe Trp
            85                  90

<210> SEQ ID NO 167
<211> LENGTH: 276
<212> TYPE: DNA
<213> ORGANISM: Lactococcus lactis subsp. lactis

<400> SEQUENCE: 167
atgaaaacca gtctctctcgt attggcatta tctgcggtta cgttattctc tgccggagga      60
attgtagctc aagctgaagg aacatggcaa catggatatg gtgttagttc ggcatattca     120
aattatcatc atggtagcaa aactcattca gccacagttg taaataataa tactggccga     180
caaggtaagg atacacaacg tgccggtgtt tgggcaaaag ctactgttgg acgtaactta     240
actgaaaaag cttcatttta ttataacttt tggtaa                                276

```
<210> SEQ ID NO 168
<211> LENGTH: 75
<212> TYPE: PRT
<213> ORGANISM: Lactococcus lactis subsp. cremoris

<400> SEQUENCE: 168

Met Lys Asn Gln Leu Asn Phe Asn Ile Val Ser Asp Glu Glu Leu Ser
1               5                   10                  15

Glu Ala Asn Gly Gly Lys Leu Thr Phe Ile Gln Ser Thr Ala Ala Gly
            20                  25                  30

Asp Leu Tyr Tyr Asn Thr Asn Thr His Lys Tyr Val Tyr Gln Gln Thr
        35                  40                  45

Gln Asn Ala Phe Gly Ala Ala Ala Asn Thr Ile Val Asn Gly Trp Met
    50                  55                  60

Gly Gly Ala Ala Gly Gly Phe Gly Leu His His
65                  70                  75

<210> SEQ ID NO 169
<211> LENGTH: 228
<212> TYPE: DNA
<213> ORGANISM: Lactococcus lactis subsp. cremoris

<400> SEQUENCE: 169
atgaaaaatc aattaaattt taatattgtt tcagatgaag aactttcaga agctaacgga    60
ggaaaattaa catttattca atcgacagcg gctggagatt tatattacaa tactaataca   120
cacaaatatg tttaccaaca aactcaaaac gcttttgggg ctgctgctaa taccattgtt   180
aatggatgga tgggtggcgc tgctggaggt ttcgggttgc accattga               228

<210> SEQ ID NO 170
<211> LENGTH: 68
<212> TYPE: PRT
<213> ORGANISM: Lactococcus lactis subsp. cremoris

<400> SEQUENCE: 170

Met Lys Asn Gln Leu Asn Phe Asn Ile Val Ser Asp Glu Glu Leu Ala
1               5                   10                  15

Glu Val Asn Gly Gly Ser Leu Gln Tyr Val Met Ser Ala Gly Pro Tyr
            20                  25                  30

Thr Trp Tyr Lys Asp Thr Arg Thr Gly Lys Thr Ile Cys Lys Gln Thr
        35                  40                  45

Ile Asp Thr Ala Ser Tyr Thr Phe Gly Val Met Ala Glu Gly Trp Gly
    50                  55                  60

Lys Thr Phe His
65

<210> SEQ ID NO 171
<211> LENGTH: 207
<212> TYPE: DNA
<213> ORGANISM: Lactococcus lactis subsp. cremoris

<400> SEQUENCE: 171
atgaaaaatc aattaaattt taatattgtt tctgatgaag aacttgcaga agttaatgga    60
ggaagcttgc agtatgttat gagtgctgga ccatatactt ggtataaaga tactagaaca   120
ggaaaaacaa tatgtaaaca gacaattgac acagcaagtt atacatttgg tgtaatggca   180
gaaggatggg gaaaaacatt ccactaa                                       207

<210> SEQ ID NO 172
```

<211> LENGTH: 63
<212> TYPE: PRT
<213> ORGANISM: Lactococcus sp. QU 12

<400> SEQUENCE: 172

Met Lys Leu Ile Asp His Leu Gly Ala Pro Arg Trp Ala Val Asp Thr
1               5                   10                  15

Ile Leu Gly Ala Ile Ala Val Gly Asn Leu Ala Ser Trp Val Leu Ala
            20                  25                  30

Leu Val Pro Gly Pro Gly Trp Ala Val Lys Ala Gly Leu Ala Thr Ala
        35                  40                  45

Ala Ala Ile Val Lys His Gln Gly Lys Ala Ala Ala Ala Trp
    50                  55                  60

<210> SEQ ID NO 173
<211> LENGTH: 192
<212> TYPE: DNA
<213> ORGANISM: Lactococcus sp. QU 12

<400> SEQUENCE: 173
atgaaattaa ttgatcattt aggtgctcca agatgggccg ttgatactat tttaggtgca      60
atcgcagttg gaacttagc aagttgggtt ctagcgcttg tccctggtcc agggtgggca     120
gtaaaagctg gtttagcaac tgctgctgcc atcgttaaac atcaaggtaa agctgccgct    180
gctgcttggt aa                                                        192

<210> SEQ ID NO 174
<211> LENGTH: 50
<212> TYPE: PRT
<213> ORGANISM: Brevibacillus sp. GI-9

<400> SEQUENCE: 174

Met Ala Cys Gln Cys Pro Asp Ala Ile Ser Gly Trp Thr His Thr Asp
1               5                   10                  15

Tyr Gln Cys His Gly Leu Glu Asn Lys Met Tyr Arg His Val Tyr Ala
            20                  25                  30

Ile Cys Met Asn Gly Thr Gln Val Tyr Cys Arg Thr Glu Trp Gly Ser
        35                  40                  45

Ser Cys
    50

<210> SEQ ID NO 175
<211> LENGTH: 153
<212> TYPE: DNA
<213> ORGANISM: Brevibacillus sp. GI-9

<400> SEQUENCE: 175
atggcttgcc aatgtccaga tgcgatctca ggttggacgc atacagatta ccagtgtcac      60
ggtttggaga taaaatgta tagacatgtt tatgcaattt gcatgaacgg tactcaagta     120
tattgcagaa cagagtgggg tagcagctgc tag                                  153

<210> SEQ ID NO 176
<211> LENGTH: 57
<212> TYPE: PRT
<213> ORGANISM: Leuconostoc pseudomesenteroides

<400> SEQUENCE: 176

Met Asn Lys Glu Tyr Asn Ser Ile Ser Asn Phe Lys Lys Ile Thr Asn
1               5                   10                  15

```
Lys Asp Leu Gln Asn Ile Asn Gly Gly Phe Ile Gly Arg Ala Ile Gly
            20                  25                  30

Asp Phe Val Tyr Phe Gly Ala Lys Gly Leu Arg Glu Ser Gly Lys Leu
        35                  40                  45

Leu Asn Tyr Tyr Tyr Lys His Lys His
    50                  55

<210> SEQ ID NO 177
<211> LENGTH: 174
<212> TYPE: DNA
<213> ORGANISM: Leuconostoc pseudomesenteroides

<400> SEQUENCE: 177
atgaataaag aatataatag cattagcaat tttaaaaaaa ttactaataa agacttgcaa      60
aacataaatg gtggatttat tggtagggca ataggtgact ttgtgtactt tggagcgaag     120
ggactaagag aatctggtaa actacttaat tattactata agcataagca ttga           174

<210> SEQ ID NO 178
<211> LENGTH: 53
<212> TYPE: PRT
<213> ORGANISM: Leuconostoc pseudomesenteroides

<400> SEQUENCE: 178

Met Lys Asn Gln Leu Met Ser Phe Glu Val Ile Ser Glu Lys Glu Leu
1               5                  10                  15

Ser Thr Val Gln Gly Gly Lys Gly Leu Gly Lys Leu Ile Gly Ile Asp
            20                  25                  30

Trp Leu Leu Gly Gln Ala Lys Asp Ala Val Lys Gln Tyr Lys Lys Asp
        35                  40                  45

Tyr Lys Arg Trp His
    50

<210> SEQ ID NO 179
<211> LENGTH: 162
<212> TYPE: DNA
<213> ORGANISM: Leuconostoc pseudomesenteroides

<400> SEQUENCE: 179
atgaaaaatc agttaatgtc tttcgaagtg atatcagaaa aagaattgtc cacggtacaa      60
ggtggcaaag gcttaggtaa actcatagga attgattggc ttttgggtca agctaaggac     120
gctgttaaac agtacaagaa ggattacaaa cgttggcact aa                        162

<210> SEQ ID NO 180
<211> LENGTH: 61
<212> TYPE: PRT
<213> ORGANISM: Leuconostoc gelidum

<400> SEQUENCE: 180

Met Met Asn Met Lys Pro Thr Glu Ser Tyr Glu Gln Leu Asp Asn Ser
1               5                  10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45

Gly Val His Arg Leu Ala Asn Gly Gly Asn Gly Phe Trp
    50                  55                  60

<210> SEQ ID NO 181
```

```
<211> LENGTH: 186
<212> TYPE: DNA
<213> ORGANISM: Leuconostoc gelidum

<400> SEQUENCE: 181
atgatgaaca tgaaacctac ggaaagctat gagcaattgg ataatagtgc tctcgaacaa    60
gtcgtaggag gtaagtatta tggtaacgga gttcattgca caaaaagtgg ttgttctgta   120
aactggggag aagccttttc agctggagta catcgtttag caaatggtgg aaatggtttc   180
tggtaa                                                              186

<210> SEQ ID NO 182
<211> LENGTH: 61
<212> TYPE: PRT
<213> ORGANISM: Leuconostoc carnosum

<400> SEQUENCE: 182

Met Asn Asn Met Lys Ser Ala Asp Asn Tyr Gln Gln Leu Asp Asn Asn
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45

Gly Val His Arg Leu Ala Asn Gly Gly Asn Gly Phe Trp
    50                  55                  60

<210> SEQ ID NO 183
<211> LENGTH: 186
<212> TYPE: DNA
<213> ORGANISM: Leuconostoc carnosum

<400> SEQUENCE: 183
atgaataaca tgaaatctgc ggataattat cagcaattgg ataataatgc tctcgaacaa    60
gtcgtaggag gtaagtatta tggtaacgga gttcattgca caaaaagtgg ttgttctgta   120
aactggggag aagccttttc agctggagta catcgtttag caaatggtgg aaatggtttc   180
tggtaa                                                              186

<210> SEQ ID NO 184
<211> LENGTH: 63
<212> TYPE: PRT
<213> ORGANISM: Leuconostoc mesenteroides

<400> SEQUENCE: 184

Met Phe Leu Val Asn Gln Leu Gly Ile Ser Lys Ser Leu Ala Asn Thr
1               5                   10                  15

Ile Leu Gly Ala Ile Ala Val Gly Asn Leu Ala Ser Trp Leu Leu Ala
            20                  25                  30

Leu Val Pro Gly Pro Gly Trp Ala Thr Lys Ala Ala Leu Ala Thr Ala
        35                  40                  45

Glu Thr Ile Val Lys His Glu Gly Lys Ala Ala Ala Ile Ala Trp
    50                  55                  60

<210> SEQ ID NO 185
<211> LENGTH: 192
<212> TYPE: DNA
<213> ORGANISM: Leuconostoc mesenteroides

<400> SEQUENCE: 185
atgttcttgg taaatcagtt agggatttca aaatcgttag ctaatactat tcttggtgca    60
```

```
attgctgttg gtaatttggc cagttggtta ttagctttgg ttcctggtcc gggttgggca      120
acaaaagcag cacttgcgac agctgaaaca attgtgaagc atgaaggaaa agcagctgct      180
attgcgtggt aa                                                          192
```

```
<210> SEQ ID NO 186
<211> LENGTH: 74
<212> TYPE: PRT
<213> ORGANISM: Bacillus licheniformis

<400> SEQUENCE: 186
```

Met Ser Lys Lys Glu Met Ile Leu Ser Trp Lys Asn Pro Met Tyr Arg
1               5                   10                  15

Thr Glu Ser Ser Tyr His Pro Ala Gly Asn Ile Leu Lys Glu Leu Gln
            20                  25                  30

Glu Glu Glu Gln His Ser Ile Ala Gly Gly Thr Ile Thr Leu Ser Thr
        35                  40                  45

Cys Ala Ile Leu Ser Lys Pro Leu Gly Asn Asn Gly Tyr Leu Cys Thr
    50                  55                  60

Val Thr Lys Glu Cys Met Pro Ser Cys Asn
65                  70

```
<210> SEQ ID NO 187
<211> LENGTH: 225
<212> TYPE: DNA
<213> ORGANISM: Bacillus licheniformis

<400> SEQUENCE: 187
atgtcaaaaa aggaaatgat tctttcatgg aaaaatccta tgtatcgcac tgaatcttct       60
tatcatccag cagggaacat ccttaaagaa ctccaggaag aggaacagca cagcatcgcc      120
ggaggcacaa tcacgctcag cacttgtgcc atcttgagca agccgttagg aaataacgga      180
tacctgtgta cagtgacaaa agaatgcatg ccaagctgta actaa                      225
```

```
<210> SEQ ID NO 188
<211> LENGTH: 266
<212> TYPE: PRT
<213> ORGANISM: Brevibacterium linens

<400> SEQUENCE: 188
```

Met Asn Asn Leu Tyr Arg Glu Leu Ala Pro Ile Pro Gly Pro Ala Trp
1               5                   10                  15

Ala Glu Ile Glu Glu Ala Arg Arg Thr Phe Lys Arg Asn Ile Ala
            20                  25                  30

Gly Arg Arg Ile Val Asp Val Ala Gly Pro Thr Gly Phe Glu Thr Ser
        35                  40                  45

Ala Val Thr Thr Gly His Ile Arg Asp Val Gln Ser Glu Thr Ser Gly
    50                  55                  60

Leu Gln Val Lys Gln Arg Ile Val Gln Glu Tyr Ile Glu Leu Arg Thr
65                  70                  75                  80

Pro Phe Thr Val Thr Arg Gln Ala Ile Asp Asp Val Ala Arg Gly Ser
                85                  90                  95

Gly Asp Ser Asp Trp Gln Pro Val Lys Asp Ala Ala Thr Thr Ile Ala
            100                 105                 110

Met Ala Glu Asp Arg Ala Ile Leu His Gly Leu Asp Ala Ala Gly Ile
        115                 120                 125

Gly Gly Ile Val Pro Gly Ser Ser Asn Ala Ala Val Ala Ile Pro Asp

Ala Val Glu Asp Phe Ala Asp Ala Val Ala Gln Ala Leu Ser Val Leu
145                 150                 155                 160

Arg Thr Val Gly Val Asp Gly Pro Tyr Ser Leu Leu Leu Ser Ser Ala
                165                 170                 175

Glu Tyr Thr Lys Val Ser Glu Ser Thr Asp His Gly Tyr Pro Ile Arg
            180                 185                 190

Glu His Leu Ser Arg Gln Leu Gly Ala Gly Glu Ile Ile Trp Ala Pro
        195                 200                 205

Ala Leu Glu Gly Ala Leu Leu Val Ser Thr Arg Gly Gly Asp Tyr Glu
    210                 215                 220

Leu His Leu Gly Gln Asp Leu Ser Ile Gly Tyr Tyr Ser His Asp Ser
225                 230                 235                 240

Glu Thr Val Glu Leu Tyr Leu Gln Glu Thr Phe Gly Phe Leu Ala Leu
                245                 250                 255

Thr Asp Glu Ser Ser Val Pro Leu Ser Leu
            260                 265

<210> SEQ ID NO 189
<211> LENGTH: 801
<212> TYPE: DNA
<213> ORGANISM: Brevibacterium linens

<400> SEQUENCE: 189
gtgaataacc tctatcgcga gcttgccccc atccccggcc cggcctgggc ggagatcgag     60
gaggaggctc gacggacatt caaacgcaat atcgccggcc gccggatcgt cgatgtcgca    120
gggcccacgg gcttcgagac ctccgcggtg accactggcc acatccgaga cgtccagtcg    180
gagacgagcg gactgcaggt taagcagcgc atcgtgcagg aatacatcga gctgcggacc    240
ccattcaccg tgactcggca ggccatcgat gacgtggccc gcgggtccgg tgactcggac    300
tggcagcccc tcaaggatgc ggccacgacg atcgcgatgg ctgaagatcg gccattctc    360 cacgggctcg atgcggccgg gatcggcgga atcgttcccg gcagctcgaa tgccgcagtg    420
gccatccccg acgccgtcga ggacttcgcg gacgccgtcg cccaggcgct gagtgtgctg    480
cgcacggtgg gagtcgacgg gccctacagc ctgttgctct cctccgcgga gtacaccaag    540
gtctccgagt ccaccgacca cggctacccg atccgcgagc acctctcccg gcagctcggc    600
gccggagaga tcatctgggc gcccgcgctc gaagggcgc tgctcgtctc cacgcgcggg     660
ggtgactacg agctccacct cggccaggac ctgtcgatcg gttactacag ccacgacagc    720
gagaccgtcg aactctatct gcaggagacc ttcggattcc tcgcgctgac cgacgaatcc    780
agtgtgcctt tgagcctctg a                                              801

<210> SEQ ID NO 190
<211> LENGTH: 71
<212> TYPE: PRT
<213> ORGANISM: Listeria innocua

<400> SEQUENCE: 190

Met Lys Lys Ala Ala Leu Lys Phe Ile Ile Val Ile Ala Ile Leu Gly
1               5                   10                  15

Phe Ser Phe Ser Phe Phe Ser Ile Gln Ser Glu Ala Lys Ser Tyr Gly
            20                  25                  30

Asn Gly Val Gln Cys Asn Lys Lys Cys Trp Val Asp Trp Gly Ser
        35                  40                  45

```
Ala Ile Ser Thr Ile Gly Asn Asn Ser Ala Ala Asn Trp Ala Thr Gly
    50                  55                  60

Gly Ala Ala Gly Trp Lys Ser
65                  70

<210> SEQ ID NO 191
<211> LENGTH: 216
<212> TYPE: DNA
<213> ORGANISM: Listeria innocua

<400> SEQUENCE: 191
ttgaagaagg cagcgttaaa atttattatt gttattgcta ttctaggttt cagttttct      60 ttctttagca tacaatctga agctaaatct tatggaaatg gagttcagtg taataagaaa     120
aaatgttggg tagattgggg tagtgctata agtactattg gaaataattc tgcagcgaat     180
tgggctacag gtggagcagc tggttggaaa agctga                               216

<210> SEQ ID NO 192
<211> LENGTH: 68
<212> TYPE: PRT
<213> ORGANISM: Bacillus sp.

<400> SEQUENCE: 192

Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
        35                  40                  45

Cys Thr Phe Thr Leu Pro Gly Gly Gly Val Cys Thr Leu Thr Ser
    50                  55                  60

Glu Cys Ile Cys
65

<210> SEQ ID NO 193
<211> LENGTH: 207
<212> TYPE: DNA
<213> ORGANISM: Bacillus sp.

<400> SEQUENCE: 193
atgagtcaag aagctatcat tcgttcatgg aaagatcctt tttcccgtga aaattctaca      60
caaaatccag ctggtaaccc attcagtgag ctgaaagaag cacaaatgga taagttagta     120
ggtgcgggag acatggaagc agcatgtact tttacattgc ctggtggcgg cggtgtttgt     180
actctaactt ctgaatgtat ttgttaa                                         207

<210> SEQ ID NO 194
<211> LENGTH: 61
<212> TYPE: PRT
<213> ORGANISM: Leuconostoc mesenteroides

<400> SEQUENCE: 194

Met Thr Asn Met Lys Ser Val Glu Ala Tyr Gln Gln Leu Asp Asn Gln
1               5                   10                  15

Asn Leu Lys Lys Val Val Gly Gly Lys Tyr Tyr Gly Asn Gly Val His
            20                  25                  30

Cys Thr Lys Ser Gly Cys Ser Val Asn Trp Gly Glu Ala Ala Ser Ala
        35                  40                  45

Gly Ile His Arg Leu Ala Asn Gly Gly Asn Gly Phe Trp
```

50 55 60

<210> SEQ ID NO 195
<211> LENGTH: 186
<212> TYPE: DNA
<213> ORGANISM: Leuconostoc mesenteroides

<400> SEQUENCE: 195

```
atgacgaata tgaagtctgt ggaagcatat cagcaattag ataaccagaa tctcaagaaa 60
gttgttggtg gaaagtatta tgggaatggt gttcactgta caaaaagtgg atgctctgtt 120
aactggggag aagctgcctc agctggcata catcgtttgg ccaatggtgg aaatggattt 180
tggtaa 186
```

<210> SEQ ID NO 196
<211> LENGTH: 68
<212> TYPE: PRT
<213> ORGANISM: Clavibacter michiganensis subsp. michiganensis

<400> SEQUENCE: 196

```
Met Asn Asp Ile Leu Glu Thr Glu Thr Pro Val Met Val Ser Pro Arg
1 5 10 15

Trp Asp Met Leu Leu Asp Ala Gly Glu Asp Thr Ser Pro Ser Val Gln
20 25 30

Thr Gln Ile Asp Ala Glu Phe Arg Arg Val Val Ser Pro Tyr Met Ser
35 40 45

Ser Ser Gly Trp Leu Cys Thr Leu Thr Ile Glu Cys Gly Thr Ile Ile
50 55 60

Cys Ala Cys Arg
65
```

<210> SEQ ID NO 197
<211> LENGTH: 207
<212> TYPE: DNA
<213> ORGANISM: Clavibacter michiganensis subsp. michiganensis

<400> SEQUENCE: 197

```
atgaacgaca tcctcgagac ggagaccccc gtcatggtca gcccccggtg ggacatgctg 60
ctcgacgcgg gcgaggacac cagcccgtcc gtccagaccc agatcgacgc ggagttccgt 120
cgcgtcgtga gcccgtacat gtccagcagc ggctggctct gcacgctcac catcgaatgt 180
ggcaccatca tctgcgcgtg tcgctga 207

<210> SEQ ID NO 198
<211> LENGTH: 69
<212> TYPE: PRT
<213> ORGANISM: Escherichia coli

<400> SEQUENCE: 198

Met Glu Leu Lys Ala Ser Glu Phe Gly Val Val Leu Ser Val Asp Ala
1 5 10 15

Leu Lys Leu Ser Arg Gln Ser Pro Leu Gly Val Gly Ile Gly Gly Gly
20 25 30

Gly Gly Gly Gly Gly Gly Gly Ser Cys Gly Gly Gln Gly Gly Gly Cys
35 40 45

Gly Gly Cys Ser Asn Gly Cys Ser Gly Gly Asn Gly Gly Ser Gly Gly
50 55 60

Ser Gly Ser His Ile
65
```

<210> SEQ ID NO 199
<211> LENGTH: 207
<212> TYPE: DNA
<213> ORGANISM: Escherichia coli

<400> SEQUENCE: 199

```
atggaattaa aagcgagtga atttggtgta gttttgtccg ttgatgctct taaattatca      60
cgccagtctc cattaggtgt tggcattggt ggtggtggcg gcggcggcgg cggcggtagc     120
tgcggtggtc aaggtggcgg ttgtggtggt tgcagcaacg gttgtagtgg tggaaacggt     180
ggcagcggcg gaagtggttc acatatc                                         207
```

<210> SEQ ID NO 200
<211> LENGTH: 7
<212> TYPE: PRT
<213> ORGANISM: Escherichia coli

<400> SEQUENCE: 200

Met Arg Thr Gly Asn Ala Asn
1               5

<210> SEQ ID NO 201
<211> LENGTH: 24
<212> TYPE: DNA
<213> ORGANISM: Escherichia coli

<400> SEQUENCE: 201

```
atgcgtactg gtaatgcaaa ctaa                                             24
```

<210> SEQ ID NO 202
<211> LENGTH: 99
<212> TYPE: PRT
<213> ORGANISM: Klebsiella pneumoniae

<400> SEQUENCE: 202

Met Arg Glu Ile Ser Gln Lys Asp Leu Asn Leu Ala Phe Gly Ala Gly
1               5                   10                  15

Glu Thr Asp Pro Asn Thr Gln Leu Leu Asn Asp Leu Gly Asn Asn Met
                20                  25                  30

Ala Trp Gly Ala Ala Leu Gly Ala Pro Gly Gly Leu Gly Ser Ala Ala
            35                  40                  45

Leu Gly Ala Ala Gly Gly Ala Leu Gln Thr Val Gly Gln Gly Leu Ile
        50                  55                  60

Asp His Gly Pro Val Asn Val Pro Ile Pro Val Leu Ile Gly Pro Ser
65                  70                  75                  80

Trp Asn Gly Ser Gly Ser Gly Tyr Asn Ser Ala Thr Ser Ser Ser Gly
                85                  90                  95

Ser Gly Ser

<210> SEQ ID NO 203
<211> LENGTH: 300
<212> TYPE: DNA
<213> ORGANISM: Klebsiella pneumoniae

<400> SEQUENCE: 203

```
atgagagaaa ttagtcaaaa ggacttaaat cttgcttttg gtgcaggaga gaccgatcca      60
aatactcaac ttctaaacga ccttggaaat aatatggcat ggggtgctgc tcttggcgct     120
cctggcggat taggatcagc agctttgggg gccgcgggag gtgcattaca aactgtaggg     180
```

```
caaggattaa ttgaccatgg tcctgtaaat gtccccatcc ctgtactcat cgggccaagc    240
tggaatggta gcggtagtgg ttataacagc gcaacatcca gttccggtag tggtagttaa    300
```

<210> SEQ ID NO 204
<211> LENGTH: 75
<212> TYPE: PRT
<213> ORGANISM: Escherichia coli

<400> SEQUENCE: 204

```
Met Arg Glu Ile Thr Glu Ser Gln Leu Arg Tyr Ile Ser Gly Ala Gly
1               5                   10                  15

Gly Ala Pro Ala Thr Ser Ala Asn Ala Ala Gly Ala Ala Ala Ile Val
            20                  25                  30

Gly Ala Leu Ala Gly Ile Pro Gly Gly Pro Leu Gly Val Val Val Gly
        35                  40                  45

Ala Val Ser Ala Gly Leu Thr Thr Ala Ile Gly Ser Thr Val Gly Ser
    50                  55                  60

Gly Ser Ala Ser Ser Ser Ala Gly Gly Gly Ser
65                  70                  75
```

<210> SEQ ID NO 205
<211> LENGTH: 228
<212> TYPE: DNA
<213> ORGANISM: Escherichia coli

<400> SEQUENCE: 205

```
atgcgagaaa taacagaatc acagttaaga tatatttccg ggcgggagg tgcgccagcg     60 acttcagcta atgccgcagg tgctgcagct attgttggag ctctcgccgg aatacctggt    120
ggtccacttg gggttgtagt tggagccgta tctgccggtt tgacaacagc aattggctcg    180
accgtgggaa gtggtagtgc cagttcttct gctggtggcg gtagctaa                 228
```

<210> SEQ ID NO 206
<211> LENGTH: 58
<212> TYPE: PRT
<213> ORGANISM: Escherichia coli

<400> SEQUENCE: 206

```
Met Ile Lys His Phe His Phe Asn Lys Leu Ser Ser Gly Lys Lys Asn
1               5                   10                  15

Asn Val Pro Ser Pro Ala Lys Gly Val Ile Gln Ile Lys Lys Ser Ala
            20                  25                  30

Ser Gln Leu Thr Lys Gly Gly Ala Gly His Val Pro Glu Tyr Phe Val
        35                  40                  45

Gly Ile Gly Thr Pro Ile Ser Phe Tyr Gly
    50                  55
```

<210> SEQ ID NO 207
<211> LENGTH: 177
<212> TYPE: DNA
<213> ORGANISM: Escherichia coli

<400> SEQUENCE: 207

```
atgattaagc attttcattt taataaactg tcttctggta aaaaaaataa tgttccatct     60
cctgcaaagg gggttataca aataaaaaaa tcagcatcgc aactcacaaa aggtggtgca    120
ggacatgtgc ctgagtattt tgtggggatt ggtacaccta tatctttcta tggctga      177
```

<210> SEQ ID NO 208
<211> LENGTH: 90
<212> TYPE: PRT
<213> ORGANISM: Escherichia coli

<400> SEQUENCE: 208

Met Tyr Met Arg Glu Leu Asp Arg Glu Glu Leu Asn Cys Val Gly Gly
1               5                   10                  15

Ala Gly Asp Pro Leu Ala Asp Pro Asn Ser Gln Ile Val Arg Gln Ile
            20                  25                  30

Met Ser Asn Ala Ala Trp Gly Pro Pro Leu Val Pro Glu Arg Phe Arg
        35                  40                  45

Gly Met Ala Val Gly Ala Ala Gly Gly Val Thr Gln Thr Val Leu Gln
    50                  55                  60

Gly Ala Ala Ala His Met Pro Val Asn Val Pro Ile Pro Lys Val Pro
65                  70                  75                  80

Met Gly Pro Ser Trp Asn Gly Ser Lys Gly
            85                  90

<210> SEQ ID NO 209
<211> LENGTH: 273
<212> TYPE: DNA
<213> ORGANISM: Escherichia coli

<400> SEQUENCE: 209
atgtatatga gagagttaga tagagaggaa ttaaattgcg ttggtggggc tggagatccg      60
cttgcagatc ctaattccca aattgtaaga cagataatgt ctaatgcggc atggggcccg     120
cctttggtgc cagagcggtt tagggggaatg gctgttggag ccgcaggtgg ggttacgcag    180
acagttcttc aaggagcagc agctcatatg ccggttaatg tccctatacc taaagttccg     240
atgggaccct catggaacgg aagtaaagga taa                                  273

<210> SEQ ID NO 210
<211> LENGTH: 50
<212> TYPE: PRT
<213> ORGANISM: Enterococcus mundtii

<400> SEQUENCE: 210

Met Ser Gln Val Val Gly Gly Lys Tyr Tyr Gly Asn Gly Val Ser Cys
1               5                   10                  15

Asn Lys Lys Gly Cys Ser Val Asp Trp Gly Lys Ala Ile Gly Ile Ile
            20                  25                  30

Gly Asn Asn Ser Ala Ala Asn Leu Ala Thr Gly Gly Ala Ala Gly Trp
        35                  40                  45

Lys Ser
    50

<210> SEQ ID NO 211
<211> LENGTH: 153
<212> TYPE: DNA
<213> ORGANISM: Enterococcus mundtii

<400> SEQUENCE: 211
atgtcacagg tagtaggtgg aaaatactac ggtaatggag tctcatgtaa taaaaaggg      60 tgcagtgttg attggggaaa agcgattggc attattggaa ataattctgc tgcgaattta    120
gctactggtg gagcagctgg ttggaaaagt taa                                 153

<210> SEQ ID NO 212

```
<211> LENGTH: 58
<212> TYPE: PRT
<213> ORGANISM: Enterococcus mundtii

<400> SEQUENCE: 212

Met Lys Lys Leu Thr Ser Lys Glu Met Ala Gln Val Val Gly Lys
1               5                   10                  15

Tyr Tyr Gly Asn Gly Leu Ser Cys Asn Lys Lys Gly Cys Ser Val Asp
                20                  25                  30

Trp Gly Lys Ala Ile Gly Ile Ile Gly Asn Asn Ser Ala Ala Asn Leu
            35                  40                  45

Ala Thr Gly Gly Ala Ala Gly Trp Lys Ser
        50                  55

<210> SEQ ID NO 213
<211> LENGTH: 177
<212> TYPE: DNA
<213> ORGANISM: Enterococcus mundtii

<400> SEQUENCE: 213
ttgaagaaat taacatcaaa agaaatggca caagtagtag gtgggaaata ctacggtaat      60
ggattatcat gtaataaaaa agggtgcagt gttgattggg gaaaagctat tggcattatt     120
ggaaataatt ctgctgcgaa tttagctact ggtggagcag ctggttggaa aagttaa       177

<210> SEQ ID NO 214
<211> LENGTH: 63
<212> TYPE: PRT
<213> ORGANISM: Streptococcus mutans

<400> SEQUENCE: 214

Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
                20                  25                  30

Ala Ser Asn Asp Asp Pro Asp Thr Arg Phe Lys Ser Trp Ser Leu Cys
            35                  40                  45

Thr Pro Gly Cys Ala Arg Thr Gly Ser Phe Asn Ser Tyr Cys Cys
        50                  55                  60

<210> SEQ ID NO 215
<211> LENGTH: 192
<212> TYPE: DNA
<213> ORGANISM: Streptococcus mutans

<400> SEQUENCE: 215
atgtcaaaca cacaattatt agaagtcctt ggtactgaaa cttttgatgt tcaagaagat      60
ctctttgctt ttgatacaac agatactact attgtggcaa gcaacgacga tccagatact     120
cgtttcaaaa gttggagcct ttgtacgcct ggttgtgcaa ggacaggtag tttcaatagt     180
tactgttgct ga                                                         192

<210> SEQ ID NO 216
<211> LENGTH: 53
<212> TYPE: PRT
<213> ORGANISM: Streptococcus mutans

<400> SEQUENCE: 216

Met Asn Lys Leu Asn Ser Asn Ala Val Val Ser Leu Asn Glu Val Ser
1               5                   10                  15
```

```
Asp Ser Glu Leu Asp Thr Ile Leu Gly Gly Asn Arg Trp Trp Gln Gly
            20                  25                  30

Val Val Pro Thr Val Ser Tyr Glu Cys Arg Met Asn Ser Trp Gln His
        35                  40                  45

Val Phe Thr Cys Cys
    50

<210> SEQ ID NO 217
<211> LENGTH: 162
<212> TYPE: DNA
<213> ORGANISM: Streptococcus mutans

<400> SEQUENCE: 217
atgaacaagt taaacagtaa cgcagtagtt tctttgaatg aagtttcaga ttctgaattg      60
gatactattt tgggtggtaa tcgttggtgg caaggtgttg tgccaacggt ctcatatgag     120
tgtcgcatga attcatggca acatgttttc acttgctgtt aa                       162

<210> SEQ ID NO 218
<211> LENGTH: 57
<212> TYPE: PRT
<213> ORGANISM: Lactococcus lactis subsp. lactis

<400> SEQUENCE: 218

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 219
<211> LENGTH: 174
<212> TYPE: DNA
<213> ORGANISM: Lactococcus lactis subsp. lactis

<400> SEQUENCE: 219
atgagtacaa agattttaa cttggatttg gtatctgttt cgaagaaaga ttcaggtgca      60
tcaccacgca ttacaagtat ttcgctatgt acacccggtt gtaaaacagg agctctgatg    120
ggttgtaaca tgaaaacagc aacttgtcat tgtagtattc acgtaagcaa ataa          174

<210> SEQ ID NO 220
<211> LENGTH: 57
<212> TYPE: PRT
<213> ORGANISM: Lactococcus lactis

<400> SEQUENCE: 220

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Val His Val Ser Lys
    50                  55

<210> SEQ ID NO 221
```

```
<211> LENGTH: 171
<212> TYPE: DNA
<213> ORGANISM: Lactococcus lactis

<400> SEQUENCE: 221
atgagtacaa aagatttcaa cttggatttg gtatctgttt cgaagaaaga ttcaggtgca    60
tcaccacgca ttacaagtat ttcgctatgt acaccggtt gtaaaacagg agctctgatg    120
ggttgtaaca tgaaaacagc aacttgtaat tgtagcgttc acgtaagcaa a            171

<210> SEQ ID NO 222
<211> LENGTH: 57
<212> TYPE: PRT
<213> ORGANISM: Lactococcus lactis

<400> SEQUENCE: 222

Met Ser Thr Lys Asp Phe Asn Leu Asp Leu Val Ser Val Ser Lys Thr
1               5                   10                  15

Asp Ser Gly Ala Ser Thr Arg Ile Thr Ser Ile Ser Leu Cys Thr Pro
            20                  25                  30

Gly Cys Lys Thr Gly Val Leu Met Gly Cys Asn Leu Lys Thr Ala Thr
        35                  40                  45

Cys Asn Cys Ser Val His Val Ser Lys
    50                  55

<210> SEQ ID NO 223
<211> LENGTH: 174
<212> TYPE: DNA
<213> ORGANISM: Lactococcus lactis

<400> SEQUENCE: 223
atgagtacaa aagatttcaa cttagatttg gtatctgttt caaaaacaga ttctggcgct    60
tcaacacgta ttaccagcat ttcgctttgt acaccaggtt gtaaaacagg tgttctgatg    120
ggatgtaacc tgaaaacagc aacttgtaat tgtagcgttc acgtaagcaa ataa          174

<210> SEQ ID NO 224
<211> LENGTH: 55
<212> TYPE: PRT
<213> ORGANISM: Streptococcus uberis

<400> SEQUENCE: 224

Met Asn Asn Glu Asp Phe Asn Leu Asp Leu Ile Lys Ile Ser Lys Glu
1               5                   10                  15

Asn Asn Ser Gly Ala Ser Pro Arg Ile Thr Ser Lys Ser Leu Cys Thr
            20                  25                  30

Pro Gly Cys Lys Thr Gly Ile Leu Met Thr Cys Pro Leu Lys Thr Ala
        35                  40                  45

Thr Cys Gly Cys His Phe Gly
    50                  55

<210> SEQ ID NO 225
<211> LENGTH: 168
<212> TYPE: DNA
<213> ORGANISM: Streptococcus uberis

<400> SEQUENCE: 225
atgaacaatg aagattttaa tttggatctc atcaaaatct caaaggaaaa caactcagga    60
gcttcacctc gaataactag taaatcatta tgtactcctg gatgtaagac gggtattttg    120
atgacttgtc cactaaaaac tgcaacctgt ggttgtcatt ttggataa                 168
```

<210> SEQ ID NO 226
<211> LENGTH: 57
<212> TYPE: PRT
<213> ORGANISM: Lactococcus lactis subsp. lactis

<400> SEQUENCE: 226

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Ile His Val Ser Lys
        50                  55

<210> SEQ ID NO 227
<211> LENGTH: 174
<212> TYPE: DNA
<213> ORGANISM: Lactococcus lactis subsp. lactis

<400> SEQUENCE: 227
atgagtacaa aagattttaa cttggatttg gtatctgttt cgaagaaaga ttcaggtgca     60
tcaccacgca ttacaagtat ttcgctatgt acacccggtt gtaaaacagg agctctgatg    120
ggttgtaaca tgaaaacagc aacttgtaat tgtagtattc acgtaagcaa ataa          174

<210> SEQ ID NO 228
<211> LENGTH: 57
<212> TYPE: PRT
<213> ORGANISM: Staphylococcus warneri

<400> SEQUENCE: 228

Met Glu Asn Ser Lys Val Met Lys Asp Ile Glu Val Ala Asn Leu Leu
1               5                   10                  15

Glu Glu Val Gln Glu Asp Glu Leu Asn Glu Val Leu Gly Ala Lys Lys
            20                  25                  30

Lys Ser Gly Val Ile Pro Thr Val Ser His Asp Cys His Met Asn Ser
        35                  40                  45

Phe Gln Phe Val Phe Thr Cys Cys Ser
        50                  55

<210> SEQ ID NO 229
<211> LENGTH: 174
<212> TYPE: DNA
<213> ORGANISM: Staphylococcus warneri

<400> SEQUENCE: 229
atggaaaatt ctaaagttat gaaggacatt gaagtagcaa atttattaga agaggttcaa     60
gaagatgaat tgaatgaagt cttaggagct aagaaaaagt caggagtaat cccaactgtg    120
tcacacgatt gccatatgaa ttctttccaa tttgtattta cttgttgttc ataa          174

<210> SEQ ID NO 230
<211> LENGTH: 58
<212> TYPE: PRT
<213> ORGANISM: Paenibacillus polymyxa

<400> SEQUENCE: 230

Met Ala Glu Asn Leu Phe Asp Leu Asp Ile Gln Val Asn Lys Ser Gln
1               5                   10                  15

Gly Ser Val Glu Pro Gln Val Leu Ser Ile Val Ala Cys Ser Ser Gly
                20                  25                  30

Cys Gly Ser Gly Lys Thr Ala Ala Ser Cys Val Glu Thr Cys Gly Asn
            35                  40                  45

Arg Cys Phe Thr Asn Val Gly Ser Leu Cys
        50                  55

<210> SEQ ID NO 231
<211> LENGTH: 177
<212> TYPE: DNA
<213> ORGANISM: Paenibacillus polymyxa

<400> SEQUENCE: 231
atggctgaaa acttatttga tctggacatt caagtaaaca aatctcaagg ttctgtagag     60
cctcaggttc tgagcattgt tgcatgttct agcggatgtg gtagcggtaa aacagctgcc    120
agttgtgttg aaacttgtgg caaccggtgc tttactaacg ttggttcact ctgctaa      177

<210> SEQ ID NO 232
<211> LENGTH: 62
<212> TYPE: PRT
<213> ORGANISM: Pediococcus acidilactici

<400> SEQUENCE: 232

Met Lys Lys Ile Glu Lys Leu Thr Glu Lys Glu Met Ala Asn Ile Ile
1               5                  10                  15

Gly Gly Lys Tyr Tyr Gly Asn Gly Val Thr Cys Gly Lys His Ser Cys
                20                  25                  30

Ser Val Asp Trp Gly Lys Ala Thr Thr Cys Ile Ile Asn Asn Gly Ala
            35                  40                  45

Met Ala Trp Ala Thr Gly Gly His Gln Gly Asn His Lys Cys
        50                  55                  60

<210> SEQ ID NO 233
<211> LENGTH: 189
<212> TYPE: DNA
<213> ORGANISM: Pediococcus acidilactici

<400> SEQUENCE: 233
atgaaaaaaa ttgaaaaatt aactgaaaaa gaaatggcca atatcattgg tggtaaatac     60
tacggtaatg gggttacttg tggcaaacat tcctgctctg ttgactgggg taaggctacc    120
acttgcataa tcaataatgg agctatggca tgggctactg gtggacatca aggtaatcat    180
aaatgctag                                                            189

<210> SEQ ID NO 234
<211> LENGTH: 60
<212> TYPE: PRT
<213> ORGANISM: Pediococcus pentosaceus

<400> SEQUENCE: 234

Met Thr Glu Ile Lys Val Leu Asn Asp Lys Glu Leu Lys Asn Val Val
1               5                  10                  15

Gly Gly Lys Tyr Tyr Gly Asn Gly Val His Cys Gly Lys Lys Thr Cys
                20                  25                  30

Tyr Val Asp Trp Gly Gln Ala Thr Ala Ser Ile Gly Lys Ile Ile Val
            35                  40                  45

Asn Gly Trp Thr Gln His Gly Pro Trp Ala His Arg
        50                  55                  60

<210> SEQ ID NO 235
<211> LENGTH: 183
<212> TYPE: DNA
<213> ORGANISM: Pediococcus pentosaceus

<400> SEQUENCE: 235
atgactgaaa ttaaagtact aaacgataag gaactaaaaa atgtcgtagg aggaaagtat    60
tacggtaacg gagtgcattg tggtaaaaag acttgctatg tggactgggg acaagctaca   120
gctagcattg gaaaaattat agtgaacgga tggacacaac acgggccttg gcacataga   180 taa                                                                 183

<210> SEQ ID NO 236
<211> LENGTH: 60
<212> TYPE: PRT
<213> ORGANISM: Staphylococcus epidermidis

<400> SEQUENCE: 236

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
    50                  55                  60

<210> SEQ ID NO 237
<211> LENGTH: 183
<212> TYPE: DNA
<213> ORGANISM: Staphylococcus epidermidis

<400> SEQUENCE: 237
atgaaaaata caaaaatttt atttgattta gaaattaaaa aagaaacaag tcaaaacact    60
gatgaacttg aacctcaaac tgctggacca gcgattagag cttctgtgaa acaatgtcag   120
aaaactttga agctacgcg tttatttaca gtgtcttgca aggaaaaaa cggatgtaaa    180 tag                                                                 183

<210> SEQ ID NO 238
<211> LENGTH: 62
<212> TYPE: PRT
<213> ORGANISM: Carnobacterium maltaromaticum

<400> SEQUENCE: 238

Met Lys Thr Val Lys Glu Leu Ser Val Lys Glu Met Gln Leu Thr Thr
1               5                   10                  15

Gly Gly Lys Tyr Tyr Gly Asn Gly Val Ser Cys Asn Lys Asn Gly Cys
            20                  25                  30

Thr Val Asp Trp Ser Lys Ala Ile Gly Ile Ile Gly Asn Asn Ala Ala
        35                  40                  45

Ala Asn Leu Thr Thr Gly Gly Ala Ala Gly Trp Asn Lys Gly
    50                  55                  60

<210> SEQ ID NO 239
<211> LENGTH: 189
<212> TYPE: DNA
<213> ORGANISM: Carnobacterium maltaromaticum

<400> SEQUENCE: 239

```
atgaaaactg ttaaagaact tagcgttaaa gaaatgcaac taactacagg aggtaagtat      60
tacggaaatg gcgtttcctg taataaaaat ggttgtactg tagattggag caaagctatt     120
gggattatag gaaacaatgc agcagcaaat ttgactacag gtggagccgc tggttggaac     180
aaaggataa                                                             189
```

<210> SEQ ID NO 240
<211> LENGTH: 69
<212> TYPE: PRT
<213> ORGANISM: Lactobacillus plantarum
<220> FEATURE:
<221> NAME/KEY: VARIANT
<222> LOCATION: 40
<223> OTHER INFORMATION: Xaa = any amino acid

<400> SEQUENCE: 240

```
Met Tyr Lys Glu Leu Thr Val Asp Glu Leu Ala Leu Ile Asp Gly Gly
1               5                   10                  15

Lys Lys Lys Lys Lys Lys Val Ala Cys Thr Trp Gly Asn Ala Ala Thr
            20                  25                  30

Ala Ala Ala Ser Gly Ala Val Xaa Gly Ile Leu Gly Gly Pro Thr Gly
        35                  40                  45

Ala Leu Ala Gly Ala Ile Trp Gly Val Ser Gln Cys Ala Ser Asn Asn
    50                  55                  60

Leu His Gly Met His
65
```

<210> SEQ ID NO 241
<211> LENGTH: 210
<212> TYPE: DNA
<213> ORGANISM: Lactobacillus plantarum
<220> FEATURE:
<221> NAME/KEY: misc_feature
<222> LOCATION: 119
<223> OTHER INFORMATION: n = a, c, t or g

<400> SEQUENCE: 241

```
atgtataaag aattaacagt tgatgaatta gcattgattg atggaggaaa aaagaagaag      60
aaaaaagtag cttgtacttg gggaaatgca gcaacagccg ctgcttctgg tgcagttang    120
ggtattcttg gtgggcctac tggtgcactg gctggagcta tctggggcgt ttcacaatgc    180
gcgtctaaca acttacacgg catgcactaa                                      210
```

<210> SEQ ID NO 242
<211> LENGTH: 56
<212> TYPE: PRT
<213> ORGANISM: Lactobacillus plantarum

<400> SEQUENCE: 242

```
Met Met Lys Lys Ile Glu Lys Leu Thr Glu Lys Glu Met Ala Asn Ile
1               5                   10                  15

Ile Gly Gly Lys Tyr Tyr Gly Asn Gly Val Thr Cys Gly Lys His Ser
            20                  25                  30

Cys Ser Val Asn Trp Gly Gln Ala Phe Ser Cys Ser Val Ser His Leu
        35                  40                  45

Ala Asn Phe Gly His Gly Lys Cys
    50                  55
```

<210> SEQ ID NO 243

<211> LENGTH: 171
<212> TYPE: DNA
<213> ORGANISM: Lactobacillus plantarum

<400> SEQUENCE: 243

```
atgatgaaaa aaattgaaaa attaactgaa aaagaaatgg ccaatatcat tggtggtaaa      60
tactatggta atggggttac ttgtggtaaa cattcctgct ctgttaactg gggccaagca     120
ttttcttgta gtgtgtcaca tttagctaac ttcggtcatg aaagtgcta a               171
```

<210> SEQ ID NO 244
<211> LENGTH: 64
<212> TYPE: PRT
<213> ORGANISM: Lactobacillus plantarum

<400> SEQUENCE: 244

```
Met Ser Lys Leu Val Lys Thr Leu Thr Val Asp Glu Ile Ser Lys Ile
1               5                   10                  15

Gln Thr Asn Gly Gly Lys Pro Ala Trp Cys Trp Tyr Thr Leu Ala Met
            20                  25                  30

Cys Gly Ala Gly Tyr Asp Ser Gly Thr Cys Tyr Met Tyr Ser His
        35                  40                  45

Cys Phe Gly Val Lys His Ser Ser Gly Gly Gly Ser Tyr His Cys
    50                  55                  60
```

<210> SEQ ID NO 245
<211> LENGTH: 195
<212> TYPE: DNA
<213> ORGANISM: Lactobacillus plantarum

<400> SEQUENCE: 245

```
atgagtaaac tagttaaaac attaactgtc gatgaaatct ctaagattca aaccaatggt      60
ggaaaacctg catggtgttg gtacacattg gcaatgtgcg gtgctggtta tgattcaggc     120
acttgtgatt atatgtattc acactgcttt ggtgtaaaac actctagcgg tggtggcggt     180
agctaccatt gttag                                                      195
```

<210> SEQ ID NO 246
<211> LENGTH: 56
<212> TYPE: PRT
<213> ORGANISM: Lactobacillus plantarum

<400> SEQUENCE: 246

```
Met Leu Gln Phe Glu Lys Leu Gln Tyr Ser Arg Leu Pro Gln Lys Lys
1               5                   10                  15

Leu Ala Lys Ile Ser Gly Gly Phe Asn Arg Gly Gly Tyr Asn Phe Gly
            20                  25                  30

Lys Ser Val Arg His Val Val Asp Ala Ile Gly Ser Val Ala Gly Ile
        35                  40                  45

Arg Gly Ile Leu Lys Ser Ile Arg
    50                  55
```

<210> SEQ ID NO 247
<211> LENGTH: 171
<212> TYPE: DNA
<213> ORGANISM: Lactobacillus plantarum

<400> SEQUENCE: 247

```
atgctacagt tgagaaaatt acaatattcc aggttgccgc aaaaaaagct tgccaaaata      60
tctggtggtt ttaatcgggg cggttataac tttggtaaaa gtgttcgaca tgttgttgat     120
```
gcaattggtt cagttgcagg cattcgtggt attttgaaaa gtattcgtta a    171

<210> SEQ ID NO 248
<211> LENGTH: 52
<212> TYPE: PRT
<213> ORGANISM: Lactobacillus plantarum

<400> SEQUENCE: 248

Met Lys Lys Phe Leu Val Leu Arg Asp Arg Glu Leu Asn Ala Ile Ser
1               5                   10                  15

Gly Gly Val Phe His Ala Tyr Ser Ala Arg Gly Val Arg Asn Asn Tyr
            20                  25                  30

Lys Ser Ala Val Gly Pro Ala Asp Trp Val Ile Ser Ala Val Arg Gly
        35                  40                  45

Phe Ile His Gly
    50

<210> SEQ ID NO 249
<211> LENGTH: 159
<212> TYPE: DNA
<213> ORGANISM: Lactobacillus plantarum

<400> SEQUENCE: 249
atgaaaaaat ttctagtttt gcgtgaccgt gaattaaatg ctatttcagg tggcgttttc    60
catgcctata gcgcgcgtgg cgttcggaat aattataaaa gtgctgttgg gcctgccgat    120
tgggtcatta gcgctgtccg aggattcatc cacggatag                           159

<210> SEQ ID NO 250
<211> LENGTH: 55
<212> TYPE: PRT
<213> ORGANISM: Lactobacillus plantarum

<400> SEQUENCE: 250

Met Thr Val Asn Lys Met Ile Lys Asp Leu Asp Val Val Asp Ala Phe
1               5                   10                  15

Ala Pro Ile Ser Asn Asn Lys Leu Asn Gly Val Val Gly Gly Gly Ala
            20                  25                  30

Trp Lys Asn Phe Trp Ser Ser Leu Arg Lys Gly Phe Tyr Asp Gly Glu
        35                  40                  45

Ala Gly Arg Ala Ile Arg Arg
    50                  55

<210> SEQ ID NO 251
<211> LENGTH: 168
<212> TYPE: DNA
<213> ORGANISM: Lactobacillus plantarum

<400> SEQUENCE: 251
atgactgtga acaaaatgat taaggatttg gatgtagtag atgcatttgc acctatttct    60
aataataagt tgaacggggt tgttggggga ggcgcttgga aaaatttctg gtctagttta    120
agaaaaggat tttatgatgg cgaagctggc agagcaatcc gtcgttaa                 168

<210> SEQ ID NO 252
<211> LENGTH: 57
<212> TYPE: PRT
<213> ORGANISM: Lactobacillus plantarum

<400> SEQUENCE: 252

Met Lys Ile Lys Leu Thr Val Leu Asn Glu Phe Glu Glu Leu Thr Ala
1               5                   10                  15

Asp Ala Glu Lys Asn Ile Ser Gly Gly Arg Arg Ser Lys Asn Gly
            20                  25                  30

Ile Gly Tyr Ala Ile Gly Tyr Ala Phe Gly Ala Val Glu Arg Ala Val
            35                  40                  45

Leu Gly Gly Ser Arg Asp Tyr Asn Lys
            50                  55

<210> SEQ ID NO 253
<211> LENGTH: 174
<212> TYPE: DNA
<213> ORGANISM: Lactobacillus plantarum

<400> SEQUENCE: 253
atgaaaatta aattaactgt tttaaatgaa tttgaagaat taactgctga cgctgaaaag      60
aatatttctg gtggccgtcg gagtcgtaaa aatggaattg atacgctat tggttatgcg      120 tttggcgcgg ttgaacgggc cgtgcttggt ggttcaaggg attataataa gtga           174

<210> SEQ ID NO 254
<211> LENGTH: 47
<212> TYPE: PRT
<213> ORGANISM: Lactobacillus plantarum

<400> SEQUENCE: 254

Met Asp Lys Phe Glu Lys Ile Ser Thr Ser Asn Leu Glu Lys Ile Ser
1               5                   10                  15

Gly Gly Asp Leu Thr Thr Lys Leu Trp Ser Ser Trp Gly Tyr Tyr Leu
            20                  25                  30

Gly Lys Lys Ala Arg Trp Asn Leu Lys His Pro Tyr Val Gln Phe
            35                  40                  45

<210> SEQ ID NO 255
<211> LENGTH: 141
<212> TYPE: DNA
<213> ORGANISM: Lactobacillus plantarum

<400> SEQUENCE: 255
atggataaat ttgaaaaaat tagtacatct aacctagaaa agatctctgg cggtgattta      60
acaaccaagt tatggagctc ttggggatat tatcttggca agaaagcacg ttggaattta      120
aagcacccat atgttcaatt t                                                141

<210> SEQ ID NO 256
<211> LENGTH: 55
<212> TYPE: PRT
<213> ORGANISM: Lactobacillus plantarum

<400> SEQUENCE: 256

Met Asn Asn Leu Asn Lys Phe Ser Thr Leu Gly Lys Ser Ser Leu Ser
1               5                   10                  15

Gln Ile Glu Gly Gly Ser Val Pro Thr Ser Val Tyr Thr Leu Gly Ile
            20                  25                  30

Lys Ile Leu Trp Ser Ala Tyr Lys His Arg Lys Thr Ile Glu Lys Ser
            35                  40                  45

Phe Asn Lys Gly Phe Tyr His
        50                  55

<210> SEQ ID NO 257

<211> LENGTH: 168
<212> TYPE: DNA
<213> ORGANISM: Lactobacillus plantarum

<400> SEQUENCE: 257

```
atgaataact tgaataaatt ttctactcta ggcaagagta gcttgtctca aattgagggc      60
ggatcagtcc caacttcagt atatacgctt ggaattaaaa ttctatggtc tgcgtataag     120
catcgcaaaa cgattgaaaa aagttttaat aaaggctttt atcattaa                  168
```

<210> SEQ ID NO 258
<211> LENGTH: 55
<212> TYPE: PRT
<213> ORGANISM: Lactobacillus plantarum

<400> SEQUENCE: 258

```
Met Asn Asn Ala Leu Ser Phe Glu Gln Gln Phe Thr Asp Phe Ser Thr
1               5                   10                  15

Leu Ser Asp Ser Glu Leu Glu Ser Val Glu Gly Gly Arg Asn Lys Leu
            20                  25                  30

Ala Tyr Asn Met Gly His Tyr Ala Gly Lys Ala Thr Ile Phe Gly Leu
        35                  40                  45

Ala Ala Trp Ala Leu Leu Ala
    50                  55
```

<210> SEQ ID NO 259
<211> LENGTH: 168
<212> TYPE: DNA
<213> ORGANISM: Lactobacillus plantarum

<400> SEQUENCE: 259

```
atgaataacg cattaagttt tgaacaacaa tttacagact tcagcacctt atcggactct      60
gaattagaat ccgttgaggg tggccgaaat aagcttgcat ataatatggg cattacgct     120
ggtaaggcaa ccatttttgg acttgcagca tgggcactcc ttgcatga                  168
```

<210> SEQ ID NO 260
<211> LENGTH: 47
<212> TYPE: PRT
<213> ORGANISM: Lactobacillus plantarum

<400> SEQUENCE: 260

```
Met Asp Lys Ile Ile Lys Phe Gln Gly Ile Ser Asp Asp Gln Leu Asn
1               5                   10                  15

Ala Val Ile Gly Gly Lys Lys Lys Lys Gln Ser Trp Tyr Ala Ala Ala
            20                  25                  30

Gly Asp Ala Ile Val Ser Phe Gly Glu Gly Phe Leu Asn Ala Trp
        35                  40                  45
```

<210> SEQ ID NO 261
<211> LENGTH: 144
<212> TYPE: DNA
<213> ORGANISM: Lactobacillus plantarum

<400> SEQUENCE: 261

```
atggataaga ttattaagtt tcaagggatt tctgatgatc aattaaatgc tgttatcggt      60
gggaaaaaga aaaacaatc ttggtacgca gcagctggtg atgcaatcgt tagttttggt     120
gaaggatttt taaatgcttg gtaa                                            144
```

<210> SEQ ID NO 262

```
<211> LENGTH: 59
<212> TYPE: PRT
<213> ORGANISM: Lactobacillus plantarum

<400> SEQUENCE: 262

Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala Lys Cys
            20                  25                  30

Lys Trp Trp Asn Ile Ser Cys Asp Leu Gly Asn Asn Gly His Val Cys
        35                  40                  45

Thr Leu Ser His Glu Cys Gln Val Ser Cys Asn
    50                  55

<210> SEQ ID NO 263
<211> LENGTH: 180
<212> TYPE: DNA
<213> ORGANISM: Lactobacillus plantarum

<400> SEQUENCE: 263
atgaaaattt ctaagattga agctcaggct cgtaaagatt tttttaaaaa aatcgatact      60
aactcgaact tattaaatgt aaatggtgcc aaatgcaagt ggtggaatat ttcgtgtgat     120
ttaggaaata atggccatgt ttgtaccttg tcacatgaat gccaagtatc ttgtaactaa     180

<210> SEQ ID NO 264
<211> LENGTH: 67
<212> TYPE: PRT
<213> ORGANISM: Lactobacillus plantarum

<400> SEQUENCE: 264

Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg Ser Gly Ile Pro Cys Thr Ile Gly Ala Ala Val Ala Ala
        35                  40                  45

Ser Ile Ala Val Cys Pro Thr Thr Lys Cys Ser Lys Arg Cys Gly Lys
    50                  55                  60

Arg Lys Lys
65

<210> SEQ ID NO 265
<211> LENGTH: 204
<212> TYPE: DNA
<213> ORGANISM: Lactobacillus plantarum

<400> SEQUENCE: 265
atgactaaaa ctagtcgtcg taagaatgct attgctaatt atttagaacc agtcgacgaa      60
aaaagtatta tgaatctttt tggggctggg gatccggaag caagatccgg aattccatgt     120
acaatcggcg cagctgtcgc agcatcaatt gcagtttgtc caactactaa gtgtagtaaa     180
cgttgtggca agcgtaagaa ataa                                            204

<210> SEQ ID NO 266
<211> LENGTH: 48
<212> TYPE: PRT
<213> ORGANISM: Lactobacillus plantarum

<400> SEQUENCE: 266
```

Met Lys Ile Gln Ile Lys Gly Met Lys Gln Leu Ser Asn Lys Glu Met
1               5                   10                  15

Gln Lys Ile Val Gly Gly Lys Ser Ser Ala Tyr Ser Leu Gln Met Gly
                20                  25                  30

Ala Thr Ala Ile Lys Gln Val Lys Lys Leu Phe Lys Lys Trp Gly Trp
            35                  40                  45

<210> SEQ ID NO 267
<211> LENGTH: 147
<212> TYPE: DNA
<213> ORGANISM: Lactobacillus plantarum

<400> SEQUENCE: 267
atgaaaattc aaattaaagg tatgaagcaa cttagtaata aggaaatgca aaaaatagta      60
ggtggaaaga gtagtgcgta ttctttgcag atgggggcaa ctgcaattaa acaggtaaag    120
aaactgttta aaaatggggg atggtaa                                         147

<210> SEQ ID NO 268
<211> LENGTH: 207
<212> TYPE: PRT
<213> ORGANISM: Propionibacterium jensenii

<400> SEQUENCE: 268

Met Asn Lys Thr His Lys Met Ala Thr Leu Val Ile Ala Ala Ile Leu
1               5                   10                  15

Ala Ala Gly Met Thr Ala Pro Thr Ala Tyr Ala Asp Ser Pro Gly Asn
                20                  25                  30

Thr Arg Ile Thr Ala Ser Glu Gln Ser Val Leu Thr Gln Ile Leu Gly
            35                  40                  45

His Lys Pro Thr Gln Thr Glu Tyr Asn Arg Tyr Val Glu Thr Tyr Gly
        50                  55                  60

Ser Val Pro Thr Glu Ala Asp Ile Asn Ala Tyr Ile Glu Ala Ser Glu
65                  70                  75                  80

Ser Glu Gly Ser Ser Ser Gln Thr Ala Ala His Asp Asp Ser Thr Ser
                85                  90                  95

Pro Gly Thr Ser Thr Glu Ile Tyr Thr Gln Ala Ala Pro Ala Arg Phe
            100                 105                 110

Ser Met Phe Phe Leu Ser Gly Thr Trp Ile Thr Arg Ser Gly Val Val
        115                 120                 125

Ser Leu Ser Leu Lys Pro Arg Lys Gly Gly Ile Gly Asn Glu Gly Asp
130                 135                 140

Glu Arg Thr Trp Lys Thr Val Tyr Asp Lys Phe His Asn Ala Gly Gln
145                 150                 155                 160

Trp Thr Arg Tyr Lys Asn Asn Gly Val Asp Ala Ser Met Lys Lys Gln
                165                 170                 175

Tyr Met Cys His Phe Lys Tyr Gly Met Val Lys Thr Pro Trp Asn Leu
            180                 185                 190

Glu Pro His Lys Lys Ala Ala Asp Val Ser Pro Val Lys Cys Asn
        195                 200                 205

<210> SEQ ID NO 269
<211> LENGTH: 624
<212> TYPE: DNA
<213> ORGANISM: Propionibacterium jensenii

<400> SEQUENCE: 269
atgaacaaaa cacacaaaat ggcgacgctg gtaattgccg cgatcttggc cgccggaatg     60

```
accgcaccaa ctgcctatgc agattctcct ggaaacacca gaattacagc cagcgagcaa      120
agcgtcctta cccagatact cggccacaaa cctacacaaa ctgaatataa ccgatacgtt      180
gagacttacg gaagcgtacc gaccgaagca gacatcaacg catatataga agcgtctgaa      240
tctgagggat catcaagtca aacggctgct cacgatgact cgacatcacc cggcacgagt      300
accgaaatct acacgcaggc agcccctgcc aggttctcaa tgttttcct gtccggaact       360 tggatcacta ggagtggtgt agtatcgctc tccttgaagc caaggaaggg tggtattggc      420
aacgaggggg acgagcgtac ctggaagact gtatacgaca aattccataa cgctgggcaa      480
tggacacgat acaagaacaa cggcgtagac gccagcatga aaaagcagta catgtgccac      540
ttcaagtacg ggatggtgaa gacgccatgg aatctggagc cccacaagaa ggctgcagac      600
gtcagtccag tcaagtgcaa ctag                                             624
```

<210> SEQ ID NO 270
<211> LENGTH: 96
<212> TYPE: PRT
<213> ORGANISM: Propionibacterium thoenii
<400> SEQUENCE: 270

```
Met Lys Lys Thr Leu Leu Arg Ser Gly Thr Ile Ala Leu Ala Thr Ala
1               5                   10                  15

Ala Ala Phe Gly Ala Ser Leu Ala Ala Ala Pro Ser Ala Met Ala Val
            20                  25                  30

Pro Gly Gly Cys Thr Tyr Thr Arg Ser Asn Arg Asp Val Ile Gly Thr
        35                  40                  45

Cys Lys Thr Gly Ser Gly Gln Phe Arg Ile Arg Leu Asp Cys Asn Asn
    50                  55                  60

Ala Pro Asp Lys Thr Ser Val Trp Ala Lys Pro Lys Val Met Val Ser
65                  70                  75                  80

Val His Cys Leu Val Gly Gln Pro Arg Ser Ile Ser Phe Glu Thr Lys
                85                  90                  95
```

<210> SEQ ID NO 271
<211> LENGTH: 291
<212> TYPE: DNA
<213> ORGANISM: Propionibacterium thoenii
<400> SEQUENCE: 271

```
atgaagaaga ccctcctgcg aagtggaacg atcgcactgg cgaccgcggc tgcatttggc       60
gcatcattgg cagccgcccc atctgccatg gccgttcctg gtggttgcac gtacacaaga      120
agcaatcgcg acgtcatcgg tacctgcaag actggaagcg gccagttccg aatccgactt      180
gactgcaaca acgctccaga caaaacttca gtctgggcca agcccaaggt aatggtgtcg      240
gttcactgtc ttgttggtca accgaggtcc atctcgttcg agaccaagtg a               291
```

<210> SEQ ID NO 272
<211> LENGTH: 255
<212> TYPE: PRT
<213> ORGANISM: Propionibacterium freudenreichii subsp freudenreii
<400> SEQUENCE: 272

```
Met Asn Thr Lys Ala Val Asn Leu Lys Ser Glu Asn Thr Thr Lys Leu
1               5                   10                  15

Val Ser Tyr Leu Thr Glu Asn Gln Leu Asp Glu Phe Ile Arg Arg Ile
            20                  25                  30
```

```
Arg Ile Asp Gly Ala Leu Val Glu Glu Val Ser Gln Asn Ala Lys Gln
            35                  40                  45

Ala Leu Asp Asn Thr Gly Leu Asn Gly Trp Ile Asn Thr Asp Cys Asp
 50                  55                  60

Glu Gly Leu Leu Ser Asp Phe Ile Ser Lys Ile Ala Ser Ala Arg Trp
 65                  70                  75                  80

Ile Pro Leu Ala Glu Ser Ile Arg Pro Ala Val Thr Asp Arg Asp Lys
                 85                  90                  95

Tyr Arg Val Ser Cys Trp Phe Tyr Gln Gly Met Asn Ile Ala Ile Tyr
            100                 105                 110

Ala Asn Ile Gly Gly Val Ala Asn Ile Ile Gly Tyr Thr Glu Ala Ala
            115                 120                 125

Val Ala Thr Leu Leu Gly Ala Val Ala Val Ala Pro Val Val Pro
 130                 135                 140

Gly Thr Pro Thr Pro Pro Lys Asp Lys Ser Ser Gln Tyr Lys Glu Val
 145                 150                 155                 160

Pro Leu Ala Val Arg Leu Ser Glu Thr Tyr His Glu Glu Gly Val Arg
                 165                 170                 175

Gly Leu Phe Asp Glu Leu Asn Tyr Ser Glu Ser Arg Met Ile Ser Thr
            180                 185                 190

Leu Arg Arg Ala Ser Thr Asp Gly Val Leu Ile Asn Ser Trp Asn Asp
            195                 200                 205

Gly Gln Asp Thr Ile Leu Leu Lys Lys Tyr Asn Phe Gln Asp Leu Gln
            210                 215                 220

Leu Thr Val Arg Ser Arg Ile Val Gly Asn Gln Thr Ile Ile Glu Glu
 225                 230                 235                 240

Cys Lys Ile Thr Asp Gly Arg Lys Thr Leu Ser Asp Glu Thr Val
                 245                 250                 255

<210> SEQ ID NO 273
<211> LENGTH: 768
<212> TYPE: DNA
<213> ORGANISM: Propionibacterium freudenreichii subsp freudenreii

<400> SEQUENCE: 273
atgaatacca aagctgtaaa tctgaagtca gaaaacacga ctaagttggt gagctacctt      60
acggaaaatc aattggatga gtttattaga aggattcgca ttgatggcgc tcttgtggaa    120
gaggtcagtc aaaatgctaa gcaggcctta gataatactg gctcaatggg ctggataaat    180
actgattgcg atgaaggcct ctctctgat ttcatttcaa agatagcaag tgctagatgg     240
attccattag ctgagtcaat tcgacctgcg gtgactgaca gggataagta tcgagtaagt    300
tgctggttct accaggggat gaatatagca atttacgcaa atatcggtgg cgtggccaat    360
attatcggct atacggaggc cgcagtcgca acactccttg gtgcagttgt ggcggtagct    420
cctgtggtcc ctggaactcc aacccctcca aaggacaaga gttcgcaata taaggaggtt    480
cccccttgccg ttcgtctttc gaaacatac cacgaagagg gagtacgagg tctattcgac    540
gagctgaact actccgagag ccgtatgatc tctactctaa ggcgagcatc aaccgatgga    600
gtcctaatta attcttggaa cgatgggcag gatacaattc tgcttaagaa gtacaatttc    660
caagacttgc aactgactgt caggagccgc attgttggga atcaaacaat aattgaagaa    720
tgcaaaatca ctgatggtag aaaaactctt tcagacgaga ctgtgtag                 768

<210> SEQ ID NO 274
<211> LENGTH: 618
```

<212> TYPE: PRT
<213> ORGANISM: Pseudomonas aeruginosa

<400> SEQUENCE: 274

```
Met Ala Arg Pro Ile Ala Asp Leu Ile His Phe Asn Ser Thr Thr Val
1               5                   10                  15

Thr Ala Ser Gly Asp Val Tyr Tyr Gly Pro Gly Gly Gly Thr Gly Ile
            20                  25                  30

Gly Pro Ile Ala Arg Pro Ile Glu His Gly Leu Asp Ser Ser Thr Glu
        35                  40                  45

Asn Gly Trp Gln Glu Phe Glu Ser Tyr Ala Asp Val Gly Val Asp Pro
    50                  55                  60

Arg Arg Tyr Val Pro Leu Gln Val Lys Glu Lys Arg Arg Glu Ile Glu
65                  70                  75                  80

Leu Gln Phe Arg Asp Ala Glu Lys Lys Leu Glu Ala Ser Val Gln Ala
                85                  90                  95

Glu Leu Asp Lys Ala Asp Ala Ala Leu Gly Pro Ala Lys Asn Leu Ala
            100                 105                 110

Pro Leu Asp Val Ile Asn Arg Ser Leu Thr Ile Val Gly Asn Ala Leu
        115                 120                 125

Gln Gln Lys Asn Gln Lys Leu Leu Leu Asn Gln Lys Lys Ile Thr Ser
    130                 135                 140

Leu Gly Ala Lys Asn Phe Leu Thr Arg Thr Ala Glu Glu Ile Gly Glu
145                 150                 155                 160

Gln Ala Val Arg Glu Gly Asn Ile Asn Gly Pro Glu Ala Tyr Met Arg
                165                 170                 175

Phe Leu Asp Arg Glu Met Glu Gly Leu Thr Ala Ala Tyr Asn Val Lys
            180                 185                 190

Leu Phe Thr Glu Ala Ile Ser Ser Leu Gln Ile Arg Met Asn Thr Leu
        195                 200                 205

Thr Ala Ala Lys Ala Ser Ile Glu Ala Ala Ala Asn Lys Ala Arg
    210                 215                 220

Glu Gln Ala Ala Ala Glu Ala Lys Arg Lys Ala Glu Glu Gln Ala Arg
225                 230                 235                 240

Gln Gln Ala Ala Ile Arg Ala Ala Asn Thr Tyr Ala Met Pro Ala Asn
                245                 250                 255

Gly Ser Val Val Ala Thr Ala Ala Gly Arg Gly Leu Ile Gln Val Ala
            260                 265                 270

Gln Gly Ala Ala Ser Leu Ala Gln Ala Ile Ser Asp Ala Ile Ala Val
        275                 280                 285

Leu Gly Arg Val Leu Ala Ser Ala Pro Ser Val Met Ala Val Gly Phe
    290                 295                 300

Ala Ser Leu Thr Tyr Ser Ser Arg Thr Ala Glu Gln Trp Gln Asp Gln
305                 310                 315                 320

Thr Pro Asp Ser Val Arg Tyr Ala Leu Gly Met Asp Ala Ala Lys Leu
                325                 330                 335

Gly Leu Pro Pro Ser Val Asn Leu Asn Ala Val Ala Lys Ala Ser Gly
            340                 345                 350

Thr Val Asp Leu Pro Met Arg Leu Thr Asn Glu Ala Arg Gly Asn Thr
        355                 360                 365

Thr Thr Leu Ser Val Val Ser Thr Asp Gly Val Ser Val Pro Lys Ala
    370                 375                 380

Val Pro Val Arg Met Ala Ala Tyr Asn Ala Thr Thr Gly Leu Tyr Glu
385                 390                 395                 400
```

Val Thr Val Pro Ser Thr Thr Ala Glu Ala Pro Pro Leu Ile Leu Thr
            405                 410                 415

Trp Thr Pro Ala Ser Pro Pro Gly Asn Gln Asn Pro Ser Ser Thr Thr
        420                 425                 430

Pro Val Val Pro Lys Pro Val Pro Val Tyr Glu Gly Ala Thr Leu Thr
            435                 440                 445

Pro Val Lys Ala Thr Pro Glu Thr Tyr Pro Gly Val Ile Thr Leu Pro
450                 455                 460

Glu Asp Leu Ile Ile Gly Phe Pro Ala Asp Ser Gly Ile Lys Pro Ile
465                 470                 475                 480

Tyr Val Met Phe Arg Asp Pro Arg Asp Val Pro Gly Ala Ala Thr Gly
            485                 490                 495

Lys Gly Gln Pro Val Ser Gly Asn Trp Leu Gly Ala Ser Gln Gly
        500                 505                 510

Glu Gly Ala Pro Ile Pro Ser Gln Ile Ala Asp Lys Leu Arg Gly Lys
            515                 520                 525

Thr Phe Lys Asn Trp Arg Asp Phe Arg Glu Gln Phe Trp Ile Ala Val
        530                 535                 540

Ala Asn Asp Pro Glu Leu Ser Lys Gln Phe Asn Pro Gly Ser Leu Ala
545                 550                 555                 560

Val Met Arg Asp Gly Gly Ala Pro Tyr Val Arg Glu Ser Glu Gln Ala
            565                 570                 575

Gly Gly Arg Ile Lys Ile Glu Ile His His Lys Val Arg Val Ala Asp
            580                 585                 590

Gly Gly Gly Val Tyr Asn Met Gly Asn Leu Val Ala Val Thr Pro Lys
        595                 600                 605

Arg His Ile Glu Ile His Lys Gly Gly Lys
    610                 615

<210> SEQ ID NO 275
<211> LENGTH: 1857
<212> TYPE: DNA
<213> ORGANISM: Pseudomonas aeruginosa

<400> SEQUENCE: 275
atggcacgac ccattgctga ccttatccac ttcaactcta caactgtcac ggcaagcgga      60
gacgtttatt acggccctgg gggaggtacc ggcattggcc ccattgccag acctatagag     120
cacggcttgg attcgtccac tgaaaatggc tggcaagagt ttgaaagtta tgctgatgtg     180
ggcgttgacc ccagacgcta tgttcctctt caggttaaag aaaaacgcag ggagatcgag     240
cttcagttcc gagatgccga gaaaaaactt gaggcgtcgg tacaagccga gctggataag     300
gctgatgccg ctcttggtcc ggcaaagaat cttgcaccat ggacgtcat caaccgcagt     360 ctgaccatcg ttggaaacgc cctccagcaa agaatcaaa actactgct gaatcagaag     420 aagattacca gcctgggtgc aaagaatttc cttacccgta cggcggaaga gatcggtgaa     480
caagcggtgc gagaaggcaa tattaacggg cctgaagcct atatgcgctt cctcgacagg     540
gaaatggaag gtctcaccgg agcttataac gtaaaactct tcaccgaagc gatcagtagt     600
ctccagatcc gcatgaatac gttgaccgcc gccaaagcaa gtattgaggc ggccgcagca     660
aacaaggcgc gtgaacaagc agcggctgag gccaaacgca aagccgaaga gcaggcccgc     720
cagcaagcgg cgataagagc tgccaatacc tatgccatgc cggccaatgg cagcgttgtc     780
gccaccgccg caggccgggg tctgatccag gtcgcacaag gcgccgcatc ccttgctcaa     840

```
gcgatctccg atgcgattgc cgtcctgggc cgggtcctgg cttcagcacc ctcggtgatg    900
gccgtgggct tgccagtct gacctactcc tcccggactg ccgagcaatg caggaccaa     960
acgcccgata gcgttcgtta cgccctgggc atggatgccg ctaaattggg gcttccccca  1020
agcgtaaacc tgaacgcggt tgcaaaagcc agcggtaccg tcgatctgcc gatgcgcctg  1080
accaacgagg cacgaggcaa cacgacgacc ctttcggtgg tcagcaccga tggtgtgagc  1140
gttccgaaag ccgttccggt ccggatggcg gcctacaatg ccacgacagg cctgtacgag  1200
gttacggttc cctctacgac cgcagaagcg ccgccactga tcctgacctg gacgccggcg  1260
agtcctccag gaaaccagaa cccttcgagt accactccgg tcgtaccgaa gccggtgccg  1320
gtatatgagg gagcgaccct tacaccggtg aaggctaccc cggaaaccta tcctggggtg  1380
attacactac cggaagacct gatcatcggc ttcccggccg actcggggat caagccgatc  1440
tatgtgatgt tcagggatcc gcgggatgta cctggtgctg cgactggcaa gggacagccc  1500
gtcagcggta attggctcgg cgccgcctct caaggtgagg gggctccaat tccaagccag  1560
attgcggata aactacgtgg taagacattc aaaaactggc gggactttcg ggaacaattc  1620
tggatagctg tggctaatga tcctgagtta agtaaacagt ttaatcctgg tagtttagct  1680
gtaatgagag atggagggc tccttatgtc agagagtcag aacaggctgg cgggagaata  1740
aagatcgaaa tccaccacaa ggttcgagta gcagatggag gcggcgttta caatatgggg  1800
aaccttgttg cagtaacgcc aaaacgtcat atagaaatcc acaagggagg gaagtga     1857
```

<210> SEQ ID NO 276
<211> LENGTH: 689
<212> TYPE: PRT
<213> ORGANISM: Pseudomonas aeruginosa

<400> SEQUENCE: 276

```
Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
```

-continued

```
            195                 200                 205
Lys Ala Arg Lys Ala Asn Val Glu Lys Val Gln Ser Glu Leu Asp
210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
                245                 250                 255

Lys Lys Leu Gln Thr Ala Asn Asn Ala Leu Ile Ala Lys Ala Pro Asn
                260                 265                 270

Ala Leu Glu Lys Gln Lys Ala Thr Tyr Asn Ala Asp Leu Leu Val Asp
                275                 280                 285

Glu Ile Ala Ser Leu Gln Ala Arg Leu Asp Lys Leu Asn Ala Glu Thr
290                 295                 300

Ala Arg Arg Lys Glu Ile Ala Arg Gln Ala Ala Ile Arg Ala Ala Asn
305                 310                 315                 320

Thr Tyr Ala Met Pro Ala Asn Gly Ser Val Val Ala Thr Ala Ala Gly
                325                 330                 335

Arg Gly Leu Ile Gln Val Ala Gln Gly Ala Ala Ser Leu Ala Gln Ala
                340                 345                 350

Ile Ser Asp Ala Ile Ala Val Leu Gly Arg Val Leu Ala Ser Ala Pro
                355                 360                 365

Ser Val Met Ala Val Gly Phe Ala Ser Leu Thr Tyr Ser Ser Arg Thr
370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
                420                 425                 430

Asn Glu Ala Arg Gly Asn Thr Thr Thr Leu Ser Val Val Ser Thr Asp
                435                 440                 445

Gly Val Ser Val Pro Lys Ala Val Pro Val Arg Met Ala Ala Tyr Asn
450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Gly Asn
                485                 490                 495

Gln Asn Pro Ser Ser Thr Thr Pro Val Val Pro Lys Pro Val Pro Val
                500                 505                 510

Tyr Glu Gly Ala Thr Leu Thr Pro Val Lys Ala Thr Pro Glu Thr Tyr
                515                 520                 525

Pro Gly Val Ile Thr Leu Pro Glu Asp Leu Ile Gly Phe Pro Ala
                530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
                580                 585                 590

Ala Asp Lys Leu Arg Gly Lys Thr Phe Lys Asn Trp Arg Asp Phe Arg
                595                 600                 605

Glu Gln Phe Trp Ile Ala Val Ala Asn Asp Pro Glu Leu Ser Lys Gln
610                 615                 620
```

```
        Phe Asn Pro Gly Ser Leu Ala Val Met Arg Asp Gly Ala Pro Tyr
        625                 630                 635                 640

Val Arg Glu Ser Glu Gln Ala Gly Gly Arg Ile Lys Ile Glu Ile His
                        645                 650                 655

His Lys Val Arg Ile Ala Asp Gly Gly Gly Val Tyr Asn Met Gly Asn
                    660                 665                 670

Leu Val Ala Val Thr Pro Lys Arg His Ile Glu Ile His Lys Gly Gly
                675                 680                 685

Lys

<210> SEQ ID NO 277
        <211> LENGTH: 2070
        <212> TYPE: DNA
        <213> ORGANISM: Pseudomonas aeruginosa

<400> SEQUENCE: 277
```

| | | | | |
|---|---|---|---|---|
| atggctgtca | atgattacga | acctggttcg | atggttatta | cacatgtgca gggtggtggg | 60 |
| cgtgacataa | tccagtatat | tcctgctcga | tcaagctacg | gtactccacc atttgtccca | 120 |
| ccaggaccaa | gtccgtatgt | cggtactgga | atgcaggagt | acaggaagct aagaagtacg | 180 |
| cttgataagt | cccattcaga | actcaagaaa | aacctgaaaa | atgaaaccct gaaggaggtt | 240 |
| gatgaactca | gagtgaagc | ggggttgcca | ggtaaagcgg | tcagtgccaa tgacatccgc | 300 |
| gatgaaaaga | gtatcgttga | tgcactcatg | gatgccaaag | caaaatcgct aaaggccatt | 360 |
| gaggatcgcc | cggccaatct | ttatacggct | tcagactttc | ctcagaagtc agagtcgatg | 420 |
| taccagagtc | agttgctggc | cagccgaaaa | ttctatggag | agttcctgga tcgccatatg | 480 |
| agtgagctgg | ccaaagcgta | cagcgccgat | atctataagg | cgcaaatcgc tatcttgaaa | 540 |
| caaacgtctc | aagagctgga | gaataaagcc | cggtcattgg | aagcagaagc ccagcgagcc | 600 |
| gctgctgagg | tggaggcgga | ctacaaggcc | aggaaggcaa | atgtcgagaa aaaagtgcag | 660 |
| tccgagcttg | accaggctgg | gaatgctttg | cctcaactga | ccaatccaac gccagagcag | 720 |
| tggcttgaac | gcgctactca | actggttacg | caggcgatcg | ccaataagaa gaaattgcag | 780 |
| actgcaaaca | atgccttgat | tgccaaggca | cccaatgcac | tggagaaaca aaaggcaacc | 840 |
| tacaacgccg | atctcctagt | ggatgaaatc | gccagcctgc | aagcacggct ggacaagctg | 900 |
| aacgccgaaa | cggcaaggcg | caaggaaatc | gctcgtcaag | cggcgatcag ggctgccaat | 960 |
| acttatgcca | tgccagccaa | tggcagcgtt | gtcgccaccg | ccgcaggccg gggtctgatc | 1020 |
| caggtcgcac | aaggcgccgc | atcccttgct | caagcgatct | ccgatgcgat tgccgtcctg | 1080 |
| ggccgggtcc | tggcttcagc | accctcggtg | atggccgtgg | gctttgccag tctgacctac | 1140 |
| tcctcccgga | ctgccgagca | atggcaggac | caaacgcccg | atagcgttcg ttacgccctg | 1200 |
| ggcatggatg | ccgctaaatt | gggcttccc | ccaagcgtaa | acctgaacgc ggttgcaaaa | 1260 |
| gccagcggta | ccgtcgatct | gccgatgcgc | ctgaccaacg | aggcacgagg caacacgacg | 1320 |
| accctttcgg | tggtcagcac | cgatggtgtg | agcgttccga | aagccgttcc ggtccggatg | 1380 |
| gcggcctaca | atgccacgac | aggcctgtac | gaggttacgg | ttccctctac gaccgcagaa | 1440 |
| gcgccgccac | tgatcctgac | ctggacgccg | gcgagtcctc | caggaaaccca gaaccccttcg | 1500 |
| agtaccactc | cggtcgtacc | gaagccggtg | ccggtatatg | agggagcgac ccttacaccg | 1560 |
| gtgaaggcta | cccccggaaac | ctatcctggg | gtgattacac | taccgaagaa cctgatcatc | 1620 |
| ggcttcccgg | ccgactcggg | gatcaagccg | atctatgtga | tgttcaggga tccgcgggat | 1680 |

```
gtacctggtg ctgcgactgg caagggacag cccgtcagcg gtaattggct cggcgccgcc    1740
tctcaaggtg aggggctcc aattccaagc cagattgcgg ataaactacg tggtaagaca     1800
ttcaaaaact ggcgggactt tcgggaacaa ttctggatag ctgtggctaa tgatcctgag    1860
ttaagtaaac agtttaatcc tggtagttta gctgtaatga gagatggagg ggctccttat    1920
gtcagagagt cagaacaggc tggcgggaga ataaagatcg aaatccacca caaggttcga   1980
atagcagatg gaggcggcgt ttacaatatg gggaaccttg ttgcagtaac gccaaaacgt    2040
catatagaaa tccacaaggg agggaagtga                                     2070
```

<210> SEQ ID NO 278
<211> LENGTH: 47
<212> TYPE: PRT
<213> ORGANISM: Ruminococcus gnavus

<400> SEQUENCE: 278

```
Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
            20                  25                  30

His Glu Cys Asn Met Asn Thr Trp Gln Phe Leu Phe Thr Cys Cys
        35                  40                  45
```

<210> SEQ ID NO 279
<211> LENGTH: 144
<212> TYPE: DNA
<213> ORGANISM: Ruminococcus gnavus

<400> SEQUENCE: 279

```
atgagaaatg acgtattaac attaacaaac ccaatggaag agaacgaact ggagcagatc    60
ttaggtggtg gcaatggtgt gttaaaaacg attagccacg aatgcaatat gaacacatgg   120
cagttcctgt ttacttgttg ctaa                                          144
```

<210> SEQ ID NO 280
<211> LENGTH: 55
<212> TYPE: PRT
<213> ORGANISM: Lactobacillus sakei

<400> SEQUENCE: 280

```
Met Lys Asn Ala Lys Ser Leu Thr Ile Gln Glu Met Lys Ser Ile Thr
1               5                   10                  15

Gly Gly Lys Tyr Tyr Gly Asn Gly Val Ser Cys Asn Ser His Gly Cys
            20                  25                  30

Ser Val Asn Trp Gly Gln Ala Trp Thr Cys Gly Val Asn His Leu Ala
        35                  40                  45

Asn Gly Gly His Gly Val Cys
        50                  55
```

<210> SEQ ID NO 281
<211> LENGTH: 168
<212> TYPE: DNA
<213> ORGANISM: Lactobacillus sakei

<400> SEQUENCE: 281

```
atgaaaaacg caaaaagcct aacaattcaa gaatgaaat ctattacagg tggtaaatac     60
tatggtaatg gcgttagctg taactctcac ggctgttcag taaattgggg gcaagcatgg   120
acttgtggag taaaccatct agctaatggc ggtcatggag tttgttaa                168
```

<210> SEQ ID NO 282
<211> LENGTH: 59
<212> TYPE: PRT
<213> ORGANISM: Lactobacillus sakei

<400> SEQUENCE: 282

Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55

<210> SEQ ID NO 283
<211> LENGTH: 180
<212> TYPE: DNA
<213> ORGANISM: Lactobacillus sakei

<400> SEQUENCE: 283
atgaataatg taaagaatt aagtatgaca gaattacaaa caattaccgg cggtgctaga      60
tcatatggca acggtgttta ctgtaataat aaaaaatgtt gggtaaatcg gggtgaagca    120
acgcaaagta ttattggtgg tatgattagc ggctgggcta gtggtttagc tggaatgtaa    180

<210> SEQ ID NO 284
<211> LENGTH: 61
<212> TYPE: PRT
<213> ORGANISM: Lactobacillus sakei

<400> SEQUENCE: 284

Met Glu Lys Phe Ile Glu Leu Ser Leu Lys Glu Val Thr Ala Ile Thr
1               5                   10                  15

Gly Gly Lys Tyr Tyr Gly Asn Gly Val His Cys Gly Lys His Ser Cys
            20                  25                  30

Thr Val Asp Trp Gly Thr Ala Ile Gly Asn Ile Gly Asn Asn Ala Ala
        35                  40                  45

Ala Asn Trp Ala Thr Gly Gly Asn Ala Gly Trp Asn Lys
    50                  55                  60

<210> SEQ ID NO 285
<211> LENGTH: 186
<212> TYPE: DNA
<213> ORGANISM: Lactobacillus sakei

<400> SEQUENCE: 285
atggaaaagt ttattgaatt atctttaaaa gaagtaacag caattacagg tggaaaatat      60
tatggtaacg gtgtacactg tggaaaacat tcatgtaccg tagactgggg aacagctatt    120
ggaaatatcg aaataatgc agctgcaaac tgggccacag gcggaaacgc tggctggaat    180
aaataa                                                                186

<210> SEQ ID NO 286
<211> LENGTH: 56
<212> TYPE: PRT
<213> ORGANISM: Streptococcus salivarius

<400> SEQUENCE: 286

Met Lys Ser Thr Asn Asn Gln Ser Ile Ala Glu Ile Ala Ala Val Asn

```
            1               5                  10                  15
Ser Leu Gln Glu Val Ser Met Glu Glu Leu Asp Gln Ile Ile Gly Ala
                20                  25                  30

Gly Asn Gly Val Val Leu Thr Leu Thr His Glu Cys Asn Leu Ala Thr
            35                  40                  45

Trp Thr Lys Lys Leu Lys Cys Cys
            50                  55

<210> SEQ ID NO 287
<211> LENGTH: 171
<212> TYPE: DNA
<213> ORGANISM: Streptococcus salivarius

<400> SEQUENCE: 287
atgaaatcaa caaataatca agtatcgca gaaattgcag cagtaaactc actacaagaa      60
gtaagtatgg aggaactaga ccaaattatt ggtgccggaa acggagtggt tcttactctt    120
actcatgaat gtaacctagc aacttggaca aaaaaactaa atgttgcta a              171

<210> SEQ ID NO 288
<211> LENGTH: 51
<212> TYPE: PRT
<213> ORGANISM: Streptococcus pyogenes serotype M28

<400> SEQUENCE: 288

Met Ser Phe Met Lys Asn Ser Lys Asp Ile Leu Thr Asn Ala Ile Glu
1               5                  10                  15

Glu Val Ser Glu Lys Glu Leu Met Glu Val Ala Gly Gly Lys Lys Gly
                20                  25                  30

Ser Gly Trp Phe Ala Thr Ile Thr Asp Asp Cys Pro Asn Ser Val Phe
            35                  40                  45

Val Cys Cys
    50

<210> SEQ ID NO 289
<211> LENGTH: 156
<212> TYPE: DNA
<213> ORGANISM: Streptococcus pyogenes serotype M28

<400> SEQUENCE: 289
atgagtttta tgaaaaattc aaaggatatt ttgactaatg ctatcgaaga agtttctgaa      60
aaagaactta tggaagtagc tggtggtaaa aaaggttccg gttggtttgc aactattact    120
gatgactgtc cgaactcagt attcgtttgt tgttaa                              156

<210> SEQ ID NO 290
<211> LENGTH: 48
<212> TYPE: PRT
<213> ORGANISM: Streptococcus salivarius

<400> SEQUENCE: 290

Met Lys Asn Ser Lys Asp Val Leu Asn Asn Ala Ile Glu Glu Val Ser
1               5                  10                  15

Glu Lys Glu Leu Met Glu Val Ala Gly Gly Lys Lys Gly Pro Gly Trp
                20                  25                  30

Ile Ala Thr Ile Thr Asp Asp Cys Pro Asn Ser Ile Phe Val Cys Cys
            35                  40                  45

<210> SEQ ID NO 291
<211> LENGTH: 147
```

<212> TYPE: DNA
<213> ORGANISM: Streptococcus salivarius

<400> SEQUENCE: 291

```
atgaaaaact caaagatgt tttgaacaat gctatcgaag aggtttctga aaaagaactt    60
atggaagtag ctggtggtaa aaaaggtcca ggttggattg caactattac tgatgactgt   120
ccaaactcaa tattcgtttg ttgttaa                                      147
```

<210> SEQ ID NO 292
<211> LENGTH: 48
<212> TYPE: PRT
<213> ORGANISM: Streptococcus salivarius

<400> SEQUENCE: 292

```
Met Lys Asn Ser Lys Asp Ile Leu Asn Asn Ala Ile Glu Glu Val Ser
1               5                   10                  15

Glu Lys Glu Leu Met Glu Val Ala Gly Gly Lys Arg Gly Ser Gly Trp
            20                  25                  30

Ile Ala Thr Ile Thr Asp Asp Cys Pro Asn Ser Val Phe Val Cys Cys
        35                  40                  45
```

<210> SEQ ID NO 293
<211> LENGTH: 147
<212> TYPE: DNA
<213> ORGANISM: Streptococcus salivarius

<400> SEQUENCE: 293

```
atgaaaaact caaagatat tttgaacaat gctatcgaag aagtttctga aaaagaactt    60
atggaagtag ctggtggtaa aagaggttca ggttggattg caactattac tgatgactgt   120
ccaaactcag tattcgtttg ttgttaa                                      147
```

<210> SEQ ID NO 294
<211> LENGTH: 62
<212> TYPE: PRT
<213> ORGANISM: Staphylococcus aureus

<400> SEQUENCE: 294

```
Met Lys Ser Ser Phe Leu Glu Lys Asp Ile Glu Glu Gln Val Thr Trp
1               5                   10                  15

Phe Glu Glu Val Ser Glu Gln Glu Phe Asp Asp Asp Ile Phe Gly Ala
            20                  25                  30

Cys Ser Thr Asn Thr Phe Ser Leu Ser Asp Tyr Trp Gly Asn Lys Gly
        35                  40                  45

Asn Trp Cys Thr Ala Thr His Glu Cys Met Ser Trp Cys Lys
    50                  55                  60
```

<210> SEQ ID NO 295
<211> LENGTH: 189
<212> TYPE: DNA
<213> ORGANISM: Staphylococcus aureus

<400> SEQUENCE: 295

```
atgaaaagtt cttttttaga aaagatata gaagaacaag tgacatggtt cgaggaagtt    60
tcagaacaag aatttgacga tgatatttt ggagcttgta gtacaaacac ttttctcttg   120
agtgactatt ggggtaataa aggaaattgg tgtactgcta ctcacgaatg tatgtcttgg   180
tgtaaataa                                                          189
```

<210> SEQ ID NO 296
<211> LENGTH: 67
<212> TYPE: PRT
<213> ORGANISM: Staphylococcus aureus

<400> SEQUENCE: 296

Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
            20                  25                  30

Tyr Ala Ala Gly Thr Pro Leu Ala Leu Leu Gly Gly Ala Ala Thr Gly
        35                  40                  45

Val Ile Gly Tyr Ile Ser Asn Gln Thr Cys Pro Thr Thr Ala Cys Thr
    50                  55                  60

Arg Ala Cys
65

<210> SEQ ID NO 297
<211> LENGTH: 204
<212> TYPE: DNA
<213> ORGANISM: Staphylococcus aureus

<400> SEQUENCE: 297
atgaaaaatg aattaggtaa gttttagaa gaaaacgaat tagagttagg taaattttca      60
gaatcagaca tgctagaaat tactgatgat gaagtatatg cagctggaac accttagcc     120 ttattgggtg gagctgccac cggggtgata ggttatattt ctaaccaaac atgtccaaca    180
actgcttgta cacgcgcttg ctag                                           204

<210> SEQ ID NO 298
<211> LENGTH: 46
<212> TYPE: PRT
<213> ORGANISM: Streptococcus pyogenes

<400> SEQUENCE: 298

Met Asn Asn Thr Ile Lys Asp Phe Asp Leu Asp Leu Lys Thr Asn Lys
1               5                   10                  15

Lys Asp Thr Ala Thr Pro Tyr Val Gly Ser Arg Tyr Leu Cys Thr Pro
            20                  25                  30

Gly Ser Cys Trp Lys Leu Val Cys Phe Thr Thr Thr Val Lys
        35                  40                  45

<210> SEQ ID NO 299
<211> LENGTH: 141
<212> TYPE: DNA
<213> ORGANISM: Streptococcus pyogenes

<400> SEQUENCE: 299
atgaataaca caattaaaga ctttgatctc gatttgaaaa caaataaaaa agacactgct      60
acaccttatg ttggtagccg ttacctatgt acccctggtt cttgttggaa attagtttgc    120
tttacaacaa ctgttaaata a                                              141

<210> SEQ ID NO 300
<211> LENGTH: 51
<212> TYPE: PRT
<213> ORGANISM: Streptococcus pyogenes

<400> SEQUENCE: 300

Met Glu Lys Asn Asn Glu Val Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50

<210> SEQ ID NO 301
<211> LENGTH: 156
<212> TYPE: DNA
<213> ORGANISM: Streptococcus pyogenes

<400> SEQUENCE: 301
atggaaaaaa ataatgaagt aatcaactct attcaagaag ttagtcttga agaactcgat       60
caaattatcg gtgctggaaa aaatggtgtg tttaaaacaa tttctcatga gtgtcatttg      120
aatacatggg cattccttgc tacttgttgt tcataa                                156

<210> SEQ ID NO 302
<211> LENGTH: 51
<212> TYPE: PRT
<213> ORGANISM: Streptococcus pyogenes serotype M49

<400> SEQUENCE: 302

Met Thr Lys Glu His Glu Ile Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50

<210> SEQ ID NO 303
<211> LENGTH: 156
<212> TYPE: DNA
<213> ORGANISM: Streptococcus pyogenes serotype M49

<400> SEQUENCE: 303
atggaaaaaa ataatgaagt aatcaactct attcaagaag ttagtcttga agaactcgat       60
caaattatcg gtgctggaaa aaatggtgtg tttaaaacaa tttctcatga gtgtcatttg      120
aatacatggg cattccttgc tacttgttgc tcataa                                156

<210> SEQ ID NO 304
<211> LENGTH: 56
<212> TYPE: PRT
<213> ORGANISM: Bacillus subtilis

<400> SEQUENCE: 304

Met Glu Lys Leu Phe Lys Glu Val Lys Leu Glu Glu Leu Glu Asn Gln
1               5                   10                  15

Lys Gly Ser Gly Leu Gly Lys Ala Gln Cys Ala Ala Leu Trp Leu Gln
            20                  25                  30

Cys Ala Ser Gly Gly Thr Ile Gly Cys Gly Gly Gly Ala Val Ala Cys
        35                  40                  45

Gln Asn Tyr Arg Gln Phe Cys Arg
    50                  55

<210> SEQ ID NO 305
<211> LENGTH: 171
<212> TYPE: DNA
<213> ORGANISM: Bacillus subtilis

<400> SEQUENCE: 305

```
atggaaaagc tatttaaaga agttaaacta gaggaactcg aaaaccaaaa aggtagtgga      60
ttaggaaaag ctcagtgtgc tgcgttgtgg ctacaatgtg ctagtggcgg tacaattggt     120
tgtggtggcg agctgttgc ttgtcaaaac tatcgtcaat tctgcagata a               171
```

<210> SEQ ID NO 306
<211> LENGTH: 56
<212> TYPE: PRT
<213> ORGANISM: Bacillus subtilis

<400> SEQUENCE: 306

```
Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45

Thr Cys Asn Cys Lys Ile Ser Lys
    50                  55
```

<210> SEQ ID NO 307
<211> LENGTH: 171
<212> TYPE: DNA
<213> ORGANISM: Bacillus subtilis

<400> SEQUENCE: 307

```
atgtcaaagt tcgatgattt cgatttggat gttgtgaaag tctctaaaca agactcaaaa      60
atcactccgc aatggaaaag tgaatcactt tgtacaccag atgtgtaac tggtgcattg     120 caaacttgct tccttcaaac actaacttgt aactgcaaaa tctctaaata a              171
```

<210> SEQ ID NO 308
<211> LENGTH: 50
<212> TYPE: PRT
<213> ORGANISM: Bacillus subtilis

<400> SEQUENCE: 308

```
Met Lys Leu Pro Val Gln Gln Val Tyr Ser Val Tyr Gly Gly Lys Asp
1               5                   10                  15

Leu Pro Lys Gly His Ser His Ser Thr Met Pro Phe Leu Ser Lys Leu
            20                  25                  30

Gln Phe Leu Thr Lys Ile Tyr Leu Leu Asp Ile His Thr Gln Pro Phe
        35                  40                  45

Phe Ile
    50
```

<210> SEQ ID NO 309
<211> LENGTH: 153
<212> TYPE: DNA
<213> ORGANISM: Bacillus subtilis

<400> SEQUENCE: 309

```
ttgaaattgc cggtgcaaca ggtctattcg gtctatgggg gtaaggatct cccaaaaggg      60
catagtcatt ctactatgcc cttttaagt aaattacaat ttttaactaa aatctacctc     120
```

-continued ttggatatac atacacaacc gtttttcatt tga    153

<210> SEQ ID NO 310
<211> LENGTH: 43
<212> TYPE: PRT
<213> ORGANISM: Bacillus subtilis

<400> SEQUENCE: 310

Met Lys Lys Ala Val Ile Val Glu Asn Lys Gly Cys Ala Thr Cys Ser
1               5                   10                  15

Ile Gly Ala Ala Cys Leu Val Asp Gly Pro Ile Pro Asp Phe Glu Ile
            20                  25                  30

Ala Gly Ala Thr Gly Leu Phe Gly Leu Trp Gly
        35                  40

<210> SEQ ID NO 311
<211> LENGTH: 132
<212> TYPE: DNA
<213> ORGANISM: Bacillus subtilis

<400> SEQUENCE: 311
atgaaaaaag ctgtcattgt agaaaacaaa ggttgtgcaa catgctcgat cggagccgct    60
tgtctagtgg acggtcctat ccctgatttt gaaattgccg gtgcaacagg tctattcggt   120
ctatgggggt aa    132

<210> SEQ ID NO 312
<211> LENGTH: 58
<212> TYPE: PRT
<213> ORGANISM: Streptococcus thermophilus

<400> SEQUENCE: 312

Met Met Asn Ala Thr Glu Asn Gln Ile Phe Val Glu Thr Val Ser Asp
1               5                   10                  15

Gln Glu Leu Glu Met Leu Ile Gly Gly Ala Asp Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55

<210> SEQ ID NO 313
<211> LENGTH: 177
<212> TYPE: DNA
<213> ORGANISM: Streptococcus thermophilus

<400> SEQUENCE: 313
atgatgaatg ctactgaaaa ccaaattttt gttgagactg tgagtgacca agaattagaa    60
atgttaattg gtggtgcaga tcgtggatgg attaagactt taacaaaaga ttgtccaaat   120
gtaatttctt caatttgtgc aggtacaatt attacagcct gtaaaaattg tgcttaa    177

<210> SEQ ID NO 314
<211> LENGTH: 64
<212> TYPE: PRT
<213> ORGANISM: Streptococcus thermophilus

<400> SEQUENCE: 314

Met Lys Gln Tyr Asn Gly Phe Glu Val Leu His Glu Leu Asp Leu Ala
1               5                   10                  15

Asn Val Thr Gly Gly Gln Ile Asn Trp Gly Ser Val Val Gly His Cys 20                  25                  30

Ile Gly Gly Ala Ile Ile Gly Gly Ala Phe Ser Gly Gly Ala Ala Ala
            35                  40                  45

Gly Val Gly Cys Leu Val Gly Ser Gly Lys Ala Ile Ile Asn Gly Leu
    50                  55                  60

<210> SEQ ID NO 315
<211> LENGTH: 195
<212> TYPE: DNA
<213> ORGANISM: Streptococcus thermophilus

<400> SEQUENCE: 315
atgaagcagt ataatggttt tgaggttcta catgaacttg acttagcaaa tgtaactggc     60
ggtcaaatta attggggatc agttgtagga cactgtatag gtggagctat tatcggaggt    120
gcattttcag gaggtgcagc ggctggagta ggatgccttg tgggagcgg aaaggcaatc    180 ataaatggat ataa                                                       195

<210> SEQ ID NO 316
<211> LENGTH: 85
<212> TYPE: PRT
<213> ORGANISM: Streptococcus thermophilus

<400> SEQUENCE: 316

Met Asn Thr Ile Thr Ile Cys Lys Phe Asp Val Leu Asp Ala Glu Leu
1               5                  10                  15

Leu Ser Thr Val Glu Gly Gly Tyr Ser Gly Lys Asp Cys Leu Lys Asp
            20                  25                  30

Met Gly Gly Tyr Ala Leu Ala Gly Ala Gly Ser Gly Ala Leu Trp Gly
        35                  40                  45

Ala Pro Ala Gly Gly Val Gly Ala Leu Pro Gly Ala Phe Val Gly Ala
    50                  55                  60

His Val Gly Ala Ile Ala Gly Gly Phe Ala Cys Met Gly Gly Met Ile
65                  70                  75                  80

Gly Asn Lys Phe Asn
                85

<210> SEQ ID NO 317
<211> LENGTH: 258
<212> TYPE: DNA
<213> ORGANISM: Streptococcus thermophilus

<400> SEQUENCE: 317
atgaatacaa taactatttg taaatttgat gttttagatg ctgaacttct ttcgacagtt     60
gagggtggat actctggtaa ggattgttta aaagacatgg gaggatatgc attggcagga    120
gctggaagtg gagctctgtg gggagctcca gcaggaggtg ttggagcact tccaggtgca    180
tttgtcggag ctcatgttgg ggcaattgca ggaggctttg catgtatggg tggaatgatt    240
ggtaataagt ttaactaa                                                  258

<210> SEQ ID NO 318
<211> LENGTH: 52
<212> TYPE: PRT
<213> ORGANISM: Bacillus cereus

<400> SEQUENCE: 318

Met Ser Glu Ile Lys Lys Ala Leu Asn Thr Leu Glu Ile Glu Asp Phe
1               5                  10                  15

```
Asp Ala Ile Glu Met Val Asp Val Asp Ala Met Pro Glu Asn Glu Ala
            20                  25                  30

Leu Glu Ile Met Gly Ala Ser Cys Thr Thr Cys Val Cys Thr Cys Ser
        35                  40                  45

Cys Cys Thr Thr
    50

<210> SEQ ID NO 319
<211> LENGTH: 159
<212> TYPE: DNA
<213> ORGANISM: Bacillus cereus

<400> SEQUENCE: 319
atgagtgaaa ttaaaaaagc attaaatacg cttgaaattg aagattttga tgcaattgaa     60
atggttgatg ttgatgctat gccagaaaac gaagcgcttg aaattatggg agcgtcatgt    120
acgacatgcg tatgtacatg cagttgttgt acaacttga                           159

<210> SEQ ID NO 320
<211> LENGTH: 47
<212> TYPE: PRT
<213> ORGANISM: Bacillus cereus

<400> SEQUENCE: 320

Met Glu Val Met Asn Asn Ala Leu Ile Thr Lys Val Asp Glu Glu Ile
1               5                   10                  15

Gly Gly Asn Ala Ala Cys Val Ile Gly Cys Ile Gly Ser Cys Val Ile
            20                  25                  30

Ser Glu Gly Ile Gly Ser Leu Val Gly Thr Ala Phe Thr Leu Gly
        35                  40                  45

<210> SEQ ID NO 321
<211> LENGTH: 144
<212> TYPE: DNA
<213> ORGANISM: Bacillus cereus

<400> SEQUENCE: 321
atggaagtta tgaacaatgc tttaattaca aaagtagatg aggagattgg aggaaacgct     60
gcttgtgtaa ttggttgtat tggcagttgc gtaattagtg aaggaattgg ttcacttgta    120
ggaacagcat ttactttagg ttaa                                           144

<210> SEQ ID NO 322
<211> LENGTH: 49
<212> TYPE: PRT
<213> ORGANISM: Bacillus cereus

<400> SEQUENCE: 322

Met Glu Val Leu Asn Lys Gln Asn Val Asn Ile Ile Pro Glu Ser Glu
1               5                   10                  15

Glu Val Gly Gly Trp Val Ala Cys Val Gly Ala Cys Gly Thr Val Cys
            20                  25                  30

Leu Ala Ser Gly Gly Val Gly Thr Glu Phe Ala Ala Ala Ser Tyr Phe
        35                  40                  45

Leu

<210> SEQ ID NO 323
<211> LENGTH: 150
<212> TYPE: DNA
<213> ORGANISM: Bacillus cereus
```

-continued

<400> SEQUENCE: 323

```
atggaagttt taaacaaaca aaatgtaaat attattccag aatctgaaga agtaggtgga    60
tgggtagcat gtgttggagc atgtggtaca gtatgtcttg ctagtggtgg tgttggaaca   120
gagtttgcag ctgcatctta tttcctataa                                   150
```

<210> SEQ ID NO 324
<211> LENGTH: 40
<212> TYPE: PRT
<213> ORGANISM: Bacillus thuringiensis

<400> SEQUENCE: 324

```
Met Glu Thr Pro Val Val Gln Pro Arg Asp Trp Thr Cys Trp Ser Cys
1               5                   10                  15
Leu Val Cys Ala Ala Cys Ser Val Glu Leu Leu Asn Leu Val Thr Ala
            20                  25                  30
Ala Thr Gly Ala Ser Thr Ala Ser
        35                  40
```

<210> SEQ ID NO 325
<211> LENGTH: 123
<212> TYPE: DNA
<213> ORGANISM: Bacillus thuringiensis

<400> SEQUENCE: 325

```
atggaaacac cagtagtaca accaagggat tggacttgtt ggagttgctt agtatgtgca    60
gcatgttctg tggaattatt aaatttagtt actgcggcaa caggggctag tactgcaagc   120
taa                                                                123
```

<210> SEQ ID NO 326
<211> LENGTH: 42
<212> TYPE: PRT
<213> ORGANISM: Rhizobium leguminosarum bv. trifolii

<400> SEQUENCE: 326

```
Met Asp Asn Lys Val Ala Lys Asn Val Glu Val Lys Lys Gly Ser Ile
1               5                   10                  15
Lys Ala Thr Phe Lys Ala Ala Val Leu Lys Ser Lys Thr Lys Val Asp
            20                  25                  30
Ile Gly Gly Ser Arg Gln Gly Cys Val Ala
        35                  40
```

<210> SEQ ID NO 327
<211> LENGTH: 129
<212> TYPE: DNA
<213> ORGANISM: Rhizobium leguminosarum bv. trifolii

<400> SEQUENCE: 327

```
atggataaca aggttgcgaa gaatgtcgaa gtgaagaagg gctccatcaa ggcgaccttc    60
aaggctgctg ttctgaagtc gaagacgaag gtcgacatcg aggtagccg tcagggctgc   120
gtcgcttaa                                                          129
```

<210> SEQ ID NO 328
<211> LENGTH: 70
<212> TYPE: PRT
<213> ORGANISM: Streptococcus uberis

<400> SEQUENCE: 328

```
Met Asn Thr Ile Glu Lys Phe Glu Asn Ile Lys Leu Phe Ser Leu Lys
```

```
 1               5                  10                 15
Lys Ile Ile Gly Gly Lys Thr Val Asn Tyr Gly Asn Gly Leu Tyr Cys
            20                 25                 30

Asn Gln Lys Lys Cys Trp Val Asn Trp Ser Glu Thr Ala Thr Thr Ile
            35                 40                 45

Val Asn Ser Ile Met Asn Gly Leu Thr Gly Gly Asn Ala Gly Trp
        50                 55                 60

His Ser Gly Gly Arg Ala
65              70
```

<210> SEQ ID NO 329
<211> LENGTH: 213
<212> TYPE: DNA
<213> ORGANISM: Streptococcus uberis

<400> SEQUENCE: 329

```
atgaatacaa ttgaaaaatt tgaaatatt  aaactttttt cactaaagaa aattatcggt      60
ggcaaaactg taaattatgg taatggcctt tattgtaacc aaaaaaaatg ctgggtaaac     120
tggtcagaaa ctgctacaac aatagtaaat aattccatca tgaacgggct cacaggtggt     180
aatgcgggtt ggcactcagg cgggagagca taa                                  213
```

<210> SEQ ID NO 330
<211> LENGTH: 76
<212> TYPE: PRT
<213> ORGANISM: Streptococcus uberis

<400> SEQUENCE: 330

```
Met Asp Ile Leu Leu Glu Leu Ala Gly Tyr Thr Gly Ile Ala Ser Gly
1               5                  10                 15

Thr Ala Lys Lys Val Val Asp Ala Ile Asp Lys Gly Ala Ala Ala Phe
            20                 25                 30

Val Ile Ile Ser Ile Ile Ser Thr Val Ile Ser Ala Gly Ala Leu Gly
        35                 40                 45

Ala Val Ser Ala Ser Ala Asp Phe Ile Ile Leu Thr Val Lys Asn Tyr
    50                 55                 60

Ile Ser Arg Asn Leu Lys Ala Gln Ala Val Ile Trp
65              70                 75
```

<210> SEQ ID NO 331
<211> LENGTH: 231
<212> TYPE: DNA
<213> ORGANISM: Streptococcus uberis

<400> SEQUENCE: 331

```
atggacattt tattagaact cgcaggatat actgggatag cctcaggtac tgcaaaaaaa      60
gttgttgatg ccattgataa aggagctgca gcctttgtta ttatttcaat tatctcaaca     120
gtaattagtg cgggagcatt gggagcagtt tcagcctcag ctgatttat  tattttaact     180
gtaaaaaatt acattagtag aaatttaaaa gcacaagctg tcatttggta a              231
```

<210> SEQ ID NO 332
<211> LENGTH: 64
<212> TYPE: PRT
<213> ORGANISM: Clostridium perfringens

<400> SEQUENCE: 332

```
Met Asp Ser Glu Leu Phe Lys Leu Met Ala Thr Gln Gly Ala Phe Ala
1               5                  10                 15
```

Ile Leu Phe Ser Tyr Leu Leu Phe Tyr Val Leu Lys Glu Asn Ser Lys
            20                  25                  30

Arg Glu Asp Lys Tyr Gln Asn Ile Ile Glu Glu Leu Thr Glu Leu Leu
        35                  40                  45

Pro Lys Ile Lys Glu Asp Val Glu Asp Ile Lys Glu Lys Leu Asn Lys
    50                  55                  60

<210> SEQ ID NO 333
<211> LENGTH: 195
<212> TYPE: DNA
<213> ORGANISM: Clostridium perfringens

<400> SEQUENCE: 333
atggatagtg aattatttaa gttaatggca acacaaggag cctttgcaat attattttcg 60
tatttattgt tttatgtttt aaaagagaat agtaaaagag aagataagta tcaaaatata 120
atagaggagc ttacagaatt attgccaaaa ataaaagaag atgtagaaga tataaaagaa 180
aaacttaata aatag 195

<210> SEQ ID NO 334
<211> LENGTH: 47
<212> TYPE: PRT
<213> ORGANISM: Micrococcus varians

<400> SEQUENCE: 334

Met Thr Asn Ala Phe Gln Ala Leu Asp Glu Val Thr Asp Ala Glu Leu
1 5 10 15

Asp Ala Ile Leu Gly Gly Gly Ser Gly Val Ile Pro Thr Ile Ser His
20 25 30

Glu Cys His Met Asn Ser Phe Gln Phe Val Phe Thr Cys Cys Ser
35 40 45

<210> SEQ ID NO 335
<211> LENGTH: 144
<212> TYPE: DNA
<213> ORGANISM: Micrococcus varians

<400> SEQUENCE: 335
atgacgaacg catttcaggc actggacgaa gtcacggacg ccgagctcga cgccatcctt 60
ggcgggggca gtggtgttat tcccacgatc agccacgagt gccacatgaa ctccttccag 120
ttcgtgttca cctgctgctc ctga 144

<210> SEQ ID NO 336
<211> LENGTH: 285
<212> TYPE: PRT
<213> ORGANISM: Streptococcus equi subsp. zooepidemicus

<400> SEQUENCE: 336

Met Lys Arg Ile Phe Phe Ala Phe Leu Ser Leu Cys Leu Phe Ile Phe
1 5 10 15

Gly Thr Gln Thr Val Ser Ala Ala Thr Tyr Thr Arg Pro Leu Asp Thr
20 25 30

Gly Asn Ile Thr Thr Gly Phe Asn Gly Tyr Pro Gly His Val Gly Val
35 40 45

Asp Tyr Ala Val Pro Val Gly Thr Pro Val Arg Ala Val Ala Asn Gly
50 55 60

Thr Val Lys Phe Ala Gly Asn Gly Ala Asn His Pro Trp Met Leu Trp
65 70 75 80

```
Met Ala Gly Asn Cys Val Leu Ile Gln His Ala Asp Gly Met His Thr
                85                  90                  95
Gly Tyr Ala His Leu Ser Lys Ile Ser Val Ser Thr Asp Ser Thr Val
            100                 105                 110
Lys Gln Gly Gln Ile Ile Gly Tyr Thr Gly Ala Thr Gly Gln Val Thr
        115                 120                 125
Gly Pro His Leu His Phe Glu Met Leu Pro Ala Asn Pro Asn Trp Gln
    130                 135                 140
Asn Gly Phe Ser Gly Arg Ile Asp Pro Thr Gly Tyr Ile Ala Asn Ala
145                 150                 155                 160
Pro Val Phe Asn Gly Thr Thr Pro Thr Glu Pro Thr Thr Pro Thr Thr
                165                 170                 175
Asn Leu Lys Ile Tyr Lys Val Asp Asp Leu Gln Lys Ile Asn Gly Ile
            180                 185                 190
Trp Gln Val Arg Asn Asn Ile Leu Val Pro Thr Asp Phe Thr Trp Val
        195                 200                 205
Asp Asn Gly Ile Ala Ala Asp Asp Val Ile Glu Val Thr Ser Asn Gly
    210                 215                 220
Thr Arg Thr Ser Asp Gln Val Leu Gln Lys Gly Gly Tyr Phe Val Ile
225                 230                 235                 240
Asn Pro Asn Asn Val Lys Ser Val Gly Thr Pro Met Lys Gly Ser Gly
                245                 250                 255
Gly Leu Ser Trp Ala Gln Val Asn Phe Thr Thr Gly Gly Asn Val Trp
            260                 265                 270
Leu Asn Thr Thr Ser Lys Asp Asn Leu Leu Tyr Gly Lys
        275                 280                 285

<210> SEQ ID NO 337
<211> LENGTH: 858
<212> TYPE: DNA
<213> ORGANISM: Streptococcus equi subsp. zooepidemicus

<400> SEQUENCE: 337
atgaaacgta tattttttgc tttcttaagt ttatgcttat ttatattcgg aacacaaacg      60
gtatctgcag ctacttatac tcggccatta gatacgggaa atatcactac agggtttaac     120
ggatacccctg tcatgttgg agtcgattat gcagtacccg ttggaactcc ggttagagca     180
gttgcaaatg gtacagtcaa atttgcaggt aatggggcta atcacccatg gatgctttgg     240
atggctggaa actgtgttct aattcaacat gctgacggga tgcatactgg atatgcacac     300
ttatcaaaaa tttcagttag cacagatagt acagttaaac aaggacaaat cataggttat     360
actggtgcca ccggccaagt taccggtcca catttgcatt ttgaaatgtt gccagcaaat     420
cctaactggc aaaatggttt ttctggaaga atagatccaa ccggatacat cgctaatgcc     480
cctgtattta atggaacaac acctacagaa cctactactc ctacaacaaa tttaaaaatc     540
tataaagttg atgatttaca aaaaattaat ggtatttggc aagtaagaaa taacatactt     600
gtaccaactg atttcacatg ggttgataat ggaattgcag cagatgatgt aattgaagta     660
actagcaatg gaacaagaac ctctgaccaa gttcttcaaa aggtggtta ttttgtcatc     720
aatcctaata atgttaaaag tgttggaact ccgatgaaag gtagtggtgg tctatcttgg     780
gctcaagtaa actttacaac aggtggaaat gtctggttaa atactactag caaagacaac     840
ttactttacg gaaaataa                                                    858
```

<210> SEQ ID NO 338
<211> LENGTH: 45
<212> TYPE: PRT
<213> ORGANISM: Myxococcus fulvus

<400> SEQUENCE: 338

Ala Asn Cys Ser Cys Ser Thr Ala Ser Asp Tyr Cys Pro Ile Leu Thr
1               5                   10                  15

Phe Cys Thr Thr Gly Thr Ala Cys Ser Tyr Thr Pro Thr Gly Cys Gly
            20                  25                  30

Thr Gly Trp Val Tyr Cys Ala Cys Asn Gly Asn Phe Tyr
        35                  40                  45

<210> SEQ ID NO 339
<211> LENGTH: 135
<212> TYPE: DNA
<213> ORGANISM: Artificial Sequence
<220> FEATURE:
<223> OTHER INFORMATION: Polynucleotide encoding the polypeptide of SEQ
      ID NO: 338

<400> SEQUENCE: 339
gcgaactgca gctgcagcac cgcgagcgat tattgcccga ttctgacctt ttgcaccacc     60
ggcaccgcgt gcagctatac cccgaccggc tgcggcaccg gctgggtgta ttgcgcgtgc    120
aacggcaact tttat                                                     135

<210> SEQ ID NO 340
<211> LENGTH: 19
<212> TYPE: PRT
<213> ORGANISM: Streptomyces griseoluteus

<400> SEQUENCE: 340

Cys Ala Asn Ser Cys Ser Tyr Gly Pro Leu Thr Trp Ser Cys Asp Gly
1               5                   10                  15

Asn Thr Lys

<210> SEQ ID NO 341
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 340

<400> SEQUENCE: 341
tgcgcgaaca gctgcagcta tggcccgctg acctggagct gcgatggcaa caccaaa       57

<210> SEQ ID NO 342
<211> LENGTH: 19
<212> TYPE: PRT
<213> ORGANISM: Streptoverticillium griseoverticillatum

<400> SEQUENCE: 342

Cys Lys Gln Ser Cys Ser Phe Gly Pro Phe Thr Phe Val Cys Asp Gly
1               5                   10                  15

Asn Thr Lys

<210> SEQ ID NO 343
<211> LENGTH: 57
<212> TYPE: DNA
<213> ORGANISM: Artificial Sequence
<220> FEATURE:
<223> OTHER INFORMATION: Polynucleotide encoding the polypeptide of SEQ -continued

ID NO: 342

<400> SEQUENCE: 343
tgcaaacaga gctgcagctt tggcccgttt acctttgtgt gcgatggcaa caccaaa    57

<210> SEQ ID NO 344
<211> LENGTH: 7
<212> TYPE: PRT
<213> ORGANISM: Carnobacterium sp.

<400> SEQUENCE: 344

Gly Ser Glu Ile Gln Pro Arg
1               5

<210> SEQ ID NO 345
<211> LENGTH: 21
<212> TYPE: DNA
<213> ORGANISM: Artificial Sequence
<220> FEATURE:
<223> OTHER INFORMATION: Polynucleotide encoding the polypeptide of SEQ
      ID NO: 344

<400> SEQUENCE: 345
ggcagcgaaa ttcagccgcg c                                            21

<210> SEQ ID NO 346
<211> LENGTH: 39
<212> TYPE: PRT
<213> ORGANISM: Lactococcus lactis subsp. lactis

<400> SEQUENCE: 346

Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
        35

<210> SEQ ID NO 347
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 346

<400> SEQUENCE: 347
ggcacctggg atgatattgg ccagggcatt ggccgcgtgg cgtattgggt gggcaaagcg    60
atgggcaaca tgagcgatgt gaaccaggcg agccgcatta accgcaaaaa aaaacat     117

<210> SEQ ID NO 348
<211> LENGTH: 35
<212> TYPE: PRT
<213> ORGANISM: Lactococcus lactis subsp. lactis

<400> SEQUENCE: 348

Lys Lys Trp Gly Trp Leu Ala Trp Val Asp Pro Ala Tyr Glu Phe Ile
1               5                   10                  15

Lys Gly Phe Gly Lys Gly Ala Ile Lys Glu Gly Asn Lys Asp Lys Trp
            20                  25                  30

Lys Asn Ile
        35

```
<210> SEQ ID NO 349
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
      ID NO: 348

<400> SEQUENCE: 349
aaaaaatggg gctggctggc gtgggtggat ccggcgtatg aatttattaa aggctttggc      60
aaaggcgcga ttaaagaagg caacaaagat aaatggaaaa acatt                    105

<210> SEQ ID NO 350
<211> LENGTH: 19
<212> TYPE: PRT
<213> ORGANISM: Streptomyces sp.

<400> SEQUENCE: 350

Cys Val Gln Ser Cys Ser Phe Gly Pro Leu Thr Trp Ser Cys Asp Gly
1               5                   10                  15

Asn Thr Lys

<210> SEQ ID NO 351
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 350

<400> SEQUENCE: 351
tgcgtgcaga gctgcagctt tggcccgctg acctggagct gcgatggcaa caccaaa        57

<210> SEQ ID NO 352
<211> LENGTH: 19
<212> TYPE: PRT
<213> ORGANISM: Actinoplanes liguriae

<400> SEQUENCE: 352

Ser Ser Gly Trp Val Cys Thr Leu Thr Ile Glu Cys Gly Thr Val Ile
1               5                   10                  15

Cys Ala Cys

<210> SEQ ID NO 353
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 352

<400> SEQUENCE: 353
agcagcggct gggtgtgcac cctgaccatt gaatgcggca ccgtgatttg cgcgtgc        57

<210> SEQ ID NO 354
<211> LENGTH: 38
<212> TYPE: PRT
<213> ORGANISM: Lactobacillus curvatus
<220> FEATURE:
<221> NAME/KEY: VARIANT
<222> LOCATION: 34
<223> OTHER INFORMATION: Xaa = any amino acid
<220> FEATURE:
<221> NAME/KEY: VARIANT
<222> LOCATION: 37
```

<223> OTHER INFORMATION: Xaa = any amino acid

<400> SEQUENCE: 354

Tyr Thr Ala Lys Gln Cys Leu Gln Ala Ile Gly Ser Cys Gly Ile Ala
1               5                   10                  15

Gly Thr Gly Ala Gly Ala Ala Gly Gly Pro Ala Gly Ala Phe Val Gly
            20                  25                  30

Ala Xaa Val Val Xaa Ile
        35

<210> SEQ ID NO 355
<211> LENGTH: 114
<212> TYPE: DNA
<213> ORGANISM: Artificial Sequence
<220> FEATURE:
<223> OTHER INFORMATION: Polynucleotide encoding the polypeptide of SEQ
      ID NO: 354
<220> FEATURE:
<221> NAME/KEY: misc_feature
<222> LOCATION: (100)..(100)
<223> OTHER INFORMATION: n=a, g, c, or t
<220> FEATURE:
<221> NAME/KEY: misc_feature
<222> LOCATION: (100)..(102)
<223> OTHER INFORMATION: triplet encoding any amino acid
<220> FEATURE:
<221> NAME/KEY: misc_feature
<222> LOCATION: (101)..(101)
<223> OTHER INFORMATION: n=a, g, c, or t
<220> FEATURE:
<221> NAME/KEY: misc_feature
<222> LOCATION: (102)..(102)
<223> OTHER INFORMATION: n=a, g, c, or t
<220> FEATURE:
<221> NAME/KEY: misc_feature
<222> LOCATION: (109)..(109)
<223> OTHER INFORMATION: n=a, g, c, or t
<220> FEATURE:
<221> NAME/KEY: misc_feature
<222> LOCATION: (109)..(111)
<223> OTHER INFORMATION: triplet encoding any amino acid
<220> FEATURE:
<221> NAME/KEY: misc_feature
<222> LOCATION: (110)..(110)
<223> OTHER INFORMATION: n=a, g, c, or t
<220> FEATURE:
<221> NAME/KEY: misc_feature
<222> LOCATION: (111)..(111)
<223> OTHER INFORMATION: n=a, g, c, or t

<400> SEQUENCE: 355
tataccgcga aacagtgcct gcaggcgatt ggcagctgcg gcattgcggg caccggcgcg      60
ggcgcggcgg gcggcccggc gggcgcgttt gtgggcgcgn nngtggtgnn natt           114

<210> SEQ ID NO 356
<211> LENGTH: 42
<212> TYPE: PRT
<213> ORGANISM: Lactobacillus sakei
<220> FEATURE:
<221> NAME/KEY: VARIANT
<222> LOCATION: 32
<223> OTHER INFORMATION: Xaa = any amino acid

<400> SEQUENCE: 356

Thr Lys Tyr Tyr Gly Asn Gly Val Tyr Cys Asn Ser Lys Lys Cys Trp
1               5                   10                  15

Val Asp Trp Gly Gln Ala Ala Gly Gly Ile Gly Gln Thr Val Val Xaa
            20                  25                  30

Gly Trp Leu Gly Gly Ala Ile Pro Gly Lys

<210> SEQ ID NO 357
<211> LENGTH: 126
<212> TYPE: DNA
<213> ORGANISM: Artificial Sequence
<220> FEATURE:
<223> OTHER INFORMATION: Polynucleotide encoding the polypeptide of SEQ
      ID NO: 356
<220> FEATURE:
<221> NAME/KEY: misc_feature
<222> LOCATION: (94)..(94)
<223> OTHER INFORMATION: n=a, g, c, or t
<220> FEATURE:
<221> NAME/KEY: misc_feature
<222> LOCATION: (94)..(96)
<223> OTHER INFORMATION: triplet encoding any amino acid
<220> FEATURE:
<221> NAME/KEY: misc_feature
<222> LOCATION: (95)..(95)
<223> OTHER INFORMATION: n=a, g, c, or t
<220> FEATURE:
<221> NAME/KEY: misc_feature
<222> LOCATION: (96)..(96)
<223> OTHER INFORMATION: n=a, g, c, or t

<400> SEQUENCE: 357
accaaatatt atggcaacgg cgtgtattgc aacagcaaaa aatgctgggt ggattggggc      60
caggcggcgg gcggcattgg ccagaccgtg gtgnnnggct ggctgggcgg cgcgattccg     120
ggcaaa                                                                126

<210> SEQ ID NO 358
<211> LENGTH: 22
<212> TYPE: PRT
<213> ORGANISM: Streptococcus mutans

<400> SEQUENCE: 358

Phe Lys Ser Trp Ser Phe Cys Thr Pro Gly Cys Ala Lys Thr Gly Ser
1               5                   10                  15

Phe Asn Ser Tyr Cys Cys
            20

<210> SEQ ID NO 359
<211> LENGTH: 132
<212> TYPE: DNA
<213> ORGANISM: Artificial Sequence
<220> FEATURE:
<223> OTHER INFORMATION: Polynucleotide encoding the polypeptide of SEQ
      ID NO: 358

<400> SEQUENCE: 359
tttaaaagct ggagcttttg caccccgggc tgcgcgaaaa ccggcagctt taacagctat      60
tgctgcttta aaagctggag cttttgcacc ccgggctgcg cgaaaaccgg cagctttaac     120
agctattgct gc                                                         132

<210> SEQ ID NO 360
<211> LENGTH: 43
<212> TYPE: PRT
<213> ORGANISM: Enterococcus mundtii

<400> SEQUENCE: 360

Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ser Ala Ala Asn
            20                  25                  30

Leu Ala Thr Gly Gly Ala Ala Gly Trp Ser Lys
        35                  40

<210> SEQ ID NO 361
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 360

<400> SEQUENCE: 361
aaatattatg gcaacggcgt gagctgcaac aaaaaaggct gcagcgtgga ttggggcaaa        60
gcgattggca ttattggcaa caacagcgcg gcgaacctgg cgaccggcgg cgcggcgggc       120
tggagcaaa                                                              129

<210> SEQ ID NO 362
<211> LENGTH: 41
<212> TYPE: PRT
<213> ORGANISM: Lactobacillus sakei
<220> FEATURE:
<221> NAME/KEY: VARIANT
<222> LOCATION: 9, 14, 33, 37
<223> OTHER INFORMATION: Xaa = any amino acid

<400> SEQUENCE: 362

Lys Tyr Tyr Gly Asn Gly Val His Xaa Gly Lys His Ser Xaa Thr Val
1               5                   10                  15

Asp Trp Gly Thr Ala Ile Gly Asn Ile Gly Asn Asn Ala Ala Ala Asn
            20                  25                  30

Xaa Ala Thr Gly Xaa Asn Ala Gly Gly
        35                  40

<210> SEQ ID NO 363
<211> LENGTH: 123
<212> TYPE: DNA
<213> ORGANISM: Artificial Sequence
<220> FEATURE:
<223> OTHER INFORMATION: Polynucleotide encoding the polypeptide of SEQ
      ID NO: 362
<220> FEATURE:
<221> NAME/KEY: misc_feature
<222> LOCATION: (25)..(25)
<223> OTHER INFORMATION: n=a, g, c, or t
<220> FEATURE:
<221> NAME/KEY: misc_feature
<222> LOCATION: (25)..(27)
<223> OTHER INFORMATION: triplet encoding any amino acid
<220> FEATURE:
<221> NAME/KEY: misc_feature
<222> LOCATION: (26)..(26)
<223> OTHER INFORMATION: n=a, g, c, or t
<220> FEATURE:
<221> NAME/KEY: misc_feature
<222> LOCATION: (27)..(27)
<223> OTHER INFORMATION: n=a, g, c, or t
<220> FEATURE:
<221> NAME/KEY: misc_feature
<222> LOCATION: (40)..(40)
<223> OTHER INFORMATION: n=a, g, c, or t
<220> FEATURE:
<221> NAME/KEY: misc_feature
<222> LOCATION: (40)..(42)
<223> OTHER INFORMATION: triplet encoding any amino acid
<220> FEATURE:
<221> NAME/KEY: misc_feature
<222> LOCATION: (41)..(41)
<223> OTHER INFORMATION: n=a, g, c, or t
<220> FEATURE:

```
<221> NAME/KEY: misc_feature
<222> LOCATION: (42)..(42)
<223> OTHER INFORMATION: n=a, g, c, or t
<220> FEATURE:
<221> NAME/KEY: misc_feature
<222> LOCATION: (97)..(97)
<223> OTHER INFORMATION: n=a, g, c, or t
<220> FEATURE:
<221> NAME/KEY: misc_feature
<222> LOCATION: (97)..(99)
<223> OTHER INFORMATION: triplet encoding any amino acid
<220> FEATURE:
<221> NAME/KEY: misc_feature
<222> LOCATION: (98)..(98)
<223> OTHER INFORMATION: n=a, g, c, or t
<220> FEATURE:
<221> NAME/KEY: misc_feature
<222> LOCATION: (99)..(99)
<223> OTHER INFORMATION: n=a, g, c, or t
<220> FEATURE:
<221> NAME/KEY: misc_feature
<222> LOCATION: (109)..(109)
<223> OTHER INFORMATION: n=a, g, c, or t
<220> FEATURE:
<221> NAME/KEY: misc_feature
<222> LOCATION: (109)..(111)
<223> OTHER INFORMATION: triplet encoding any amino acid
<220> FEATURE:
<221> NAME/KEY: misc_feature
<222> LOCATION: (110)..(110)
<223> OTHER INFORMATION: n=a, g, c, or t
<220> FEATURE:
<221> NAME/KEY: misc_feature
<222> LOCATION: (111)..(111)
<223> OTHER INFORMATION: n=a, g, c, or t

<400> SEQUENCE: 363
aaatattatg gcaacggcgt gcatnnnggc aaacatagcn nnaccgtgga ttggggcacc      60
gcgattggca acattggcaa caacgcggcg gcgaacnnng cgaccggcnn naacgcgggc     120
ggc                                                                  123

<210> SEQ ID NO 364
<211> LENGTH: 31
<212> TYPE: PRT
<213> ORGANISM: Lactobacillus paracasei

<400> SEQUENCE: 364

Gly Met Ser Gly Tyr Ile Gln Gly Ile Pro Asp Phe Leu Lys Gly Tyr
1               5                   10                  15

Leu His Gly Ile Ser Ala Ala Asn Lys His Lys Lys Gly Arg Leu
            20                  25                  30

<210> SEQ ID NO 365
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 364

<400> SEQUENCE: 365
ggcatgagcg gctatattca gggcattccg gattttctga aaggctatct gcatggcatt      60
agcgcggcga acaaacataa aaaaggccgc ctg                                   93

<210> SEQ ID NO 366
<211> LENGTH: 31
<212> TYPE: PRT
<213> ORGANISM: Leuconostoc mesenteroides
```

<400> SEQUENCE: 366

Lys Gly Lys Gly Phe Trp Ser Trp Ala Ser Lys Ala Thr Ser Trp Leu
1               5                   10                  15

Thr Gly Pro Gln Gln Pro Gly Ser Pro Leu Leu Lys Lys His Arg
            20                  25                  30

<210> SEQ ID NO 367
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 366

<400> SEQUENCE: 367
aaaggcaaag gcttttggag ctgggcgagc aaagcgacca gctggctgac cggcccgcag      60
cagccgggca gcccgctgct gaaaaaacat cgc                                  93

<210> SEQ ID NO 368
<211> LENGTH: 43
<212> TYPE: PRT
<213> ORGANISM: Leuconostoc mesenteroides

<400> SEQUENCE: 368

Lys Asn Tyr Gly Asn Gly Val His Cys Thr Lys Lys Gly Cys Ser Val
1               5                   10                  15

Asp Trp Gly Tyr Ala Trp Thr Asn Ile Ala Asn Asn Ser Val Met Asn
            20                  25                  30

Gly Leu Thr Gly Gly Asn Ala Gly Trp His Asn
        35                  40

<210> SEQ ID NO 369
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 368

<400> SEQUENCE: 369
aaaaactatg gcaacggcgt gcattgcacc aaaaaaggct gcagcgtgga ttggggctat      60
gcgtggacca acattgcgaa caacagcgtg atgaacggcc tgaccggcgg caacgcgggc     120
tggcataac                                                            129

<210> SEQ ID NO 370
<211> LENGTH: 47
<212> TYPE: PRT
<213> ORGANISM: Bacillus subtilis

<400> SEQUENCE: 370

Ala Ile Lys Leu Val Gln Ser Pro Asn Gly Asn Phe Ala Ala Ser Phe
1               5                   10                  15

Val Leu Asp Gly Thr Lys Trp Ile Phe Lys Ser Lys Tyr Tyr Asp Ser
            20                  25                  30

Ser Lys Gly Tyr Trp Val Gly Ile Tyr Glu Val Trp Asp Arg Lys
        35                  40                  45

<210> SEQ ID NO 371
<211> LENGTH: 141
<212> TYPE: DNA
<213> ORGANISM: Artificial Sequence

```
<220> FEATURE:
<223> OTHER INFORMATION: Polynucleotide encoding the polypeptide of SEQ
      ID NO: 370

<400> SEQUENCE: 371
gcgattaaac tggtgcagag cccgaacggc aactttgcgg cgagctttgt gctggatggc    60
accaaatgga ttttaaaag caaatattat gatagcagca aaggctattg ggtgggcatt   120
tatgaagtgt gggatcgcaa a                                             141

<210> SEQ ID NO 372
<211> LENGTH: 12
<212> TYPE: PRT
<213> ORGANISM: Bacillus licheniformis
<220> FEATURE:
<221> NAME/KEY: VARIANT
<222> LOCATION: 7
<223> OTHER INFORMATION: Xaa = any amino acid

<400> SEQUENCE: 372

Ile Ser Leu Glu Ile Cys Xaa Ile Phe His Asp Asn
1               5                   10

<210> SEQ ID NO 373
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 372
<220> FEATURE:
<221> NAME/KEY: misc_feature
<222> LOCATION: (19)..(19)
<223> OTHER INFORMATION: n=a, g, c, or t
<220> FEATURE:
<221> NAME/KEY: misc_feature
<222> LOCATION: (19)..(21)
<223> OTHER INFORMATION: triplet encoding any amino acid
<220> FEATURE:
<221> NAME/KEY: misc_feature
<222> LOCATION: (20)..(20)
<223> OTHER INFORMATION: n=a, g, c, or t
<220> FEATURE:
<221> NAME/KEY: misc_feature
<222> LOCATION: (21)..(21)
<223> OTHER INFORMATION: n=a, g, c, or t

<400> SEQUENCE: 373
attagcctgg aaatttgcnn natttttcat gataac                             36

<210> SEQ ID NO 374
<211> LENGTH: 37
<212> TYPE: PRT
<213> ORGANISM: Lactococcus lactis subsp. lactis

<400> SEQUENCE: 374

Thr Ser Tyr Gly Asn Gly Val His Cys Asn Lys Ser Lys Cys Trp Ile
1               5                   10                  15

Asp Val Ser Glu Leu Glu Thr Tyr Lys Ala Gly Thr Val Ser Asn Pro
            20                  25                  30

Lys Asp Ile Leu Trp
        35

<210> SEQ ID NO 375
<211> LENGTH: 111
<212> TYPE: DNA
<213> ORGANISM: Artificial Sequence
<220> FEATURE:
```

```
<223> OTHER INFORMATION: Polynucleotide encoding the polypeptide of SEQ
      ID NO: 374

<400> SEQUENCE: 375
accagctatg gcaacggcgt gcattgcaac aaaagcaaat gctggattga tgtgagcgaa       60
ctggaaacct ataaagcggg caccgtgagc aacccgaaag atattctgtg g               111

<210> SEQ ID NO 376
<211> LENGTH: 9
<212> TYPE: PRT
<213> ORGANISM: Serratia plymuthica

<400> SEQUENCE: 376

Asp Tyr His His Gly Val Arg Val Leu
1               5

<210> SEQ ID NO 377
<211> LENGTH: 27
<212> TYPE: DNA
<213> ORGANISM: Artificial Sequence
<220> FEATURE:
<223> OTHER INFORMATION: Polynucleotide encoding the polypeptide of SEQ
      ID NO: 376

<400> SEQUENCE: 377
gattatcatc atggcgtgcg cgtgctg                                           27

<210> SEQ ID NO 378
<211> LENGTH: 15
<212> TYPE: PRT
<213> ORGANISM: Halobacterium sp.

<400> SEQUENCE: 378

Asp Ile Asp Ile Thr Gly Cys Ser Ala Cys Lys Tyr Ala Ala Gly
1               5                   10                  15

<210> SEQ ID NO 379
<211> LENGTH: 45
<212> TYPE: DNA
<213> ORGANISM: Artificial Sequence
<220> FEATURE:
<223> OTHER INFORMATION: Polynucleotide encoding the polypeptide of SEQ
      ID NO: 378

<400> SEQUENCE: 379
gatattgata ttaccggctg cagcgcgtgc aaatatgcgg cgggc                       45

<210> SEQ ID NO 380
<211> LENGTH: 12
<212> TYPE: PRT
<213> ORGANISM: Bacillus subtilis
<220> FEATURE:
<221> NAME/KEY: VARIANT
<222> LOCATION: 1, 2, 6
<223> OTHER INFORMATION: Xaa = any amino acid

<400> SEQUENCE: 380

Xaa Xaa Lys Glu Ile Xaa His Ile Phe His Asp Asn
1               5                   10

<210> SEQ ID NO 381
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
```

```
                ID NO: 380
<220> FEATURE:
<221> NAME/KEY: misc_feature
<222> LOCATION: (1)..(1)
<223> OTHER INFORMATION: n=a, g, c, or t
<220> FEATURE:
<221> NAME/KEY: misc_feature
<222> LOCATION: (1)..(3)
<223> OTHER INFORMATION: triplet encoding any amino acid
<220> FEATURE:
<221> NAME/KEY: misc_feature
<222> LOCATION: (2)..(2)
<223> OTHER INFORMATION: n=a, g, c, or t
<220> FEATURE:
<221> NAME/KEY: misc_feature
<222> LOCATION: (3)..(3)
<223> OTHER INFORMATION: n=a, g, c, or t
<220> FEATURE:
<221> NAME/KEY: misc_feature
<222> LOCATION: (4)..(4)
<223> OTHER INFORMATION: n=a, g, c, or t
<220> FEATURE:
<221> NAME/KEY: misc_feature
<222> LOCATION: (4)..(6)
<223> OTHER INFORMATION: triplet encoding any amino acid
<220> FEATURE:
<221> NAME/KEY: misc_feature
<222> LOCATION: (5)..(5)
<223> OTHER INFORMATION: n=a, g, c, or t
<220> FEATURE:
<221> NAME/KEY: misc_feature
<222> LOCATION: (6)..(6)
<223> OTHER INFORMATION: n=a, g, c, or t
<220> FEATURE:
<221> NAME/KEY: misc_feature
<222> LOCATION: (16)..(16)
<223> OTHER INFORMATION: n=a, g, c, or t
<220> FEATURE:
<221> NAME/KEY: misc_feature
<222> LOCATION: (16)..(18)
<223> OTHER INFORMATION: triplet encoding any amino acid
<220> FEATURE:
<221> NAME/KEY: misc_feature
<222> LOCATION: (17)..(17)
<223> OTHER INFORMATION: n=a, g, c, or t
<220> FEATURE:
<221> NAME/KEY: misc_feature
<222> LOCATION: (18)..(18)
<223> OTHER INFORMATION: n=a, g, c, or t

<400> SEQUENCE: 381
nnnnnnaaag aaattnnnca tatttttcat gataac                              36

<210> SEQ ID NO 382
<211> LENGTH: 12
<212> TYPE: PRT
<213> ORGANISM: Lactobacillus curvatus

<400> SEQUENCE: 382

Thr Pro Val Val Asn Pro Pro Phe Leu Gln Gln Thr
1               5                   10

<210> SEQ ID NO 383
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 382

<400> SEQUENCE: 383
accccggtgg tgaacccgcc gtttctgcag cagacc                              36
```

```
<210> SEQ ID NO 384
<211> LENGTH: 10
<212> TYPE: PRT
<213> ORGANISM: Lactobacillus curvatus
<220> FEATURE:
<221> NAME/KEY: VARIANT
<222> LOCATION: 10
<223> OTHER INFORMATION: Xaa = any amino acid

<400> SEQUENCE: 384

Val Ala Pro Phe Pro Glu Gln Phe Leu Xaa
1               5                   10

<210> SEQ ID NO 385
<211> LENGTH: 30
<212> TYPE: DNA
<213> ORGANISM: Artificial Sequence
<220> FEATURE:
<223> OTHER INFORMATION: Polynucleotide encoding the polypeptide of SEQ
      ID NO: 384
<220> FEATURE:
<221> NAME/KEY: misc_feature
<222> LOCATION: (28)..(28)
<223> OTHER INFORMATION: n=a, g, c, or t
<220> FEATURE:
<221> NAME/KEY: misc_feature
<222> LOCATION: (28)..(30)
<223> OTHER INFORMATION: triplet encoding any amino acid
<220> FEATURE:
<221> NAME/KEY: misc_feature
<222> LOCATION: (29)..(29)
<223> OTHER INFORMATION: n=a, g, c, or t
<220> FEATURE:
<221> NAME/KEY: misc_feature
<222> LOCATION: (30)..(30)
<223> OTHER INFORMATION: n=a, g, c, or t

<400> SEQUENCE: 385
gtggcgccgt tccggaaca gtttctgnnn                                         30

<210> SEQ ID NO 386
<211> LENGTH: 9
<212> TYPE: PRT
<213> ORGANISM: Lactobacillus curvatus

<400> SEQUENCE: 386

Asn Ile Pro Gln Leu Thr Pro Thr Pro
1               5

<210> SEQ ID NO 387
<211> LENGTH: 27
<212> TYPE: DNA
<213> ORGANISM: Artificial Sequence
<220> FEATURE:
<223> OTHER INFORMATION: Polynucleotide encoding the polypeptide of SEQ
      ID NO: 386

<400> SEQUENCE: 387
aacattccgc agctgacccc gaccccg                                           27

<210> SEQ ID NO 388
<211> LENGTH: 18
<212> TYPE: PRT
<213> ORGANISM: Bacillus thuringiensis subsp. entomocidus
<220> FEATURE:
<221> NAME/KEY: VARIANT
<222> LOCATION: 4, 7, 10
<223> OTHER INFORMATION: Xaa = any amino acid

<400> SEQUENCE: 388
```

Asp Trp Thr Xaa Trp Ser Xaa Leu Val Xaa Ala Ala Cys Ser Val Glu
1               5                   10                  15

Leu Leu

<210> SEQ ID NO 389
<211> LENGTH: 54
<212> TYPE: DNA
<213> ORGANISM: Artificial Sequence
<220> FEATURE:
<223> OTHER INFORMATION: Polynucleotide encoding the polypeptide of SEQ
      ID NO: 388
<220> FEATURE:
<221> NAME/KEY: misc_feature
<222> LOCATION: (10)..(10)
<223> OTHER INFORMATION: n=a, g, c, or t
<220> FEATURE:
<221> NAME/KEY: misc_feature
<222> LOCATION: (10)..(12)
<223> OTHER INFORMATION: triplet encoding any amino acid
<220> FEATURE:
<221> NAME/KEY: misc_feature
<222> LOCATION: (11)..(11)
<223> OTHER INFORMATION: n=a, g, c, or t
<220> FEATURE:
<221> NAME/KEY: misc_feature
<222> LOCATION: (12)..(12)
<223> OTHER INFORMATION: n=a, g, c, or t
<220> FEATURE:
<221> NAME/KEY: misc_feature
<222> LOCATION: (19)..(19)
<223> OTHER INFORMATION: n=a, g, c, or t
<220> FEATURE:
<221> NAME/KEY: misc_feature
<222> LOCATION: (19)..(21)
<223> OTHER INFORMATION: triplet encoding any amino acid
<220> FEATURE:
<221> NAME/KEY: misc_feature
<222> LOCATION: (20)..(20)
<223> OTHER INFORMATION: n=a, g, c, or t
<220> FEATURE:
<221> NAME/KEY: misc_feature
<222> LOCATION: (21)..(21)
<223> OTHER INFORMATION: n=a, g, c, or t
<220> FEATURE:
<221> NAME/KEY: misc_feature
<222> LOCATION: (28)..(28)
<223> OTHER INFORMATION: n=a, g, c, or t
<220> FEATURE:
<221> NAME/KEY: misc_feature
<222> LOCATION: (28)..(30)
<223> OTHER INFORMATION: triplet encoding any amino acid
<220> FEATURE:
<221> NAME/KEY: misc_feature
<222> LOCATION: (29)..(29)
<223> OTHER INFORMATION: n=a, g, c, or t
<220> FEATURE:
<221> NAME/KEY: misc_feature
<222> LOCATION: (30)..(30)
<223> OTHER INFORMATION: n=a, g, c, or t

<400> SEQUENCE: 389
gattggaccn nntggagcnn nctggtgnnn gcggcgtgca gcgtggaact gctg         54

<210> SEQ ID NO 390
<211> LENGTH: 30
<212> TYPE: PRT
<213> ORGANISM: Lactobacillus curvatus

<400> SEQUENCE: 390

Ala Tyr Pro Gly Asn Gly Val His Cys Gly Lys Tyr Ser Cys Thr Val
1               5                   10                  15

Asp Lys Gln Thr Ala Ile Gly Asn Ile Gly Asn Asn Ala Ala
            20                  25                  30

<210> SEQ ID NO 391
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 390

<400> SEQUENCE: 391
gcgtatccgg gcaacggcgt gcattgcggc aaatatagct gcaccgtgga taaacagacc      60
gcgattggca acattggcaa caacgcggcg                                       90

<210> SEQ ID NO 392
<211> LENGTH: 43
<212> TYPE: PRT
<213> ORGANISM: Carnobacterium divergens

<400> SEQUENCE: 392

Thr Lys Tyr Tyr Gly Asn Gly Val Tyr Cys Asn Ser Lys Lys Cys Trp
1               5                   10                  15

Val Asp Trp Gly Thr Ala Gln Gly Cys Ile Asp Val Val Ile Gly Gln
            20                  25                  30

Leu Gly Gly Gly Ile Pro Gly Lys Gly Lys Cys
        35                  40

<210> SEQ ID NO 393
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 392

<400> SEQUENCE: 393
accaaatatt atggcaacgg cgtgtattgc aacagcaaaa aatgctgggt ggattggggc      60
accgcgcagg gctgcattga tgtggtgatt ggccagctgg gcggcggcat tccgggcaaa     120
ggcaaatgc                                                             129

<210> SEQ ID NO 394
<211> LENGTH: 62
<212> TYPE: PRT
<213> ORGANISM: Enterococcus sp.

<400> SEQUENCE: 394

Asn Arg Trp Tyr Cys Asn Ser Ala Ala Gly Gly Val Gly Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
        35                  40                  45

Lys Ala Cys Lys Ser Phe Pro Gly Ser Gly Trp Ala Ser Gly
    50                  55                  60

<210> SEQ ID NO 395
<211> LENGTH: 186
<212> TYPE: DNA
<213> ORGANISM: Artificial Sequence
<220> FEATURE:
<223> OTHER INFORMATION: Polynucleotide encoding the polypeptide of SEQ
      ID NO: 394

<400> SEQUENCE: 395

```
aaccgctggt attgcaacag cgcggcgggc ggcgtgggcg gcgcggcggt gtgcggcctg      60
gcgggctatg tgggcgaagc gaaagaaaac attgcgggcg aagtgcgcaa aggctggggc     120
atggcgggcg gctttaccca taacaaagcg tgcaaaagct ttccgggcag cggctgggcg     180
agcggc                                                                186
```

<210> SEQ ID NO 396
<211> LENGTH: 39
<212> TYPE: PRT
<213> ORGANISM: Enterococcus faecium

<400> SEQUENCE: 396

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
        35

<210> SEQ ID NO 397
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 396

<400> SEQUENCE: 397

```
accaccaaaa actatggcaa cggcgtgtgc aacagcgtga actggtgcca gtgcggcaac      60
gtgtgggcga gctgcaacct ggcgaccggc tgcgcggcgt ggctgtgcaa actggcg       117
```

<210> SEQ ID NO 398
<211> LENGTH: 30
<212> TYPE: PRT
<213> ORGANISM: Paenibacillus polymyxa

<400> SEQUENCE: 398

Ala Ser Ile Ile Lys Thr Thr Ile Lys Val Ser Lys Ala Val Cys Lys
1               5                   10                  15

Thr Leu Thr Cys Ile Cys Thr Gly Ser Cys Ser Asn Cys Lys
            20                  25                  30

<210> SEQ ID NO 399
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 398

<400> SEQUENCE: 399

```
gcgagcatta ttaaaaccac cattaaagtg agcaaagcgg tgtgcaaaac cctgacctgc      60
atttgcaccg gcagctgcag caactgcaaa                                      90
```

<210> SEQ ID NO 400
<211> LENGTH: 31
<212> TYPE: PRT
<213> ORGANISM: Staphylococcus epidermidis

<400> SEQUENCE: 400

```
Ser Ala Ser Ile Val Lys Thr Thr Ile Lys Ala Ser Lys Lys Leu Cys
1               5                   10                  15

Arg Gly Phe Thr Leu Thr Cys Gly Cys His Phe Thr Gly Lys Lys
            20                  25                  30
```

<210> SEQ ID NO 401
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 400

<400> SEQUENCE: 401
agcgcgagca ttgtgaaaac caccattaaa gcgagcaaaa aactgtgccg cggctttacc      60
ctgacctgcg gctgccattt taccggcaaa aaa                                   93

<210> SEQ ID NO 402
<211> LENGTH: 43
<212> TYPE: PRT
<213> ORGANISM: Enterococcus faecium

<400> SEQUENCE: 402

```
Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ala Ala Ala Asn
            20                  25                  30

Leu Thr Thr Gly Gly Lys Ala Ala Trp Ala Cys
        35                  40
```

<210> SEQ ID NO 403
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 402

<400> SEQUENCE: 403
aaatattatg gcaacggcgt gagctgcaac aaaaaaggct gcagcgtgga ttggggcaaa      60
gcgattggca ttattggcaa caacgcggcg gcgaacctga ccaccggcgg caaagcggcg     120
tgggcgtgc                                                             129

<210> SEQ ID NO 404
<211> LENGTH: 39
<212> TYPE: PRT
<213> ORGANISM: Paenibacillus polymyxa

<400> SEQUENCE: 404

```
Ala Thr Tyr Tyr Gly Asn Gly Leu Tyr Cys Asn Lys Gln Lys His Tyr
1               5                   10                  15

Thr Trp Val Asp Trp Asn Lys Ala Ser Arg Glu Ile Gly Lys Ile Thr
            20                  25                  30

Val Asn Gly Trp Val Gln His
        35
```

<210> SEQ ID NO 405
<211> LENGTH: 117
<212> TYPE: DNA
<213> ORGANISM: Artificial Sequence
<220> FEATURE:
<223> OTHER INFORMATION: Polynucleotide encoding the polypeptide of SEQ

ID NO: 404

<400> SEQUENCE: 405
gcgacctatt atggcaacgg cctgtattgc aacaaacaga acattatac ctgggtggat        60 tggaacaaag cgagccgcga aattggcaaa attaccgtga acggctgggt gcagcat         117

<210> SEQ ID NO 406
<211> LENGTH: 35
<212> TYPE: PRT
<213> ORGANISM: Bacillus circulans

<400> SEQUENCE: 406

Val Asn Tyr Gly Asn Gly Val Ser Cys Ser Lys Thr Lys Cys Ser Val
1               5                   10                  15

Asn Trp Gly Ile Ile Thr His Gln Ala Phe Arg Val Thr Ser Gly Val
            20                  25                  30

Ala Ser Gly
        35

<210> SEQ ID NO 407
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
      ID NO: 406

<400> SEQUENCE: 407
gtgaactatg gcaacggcgt gagctgcagc aaaaccaaat gcagcgtgaa ctggggcatt        60
attacccatc aggcgtttcg cgtgaccagc ggcgtggcga gcggc                       105

<210> SEQ ID NO 408
<211> LENGTH: 30
<212> TYPE: PRT
<213> ORGANISM: Paenibacillus polymyxa

<400> SEQUENCE: 408

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30

<210> SEQ ID NO 409
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 408

<400> SEQUENCE: 409
tttgtgtatg gcaacggcgt gaccagcatt ctggtgcagg cgcagtttct ggtgaacggc        60
cagcgccgct tttttatac cccggataaa                                          90

<210> SEQ ID NO 410
<211> LENGTH: 13
<212> TYPE: PRT
<213> ORGANISM: Lactobacillus rhamnosus

<400> SEQUENCE: 410

Ala Val Pro Ala Val Arg Lys Thr Asn Glu Thr Leu Asp
1               5                   10

<210> SEQ ID NO 411
<211> LENGTH: 39
<212> TYPE: DNA
<213> ORGANISM: Artificial Sequence
<220> FEATURE:
<223> OTHER INFORMATION: Polynucleotide encoding the polypeptide of SEQ
      ID NO: 410

<400> SEQUENCE: 411
gcggtgccgg cggtgcgcaa aaccaacgaa accctggat                           39

<210> SEQ ID NO 412
<211> LENGTH: 69
<212> TYPE: PRT
<213> ORGANISM: Bacillus licheniformis

<400> SEQUENCE: 412

Met Lys Asn Ser Ala Ala Arg Glu Ala Phe Lys Gly Ala Asn His Pro
1               5                   10                  15

Ala Gly Met Val Ser Glu Glu Leu Lys Ala Leu Val Gly Gly Asn
            20                  25                  30

Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys Pro Thr Thr Lys
    50                  55                  60

Cys Thr Ser Arg Cys
65

<210> SEQ ID NO 413
<211> LENGTH: 207
<212> TYPE: DNA
<213> ORGANISM: Artificial Sequence
<220> FEATURE:
<223> OTHER INFORMATION: Polynucleotide encoding the polypeptide of SEQ
      ID NO: 412

<400> SEQUENCE: 413
atgaaaaaca gcgcggcgcg cgaagcgttt aaaggcgcga accatccggc gggcatggtg     60
agcgaagaag aactgaaagc gctggtgggc ggcaacgatg tgaacccgga aaccacccg    120 gcgaccacca gcagctggac ctgcattacc gcgggcgtga ccgtgagcgc gagcctgtgc    180
ccgaccacca atgcaccag ccgctgc                                         207

<210> SEQ ID NO 414
<211> LENGTH: 36
<212> TYPE: PRT
<213> ORGANISM: Lactobacillus plantarum

<400> SEQUENCE: 414

Lys Tyr Tyr Gly Asn Gly Leu Ser Cys Ser Lys Lys Gly Cys Thr Val
1               5                   10                  15

Asn Trp Gly Gln Ala Phe Ser Cys Gly Val Asn Arg Val Ala Thr Ala
            20                  25                  30

Gly His Gly Lys
        35

<210> SEQ ID NO 415
<211> LENGTH: 108
<212> TYPE: DNA
<213> ORGANISM: Artificial Sequence
<220> FEATURE:

<223> OTHER INFORMATION: Polynucleotide encoding the polypeptide of SEQ
ID NO: 414

<400> SEQUENCE: 415
aaatattatg gcaacggcct gagctgcagc aaaaaaggct gcaccgtgaa ctggggccag        60
gcgtttagct gcggcgtgaa ccgcgtggcg accgcgggcc atggcaaa                    108

<210> SEQ ID NO 416
<211> LENGTH: 24
<212> TYPE: PRT
<213> ORGANISM: Lactobacillus acidophilus

<400> SEQUENCE: 416

Gly Asn Pro Lys Val Ala His Cys Ala Ser Gln Ile Gly Arg Ser Thr
1               5                   10                  15

Ala Trp Gly Ala Val Ser Gly Ala
            20

<210> SEQ ID NO 417
<211> LENGTH: 72
<212> TYPE: DNA
<213> ORGANISM: Artificial Sequence
<220> FEATURE:
<223> OTHER INFORMATION: Polynucleotide encoding the polypeptide of SEQ
ID NO: 416

<400> SEQUENCE: 417
ggcaacccga aagtggcgca ttgcgcgagc cagattggcc gcagcaccgc gtggggcgcg        60
gtgagcggcg cg                                                           72

<210> SEQ ID NO 418
<211> LENGTH: 40
<212> TYPE: PRT
<213> ORGANISM: Enterococcus faecalis

<400> SEQUENCE: 418

Trp Leu Pro Pro Ala Gly Leu Leu Gly Arg Cys Gly Arg Trp Phe Arg
1               5                   10                  15

Pro Trp Leu Leu Trp Leu Gln Ser Gly Ala Gln Tyr Lys Trp Leu Gly
            20                  25                  30

Asn Leu Phe Gly Leu Gly Pro Lys
        35                  40

<210> SEQ ID NO 419
<211> LENGTH: 120
<212> TYPE: DNA
<213> ORGANISM: Artificial Sequence
<220> FEATURE:
<223> OTHER INFORMATION: Polynucleotide encoding the polypeptide of SEQ
ID NO: 418

<400> SEQUENCE: 419
tggctgccgc cggcgggcct gctgggccgc tgcggccgct ggtttcgccc gtggctgctg        60
tggctgcaga gcggcgcgca gtataaatgg ctgggcaacc tgtttggcct gggcccgaaa       120

<210> SEQ ID NO 420
<211> LENGTH: 40
<212> TYPE: PRT
<213> ORGANISM: Anabaena variabilis

<400> SEQUENCE: 420

Asn Leu Asp Gln Trp Leu Thr Glu Gln Val His Glu Phe Gln Asp Met

```
            1               5                  10                  15
Tyr Leu Glu Pro Gln Ala Ile Ser Asn Gln Asp Ile Thr Phe Lys Leu
                    20                  25                  30

Ser Asp Leu Asp Phe Ile His Asn
            35                  40
```

<210> SEQ ID NO 421
<211> LENGTH: 124
<212> TYPE: DNA
<213> ORGANISM: Anabaena variabilis

<400> SEQUENCE: 421

```
taatttagat cagtggttaa cagaacaagt tcatgagttt caagatatgt acttggaacc    60
acaagcaata tccaatcaag acattacctt caaactatct gacctagatt ttattcataa   120
ttga                                                                124
```

<210> SEQ ID NO 422
<211> LENGTH: 40
<212> TYPE: PRT
<213> ORGANISM: Nostoc sp

<400> SEQUENCE: 422

```
Asn Leu Asp Gln Trp Leu Thr Glu Gln Val His Glu Phe Gln Asp Met
1               5                   10                  15

Tyr Leu Glu Pro Gln Ala Ile Ser Asn Gln Asp Ile Thr Phe Lys Leu
                    20                  25                  30

Ser Asp Leu Asp Phe Ile His Asn
            35                  40
```

<210> SEQ ID NO 423
<211> LENGTH: 123
<212> TYPE: DNA
<213> ORGANISM: Nostoc sp

<400> SEQUENCE: 423

```
aatttagatc aatggttaac agaacaagtt catgagtttc aagatatgta cttggaacca    60
caagcaatat ccaatcaaga cattaccttc aaactgtcag acctagattt tattcataat   120
tga                                                                 123
```

<210> SEQ ID NO 424
<211> LENGTH: 7
<212> TYPE: PRT
<213> ORGANISM: Nostoc azollae

<400> SEQUENCE: 424

```
His Arg Glu Lys Lys Ser Ala
1               5
```

<210> SEQ ID NO 425
<211> LENGTH: 24
<212> TYPE: DNA
<213> ORGANISM: Nostoc azollae

<400> SEQUENCE: 425

```
cacagagaga aaaaatcagc atag                                           24
```

<210> SEQ ID NO 426
<211> LENGTH: 23
<212> TYPE: PRT
<213> ORGANISM: Acaryochloris marina

<400> SEQUENCE: 426

Thr Ser Asn Asn Trp Leu Ala Lys Asn Tyr Leu Ser Met Trp Asn Lys
1               5                   10                  15

Lys Ser Ser Asn Pro Asn Leu
            20

<210> SEQ ID NO 427
<211> LENGTH: 72
<212> TYPE: DNA
<213> ORGANISM: Acaryochloris marina

<400> SEQUENCE: 427
acaagcaata actggctagc caaaaactat ctttctatgt ggaataaaaa gagcagtaat      60
ccaaaccttt ag                                                         72

<210> SEQ ID NO 428
<211> LENGTH: 6
<212> TYPE: PRT
<213> ORGANISM: Cyanothece

<400> SEQUENCE: 428

Phe Arg Tyr Phe Trp Trp
1               5

<210> SEQ ID NO 429
<211> LENGTH: 21
<212> TYPE: DNA
<213> ORGANISM: Cyanothece

<400> SEQUENCE: 429
tttagatatt tttggtggta a                                               21

<210> SEQ ID NO 430
<211> LENGTH: 6
<212> TYPE: PRT
<213> ORGANISM: Cyanothece

<400> SEQUENCE: 430

Phe Arg Tyr Phe Trp Trp
1               5

<210> SEQ ID NO 431
<211> LENGTH: 21
<212> TYPE: DNA
<213> ORGANISM: Cyanothece

<400> SEQUENCE: 431
tttagatatt tttggtggta a                                               21

<210> SEQ ID NO 432
<211> LENGTH: 9
<212> TYPE: PRT
<213> ORGANISM: Cyanothece

<400> SEQUENCE: 432

Cys Gly Glu Lys Trp Arg Ile Phe Ser
1               5

<210> SEQ ID NO 433
<211> LENGTH: 27
<212> TYPE: DNA
<213> ORGANISM: Cyanothece

<400> SEQUENCE: 433
tgtggagaaa aatggagaat ttttagc 27

<210> SEQ ID NO 434
<211> LENGTH: 8
<212> TYPE: PRT
<213> ORGANISM: Cyanothece

<400> SEQUENCE: 434

Phe Arg Leu Gln Leu Trp Gln Phe
1               5

<210> SEQ ID NO 435
<211> LENGTH: 24
<212> TYPE: DNA
<213> ORGANISM: Cyanothece

<400> SEQUENCE: 435
tttcgcttac aactgtggca attt 24

<210> SEQ ID NO 436
<211> LENGTH: 16
<212> TYPE: PRT
<213> ORGANISM: Cyanothece

<400> SEQUENCE: 436

Leu Gly Cys Asn Gln Ser Ser Ile Trp Ser Ile Phe Phe Trp Asn His
1               5                   10                  15

<210> SEQ ID NO 437
<211> LENGTH: 51
<212> TYPE: DNA
<213> ORGANISM: Cyanothece

<400> SEQUENCE: 437
ctaggatgta accagagcag tatctggtca attttttct ggaatcatta a 51

<210> SEQ ID NO 438
<211> LENGTH: 40
<212> TYPE: PRT
<213> ORGANISM: Microcoleus chthonoplastes

<400> SEQUENCE: 438

Tyr Asn Leu Gln Gly Leu Pro Ala Ile Glu Ser Glu Asp Cys Ile Pro
1               5                   10                  15
Asp Ser Val Ala Pro Ser Asp Trp Phe Ser Gly Val Ser Ser Leu
            20                  25                  30
Phe Asn Arg Leu Thr Gly Leu Gly
        35                  40

<210> SEQ ID NO 439
<211> LENGTH: 123
<212> TYPE: DNA
<213> ORGANISM: Microcoleus chthonoplastes

<400> SEQUENCE: 439
tataacctac aggggttgcc agcaattgag tcagaagact gtatcccaga ttctgtagcg 60
ccttcggatg attggttttc aggcgtatcg tctctgttta accgcttgac tgggttgggt 120
tag 123

```
<210> SEQ ID NO 440
<211> LENGTH: 37
<212> TYPE: PRT
<213> ORGANISM: Nostoc sp

<400> SEQUENCE: 440

Trp Met Ala Ile Arg Arg Ile Leu Arg Cys His Pro Phe His Pro Gly
1               5                   10                  15

Gly Tyr Asp Pro Val Pro Glu Leu Gly Glu His Cys Cys His His Asp
            20                  25                  30

Ser Gly Asn Lys Gly
        35

<210> SEQ ID NO 441
<211> LENGTH: 114
<212> TYPE: DNA
<213> ORGANISM: Nostoc sp

<400> SEQUENCE: 441
tggatggcga ttcgccgcat tttgcgttgt catccattcc acccaggggg ttatgatcct     60
gtaccagagt tgggtgagca ttgttgtcat catgatagcg ggaataaggg gtga           114

<210> SEQ ID NO 442
<211> LENGTH: 35
<212> TYPE: PRT
<213> ORGANISM: Anabaena variabilis

<400> SEQUENCE: 442

Trp Met Gly Ile Arg Arg Ile Leu Arg Cys His Pro Phe His Pro Gly
1               5                   10                  15

Gly Tyr Asp Pro Val Pro Glu Val Gly Glu His Cys Cys His His Asp
            20                  25                  30

Ser Gly Lys
        35

<210> SEQ ID NO 443
<211> LENGTH: 108
<212> TYPE: DNA
<213> ORGANISM: Anabaena variabilis

<400> SEQUENCE: 443
tggatgggga ttcgccgcat tttgcgttgt catccattcc acccaggcgg ttatgatcct     60
gtaccagagg tgggtgagca ttgttgtcat catgatagcg ggaagtag                 108

<210> SEQ ID NO 444
<211> LENGTH: 48
<212> TYPE: PRT
<213> ORGANISM: Nodularia spumigena

<400> SEQUENCE: 444

Trp Met Ala Thr Arg Arg Ile Leu Arg Cys His Pro Phe His Pro Gly
1               5                   10                  15

Gly Tyr Asp Pro Val Pro Glu Val Lys His Asn Cys Cys Asp Gln His
            20                  25                  30

Leu Ser Asp Ser Gly Lys Gln Thr Thr Glu Asp His His Lys Gly Ser
        35                  40                  45

<210> SEQ ID NO 445
<211> LENGTH: 147
<212> TYPE: DNA
<213> ORGANISM: Nodularia spumigena
```

<400> SEQUENCE: 445
tggatggcga ctcggcggat tttgcgttgt catcccttcc atcctggtgg atatgatcca    60
gttccagagg taaaacacaa ttgctgcgat cagcatctgt ccgattctgg gaaacagacc   120
acagaagacc atcacaaagg ctcgtag                                       147

<210> SEQ ID NO 446
<211> LENGTH: 34
<212> TYPE: PRT
<213> ORGANISM: Nostoc azollae

<400> SEQUENCE: 446

Trp Met Ala Thr Leu Arg Ile Leu Arg Cys His Pro Phe His Pro Gly
1               5                   10                  15

Gly Tyr Asp Pro Val Pro Gly Leu Ala Glu Lys Ser Cys Cys Asp His
            20                  25                  30

His Asp

<210> SEQ ID NO 447
<211> LENGTH: 105
<212> TYPE: DNA
<213> ORGANISM: Nostoc azollae

<400> SEQUENCE: 447
tggatggcaa ctttgcggat tttacgctgt catcctttcc atcctggtgg ttatgatcct    60
gtaccaggac tagcggaaaa atcctgttgt gaccatcatg attga                  105

<210> SEQ ID NO 448
<211> LENGTH: 28
<212> TYPE: PRT
<213> ORGANISM: Synechococcus

<400> SEQUENCE: 448

Trp Leu Thr Ala Lys Arg Phe Cys Arg Cys His Pro Leu His Pro Gly
1               5                   10                  15

Gly Tyr Asp Pro Val Pro Glu Lys Lys Ser Val Leu
            20                  25

<210> SEQ ID NO 449
<211> LENGTH: 87
<212> TYPE: DNA
<213> ORGANISM: Synechococcus

<400> SEQUENCE: 449
tggctaacag ccaagcgctt ttgtcgctgt catccgcttc atcctggcgg tatgatccg    60 gtaccggaga agaaatcggt actctaa                                       87

<210> SEQ ID NO 450
<211> LENGTH: 23
<212> TYPE: PRT
<213> ORGANISM: Prochlorococcus marinus

<400> SEQUENCE: 450

Trp Leu Thr Leu Arg Arg Leu Ser Arg Cys His Pro Phe Thr Pro Cys
1               5                   10                  15

Gly Cys Asp Pro Val Pro Asp
            20

<210> SEQ ID NO 451

<211> LENGTH: 72
<212> TYPE: DNA
<213> ORGANISM: Prochlorococcus marinus

<400> SEQUENCE: 451
tggctcaccc tgcggcgcct gtctcgttgc catccttta cccctgtgg ttgcgacccg    60 gtgcctgatt aa                                                      72

<210> SEQ ID NO 452
<211> LENGTH: 69
<212> TYPE: PRT
<213> ORGANISM: Escherichia coli

<400> SEQUENCE: 452

Met Ser Tyr Lys Lys Leu Tyr Gln Leu Thr Ala Ile Phe Ser Leu Pro
1               5                   10                  15

Leu Thr Ile Leu Leu Val Ser Leu Ser Ser Leu Arg Ile Val Gly Glu
            20                  25                  30

Gly Asn Ser Tyr Val Asp Val Phe Leu Ser Phe Ile Ile Phe Leu Gly
        35                  40                  45

Phe Ile Glu Leu Ile His Gly Ile Arg Lys Ile Leu Val Trp Ser Gly
    50                  55                  60

Trp Lys Asn Gly Ser
65

<210> SEQ ID NO 453
<211> LENGTH: 210
<212> TYPE: DNA
<213> ORGANISM: Escherichia coli

<400> SEQUENCE: 453
atgagttata aaaactgta ccaattgacg gctatattta gtttacctct tactatctta    60 ttggttcac tttcatccct tcggattgtt ggcgaaggga attcttatgt tgacgttttt   120
ctaagcttta taatatttct tggttttatt gagctgattc atgggattcg aaagattttg   180
gtctggtcag gctggaaaaa cggaagttaa                                   210

<210> SEQ ID NO 454
<211> LENGTH: 85
<212> TYPE: PRT
<213> ORGANISM: Escherichia coli

<400> SEQUENCE: 454

Met Gly Leu Lys Leu Asp Leu Thr Trp Phe Asp Lys Ser Thr Glu Asp
1               5                   10                  15

Phe Lys Gly Glu Glu Tyr Ser Lys Asp Phe Gly Asp Asp Gly Ser Val
            20                  25                  30

Met Glu Ser Leu Gly Val Pro Phe Lys Asp Asn Val Asn Asn Gly Cys
        35                  40                  45

Phe Asp Val Ile Ala Glu Trp Val Pro Leu Leu Gln Pro Tyr Phe Asn
    50                  55                  60

His Gln Ile Asp Ile Ser Asp Asn Glu Tyr Phe Val Ser Phe Asp Tyr
65                  70                  75                  80

Arg Asp Gly Asp Trp
                85

<210> SEQ ID NO 455
<211> LENGTH: 258
<212> TYPE: DNA

<213> ORGANISM: Escherichia coli

<400> SEQUENCE: 455

```
atgggactta aattggattt aacttggttt gataaaagta cagaagattt taagggtgag    60
gagtattcaa aagattttgg agatgacggt tcagttatgg aaagtctagg tgtgccttt   120
aaggataatg ttaataacgg ttgctttgat gttatagctg aatgggtacc tttgctacaa   180
ccatacttta atcatcaaat tgatatttcc gataatgagt attttgtttc gtttgattat   240
cgtgatggtg attggtga                                                 258
```

<210> SEQ ID NO 456
<211> LENGTH: 113
<212> TYPE: PRT
<213> ORGANISM: Escherichia coli

<400> SEQUENCE: 456

```
Met Ser Leu Arg Tyr Tyr Ile Lys Asn Ile Leu Phe Gly Leu Tyr Cys
1               5                   10                  15
Thr Leu Ile Tyr Ile Tyr Leu Ile Thr Lys Asn Ser Glu Gly Tyr Tyr
            20                  25                  30
Phe Leu Val Ser Asp Lys Met Leu Tyr Ala Ile Val Ile Ser Thr Ile
        35                  40                  45
Leu Cys Pro Tyr Ser Lys Tyr Ala Ile Glu Tyr Ile Ala Phe Asn Phe
    50                  55                  60
Ile Lys Lys Asp Phe Phe Glu Arg Arg Lys Asn Leu Asn Asn Ala Pro
65                  70                  75                  80
Val Ala Lys Leu Asn Leu Phe Met Leu Tyr Asn Leu Leu Cys Leu Val
                85                  90                  95
Leu Ala Ile Pro Phe Gly Leu Leu Gly Leu Phe Ile Ser Ile Lys Asn
            100                 105                 110
Asn
```

<210> SEQ ID NO 457
<211> LENGTH: 342
<212> TYPE: DNA
<213> ORGANISM: Escherichia coli

<400> SEQUENCE: 457

```
atgagcttaa gatactacat aaaaaatatt ttatttggcc tgtactgcac acttatatat    60
ataaccttaa taacaaaaaa cagcgaaggg tattatttcc ttgtgtcaga taagatgcta   120
tatgcaatag tgataagcac tattctatgt ccatattcaa aatatgctat tgaatacata   180
gcttttaact tcataaagaa agatttttc gaaagaagaa aaaacctaaa taacgccccc    240
gtagcaaaat taaacctatt tatgctatat aatctacttt gtttggtcct agcaatccca   300
tttggattgc taggactttt tatatcaata aagaataatt aa                     342
```

<210> SEQ ID NO 458
<211> LENGTH: 85
<212> TYPE: PRT
<213> ORGANISM: Escherichia coli

<400> SEQUENCE: 458

```
Met Gly Leu Lys Leu His Ile His Trp Phe Asp Lys Lys Thr Glu Glu
1               5                   10                  15
Phe Lys Gly Gly Glu Tyr Ser Asp Phe Gly Asp Asp Gly Ser Val
            20                  25                  30
```

Ile Glu Ser Leu Gly Met Pro Leu Lys Asp Asn Ile Asn Asn Gly Trp
             35                  40                  45

Phe Asp Val Glu Lys Pro Trp Val Ser Ile Leu Gln Pro His Phe Lys
 50                  55                  60

Asn Val Ile Asp Ile Ser Lys Phe Asp Tyr Phe Val Ser Phe Val Tyr
 65                  70                  75                  80

Arg Asp Gly Asn Trp
             85

<210> SEQ ID NO 459
<211> LENGTH: 258
<212> TYPE: DNA
<213> ORGANISM: Escherichia coli

<400> SEQUENCE: 459
atggggctta aattacatat tcattggttt gataagaaaa ccgaagagtt taaaggcggt      60
gaatactcaa aagacttcgg tgatgatggt tctgtcattg aaagtctggg atgcctttta     120
aaggataata ttaataatgg ttggtttgat gttgaaaaac catgggtttc gatattacag     180
ccacacttta aaaatgtaat cgatattagt aaatttgatt actttgtatc ctttgtttac     240
cgggatggta actggtaa                                                   258

<210> SEQ ID NO 460
<211> LENGTH: 86
<212> TYPE: PRT
<213> ORGANISM: Escherichia coli

<400> SEQUENCE: 460

Met Glu Leu Lys His Ser Ile Ser Asp Tyr Thr Glu Ala Glu Phe Leu
 1               5                  10                  15

Glu Phe Val Lys Lys Ile Cys Arg Ala Glu Gly Ala Thr Glu Glu Asp
             20                  25                  30

Asp Asn Lys Leu Val Arg Glu Phe Glu Arg Leu Thr Glu His Pro Asp
         35                  40                  45

Gly Ser Asp Leu Ile Tyr Tyr Pro Arg Asp Asp Arg Glu Asp Ser Pro
 50                  55                  60

Glu Gly Ile Val Lys Glu Ile Lys Glu Trp Arg Ala Ala Asn Gly Lys
 65                  70                  75                  80

Ser Gly Phe Lys Gln Gly
             85

<210> SEQ ID NO 461
<211> LENGTH: 261
<212> TYPE: DNA
<213> ORGANISM: Escherichia coli

<400> SEQUENCE: 461
atggaactga acatagtat tagtgattat accgaggctg aatttctgga gtttgtaaaa       60
aaaatatgta gagctgaagg tgctactgaa gaggatgaca taaaattagt gagagagttt     120
gagcgattaa ctgagcaccc agatggttca gatctgattt attatcctcg cgatgacagg     180
gaagatagtc ctgaagggat tgtcaaggaa attaagaat ggcgagctgc taacggtaag      240
tcaggattta aacagggctg a                                               261

<210> SEQ ID NO 462
<211> LENGTH: 178
<212> TYPE: PRT
<213> ORGANISM: Citrobacter freundii

<400> SEQUENCE: 462

Met Met Asn Glu His Ser Ile Asp Thr Asp Asn Arg Lys Ala Asn Asn
1               5                   10                  15

Ala Leu Tyr Leu Phe Ile Ile Ile Gly Leu Ile Pro Leu Leu Cys Ile
            20                  25                  30

Phe Val Val Tyr Tyr Lys Thr Pro Asp Ala Leu Leu Leu Arg Lys Ile
        35                  40                  45

Ala Thr Ser Thr Glu Asn Leu Pro Ser Ile Thr Ser Ser Tyr Asn Pro
    50                  55                  60

Leu Met Thr Lys Val Met Asp Ile Tyr Cys Lys Thr Ala Pro Phe Leu
65                  70                  75                  80

Ala Leu Ile Leu Tyr Ile Leu Thr Phe Lys Ile Arg Lys Leu Ile Asn
                85                  90                  95

Asn Thr Asp Arg Asn Thr Val Leu Arg Ser Cys Leu Leu Ser Pro Leu
            100                 105                 110

Val Tyr Ala Ala Ile Val Tyr Leu Phe Cys Phe Arg Asn Phe Glu Leu
        115                 120                 125

Thr Thr Ala Gly Arg Pro Val Arg Leu Met Ala Thr Asn Asp Ala Thr
    130                 135                 140

Leu Leu Leu Phe Tyr Ile Gly Leu Tyr Ser Ile Ile Phe Thr Thr
145                 150                 155                 160

Tyr Ile Thr Leu Phe Thr Pro Val Thr Ala Phe Lys Leu Leu Lys Lys
                165                 170                 175

Arg Gln

<210> SEQ ID NO 463
<211> LENGTH: 537
<212> TYPE: DNA
<213> ORGANISM: Citrobacter freundii

<400> SEQUENCE: 463
atgatgaatg aacactcaat agatacggac aacagaaagg ccaataacgc attgtattta      60
tttataataa tcggattaat accattattg tgcattttg ttgtttacta caaaacgcca      120
gacgctttac ttttacgtaa aattgctaca agcactgaga atctcccgtc aataacatcc     180
tcctacaacc cattaatgac aaaggttatg gatatttatt gtaaaacagc gcctttcctt     240
gccttaatac tatacatcct aacctttaaa atcagaaaat taatcaacaa caccgacagg    300
aacactgtac ttagatcttg tttattaagt ccattggtct atgcagcaat tgtttatcta    360
ttctgcttcc gaattttga gttaacaaca gccggaaggc ctgtcagatt aatggccacc     420
aatgacgcaa cactattgtt atttatatt ggtctgtact caataatttt ctttacaacc    480
tatatcacgc tattcacacc agtcactgca tttaaattat taaaaaaag gcagtaa       537

<210> SEQ ID NO 464
<211> LENGTH: 111
<212> TYPE: PRT
<213> ORGANISM: Escherichia coli

<400> SEQUENCE: 464

Met Asn Arg Lys Tyr Tyr Phe Asn Asn Met Trp Trp Gly Trp Val Thr
1               5                   10                  15

Gly Gly Tyr Met Leu Tyr Met Ser Trp Asp Tyr Glu Phe Lys Tyr Arg
            20                  25                  30

Leu Leu Phe Trp Cys Ile Ser Leu Cys Gly Met Val Leu Tyr Pro Val

```
                35                  40                  45
Ala Lys Trp Tyr Ile Glu Asp Thr Ala Leu Lys Phe Thr Arg Pro Asp
 50                  55                  60

Phe Trp Asn Ser Gly Phe Phe Ala Asp Thr Pro Gly Lys Met Gly Leu
 65                  70                  75                  80

Leu Ala Val Tyr Thr Gly Thr Val Phe Ile Leu Ser Leu Pro Leu Ser
                 85                  90                  95

Met Ile Tyr Ile Leu Ser Val Ile Ile Lys Arg Leu Ser Val Arg
            100                 105                 110

<210> SEQ ID NO 465
<211> LENGTH: 336
<212> TYPE: DNA
<213> ORGANISM: Escherichia coli

<400> SEQUENCE: 465
atgaacagaa aatattattt taataatatg tggtggggat gggtgacggg gggatatatg      60
ctgtatatgt catgggatta tgagtttaaa tacagattac tgttctggtg tatttctctc     120
tgcggaatgg ttttgtatcc ggttgcaaaa tggtatattg aagatacagc tctaaaattt     180
acccggcctg atttctggaa cagcggtttt tttgctgata cacctggaaa aatggggttg     240
cttgcggttt atacgggtac tgttttcata ttatctcttc cgttaagtat gatatatatt     300
ctttctgtta ttataaaaag gctgtctgta agatag                               336

<210> SEQ ID NO 466
<211> LENGTH: 115
<212> TYPE: PRT
<213> ORGANISM: Escherichia coli

<400> SEQUENCE: 466

Met Lys Leu Asp Ile Ser Val Lys Tyr Leu Leu Lys Ser Leu Ile Pro
 1               5                  10                  15

Ile Leu Ile Ile Leu Thr Val Phe Tyr Leu Gly Trp Lys Asp Asn Gln
            20                  25                  30

Glu Asn Ala Arg Met Phe Tyr Ala Phe Ile Gly Cys Ile Ile Ser Ala
        35                  40                  45

Ile Thr Phe Pro Phe Ser Met Arg Ile Ile Gln Lys Met Val Ile Arg
 50                  55                  60

Phe Thr Gly Lys Glu Phe Trp Gln Lys Asp Phe Phe Thr Asn Pro Val
 65                  70                  75                  80

Gly Gly Ser Leu Thr Ala Ile Phe Glu Leu Phe Cys Phe Val Ile Ser
                 85                  90                  95

Val Pro Val Val Ala Ile Tyr Leu Ile Phe Ile Leu Cys Lys Ala Leu
            100                 105                 110

Ser Gly Lys
        115

<210> SEQ ID NO 467
<211> LENGTH: 348
<212> TYPE: DNA
<213> ORGANISM: Escherichia coli

<400> SEQUENCE: 467
atgaaactgg atatatctgt aaagtattta ctgaaaagcc tgataccaat cctcattatt      60
cttacagttt tttatctggg atggaaagat aaccaggaaa atgcaagaat gttttatgcg     120
ttcatcggat gcattatcag tgccattact tttcctttttt caatgaggat aatacagaaa     180
```

```
atggtaataa ggtttacagg gaaagaattc tggcaaaaag acttctttac aaatccagtt      240
ggcggaagct taactgcaat atttgaatta ttctgtttcg ttatatcagt tcctgtggtt      300
gccatttact taatttttat actctgcaaa gcccttttcag gaaaatga                 348
```

<210> SEQ ID NO 468
<211> LENGTH: 131
<212> TYPE: PRT
<213> ORGANISM: Escherichia coli

<400> SEQUENCE: 468

```
Met His Asn Thr Leu Leu Glu Lys Ile Ile Ala Tyr Leu Ser Leu Pro
  1               5                  10                  15

Gly Phe His Ser Leu Asn Asn Pro Pro Leu Ser Glu Ala Phe Asn Leu
                 20                  25                  30

Tyr Val His Thr Ala Pro Leu Ala Ala Thr Ser Leu Phe Ile Phe Thr
             35                  40                  45

His Lys Glu Leu Glu Leu Lys Pro Lys Ser Ser Pro Leu Arg Ala Leu
         50                  55                  60

Lys Ile Leu Thr Pro Phe Thr Ile Leu Tyr Ile Ser Met Ile Tyr Cys
 65                  70                  75                  80

Phe Leu Leu Thr Asp Thr Glu Leu Thr Leu Ser Ser Lys Thr Phe Val
                 85                  90                  95

Leu Ile Val Lys Lys Arg Ser Val Phe Val Phe Leu Tyr Asn Thr
                100                 105                 110

Ile Tyr Trp Asp Ile Tyr Ile His Ile Phe Val Leu Leu Val Pro Tyr
            115                 120                 125

Arg Asn Ile
        130
```

<210> SEQ ID NO 469
<211> LENGTH: 396
<212> TYPE: DNA
<213> ORGANISM: Escherichia coli

<400> SEQUENCE: 469

```
atgcacaata cactcctcga aaaatcatc gcatacctat ccctaccagg atttcattca       60
ttaaacaacc cgcccctaag cgaagcattc aatctctatg ttcatacagc cccttttagct    120 gcaaccagct tattcatatt cacacacaaa gaattagagt taaaaccaaa gtcgtcacct    180
ctgcgggcac taaagatatt aactcctttc actattcttt atatatccat gatatactgt    240
ttcttgctaa ctgacacaga actaaccttg tcatcaaaaa catttgtatt aatagtcaaa    300
aaacgatctg ttttttgtctt ttttctatat aacactatat attgggatat atatattcac    360
atatttgtac tttggttcc ttataggaac atataa                               396
```

<210> SEQ ID NO 470
<211> LENGTH: 85
<212> TYPE: PRT
<213> ORGANISM: Escherichia coli

<400> SEQUENCE: 470

```
Met Glu Leu Lys Asn Ser Ile Ser Asp Tyr Thr Glu Thr Glu Phe Lys
  1               5                  10                  15

Lys Ile Ile Glu Asp Ile Ile Asn Cys Glu Gly Asp Glu Lys Lys Gln
                 20                  25                  30

Asp Asp Asn Leu Glu His Phe Ile Ser Val Thr Glu His Pro Ser Gly
```

```
                    35                  40                  45
Ser Asp Leu Ile Tyr Tyr Pro Glu Gly Asn Asn Asp Gly Ser Pro Glu
 50                  55                  60

Ala Val Ile Lys Glu Ile Lys Glu Trp Arg Ala Ala Asn Gly Lys Ser
 65                  70                  75                  80

Gly Phe Lys Gln Gly
                 85

<210> SEQ ID NO 471
<211> LENGTH: 258
<212> TYPE: DNA
<213> ORGANISM: Escherichia coli

<400> SEQUENCE: 471
atggaactga aaacagcat tagtgattac actgaaactg aattcaaaaa aattattgaa      60
gacatcatca attgtgaagg tgatgaaaaa aacaggatg ataacctcga gcattttata     120
agtgttactg agcatcctag tggttctgat ctgatttatt acccagaagg taataatgat    180
ggtagccctg aagctgttat taaagagatt aaagaatggc gagctgctaa cggtaagtca    240
ggatttaaac agggctga                                                  258

<210> SEQ ID NO 472
<211> LENGTH: 98
<212> TYPE: PRT
<213> ORGANISM: Lactococcus lactis subsp. lactis

<400> SEQUENCE: 472

Met Lys Lys Lys Gln Ile Glu Phe Glu Asn Glu Leu Arg Ser Met Leu
  1               5                  10                  15

Ala Thr Ala Leu Glu Lys Asp Ile Ser Gln Glu Glu Arg Asn Ala Leu
                 20                  25                  30

Asn Ile Ala Glu Lys Ala Leu Asp Asn Ser Glu Tyr Leu Pro Lys Ile
                 35                  40                  45

Ile Leu Asn Leu Arg Lys Ala Leu Thr Pro Leu Ala Ile Asn Arg Thr
 50                  55                  60

Leu Asn His Asp Leu Ser Glu Leu Tyr Lys Phe Ile Thr Ser Ser Lys
 65                  70                  75                  80

Ala Ser Asn Lys Asn Leu Gly Gly Gly Leu Ile Met Ser Trp Gly Arg
                 85                  90                  95

Leu Phe

<210> SEQ ID NO 473
<211> LENGTH: 297
<212> TYPE: DNA
<213> ORGANISM: Lactococcus lactis subsp. lactis

<400> SEQUENCE: 473
atgaaaaaaa aacaaataga atttgaaaac gagctaagaa gtatgttggc taccgccctt      60
gaaaaagaca ttagtcaaga ggaaagaaat gctctgaata ttgcagaaaa ggcgcttgac     120
aattctgaat atttaccaaa aattattta aacctcagaa agccctaac tccattagct       180 ataaatcgaa cacttaacca tgatttatct gaactgtata attcattac aagttccaaa     240 gcatcaaaca aaaatttagg tggtggttta attatgtcgt ggggacgact attctaa      297

<210> SEQ ID NO 474
<211> LENGTH: 98
<212> TYPE: PRT
```

<213> ORGANISM: Lactococcus lactis subsp. cremoris

<400> SEQUENCE: 474

```
Met Lys Lys Lys Gln Ile Glu Phe Glu Asn Glu Leu Arg Ser Met Leu
1               5                   10                  15
Ala Thr Ala Leu Glu Lys Asp Ile Ser Gln Glu Glu Arg Asn Ala Leu
            20                  25                  30
Asn Ile Ala Glu Lys Ala Leu Asp Asn Ser Glu Tyr Leu Pro Lys Ile
        35                  40                  45
Ile Leu Asn Leu Arg Lys Ala Leu Thr Pro Leu Ala Ile Asn Arg Thr
    50                  55                  60
Leu Asn His Asp Leu Ser Glu Leu Tyr Lys Phe Ile Thr Ser Ser Lys
65                  70                  75                  80
Ala Ser Asn Lys Asn Leu Gly Gly Gly Leu Ile Met Ser Trp Gly Arg
                85                  90                  95
Leu Phe
```

<210> SEQ ID NO 475
<211> LENGTH: 297
<212> TYPE: DNA
<213> ORGANISM: Lactococcus lactis subsp. cremoris

<400> SEQUENCE: 475

| | |
|---|---|
| atgaaaaaaa aacaaataga atttgaaaac gagctaagaa gtatgttggc taccgccctt | 60 |
| gaaaagaca ttagtcaaga ggaaagaaat gctctgaata ttgcagaaaa ggcgcttgac | 120 |
| aattctgaat atttaccaaa aattattta aacctcagaa aagccctaac tccattagct | 180 |
| ataaatcgaa cacttaacca tgatttatct gaactgtata aattcattac aagttccaaa | 240 |
| gcatcaaaca aaaatttagg tggtggttta attatgtcgt ggggacgact attctaa | 297 |

<210> SEQ ID NO 476
<211> LENGTH: 87
<212> TYPE: PRT
<213> ORGANISM: Escherichia coli

<400> SEQUENCE: 476

```
Met Asn Lys Met Ala Met Ile Asp Leu Ala Lys Leu Phe Leu Ala Ser
1               5                   10                  15
Lys Ile Thr Ala Ile Glu Phe Ser Glu Arg Ile Cys Val Glu Arg Arg
            20                  25                  30
Arg Leu Tyr Gly Val Lys Asp Leu Ser Pro Asn Ile Leu Asn Cys Gly
        35                  40                  45
Glu Glu Leu Phe Met Ala Ala Glu Arg Phe Glu Pro Asp Ala Asp Arg
    50                  55                  60
Ala Asn Tyr Glu Ile Asp Asp Asn Gly Leu Lys Val Glu Val Arg Ser
65                  70                  75                  80
Ile Leu Glu Lys Phe Lys Leu
                85
```

<210> SEQ ID NO 477
<211> LENGTH: 249
<212> TYPE: DNA
<213> ORGANISM: Escherichia coli

<400> SEQUENCE: 477

| | |
|---|---|
| atgatcgatt tggcgaaatt attttttagct tcgaaaatta cagtgattga gttttcagag | 60 |
| cgaatttgtg ttgaacggag aagattgtat ggtgttaagg atttgtctcc gaatatatta | 120 |

```
aattgtgggg aagagttgtc tatggctgct gagcgatttg agcctgatgc agatagggct    180
aattatgaaa ttgatgataa tggacttaag gtcgaggtcc gatctatctt ggaaaaactt    240
aaatcataa                                                            249
```

<210> SEQ ID NO 478
<211> LENGTH: 83
<212> TYPE: PRT
<213> ORGANISM: Escherichia coli

<400> SEQUENCE: 478

```
Met Lys Leu Ser Pro Lys Ala Ala Ile Glu Val Cys Asn Glu Ala Ala
1               5                   10                  15

Lys Lys Gly Leu Trp Ile Leu Gly Ile Asp Gly Gly His Trp Leu Asn
            20                  25                  30

Pro Gly Phe Arg Ile Asp Ser Ser Ala Ser Trp Thr Tyr Asp Met Pro
        35                  40                  45

Glu Glu Tyr Lys Ser Lys Ile Pro Glu Asn Asn Arg Leu Ala Ile Glu
    50                  55                  60

Asn Ile Lys Asp Asp Ile Glu Asn Gly Tyr Thr Ala Phe Ile Ile Thr
65                  70                  75                  80

Leu Lys Met
```

<210> SEQ ID NO 479
<211> LENGTH: 243
<212> TYPE: DNA
<213> ORGANISM: Escherichia coli

<400> SEQUENCE: 479

```
atgaagttat caccaaaagc tgcaatagaa gtttgtaatg aagcagcgaa aaaaggctta    60
tggattttgg gcattgatgg tgggcattgg ctgaatcctg gattcaggat agatagttca    120
gcatcatgga catatgatat gccggagaat acaaatcaaa atccctgaa ataatagat     180 tggctattga aaatattaaa gatgatattg agaatggata cactgctttc attatcacgt    240
taa                                                                  243
```

<210> SEQ ID NO 480
<211> LENGTH: 85
<212> TYPE: PRT
<213> ORGANISM: Escherichia coli

<400> SEQUENCE: 480

```
Met Gly Leu Lys Leu His Ile Asn Trp Phe Asp Lys Arg Thr Glu Glu
1               5                   10                  15

Phe Lys Gly Gly Glu Tyr Ser Lys Asp Phe Gly Asp Asp Gly Ser Val
            20                  25                  30

Ile Glu Arg Leu Gly Met Pro Phe Lys Asp Asn Ile Asn Asn Gly Trp
        35                  40                  45

Phe Asp Val Ile Ala Glu Trp Val Pro Leu Leu Gln Pro Tyr Phe Asn
    50                  55                  60

His Gln Ile Asp Ile Ser Asp Asn Glu Tyr Phe Val Ser Phe Asp Tyr
65                  70                  75                  80

Arg Asp Gly Asp Trp
                85
```

<210> SEQ ID NO 481
<211> LENGTH: 258

```
<212> TYPE: DNA
<213> ORGANISM: Escherichia coli

<400> SEQUENCE: 481
atggggctta aattacatat taattggttt gataagacga ccgaggaatt taaaggtggt    60
gagtattcaa aagattttgg agatgatggc tcggtcattg aacgtcttgg aatgccttta   120
aaagataata tcaataatgg ttggtttgat gttatagctg aatgggtacc tttgctacaa   180
ccatacttta atcatcaaat tgatatttcc gataatgagt attttgtttc gtttgattat   240
cgtgatggtg attggtga                                                  258

<210> SEQ ID NO 482
<211> LENGTH: 85
<212> TYPE: PRT
<213> ORGANISM: Escherichia coli

<400> SEQUENCE: 482

Met Glu Leu Lys Lys Ser Ile Gly Asp Tyr Thr Glu Thr Phe Lys
1               5                   10                  15

Lys Ile Ile Glu Asn Ile Ile Asn Cys Glu Gly Asp Glu Lys Lys Gln
            20                  25                  30

Asp Asp Asn Leu Glu His Phe Ile Ser Val Thr Glu His Pro Ser Gly
        35                  40                  45

Ser Asp Leu Ile Tyr Tyr Pro Glu Gly Asn Asn Asp Gly Ser Pro Glu
    50                  55                  60

Ala Val Ile Lys Glu Ile Lys Glu Trp Arg Ala Ala Asn Gly Lys Ser
65                  70                  75                  80

Gly Phe Lys Gln Gly
                85

<210> SEQ ID NO 483
<211> LENGTH: 258
<212> TYPE: DNA
<213> ORGANISM: Escherichia coli

<400> SEQUENCE: 483
gtggagctaa agaaaagtat tggtgattac actgaaaccg aattcaaaaa aattattgaa    60
aacatcatca attgtgaagg tgatgaaaaa aaacaggatg ataacctcga gcattttata   120
agtgttactg agcatcctag tggttctgat ctgatttatt acccagaagg taataatgat   180
ggtagccctg aagctgttat taaagagatt aaagaatggc gagctgctaa cggtaagtca   240
ggatttaaac agggctga                                                  258

<210> SEQ ID NO 484
<211> LENGTH: 86
<212> TYPE: PRT
<213> ORGANISM: Escherichia coli

<400> SEQUENCE: 484

Met Glu Leu Lys His Ser Ile Ser Asp Tyr Thr Glu Ala Glu Phe Leu
1               5                   10                  15

Gln Leu Val Thr Thr Ile Cys Asn Ala Asp Thr Ser Ser Glu Glu Glu
            20                  25                  30

Leu Val Lys Leu Val Thr His Phe Glu Glu Met Thr Glu His Pro Ser
        35                  40                  45

Gly Ser Asp Leu Ile Tyr Tyr Pro Lys Glu Gly Asp Asp Ser Pro
    50                  55                  60
```

Ser Gly Ile Val Asn Thr Val Lys Gln Trp Arg Ala Ala Asn Gly Lys
65                  70                  75                  80

Ser Gly Phe Lys Gln Gly
            85

<210> SEQ ID NO 485
<211> LENGTH: 261
<212> TYPE: DNA
<213> ORGANISM: Escherichia coli

<400> SEQUENCE: 485
atggaactga agcatagcat tagtgattat acagaagctg aattttaca acttgtaaca      60 acaatttgta atgcgaacac ttccagtgaa gaagaactgg ttaaattggt tacacactttt   120 gaggaaatga ctgagcaccc tagtggtagt gatttaatat attacccaaa agaaggtgat    180
gatgactcac cttcaggtat tgtaaacaca gtaaacaat ggcgagccgc taacggtaag     240
tcaggattta aacagggcta a                                              261

<210> SEQ ID NO 486
<211> LENGTH: 141
<212> TYPE: PRT
<213> ORGANISM: Escherichia coli

<400> SEQUENCE: 486

Met Leu Thr Leu Tyr Gly Tyr Ile Arg Asn Val Phe Leu Tyr Arg Met
1               5                   10                  15

Asn Asp Arg Ser Cys Gly Asp Phe Met Lys Val Ile Ser Met Lys Phe
            20                  25                  30

Ile Phe Ile Leu Thr Ile Ile Ala Leu Ala Ala Val Phe Phe Trp Ser
        35                  40                  45

Glu Asp Lys Gly Pro Ala Cys Tyr Gln Val Ser Asp Glu Gln Ala Arg
    50                  55                  60

Thr Phe Val Lys Asn Asp Tyr Leu Gln Arg Met Lys Arg Trp Asp Asn
65                  70                  75                  80

Asp Val Gln Leu Leu Gly Thr Glu Ile Pro Lys Ile Thr Trp Glu Lys
                85                  90                  95

Ile Glu Arg Ser Leu Thr Asp Val Glu Asp Glu Lys Thr Leu Leu Val
            100                 105                 110

Pro Phe Lys Ala Glu Gly Pro Asp Gly Lys Arg Met Tyr Tyr Gly Met
        115                 120                 125

Tyr His Cys Glu Glu Gly Tyr Val Glu Tyr Ala Asn Asp
    130                 135                 140

<210> SEQ ID NO 487
<211> LENGTH: 354
<212> TYPE: DNA
<213> ORGANISM: Escherichia coli

<400> SEQUENCE: 487
atgaaagtaa ttagcatgaa atttatttt attttaacga ttattgctct tgctgctgtt     60
tttttctggt ctgaagataa aggtccggca tgctatcagg tcagcgatga acaggccaga   120
acgtttgtaa aaaatgatta cctgcaaaga atgaaacgct gggacaacga tgtacaactt   180
cttggtacag aaatcccgaa aattacatgg gaaaagattg agagaagttt aacagatgtt   240
gaagatgaaa aacacttcct gtcccattt aaagctgaag cccggacgg taagagaatg     300 tattatggca tgtaccattg tgaggaggga tatgttgaat atgcgaatga ctaa          354

<210> SEQ ID NO 488
<211> LENGTH: 175
<212> TYPE: PRT
<213> ORGANISM: Escherichia coli

<400> SEQUENCE: 488

Met Thr Ser Asn Lys Asp Lys Asn Lys Lys Ala Asn Glu Ile Leu Tyr
1               5                   10                  15

Ala Phe Ser Ile Ile Gly Ile Ile Pro Leu Met Ala Ile Leu Ile Leu
            20                  25                  30

Arg Ile Asn Asp Pro Tyr Ser Gln Val Leu Tyr Tyr Leu Tyr Asn Lys
        35                  40                  45

Val Ala Phe Leu Pro Ser Ile Thr Ser Leu His Asp Pro Val Met Thr
    50                  55                  60

Thr Leu Met Ser Asn Tyr Asn Lys Thr Ala Pro Val Met Gly Ile Leu
65                  70                  75                  80

Val Phe Leu Cys Thr Tyr Lys Thr Arg Glu Ile Ile Lys Pro Val Thr
                85                  90                  95

Arg Lys Leu Val Val Gln Ser Cys Phe Trp Gly Pro Val Phe Tyr Ala
            100                 105                 110

Ile Leu Ile Tyr Ile Thr Leu Phe Tyr Asn Leu Glu Leu Thr Thr Ala
        115                 120                 125

Gly Gly Phe Phe Lys Leu Leu Ser His Asn Val Ile Thr Leu Phe Ile
    130                 135                 140

Leu Tyr Cys Ser Ile Tyr Phe Thr Val Leu Thr Met Thr Tyr Ala Ile
145                 150                 155                 160

Leu Leu Met Pro Leu Leu Val Ile Lys Tyr Phe Lys Gly Arg Gln
                165                 170                 175

<210> SEQ ID NO 489
<211> LENGTH: 528
<212> TYPE: DNA
<213> ORGANISM: Escherichia coli

<400> SEQUENCE: 489
atgaccagca ataaagataa gaacaagaaa gcaaacgaaa tattatatgc attttccata      60
atcgggatta ttccattaat ggctatatta tacttcgaa taaatgatcc atattctcaa     120
gtgctgtact acttatataa taaggtggca tttctccctt ctattacatc attgcatgat    180
cccgtcatga caacacttat gtcaaactac aacaagacag cgccagttat gggtattctc    240 gttttttcttt gcacatataa gacaagagaa atcataaagc cagtaacaag aaaacttgtt   300
gtgcaatcct gtttctgggg gcccgttttt tatgccattc tgatttatat cacactgttc    360
tataatctgg aactaacaac agcaggtggt tttttttaaat tattatctca taatgtcatc   420
actctgttta ttttatattg ctccatttac tttactgttt taaccatgac atatgcgatt   480
ttactgatgc cattacttgt cattaaatat tttaaaggga ggcagtaa                 528

<210> SEQ ID NO 490
<211> LENGTH: 78
<212> TYPE: PRT
<213> ORGANISM: Escherichia coli

<400> SEQUENCE: 490

Met Asp Arg Lys Arg Thr Lys Leu Glu Leu Leu Phe Ala Phe Ile Ile
1               5                   10                  15

Asn Ala Thr Ala Ile Tyr Ile Ala Leu Ala Ile Tyr Asp Cys Val Phe

```
                    20                  25                  30
Arg Gly Lys Asp Phe Leu Ser Met His Thr Phe Cys Phe Ser Ala Leu
            35                  40                  45
Met Ser Ala Ile Cys Tyr Phe Val Gly Asp Asn Tyr Tyr Ser Ile Ser
        50                  55                  60
Asp Lys Ile Lys Arg Arg Ser Tyr Glu Asn Ser Asp Ser Lys
65                  70                  75
```

<210> SEQ ID NO 491
<211> LENGTH: 237
<212> TYPE: DNA
<213> ORGANISM: Escherichia coli

<400> SEQUENCE: 491

```
atggatagaa aaagaacaaa attagagttg ttatttgcat ttataataaa tgccaccgca      60
atatatattg cattagctat atatgattgt gttttagag  gaaaggactt tttatccatg     120
catacatttt gcttctctgc attaatgtct gcaatatgtt actttgttgg tgataattat    180
tattcaatat ccgataagat aaaaaggaga tcatatgaga actctgactc taaatga       237
```

<210> SEQ ID NO 492
<211> LENGTH: 113
<212> TYPE: PRT
<213> ORGANISM: Shigella sonnei

<400> SEQUENCE: 492

```
Met Ser Leu Arg Tyr Tyr Ile Lys Asn Ile Leu Phe Gly Leu Tyr Cys
1               5                   10                  15

Ala Leu Ile Tyr Ile Tyr Leu Ile Thr Lys Asn Asn Glu Gly Tyr Tyr
            20                  25                  30

Phe Leu Ala Ser Asp Lys Met Leu Tyr Ala Ile Val Ile Ser Thr Ile
        35                  40                  45

Leu Cys Pro Tyr Ser Lys Tyr Ala Ile Glu His Ile Phe Phe Lys Phe
    50                  55                  60

Ile Lys Lys Asp Phe Phe Arg Lys Arg Lys Asn Leu Asn Lys Cys Pro
65                  70                  75                  80

Arg Gly Lys Ile Lys Pro Tyr Leu Cys Val Tyr Asn Leu Leu Cys Leu
                85                  90                  95

Val Leu Ala Ile Pro Phe Gly Leu Leu Gly Leu Val Tyr Ile Asn Lys
            100                 105                 110

Glu
```

<210> SEQ ID NO 493
<211> LENGTH: 342
<212> TYPE: DNA
<213> ORGANISM: Shigella sonnei

<400> SEQUENCE: 493

```
atgagtttaa gatactacat aaaaaatatt ttgtttggcc tatactgcgc acttatatat      60 ataccttaa  acaaaaaaa  caacgaaggg tattatttcc tagcgtcaga taagatgcta    120
tacgcaatag tgataagcac tattctatgc ccatattcaa aatatgctat tgaacacata    180
ttttttaagt tcataaagaa agatttttc  agaaaaagaa aaaacctaaa taatgcccc     240 cgtggcaaaa ttaaaccgta tttatgcgta tacaatctac tttgtttggt cctagcaatc    300
ccatttggat tgctaggact tgtttatatc aataaagaat aa                       342
```

<210> SEQ ID NO 494
<211> LENGTH: 113
<212> TYPE: PRT
<213> ORGANISM: Escherichia coli

<400> SEQUENCE: 494

Met Ser Leu Arg Tyr Tyr Ile Lys Asn Ile Leu Phe Gly Leu Tyr Cys
1               5                   10                  15

Thr Leu Ile Tyr Ile Tyr Leu Ile Thr Lys Asn Ser Glu Glu Tyr Tyr
            20                  25                  30

Phe Leu Val Thr Asp Lys Met Leu Tyr Ala Ile Val Ile Ser Thr Ile
        35                  40                  45

Leu Cys Pro Tyr Ser Lys Tyr Ala Ile Glu His Ile Ala Phe Asn Phe
    50                  55                  60

Ile Lys Lys His Phe Phe Glu Arg Arg Lys Asn Leu Asn Asn Ala Pro
65                  70                  75                  80

Val Ala Lys Leu Asn Leu Phe Met Leu Tyr Asn Leu Leu Cys Leu Val
                85                  90                  95

Leu Ala Ile Pro Phe Gly Leu Leu Gly Leu Phe Ile Ser Ile Lys Asn
            100                 105                 110

Asn

<210> SEQ ID NO 495
<211> LENGTH: 342
<212> TYPE: DNA
<213> ORGANISM: Escherichia coli

<400> SEQUENCE: 495
atgagcttaa gatactacat aaaaaatatt ttatttggcc tgtactgcac acttatatat      60
atataccttc taacaaaaaa cagcgaagag tattatttcc ttgtgacaga taagatgcta     120
tatgcaatag tgataagcac tattctatgt ccatattcaa aatatgctat tgaacacata     180
gcttttaact tcataaagaa acattttttc gaaagaagaa aaaacctaaa taacgccccc     240
gtagcaaaat taaacctatt tatgctatat aatctacttt gtttggtcct agcaatccca     300
tttggattgc taggactttt tatatcaata aagaataatt aa                        342

<210> SEQ ID NO 496
<211> LENGTH: 113
<212> TYPE: PRT
<213> ORGANISM: Leuconostoc gelidum

<400> SEQUENCE: 496

Met Arg Lys Asn Asn Ile Leu Leu Asp Asp Ala Lys Ile Tyr Thr Asn
1               5                   10                  15

Lys Leu Tyr Leu Leu Ile Asp Arg Lys Asp Ala Gly Tyr Gly
            20                  25                  30

Asp Ile Cys Asp Val Leu Phe Gln Val Ser Lys Lys Leu Asp Ser Thr
        35                  40                  45

Lys Asn Val Glu Ala Leu Ile Asn Arg Leu Val Asn Tyr Ile Arg Ile
    50                  55                  60

Thr Ala Ser Thr Asn Arg Ile Lys Phe Ser Lys Asp Glu Glu Ala Val
65                  70                  75                  80

Ile Ile Glu Leu Gly Val Ile Gly Gln Lys Ala Gly Leu Asn Gly Gln
                85                  90                  95

Tyr Met Ala Asp Phe Ser Asp Lys Ser Gln Phe Tyr Ile Phe Glu
            100                 105                 110

Arg

<210> SEQ ID NO 497
<211> LENGTH: 342
<212> TYPE: DNA
<213> ORGANISM: Leuconostoc gelidum

<400> SEQUENCE: 497

```
ttgagaaaaa ataacatttt attggacgat gctaaaatat acacgaacaa actctatttg      60
ctattaatcg atagaaaaga tgacgctggg tatggagata tttgtgatgt tttgtttcag     120
gtatccaaaa aattagatag cacaaaaaat gtagaagcat tgattaaccg attggtcaat     180
tatatacgaa ttaccgcttc aacaaacaga attaagtttt caaaagatga agaggctgta     240
attatagaac ttggtgtaat tggtcagaag gctggattaa acggccaata catggctgat     300
ttttctgaca aatctcagtt ttatagtatc tttgaaagat aa                        342
```

<210> SEQ ID NO 498
<211> LENGTH: 91
<212> TYPE: PRT
<213> ORGANISM: Lactococcus lactis subsp. cremoris

<400> SEQUENCE: 498

```
Met Lys Lys Lys Val Asp Thr Glu Lys Gln Ile Thr Ser Trp Ala Ser
1               5                   10                  15
Asp Leu Ala Ser Lys Asn Glu Thr Lys Val Gln Glu Lys Leu Ile Leu
            20                  25                  30
Ser Ser Tyr Ile Gln Asp Ile Glu Asn His Val Tyr Phe Pro Lys Ala
        35                  40                  45
Met Ile Ser Leu Glu Lys Lys Leu Arg Asp Gln Asn Asn Ile Cys Ala
    50                  55                  60
Leu Ser Lys Glu Val Asn Gln Phe Tyr Phe Lys Val Val Glu Val Asn
65                  70                  75                  80
Gln Arg Lys Ser Trp Met Val Gly Leu Ile Val
            85                  90
```

<210> SEQ ID NO 499
<211> LENGTH: 276
<212> TYPE: DNA
<213> ORGANISM: Lactococcus lactis subsp. cremoris

<400> SEQUENCE: 499

```
atgaaaaaaa aagttgatac agaaaaacaa attacttctt gggcatctga cttagcttcc      60
aaaaatgaaa caaaggttca gaaaaatta atactgtctt cttatattca ggacatcgaa      120
aaccatgttt actttccaaa agcaatgatt tctttagaaa aaaaattacg agaccaaaat     180
aatatttgcg ctttatcaaa agaagtcaat cagtttttatt ttaaagttgt tgaagtaaat     240
caaagaaaat cctggatggt aggtttgata gtttaa                               276
```

<210> SEQ ID NO 500
<211> LENGTH: 112
<212> TYPE: PRT
<213> ORGANISM: Pediococcus acidilactici

<400> SEQUENCE: 500

```
Met Asn Lys Thr Lys Ser Glu His Ile Lys Gln Gln Ala Leu Asp Leu
1               5                   10                  15
Phe Thr Arg Leu Gln Phe Leu Leu Gln Lys His Asp Thr Ile Glu Pro
            20                  25                  30
```

Tyr Gln Tyr Val Leu Asp Ile Leu Glu Thr Gly Ile Ser Lys Thr Lys
            35                  40                  45

His Asn Gln Gln Thr Pro Glu Arg Gln Ala Arg Val Val Tyr Asn Lys
         50                  55                  60

Ile Ala Ser Gln Ala Leu Val Asp Lys Leu His Phe Thr Ala Glu Glu
65                  70                  75                  80

Asn Lys Val Leu Ala Ala Ile Asn Glu Leu Ala His Ser Gln Lys Gly
                85                  90                  95

Trp Gly Glu Phe Asn Met Leu Asp Thr Thr Asn Thr Trp Pro Ser Gln
            100                 105                 110

<210> SEQ ID NO 501
<211> LENGTH: 339
<212> TYPE: DNA
<213> ORGANISM: Pediococcus acidilactici

<400> SEQUENCE: 501
atgaataaga ctaagtcgga acatattaaa caacaagctt tggacttatt tactaggcta    60 cagttttac tacagaagca cgatactatc gaaccttacc agtacgtttt agatattctg    120
gagactggta tcagtaaaac taaacataac cagcaaacgc ctgaacgaca agctcgtgta    180
gtctacaaca agattgccag ccaagcgtta gtagataagt tacattttac tgccgaagaa    240
aacaaagttc tagcagccat caatgaattg gcgcattctc aaaagggtg gggcgagttt    300 aacatgctag atactaccaa tacgtggcct agccaatag                           339

<210> SEQ ID NO 502
<211> LENGTH: 88
<212> TYPE: PRT
<213> ORGANISM: Carnobacterium maltaromaticum

<400> SEQUENCE: 502

Met Ile Lys Asp Glu Lys Ile Asn Lys Ile Tyr Ala Leu Val Lys Ser
1               5                   10                  15

Ala Leu Asp Asn Thr Asp Val Lys Asn Asp Lys Lys Leu Ser Leu Leu
            20                  25                  30

Leu Met Arg Ile Gln Glu Thr Ser Ile Asn Gly Glu Leu Phe Tyr Asp
        35                  40                  45

Tyr Lys Lys Glu Leu Gln Pro Ala Ile Ser Met Tyr Ser Ile Gln His
    50                  55                  60

Asn Phe Arg Val Pro Asp Asp Leu Val Lys Leu Leu Ala Leu Val Gln
65                  70                  75                  80

Thr Pro Lys Ala Trp Ser Gly Phe
                85

<210> SEQ ID NO 503
<211> LENGTH: 267
<212> TYPE: DNA
<213> ORGANISM: Carnobacterium maltaromaticum

<400> SEQUENCE: 503
atgataaaag atgaaaaaat aaataaaatc tatgctttag ttaagagcgc acttgataat    60
acggatgtta agaatgataa aaaactttct ttacttctta tgagaataca agaaacatca    120
attaatggag aactatttta cgattataaa aagaattac agccagctat tagtatgtac    180
tctattcaac ataactttcg ggttcctgac gatctagtaa aactgttagc attagttcaa    240
acacctaaag cttggtcagg gtttttaa                                      267

<210> SEQ ID NO 504
<211> LENGTH: 111
<212> TYPE: PRT
<213> ORGANISM: Carnobacterium maltaromaticum

<400> SEQUENCE: 504

```
Met Asp Ile Lys Ser Gln Thr Leu Tyr Leu Asn Leu Ser Glu Ala Tyr
1               5                   10                  15
Lys Asp Pro Glu Val Lys Ala Asn Glu Phe Leu Ser Lys Leu Val Val
            20                  25                  30
Gln Cys Ala Gly Lys Leu Thr Ala Ser Asn Ser Glu Asn Ser Tyr Ile
        35                  40                  45
Glu Val Ile Ser Leu Leu Ser Arg Gly Ile Ser Ser Tyr Tyr Leu Ser
    50                  55                  60
His Lys Arg Ile Ile Pro Ser Ser Met Leu Thr Ile Tyr Thr Gln Ile
65                  70                  75                  80
Gln Lys Asp Ile Lys Asn Gly Asn Ile Asp Thr Glu Lys Leu Arg Lys
                85                  90                  95
Tyr Glu Ile Ala Lys Gly Leu Met Ser Val Pro Tyr Ile Tyr Phe
            100                 105                 110
```

<210> SEQ ID NO 505
<211> LENGTH: 336
<212> TYPE: DNA
<213> ORGANISM: Carnobacterium maltaromaticum

<400> SEQUENCE: 505

```
atggatataa agtctcaaac attatatttg aatctaagcg aggcatataa agaccctgaa      60
gtaaaagcta atgaattctt atcaaaatta gttgtacaat gtgctgggaa attaacagct     120
tcaaacagtg agaacagtta tattgaagta atatcattgc tatctagggg tatttctagt     180
tattatttat cccataaacg tataattcct tcaagtatgt taactatata tactcaaata     240
caaaaggata taaaaaacgg gaatattgac accgaaaaat taaggaaata tgagatagca     300
aaaggattaa tgtccgttcc ttatatatat ttctaa                               336
```

<210> SEQ ID NO 506
<211> LENGTH: 245
<212> TYPE: PRT
<213> ORGANISM: Lactococcus lactis subsp. lactis

<400> SEQUENCE: 506

```
Met Arg Arg Tyr Leu Ile Leu Ile Val Ala Leu Ile Gly Ile Thr Gly
1               5                   10                  15
Leu Ser Gly Cys Tyr Gln Thr Ser His Lys Lys Val Arg Phe Asp Glu
            20                  25                  30
Gly Ser Tyr Thr Asn Phe Ile Tyr Asp Asn Lys Ser Tyr Phe Val Thr
        35                  40                  45
Asp Lys Glu Ile Pro Gln Glu Asn Val Asn Asn Ser Lys Val Lys Phe
    50                  55                  60
Tyr Lys Leu Leu Ile Val Asp Met Lys Ser Glu Lys Leu Leu Ser Ser
65                  70                  75                  80
Ser Asn Lys Asn Ser Val Thr Leu Val Leu Asn Asn Ile Tyr Glu Ala
                85                  90                  95
Ser Asp Lys Ser Leu Cys Met Gly Ile Asn Asp Arg Tyr Tyr Lys Ile
            100                 105                 110
```

-continued

```
Leu Pro Glu Ser Asp Lys Gly Ala Val Lys Ala Leu Arg Leu Gln Asn
            115                 120                 125

Phe Asp Val Thr Ser Asp Ile Ser Asp Asn Phe Val Ile Asp Lys
    130                 135                 140

Asn Asp Ser Arg Lys Ile Asp Tyr Met Gly Asn Ile Tyr Ser Ile Ser
145                 150                 155                 160

Asp Thr Thr Val Ser Asp Glu Glu Leu Gly Glu Tyr Gln Asp Val Leu
                165                 170                 175

Ala Glu Val Arg Val Phe Asp Ser Val Ser Gly Lys Ser Ile Pro Arg
            180                 185                 190

Ser Glu Trp Gly Arg Ile Asp Lys Asp Gly Ser Asn Ser Lys Gln Ser
        195                 200                 205

Arg Thr Glu Trp Asp Tyr Gly Glu Ile His Ser Ile Arg Gly Lys Ser
    210                 215                 220

Leu Thr Glu Ala Phe Ala Val Glu Ile Asn Asp Asp Phe Lys Leu Ala
225                 230                 235                 240

Thr Lys Val Gly Asn
                245

<210> SEQ ID NO 507
<211> LENGTH: 738
<212> TYPE: DNA
<213> ORGANISM: Lactococcus lactis subsp. lactis

<400> SEQUENCE: 507
atgagaagat atttaatact tattgtggcc ttaataggga taacaggttt atcagggtgt      60
tatcaaacaa gtcataaaaa ggtgaggttt gacgaaggaa gttatactaa tttattttat    120
gataataaat cgtatttcgt aactgataag gagattcctc aggagaacgt taacaattcc    180
aaagtaaaat tttataagct gttgattgtt gacatgaaaa gtgagaaact tttatcaagt    240
agcaacaaaa atagtgtgac tttggtctta ataatatttt atgaggcttc tgacaagtcg    300
ctatgtatgg gtattaacga cagatactat aagatacttc agaaagtgaa taaggggggcg    360 gtcaaagctt tgagattaca aaactttgat gtgacaagcg atatttctga tgataatttt    420
gttattgata aaaatgattc acgaaaaatt gactatatgg gaaatattta cagtatatcg    480
gacaccaccg tatctgatga agaattggga gaatatcagg atgttttagc tgaagtacgt    540
gtgtttgatt cagttagtgg caaaagtatc ccgaggtctg aatgggggag aattgataag    600
gatggttcaa attccaaaca gagtaggacg gaatgggatt atggcgaaat ccattctatt    660
agaggaaaat ctcttactga agcatttgcc gttgagataa atgatgattt taagcttgca    720
acgaaggtag gaaactag                                                  738

<210> SEQ ID NO 508
<211> LENGTH: 261
<212> TYPE: PRT
<213> ORGANISM: Rhizobium leguminosarum bv. trifolii

<400> SEQUENCE: 508

Met Asn Asp Glu Ile Cys Leu Thr Gly Gly Gly Arg Thr Thr Val Thr
1               5                   10                  15

Arg Arg Gly Gly Val Val Tyr Arg Glu Gly Gly Pro Trp Ser Ser Thr
            20                  25                  30

Val Ile Ser Leu Leu Arg His Leu Glu Ala Ser Gly Phe Ala Glu Ala
        35                  40                  45

Pro Ser Val Val Gly Thr Gly Phe Asp Glu Arg Gly Arg Glu Thr Leu
```

```
                50                  55                  60
Ser Phe Ile Glu Gly Glu Phe Val His Pro Gly Pro Trp Ser Glu Glu
 65                  70                  75                  80

Ala Phe Pro Gln Phe Gly Met Met Leu Arg Arg Leu His Asp Ala Thr
                 85                  90                  95

Ala Ser Phe Lys Pro Pro Glu Asn Ser Met Trp Arg Asp Trp Phe Gly
            100                 105                 110

Arg Asn Leu Gly Glu Gly Gln His Val Ile Gly His Cys Asp Thr Gly
            115                 120                 125

Pro Trp Asn Ile Val Cys Arg Ser Gly Leu Pro Val Gly Leu Ile Asp
        130                 135                 140

Trp Glu Val Ala Gly Pro Val Arg Ala Asp Ile Glu Leu Ala Gln Ala
145                 150                 155                 160

Cys Trp Leu Asn Ala Gln Leu Tyr Asp Asp Ile Ala Glu Arg Val
            165                 170                 175

Gly Leu Gly Ser Val Thr Met Arg Ala His Gln Val Arg Leu Leu Leu
            180                 185                 190

Asp Gly Tyr Gly Leu Ser Arg Lys Gln Arg Gly Gly Phe Val Asp Lys
        195                 200                 205

Leu Ile Thr Phe Ala Val His Asp Ala Ala Glu Gln Ala Lys Glu Ala
210                 215                 220

Ala Val Thr Pro Glu Ser Asn Asp Ala Glu Pro Leu Trp Ala Ile Ala
225                 230                 235                 240

Trp Arg Thr Arg Ser Ala Ser Trp Met Leu His His Arg Gln Thr Leu
            245                 250                 255

Glu Ala Ala Leu Ala
            260

<210> SEQ ID NO 509
<211> LENGTH: 786
<212> TYPE: DNA
<213> ORGANISM: Rhizobium leguminosarum bv. trifolii

<400> SEQUENCE: 509
atgaatgatg agatttgcct gacaggtggc ggacgaacga ctgtcacgcg gcgcggcgga     60
gtcgtgtatc gcgaaggcgg cccgtggtca tcaaccgtca tttcgctcct gcggcatctg    120
gaagcctctg gcttcgctga agctccttcc gttgtcggca ccggtttcga tgagcgcggc    180
cgggagacat tatcgtttat cgagggtgag tttgttcacc aggcccttg tcggaggag     240 gcttttccgc aatttggaat gatgttgcgg cgactgcacg atgccaccgc tcgttcaaa    300 cctcccgaaa actcgatgtg gcgcgattgg ttcgggcgta acctcggtga gggtcaacac    360
gtaataggac actgcgacac aggcccatgg aacattgttt gccggtcagg attgcctgtc    420
gggttgatag attgggaggt ggctgggcct gtcagggcgg atatcgaatt ggcccaggct    480
tgttggctga atgcccagct ctacgatgac gacattgcgg agagggtcgg attaggctct    540
gtgaccatga gagcgcatca agttcgcctg ctgcttgacg gctatggtct gtctcggaag    600
caacgcggcg gcttcgtcga caagctaatc acgttcgcag ttcacgatgc ggccgagcag    660
gcgaaagagg cggctgtcac gccagagtcg aacgatgcgg aaccgctatg gcaattgcc     720 tggcgcacta gaagtgcctc ctggatgctc catcatcggc aaacactgga agcagcgctg    780
gcatag                                                               786

<210> SEQ ID NO 510
```

<211> LENGTH: 436
<212> TYPE: PRT
<213> ORGANISM: Bacillus subtilis

<400> SEQUENCE: 510

| | | | | | | | | | | | | | | |
|---|---|---|---|---|---|---|---|---|---|---|---|---|---|---|
| Met | Asn | Asn | Ile | Ile | Pro | Ile | Met | Ser | Leu | Leu | Phe | Lys | Gln | Leu | Tyr |
| 1 | | | | 5 | | | | | 10 | | | | | 15 | |
| Ser | Arg | Gln | Gly | Lys | Lys | Asp | Ala | Ile | Arg | Ile | Ala | Ala | Gly | Leu | Val |
| | | | 20 | | | | | 25 | | | | | 30 | | |
| Ile | Leu | Ala | Val | Phe | Glu | Ile | Gly | Leu | Ile | Arg | Gln | Ala | Gly | Ile | Asp |
| | | 35 | | | | | 40 | | | | | 45 | | | |
| Glu | Ser | Val | Leu | Arg | Lys | Thr | Tyr | Ile | Ile | Leu | Ala | Leu | Leu | Leu | Met |
| 50 | | | | | 55 | | | | | 60 | | | | | |
| Asn | Thr | Tyr | Met | Val | Phe | Leu | Ser | Val | Thr | Ser | Gln | Trp | Lys | Glu | Ser |
| 65 | | | | 70 | | | | | 75 | | | | | 80 | |
| Tyr | Met | Lys | Leu | Ser | Cys | Leu | Leu | Pro | Ile | Ser | Ser | Arg | Ser | Phe | Trp |
| | | | 85 | | | | | 90 | | | | | 95 | | |
| Leu | Ala | Gln | Ser | Val | Val | Leu | Phe | Val | Asp | Thr | Cys | Leu | Arg | Arg | Thr |
| | | | 100 | | | | | 105 | | | | | 110 | | |
| Leu | Phe | Phe | Phe | Ile | Leu | Pro | Leu | Phe | Leu | Phe | Gly | Asn | Gly | Thr | Leu |
| | | 115 | | | | | 120 | | | | | 125 | | | |
| Ser | Gly | Ala | Gln | Thr | Leu | Phe | Trp | Leu | Gly | Arg | Phe | Ser | Phe | Phe | Thr |
| 130 | | | | | 135 | | | | | 140 | | | | | |
| Val | Tyr | Ser | Ile | Ile | Phe | Gly | Val | Val | Leu | Ser | Asn | His | Phe | Val | Lys |
| 145 | | | | | 150 | | | | | 155 | | | | | 160 |
| Lys | Lys | Asn | Leu | Met | Phe | Leu | Leu | His | Ala | Ala | Ile | Phe | Ala | Cys | Val |
| | | | | 165 | | | | | 170 | | | | | 175 | |
| Cys | Ile | Ser | Ala | Ala | Leu | Met | Pro | Ala | Ala | Thr | Ile | Pro | Leu | Cys | Ala |
| | | | 180 | | | | | 185 | | | | | 190 | | |
| Val | His | Ile | Leu | Trp | Ala | Val | Val | Ile | Asp | Phe | Pro | Val | Phe | Leu | Gln |
| | | | 195 | | | | | 200 | | | | | 205 | | |
| Ala | Pro | Pro | Gln | Gln | Gly | Lys | Met | His | Ser | Phe | Met | Arg | Arg | Ser | Glu |
| | | 210 | | | | | 215 | | | | | 220 | | | |
| Phe | Ser | Phe | Tyr | Lys | Arg | Glu | Trp | Asn | Arg | Phe | Ile | Ser | Ser | Lys | Ala |
| 225 | | | | | 230 | | | | | 235 | | | | | 240 |
| Met | Leu | Leu | Asn | Tyr | Ala | Val | Met | Ala | Val | Phe | Ser | Gly | Phe | Phe | Ser |
| | | | | 245 | | | | | 250 | | | | | 255 | |
| Phe | Gln | Met | Met | Asn | Thr | Gly | Ile | Phe | Asn | Gln | Gln | Val | Ile | Tyr | Ile |
| | | | 260 | | | | | 265 | | | | | 270 | | |
| Val | Ile | Ser | Ala | Leu | Leu | Leu | Ile | Cys | Ser | Pro | Ile | Ala | Leu | Leu | Tyr |
| | | 275 | | | | | 280 | | | | | 285 | | | |
| Ser | Ile | Glu | Lys | Asn | Asp | Arg | Met | Leu | Leu | Ile | Thr | Leu | Pro | Ile | Lys |
| | 290 | | | | | 295 | | | | | 300 | | | | |
| Arg | Lys | Thr | Met | Phe | Trp | Ala | Lys | Tyr | Arg | Phe | Tyr | Ser | Gly | Leu | Leu |
| 305 | | | | | 310 | | | | | 315 | | | | | 320 |
| Ala | Gly | Gly | Phe | Leu | Leu | Val | Val | Met | Ile | Val | Gly | Phe | Ile | Ser | Gly |
| | | | | 325 | | | | | 330 | | | | | 335 | |
| Arg | Ser | Ile | Ser | Val | Leu | Thr | Phe | Leu | Gln | Cys | Ile | Glu | Leu | Leu | Leu |
| | | | 340 | | | | | 345 | | | | | 350 | | |
| Ala | Gly | Ala | Tyr | Ile | Arg | Leu | Thr | Ala | Asp | Glu | Lys | Arg | Pro | Ser | Phe |
| | | | 355 | | | | | 360 | | | | | 365 | | |
| Ser | Trp | Gln | Thr | Glu | Gln | Gln | Leu | Trp | Ser | Gly | Phe | Ser | Lys | Tyr | Arg |
| | 370 | | | | | 375 | | | | | 380 | | | | |
| Ser | Tyr | Leu | Phe | Cys | Leu | Pro | Leu | Phe | Leu | Ala | Ile | Leu | Ala | Gly | Thr |

```
385                 390                 395                 400
Ala Val Ser Leu Ala Val Ile Pro Ile Ala Gly Leu Val Ile Tyr
                405                 410                 415

Tyr Leu Gln Lys Gln Asp Gly Gly Phe Phe Asp Thr Ser Lys Arg Glu
                420                 425                 430

Arg Leu Gly Ser
        435
```

<210> SEQ ID NO 511
<211> LENGTH: 1000
<212> TYPE: DNA
<213> ORGANISM: Bacillus subtilis

<400> SEQUENCE: 511

```
atgaataaca taatccctat catgtctttg ctgttcaaac agctttacag ccggcaaggg      60
aaaaaggacg ccatccgcat tgccgcaggc cttgtcattc tggccgtgtt tgaaatcggg     120
ctgatccgcc aggccggcat tgatgaatcg gtgttgcgca aaacgtatat catactcgcg     180
cttcttttga tgaacacata tggtgtgttt ctttccgtga catcacaatg gaaggaatct     240
tatatgaagc tgagctgcct gctgccgatt cttcacgga gcttttggct cgcccagagt      300
gtcgttttgt ttgtcgatac ctgtttgaga agaactttat tcttttttat tttaccgctg     360
ttcttatttg gaaacggaac gctgtcaggg gcgcaaacat tgtttggct cggcaggttt      420
tcgttttta ccgtttactc cattattttc ggagttgtgc taagcaacca cttcgtcaaa      480
aagaagaact tgatgtttct gctgcatgcg gcgatattcg cctgtgtatg tatcagcgcc     540
gctttgatgc cggccgccac gattccgctt tgcgcggttc atatcctgtg gcggtggtc      600
attgactttc ctgtctttct gcaggcgcct ccgcagcagg gcaagatgca ttcatttatg     660
cggcgatctg aattttcgtt ttacaaaaga gaatggaacc gatttatctc ttctaaagcg     720
atgctgttaa attacgcggt aatggcggta ttcagcggct tctttttcgtt ccagatgatg    780
aacaccggca tcttcaatca gcaagtgatt tatatcgtga tttccgcgct tttgctcatc    840
tgctcgccga tcgcccttttt gtattcgatt gaaaaaaatg accgatgct gctcatcacg     900
cttccgatca agcgaaaaac gatgtttggg gcgaaatatc gcttttattc aggcctattg    960
gcaggcggat ttctccttgt cgtgatgatt gtgggtttca                          1000
```

<210> SEQ ID NO 512
<211> LENGTH: 239
<212> TYPE: PRT
<213> ORGANISM: Bacillus subtilis

<400> SEQUENCE: 512

```
Met Ser Ile Leu Asp Ile His Asp Val Ser Val Trp Tyr Glu Arg Asp
1               5                   10                  15

Asn Val Ile Leu Glu Gln Val Asp Leu His Leu Glu Lys Gly Ala Val
                20                  25                  30

Tyr Gly Leu Leu Gly Val Asn Gly Ala Gly Lys Thr Thr Leu Ile Asn
            35                  40                  45

Thr Leu Thr Gly Val Asn Arg Asn Phe Ser Gly Arg Phe Thr Leu Cys
        50                  55                  60

Gly Ile Glu Ala Glu Ala Gly Met Pro Gln Lys Thr Ser Asp Gln Leu
65                  70                  75                  80

Lys Thr His Arg Tyr Phe Ala Asp Tyr Pro Leu Leu Phe Thr Glu
                85                  90                  95
```

```
Ile Thr Ala Lys Asp Tyr Val Ser Phe Val His Ser Leu Tyr Gln Lys
            100                 105                 110

Asp Phe Ser Glu Gln Gln Phe Ala Ser Leu Ala Glu Ala Phe His Phe
        115                 120                 125

Ser Lys Tyr Ile Asn Arg Arg Ile Ser Glu Leu Ser Leu Gly Asn Arg
    130                 135                 140

Gln Lys Val Val Leu Met Thr Gly Leu Leu Leu Arg Ala Pro Leu Phe
145                 150                 155                 160

Ile Leu Asp Glu Pro Leu Val Gly Leu Asp Val Glu Ser Ile Glu Val
                165                 170                 175

Phe Tyr Gln Lys Met Arg Glu Tyr Cys Glu Ala Gly Gly Thr Ile Leu
            180                 185                 190

Phe Ser Ser His Leu Leu Asp Val Val Gln Arg Phe Cys Asp Tyr Ala
        195                 200                 205

Ala Ile Leu His Asn Lys Gln Ile Gln Lys Val Ile Pro Ile Gly Glu
    210                 215                 220

Glu Thr Asp Leu Arg Arg Glu Phe Phe Glu Val Ile Gly His Glu
225                 230                 235
```

<210> SEQ ID NO 513
<211> LENGTH: 716
<212> TYPE: DNA
<213> ORGANISM: Bacillus subtilis

<400> SEQUENCE: 513

```
gcatttggga tatacacgat gtatccgttt ggtatgaacg ggacaacgtc atcttagagc    60
acgtggactt acacttagaa aaaggcgccg tttacggatt gcttggggta aacggtgccg   120
gcaaaacaac actgatcaat acgctgacag gagtgaaccg caattacagc gggggcttta   180
cgctgtgcgg cattgaagct gaggccggca tgccgcagaa acatcagat caactgaaga   240
ttcaccgtta cttcgccgct gattatccgc tgctgtttac agaaattacg gcgaaggact   300
atgtgtcttt cgtccattcg ctttatcaaa aggattttc agagcgacag tttgccagtt   360
tggctgaggc ctttcatttt tcaaaataca tcaacaggag aatctcggag ctgtccttgg   420
ggaacaggca aaaggttgtg ttgatgacag gattattgct gcgggctccc ctgtttattt   480
tggatgagcc gctcgtcggt ttggatgtgg aatcaataga ggtcttttat cagaaaatgc   540
gggagtactg tgaggaaggc ggaaccattt tgttttcttc ccatctgctc gatgtcgtgc   600
agagatttg tgattttgcg gccattctgc acaacaaaca gatccaaaag gtcattccga   660
ttggggagga gaccgatctg cggcgggaat tttttgaggt tatcggccat gaataa       716
```

<210> SEQ ID NO 514
<211> LENGTH: 53
<212> TYPE: PRT
<213> ORGANISM: Bacillus subtilis

<400> SEQUENCE: 514

```
Met Ser Pro Ala Gln Arg Arg Ile Leu Leu Tyr Ile Leu Ser Phe Ile
1               5                   10                  15

Phe Val Ile Gly Ala Val Val Tyr Phe Val Lys Ser Asp Tyr Leu Phe
            20                  25                  30

Thr Leu Ile Phe Ile Ala Ile Ala Ile Leu Phe Gly Met Arg Ala Arg
        35                  40                  45

Lys Ala Asp Ser Arg
    50
```

<210> SEQ ID NO 515
<211> LENGTH: 162
<212> TYPE: DNA
<213> ORGANISM: Bacillus subtilis

<400> SEQUENCE: 515
ttgtcaccag cacaaagaag aattttactg tatatccttt catttatctt tgtcatcggc     60
gcagtcgtct attttgtcaa aagcgattat ctgtttacgc tgattttcat tgccattgcc    120
attctgttcg ggatgcgcgc gcggaaggct gactcgcgat ga                       162

<210> SEQ ID NO 516
<211> LENGTH: 87
<212> TYPE: PRT
<213> ORGANISM: Escherichia coli

<400> SEQUENCE: 516

Met Glu Leu Lys Asn Ser Ile Ser Asp Tyr Thr Glu Ala Glu Phe Val
1               5                   10                  15

Gln Leu Leu Lys Glu Ile Glu Lys Glu Asn Val Ala Ala Thr Asp Asp
                20                  25                  30

Val Leu Asp Val Leu Leu Glu His Phe Val Lys Ile Thr Glu His Pro
            35                  40                  45

Asp Gly Thr Asp Leu Ile Tyr Tyr Pro Ser Asn Arg Asp Asp Ser
        50                  55                  60

Pro Glu Gly Ile Val Lys Glu Ile Lys Glu Trp Arg Ala Ala Asn Gly
65                  70                  75                  80

Lys Pro Gly Phe Lys Gln Gly
                85

<210> SEQ ID NO 517
<211> LENGTH: 264
<212> TYPE: DNA
<213> ORGANISM: Escherichia coli

<400> SEQUENCE: 517
atggaactga aaaatagtat tagtgattac acagaggctg agtttgttca acttcttaag     60
gaaattgaaa aagagaatgt tgctgcaact gatgatgtgt tagatgtgtt actcgaacac    120
tttgtaaaaa ttactgagca tccagatgga acggatctga tttattatcc tagtgataat    180
agagacgata gccccgaagg gattgtcaag gaaattaaag aatggcgagc tgctaacggt    240
aagccaggat ttaaacaggg ctga                                           264

<210> SEQ ID NO 518
<211> LENGTH: 87
<212> TYPE: PRT
<213> ORGANISM: Pseudomonas aeruginosa

<400> SEQUENCE: 518

Met Lys Ser Lys Ile Ser Glu Tyr Thr Glu Lys Glu Phe Leu Glu Phe
1               5                   10                  15

Val Glu Asp Ile Tyr Thr Asn Asn Lys Lys Phe Pro Thr Glu Glu
                20                  25                  30

Ser His Ile Gln Ala Val Leu Glu Phe Lys Lys Leu Thr Glu His Pro
            35                  40                  45

Ser Gly Ser Asp Leu Leu Tyr Tyr Pro Asn Glu Asn Arg Glu Asp Ser
        50                  55                  60

Pro Ala Gly Val Val Lys Glu Val Lys Glu Trp Arg Ala Ser Lys Gly 65                70                75                80

Leu Pro Gly Phe Lys Ala Gly
                    85

<210> SEQ ID NO 519
<211> LENGTH: 264
<212> TYPE: DNA
<213> ORGANISM: Pseudomonas aeruginosa

<400> SEQUENCE: 519
atgaagtcca agatttccga atatacggaa aaagagtttc ttgagtttgt tgaagacata    60
tacacaaaca ataagaaaaa gttccctacc gaggagtctc atattcaagc cgtgcttgaa   120
tttaaaaaac taacggaaca cccaagcggc tcagaccttc tttactaccc caacgaaaat   180
agagaagata gcccagctgg agttgtaaag gaagttaaag aatggcgtgc ttccaagggg   240
cttcctggct taaggccgg ttag                                           264

<210> SEQ ID NO 520
<211> LENGTH: 87
<212> TYPE: PRT
<213> ORGANISM: Pseudomonas aeruginosa

<400> SEQUENCE: 520

Met Lys Ser Lys Ile Ser Glu Tyr Thr Glu Lys Glu Phe Leu Glu Phe
1               5                   10                  15

Val Lys Asp Ile Tyr Thr Asn Asn Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

Leu Pro Gly Phe Lys Ala Gly
                    85

<210> SEQ ID NO 521
<211> LENGTH: 264
<212> TYPE: DNA
<213> ORGANISM: Pseudomonas aeruginosa

<400> SEQUENCE: 521
atgaagtcca agatttccga atatacggaa aaagagtttc ttgagtttgt taaagacata    60
tacacaaaca ataagaaaaa gttccctacc gaggagtctc atattcaagc cgtgcttgaa   120
tttaaaaaac taacggaaca cccaagcggc tcagaccttc tttactaccc caacgaaaat   180
agagaagata gcccagctgg agttgtaaag gaagttaaag aatggcgtgc ttccaagggg   240
cttcctggct taaggccgg ttag                                           264

<210> SEQ ID NO 522
<211> LENGTH: 95
<212> TYPE: PRT
<213> ORGANISM: Enterococcus hirae

<400> SEQUENCE: 522

Met Asp Phe Thr Lys Glu Glu Lys Leu Leu Asn Ala Ile Ser Lys Val
1               5                   10                  15

Tyr Asn Glu Ala Thr Ile Asp Asp Tyr Pro Asp Leu Lys Glu Lys Leu

```
                20                  25                  30
Phe Leu Tyr Ser Lys Glu Ile Ser Glu Gly Lys Ser Val Gly Glu Val
            35                  40                  45

Ser Met Lys Leu Ser Ser Phe Leu Gly Arg Tyr Ile Leu Lys His Lys
        50                  55                  60

Phe Gly Leu Pro Lys Ser Leu Ile Glu Leu Gln Ile Val Ser Lys
65                  70                  75                  80

Glu Ser Gln Val Tyr Arg Gly Trp Ala Ser Ile Gly Ile Trp Ser
                85                  90                  95

<210> SEQ ID NO 523
<211> LENGTH: 288
<212> TYPE: DNA
<213> ORGANISM: Enterococcus hirae

<400> SEQUENCE: 523
atggatttta ctaaagaaga aaacttttta aatgcaatta gtaaagtata caatgaagca      60
actatagatg actatcctga cttaaaagaa aagctctttc tttattctaa agaaatcagt     120
gagggaaaaa gtgttggtga agttagtatg aaattaagta gttttcttgg aagatatatt     180
ttaaaacata aatttggatt acctaaatct ttaatagaat acaagaaat tgttagtaag     240 gaatctcaag tatatagagg atgggcttct attggtattt ggagttaa                  288

<210> SEQ ID NO 524
<211> LENGTH: 113
<212> TYPE: PRT
<213> ORGANISM: Leuconostoc mesenteroides

<400> SEQUENCE: 524

Met Lys Lys Lys Tyr Arg Tyr Leu Glu Asp Ser Lys Asn Tyr Thr Ser
1               5                   10                  15

Thr Leu Tyr Ser Leu Leu Val Asp Asn Val Asp Lys Pro Gly Tyr Ser
            20                  25                  30

Asp Ile Cys Asp Val Leu Leu Gln Val Ser Lys Lys Leu Asp Asn Thr
        35                  40                  45

Gln Ser Val Glu Ala Leu Ile Asn Arg Leu Val Asn Tyr Ile Arg Ile
    50                  55                  60

Thr Ala Ser Thr Tyr Lys Ile Ile Phe Ser Lys Lys Glu Glu Leu
65                  70                  75                  80

Ile Ile Lys Leu Gly Val Ile Gly Gln Lys Ala Gly Leu Asn Gly Gln
                85                  90                  95

Tyr Met Ala Asp Phe Ser Asp Lys Ser Gln Phe Tyr Ser Val Phe Asp
            100                 105                 110

Gln

<210> SEQ ID NO 525
<211> LENGTH: 342
<212> TYPE: DNA
<213> ORGANISM: Leuconostoc mesenteroides

<400> SEQUENCE: 525
ttgaaaaaaa agtatcggta tttagaagat agcaaaaatt acactagtac actctattct      60
ctgttagttg ataatgttga caaacctgga tactcagata tttgcgatgt tttgcttcaa     120
gtttctaaga agttggataa tactcaaagt gttgaagcgc taattaatcg attggttaat     180
tatattcgta ttactgcttc aacatacaaa attatttttt caaaaaaaga agaggaattg     240
```

```
attataaaac ttggtgttat tggacaaaaa gctggactta atggtcagta tatggctgat    300 tttcagaca agtctcagtt ttacagcgtt ttcgatcagt aa                        342
```

<210> SEQ ID NO 526
<211> LENGTH: 93
<212> TYPE: PRT
<213> ORGANISM: Escherichia coli

<400> SEQUENCE: 526

```
Met Ser Phe Leu Asn Phe Ala Phe Ser Pro Val Phe Phe Ser Ile Met
1               5                   10                  15

Ala Cys Tyr Phe Ile Val Trp Arg Asn Lys Arg Asn Glu Phe Val Cys
            20                  25                  30

Asn Arg Leu Leu Ser Ile Ile Ile Ser Phe Leu Ile Cys Phe Ile
        35                  40                  45

Tyr Pro Trp Leu Asn Tyr Lys Ile Glu Val Lys Tyr Tyr Ile Phe Glu
    50                  55                  60

Gln Phe Tyr Leu Phe Cys Phe Leu Ser Ser Leu Val Ala Val Val Ile
65                  70                  75                  80

Asn Leu Ile Val Tyr Phe Ile Leu Tyr Arg Arg Cys Ile
                85                  90
```

<210> SEQ ID NO 527
<211> LENGTH: 282
<212> TYPE: DNA
<213> ORGANISM: Escherichia coli

<400> SEQUENCE: 527

```
atgagttttc ttaattttgc attttctcct gtattcttct ccattatggc gtgttatttc    60
attgtatgga gaaataaacg aaacgaattt gtctgcaata gattgctatc aattataata   120 atatctttt tgatatgctt catatatcca tggctaaatt acaaaatcga agttaaatat    180
tatatatttg aacagtttta tcttttttgt ttttatcgt cactcgtggc tgttgtaata    240
aacctaattg tatactttat attatacagg agatgtatat ga                      282
```

<210> SEQ ID NO 528
<211> LENGTH: 96
<212> TYPE: PRT
<213> ORGANISM: Escherichia coli

<400> SEQUENCE: 528

```
Met His Leu Lys Tyr Tyr Leu His Asn Leu Pro Glu Ser Leu Ile Pro
1               5                   10                  15

Trp Ile Leu Ile Leu Ile Phe Asn Asp Asn Asp Asn Thr Pro Leu Leu
            20                  25                  30

Phe Ile Phe Ile Ser Ser Ile His Val Leu Leu Tyr Pro Tyr Ser Lys
        35                  40                  45

Leu Thr Ile Ser Arg Tyr Ile Lys Glu Asn Thr Lys Leu Lys Lys Glu
    50                  55                  60

Pro Trp Tyr Leu Cys Lys Leu Ser Ala Leu Phe Tyr Leu Leu Met Ala
65                  70                  75                  80

Ile Pro Val Gly Leu Pro Ser Phe Ile Tyr Tyr Thr Leu Lys Arg Asn
                85                  90                  95
```

<210> SEQ ID NO 529
<211> LENGTH: 291
<212> TYPE: DNA
<213> ORGANISM: Escherichia coli

<400> SEQUENCE: 529

```
atgcatttaa aatactacct acataattta cctgaatcac ttataccatg gattcttatt      60
ttaatattta acgacaatga taacactcct ttgttattta tatttatatc atcaatacat     120
gtattgctat atccatactc taaattaacc atatctagat atatcaaaga aaatacaaag     180
ttaaaaaaag aaccctggta cttatgcaag ttatctgcat tgtttttattt attaatggca    240
atcccagtag gattgccaag tttcatatat tacactctaa agagaaatta a              291
```

<210> SEQ ID NO 530
<211> LENGTH: 344
<212> TYPE: PRT
<213> ORGANISM: Escherichia coli

<400> SEQUENCE: 530

```
Met Met Ile Gln Ser His Pro Leu Leu Ala Ala Pro Leu Ala Val Gly
1               5                   10                  15

Asp Thr Ile Gly Phe Phe Ser Ser Ala Pro Ala Thr Val Thr Ala
            20                  25                  30

Lys Asn Arg Phe Phe Arg Gly Val Glu Phe Leu Gln Arg Lys Gly Phe
        35                  40                  45

Lys Leu Val Ser Gly Lys Leu Thr Gly Lys Thr Asp Phe Tyr Arg Ser
    50                  55                  60

Gly Thr Ile Lys Glu Arg Ala Gln Glu Phe Asn Glu Leu Val Tyr Asn
65                  70                  75                  80

Pro Asp Ile Thr Cys Ile Met Ser Thr Ile Gly Gly Asp Asn Ser Asn
                85                  90                  95

Ser Leu Leu Pro Phe Leu Asp Tyr Asp Ala Ile Ile Ala Asn Pro Lys
            100                 105                 110

Ile Ile Ile Gly Tyr Ser Asp Thr Thr Ala Leu Leu Ala Gly Ile Tyr
        115                 120                 125

Ala Lys Thr Gly Leu Ile Thr Phe Tyr Gly Pro Ala Leu Ile Pro Ser
    130                 135                 140

Phe Gly Glu His Pro Pro Leu Val Asp Ile Thr Tyr Glu Ser Phe Ile
145                 150                 155                 160

Lys Ile Leu Thr Arg Lys Gln Ser Gly Ile Tyr Thr Tyr Thr Leu Pro
                165                 170                 175

Glu Lys Trp Ser Asp Glu Ser Ile Asn Trp Asn Glu Asn Lys Ile Leu
            180                 185                 190

Arg Pro Lys Lys Leu Tyr Lys Asn Asn Cys Ala Phe Tyr Gly Ser Gly
        195                 200                 205

Lys Val Glu Gly Arg Val Ile Gly Gly Asn Leu Asn Thr Leu Thr Gly
    210                 215                 220

Ile Trp Gly Ser Glu Trp Met Pro Glu Ile Leu Asn Gly Asp Ile Leu
225                 230                 235                 240

Phe Ile Glu Asp Ser Arg Lys Ser Ile Ala Thr Ile Glu Arg Leu Phe
                245                 250                 255

Ser Met Leu Lys Leu Asn Arg Val Phe Asp Lys Val Ser Ala Ile Ile
            260                 265                 270

Leu Gly Lys His Glu Leu Phe Asp Cys Ala Gly Ser Lys Arg Arg Pro
        275                 280                 285

Tyr Glu Val Leu Thr Glu Val Leu Asp Gly Lys Gln Ile Pro Val Leu
    290                 295                 300

Asp Gly Phe Asp Cys Ser His Thr His Pro Met Leu Thr Leu Pro Leu
```

```
                305                 310                 315                 320
Gly Val Lys Leu Ala Ile Asp Phe Asp Asn Lys Asn Ile Ser Ile Thr
                    325                 330                 335
Glu Gln Tyr Leu Ser Thr Glu Lys
                340

<210> SEQ ID NO 531
<211> LENGTH: 1000
<212> TYPE: DNA
<213> ORGANISM: Escherichia coli

<400> SEQUENCE: 531
atgatgatac aatctcatcc actactggcc gctcccctgg cagtaggaga tacaattggt      60
ttctttttcat catctgctcc ggcaacagtt actgcaaaaa atcgtttttt tcggggagtt    120
gagtttcttc agagaaaggg atttaagctg gtatcaggga gcttaccgg taaaacagat     180
ttttatcgtt caggtactat taaagaaaga gctcaagaat ttaatgagtt agtctacaat    240
cctgatatta cctgtataat gtcaacgatc ggtggagata cagtaattc actactaccg    300
tttctggact atgatgctat cattgcaaac cccaaaatta tcataggtta ctcagataca    360
actgctttat tagcaggaat atatgcaaaa acagggttaa taacattcta tggaccagct    420
cttattcctt cgtttggtga acatccacct cttgtggata taacatatga atcatttatt    480
aaaatactaa caagaaaaca atcaggaata tatacctaca cattacctga aaagtggagt    540
gatgagagca taaactggaa tgaaaacaag atattaaggc ctaagaagct atataaaaac    600
aactgtgcct tttatggttc cggaaaagtt gaggggcgtg taattggagg aaatctaaat    660
actttgacag gtatatgggg gagtgaatgg atgcctgaaa ttcttaatgg agatatattg    720
tttattgagg acagtcggaa aagcattgca acaattgaac gattattctc tatgctaaag    780
cttaatcgcg tgtttgataa agttagtgca ataatactcg ggaaacatga gcttttttgat   840
tgtgcaggaa gtaaacgcag accatatgaa gtattaacag aggtattaga tgggaaacag    900
attcctgtac tggatggatt tgattgttca catacacatc caatgctaac tcttccactt    960
ggtgtaaaat tagctattga ctttgacaac aaaaatatat                         1000

<210> SEQ ID NO 532
<211> LENGTH: 90
<212> TYPE: PRT
<213> ORGANISM: Lactobacillus sakei

<400> SEQUENCE: 532

Met Lys Ala Asp Tyr Lys Lys Ile Asn Ser Ile Leu Thr Tyr Thr Ser
1               5                   10                  15
Thr Ala Leu Lys Asn Pro Lys Ile Ile Lys Asp Lys Asp Leu Val Val
                20                  25                  30
Leu Leu Thr Ile Ile Gln Glu Glu Ala Lys Gln Asn Arg Ile Phe Tyr
            35                  40                  45
Asp Tyr Lys Arg Lys Phe Arg Pro Ala Val Thr Arg Phe Thr Ile Asp
        50                  55                  60
Asn Asn Phe Glu Ile Pro Asp Cys Leu Val Lys Leu Leu Ser Ala Val
65                  70                  75                  80
Glu Thr Pro Lys Ala Trp Ser Gly Phe Ser
                85                  90

<210> SEQ ID NO 533
<211> LENGTH: 268
```

```
<212> TYPE: DNA
<213> ORGANISM: Lactobacillus sakei

<400> SEQUENCE: 533
ggcagattat aaaaaaataa attcaatact aacttacaca tctactgctt taaaaaaccc      60
taaaattata aaagataaag atttagtagt ccttctaact attattcaag aagaagccaa     120
acaaaataga atcttttatg attataaaag aaaatttcgt ccagcggtta ctcgctttac     180
aattgataat aattttgaga ttcctgattg tttggttaaa ctactgtcag ctgttgaaac     240
acctaaggcg tggtctggat ttagttag                                        268

<210> SEQ ID NO 534
<211> LENGTH: 83
<212> TYPE: PRT
<213> ORGANISM: Escherichia coli

<400> SEQUENCE: 534

Met Lys Leu Ser Pro Lys Ala Ala Ile Glu Val Cys Asn Glu Ala Ala
 1               5                  10                  15

Lys Lys Gly Leu Trp Ile Leu Gly Ile Asp Gly Gly His Trp Leu Asn
                20                  25                  30

Pro Gly Phe Arg Ile Asp Ser Ser Ala Ser Trp Thr Tyr Asp Met Pro
            35                  40                  45

Glu Glu Tyr Lys Ser Lys Thr Pro Glu Asn Asn Arg Leu Ala Ile Glu
        50                  55                  60

Asn Ile Lys Asp Asp Ile Glu Asn Gly Tyr Thr Ala Phe Ile Ile Thr
65                  70                  75                  80

Leu Lys Met

<210> SEQ ID NO 535
<211> LENGTH: 251
<212> TYPE: DNA
<213> ORGANISM: Escherichia coli

<400> SEQUENCE: 535
tgaagttatc accaaaagct gcaatagaag tttgtaatga agcagcgaaa aaaggcttat      60
ggattttggg cattgatggt gggcattggc tgaatcctgg attcaggata gatagttcag     120
catcatggac atatgatatg ccggaggaat acaaatcaaa acccctgaa ataatagat      180
tggctattga aaatattaaa gatgatattg agaatggata cactgctttc attatcacgt     240
taaagatgta a                                                         251

<210> SEQ ID NO 536
<211> LENGTH: 436
<212> TYPE: PRT
<213> ORGANISM: Bacillus subtilis

<400> SEQUENCE: 536

Met Asn Asn Ile Phe Pro Ile Met Ser Leu Leu Phe Lys Gln Leu Tyr
 1               5                  10                  15

Ser Arg Gln Gly Lys Lys Asp Ala Ile Arg Ile Ala Ala Gly Leu Val
                20                  25                  30

Ile Leu Ala Val Phe Glu Ile Gly Leu Ile Arg Gln Ala Gly Ile Asp
            35                  40                  45

Glu Ser Val Leu Gly Lys Thr Tyr Ile Ile Leu Ala Leu Leu Leu Met
        50                  55                  60

Asn Thr Tyr Met Val Phe Leu Ser Val Thr Ser Gln Trp Lys Glu Ser
```

```
              65                  70                  75                  80

Tyr Met Lys Leu Ser Cys Leu Leu Pro Ile Ser Ser Arg Ser Phe Trp
                     85                  90                  95

Leu Ala Gln Ser Val Val Leu Phe Val Asp Thr Cys Leu Arg Arg Thr
                    100                 105                 110

Leu Phe Phe Phe Ile Leu Pro Leu Phe Leu Phe Gly Asn Gly Thr Leu
                    115                 120                 125

Ser Gly Ala Gln Thr Leu Phe Trp Leu Gly Arg Phe Ser Phe Phe Thr
    130                 135                 140

Val Tyr Ser Ile Leu Phe Gly Val Met Leu Ser Asn His Phe Val Lys
    145                 150                 155                 160

Lys Lys Asn Ser Met Phe Leu Leu His Ala Ala Val Phe Ala Phe Val
                    165                 170                 175

Cys Leu Ser Ala Ala Phe Met Pro Ala Val Thr Ile Pro Leu Cys Ala
                    180                 185                 190

Val His Met Leu Trp Ala Val Ile Ile Asp Phe Pro Val Phe Leu Gln
                    195                 200                 205

Ala Pro Pro His Gln Ser Lys Met His Phe Phe Met Arg Arg Ser Glu
                    210                 215                 220

Phe Ser Phe Tyr Lys Arg Glu Trp Asn Arg Phe Ile Ser Ser Lys Ala
    225                 230                 235                 240

Met Leu Leu Asn Tyr Val Val Met Ala Ala Phe Ser Gly Phe Phe Ser
                    245                 250                 255

Phe Gln Met Met Asn Thr Gly Ile Phe Asn Gln Gln Val Ile Tyr Ile
                    260                 265                 270

Val Ile Ser Ala Leu Leu Leu Ile Cys Ser Pro Ile Ala Leu Leu Tyr
                    275                 280                 285

Ser Ile Glu Lys Asn Asp Arg Met Leu Leu Ile Thr Leu Pro Ile Lys
                    290                 295                 300

Arg Arg Thr Met Phe Trp Ala Lys Tyr Arg Phe Tyr Ser Gly Leu Leu
    305                 310                 315                 320

Ala Gly Gly Phe Leu Leu Val Ala Ile Ile Val Gly Phe Ile Ser Gly
                    325                 330                 335

Arg Pro Ile Ser Ala Leu Thr Phe Val Gln Cys Met Glu Leu Leu Leu
                    340                 345                 350

Ala Gly Ala Phe Ile Arg Leu Thr Ala Asp Glu Lys Arg Pro Ser Phe
                    355                 360                 365

Gly Trp Gln Thr Glu Gln Gln Leu Trp Ser Gly Phe Ser Lys Tyr Arg
    370                 375                 380

Ser Tyr Leu Phe Cys Leu Pro Leu Phe Leu Ala Thr Leu Ala Gly Thr
    385                 390                 395                 400

Ala Val Ser Leu Ala Val Ile Pro Ile Ala Ala Leu Ile Ile Val Tyr
                    405                 410                 415

Tyr Leu Gln Lys Gln Asp Gly Gly Phe Phe Asp Thr Ser Lys Arg Glu
                    420                 425                 430

Arg Ile Gly Ser
            435

<210> SEQ ID NO 537
<211> LENGTH: 1000
<212> TYPE: DNA
<213> ORGANISM: Bacillus subtilis

<400> SEQUENCE: 537
```

-continued

| | |
|---|---|
| ttggggagga gaccgatctg cggcgggaat tttttgaggt tatcggccat gaataacata | 60 |
| ttccccatca tgtcgttgct gttcaaacag ctgtacagcc ggcaagggaa aaaggacgct | 120 |
| atccgcattg ctgcagggct tgtgattctc gccgtgtttg aaatcgggct gatccgacaa | 180 |
| gccggcattg acgaatcggt gttgggaaaa acgtatatca tattggcgct tctcttaatg | 240 |
| aacacgtata tggtgtttct ttccgtgaca tcacaatgga aggaatctta tatgaagctg | 300 |
| agctgtctgc tgccgatttc atcacggagc ttttggctcg cccagagtgt cgttctgttt | 360 |
| gtcgatacct gtttgagaag aacgttattc tttttttattt taccgctgtt cttatttgga | 420 |
| aacggaacgc tgtcaggggc gcaaacattg ttttggcttg gcagatttc gttttttacc | 480 |
| gtttactcga ttctattcgg agttatgcta agcaaccatt tcgtcaaaaa gaagaactcg | 540 |
| atgtttctgc tgcatgcggc ggtattcgcc tttgtatgcc tcagtgccgc ttttatgccg | 600 |
| gccgtcacga tcccgctatg cgcggttcac atgctatggg cggtgatcat tgactttccg | 660 |
| gtctttctgc aggcgcctcc gcatcagagc aagatgcatt ttttatgcg gcgatctgaa | 720 |
| ttttcgtttt acaaaagaga atggaaccga tttatttctt ctaaagcgat gctgttaaat | 780 |
| tacgtggtga tggcggcgtt cagcggattc ttttcgttcc agatgatgaa cactggcatc | 840 |
| ttcaatcagc aagtgattta tattgtgatt tccgctctat tgctgatttg ctcgccgatc | 900 |
| gcccttttgt actctattga aaaaaacgat cgcatgctgc tcatcacgct tccaattaaa | 960 |
| agaagaacga tgttttgggc gaaatatcgc ttttattcag | 1000 |

<210> SEQ ID NO 538
<211> LENGTH: 580
<212> TYPE: PRT
<213> ORGANISM: Escherichia coli

<400> SEQUENCE: 538

Met Glu Arg Lys Gln Lys Asn Ser Leu Phe Asn Tyr Ile Tyr Ser Leu
1               5                   10                  15

Met Asp Val Arg Gly Lys Phe Leu Phe Phe Ser Met Leu Phe Ile Thr
            20                  25                  30

Ser Leu Ser Ser Ile Ile Ile Ser Ile Ser Pro Leu Ile Leu Ala Lys
        35                  40                  45

Ile Thr Asp Leu Leu Ser Gly Ser Leu Ser Asn Phe Ser Tyr Glu Tyr
    50                  55                  60

Leu Val Leu Leu Ala Cys Leu Tyr Met Phe Cys Val Ile Ser Asn Lys
65                  70                  75                  80

Ala Ser Val Phe Leu Phe Met Ile Leu Gln Ser Ser Leu Arg Ile Asn
                85                  90                  95

Met Gln Lys Lys Met Ser Leu Lys Tyr Leu Arg Glu Leu Tyr Asn Glu
            100                 105                 110

Asn Ile Thr Asn Leu Ser Lys Asn Asn Ala Gly Tyr Thr Thr Gln Ser
        115                 120                 125

Leu Asn Gln Ala Ser Asn Asp Ile Tyr Ile Leu Val Arg Asn Val Ser
    130                 135                 140

Gln Asn Ile Leu Ser Pro Val Ile Gln Leu Ile Ser Thr Ile Val Val
145                 150                 155                 160

Val Leu Ser Thr Lys Asp Trp Phe Ser Ala Gly Val Phe Phe Leu Tyr
                165                 170                 175

Ile Leu Val Phe Val Ile Phe Asn Thr Arg Leu Thr Gly Ser Leu Ala
            180                 185                 190

Ser Leu Arg Lys His Ser Met Asp Ile Thr Leu Asn Ser Tyr Ser Leu

```
                195                 200                 205
Leu Ser Asp Thr Val Asp Asn Met Ile Ala Lys Lys Asn Asn Ala
210                 215                 220
Leu Arg Leu Ile Ser Glu Arg Tyr Glu Asp Ala Leu Thr Gln Glu Asn
225                 230                 235                 240
Asn Ala Gln Lys Lys Tyr Trp Leu Leu Ser Lys Val Leu Leu Leu
                245                 250                 255
Asn Ser Leu Leu Ala Val Ile Leu Phe Gly Ser Val Phe Ile Tyr Asn
            260                 265                 270
Ile Leu Gly Val Leu Asn Gly Val Val Ser Ile Gly His Phe Ile Met
            275                 280                 285
Ile Thr Ser Tyr Ile Ile Leu Leu Ser Thr Pro Val Glu Asn Ile Gly
            290                 295                 300
Ala Leu Leu Ser Glu Ile Arg Gln Ser Met Ser Ser Leu Ala Gly Phe
305                 310                 315                 320
Ile Gln Arg His Ala Glu Asn Lys Ala Thr Ser Pro Ser Ile Pro Phe
                325                 330                 335
Leu Asn Met Glu Arg Lys Leu Asn Leu Ser Ile Arg Glu Leu Ser Phe
            340                 345                 350
Ser Tyr Ser Asp Asp Lys Lys Ile Leu Asn Ser Val Ser Leu Asp Leu
            355                 360                 365
Phe Thr Gly Lys Met Tyr Ser Leu Thr Gly Pro Ser Gly Ser Gly Lys
370                 375                 380
Ser Thr Leu Val Lys Ile Ile Ser Gly Tyr Tyr Lys Asn Tyr Phe Gly
385                 390                 395                 400
Asp Ile Tyr Leu Asn Asp Ile Ser Leu Arg Asn Ile Ser Asp Glu Asp
                405                 410                 415
Leu Asn Asp Ala Ile Tyr Tyr Leu Thr Gln Asp Tyr Ile Phe Met
            420                 425                 430
Asp Thr Leu Arg Phe Asn Leu Arg Leu Ala Asn Tyr Asp Ala Ser Glu
            435                 440                 445
Asn Glu Ile Phe Lys Val Leu Lys Leu Ala Asn Leu Ser Val Val Asn
            450                 455                 460
Asn Glu Pro Val Ser Leu Asp Thr His Leu Ile Asn Arg Gly Asn Asn
465                 470                 475                 480
Tyr Ser Gly Gly Gln Lys Gln Arg Ile Ser Leu Ala Arg Leu Phe Leu
                485                 490                 495
Arg Lys Pro Ala Ile Ile Ile Asp Glu Ala Thr Ser Ala Leu Asp
            500                 505                 510
Tyr Ile Asn Glu Ser Glu Ile Leu Ser Ser Ile Arg Thr His Phe Pro
            515                 520                 525
Asp Ala Leu Ile Ile Asn Ile Ser His Arg Ile Asn Leu Leu Glu Cys
            530                 535                 540
Ser Asp Cys Val Tyr Val Leu Asn Glu Gly Asn Ile Val Ala Ser Gly
545                 550                 555                 560
His Phe Arg Asp Leu Met Val Ser Asn Glu Tyr Ile Ser Gly Leu Ala
                565                 570                 575
Ser Val Thr Glu
            580

<210> SEQ ID NO 539
<211> LENGTH: 1000
<212> TYPE: DNA
<213> ORGANISM: Escherichia coli
```

-continued

<400> SEQUENCE: 539

```
atggaaagaa aacagaaaaa ctcattattt aattatattt attcattaat ggatgtaaga    60
ggtaaatttt tattctttttc catgttattc attacatcat tatcatcgat aatcatatct   120
atttcaccat tgattcttgc aaagattaca gatttactgt ctggctcatt gtcaaatttt   180
agttatgaat atctggtttt acttgcctgt ttatacatgt tttgcgttat atctaataaa   240
gcaagtgttt ttttatttat gatactgcaa agtagtctac gtattaacat gcagaaaaaa   300
atgtcgctaa agtatttgag agaattgtat aacgaaaata taactaactt gagtaaaaat   360
aatgctggat atacaacgca aagtcttaac caggcttcaa atgacattta tattcttgtg   420
agaaatgttt cccagaatat cctgtcacct gttatacaac ttatttccac tattgttgtt   480
gttttatcta cgaaggactg gttttctgcc ggtgtgtttt ttctctatat ctggtatttt   540
gtaatttttta ataccagact gactggcagt ttagcgtctc tcagaaaaca cagcatggat   600
atcactctta actcttatag tctgttatct gatactgttg ataacatgat agcagctaaa   660
aagaataatg cattaagact tatttctgaa cgttatgaag atgctctcac tcaggaaaac   720
aatgctcaga aaaatactg gttactcagt tctaaagttc ttttattgaa ctctttactt   780
gctgtaatat tatttggttc tgtattcata tataatattt taggtgtgct gaatggtgta   840
gttagtatcg ccacttcat tatgattaca tcatatatca ttcttctttc aacgccagtg   900
gaaaatatag gggcattgct aagtgagatc aggcagtcaa tgtctagcct ggcaggtttt   960
attcaacgtc atgccgagaa taaagccaca tctccttcaa                        1000
```

<210> SEQ ID NO 540
<211> LENGTH: 95
<212> TYPE: PRT
<213> ORGANISM: Klebsiella pneumoniae

<400> SEQUENCE: 540

```
Met Thr Leu Leu Ser Phe Gly Phe Ser Pro Val Phe Phe Ser Val Met
1               5                   10                  15

Ala Phe Cys Ile Ile Ser Arg Ser Lys Phe Tyr Pro Gln Arg Thr Arg
            20                  25                  30

Asn Lys Val Ile Val Leu Ile Leu Leu Thr Phe Phe Ile Cys Phe Leu
        35                  40                  45

Tyr Pro Leu Thr Lys Val Tyr Leu Val Gly Ser Tyr Gly Ile Phe Asp
    50                  55                  60

Lys Phe Tyr Leu Phe Cys Phe Ile Ser Thr Leu Ile Ala Ile Ala Ile
65                  70                  75                  80

Asn Val Val Ile Leu Thr Ile Asn Gly Ala Lys Asn Glu Arg Asn
                85                  90                  95
```

<210> SEQ ID NO 541
<211> LENGTH: 288
<212> TYPE: DNA
<213> ORGANISM: Klebsiella pneumoniae

<400> SEQUENCE: 541

```
atgacattac tttcatttgg attttctcct gttttctttt cagtcatggc gttctgtatc    60
atttcacgta gtaaattcta tccgcagaga acgcgaaaca aagttattgt tctgattta   120
ctaactttt ttatttgttt tttatatcca ttaacaaaag tgtatctggt gggaagttac   180
ggtatatttg acaaattcta cctctttttgc tttatttcta cgttaattgc aatagcaatt   240
```
aacgtagtga tacttacaat aaatggagct aagaatgaga gaaattag                          288

<210> SEQ ID NO 542
<211> LENGTH: 13
<212> TYPE: RNA
<213> ORGANISM: Artificial Sequence
<220> FEATURE:
<223> OTHER INFORMATION: Kozak sequence

<400> SEQUENCE: 542
gccgccrcca ugg                                                                13

<210> SEQ ID NO 543
<211> LENGTH: 6
<212> TYPE: RNA
<213> ORGANISM: Artificial Sequence
<220> FEATURE:
<223> OTHER INFORMATION: Shine-Delgarno sequence

<400> SEQUENCE: 543 ggaggu                                                                         6

<210> SEQ ID NO 544
<211> LENGTH: 30
<212> TYPE: DNA
<213> ORGANISM: Artificial Sequence
<220> FEATURE:
<223> OTHER INFORMATION: Lead promoter

<400> SEQUENCE: 544
gaaaaccttg tcaatgaaga gcgatctatg                                              30

<210> SEQ ID NO 545
<211> LENGTH: 30
<212> TYPE: DNA
<213> ORGANISM: Artificial Sequence
<220> FEATURE:
<223> OTHER INFORMATION: FecA promoter

<400> SEQUENCE: 545
ttctcgttcg actcatagct gaacacaaca                                              30

<210> SEQ ID NO 546
<211> LENGTH: 16
<212> TYPE: DNA
<213> ORGANISM: Artificial Sequence
<220> FEATURE:
<223> OTHER INFORMATION: Cu-sensitive promoter

<400> SEQUENCE: 546
atgacaaaat tgtcat                                                             16

<210> SEQ ID NO 547
<211> LENGTH: 30
<212> TYPE: DNA
<213> ORGANISM: Artificial Sequence
<220> FEATURE:
<223> OTHER INFORMATION: Fe promoter

<400> SEQUENCE: 547
accaatgctg ggaacggcca gggcacctaa                                              30

<210> SEQ ID NO 548
<211> LENGTH: 30
<212> TYPE: DNA
<213> ORGANISM: Artificial Sequence

```
<220> FEATURE:
<223> OTHER INFORMATION: Fe and UV promoters

<400> SEQUENCE: 548
ctgaaagcgc ataccgctat ggagggggtt                                30

<210> SEQ ID NO 549
<211> LENGTH: 30
<212> TYPE: DNA
<213> ORGANISM: Artificial Sequence
<220> FEATURE:
<223> OTHER INFORMATION: PrFe (PI + PII rus operon)

<400> SEQUENCE: 549
tagatatgcc tgaaagcgca taccgctatg                                30

<210> SEQ ID NO 550
<211> LENGTH: 30
<212> TYPE: DNA
<213> ORGANISM: Artificial Sequence
<220> FEATURE:
<223> OTHER INFORMATION: Lux cassette right promoter

<400> SEQUENCE: 550
tgttatagtc gaatacctct ggcggtgata                                30

<210> SEQ ID NO 551
<211> LENGTH: 30
<212> TYPE: DNA
<213> ORGANISM: Artificial Sequence
<220> FEATURE:
<223> OTHER INFORMATION: P(Las) TetO

<400> SEQUENCE: 551
ttttggtaca ctccctatca gtgatagaga                                30

<210> SEQ ID NO 552
<211> LENGTH: 30
<212> TYPE: DNA
<213> ORGANISM: Artificial Sequence
<220> FEATURE:
<223> OTHER INFORMATION: P(Las) CIO

<400> SEQUENCE: 552 cttttttggta cactacctct ggcggtgata                               30

<210> SEQ ID NO 553
<211> LENGTH: 30
<212> TYPE: DNA
<213> ORGANISM: Artificial Sequence
<220> FEATURE:
<223> OTHER INFORMATION: P(Rhl)

<400> SEQUENCE: 553
tacgcaagaa aatggtttgt tatagtcgaa                                30

<210> SEQ ID NO 554
<211> LENGTH: 30
<212> TYPE: DNA
<213> ORGANISM: Artificial Sequence
<220> FEATURE:
<223> OTHER INFORMATION: Double Promoter (LuxR/HSL, positive / cI,
      negative)

<400> SEQUENCE: 554
cgtgcgtgtt gataacaccg tgcgtgttga                                30
```

```
<210> SEQ ID NO 555
<211> LENGTH: 30
<212> TYPE: DNA
<213> ORGANISM: Artificial Sequence
<220> FEATURE:
<223> OTHER INFORMATION: P2 promoter in agr operon from S. aureus

<400> SEQUENCE: 555
agattgtact aaatcgtata atgacagtga                                          30

<210> SEQ ID NO 556
<211> LENGTH: 30
<212> TYPE: DNA
<213> ORGANISM: Artificial Sequence
<220> FEATURE:
<223> OTHER INFORMATION: plux-cI hybrid promoter

<400> SEQUENCE: 556
gtgttgatgc ttttatcacc gccagtggta                                          30

<210> SEQ ID NO 557
<211> LENGTH: 30
<212> TYPE: DNA
<213> ORGANISM: Artificial Sequence
<220> FEATURE:
<223> OTHER INFORMATION: plux-lac hybrid promoter

<400> SEQUENCE: 557
agtgtgtgga attgtgagcg gataacaatt                                          30

<210> SEQ ID NO 558
<211> LENGTH: 30
<212> TYPE: DNA
<213> ORGANISM: Artificial Sequence
<220> FEATURE:
<223> OTHER INFORMATION: CinR, CinL and glucose controlled promotor

<400> SEQUENCE: 558
acatcttaaa agttttagta tcatattcgt                                          30

<210> SEQ ID NO 559
<211> LENGTH: 30
<212> TYPE: DNA
<213> ORGANISM: Artificial Sequence
<220> FEATURE:
<223> OTHER INFORMATION: RhlR promoter repressible by CI

<400> SEQUENCE: 559
tacgcaagaa aatggtttgt tatagtcgaa                                          30

<210> SEQ ID NO 560
<211> LENGTH: 30
<212> TYPE: DNA
<213> ORGANISM: Artificial Sequence
<220> FEATURE:
<223> OTHER INFORMATION: Reverse Lux Promoter

<400> SEQUENCE: 560
tcttgcgtaa acctgtacga tcctacaggt                                          30

<210> SEQ ID NO 561
<211> LENGTH: 30
<212> TYPE: DNA
<213> ORGANISM: Artificial Sequence
<220> FEATURE:
```

<223> OTHER INFORMATION: rhlI promoter

<400> SEQUENCE: 561
atcctccttt agtcttcccc ctcatgtgtg                                              30

<210> SEQ ID NO 562
<211> LENGTH: 30
<212> TYPE: DNA
<213> ORGANISM: Artificial Sequence
<220> FEATURE:
<223> OTHER INFORMATION: lasI promoter

<400> SEQUENCE: 562
taaaattatg aaatttgcat aaattcttca                                              30

<210> SEQ ID NO 563
<211> LENGTH: 30
<212> TYPE: DNA
<213> ORGANISM: Artificial Sequence
<220> FEATURE:
<223> OTHER INFORMATION: LuxR+3OC6HSL independent R0065

<400> SEQUENCE: 563
gtgttgacta ttttacctct ggcggtgata                                              30

<210> SEQ ID NO 564
<211> LENGTH: 30
<212> TYPE: DNA
<213> ORGANISM: Artificial Sequence
<220> FEATURE:
<223> OTHER INFORMATION: LasR/LasI Inducible & RHLR/RHLI repressible
      Promoter

<400> SEQUENCE: 564
gaaatctggc agttttggt acacgaaagc                                               30

<210> SEQ ID NO 565
<211> LENGTH: 30
<212> TYPE: DNA
<213> ORGANISM: Artificial Sequence
<220> FEATURE:
<223> OTHER INFORMATION: pLux/cI Hybrid Promoter

<400> SEQUENCE: 565
acaccgtgcg tgttgatata gtcgaataaa                                              30

<210> SEQ ID NO 566
<211> LENGTH: 30
<212> TYPE: DNA
<213> ORGANISM: Artificial Sequence
<220> FEATURE:
<223> OTHER INFORMATION: pLas promoter

<400> SEQUENCE: 566
aaaattatga aatttgtata aattcttcag                                              30

<210> SEQ ID NO 567
<211> LENGTH: 30
<212> TYPE: DNA
<213> ORGANISM: Artificial Sequence
<220> FEATURE:
<223> OTHER INFORMATION: pLas/cI Hybrid Promoter

<400> SEQUENCE: 567
ggttcttttt ggtacctctg gcggtgataa                                              30

<210> SEQ ID NO 568
<211> LENGTH: 30
<212> TYPE: DNA
<213> ORGANISM: Artificial Sequence
<220> FEATURE:
<223> OTHER INFORMATION: pLas/Lux Hybrid Promoter

<400> SEQUENCE: 568
tgtaggatcg tacaggtata aattcttcag                               30

<210> SEQ ID NO 569
<211> LENGTH: 30
<212> TYPE: DNA
<213> ORGANISM: Artificial Sequence
<220> FEATURE:
<223> OTHER INFORMATION: pLux

<400> SEQUENCE: 569
caagaaaatg gtttgttata gtcgaataaa                               30

<210> SEQ ID NO 570
<211> LENGTH: 30
<212> TYPE: DNA
<213> ORGANISM: Artificial Sequence
<220> FEATURE:
<223> OTHER INFORMATION: pLux/Las Hybrid Promoter

<400> SEQUENCE: 570
ctatctcatt tgctagtata gtcgaataaa                               30

<210> SEQ ID NO 571
<211> LENGTH: 30
<212> TYPE: DNA
<213> ORGANISM: Artificial Sequence
<220> FEATURE:
<223> OTHER INFORMATION: Hybrid promoter: HSL-LuxR activated, P22 C2
      repressed

<400> SEQUENCE: 571
tagtttataa tttaagtgtt ctttaatttc                               30

<210> SEQ ID NO 572
<211> LENGTH: 30
<212> TYPE: DNA
<213> ORGANISM: Artificial Sequence
<220> FEATURE:
<223> OTHER INFORMATION: PAI+LasR -> LuxI (AI)

<400> SEQUENCE: 572
caccttcggg tgggcctttc tgcgtttata                               30

<210> SEQ ID NO 573
<211> LENGTH: 30
<212> TYPE: DNA
<213> ORGANISM: Artificial Sequence
<220> FEATURE:
<223> OTHER INFORMATION: PAI+LasR -> LasI & AI+LuxR --[m]LasI

<400> SEQUENCE: 573
aataactctg atagtgctag tgtagatctc                               30

<210> SEQ ID NO 574
<211> LENGTH: 30
<212> TYPE: DNA
<213> ORGANISM: Artificial Sequence
<220> FEATURE:

```
<223> OTHER INFORMATION: PAI+LasR -> LasI+GFP & AI+LuxR --[\m]LasI+GFP

<400> SEQUENCE: 574
caccttcggg tgggcctttc tgcgtttata                                    30

<210> SEQ ID NO 575
<211> LENGTH: 30
<212> TYPE: DNA
<213> ORGANISM: Artificial Sequence
<220> FEATURE:
<223> OTHER INFORMATION: Complex QS -> LuxI & LasI circuit

<400> SEQUENCE: 575
caccttcggg tgggcctttc tgcgtttata                                    30

<210> SEQ ID NO 576
<211> LENGTH: 30
<212> TYPE: DNA
<213> ORGANISM: Artificial Sequence
<220> FEATURE:
<223> OTHER INFORMATION: position 3 mutated promoter lux pR-3 (luxR &
      HSL regulated)

<400> SEQUENCE: 576
caagaaaatg gtttgttata gtcgaataaa                                    30

<210> SEQ ID NO 577
<211> LENGTH: 30
<212> TYPE: DNA
<213> ORGANISM: Artificial Sequence
<220> FEATURE:
<223> OTHER INFORMATION: position 5 mutated promoter lux pR-5 (luxR &
      HSL regulated)

<400> SEQUENCE: 577
caagaaaatg gtttgttata gtcgaataaa                                    30

<210> SEQ ID NO 578
<211> LENGTH: 30
<212> TYPE: DNA
<213> ORGANISM: Artificial Sequence
<220> FEATURE:
<223> OTHER INFORMATION: position 3&5 mutated promoter lux pR-3/5
      (luxR & HSL regulated)

<400> SEQUENCE: 578
caagaaaatg gtttgttata gtcgaataaa                                    30

<210> SEQ ID NO 579
<211> LENGTH: 30
<212> TYPE: DNA
<213> ORGANISM: Artificial Sequence
<220> FEATURE:
<223> OTHER INFORMATION: Promoter (HSL-mediated luxR repressor)

<400> SEQUENCE: 579
ttgacacctg taggatcgta caggtataat                                    30

<210> SEQ ID NO 580
<211> LENGTH: 30
<212> TYPE: DNA
<213> ORGANISM: Artificial Sequence
<220> FEATURE:
<223> OTHER INFORMATION: Promoter (luxR & HSL regulated -- lux pR)

<400> SEQUENCE: 580
```
caagaaaatg gtttgttata gtcgaataaa                                    30

<210> SEQ ID NO 581
<211> LENGTH: 30
<212> TYPE: DNA
<213> ORGANISM: Artificial Sequence
<220> FEATURE:
<223> OTHER INFORMATION: Promoter (luxR & HSL regulated -- lux pL)

<400> SEQUENCE: 581
cacgcaaaac ttgcgacaaa caataggtaa                                    30

<210> SEQ ID NO 582
<211> LENGTH: 30
<212> TYPE: DNA
<213> ORGANISM: Artificial Sequence
<220> FEATURE:
<223> OTHER INFORMATION: Promoter (RhlR & C4-HSL regulated)

<400> SEQUENCE: 582
gttagctttc gaattggcta aaaagtgttc                                    30

<210> SEQ ID NO 583
<211> LENGTH: 30
<212> TYPE: DNA
<213> ORGANISM: Artificial Sequence
<220> FEATURE:
<223> OTHER INFORMATION: Promoter (cinR and HSL regulated)

<400> SEQUENCE: 583
ccattctgct ttccacgaac ttgaaaacgc                                    30

<210> SEQ ID NO 584
<211> LENGTH: 30
<212> TYPE: DNA
<213> ORGANISM: Artificial Sequence
<220> FEATURE:
<223> OTHER INFORMATION: Promoter (LasR & PAI regulated)

<400> SEQUENCE: 584
ggccgcgggt tcttttggt acacgaaagc                                     30

<210> SEQ ID NO 585
<211> LENGTH: 30
<212> TYPE: DNA
<213> ORGANISM: Artificial Sequence
<220> FEATURE:
<223> OTHER INFORMATION: Promoter, Standard (luxR and HSL regulated --
      lux pR)

<400> SEQUENCE: 585
aagaaaatgg tttgttgata ctcgaataaa                                    30

<210> SEQ ID NO 586
<211> LENGTH: 30
<212> TYPE: DNA
<213> ORGANISM: Artificial Sequence
<220> FEATURE:
<223> OTHER INFORMATION: P(Bla)

<400> SEQUENCE: 586
gtttatacat aggcgagtac tctgttatgg                                    30

<210> SEQ ID NO 587
<211> LENGTH: 30
<212> TYPE: DNA

```
<213> ORGANISM: Artificial Sequence
<220> FEATURE:
<223> OTHER INFORMATION: P(Cat)

<400> SEQUENCE: 587
agaggttcca actttcacca taatgaaaca                                        30

<210> SEQ ID NO 588
<211> LENGTH: 30
<212> TYPE: DNA
<213> ORGANISM: Artificial Sequence
<220> FEATURE:
<223> OTHER INFORMATION: P(Kat)

<400> SEQUENCE: 588
taaacaacta acggacaatt ctacctaaca                                        30

<210> SEQ ID NO 589
<211> LENGTH: 30
<212> TYPE: DNA
<213> ORGANISM: Artificial Sequence
<220> FEATURE:
<223> OTHER INFORMATION: Template for Building Primer Family Member

<400> SEQUENCE: 589
acatcaagcc aaattaaaca ggattaacac                                        30

<210> SEQ ID NO 590
<211> LENGTH: 30
<212> TYPE: DNA
<213> ORGANISM: Artificial Sequence
<220> FEATURE:
<223> OTHER INFORMATION: Reverse lambda cI-regulated promoter

<400> SEQUENCE: 590
gaggtaaaat agtcaacacg cacggtgtta                                        30

<210> SEQ ID NO 591
<211> LENGTH: 30
<212> TYPE: DNA
<213> ORGANISM: Artificial Sequence
<220> FEATURE:
<223> OTHER INFORMATION: Key Promoter absorbs 3

<400> SEQUENCE: 591
caggccggaa taactcccta taatgcgcca                                        30

<210> SEQ ID NO 592
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 592
ggctagctca gtcctaggta cagtgctagc                                        30

<210> SEQ ID NO 593
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 593
agctagctca gtcctaggta ttatgctagc                                        30
```

<210> SEQ ID NO 594
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 594
agctagctca gtcctaggta ctgtgctagc                                    30

<210> SEQ ID NO 595
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 595
agctagctca gtcctaggga ttatgctagc                                    30

<210> SEQ ID NO 596
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 596
agctagctca gtcctaggta ttgtgctagc                                    30

<210> SEQ ID NO 597
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 597
ggctagctca gtcctaggta ctatgctagc                                    30

<210> SEQ ID NO 598
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 598
ggctagctca gtcctaggta tagtgctagc                                    30

<210> SEQ ID NO 599
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 599
ggctagctca gccctaggta ttatgctagc                                    30

<210> SEQ ID NO 600
<211> LENGTH: 30
<212> TYPE: DNA
<213> ORGANISM: Artificial Sequence
<220> FEATURE:

<223> OTHER INFORMATION: constitutive promoter family member

<400> SEQUENCE: 600
agctagctca gtcctaggta taatgctagc                                              30

<210> SEQ ID NO 601
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 601
agctagctca gtcctaggga ctgtgctagc                                              30

<210> SEQ ID NO 602
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 602
ggctagctca gtcctaggta caatgctagc                                              30

<210> SEQ ID NO 603
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 603
ggctagctca gtcctaggta tagtgctagc                                              30

<210> SEQ ID NO 604
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 604
agctagctca gtcctaggga ttatgctagc                                              30

<210> SEQ ID NO 605
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 605
ggctagctca gtcctaggga ttatgctagc                                              30

<210> SEQ ID NO 606
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 606
ggctagctca gtcctaggta caatgctagc                                              30

```
<210> SEQ ID NO 607
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 607
agctagctca gcccttggta caatgctagc                                     30

<210> SEQ ID NO 608
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 608
agctagctca gtcctaggga ctatgctagc                                     30

<210> SEQ ID NO 609
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 609
agctagctca gtcctaggga ttgtgctagc                                     30

<210> SEQ ID NO 610
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 610
ggctagctca gtcctaggta ttgtgctagc                                     30

<210> SEQ ID NO 611
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 611
agctagctca gtcctaggta taatgctagc                                     30

<210> SEQ ID NO 612
<211> LENGTH: 30
<212> TYPE: DNA
<213> ORGANISM: Artificial Sequence
<220> FEATURE:
<223> OTHER INFORMATION: 1bp mutant from J23107

<400> SEQUENCE: 612
ggctagctca gtcctaggta ttatgctagc                                     30

<210> SEQ ID NO 613
<211> LENGTH: 30
<212> TYPE: DNA
<213> ORGANISM: Artificial Sequence
<220> FEATURE:
<223> OTHER INFORMATION: 1bp mutant from J23114
```

```
<400> SEQUENCE: 613
ggctagctca gtcctaggta caatgctagc                                              30

<210> SEQ ID NO 614
<211> LENGTH: 30
<212> TYPE: DNA
<213> ORGANISM: Artificial Sequence
<220> FEATURE:
<223> OTHER INFORMATION: pBAD reverse

<400> SEQUENCE: 614
aaagtgtgac gccgtgcaaa taatcaatgt                                              30

<210> SEQ ID NO 615
<211> LENGTH: 30
<212> TYPE: DNA
<213> ORGANISM: Artificial Sequence
<220> FEATURE:
<223> OTHER INFORMATION: NikR promoter, a protein of the ribbon helix-
      helix family of trancription factors that repress expre

<400> SEQUENCE: 615
gacgaatact taaaatcgtc atacttattt                                              30

<210> SEQ ID NO 616
<211> LENGTH: 30
<212> TYPE: DNA
<213> ORGANISM: Artificial Sequence
<220> FEATURE:
<223> OTHER INFORMATION: lacq_Promoter

<400> SEQUENCE: 616
aaacctttcg cggtatggca tgatagcgcc                                              30

<210> SEQ ID NO 617
<211> LENGTH: 30
<212> TYPE: DNA
<213> ORGANISM: Artificial Sequence
<220> FEATURE:
<223> OTHER INFORMATION: lacIQ - promoter sequence

<400> SEQUENCE: 617
tgatagcgcc cggaagagag tcaattcagg                                              30

<210> SEQ ID NO 618
<211> LENGTH: 30
<212> TYPE: DNA
<213> ORGANISM: Artificial Sequence
<220> FEATURE:
<223> OTHER INFORMATION: E. Coli CreABCD phosphate sensing operon
      promoter

<400> SEQUENCE: 618
ttatttaccg tgacgaacta attgctcgtg                                              30

<210> SEQ ID NO 619
<211> LENGTH: 30
<212> TYPE: DNA
<213> ORGANISM: Artificial Sequence
<220> FEATURE:
<223> OTHER INFORMATION: GlnRS promoter

<400> SEQUENCE: 619
catacgccgt tatacgttgt ttacgctttg                                              30
```

```
<210> SEQ ID NO 620
<211> LENGTH: 30
<212> TYPE: DNA
<213> ORGANISM: Artificial Sequence
<220> FEATURE:
<223> OTHER INFORMATION: Constitutive weak promoter of lacZ

<400> SEQUENCE: 620
ttatgcttcc ggctcgtatg ttgtgtggac                                      30

<210> SEQ ID NO 621
<211> LENGTH: 30
<212> TYPE: DNA
<213> ORGANISM: Artificial Sequence
<220> FEATURE:
<223> OTHER INFORMATION: Mutated LacZ promoter

<400> SEQUENCE: 621
ttatgcttcc ggctcgtatg gtgtgtggac                                      30

<210> SEQ ID NO 622
<211> LENGTH: 30
<212> TYPE: DNA
<213> ORGANISM: Artificial Sequence
<220> FEATURE:
<223> OTHER INFORMATION: constitutive promoter with (TA)10 between -10
      and -35 elements

<400> SEQUENCE: 622
atatatatat atatataatg gaagcgtttt                                      30

<210> SEQ ID NO 623
<211> LENGTH: 30
<212> TYPE: DNA
<213> ORGANISM: Artificial Sequence
<220> FEATURE:
<223> OTHER INFORMATION: constitutive promoter with (TA)9 between -10
      and -35 elements

<400> SEQUENCE: 623
atatatatat atatataatg gaagcgtttt                                      30

<210> SEQ ID NO 624
<211> LENGTH: 30
<212> TYPE: DNA
<213> ORGANISM: Artificial Sequence
<220> FEATURE:
<223> OTHER INFORMATION: constitutive promoter with (C)10 between -10
      and -35 elements

<400> SEQUENCE: 624
ccccgaaagc ttaagaatat aattgtaagc                                      30

<210> SEQ ID NO 625
<211> LENGTH: 30
<212> TYPE: DNA
<213> ORGANISM: Artificial Sequence
<220> FEATURE:
<223> OTHER INFORMATION: constitutive promoter with (C)12 between -10
      and -35 elements

<400> SEQUENCE: 625
ccccgaaagc ttaagaatat aattgtaagc                                      30

<210> SEQ ID NO 626
<211> LENGTH: 30
<212> TYPE: DNA
```

```
<213> ORGANISM: Artificial Sequence
<220> FEATURE:
<223> OTHER INFORMATION: optimized (TA) repeat constitutive promoter
      with 13 bp between -10 and -35 elements

<400> SEQUENCE: 626
tgacaatata tatatatata taatgctagc                                     30

<210> SEQ ID NO 627
<211> LENGTH: 30
<212> TYPE: DNA
<213> ORGANISM: Artificial Sequence
<220> FEATURE:
<223> OTHER INFORMATION: optimized (TA) repeat constitutive promoter
      with 15 bp between -10 and -35 elements

<400> SEQUENCE: 627
acaatatata tatatatata taatgctagc                                     30

<210> SEQ ID NO 628
<211> LENGTH: 30
<212> TYPE: DNA
<213> ORGANISM: Artificial Sequence
<220> FEATURE:
<223> OTHER INFORMATION: optimized (TA) repeat constitutive promoter
      with 17 bp between -10 and -35 elements

<400> SEQUENCE: 628
aatatatata tatatatata taatgctagc                                     30

<210> SEQ ID NO 629
<211> LENGTH: 30
<212> TYPE: DNA
<213> ORGANISM: Artificial Sequence
<220> FEATURE:
<223> OTHER INFORMATION: optimized (TA) repeat constitutive promoter
      with 19 bp between -10 and -35 elements

<400> SEQUENCE: 629
tatatatata tatatatata taatgctagc                                     30

<210> SEQ ID NO 630
<211> LENGTH: 30
<212> TYPE: DNA
<213> ORGANISM: Artificial Sequence
<220> FEATURE:
<223> OTHER INFORMATION: optimized (TA) repeat constitutive promoter
      with 21 bp between -10 and -35 elements

<400> SEQUENCE: 630
tatatatata tatatatata taatgctagc                                     30

<210> SEQ ID NO 631
<211> LENGTH: 30
<212> TYPE: DNA
<213> ORGANISM: Artificial Sequence
<220> FEATURE:
<223> OTHER INFORMATION: optimized (A) repeat constitutive promoter with
      17 bp between -10 and -35 elements

<400> SEQUENCE: 631
aaaaaaaaaa aaaaaaaata taatgctagc                                     30

<210> SEQ ID NO 632
<211> LENGTH: 30
<212> TYPE: DNA
<213> ORGANISM: Artificial Sequence
```

```
<220> FEATURE:
<223> OTHER INFORMATION: optimized (A) repeat constitutive promoter with
      18 bp between -10 and -35 elements

<400> SEQUENCE: 632
aaaaaaaaaa aaaaaaaata taatgctagc                                     30

<210> SEQ ID NO 633
<211> LENGTH: 30
<212> TYPE: DNA
<213> ORGANISM: Artificial Sequence
<220> FEATURE:
<223> OTHER INFORMATION: J23101:GFP

<400> SEQUENCE: 633
caccttcggg tgggcctttc tgcgtttata                                     30

<210> SEQ ID NO 634
<211> LENGTH: 30
<212> TYPE: DNA
<213> ORGANISM: Artificial Sequence
<220> FEATURE:
<223> OTHER INFORMATION: J23119:IFP

<400> SEQUENCE: 634
caccttcggg tgggcctttc tgcgtttata                                     30

<210> SEQ ID NO 635
<211> LENGTH: 30
<212> TYPE: DNA
<213> ORGANISM: Artificial Sequence
<220> FEATURE:
<223> OTHER INFORMATION: J23119:HO1

<400> SEQUENCE: 635
caccttcggg tgggcctttc tgcgtttata                                     30

<210> SEQ ID NO 636
<211> LENGTH: 30
<212> TYPE: DNA
<213> ORGANISM: Artificial Sequence
<220> FEATURE:
<223> OTHER INFORMATION: Infrared signal reporter (J23119:IFP:J23119:
      HO1)

<400> SEQUENCE: 636
caccttcggg tgggcctttc tgcgtttata                                     30

<210> SEQ ID NO 637
<211> LENGTH: 30
<212> TYPE: DNA
<213> ORGANISM: Artificial Sequence
<220> FEATURE:
<223> OTHER INFORMATION: Double terminator + constitutive promoter

<400> SEQUENCE: 637
ggctagctca gtcctaggta cagtgctagc                                     30

<210> SEQ ID NO 638
<211> LENGTH: 30
<212> TYPE: DNA
<213> ORGANISM: Artificial Sequence
<220> FEATURE:
<223> OTHER INFORMATION: Double terminator + Constitutive promoter +
      Strong RBS

<400> SEQUENCE: 638
```

```
tgctagctac tagagattaa agaggagaaa                                    30

<210> SEQ ID NO 639
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 639
ttgtgagcgg ataacaagat actgagcaca                                    30

<210> SEQ ID NO 640
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 640
ttgtgagcgg ataacaagat actgagcaca                                    30

<210> SEQ ID NO 641
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 641
ttgtgagcgg ataacaagat actgagcaca                                    30

<210> SEQ ID NO 642
<211> LENGTH: 30
<212> TYPE: DNA
<213> ORGANISM: Artificial Sequence
<220> FEATURE:
<223> OTHER INFORMATION: M13K07 gene I promoter

<400> SEQUENCE: 642
cctgttttta tgttattctc tctgtaaagg                                    30

<210> SEQ ID NO 643
<211> LENGTH: 30
<212> TYPE: DNA
<213> ORGANISM: Artificial Sequence
<220> FEATURE:
<223> OTHER INFORMATION: M13K07 gene II promoter

<400> SEQUENCE: 643
aaatatttgc ttatacaatc ttcctgtttt                                    30

<210> SEQ ID NO 644
<211> LENGTH: 30
<212> TYPE: DNA
<213> ORGANISM: Artificial Sequence
<220> FEATURE:
<223> OTHER INFORMATION: M13K07 gene III promoter

<400> SEQUENCE: 644
gctgataaac cgatacaatt aaaggctcct                                    30

<210> SEQ ID NO 645
<211> LENGTH: 30
<212> TYPE: DNA
```

```
<213> ORGANISM: Artificial Sequence
<220> FEATURE:
<223> OTHER INFORMATION: M13K07 gene IV promoter

<400> SEQUENCE: 645
ctcttctcag cgtcttaatc taagctatcg                              30

<210> SEQ ID NO 646
<211> LENGTH: 30
<212> TYPE: DNA
<213> ORGANISM: Artificial Sequence
<220> FEATURE:
<223> OTHER INFORMATION: M13K07 gene V promoter

<400> SEQUENCE: 646
atgagccagt tcttaaaatc gcataaggta                              30

<210> SEQ ID NO 647
<211> LENGTH: 30
<212> TYPE: DNA
<213> ORGANISM: Artificial Sequence
<220> FEATURE:
<223> OTHER INFORMATION: M13K07 gene VI promoter

<400> SEQUENCE: 647
ctattgattg tgacaaaata aacttattcc                              30

<210> SEQ ID NO 648
<211> LENGTH: 30
<212> TYPE: DNA
<213> ORGANISM: Artificial Sequence
<220> FEATURE:
<223> OTHER INFORMATION: M13K07 gene VIII promoter

<400> SEQUENCE: 648
gtttcgcgct tggtataatc gctgggggtc                              30

<210> SEQ ID NO 649
<211> LENGTH: 30
<212> TYPE: DNA
<213> ORGANISM: Artificial Sequence
<220> FEATURE:
<223> OTHER INFORMATION: M13110

<400> SEQUENCE: 649
ctttgcttct gactataata gtcagggtaa                              30

<210> SEQ ID NO 650
<211> LENGTH: 30
<212> TYPE: DNA
<213> ORGANISM: Artificial Sequence
<220> FEATURE:
<223> OTHER INFORMATION: Modified promoter sequence of g3.

<400> SEQUENCE: 650
aaaccgatac aattaaaggc tcctgctagc                              30

<210> SEQ ID NO 651
<211> LENGTH: 30
<212> TYPE: DNA
<213> ORGANISM: Artificial Sequence
<220> FEATURE:
<223> OTHER INFORMATION: Constitutive Promoter I

<400> SEQUENCE: 651
caccacactg atagtgctag tgtagatcac                              30
```

<210> SEQ ID NO 652
<211> LENGTH: 30
<212> TYPE: DNA
<213> ORGANISM: Artificial Sequence
<220> FEATURE:
<223> OTHER INFORMATION: Constitutive Promoter II

<400> SEQUENCE: 652
gccggaataa ctccctataa tgcgccacca                                    30

<210> SEQ ID NO 653
<211> LENGTH: 30
<212> TYPE: DNA
<213> ORGANISM: Artificial Sequence
<220> FEATURE:
<223> OTHER INFORMATION: --Specify Parts List--

<400> SEQUENCE: 653
ttgacaagct tttcctcagc tccgtaaact                                    30

<210> SEQ ID NO 654
<211> LENGTH: 30
<212> TYPE: DNA
<213> ORGANISM: Artificial Sequence
<220> FEATURE:
<223> OTHER INFORMATION: Full-length stationary phase osmY promoter

<400> SEQUENCE: 654
ggtttcaaaa ttgtgatcta tatttaacaa                                    30

<210> SEQ ID NO 655
<211> LENGTH: 30
<212> TYPE: DNA
<213> ORGANISM: Artificial Sequence
<220> FEATURE:
<223> OTHER INFORMATION: Minimal stationary phase osmY promoter

<400> SEQUENCE: 655
ggtttcaaaa ttgtgatcta tatttaacaa                                    30

<210> SEQ ID NO 656
<211> LENGTH: 30
<212> TYPE: DNA
<213> ORGANISM: Artificial Sequence
<220> FEATURE:
<223> OTHER INFORMATION: htpG Heat Shock Promoter

<400> SEQUENCE: 656
tctattccaa taaagaaatc ttcctgcgtg                                    30

<210> SEQ ID NO 657
<211> LENGTH: 30
<212> TYPE: DNA
<213> ORGANISM: Artificial Sequence
<220> FEATURE:
<223> OTHER INFORMATION: Promoter veg a constitutive promoter for B.
      subtilis

<400> SEQUENCE: 657
aaaaatgggc tcgtgttgta caataaatgt                                    30

<210> SEQ ID NO 658
<211> LENGTH: 30
<212> TYPE: DNA
<213> ORGANISM: Artificial Sequence

```
<220> FEATURE:
<223> OTHER INFORMATION: Promoter 43 a constitutive promoter for B.
      subtilis

<400> SEQUENCE: 658
aaaaaaagcg cgcgattatg taaaatataa                                30

<210> SEQ ID NO 659
<211> LENGTH: 30
<212> TYPE: DNA
<213> ORGANISM: Artificial Sequence
<220> FEATURE:
<223> OTHER INFORMATION: Strong constitutive promoter for Bacillus
      subtilis

<400> SEQUENCE: 659
aattgcagta ggcatgacaa aatggactca                                30

<210> SEQ ID NO 660
<211> LENGTH: 30
<212> TYPE: DNA
<213> ORGANISM: Artificial Sequence
<220> FEATURE:
<223> OTHER INFORMATION: PliaG

<400> SEQUENCE: 660
caagcttttc ctttataata gaatgaatga                                30

<210> SEQ ID NO 661
<211> LENGTH: 30
<212> TYPE: DNA
<213> ORGANISM: Artificial Sequence
<220> FEATURE:
<223> OTHER INFORMATION: PlepA

<400> SEQUENCE: 661
tctaagctag tgtattttgc gtttaatagt                                30

<210> SEQ ID NO 662
<211> LENGTH: 30
<212> TYPE: DNA
<213> ORGANISM: Artificial Sequence
<220> FEATURE:
<223> OTHER INFORMATION: Pveg

<400> SEQUENCE: 662
aatgggctcg tgttgtacaa taaatgtagt                                30

<210> SEQ ID NO 663
<211> LENGTH: 30
<212> TYPE: DNA
<213> ORGANISM: Artificial Sequence
<220> FEATURE:
<223> OTHER INFORMATION: Promoter ctc for B. subtilis

<400> SEQUENCE: 663
atccttatcg ttatgggtat tgtttgtaat                                30

<210> SEQ ID NO 664
<211> LENGTH: 30
<212> TYPE: DNA
<213> ORGANISM: Artificial Sequence
<220> FEATURE:
<223> OTHER INFORMATION: Promoter gsiB for B. subtilis

<400> SEQUENCE: 664
```

```
<210> SEQ ID NO 665
<211> LENGTH: 30
<212> TYPE: DNA
<213> ORGANISM: Artificial Sequence
<220> FEATURE:
<223> OTHER INFORMATION: Promoter 43 a constitutive promoter for B.
      subtilis

<400> SEQUENCE: 665
aaaaaaagcg cgcgattatg taaaatataa                                30

<210> SEQ ID NO 666
<211> LENGTH: 30
<212> TYPE: DNA
<213> ORGANISM: Artificial Sequence
<220> FEATURE:
<223> OTHER INFORMATION: Pspv2 from Salmonella

<400> SEQUENCE: 666
tacaaaataa ttccctgca aacattatca                                 30

<210> SEQ ID NO 667
<211> LENGTH: 30
<212> TYPE: DNA
<213> ORGANISM: Artificial Sequence
<220> FEATURE:
<223> OTHER INFORMATION: Pspv from Salmonella

<400> SEQUENCE: 667
tacaaaataa ttccctgca aacattatcg                                 30

<210> SEQ ID NO 668
<211> LENGTH: 30
<212> TYPE: DNA
<213> ORGANISM: Artificial Sequence
<220> FEATURE:
<223> OTHER INFORMATION: T7 promoter (strong promoter from T7
      bacteriophage)

<400> SEQUENCE: 668
agggaataca agctacttgt tcttttttgca                               30

<210> SEQ ID NO 669
<211> LENGTH: 23
<212> TYPE: DNA
<213> ORGANISM: Artificial Sequence
<220> FEATURE:
<223> OTHER INFORMATION: T7 Promoter

<400> SEQUENCE: 669
taatacgact cactataggg aga                                       23

<210> SEQ ID NO 670
<211> LENGTH: 28
<212> TYPE: DNA
<213> ORGANISM: Artificial Sequence
<220> FEATURE:
<223> OTHER INFORMATION: T7 Promoter

<400> SEQUENCE: 670
gaatttaata cgactcacta tagggaga                                  28

<210> SEQ ID NO 671
<211> LENGTH: 19
```

```
<212> TYPE: DNA
<213> ORGANISM: Artificial Sequence
<220> FEATURE:
<223> OTHER INFORMATION: T7 consensus -10 and rest

<400> SEQUENCE: 671
taatacgact cactatagg                                            19

<210> SEQ ID NO 672
<211> LENGTH: 30
<212> TYPE: DNA
<213> ORGANISM: Artificial Sequence
<220> FEATURE:
<223> OTHER INFORMATION: overlapping T7 promoter

<400> SEQUENCE: 672
gagtcgtatt aatacgactc actataggg                                 30

<210> SEQ ID NO 673
<211> LENGTH: 30
<212> TYPE: DNA
<213> ORGANISM: Artificial Sequence
<220> FEATURE:
<223> OTHER INFORMATION: more overlapping T7 promoter

<400> SEQUENCE: 673
agtgagtcgt actacgactc actataggg                                 30

<210> SEQ ID NO 674
<211> LENGTH: 30
<212> TYPE: DNA
<213> ORGANISM: Artificial Sequence
<220> FEATURE:
<223> OTHER INFORMATION: weaken overlapping T7 promoter

<400> SEQUENCE: 674
gagtcgtatt aatacgactc tctataggg                                 30

<210> SEQ ID NO 675
<211> LENGTH: 23
<212> TYPE: DNA
<213> ORGANISM: Artificial Sequence
<220> FEATURE:
<223> OTHER INFORMATION: T7 Consensus Promoter Sequence

<400> SEQUENCE: 675
taatacgact cactataggg aga                                       23

<210> SEQ ID NO 676
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 676
ttatacgact cactataggg aga                                       23

<210> SEQ ID NO 677
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 677
```

```
gaatacgact cactataggg aga                                           23
```

<210> SEQ ID NO 678
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 678

```
taatacgtct cactataggg aga                                           23
```

<210> SEQ ID NO 679
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 679

```
tcatacgact cactataggg aga                                           23
```

<210> SEQ ID NO 680
<211> LENGTH: 30
<212> TYPE: DNA
<213> ORGANISM: Artificial Sequence
<220> FEATURE:
<223> OTHER INFORMATION: T7 strong promoter

<400> SEQUENCE: 680

```
taatacgact cactataggg agaccacaac                                    30
```

<210> SEQ ID NO 681
<211> LENGTH: 30
<212> TYPE: DNA
<213> ORGANISM: Artificial Sequence
<220> FEATURE:
<223> OTHER INFORMATION: T7 weak binding and processivity

<400> SEQUENCE: 681

```
taattgaact cactaaaggg agaccacagc                                    30
```

<210> SEQ ID NO 682
<211> LENGTH: 30
<212> TYPE: DNA
<213> ORGANISM: Artificial Sequence
<220> FEATURE:
<223> OTHER INFORMATION: T7 weak binding promoter

<400> SEQUENCE: 682

```
cgaagtaata cgactcacta ttagggaaga                                    30
```

<210> SEQ ID NO 683
<211> LENGTH: 30
<212> TYPE: DNA
<213> ORGANISM: Artificial Sequence
<220> FEATURE:
<223> OTHER INFORMATION: pCyc (Medium) Promoter

<400> SEQUENCE: 683

```
acaaacacaa atacacacac taaattaata                                    30
```

<210> SEQ ID NO 684
<211> LENGTH: 30
<212> TYPE: DNA
<213> ORGANISM: Artificial Sequence

```
<220> FEATURE:
<223> OTHER INFORMATION: pAdh (Strong) Promoter

<400> SEQUENCE: 684
ccaagcatac aatcaactat ctcatataca                                      30

<210> SEQ ID NO 685
<211> LENGTH: 30
<212> TYPE: DNA
<213> ORGANISM: Artificial Sequence
<220> FEATURE:
<223> OTHER INFORMATION: pSte5 (Weak) Promoter

<400> SEQUENCE: 685
gatacaggat acagcggaaa caacttttaa                                      30

<210> SEQ ID NO 686
<211> LENGTH: 30
<212> TYPE: DNA
<213> ORGANISM: Artificial Sequence
<220> FEATURE:
<223> OTHER INFORMATION: yeast ADH1 promoter

<400> SEQUENCE: 686
tttcaagcta taccaagcat acaatcaact                                      30

<210> SEQ ID NO 687
<211> LENGTH: 30
<212> TYPE: DNA
<213> ORGANISM: Artificial Sequence
<220> FEATURE:
<223> OTHER INFORMATION: cyc100 minimal promoter

<400> SEQUENCE: 687
cctttgcagc ataaattact atacttctat                                      30

<210> SEQ ID NO 688
<211> LENGTH: 30
<212> TYPE: DNA
<213> ORGANISM: Artificial Sequence
<220> FEATURE:
<223> OTHER INFORMATION: cyc70 minimal promoter

<400> SEQUENCE: 688
cctttgcagc ataaattact atacttctat                                      30

<210> SEQ ID NO 689
<211> LENGTH: 30
<212> TYPE: DNA
<213> ORGANISM: Artificial Sequence
<220> FEATURE:
<223> OTHER INFORMATION: cyc43 minimal promoter

<400> SEQUENCE: 689
cctttgcagc ataaattact atacttctat                                      30

<210> SEQ ID NO 690
<211> LENGTH: 30
<212> TYPE: DNA
<213> ORGANISM: Artificial Sequence
<220> FEATURE:
<223> OTHER INFORMATION: cyc28 minimal promoter

<400> SEQUENCE: 690
cctttgcagc ataaattact atacttctat                                      30
```

<210> SEQ ID NO 691
<211> LENGTH: 30
<212> TYPE: DNA
<213> ORGANISM: Artificial Sequence
<220> FEATURE:
<223> OTHER INFORMATION: cyc16 minimal promoter

<400> SEQUENCE: 691
cctttgcagc ataaattact atacttctat                                30

<210> SEQ ID NO 692
<211> LENGTH: 30
<212> TYPE: DNA
<213> ORGANISM: Artificial Sequence
<220> FEATURE:
<223> OTHER INFORMATION: pPGK1

<400> SEQUENCE: 692
ttatctactt tttacaacaa atataaaaca                                30

<210> SEQ ID NO 693
<211> LENGTH: 30
<212> TYPE: DNA
<213> ORGANISM: Artificial Sequence
<220> FEATURE:
<223> OTHER INFORMATION: pCYC Yeast Promoter

<400> SEQUENCE: 693
acaaacacaa atacacacac taaattaata                                30

<210> SEQ ID NO 694
<211> LENGTH: 30
<212> TYPE: DNA
<213> ORGANISM: Artificial Sequence
<220> FEATURE:
<223> OTHER INFORMATION: Yeast GPD (TDH3) Promoter

<400> SEQUENCE: 694
gtttcgaata aacacacata aacaaacaaa                                30

<210> SEQ ID NO 695
<211> LENGTH: 30
<212> TYPE: DNA
<213> ORGANISM: Artificial Sequence
<220> FEATURE:
<223> OTHER INFORMATION: yeast mid-length ADH1 promoter

<400> SEQUENCE: 695
ccaagcatac aatcaactat ctcatataca                                30

<210> SEQ ID NO 696
<211> LENGTH: 30
<212> TYPE: DNA
<213> ORGANISM: Artificial Sequence
<220> FEATURE:
<223> OTHER INFORMATION: Yeast CLB1 promoter region, G2/M cell cycle
      specific

<400> SEQUENCE: 696
accatcaaag gaagctttaa tcttctcata                                30

<210> SEQ ID NO 697
<211> LENGTH: 30
<212> TYPE: DNA
<213> ORGANISM: Artificial Sequence
<220> FEATURE:

```
<223> OTHER INFORMATION: CMV promoter

<400> SEQUENCE: 697
agaacccact gcttactggc ttatcgaaat                                    30

<210> SEQ ID NO 698
<211> LENGTH: 30
<212> TYPE: DNA
<213> ORGANISM: Artificial Sequence
<220> FEATURE:
<223> OTHER INFORMATION: Ubc Promoter

<400> SEQUENCE: 698
ggccgttttt ggcttttttg ttagacgaag                                    30
```

CONTROLLED GROWTH OF MICROORGANISMS

RELATED APPLICATIONS

This Application is a continuation of U.S. patent application Ser. No. 15/087,706, filed Mar. 31, 2016, which is a divisional of U.S. patent application Ser. No. 14/459,810, filed Aug. 14, 2014, issued May 10, 2016 as U.S. Pat. No. 9,333,227, which claims the benefit of U.S. Provisional Application Ser. No. 61/867,510, filed on Aug. 19, 2013, each of which is hereby incorporated by reference in its entirety.

REFERENCE TO SEQUENCE LISTING

The present application is being filed along with a Sequence Listing in electronic format. The Sequence Listing is provided as a file entitled SEQUENCESYNG001A.TXT, created and last saved on Aug. 11, 2014, which is 380,081 bytes in size, and updated by a file entitled SYNG001C1REPLACEMENT.TXT, created and last saved on Mar. 11, 2019, which is 383,499 bytes in size. The information in the electronic format of the Sequence Listing is incorporated herein by reference in its entirety.

BACKGROUND

Humans have used microbial organisms to generate products since the beginning of human history, for example in processing foods such as cheese, beer, and wine. During the centuries, microbial organism-mediated processes have been studied and scaled-up, often by controlling fermentation conditions or identification of phenotypic characteristics of microbial organisms.

Presently, many products are produced using a process that involves microbial organisms. In laboratories, and in some pharmaceutical manufacturing processes, microbial organisms, including genetically engineered microbial organisms, can be cultured in sterile, controlled environments. On the other hand, feedstocks used for various industrial processes involving microorganisms are not sterile, and may contain a variety of strains and species of microorganisms. As such, genetically engineered microorganisms for laboratory and pharmaceutical processes are not necessarily suited for processes, such as industrial processes, which involve using feedstocks or which are exposed to other microorganisms in the environment which could potentially contaminate the culture and which may also involve, changing environmental conditions. Herein microorganisms which have been engineered to control their own growth and the growth of other microorganisms and/or to respond to changes in their environment are described. Such microorganisms are suitable for growth in non-sterile, less rigidly controlled feedstocks. Such microorganisms can be useful for robust, consistent production of a desired product across a range of different feedstocks and environments.

FIELD

Embodiments herein relate generally to the control of growth of microorganisms. More particularly, some embodiments herein relate to microorganisms engineered for regulated growth in response to other microorganisms and/or conditions of the culture environment, and methods of making and using such engineered microorganisms.

SUMMARY

One embodiment disclosed herein includes a first microbial cell comprising a nucleic acid encoding a secreted bacteriocin which controls the growth of a second microbial cell and a nucleic acid which confers resistance to the secreted bacteriocin is provided, in which the first microbial cell has been genetically engineered to allow the expression or activity of the nucleic acid which confers resistance to the bacteriocin to be regulated. According to some aspects of this embodiment, the expression or activity of the nucleic acid which confers resistance to the bacteriocin is reduced to a level which causes the first microbial cell to be neutralized by the bacteriocin if the first microbial cell is released from a desired growth environment. According to some aspects of this embodiment, the first microbial cell has been genetically engineered to make a desired product. According to some aspects of this embodiment, the secreted bacteriocin further has been selected to maintain at least one condition within a culture in which the first microbial cell is producing the desired product. According to some aspects of this embodiment, the culture comprises at least one invading microbial organism. According to some aspects of this embodiment, the at least one condition of the culture comprises controlling the growth of the second microbial cell, wherein the second microbial cell is a common contaminate of the culture. According to some aspects of this embodiment, the second microbial cell is a different strain, species or genus than the first microbial cell. According to some aspects of this embodiment, the microbial cell further comprises a nucleic acid encoding a second secreted bacteriocin which controls the growth of a third microbial cell and a nucleic acid which confers resistance to the secreted second bacteriocin, and also the first microbial cell has been genetically engineered to allow the expression or activity of the nucleic acid which confers resistance to the bacteriocin to be regulated. According to some aspects of this embodiment, the bacteriocin kills the second microbial cell. According to some aspects of this embodiment, the bacteriocin reduces the growth rate of the second microbial cell. According to some aspects of this embodiment, the bacteriocin arrests the growth of the second microbial cell. According to some aspects of this embodiment, the transcription of the nucleic acid conferring resistance to the bacteriocin is under the control of a regulatable promoter. According to some aspects of this embodiment, the activity of a polypeptide encoded by the nucleic acid conferring resistance to the bacteriocin is regulatable. According to some aspects of this embodiment, the nucleic acid encoding the bacteriocin is on a chromosome of the microbial cell. According to some aspects of this embodiment, the nucleic acid conferring resistance to the bacteriocin is on a plasmid. According to some aspects of this embodiment, the nucleic acid encoding the bacteriocin is on a chromosome of the microbial cell, and the nucleic acid conferring resistance to the bacteriocin is on a plasmid. According to some aspects of this embodiment, the nucleic acid encoding the bacteriocin and the nucleic acid conferring resistance to the bacteriocin are on one or more plasmids. According to some aspects of this embodiment, the first microbial cell is selected from the group consisting of bacteria, yeast, and algae, for example photosynthetic microalgae.

Another embodiment disclosed herein includes a method of controlling the growth of a second microbial cell in a culture medium, in which the method includes comprising culturing a first microbial cell as described herein in a culture medium comprising the second microbial cell under conditions in which the first microbial cell produces a bacteriocin at a level sufficient to control the growth of the second microbial cell. According to some aspects of this embodiment, the culture is maintained continually for at least 30 days, for example at least 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 days. According to some aspects of this embodiment, the method further includes detecting at least one change in the culture medium, the change comprising a presence or increase in the levels or activity of a third microbial cell, and reengineering the first microbial cell in response to the change to produce a second bacteriocin at a level sufficient to control the growth of the third microbial cell.

Another embodiment disclosed herein includes a method of detecting a presence, absence, or amount of a molecule in a culture is provided. The method can comprise culturing a first genetically engineered microbial cell comprising a bacteriocin under the control of a genetically regulatable promoter, such that the regulatable promoter is regulated by the molecule so that either (a) the regulatable promoter drives transcription in the presence of the molecule, but not in the absence of the molecule; or (b) the regulatable promoter drives transcription in the absence of the molecule, but not in the presence of the molecule. The method can comprise isolating an amount of genomic nucleic acid of the first microbial cell from the culture. The method can comprise detecting from the amount of genomic nucleic acid, a presence, absence, or quantity of a nucleic acid sequence characteristic of the first microbial cell. According to some aspects of this embodiment, the method further includes comparing the quantity of the nucleic acid sequence characteristic of the first microbial cell to a quantity of a reference nucleic acid sequence.

Another embodiment disclosed herein includes a genetically engineered vector comprising a nucleic acid conferring resistance to a bacteriocin, in which the expression or activity of the nucleic acid is configured to change in response to the presence, level or absence of a component of a feedstock. According to some aspects of this embodiment, the vector further comprises a nucleic acid encoding the bacteriocin. According to some aspects of this embodiment, the vector further comprises a nucleic acid which encodes a desired product.

Another embodiment disclosed herein includes a kit, which can includes a plurality of strains of a genetically engineered microbial organism, in which each strain has been genetically engineered to allow the expression or activity of a nucleic acid which confers resistance to a different bacteriocin to be regulated.

Another embodiment disclosed herein includes a method of identifying at least one bacteriocin which modulates the growth of at least one microbial cell in an industrial culture medium, in which the method includes contacting the industrial culture medium with a medium or composition comprising the at least one bacteriocin; and determining whether the at least one bacteriocin has a desired effect on the growth of the at least one microbial cell. According to some aspects of this embodiment, the method includes contacting the industrial culture medium with at least one bacteriocin produced by a first microbial cell as described herein. According to some aspects of this embodiment, the at least one bacteriocin produced by the first microbial cell is in a supernatant obtained from a culture comprising the first microbial cell. According to some aspects of this embodiment, the method further includes constructing a genetically engineered microbial cell to produce at least one bacteriocin which has been determined to have a desired effect on the growth of the at least one microbial cell. According to some aspects of this embodiment, the at least one microbial cell is an organism which is a common invader of the industrial culture medium. According to some aspects of this embodiment, the at least one microbial cell is an organism which has newly invaded an existing industrial culture.

Another embodiment disclosed herein includes a system for neutralizing undesired microbial organisms in a culture medium. The system can comprise a first environment comprising a culture medium, and a second environment comprising a second microbial organism that secretes two or more different bacteriocins, in which the second microbial organism comprises immunity modulators for each of the two or more different bacteriocins, in which the second environment is in fluid communication with the first environment, in which the second environment is physically separated from the first environment so that the second microbial organism cannot move from the second environment to the first environment, and in which the secreted two or more different bacteriocins enter the culture medium of the first environment. According to some aspects of this embodiment, the system further comprises a first microbial organism in the culture medium, in which the first microbial organism does not secrete the two or more different bacteriocins, and in which the first microbial organism is not neutralized by any of the two or more different bacteriocins. According to some aspects of this embodiment, the first microbial organism is non-GMO. According to some aspects of this embodiment, the first microbial organism ferments a component of the culture medium. According to some aspects of this embodiment, the first microbial organism decontaminates the culture medium. According to some aspects of this embodiment, the first microbial organism conducts photosynthesis, and the photosynthesis comprises a substrate comprised by the culture medium. According to some aspects of this embodiment, the second environment is separated from the first environment by at least one of a membrane, a mesh, a filter, or a valve that is permeable to the two or more different bacteriocins, but is not permeable to the second microbial organisms. According to some aspects of this embodiment, the second microbial organism secretes at least 3 bacteriocins, for example at least 3, 4, 5, 6, 7, 8, 9, 10, 11, 12, 13, 14, 15, 16, 17, 18, 19, or 20 bacteriocins. According to some aspects of this embodiment, the second environment comprises at least a third microbial organism that is different from the second microbial organism, and also secretes bacteriocins. According to some aspects of this embodiment, the third microbial organism secretes at least 2 bacteriocins, for example at least 2, 3, 4, 5, 6, 7, 8, 9, 10, 11, 12, 13, 14, 15, 16, 17, 18, 19, or 20 bacteriocins. Another embodiment disclosed herein includes a method of storing a feedstock. The method can comprise providing a feedstock, providing a first microbial organism, in which the first microbial organism secretes two or more different bacteriocins, contacting the feedstock with the bacteriocins, and storing the feedstock for a desired period of time. According to some aspects of this embodiment, contacting the feedstock with the bacteriocins comprises contacting the feedstock with the microbial organism. According to some aspects of this embodiment, contacting the feedstock with the bacteriocins comprises placing the microbial organism in fluid communication with the feedstock, while maintaining physical separation between the microbial organism and the feedstock, so that the bacteriocins contact the feedstock, but the microbial organism does not directly contact the feedstock. According to some aspects of this embodiment, the separation is maintained by at least one or more of a membrane, a mesh, a filter, or a valve that is permeable to the two or more different bacteriocins, but is not permeable to the first microbial organism. According to some aspects of this embodiment, the method further comprises fermenting the feedstock with a second microbial organism prior to or concurrently with contacting the feedstock with the bacteriocins. According to some aspects of this embodiment, the fermentation comprises at least one of producing a desired component in the feedstock or removing an undesired component from the feedstock. According to some aspects of this embodiment, the desired period of time comprises at least one month, for example at least one, two, three, four, five, six, seven, eight, nine, ten, eleven, or twelve months. According to some aspects of this embodiment, the desired period of time comprises at least six months, for example six, seven, eight nine, ten, eleven, or twelve months. According to some aspects of this embodiment, the first microbial organism secretes at least 3 bacteriocins, for example at least 3, 4, 5, 6, 7, 8, 9, 10, 11, 12, 13, 14, 15, 16, 17, 18, 19, or 20 bacteriocins.

DETAILED DESCRIPTION

Figure 1:
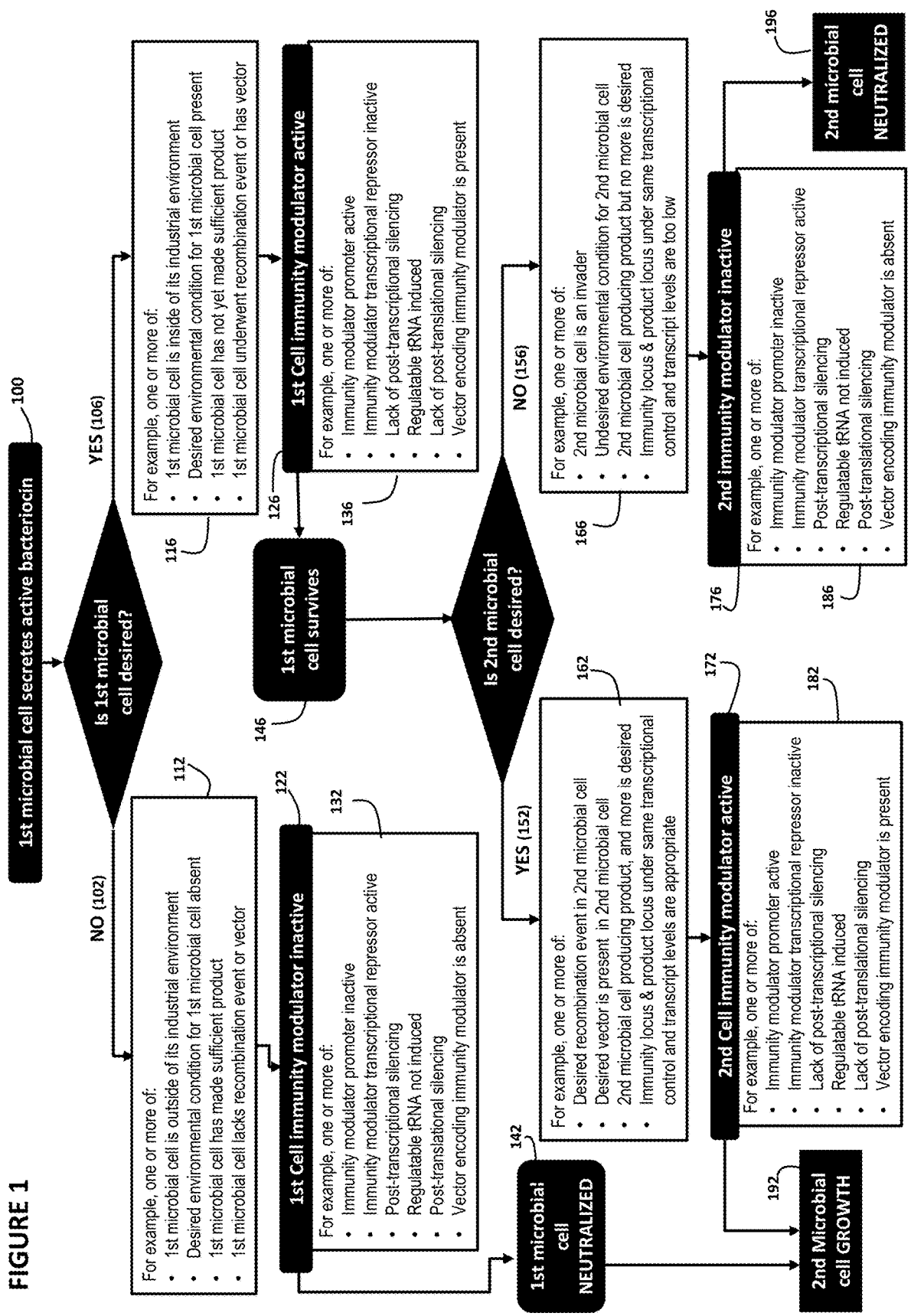
FIG. 1 is a flow diagram depicting options for configuring a microbial cell to control the growth of a second microbial cell according to some of the embodiments herein.

According to some of the embodiments herein, genetically engineered microbial organisms are provided. In some embodiments, the microbial organisms are engineered to control the growth of the microbial population in an environment such as those employing a feedstock. As used herein, "neutralizing" activity (and variations of the same root word) of bacteriocins can refer to either arrest of microbial reproduction, or cytotoxicity. Microbial organisms can be engineered to produce bacteriocins, which are secreted polypeptides that can neutralize microorganisms. However, microbial organisms that produce bacteriocin immunity modulators can resist certain bacteriocins. Thus, in some embodiments, a first microbial organism is engineered to secrete bacteriocins. In some embodiments, the particular bacteriocins are selected based on the type of microbial cell, the types of microbial cells being regulated, the composition of the culture medium, or geographic location (for example, to target particular contaminating microbial organisms associated with a particular type of culture medium and/or geographical location). Other microbial organisms that possess desired characteristics for a particular environment can produce bacteriocin immunity modulators (and thus survive in the presence of bacteriocins), while undesired other microbial organisms (for example contaminants, microbial organisms that have lost a desired characteristic or organisms which are involved in an industrial process but whose growth or production of a particular product is not desired under the prevailing conditions) fail to produce bacteriocin immunity modulators, and are thus neutralized by the bacteriocins.

Microbial Organisms

According to some aspects, genetically engineered microorganisms are provided. As used herein, genetically engineered "microbial organism," "microorganism," and variations of these root terms (such as pluralizations and the like), encompasses genetic modification of any naturally-occurring species or fully synthetic prokaryotic or eukaryotic unicellular organism, as well as Archae species. Thus, this expression can refer to cells of bacterial species, fungal species, and algae.

Exemplary microorganisms that can be used in accordance with embodiments herein include, but are not limited to, bacteria, yeast, and algae, for example photosynthetic microalgae. Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," Science 329: 52-56, hereby incorporated by reference in its entirety). As such, in some embodiments, the microorganism is fully synthetic. A desired combination of genetic elements, including elements that regulate gene expression, and elements encoding gene products (for example bacteriocins, immunity modulators, poison, antidote, and industrially useful molecules) can be assembled on a desired chassis into a partially or fully synthetic microorganism. Description of genetically engineered microbial organisms for industrial applications can also be found in Wright, et al. (2013) "Building-in biosafety for synthetic biology" *Microbiology* 159: 1221-1235.

A variety of bacterial species and strains can be used in accordance with embodiments herein, and genetically modified variants, or synthetic bacteria based on a "chassis" of a known species can be provided. Exemplary bacteria with industrially applicable characteristics, which can be used in accordance with embodiments herein include, but are not limited to, *Bacillus* species (for example *Bacillus coagulans*, *Bacillus subtilis*, and *Bacillus licheniformis*), *Paenibacillus* species, *Streptomyces* species, *Micrococcus* species, *Corynebacterium* species, *Acetobacter* species, *Cyanobacteria* species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus*, *Pseudomonas stutzeri*, *Clostridium thermocellus*, and *Escherichia coli*.

A variety of yeast species and strains can be used in accordance with embodiments herein, and genetically modified variants, or synthetic yeast based on a "chassis" of a known species can be provided. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces japonicas*), *Pichia* or *Hansenula* species (for example, *Pichia pastoris* or *Hansenula polymorpha*) species, and *Brettanomyces* species (for example, *Brettanomyces claussenii*).

A variety of algae species and strains can be used in accordance with embodiments herein, and genetically modified variants, or synthetic algae based on a "chassis" of a known species can be created. In some embodiments, the algae comprises photosynthetic microalgae. Exemplary algae species that can be useful for biofuels, and can be used in accordance with embodiments herein, include *Botryococcus braunii, Chlorella* species, *Dunaliella tertiolecta, Gracilaria* species, *Pleurochrysis carterae*, and *Sargassum* species. Additionally, many algaes can be useful for food products, fertilizer products, waste neutralization, environmental remediation, and carbohydrate manufacturing (for example, biofuels).

Bacteriocins

As used herein, "bacteriocin," and variations of this root term, refers to a polypeptide that is secreted by a host cell and can neutralize at least one cell other than the individual host cell in which the polypeptide is made, including cells clonally related to the host cell and other microbial cells. As used herein, "bacteriocin" also encompasses a cell-free or chemically synthesized version of such a polypeptide. A cell that expresses a particular "immunity modulator" (discussed in more detail herein) is immune to the neutralizing effects of a particular bacteriocin or group of bacteriocins. As such, bacteriocins can neutralize a cell producing the bacteriocin and/or other microbial cells, so long as these cells do not produce an appropriate immunity modulator. As such, a host cell can exert cytotoxic or growth-inhibiting effects on a plurality of other microbial organisms by secreting bacteriocins. In some embodiments, a bacteriocin is produced by the translational machinery (e.g. a ribosome, etc.) of a microbial cell. In some embodiments, a bacteriocin is chemically synthesized. Some bacteriocins can be derived from a polypeptide precursor. The polypeptide precursor can undergo cleavage (for example processing by a protease) to yield the polypeptide of the bacteriocin itself. As such, in some embodiments, a bacteriocin is produced from a precursor polypeptide. In some embodiments, a bacteriocin comprises a polypeptide that has undergone post-translational modifications, for example cleavage, or the addition of one or more functional groups.

"Antibiotic," and variations of this root term, refers to a metabolite, or an intermediate of a metabolic pathway which can kill or arrest the growth of at least one microbial cell. Some antibiotics can be produced by microbial cells, for example bacteria. Some antibiotics can be synthesized chemically. It is understood that bacteriocins are distinct from antibiotics, at least in that bacteriocins refer to gene products (which, in some embodiments, undergo additional post-translational processing) or synthetic analogs of the same, while antibiotics refer to intermediates or products of metabolic pathways or synthetic analogs of the same.

Neutralizing activity of bacteriocins can include arrest of microbial reproduction, or cytotoxicity. Some bacteriocins have cytotoxic activity (e.g. "bacteriocide" effects), and thus can kill microbial organisms, for example bacteria, yeast, algae, synthetic micoorganisms, and the like. Some bacteriocins can inhibit the reproduction of microbial organisms (e.g. "bacteriostatic" effects), for example bacteria, yeast, algae, synthetic micoorganisms, and the like, for example by arresting the cell cycle.

It is noted that non-bacteriocin approaches have been proposed to target various microbial organisms. For example, KAMORAN™ chemical has been proposed to target Lactic Acid Bacteria (LAB) family bacteria (see Union Nationale des Groupements de Distillateurs D'Alcool, (2005) "Kamoran"). It is noted that phage has also been proposed to target LAB family bacteria (see U.S. Pub. No. 2010/0330041). It is noted that pesticides have been proposed to target various contaminating microbial organisms (see McBride et al., "Contamination Management in Low Cost Open Algae Ponds for Biofuels Production" Industrial Biotechnology 10: 221-227 (2014)). However, bacteriocins can provide numerous advantages over chemicals, pesticides, or phages. For example, bacteriocins can avoid potentially toxic runoff or byproduct in a feedstock. For example, bacteriocins can have higher efficacy against particular undesired microbial organisms than phages, chemicals, or pesticides. For example, bacteriocins can be produced by microbial organisms that undergo logarithmic growth, and thus can readily be scaled-up or scaled down, whereas the scalability of phages or chemical/pesticide systems can be more limited. For example, bacteriocins can allow for precise control over which organisms are neutralized and which are not, for example to avoid neutralization of industrially useful microbial organisms in the culture medium. For example, phages can be difficult to produce at an industrial scale, and also can be difficult to control, in that phages can be infectious, can raise questions of gene control, and in that conservation of phages can be difficult. On the other hand, bacteriocins in accordance with some embodiments herein can comprise part of an industrial process and thus can be involved in gene containment and/or control a fermentation process via bacteriostatic activity. Additionally, the susceptibility of the microbial organisms involved in the industrial process can be tuned via immunity control. Additionally, bacteriocins typically have a low level of toxicity for industrial applications such as human or animal food, and it is contemplated that bacteriocins in accordance with some embodiments herein are suitable for use as a food preservative, such as an additive.

In some embodiments, a particular neutralizing activity (e.g. cytoxicity or arrest of microbial reproduction) is selected based on the type of microbial regulation that is desired. As such in some embodiments, microbial cells are engineered to express particular bacteriocins or combination of bacteriocins. For example, in some embodiments, microbial cells are engineered to express particular bacteriocins based on the cells being regulated. In some embodiments, for example if contaminating cells are to be killed at least one cytotoxic bacteriocin is provided. In some embodiments, a bacteriocin or combination of bacteriocins which is effective against contaminants which commonly occur in a particular culture, or a particular geographic location, or a particular type of culture grown in a particular geographic location are selected. In some embodiments, for example embodiments in which reversible regulation of microbial cell ratios is desired, a bacteriocin that inhibits microbial reproduction is provided. Without being limited by any particular theory, many bacteriocins can have neutralizing activity against microbial organisms that typically occupy the same ecological niche as the species that produces the bacteriocin. As such, in some embodiments, when a particular spectrum of bacteriocin activity is desired, a bacteriocin is selected from a host species that occupies the same (or similar) ecological niche as the microbial organism or organisms targeted by the bacteriocin.

In some embodiments, one or more bacteriocin activities are selected in advance of culture growth, and one or more microbial organisms are engineered to generate a desired culture environment. In some embodiments, bacteriocins may be selected based on their ability to neutralize one or more invading organisms which are likely to attempt to grow in a particular culture. In another embodiment, in an industrial environment in which strain A makes intermediate A, and strain B converts intermediate A into intermediate B, strains A and B can be engineered so that an abundance of intermediate A shifts the equilibrium to favor strain B by generating a bacteriocin activity profile such that growth of strain A is inhibited or prevented under these conditions, while a lack of intermediate A shifts the equilibrium to favor strain A by generating a bacteriocin activity profile such that growth of strain B is inhibited or prevented. In some embodiments, one or more bacteriocin activities are selected based on one or more conditions of an existing culture environment. For example, if particular invaders are identified in a culture environment, "neutralizer" microorganisms can be engineered to produce bacteriocins to neutralize the identified invaders. In some embodiments, genetically engineered cells that produce bacteriocins are added to an existing culture to re-equilibrate the culture, for example if a growth of a particular microbial cell type in the microbial cell culture is too high. In some embodiments, genetically engineered cells that produce bacteriocins are added to an existing culture to neutralize all or substantially all of the microbial cells in a culture, for example to eliminate an industrial culture in a culture environment so that a new industrial culture can be introduced to the culture environment.

For example, in some embodiments, an anti-fungal activity (such as anti-yeast activity) is desired. A number of bacteriocins with anti-fungal activity have been identified. For example, bacteriocins from *Bacillus* have been shown to have neutralizing activity against yeast strains (see Adetunji and Olaoye (2013) Malaysian Journal of Microbiology 9: 130-13, hereby incorporated by reference in its entirety), an *Enterococcus faecalis* peptide (WLPPAGLL-GRCGRWFRPWLLWLQ SGAQY KWLGNLFGLGPK, SEQ ID NO: 1) has been shown to have neutralizing activity against *Candida* species (see Shekh and Roy (2012) BMC Microbiology 12: 132, hereby incorporated by reference in its entirety), and bacteriocins from *Pseudomonas* have been shown to have neutralizing activity against fungi such as *Curvularia lunata, Fusarium* species, *Helminthosporium* species, and *Biopolaris* species (Shalani and Srivastava (2008) The Internet Journal of Microbiology. Volume 5 Number 2. DOI: 10.5580/27dd—accessible on the worldwide web at archive.ispub.com/journal/the-internet-journal-of-microbiology/volume-5-number-2/screening-for-antifungal-activity-of-pseudomonas-fluorescens-against-phytopathogenic-fungi.html#sthash.d0Ys03UO.1DKuT1US.dpuf, hereby incorporated by reference in its entirety). By way of example, botrycidin AJ1316 (see Zuber, P et al. (1993) Peptide Antibiotics. In *Bacillus subtilis* and Other Gram-Positive Bacteria: Biochemistry, Physiology, and Molecular Genetics ed Sonenshein et al., pp. 897-916, American Society for Microbiology, hereby incorporated by reference in its entirety) and alirin B1 (see Shenin et al. (1995) Antibiot Khimioter 50: 3-7, hereby incorporated by reference in its entirety) from *B. subtilis* have been shown to have antifungal activities. As such, in some embodiments, for example embodiments in which neutralization of a fungal microbial organism is desired, a bacteriocin comprises at least one of botrycidin AJ1316 or alirin B1.

For example, in some embodiments, bacteriocin activity in a culture of cyanobacteria is desirable. In some embodiments, bacteriocins are provided to neutralize cyanobacteria. In some embodiments, bacteriocins are provided to neutralize invading microbial organisms typically found in a cyanobacteria culture environment. Clusters of conserved bacteriocin polypeptides have been identified in a wide variety of cyanobacteria species. For example, at least 145 putative bacteriocin gene clusters have been identified in at least 43 cyanobacteria species, as reported in Wang et al. (2011), Genome Mining Demonstrates the Widespread Occurrence of Gene Clusters Encoding Bacteriocins in Cyanobacteria. PLoS ONE 6(7): e22384, hereby incorporated by reference in its entirety. Exemplary cyanobacteria bacteriocins are shown in Table 1.2, as SEQ ID NO's 420, 422, 424, 426, 428, 30, 432, 434, 436, 438, 440, 442, 444, 446, 448, and 450.

In some embodiments, the host cell itself is a microbial cell. In some embodiments, bacteriocins neutralize cells of a different species or strain from the host cell. In some embodiments, bacteriocins neutralize cells of the same species or strain as the host cell if these cells lack an appropriate immunity modulator. As bacteriocins can mediate neutralization of both host and non-host microbial organisms, the skilled artisan will readily appreciate that a bacteriocin is distinct from poison-antidote systems (described in more detail herein), which involve an endogenous mechanism by which a host microorganism can neutralize only itself. In other words, bacteriocins can neutralize cells other than the cell in which they are produced (for example, bacteriocins can be selected and/or engineered to act as an ecological niche protector), while poison molecules kill only the individual cell in which they are produced (for example, to act as suicidal systems).

A number of bacteriocins have been identified and characterized. Without being limited by any particular theory, exemplary bacteriocins can be classified as "class I" bacteriocins, which typically undergo post-translational modification, and "class II" bacteriocins, which are typically unmodified. Additionally, exemplary bacteriocins in each class can be categorized into various subgroups, as summarized in Table 1.1, which is adapted from Cotter, P. D. et al. "Bacteriocins—a viable alternative to antibiotics" *Nature Reviews Microbiology* 11: 95-105, hereby incorporated by reference in its entirety.

Without being limited by any particular theory, bacteriocins can effect neutralization of a target microbial cell in a variety of ways. For example, a bacteriocin can permeablize a cell wall, thus depolarizing the cell wall and interfering with respiration.

TABLE 1.1

Classification of Exemplary Bacteriocins

| Group | Distinctive feature | Examples |
|---|---|---|
| Class I (typically modified) | | |
| MccC7-C51-type bacteriocins | Is covalently attached to a carboxy-terminal aspartic acid | MccC7-C51 |
| Lasso peptides | Have a lasso structure | MccJ25 |
| Linear azole- or azoline-containing peptides | Possess heterocycles but not other modifications | MccB17 |
| Lantibiotics | Possess lanthionine bridges | Nisin, planosporicin, mersacidin, actagardine, mutacin 1140 |
| Linaridins | Have a linear structure and contain dehydrated amino acids | Cypemycin |
| Proteusins | Contain multiple hydroxylations, epimerizations and methylations | Polytheonamide A |
| Sactibiotics | Contain sulphur-α-carbon linkages | Subtilosin A, thuricin CD |
| Patellamide-like cyanobactins | Possess heterocycles and undergo macrocyclization | Patellamide A |
| Anacyclamide-like cyanobactins | Cyclic peptides consisting of proteinogenic amino acids with prenyl attachments | Anacyclamide A10 |
| Thiopeptides | Contain a central pyridine, dihydropyridine or piperidine ring as well as heterocycles | Thiostrepton, nocathiacin I, GE2270 A, philipimycin |
| Bottromycins | Contain macrocyclic amidine, a decarboxylated carboxy-terminal thiazole and carbon-methylated amino acids | Bottromycin A2 |
| Glycocins | Contain S-linked glycopeptides | Sublancin 168 |
| Class II (typically unmodified or cyclic) | | |
| IIa peptides (pediocin PA-1-like bacteriocins) | Possess a conserved YGNGV motif (in which N represents any amino acid) | Pediocin PA-1, enterocin CRL35, carnobacteriocin BM1 |
| IIb peptides | Two unmodified peptides are required for activity | ABP118, lactacin F |
| IIc peptides | Cyclic peptides | Enterocin AS-48 |
| IId peptides | Unmodified, linear, non-pediocin-like, single-peptide bacteriocins | MccV, MccS, epidermicin NI01, lactococcin A |
| IIe peptides | Contain a serine-rich carboxy-terminal region with a non-ribosomal siderophore-type modification | MccE492, MccM |

A number of bacteriocins can be used in accordance with embodiments herein. Exemplary bacteriocins are shown in Table 1.2. In some embodiments, at least one bacteriocin comprising a polypeptide sequence of Table 1.2 is provided. As shown in Table 1.2, some bacteriocins function as pairs of molecules. As such, it will be understood that unless explicitly stated otherwise, when a functional "bacteriocin" or "providing a bacteriocin," or the like is discussed herein, functional bacteriocin pairs are included along with bacteriocins that function individually. With reference to Table 1.2, "organisms of origin" listed in parentheses indicate alternative names and/or strain information for organisms known the produce the indicated bacteriocin.

Embodiments herein also include peptides and proteins with identity to bacteriocins described in Table 1.2. The term "identity" is meant to include nucleic acid or protein sequence homology or three-dimensional homology. Several techniques exist to determine nucleic acid or polypeptide sequence homology and/or three-dimensional homology to polypeptides. These methods are routinely employed to discover the extent of identity that one sequence, domain, or model has to a target sequence, domain, or model. A vast range of functional bacteriocins can incorporate features of bacteriocins disclosed herein, thus providing for a vast degree of identity to the bacteriocins in Table 1.2. In some embodiments, a bacteriocin has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 1.2. Percent identity may be determined using the BLAST software (Altschul, S. F., et al. (1990) "Basic local alignment search tool." J. Mol. Biol. 215:403-410, accessible on the world wide web at blast.ncbi.nlm.nih.gov) with the default parameters.

In some embodiments, a polynucleotide encoding a bacteriocin as described herein is provided. In some embodiments, the polynucleotide is comprised within an expression vector. In some embodiments, the polynucleotide or expression vector is in a microbial cell. Exemplary polynucleotide sequences encoding the polypeptides of table 1.2 are indicated in table 1.2. SEQ ID NOs: 341 to 419 (odd SEQ ID numbers) represent exemplary polynucleotides based on the reverse translation of the respective polypeptide. The skilled artisan will readily understand that more than one polynucleotide can encode a particular polypeptide. For example, the genetic code is degenerate, and moreover, codon usage can vary based on the particular organism in which the gene product is being expressed. In some embodiments, a polynucleotide encoding a bacteriocin is selected based on the codon usage of the organism expressing the bacteriocin. In some embodiments, a polynucleotide encoding a bacteriocin is codon optimized based on the particular organism expressing the bacteriocin.

While the bacteriocins in Table 1.2 are naturally-occurring, the skilled artisan will appreciate that variants of the bacteriocins of Table 1.2, naturally-occurring bacteriocins other than the bacteriocins of Table 1.2 or variants thereof, or synthetic bacteriocins can be used according to some embodiments herein. In some embodiments, such variants have enhanced or decreased levels of cytotoxic or growth inhibition activity on the same or a different microorganism or species of microorganism relative to the wild type protein. Several motifs have been recognized as characteristic of bacteriocins. For example, the motif YGXGV (SEQ ID NO: 2), wherein X is any amino acid residue, is a N-terminal consensus sequence characteristic of class IIa bacteriocins. Accordingly, in some embodiments, a synthetic bacteriocin comprises an N-terminal sequence with at least about 50% identity to SEQ ID NO: 2, for example at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2. In some embodiments, a synthetic bacteriocin comprises a N-terminal sequence comprising SEQ ID NO: 2. Additionally, some class IIb bacteriocins comprise a GxxxG motif. Without being limited by any particular theory, it is believed that the GxxxG motif can mediate association between helical proteins in the cell membrane, for example to facilitate bacterioncin-mediated neutralization through cell membrane interactions. As such, in some embodiments, the bacteriocin comprises a motif that facilitates interactions with the cell membrane. In some embodiments, the bacteriocin comprises a GxxxG motif. Optionally, the bacteriocin comprising a GxxxG motif can comprise a helical structure. In addition to structures described herein, "bacteriocin" as used herein also encompasses structures that have substantially the same effect on microbial cells as any of the bacteriocins explicitly provided herein.

It has been shown that fusion polypeptides comprising two or more bacteriocins or portions thereof can have neutralizing activity against a broader range of microbial organisms than either individual bacteriocin. For example, it has been shown that a hybrid bacteriocin, Ent35-MccV (GKYYGNGVSCNKKGCSVDWGRAIGIIGNNSAAN-LATGGAAGWKSGGGASGRDIAM AIGTLSGQFVAG-GIGAAAGGVAGGAIYDYASTHKPNPAMSPSGLGG-TIKQKPEGIPSE AWNYAAGRLCNWSPNNLSDVCL, SEQ ID NO: 3), displays antimicrobial activity against pathogenic Gram-positive and Gram-negative bacteria (Acuña et al. (2012), FEBS Open Bio, 2: 12-19). It is noted that that Ent35-MccV fusion bacteriocin comprises, from N-terminus to C-terminus, an N-terminal glycine, Enterocin CRL35, a linker comprising three glycines, and a C-terminal Microcin V. It is contemplated herein that bacteriocins can comprise fusions of two or more polypeptides having bacteriocin activity. In some embodiments, a fusion polypeptide of two or more bacteriocins is provided. In some embodiments, the two or more bacteriocins comprise polypeptides from Table 1.2, or modifications thereof. In some embodiments, the fusion polypeptide comprising of two or more bacteriocins has a broader spectrum of activity than either individual bacteriocin, for example having neutralizing activity against more microbial organisms, neutralizing activity under a broader range of environmental conditions, and/or a higher efficiency of neutralization activity. In some embodiments, a fusion of two or more bacteriocins is provided, for example two, three, four, five, six, seven, eight, nine, or ten bacteriocins. In some embodiments, two or more bacteriocin polypeptides are fused to each other via a covalent bond, for example a peptide linkage. In some embodiments, a linker is positioned between the two bacteriocin polypeptides. In some embodiments, the linker comprises one or glycines, for example about 1, 2, 3, 4, 5, 6, 7, 8, 9, 10, 11, 12, 13, 14, 15, 16, 17, 18, 19, or 20 glycines. In some embodiments, the linker is cleaved within the cell to produce the individual bacteriocins included in the fusion protein. In some embodiments, a bacteriocin as provided herein is modified to provide a desired spectrum of activity relative to the unmodified bacteriocin. For example, the modified bacteriocin may have enhanced or decreased activity agains the same organisms as the unmodified bacteriocin. Alternatively, the modified bacteriocin may have enhanced activity against an organism against which the unmodified bacteriocin has less activity or no activity.

TABLE 1.2

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 4 | Acidocin 8912 | Unclassified | MISSHQKTL TDKELALISG GKTHYPTNA WKSLWKGF WESLRYTDGF | *Lactobacillus acidophilus* | 5 | ATGATTTCATC TCATCAAAAA ACGTTAACTG ATAAAGAATT AGCATTAATTT CTGGGGGGAA AACGCACTAC CCGACTAATG CATGGAAAAG TCTTTGGAAA GGTTTCTGGG AAAGCCTTCG TTATACTGAC GGTTTTTAG |
| 6 | Acidocin A | class IIA/YG NGV | MISMISSHQ KTLTDKELA LISGGKTYY GTNGVHCTK KSLWGKVRL KNVIPGTLC RKQSLPIKQ DLKILLGWA TGAFGKTFH | *Lactobacillus acidophilus* | 7 | ATGATTTCAAT GATTTCATCTC ATCAAAAAAC GTTAACTGAT AAAGAATTAG CATTAATTTCT GGGGGGAAAA CGTACTATGG TACTAATGGT GTGCATTGTA CTAAAAAGAG TCTTTGGGGT AAAGTACGCT TAAAAAACGT GATTCCTGGA ACTCTTTGTCG TAAGCAATCG TTGCCGATCA AACAGGATTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAAAATTTTA CTGGGCTGGG CTACAGGTGC TTTTGGCAAG ACATTTCATTAA |
| 8 | Acidocin B (AcdB) | Unclassified | MDKKTKILF EVLYIICIIGP QFILFVTAKN NMYQLVGSF VGIVWFSYIF WYIFFKQHK KM | Lactobacillus acidophilus | 9 | ATGGATAAGA AAACAAAAAT ATTATTTGAA GTATTATACAT CATCTGTATA ATAGGCCCTC AATTTATATTA TTTGTGACTGC AAAAAACAAT ATGTATCAGT TGGTGGGTTC GTTTGTTGGA ATAGTATGGT TTTCGTATATT TTTTGGTATAT TTTTTTCAAAC AACATAAAAA AATGTAG |
| 10 | Acidocin LF221B (Gassericin K7 B) | Unclassified | MALKTLEKH ELRNVMGG NKWGNAVI GAATGATRG VSWCRGFGP WGMTACAL GGAAIGGYL GYKSN | Lactobacillus gasseri | 11 | ATGGCTTTAA AAACATTAGA AAAACATGAA TTAAGAAATG TAATGGGTGG AAACAAGTGG GGGAATGCTG TAATAGGAGC TGCTACGGGA GCTACTCGCG GAGTAAGTTG GTGCAGAGGA TTCGGACCAT GGGGAATGAC TGCCTGTGCG TTAGGAGGTG CTGCAATTGG AGGATATCTG GGATATAAGA GTAATTAA |
| 12 | Aureocin A53 | Unclassified | MSWLNFLK YIAKYGKKA VSAAWKYK GKVLEWLN VGPTLEWV WQKLKKIAGL | Staphylococcus aureus | 13 | ATGAGTTGGT TAAATTTTTA AAATACATCG CTAAATATGG CAAAAAAGCG GTATCTGCTG CTTGGAAGTA CAAAGGTAAA GTATTAGAAT GGCTTAATGT TGGTCCTACTC TTGAATGGGT ATGGCAAAAA TTAAAGAAAA TTGCTGGATT ATAA |
| 14 | Avicin A | class IIA/YG NGV | MTRSKKLNL REMKNVVG GTYYGNGVS CNKKGCSVD WGKAISIIGN NSAANLATG GAAGWKS | Enterococcus avium (Streptococcus avium) | 15 | ATGACAAGAT CAAAAAAATT AAATTTACGC GAAATGAAGA ATGTTGTTGG TGGTACCTAC TATGGAAATG GTGTATCTTGT AACAAGAAAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCTGTTCAGTT GACTGGGGCA AAGCCATCAG TATTATAGGA AATAATTCCG CAGCAAACTT AGCAACTGGT GGTGCTGCTG GTTGGAAGTC ATAA |
| 16 | Bacteriocin 31 | Unclassified | MKKKLVICG IIGIGFTALG TNVEAATYY GNGLYCNK QKCWVDWN KASREIGKII VNGWVQHG PWAPR | Enterococcus faecalis (Streptococcus faecalis) | 17 | ATGAAAAAGA AATTAGTTATT TGTGGCATTA TTGGGATTGG TTTTACAGCAT TAGGAACAAA TGTAGAAGCT GCTACGTATT ACGGAAATGG TTTATATTGTA ATAAGCAAAA ATGTTGGGTA GACTGGAATA AAGCTTCAAG GGAAATTGGA AAAATTATTG TTAATGGTTG GGTACAACAT GGCCCTTGGG CTCCTAGATAG |
| 18 | Bacteriocin J46 | Unclassified | MKEQNSFNL LQEVTESEL DLILGAKGG SGVIHTISHE VIYNSWNFV FTCCS | Lactococcus lactis | 19 | ATGAAAGAAC AAAACTCTTTT AATCTTCTTCA AGAAGTGACA GAAAGTGAAT TGGACCTTATT TTAGGTGCAA AAGGCGGCAG TGGAGTTATT CATACAATTTC TCATGAAGTA ATATATAATA GCTGGAACTT TGTATTTACTT GCTGCTCTTAA |
| 20 | Bacteriocin T8 | class IIa | MKKKVLKH CVILGILGTC LAGIGTGIKV DAATYYGN GLYCNKEKC WVDWNQAK GEIGKIIVNG WVNHGPWA PRR | Enterococcus faecium (Streptococcus faecium) | 21 | ATGAAAAAGA AAGTATTAAA ACATTGTGTT ATTCTAGGAA TATTAGGAAC TTGTCTAGCTG GCATCGGTAC AGGAATAAAA GTTGATGCAG CTACTTACTAT GGAAATGGTC TTTATTGTAAC AAAGAAAAT GTTGGGTAGA TTGGAATCAA GCTAAAGGAG AAATTGGAAA AATTATTGTTA ATGGTTGGGT TAATCATGGT CCATGGGCAC CTAGAAGGTAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 22 | Boticin B | Unclassified | MQKPEIISAD LGLCAVNEF VALAAIPGG AATFAVCQ MPNLDEIVS NAAYV | Clostridium botulinum | 23 | ATGCAAAAAC CAGAAATTAT TAGTGCTGAT TTAGGGCTTT GTGCAGTTAA TGAATTTGTA GCTCTTGCTGC CATTCCTGGT GGTGCTGCTA CATTTGCAGT ATGCCAAATG CCAAACTTGG ATGAGATTGT TAGTAATGCA GCATATGTTT AA |
| 24 | Bovicin HJ50 | Lantibiotic | MMNATENQI FVETVSDQE LEMLIGGAD RGWIKTLTK DCPNVISSIC AGTIITACKN CA | Streptococcus equinus (Streptococcus bovis) | 25 | ATGATGAATG CTACTGAAAA CCAAATTTTTG TTGAGACTGT GAGTGACCAA GAATTAGAAA TGTTAATTGGT GGTGCAGATC GTGGATGGAT TAAGACTTTA ACAAAAGATT GTCCAAATGT AATTTCTTCAA TTTGTGCAGG TACAATTATA CAGCTTGTAA AAATTGTGCT TAA |
| 26 | Brochocin-c | Unclassified | MHKVKKLN NQELQQIVG GYSSKDCLK DIGKGIGAG TVAGAAGG GLAAGLGAI PGAFVGAHF GVIGGSAACI GGLLGN | Brochothrix campestris | 27 | ATGCACAAGG TAAAAAAATT AAACAATCAA GAGTTACAAC AGATCGTGGG AGGTTACAGT TCAAAAGATT GTCTAAAAGA TATTGGTAAA GGAATTGGTG CTGGTACAGT AGCTGGGGCA GCCGGCGGTG GCCTAGCTGC AGGATTAGGT GCTATCCCAG GAGCATTCGT TGGAGCACAT TTTGGAGTAA TCGGCGGATC TGCCGCATGC ATTGGTGGAT TATTAGGTAA CTAG |
| 28 | Butyrivibriocin AR10 | Unclassified | MSKKQIMSN CISIALLIALI PNIYFIADKM GIQLAPAWY QDIVNWVSA GGTLTTGFAI IVGVTVPAW IAEAAAAFGI ASA | Butyrivibrio fibrisolvens | 29 | ATGAGTAAAA AACAAATTAT GAGTAACTGT ATATCAATTG CATTATTAATA GCACTAATTC CTAATATCTAT TTTATTGCAG ATAAAATGGG AATTCAGTTA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCACCTGCTT GGTATCAAGA TATTGTGAATT GGGTATCTGC TGGTGGAACA CTTACTACTG GTTTTGCGATT ATTGTAGGAG TTACAGTACC GGCATGGATA GCAGAAGCAG CTGCAGCTTTT GGTATAGCTT CAGCATGA |
| 30 | Butyrivibriocin OR79 | Lantibiotic | MNKELNALT NPIDEKELEQ ILGGGNGVI KTISHECHM NTWQFIFTC CS | Butyrivibrio fibrisolvens | 31 | ATGAACAAAG AACTTAATGC ACTTACAAAT CCTATTGACG AGAAGGAGCT TGAGCAGATC CTCGGTGGTG GCAATGGTGT CATCAAGACA ATCAGCCACG AGTGCCACAT GAACACATGG CAGTTCATTTT CACATGTTGC TCTTAA |
| 32 | Carnobacteriocin B2 (Carnocin CP52) | class IIA/YG NGV | MNSVKELN VKEMKQLH GGVNYGNG VSCSKTKCS VNWGQAFQ ERYTAGINSF VSGVASGAG SIGRRP | Carnobacterium maltaromaticum (Carnobacterium piscicola) | 33 | ATGAATAGCG TAAAAGAATT AAACGTGAAA GAAATGAAAC AATTACACGG TGGAGTAAAT TATGGTAATG GTGTTTCTTGC AGTAAAACAA AATGTTCAGT TAACTGGGGA CAAGCCTTTC AAGAAAGATA CACAGCTGGA ATTAACTCATT TGTAAGTGGA GTCGCTTCTG GGGCAGGATC CATTGGTAGG AGACCGTAA |
| 34 | Carnobacteriocin BM1 (Carnobacteriocin B1) | class IIA/YG NGV | MKSVKELNK KEMQQINGG AISYGNGVY CNKEKCWV NKAENKQAI TGIVIGGWA SSLAGMGH | Carnobacterium maltaromaticum (Carnobacterium piscicola) | 35 | ATGAAAAGCG TTAAAGAACT AAATAAAAA GAAATGCAAC AAATTAATGG TGGAGCTATC TCTTATGGCA ATGGTGTTTAT TGTAACAAAG AGAAATGTTG GGTAAACAAG GCAGAAAACA AACAAGCTAT TACTGGAATA GTTATCGGTG GATGGGCTTC TAGTTTAGCA GGAATGGGAC ATTAA |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| 36 | Carnobacteriocin-A (Piscicolin-61) | class IIc, non subgrouped bacteriocins (problematic) | MNNVKELSI KEMQQVTG GDQMSDGV NYGKGSSLS KGGAKCGL GIVGGLATIP SGPLGWLAG AAGVINSCMK | Carnobacterium maltaromaticum (Carnobacterium piscicola) | 37 | ATGAATAATG TAAAAGAGTT AAGTATTAAA GAAATGCAAC AAGTTACTGG TGGAGACCAA ATGTCAGATG GTGTAAATTA TGGAAAAGGC TCTAGCTTATC AAAAGGTGGT GCCAAATGTG GTTTAGGGAT CGTCGGCGGA TTAGCTACTAT CCCTTCAGGT CCTTTAGGCT GGTTAGCCGG AGCAGCAGGT GTAATTAATA GCTGTATGAA ATAA |
| 38 | Carnocyclin-A | Unclassified | MLYELVAY GIAQGTAEK VVSLINAGL TVGSIISILG GVTVGLSGV FTAVKAAIA KQGIKKAIQL | Carnobacterium maltaromaticum (Carnobacterium piscicola) | 39 | ATGTTATATG AATTAGTTGC ATATGGTATC GCACAAGGTA CAGCTGAAAA GGTTGTAAGT CTAATTAACG CAGGTTTAAC AGTAGGGTCT ATTATTTCAAT TTTGGGTGGG GTCACAGTCG GTTTATCAGG TGTCTTCACA GCAGTTAAAG CAGCAATTGC TAAACAAGGA ATAAAAAAG CAATTCAATT ATAA |
| 40 | Carocin D | Unclassified | MIKYRLYAP NDGDTMTV SGGGGWVS NDDRKGGN DRDNGKGG SAVDFSKNP EKQAIVNPY LAIAIPMPVY PLYGKLGFTI NTTAIETELA NVRAAINTK LATLSAVIGR SLPVVGRVF GVTAAGMW PSSTAPSSLD SIYNQAHQQ ALAQLAAQQ GVLNKGYN VTAMPAGFV SSLPVSEIKS LPTAPASLLA QSVINTELSQ RQLALTQPT TNAPVANIP VVKAEKTA MPGVYSAKI IAGEPAFQIK VDNTKPALA | Pectobacterium carotovorum subsp. carotovorum (Erwinia carotovora subsp. carotovora) | 41 | ATGATTAAAT ACCGTTTATAT GCTCCAAATG ATGGAGACAC CATGACAGTG AGTGGTGGTG GTGGTTGGGT TTCAAACGAT GATCGCAAAG GTGGTAATGA CAGGGACAAT GGCAAAGGTG GTTCTGCCGTT GATTTTAGTA AAAATCCAGA AAAGCAGGCT ATCGTTAATCC CTATTTGGCA ATCGCGATAC CGATGCCGGT CTACCCTCTTT ATGGAAAGCT AGGGTTCACA ATAAATACGA CGGCAATTGA GACTGAACTC GCAAATGTCA GAGCAGCAAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | QNPPKVKDD | | | TAACACTAAA |
| | | | IQVSSFLSSP | | | CTTGCAACAC |
| | | | VADTHHAFI | | | TCAGTGCAGT |
| | | | DFGSDHEPV | | | GATTGGCAGA |
| | | | YVSLSKIVT | | | TCACTTCCGGT |
| | | | AEEEKKQVE | | | CGTTGGGCGG |
| | | | EAKRREQEW | | | GTATTTGGTG |
| | | | LLRHPITAAE | | | TTACTGCCGC |
| | | | RKLTEIRQVI | | | CGGAATGTGG |
| | | | SFAQQLKES | | | CCTTCTAGTAC |
| | | | SVATISEKTK | | | CGCTCCCAGT |
| | | | TVAVYQEQ | | | AGTCTCGATT |
| | | | VNTAAKNR | | | CTATATACAA |
| | | | DNFYNQNR | | | TCAAGCACAT |
| | | | GLLSAGITG | | | CAGCAGGCTT |
| | | | GPGYPIYLA | | | TAGCCCAGTT |
| | | | LWQTMNNF | | | AGCTGCTCAA |
| | | | HQAYFRANN | | | CAGGGAGTAT |
| | | | ALEQESHVL | | | TAAATAAAGG |
| | | | NLARSDLAK | | | GTATAACGTT |
| | | | AEQLLAENN | | | ACAGCAATGC |
| | | | RLQVETERT | | | CTGCAGGTTT |
| | | | LAEEKEIKR | | | CGTCAGCAGT |
| | | | NRVNVSTFG | | | TTGCCTGTTAG |
| | | | TVQTQLSKL | | | TGAAATCAAA |
| | | | LSDFYAVTS | | | TCATTGCCAA |
| | | | LSQSVPSGA | | | CAGCTCCCGC |
| | | | LASFSYNPQ | | | CAGTTTACTG |
| | | | GMIGSGKIV | | | GCACAAAGTG |
| | | | GKDVDVLFS | | | TGATTAATAC |
| | | | IPVKDIPGYK | | | CGAACTTTCCC |
| | | | SPINLDDLAK | | | AGCGTCAACT |
| | | | KNGSLDLPIR | | | GGCTCTTACTC |
| | | | LAFSDENGE | | | AGCCCACGAC |
| | | | RVLRAFKAD | | | GAATGCACCA |
| | | | SLRIPSSVRG | | | GTCGCGAATA |
| | | | VAGSYDKNT | | | TTCCCGTAGTT |
| | | | GIFSAEIDGV | | | AAAGCAGAGA |
| | | | SSRLVLENP | | | AAACAGCAAT |
| | | | AFPPTGNVG | | | GCCAGGTGTG |
| | | | NTGNTAPDY | | | TATTCAGCGA |
| | | | KALLNTGVD | | | AAATTATTGCT |
| | | | VKPVDKITV | | | GGTGAGCCTG |
| | | | TVTPVADPV | | | CATTCCAAAT |
| | | | DIDDYIIWLP | | | CAAGGTCGAT |
| | | | TASGSGVEPI | | | AATACCAAAC |
| | | | YVVFNSNPY | | | CTGCTTTGGC |
| | | | GGTEKGKYS | | | ACAGAATCCG |
| | | | KRYYNPDKA | | | CCGAAAGTAA |
| | | | GGPILELDW | | | AAGATGATAT |
| | | | KNVKIDHAG | | | TCAGGTATCTT |
| | | | VDNVKLHT | | | CTTTCCTTTCC |
| | | | GRFKASVEN | | | TCGCCAGTAG |
| | | | KVMIERLENI | | | CTGATACGCA |
| | | | LNGQITATD | | | CCATGCATTTA |
| | | | TDKRFYTHE | | | TTGATTTTGGC |
| | | | LRELNRYRN | | | AGCGATCATG |
| | | | LGIKDGEVP | | | AACCGGTATA |
| | | | SSIQEESAV | | | CGTGTCTCTTT |
| | | | WNDTHTAT | | | CAAAGATCGT |
| | | | LEDYKINEK | | | GACAGCCGAG |
| | | | EQPLYTDAA | | | GAGGAGAAAA |
| | | | LQAAYEQEL | | | AACAGGTTGA |
| | | | KDALGGKHG | | | AGAGGCCAAG |
| | | | | | | CGCCGTGAGC |
| | | | | | | AGGAGTGGTT |
| | | | | | | GTTGCGTCAT |
| | | | | | | CCAATTACAG |
| | | | | | | CTGCGGAGCG |
| | | | | | | AAAATTAACT |
| | | | | | | GAAATCCGCC |
| | | | | | | AAGTGATCTC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TTTTGCTCAAC AGCTAAAAGA AAGCTCTGTC GCAACCATTT CAGAAAAAAC TAAAACTGTT GCGGTTTACC AAGAACAGGT GAATACCGCT GCAAAAAATC GCGACAATTT TTATAATCAA AATAGAGGTC TGTTAAGTGC GGGTATAACT GGGGGACCGG GATATCCTATT TATCTTGCTTT ATGGCAAACG ATGAATAACT TTCATCAGGC TTATTTCAGA GCAAATAATG CATTGGAACA AGAGAGTCAT GTTCTGAACC TGGCTCGTTCT GATCTGGCTA AGGCTGAGCA ATTGCTTGCTG AGAATAATCG ACTTCAGGTT GAAACGGAGC GAACGCTTGC CGAAGAAAAA GAGATAAAAC GCAACAGGGT TAATGTATCA ACATTTGGCA CAGTGCAAAC TCAACTTAGT AAATTGCTGT CAGATTTTTAT GCTGTTACAT CACTTTCCCAA AGTGTTCCTTC GGGGGCATTA GCCTCTTTTTC ATATAATCCA CAAGGGATGA TTGGCAGCGG TAAGATTGTT GGGAAGGATG TCGATGTTTTA TTTTCCATCCC AGTAAAAGAT ATTCCGGGAT ATAAATCTCCT ATTAACTTGG ACGATTTAGC CAAGAAAAAT GGAAGTCTGG ATCTTCCCATT CGTCTGGCAT TTTCTGATGA GAATGGAGAA AGGGTTCTTC GGGCATTCAA AGCGGATAGT CTGCGAATCC CTTCGAGTGT CAGAGGTGTA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCGGGCAGTT ATGACAAAAA TACGGGTATT TTTAGTGCAG AAATTGATGG TGTTTCATCTC GCCTTGTACT GGAAAACCCA GCGTTTCCTCC GACCGGAAAT GTCGGTAATA CGGGTAATAC TGCACCTGAC TATAAAGCAT TACTGAATAC TGGTGTTGAT GTTAAACCTG TTGATAAAAT CACAGTTACG GTAACACCAG TTGCTGATCC AGTGGATATT GATGACTATA TAATCTGGTT GCCAACTGCG TCTGGTTCTG GCGTGGAACC CATTTATGTCG TGTTTAACAG TAATCCGTAT GGTGGGACGG AAAAAGGAAA ATATAGCAAA CGTTATTATAA TCCAGATAAG GCAGGCGGTC CGATCTTGGA GCTGGATTGG AAAAACGTTA AGATTGACCA TGCAGGTGTG GACAATGTTA AATTACACAC AGGGCGTTTC AAAGCGTCGG TTGAAAACAA AGTGATGATT GAACGTTTGG AAAACATACT GAATGGTCAA ATCACGGCCA CGGATACTGA CAAGCGATTC TATACGCATG AATTAAGAGA GTTAAACCGC TACAGAAATT TAGGCATCAA AGACGGTGAA GTGCCTAGTA GCATTCAAGA AGAAAGCGCT GTTTGGAACG ACACACACAC AGCGACGCTT GAAGACTACA AAATTAATGA GAAAGAGCAA CCGTTGTACA CTGATGCTGC TTTGCAGGCA GCCTACGAAC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AGGAACTCAA AGACGCATTA GGAGGGAAAC ATGGCTAA |
| 42 | Cerein 7B | Unclassified | MENLQMLT EEELMEIEG GGWWNSWG KCVAGTIGG AGTGGLGGA AAGSAVPVI GTGIGGAIG GVSGGLTGA ATFC | Bacillus cereus | 43 | ATGGAAAACT TACAAATGTT AACTGAAGAA GAATTAATGG AAATTGAAGG TGGAGGCTGG TGGAATAGCT GGGGTAAATG TGTTGCTGGA ACTATCGGTG GAGCTGGAAC TGGTGGTTTA GGTGGAGCTG CTGCAGGTTC AGCTGTTCCG GTTATTGGTA CTGGTATTGG TGGCGCTATT GGTGGAGTTA GCGGTGGCCT TACAGGTGCA GCTACTTTTG CTAA |
| 44 | Cinnamycin (Lanthiopeptin) | Lantibiotic | MTASILQQS VVDADFRAA LLENPAAFG ASAAALPTP VEAQDQASL DFWTKDIAA TEAFACRQS CSFGPFTFVC DGNTK | Streptoverticillium griseoverticillatum | 45 | ATGACCGCTT CCATTCTTCAG CAGTCCGTCG TGGACGCCGA CTTCCGCGCG GCGCTGCTTG AGAACCCCGC CGCCTTCGGC GCTTCCGCCG CGGCCCTGCC CACGCCCGTC GAGGCCCAGG ACCAGGCGTC CCTTGACTTCT GGACCAAGGA CATCGCCGCC ACGGAAGCCT TCGCCTGCCG CCAGAGCTGC AGCTTCGGCC CGTTCACCTTC GTGTGCGACG GCAACACCAA GTAA |
| 46 | Circularin A | Unclassified | MSLLALVAG TLGVSQSIAT TVVSIVLTGS TLISIILGITAI LSGGVDAIL EIGWSAFVA TVKKIVAER GKAAAIAW | Geobacillus kaustophilus (strain HTA426) | 47 | ATGAGTTTGC TGGCGCTTGT TGCCGGGACG CTCGGCGTGT CACAGTCAAT CGCGACGACG GTTGTTTCGAT TGTGTTGACC GGCTCCACTC TCATTTCTATT ATTCTTGGGA TCACCGCTATT TTGTCAGGTG GAGTCGACGC CATTTTGGAA ATTGGGTGGT CAGCTTTTGTC GCGACGGTGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAAAAATAGT GGCGGAACGA GGAAAAGCGG CAGCGATTGC ATGGTAA |
| 48 | Closticin 574 | Unclassified | MRKVFLRSII STLVMCAFV SSSFSVNAD ESKPNDEKII NNIENVTTT KDIVKSNKN NIVYLDEGV MSIPLSGRKP IAIKDDNNK EDLTVTLPIK NTGDISKISS NGTILYKNN SSNSSNIALQ PKNDGFKAL ININDKLAN KEYEFTFNL PKNSKLISAA TYLGKEYDT KEVFVVDKN NIITSIISPAW AKDANGHN VSTYYKIVS NNKLVQVV EFTENTAFP VVADPNWT KIGKCAGSIA WAIGSGLFG GAKLIKIKKY IAELGGLQK AAKLLVGAT TWEEKLHAG GYALINLAA ELTGVAGIQ ANCF | *Clostridium tyrobutyricum* | 49 | TTGAGAAAAG TATTTTTAAGA TCAATAATTTC AACATTAGTT ATGTGTGCAT TTGTTTCAAGC AGCTTTTCAGT AAATGCGGAT GAAAGCAAAC CAAATGATGA AAAAATAATT AATAACATAG AAAACGTTAC TACTACTAAA GATATTGTAA AAAGTAATAA AATAATATT GTATATTTAG ATGAAGGTGT AATGAGTATT CCATTGTCTG GGAGAAAACC CATTGCTATTA AAGATGATAA TAATAAAGAA GATTTAACTG TTACATTACCT ATTAAGAATA CTGGAGATAT ATCTAAAATT AGTAGTAATG GTACTATTCTG TATAAAAATA ATAGTAGTAA TTCATCTAATA TAGCTTTACA ACCTAAAAAT GATGGATTTA AGGCTTTAAT AAATATTAAT GATAAGTTAG CTAATAAAGA ATATGAATTT ACATTTAATTT ACCCAAAAAC AGTAAATTAA TTAGTGCTGC CACATATTTG GGTAAAGAAT ATGATACAAA AGAAGTATTT GTAGTAGACA AAAATAATAT AATTACGAGT ATTATTAGTCC AGCTTGGGCT AAAGATGCAA ATGGACATAA TGTTTCTACTT ATTATAAGAT AGTATCGAAT AATAAATTAG TACAAGTTGT TGAATTCACA GAAAATACTG CATTCCCGGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGTAGCTGAT CCTAATTGGA CTAAAATTGG GAAATGCGCT GGGTCAATAG CATGGGCTAT AGGTTCTGGC CTTTTTGGTGG AGCAAAGCTA ATTAAAATAA AAAAATATAT AGCAGAGCTT GGAGGACTTC AAAAAGCAGC TAAATTATTA GTTGGTGCAA CCACTTGGGA AGAAAAATTA CACGCAGGCG GTTATGCATT AATTAACTTA GCTGCTGAGC TAACAGGTGT AGCAGGTATA CAAGCAAATT GTTTTTAA |
| 50 | Coagulin A | Unclassified | MKKIEKLTE KEMANIIGG KYYGNGVT CGKHSCSVD WGKATTCII NNGAMAWA TGGHQGTH KC | Bacillus coagulans | 51 | ATGAAAAAAA TTGAAAAATT AACTGAAAAA GAAATGGCCA ATATCATTGG TGGTAAATAC TACGGTAATG GGGTTACTTG TGGCAAACAT TCCTGCTCTGT TGACTGGGGT AAGGCTACCA CCTGCATAAT CAATAATGGA GCTATGGCAT GGGCTACTGG TGGACATCAA GGTACTCATA AATGCTAG |
| 52 | Colicin-10 | Unclassified | MDKVTDNSP DVESTESTE GSFPTVGVD TGDTITATL ATGTENVGG GGGAFGGAS ESSAAIHATA KWSTAQLKK HQAEQAAR AAAAEAALA KAKSQRDAL TQRLKDIVN DALRANAAR SPSVTDLAH ANNMAMQA EAERLRLAK AEQKAREEA EAAEKALRE AERQRDEIA RQQAETAHL LAMAEAAEA EKNRQDSLD EEHRAVEVA EKKLAEAKA ELAKAESDV | Escherichia coli | 53 | ATGGATAAAG TCACTGATAA TTCTCCAGAT GTGGAGAGCA CAGAATCTAC TGAGGGGTCA TTCCCAACTGT TGGGGTTGAT ACTGGCGATA CGATTACAGC GACGCTTGCA ACTGGAACTG AAAATGTTGG TGGAGGCGGT GGAGCATTTG GTGGGGCCAG TGAAAGTTCT GCTGCGATAC ATGCAACCGC TAAATGGTCT ACCGCGCAGT TGAAAAAACA TCAGGCTGAA CAGGCTGCCC GTGCTGCTGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | QSKQAIVSR | | | GGCTGAGGCA |
| | | | VAGELENAQ | | | GCATTGGCAA |
| | | | KSVDVKVTG | | | AAGCGAAATC |
| | | | FPGWRDVQ | | | TCAGCGTGAT |
| | | | KKLERQLQD | | | GCCCTGACTC |
| | | | KKNEYSSVT | | | AACGTCTCAA |
| | | | NALNSAVSI | | | GGATATTGTT |
| | | | RDAKKTEVQ | | | AATGACGCTT |
| | | | NAEIKLKEA | | | TACGTGCTAA |
| | | | KDALEKSQV | | | TGCCGCTCGT |
| | | | KDSVDTMV | | | AGTCCATCAG |
| | | | GFYQYITEQ | | | TAACTGACCTT |
| | | | YGEKYSRIA | | | GCTCATGCCA |
| | | | QDLAEKAKG | | | ATAATATGGC |
| | | | SKFNSVDEA | | | AATGCAGGCA |
| | | | LAAFEKYKN | | | GAGGCTGAGC |
| | | | VLDKKFSKV | | | GTTTGCGCCTT |
| | | | DRDDIFNAL | | | GCGAAGGCAG |
| | | | ESITYDEWA | | | AGCAAAAGC |
| | | | KHLEKISRAL | | | CCGTGAAGAA |
| | | | KVTGYLSFG | | | GCTGAAGCAG |
| | | | YDVWDGTL | | | CAGAAAAAGC |
| | | | KGLKTGDW | | | GCTCCGGGAA |
| | | | KPLFVTLEKS | | | GCAGAACGCC |
| | | | AVDFGVAKI | | | AACGTGATGA |
| | | | VALMFSFIV | | | GATTGCCCGC |
| | | | GAPLGFWGI | | | CAACAGGCTG |
| | | | AIITGIVSSYI | | | AAACCGCGCA |
| | | | GDDELNKLN | | | TTTGTTAGCA |
| | | | ELLGI | | | ATGGCGGAGG |
| | | | | | | CAGCAGAGGC |
| | | | | | | TGAGAAAAAT |
| | | | | | | CGACAGGATT |
| | | | | | | CTCTTGATGA |
| | | | | | | AGAGCATCGG |
| | | | | | | GCTGTGGAAG |
| | | | | | | TGGCAGAGAA |
| | | | | | | GAAGCTGGCT |
| | | | | | | GAGGCTAAAG |
| | | | | | | CTGAACTGGC |
| | | | | | | GAAGGCCGAA |
| | | | | | | AGCGATGTAC |
| | | | | | | AGAGTAAGCA |
| | | | | | | AGCGATTGTT |
| | | | | | | TCCAGAGTTG |
| | | | | | | CAGGGGAGCT |
| | | | | | | TGAAAACGCT |
| | | | | | | CAAAAAAGTG |
| | | | | | | TTGATGTGAA |
| | | | | | | GGTTACCGGA |
| | | | | | | TTTCCTGGATG |
| | | | | | | GCGTGATGTT |
| | | | | | | CAGAAAAAAC |
| | | | | | | TGGAGAGACA |
| | | | | | | ATTGCAGGAT |
| | | | | | | AAGAAGAATG |
| | | | | | | AATATTCGTC |
| | | | | | | AGTGACGAAT |
| | | | | | | GCTCTTAATTC |
| | | | | | | TGCTGTTAGC |
| | | | | | | ATTAGAGATG |
| | | | | | | CTAAAAAAAC |
| | | | | | | AGAAGTTCAG |
| | | | | | | AATGCTGAGA |
| | | | | | | TAAAATTAAA |
| | | | | | | AGAAGCTAAG |
| | | | | | | GATGCTCTTG |
| | | | | | | AGAAGAGTCA |
| | | | | | | GGTAAAAGAC |
| | | | | | | TCTGTTGATAC |
| | | | | | | TATGGTTGGG |
| | | | | | | TTTTATCAATA |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | | | | TATAACCGAA CAATATGGGG AAAAATATTC CAGAATAGCT CAGGATTTAG CTGAAAAGGC GAAGGGTAGT AAATTTAATA GTGTTGATGA AGCACTTGCT GCATTTGAAA AGTATAAAAA TGTACTGGAT AAGAAATTCA GTAAGGTTGA TAGGGATGAT ATTTTTAATGC TTTAGAGTCT ATTACTTATGA TGAGTGGGCC AAGCATCTAG AAAAGATCTC TAGGGCTCTT AAGGTTACTG GATATTTGTCT TTCGGGTATG ATGTATGGGA TGGTACCCTA AAGGGATTAA AAACAGGAGA CTGGAAGCCT TTATTTGTCAC TCTGGAGAAG AGCGCGGTAG ATTTCGGCGT GGCAAAAATT GTGGCATTAA TGTTTAGTTTT ATTGTTGGTG CGCCTCTTGG CTTCTGGGGA ATTGCAATTAT CACAGGTATT GTTTCTTCTTA CATAGGGGAT GATGAGTTGA ACAAGCTTAA TGAATTACTA GGTATTTAA |
| 54 | Colicin-E1 | Unclassified | METAVAYY KDGVPYDD KGQVIITLLN GTPDGSGSG GGGGKGGS KSESSAAIHA TAKWSTAQL KKTQAEQAA RAKAAAEAQ AKAKANRD ALTQRLKDI VNEALRHNA SRTPSATELA HANNAAMQ AEDERLRLA KAEEKARKE AEAAEKAFQ EAEQRRKEI EREKAETER QLKLAEAEE KRLAALSEE AKAVEIAQK | Escherichia coli | 55 | ATGGAAACCG CGGTAGCGTA CTATAAAGAT GGTGTTCCTTA TGATGATAAG GGACAGGTAA TTATTACTCTT TTGAATGGTA CTCCTGACGG GAGTGGCTCT GGCGGCGGAG GTGGAAAAGG AGGCAGTAAA AGTGAAAGTT CTGCAGCTAT TCATGCAACT GCTAAATGGT CTACTGCTCA ATTAAAGAAA ACACAGGCAG AGCAGGCTGC CCGGGCAAAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | KLSAAQSEV | | | GCTGCAGCGG |
| | | | VKMDGEIKT | | | AAGCACAGGC |
| | | | LNSRLSSSIH | | | GAAAGCAAAG |
| | | | ARDAEMKTL | | | GCAAACAGGG |
| | | | AGKRNELAQ | | | ATGCGCTGAC |
| | | | ASAKYKELD | | | TCAGCGCCTG |
| | | | ELVKKLSPR | | | AAGGATATCG |
| | | | ANDPLQNRP | | | TGAATGAGGC |
| | | | FFEATRRRV | | | TCTTCGTCACA |
| | | | GAGKIREEK | | | ATGCCTCACG |
| | | | QKQVTASET | | | TACGCCTTCA |
| | | | RINRINADIT | | | GCAACAGAGC |
| | | | QIQKAISQVS | | | TTGCTCATGCT |
| | | | NNRNAGIAR | | | AATAATGCAG |
| | | | VHEAEENLK | | | CTATGCAGGC |
| | | | KAQNNLLNS | | | GGAAGACGAG |
| | | | QIKDAVDAT | | | CGTTTGCGCCT |
| | | | VSFYQTLTE | | | TGCGAAAGCA |
| | | | KYGEKYSK | | | GAAGAAAAAG |
| | | | MAQELADKS | | | CCCGTAAAGA |
| | | | KGKKIGNVN | | | AGCGGAAGCA |
| | | | EALAAFEKY | | | GCAGAAAAGG |
| | | | KDVLNKKFS | | | CTTTTCAGGA |
| | | | KADRDAIFN | | | AGCAGAACAA |
| | | | ALASVKYDD | | | CGACGTAAAG |
| | | | WAKHLDQF | | | AGATTGAACG |
| | | | AKYLKITGH | | | GGAGAAGGCT |
| | | | VSFGYDVVS | | | GAAACAGAAC |
| | | | DILKIKDTGD | | | GCCAGTTGAA |
| | | | WKPLFLTLE | | | ACTGGCTGAA |
| | | | KKAADAGVS | | | GCTGAAGAGA |
| | | | YVVALLFSL | | | AACGACTGGC |
| | | | LAGTTLGIW | | | TGCATTGAGT |
| | | | GIAIVTGILC | | | GAAGAAGCTA |
| | | | SYIDKNKLN | | | AAGCTGTTGA |
| | | | TINEVLGI | | | GATCGCCCAA |
| | | | | | | AAAAAACTTT |
| | | | | | | CTGCTGCACA |
| | | | | | | ATCTGAAGTG |
| | | | | | | GTGAAAATGG |
| | | | | | | ATGGAGAGAT |
| | | | | | | TAAGACTCTC |
| | | | | | | AATTCTCGTTT |
| | | | | | | AAGCTCCAGT |
| | | | | | | ATCCATGCCC |
| | | | | | | GTGATGCAGA |
| | | | | | | AATGAAAACG |
| | | | | | | CTCGCTGGAA |
| | | | | | | AACGAAATGA |
| | | | | | | ACTGGCTCAG |
| | | | | | | GCATCCGCTA |
| | | | | | | AATATAAAGA |
| | | | | | | ACTGGATGAG |
| | | | | | | CTGGTCAAAA |
| | | | | | | AACTATCACC |
| | | | | | | AAGAGCCAAT |
| | | | | | | GATCCGCTTC |
| | | | | | | AGAACCGTCC |
| | | | | | | TTTTTTTGAAG |
| | | | | | | CAACCAGACG |
| | | | | | | ACGGGTTGGG |
| | | | | | | GCCGGTAAGA |
| | | | | | | TTAGAGAAGA |
| | | | | | | AAAACAAAAA |
| | | | | | | CAGGTAACAG |
| | | | | | | CATCAGAAAC |
| | | | | | | ACGTATTAAC |
| | | | | | | CGGATAAATG |
| | | | | | | CTGATATAAC |
| | | | | | | TCAGATCCAG |
| | | | | | | AAGGCTATTT |
| | | | | | | CTCAGGTCAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TAATAATCGT AATGCCGGTA TCGCTCGTGTT CATGAAGCTG AAGAAAATTT GAAAAAAGCA CAGAATAATC TCCTTAATTCA CAGATTAAGG ATGCTGTTGA TGCAACAGTT AGCTTTTATCA AACGCTGACT GAAAAATATG GTGAAAAATA TTCGAAAATG GCACAGGAAC TTGCTGATAA GTCTAAAGGT AAGAAAATCG GCAATGTGAA TGAAGCTCTC GCTGCTTTTGA AAAATACAAG GATGTTTTAA ATAAGAAATT CAGCAAAGCC GATCGTGATG CTATTTTTAAT GCGTTGGCAT CGGTGAAGTA TGATGACTGG GCTAAACATT TAGATCAGTT TGCCAAGTAC TTGAAGATTA CGGGGCATGT TTCTTTTGGAT ATGATGTGGT ATCTGATATCC TAAAAATTAA GGATACAGGT GACTGGAAGC CACTATTTCTT ACATTAGAGA AGAAAGCTGC AGATGCAGGG GTGAGTTATG TTGTTGCTTTA CTTTTTAGCTT GCTTGCTGGA ACTACATTAG GTATTTGGGG TATTGCTATTG TTACAGGAAT TCTATGCTCCT ATATTGATAA GAATAAACTT AATACTATAA ATGAGGTGTT AGGGATTTAA |
| 56 | Colicin-Ia | Unclassified | MSDPVRITN PGAESLGYD SDGHEIMAV DIYVNPPRV DVFHGTPPA WSSFGNKTI WGGNEWVD DSPTRSDIEK RDKEITAYK NTLSAQQKE | Escherichia coli | 57 | ATGTCTGACC CTGTACGTATT ACAAATCCCG GTGCAGAATC GCTGGGGTAT GATTCAGATG GCCATGAAAT TATGGCCGTT GATATTTATGT AAACCCTCCA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | NENKRTEAG | | | CGTGTCGATG |
| | | | KRLSAAIAA | | | TCTTTCATGGT |
| | | | REKDENTLK | | | ACCCCGCCTG |
| | | | TLRAGNADA | | | CATGGAGTTC |
| | | | ADITRQEFRL | | | CTTCGGGAAC |
| | | | LQAELREYG | | | AAAACCATCT |
| | | | FRTEIAGYD | | | GGGGCGGAAA |
| | | | ALRLHTESR | | | CGAGTGGGTT |
| | | | MLFADADSL | | | GATGATTCCC |
| | | | RISPREARSL | | | CAACCCGAAG |
| | | | IEQAEKRQK | | | TGATATCGAA |
| | | | DAQNADKK | | | AAAAGGGACA |
| | | | AADMLAEY | | | AGGAAATCAC |
| | | | ERRKGILDT | | | AGCGTACAAA |
| | | | RLSELEKNG | | | AACACGCTCA |
| | | | GAALAVLDA | | | GCGCGCAGCA |
| | | | QQARLLGQQ | | | GAAAGAGAAT |
| | | | TRNDRAISE | | | GAGAATAAGC |
| | | | ARNKLSSVT | | | GTACTGAAGC |
| | | | ESLNTARNA | | | CGGAAAACGC |
| | | | LTRAEQQLT | | | CTCTCTGCGG |
| | | | QQKNTPDGK | | | CGATTGCTGC |
| | | | TIVSPEKFPG | | | AAGGGAAAAA |
| | | | RSSTNHSIVV | | | GATGAAAACA |
| | | | SGDPRFAGTI | | | CACTGAAAAC |
| | | | KITTSAVIDN | | | ACTCCGTGCC |
| | | | RANLNYLLS | | | GGAAACGCAG |
| | | | HSGLDYKRN | | | ATGCCGCTGA |
| | | | ILNDRNPVV | | | TATTACACGA |
| | | | TEDVEGDKK | | | CAGGAGTTCA |
| | | | IYNAEVAEW | | | GACTCCTGCA |
| | | | DKLRQRLLD | | | GGCAGAGCTG |
| | | | ARNKITSAES | | | AGAGAATACG |
| | | | AVNSARNNL | | | GATTCCGTAC |
| | | | SARTNEQKH | | | TGAAATCGCC |
| | | | ANDALNALL | | | GGATATGACG |
| | | | KEKENIRNQ | | | CCCTCCGGCT |
| | | | LSGINQKIAE | | | GCATACAGAG |
| | | | EKRKQDELK | | | AGCCGGATGC |
| | | | ATKDAINFT | | | TGTTTGCTGAT |
| | | | TEFLKSVSE | | | GCTGATTCTCT |
| | | | KYGAKAEQL | | | TCGTATATCTC |
| | | | AREMAGQA | | | CCCGGGAGGC |
| | | | KGKKIRNVE | | | CAGGTCGTTA |
| | | | EALKTYEKY | | | ATCGAACAGG |
| | | | RADINKKIN | | | CTGAAAAACG |
| | | | AKDRAAIAA | | | GCAGAAGGAT |
| | | | ALESVKLSDI | | | GCGCAGAACG |
| | | | SSNLRFSR | | | CAGACAAGAA |
| | | | GLGYAGKFT | | | GGCCGCTGAT |
| | | | SLADWITEF | | | ATGCTTGCTG |
| | | | GKAVRTEN | | | AATACGAGCG |
| | | | WRPLFVKTE | | | CAGAAAAGGT |
| | | | TIIAGNAATA | | | ATTCTGGACA |
| | | | LVALVFSILT | | | CCCGGTTGTC |
| | | | GSALGIIGYG | | | AGAGCTGGAA |
| | | | LLMAVTGAL | | | AAAAATGGCG |
| | | | IDESLVEKA | | | GGGCAGCCCT |
| | | | NKFWGI | | | TGCCGTTCTTG |
| | | | | | | ATGCACAACA |
| | | | | | | GGCCCGTCTG |
| | | | | | | CTCGGGCAGC |
| | | | | | | AGACACGGAA |
| | | | | | | TGACAGGGCC |
| | | | | | | ATTTCAGAGG |
| | | | | | | CCCGGAATAA |
| | | | | | | ACTCAGTTCA |
| | | | | | | GTGACGGAAT |
| | | | | | | CGCTTAACAC |
| | | | | | | GGCCCGTAAT |
| | | | | | | GCATTAACCA |
| | | | | | | GAGCTGAACA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ACAGCTGACG CAACAGAAAA ACACGCCTGA CGGCAAAACG ATAGTTTCCCC TGAAAAATTC CCGGGGCGTT CATCAACAAA TGATTCTATTG TTGTGAGCGG TGATCCGAGA TTTGCCGGTA CGATAAAAAT CACAACCAGC GCAGTCATCG ATAACCGTGC AAACCTGAAT TATCTTCTGAG CCATTCCGGT CTGGACTATA AACGCAATAT TCTGAATGAC CGGAATCCGG TGGTGACAGA GGATGTGGAA GGTGACAAGA AAATTTATAA TGCTGAAGTT GCTGAATGGG ATAAGTTACG GCAAAGATTG CTTGATGCCA GAAATAAAAT CACCTCTGCT GAATCTGCGG TAAATTCGGC GAGAAATAAC CTCAGTGCCA GAACAAATGA GCAAAAGCAT GCAAATGACG CTCTTAATGCC CTGTTGAAGG AAAAAGAGAA TATCCGTAAC CAGCTTTCCG GCATCAATCA GAAGATAGCG GAAGAGAAAA GAAAACAGGA TGAACTGAAG GCAACGAAAG ACGCAATTAA TTTCACAACA GAGTTCCTGA AATCAGTTTC AGAAAAATAT GGTGCAAAAG CTGAGCAGTT AGCCAGAGAG ATGGCCGGGC AGGCTAAAGG GAAGAAAATA CGTAATGTTG AAGAGGCATT AAAAACGTAT GAAAAGTACC GGGCTGACAT TAACAAAAAA ATTAATGCAA AAGATCGTGC AGCGATTGCC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCAGCCCTTG AGTCTGTGAA GCTGTCTGAT ATATCGTCTA ATCTGAACAG ATTCAGTCGG GGACTGGGAT ATGCAGGAAA ATTTACAAGT CTTGCTGACT GGATCACTGA GTTTGGTAAG GCTGTCCGGA CAGAGAACTG GCGTCCTCTTT TTGTTAAAAC AGAAACCATC ATAGCAGGCA ATGCCGCAAC GGCTCTTGTG GCACTGGTCT TCAGTATTCTT ACCGGAAGCG CTTTAGGCATT ATCGGGTATG GTTTACTGAT GGCTGTCACC GGTGCGCTGA TTGATGAATC GCTTGTGGAA AAAGCGAATA AGTTCTGGGG TATTTAA |
| 58 | Colicin-Ib | Unclassified | MSDPVRITN PGAESLGYD SDGHEIMAV DIYVNPPRV DVFHGTPPA WSSFGNKTI WGGNEWVD DSPTRSDIEK RDKEITAYK NTLSAQQKE NENKRTEAG KRLSAAIAA REKDENTLK TLRAGNADA ADITRQEFRL LQAELREYG FRTEIAGYD ALRLHTESR MLFADADSL RISPREARSL IEQAEKRQK DAQNADKK AADMLAEY ERRKGILDT RLSELEKNG GAALAVLDA QQARLLGQQ TRNDRAISE ARNKLSSVT ESLKTARNA LTRAEQQLT QQKNTPDGK TIVSPEKFPG RSSTNHSIVV SGDPRFAGTI KITTSAVIDN RANLNYLLT HSGLDYKRN | Escherichia coli | 59 | ATGTCTGACC CTGTACGTATT ACAAATCCCG GTGCAGAATC GCTGGGATAT GATTCAGATG GCCATGAAAT TATGGCCGTT GATATTTATGT AAACCCTCCA CGTGTCGATG TCTTTCATGGT ACCCCGCCTG CATGGAGTTC CTTCGGGAAC AAAACCATCT GGGGTGGAAA CGAGTGGGTC GATGATTCCC CAACCCGAAG TGATATCGAA AAAAGGGACA AGGAAATCAC AGCGTACAAA AACACGCTCA GCGCGCAGCA GAAAGAGAAT GAGAATAAGC GTACTGAAGC TGGAAAACGC CTTTCTGCGGC AATTGCTGCA AGGGAAAAAG ATGAAAACAC ACTGAAAACA CTCCGTGCCG GAAACGCAGA TGCCGCTGAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | ILNDRNPVV | | | ATTACACGAC |
| | | | TEDVEGDKK | | | AGGAGTTCAG |
| | | | IYNAEVAEW | | | ACTCCTGCAG |
| | | | DKLRQRLLD | | | GCAGAGCTGA |
| | | | ARNKITSAES | | | GAGAATACGG |
| | | | AINSARNNV | | | ATTCCGTACT |
| | | | SARTNEQKH | | | GAAATCGCCG |
| | | | ANDALNALL | | | GATATGATGC |
| | | | KEKENIRSQ | | | CCTCCGGCTG |
| | | | LADINQKIAE | | | CATACAGAGA |
| | | | EKRKRDEIN | | | GCCGGATGCT |
| | | | MVKDAIKLT | | | GTTTGCTGAT |
| | | | SDFYRTIYDE | | | GCTGATTCTCT |
| | | | FGKQASELA | | | TCGTATATCTC |
| | | | KELASVSQG | | | CCCGCGAGGC |
| | | | KQIKSVDDA | | | CAGGTCGTTA |
| | | | LNAFDKFRN | | | ATCGAACAGG |
| | | | NLNKKYNIQ | | | CTGAAAAACG |
| | | | DRMAISKAL | | | GCAGAAGGAT |
| | | | EAINQVHMA | | | GCGCAGAACG |
| | | | ENFKLFSKAF | | | CAGACAAGAA |
| | | | GFTGKVIER | | | GGCCGCTGAT |
| | | | YDVAVELQK | | | ATGCTTGCTG |
| | | | AVKTDNWR | | | AATACGAGCG |
| | | | PFFVKLESLA | | | CAGAAAAGGT |
| | | | AGRAASAVT | | | ATTCTGGACA |
| | | | AWAFSVML | | | CGCGGTTGTC |
| | | | GTPVGILGF | | | AGAGCTGGAA |
| | | | AIIMAAVSA | | | AAAAATGGCG |
| | | | LVNDKFIEQ | | | GGGCAGCCCT |
| | | | VNKLIGI | | | TGCCGTTCTTG |
| | | | | | | ATGCACAACA |
| | | | | | | GGCCCGTCTG |
| | | | | | | CTCGGGCAGC |
| | | | | | | AGACACGGAA |
| | | | | | | TGACAGGGCC |
| | | | | | | ATTTCAGAGG |
| | | | | | | CCCGGAATAA |
| | | | | | | ACTCAGTTCG |
| | | | | | | GTGACGGAAT |
| | | | | | | CGCTTAAGAC |
| | | | | | | GGCCCGTAAT |
| | | | | | | GCATTAACCA |
| | | | | | | GAGCTGAACA |
| | | | | | | ACAGCTGACG |
| | | | | | | CAACAGAAAA |
| | | | | | | ACACGCCTGA |
| | | | | | | CGGCAAAACG |
| | | | | | | ATAGTTTCCCC |
| | | | | | | TGAAAAATTC |
| | | | | | | CCGGGGCGTT |
| | | | | | | CATCAACAAA |
| | | | | | | TCATTCTATTG |
| | | | | | | TTGTGAGTGG |
| | | | | | | TGATCCGAGG |
| | | | | | | TTTGCCGGTA |
| | | | | | | CGATAAAAAT |
| | | | | | | CACAACCAGC |
| | | | | | | GCGGTCATCG |
| | | | | | | ATAACCGTGC |
| | | | | | | AAACCTGAAT |
| | | | | | | TATCTTCTGAC |
| | | | | | | CCATTCCGGT |
| | | | | | | CTGGACTATA |
| | | | | | | AACGCAATAT |
| | | | | | | TCTGAATGAC |
| | | | | | | CGGAATCCGG |
| | | | | | | TGGTGACAGA |
| | | | | | | GGATGTGGAA |
| | | | | | | GGTGACAAGA |
| | | | | | | AAATTTATAA |
| | | | | | | TGCTGAAGTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCTGAATGGG ATAAGTTACG GCAACGATTG CTTGATGCCA GAAATAAAAT CACCTCTGCT GAATCTGCGA TAAATTCGGC GAGAAATAAC GTCAGTGCCA GAACAAATGA ACAAAAGCAT GCAAATGACG CTCTTAATGCC CTGTTGAAGG AAAAAGAGAA TATCCGTAGC CAGCTTGCTG ACATCAATCA GAAAATAGCT GAAGAGAAAA GAAAAAGGGA TGAAATAAAT ATGGTAAAGG ATGCCATAAA ACTCACCTCTG ATTTCTACAG AACGATATAT GATGAGTTCG GTAAACAAGC ATCCGAACTT GCTAAGGAGC TGGCTTCTGTA TCTCAAGGGA AACAGATTAA GAGTGTGGAT GATGCACTGA ACGCTTTTGAT AAATTCCGTA ATAATCTGAA CAAGAAATAT AACATACAAG ATCGCATGGC CATTTCTAAA GCCCTGGAAG CTATTAATCA GGTCCATATG GCGGAGAATT TTAAGCTGTTC AGTAAGGCAT TTGGTTTTACC GGAAAAGTTA TTGAACGTTA TGATGTTGCT GTGGAGTTAC AAAAGGCTGT AAAAACGGAC AACTGGCGTC CATTTTTTGTA AAACTTGAAT CACTGGCAGC AGGAAGAGCT GCTTCAGCAG TTACAGCATG GGCGTTTTCC GTCATGCTGG GAACCCCTGT AGGTATTCTG GGTTTTGCAA TTATTATGGC GGCTGTGAGT GCGCTTGTTA |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | | | | ATGATAAGTT TATTGAGCAG GTCAATAAAC TTATTGGTATC TGA |
| 60 | Colicin-M | Unclassified | METLTVHAP SPSTNLPSYG NGAFSLSAP HVPGAGPLL VQVVYSFFQ SPNMCLQAL TQLEDYIKK HGASNPLTL QIISTNIGYF CNADRNLVL HPGISVYDA YHFAKPAPS QYDYRSMN MKQMSGNV TTPIVALAH YLWGNGAE RSVNIANIGL KISPMKINQI KDIIKSGVV GTFPVSTKFT HATGDYNVI TGAYLGNIT LKTEGTLTIS ANGSWTYN GVVRSYDD KYDFNASTH RGIIGESLTR LGAMFSGKE YQILLPGEIH IKESGKR | Escherichia coli | 61 | ATGGAAACCT TAACTGTTCAT GCACCATCAC CATCAACTAA CTTACCAAGTT ATGGCAATGG TGCATTTTCTC TTTCAGCACC ACATGTGCCT GGTGCTGGCC CTCTTTTAGTC CAGGTTGTTT ATAGTTTTTC CAGAGTCCAA ACATGTGTCTT CAGGCTTTAA CTCAACTTGA GGATTACATC AAAAAACATG GGCCAGCAA CCCTCTCACAT TGCAGATCAT ATCGACAAAT ATTGGTTACTT CTGTAACGCC GACCGAAATC TGGTTCTTCAC CCTGGAATAA GCGTTTATGA CGCTTACCACT TCGCAAAACC AGCGCCAAGT CAATATGACT ATCGCTCAAT GAATATGAAA CAAATGAGCG GTAATGTCAC TACACCAATT GTGGCGCTTG CTCACTATTTA TGGGGTAATG GCGCTGAAAG GAGCGTTAAT ATCGCCAACA TTGGTCTTAA AATTTCCCCTA TGAAAATTAA TCAGATAAAA GACATTATAA AATCTGGTGT AGTAGGCACA TTCCCTGTTTC TACAAAGTTC ACACATGCCA CTGGTGATTA TAATGTTATTA CCGGTGCATA TCTTGGTAAT ATCACACTGA AAACAGAAGG TACTTTAACTA TCTCTGCCAAT GGCTCCTGGA CTTACAATGG CGTTGTTCGTT CATATGATGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TAAATACGAT TTTAACGCCA GCACTCACCG TGGCATTATC GGAGAGTCGC TCACAAGGCT CGGGGCGATG TTTTCTGGTAA AGAGTACCAG ATACTGCTTCC TGGTGAAATT CACATTAAAG AAAGTGGTAA GCGATAA |
| 62 | Colicin-N | Unclassified | MGSNGADN AHNNAFGG GKNPGIGNT SGAGSNGSA SSNRGNSNG WSWSNKPH KNDGFHSDG SYHITFHGD NNSKPKPGG NSGNRGNN GDGASAKV GEITITPDNS KPGRYISSNP EYSLLAKLID AESIKGTEV YTFHTRKGQ YVKVTVPDS NIDKMRVDY VNWKGPKY NNKLVKRFV SQFLLFRKEE KEKNEKEAL LKASELVSG MGDKLGEY LGVKYKNV AKEVANDIK NFHGRNIRS YNEAMASLN KVLANPKM KVNKSDKD AIVNAWKQ VNAKDMAN KIGNLGKAF KVADLAIKV EKIREKSIEG YNTGNWGP LLLEVESWII GGVVAGVAI SLFGAVLSFL PISGLAVTAL GVIGIMTISY LSSFIDANRV SNINNIISSVIR | Escherichia coli | 63 | GCAAATCGAG TTTCGAATATA AATAACATTA TATCTAGTGTT ATTCGATGA |
| 64 | Colicin-V (Microcin-V) | Unclassified | MRTLTLNEL DSVSGGASG RDIAMAIGT LSGQFVAGG IGAAAGGVA GGAIYDYAS THKPNPAMS PSGLGGTIK QKPEGIPSEA WNYAAGRL CNWSPNNLS DVCL | Escherichia coli | 65 | ATGAGAACTC TGACTCTAAA TGAATTAGAT TCTGTTTCTGG TGGTGCTTCA GGGCGTGATA TTGCGATGGC TATAGGAACA CTATCCGGAC AATTTGTTGC AGGAGGAATT GGAGCAGCTG CTGGGGGTGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGCTGGAGGT GCAATATATG ACTATGCATC CACTCACAAA CCTAATCCTGC AATGTCTCCAT CCGGTTTAGG AGGAACAATT AAGCAAAAAC CCGAAGGGAT ACCTTCAGAA GCATGGAACT ATGCTGCGGG AAGATTGTGT AATTGGAGTC CAAATAATCT TAGTGATGTTT GTTTATAA |
| 66 | Columbicin A | Lantibiotic | MMNATENQI FVETVSDQE LEMLIGGAG RGWIKTLTK DCPNVISSIC AGTIITACKN CA | Enterococcus columbae | 67 | ATGATGAATG CTACTGAAAA CCAAATTTTTG TTGAGACTGT GAGTGACCAA GAATTAGAAA TGTTAATTGG GGTGCAGGTC GTGGATGGAT TAAGACTTTA ACAAAAGATT GTCCAAATGT GATTTCTTCAA TTTGTGCAGG TACAATTATTA CAGCTTGTAA AAATTGTGCT TAA |
| 68 | Curvacin-A | class IIA/YG NGV | MNNVKELS MTELQTITG GARSYGNG VYCNNKKC WVNRGEAT QSIIGGMISG WASGLAGM | Lactobacillus curvatus | 69 | ATGAATAATG TAAAAGAATT AAGTATGACA GAATTACAAA CAATTACCGG CGGTGCTAGA TCATATGGCA ACGGTGTTTA CTGTAATAAT AAAAAATGTT GGGTAAATCG GGGTGAAGCA ACGCAAAGTA TTATTGGTGG TATGATTAGC GGCTGGGCTA GTGGTTTAGC TGGAATGTAA |
| 70 | Cypemycin | Unclassified | MRSEMTLTS TNSAEALAA QDFANTVLS AAAPGFHAD CETPAMATP ATPTVAQFV IQGSTICLVC | Streptomyces sp. | 71 | GTGCGATCTG AGATGACTCT TACGAGCACG AATTCCGCTG AGGCTCTGGC GGCGCAGGAC TTTGCGAACA CCGTTCTCAG CGCGGCGGCC CCGGGCTTCC ACGCGGACTG CGAGACGCCG GCCATGGCCA CCCCGGCCAC GCCGACCGTC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCCCAGTTCG TGATCCAGGG CAGCACGATC TGCCTGGTCT GCTGA |
| 72 | Cytolysin | Lantibiotic | MVNSKDLR NPEFRKAQG LQFVDEVNE KELSSLAGS GDVHAQTT WPCATVGVS VALCPTTKC TSQC | Bacillus halodurans (strain ATCC BAA-125/ DSM 18197/ FERM 7344/ JCM 9153/ C-125) | 73 | ATGGTAAATT CAAAAGATTT GCGTAATCCT GAATTCCGCA AAGCCCAAGG TCTACAATTCG TTGACGAGGT GAACGAGAAG GAACTTTCGT CTCTAGCTGG TTCAGGAGAT GTGCATGCAC AAACAACTTG GCCTTGCGCT ACAGTTGGTG TCTCCGTAGC CTTGTGCCCA ACTACAAAGT GTACAAGCCA GTGCTAA |
| 74 | Divercin V41 | class IIa/YGN GV | MKNLKEGSY TAVNTDELK SINGGTKYY GNGVYCNS KKCWVDWG QASGCIGQT VVGGWLGG AIPGKC | Carnobacterium divergens (Lactobacillus divergens) | 75 | ATGAAAAACT TAAAAGAAGG TTCATACACTG CTGTTAATACT GATGAATTAA AAAGTATCAA TGGTGGAACA AAATATTATG GGAATGGCGT TTATTGCAATT CTAAAAAATG TTGGGTAGAT TGGGGACAAG CTTCAGGTTGT ATCGGTCAAA CTGTTGTTGG CGGATGGCTA GGCGGAGCTA TACCAGGTAA ATGCTAA |
| 76 | Divergicin 750 | Unclassified | MIKREKNRT ISSLGYEEIS NHKLQEIQG GKGILGKLG VVQAGVDF VSGVWAGIK QSAKDHPNA | Carnobacterium divergens (Lactobacillus divergens) | 77 | ATGATTAAAA GAGAAAAGAA CAGAACAATT TCTTCCCTTGG TTATGAAGAA ATTTCTAATCA TAAATTGCAA GAAATACAAG GTGGAAAAGG AATTCTTGGT AAACTAGGAG TAGTACAGGC AGGAGTGGAT TTTGTATCAG GAGTGTGGGC TGGAATAAAA CAGTCTGCCA AAGATCATCC TAATGCGTAA |
| 78 | Divergicin A | Class IIc | MKKQILKGL VIVVCLSGA TFFSTPQQAS AAAPKITQK | Carnobacterium divergens (Lactobacillus divergens) | 79 | ATGAAAAAAC AAATTTTAAA AGGGTTGGTT ATAGTTGTTTG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | QKNCVNGQ LGGMLAGA LGGPGGVVL GGIGGAIAG GCFN | | | TTTATCTGGG GCAACATTTT CTCAACACCA CAACAAGCTT CTGCTGCTGC ACCGAAAATT ACTCAAAAAC AAAAAAATTG TGTTAATGGA CAATTAGGTG GAATGCTTGC TGGAGCTTTG GGTGGACCTG GCGGAGTTGT GTTAGGTGGT ATAGGTGGTG CAATAGCAGG AGGTTGTTTTA ATTAA |
| 80 | Durancin Q | Unclassified | MQTIKELNT MELQEIIGGE NDHRMPYEL NRPNNLSKG GAKCAAGIL GAGLGAVG GGPGGFISA GISAVLGCM | Enterococcus durans | 81 | ATGCAAACGA TCAAAGAATT GAACACGATG GAATTACAAG AAATAATTGG AGGTGAAAAT GACCATCGGA TGCCTTACGA ATTGAACCGT CCAAATAATT TATCCAAAGG TGGGGCTAAG TGTGCTGCTG GAATACTTGG CGCTGGACTA GGCGCAGTAG GCGGTGGACC TGGCGGATTT ATTAGTGCCG GAATCAGTGC TGTTCTTGGTT GTATGTAA |
| 82 | Durancin TW-49M | Unclassified | MQTIKELNT MELQKIIGG ENDHRMPYE LNRPNNLSK GGAKCAAGI LGAGLGAVG GGPGGFISA GISAVLGCM | Enterococcus durans | 83 | ATGCAAACGA TCAAAGAATT GAACACGATG GAATTACAAA AAATAATTGG AGGTGAAAAT GACCATCGGA TGCCTTACGA ATTGAACCGT CCAAATAATT TATCCAAAGG TGGAGCTAAG TGCGCTGCCG GAATACTTGG TGCTGGATTA GGCGCAGTAG GCGGTGGACC TGGCGGATTT ATTAGTGCCG GAATCAGTGC TGTTCTTGGTT GTATGTAA |
| 84 | Dysgalacticin | Unclassified | MKKLKRLVI SLVTSLLVIS STVPALVYA NETNNFAET QKEITTNSEA TLTNEDYTK | Streptococcus dysgalactiae subsp. equisimilis (Streptococcus equisimilis) | 85 | ATGAAAAAAT TAAAACGTCT TGTTATCTCTC TTGTTACTTCA TTACTAGTAAT TTCAAGTACA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | LTSEVKTIYT NLIQYDQTK NKFYVDEDK TEQYYNYD DESIKGVYL MKDSLNDEL NNNNSSNYS EIINQKISEID YVLQGNDIN NLIPSNTRVK RSADFSWIQ RCLEEAWGY AISLVTLKGI INLFKAGKFE AAAAKLASA TAGRIAGMA ALFAFVATC GATTVS | | | GTTCCAGCAC TTGTTTACGCT AATGAAACAA ATAACTTTGC AGAAACTCAA AAAGAAATTA CAACAAATTC AGAAGCAACA TTAACCAATG AAGACTACAC TAAATTAACTT CCGAAGTAAA AACAATTTAT ACAAATCTGA TTCAATACGA CCAAACAAAA AACAAATTTT ACGTCGATGA AGACAAAACT GAACAATATT ATAACTACGA TGATGAAAGT ATAAAAGGGG TTTATCTCATG AAAGATAGTT TGAACGATGA GTTAAACAAT AATAACTCTTC AAACTATTCT GAAATAATTA ATCAAAAAAT CTCTGAAATT GACTATGTCC TTCAAGGAAA CGATATAAAT AATTTAATTCC TAGCAATACC AGAGTAAAAA GATCAGCAGA TTTTTCTTGGA TTCAAAGATG TCTAGAAGAA GCATGGGGAT ATGCTATTAG TCTAGTTACTC TAAAAGGAAT AATCAATCTA TTTAAAGCAG GAAAATTTGA AGCTGCTGCT GCTAAATTAG CTTCTGCTACA GCAGGTAGAA TCGCTGGAAT GGCTGCCTTA TTTGCTTTCGT AGCAACTTGC GGTGCGACAA CTGTATCATAA |
| 86 | Enterocin 1071A | Unclassified | MKQYKVLN EKEMKKPIG GESVFSKIGN AVGPAAYWI LKGLGNMSD VNQADRINR KKH | Enterococcus faecalis (Streptococcus faecalis) | 87 | ATGAAGCAAT ATAAAGTATT GAATGAAAAA GAAATGAAAA AACCTATTGG GGGAGAGTCG GTTTTTAGTAA AATAGGTAAT GCTGTAGGTC CAGCTGCTTA TTGGATTTTAA AAGGATTAGG |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | | | | TAATATGAGT GATGTAAACC AAGCTGATAG AATTAATAGA AAGAAACATT AA |
| 88 | Enterocin 7A (Enterocin L50A) | bacteriocins without sequence leader | MGAIAKLVA KFGWPIVKK YYKQIMQFI GEGWAINKII DWIKKHI | Enterococcus faecalis (Streptococcus faecalis) | 89 | ATGGGAGCAA TCGCAAAATT AGTAGCAAAG TTTGGATGGC CAATTGTTAA AAAGTATTAC AAACAAATTA TGCATTTATT GGAGAAGGAT GGGCAATTAA CAAAATTATT GATTGGATCA AAAAACATAT TTAA |
| 90 | Enterocin 7B | Unclassified | MGAIAKLVA KFGWPFIKK FYKQIMQFIG QGWTIDQIE KWLKRH | Enterococcus faecalis (Streptococcus faecalis) | 91 | ATGGGAGCAA TCGCAAAATT AGTAGCAAAG TTTGGATGGC CATTTATTAAA AAATTCTACA AACAAATTAT GCAGTTTATC GGACAAGGAT GGACAATAGA TCAAATTGAA AAATGGTTAA AAAGACATTGA |
| 92 | Enterocin 96 | Class II | MLNKKLLEN GVVNAVTID ELDAQFGGM SKRDCNLMK ACCAGQAVT YAIHSLLNRL GGDSSDPAG CNDIVRKYCK | Enterococcus faecalis (strain ATCC 700802/ V583) | 93 | ATGTTAAATA AAAAATTATT AGAAAATGGT GTAGTAAATG CTGTAACAAT TGATGAACTT GATGCTCAAT TTGGTGGAAT GAGCAAACGT GATTGTAACT TGATGAAGGC GTGTTGTGCT GGACAAGCAG TAACATATGC TATTCATAGTC TTTTAAATCGA TTAGGTGGAG ACTCTAGTGA TCCAGCTGGT TGTAATGATA TTGTAAGAAA ATATTGTAAA TAA |
| 94 | Enterocin A | Class IIa, IIc (problematic) | MKHLKILSIK ETQLIYGGT THSGKYYGN GVYCTKNKC TVDWAKAT TCIAGMSIG GFLGGAIPG KC | Enterococcus faecium (Streptococcus faecium) | 95 | ATGAAACATT TAAAAATTTT GTCTATTAAA GAGACACAAC TTATCTATGG GGGTACCACT CATAGTGGAA AATATTATGG AAATGGAGTG TATTGCACTA AAAATAAATG TACGGTCGAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGGGCCAAGG CAACTACTTGT ATTGCAGGAA TGTCTATAGG TGGTTTTTTAG GTGGAGCAAT TCCAGGGAAG TGC |
| 96 | Enterocin AS-48 (BACTERIOCINAS-48) | Unclassified | MVKENKFSK IFILMALSFL GLALFSASL QFLPIAHMA KEFGIPAAV AGTVLNVVE AGGWVTTIV SILTAVGSG GLSLLAAAG RESIKAYLK KEIKKKGKR AVIAW | Enterococcus faecalis (Streptococcus faecalis) | 97 | ATGGTTAAAG AAAATAAATT TTCTAAGATTT TTATTTTAATG GCTTTGAGTTT TTTGGGGTTA GCCTTGTTTAG TGCAAGTCTT CAGTTTTTGCC CATTGCACAT ATGGCTAAAG AGTTCGGTAT ACCAGCAGCA GTTGCAGGAA CTGTGCTTAAT GTAGTTGAAG CTGGTGGATG GGTCACTACT ATTGTATCAAT TCTTACTGCTG TAGGTAGCGG AGGTCTTTCTT TACTCGCTGC AGCAGGAAGA GAGTCAATTA AAGCATACCT TAAGAAAGAA ATTAAGAAAA AAGGAAAAAG AGCAGTTATT GCTTGGTAA |
| 98 | Enterocin B | class IIc, non subgrouped bacteriocins (problematic) | MQNVKELST KEMKQIIGG ENDHRMPNE LNRPNNLSK GGAKCGAAI AGGLFGIPK GPLAWAAGL ANVYSKCN | Enterococcus faecium (Streptococcus faecium) | 99 | ATGCAAAATG TAAAAGAATT AAGTACGAAA GAGATGAAAC AAATTATCGG TGGAGAAAAT GATCACAGAA TGCCTAATGA GTTAAATAGA CCTAACAACT TATCTAAAGG TGGAGCAAAA TGTGGTGCTG CAATTGCTGG GGGATTATTT GGAATCCCAA AAGGACCACT AGCATGGGCT GCTGGGTTAG CAAATGTATA CTCTAAATGC AACTAA |
| 100 | Enterocin CRL35 (Mundticin KS) | Class IIa | MKKLTSKE MAQVVGGK YYGNGVSC NKKGCSVD WGKAIGIIGN NSAANLATG GAAGWKS | Enterococcus mundtii | 101 | TTGAAGAAAT TAACATCAAA AGAAATGGCA CAAGTAGTAG GTGGAAAATA CTACGGTAAT GGAGTCTCAT GTAATAAAAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AGGGTGCAGT GTTGATTGGG GAAAAGCTAT TGGCATTATT GGAAATAATT CTGCTGCGAA TTTAGCTACTG GTGGAGCAGC TGGTTGGAAA AGTTAA |
| 102 | Enterocin EJ97 | Unclassified | MLAKIKAMI KKFPNPYTL AAKLTTYEI NWYKQQYG RYPWERPVA | Enterococcus faecalis (Streptococcus faecalis) | 103 | ATGTTAGCAA AAATTAAAGC GATGATTAAG AAGTTTCCGA ACCCTTATACT TTAGCAGCTA AGCTAACGAC TTACGAAATT AATTGGTATA AACAACAATA CGGTCGTTAT CCTTGGGAGC GCCCTGTAGC ATAA |
| 104 | Enterocin P | Class IIa, IIb and IIc (problematic) | MRKKLFSLA LIGIFGLVVT NFGTKVDAA TRSYGNGVY CNNSKCWV NWGEAKENI AGIVISGWA SGLAGMGH | Enterococcus faecium (Streptococcus faecium) | 105 | ATGAGAAAAA AATTATTTAGT TTAGCTCTTAT TGGAATATTT GGGTTAGTTG TGACAAATTTT GGTACAAAAG TTGATGCAGC TACGCGTTCA TATGGTAATG GTGTTTATTGT AATAATAGTA AATGCTGGGT TAACTGGGGA GAAGCTAAAG AGAATATTGC AGGAATCGTT ATTAGTGGCT GGGCTTCTGG TTTGGCAGGT ATGGGACATT AA |
| 106 | Enterocin Q | Class IIc | MNFLKNGIA KWMTGAEL QAYKKKYG CLPWEKISC | Enterococcus faecium (Streptococcus faecium) | 107 | ATGAATTTTCT TAAAAATGGT ATCGCAAAAT GGATGACCGG TGCTGAATTG CAAGCGTATA AAAAGAAATA TGGATGCTTG CCATGGGAAA AAATTTCTTGT TAA |
| 108 | Enterocin SE-K4 | Class IIa | MKKKLVKG LVICGMIGIG FTALGTNVE AATYYGNG VYCNKQKC WVDWSRAR SEIIDRGVKA YVNGFTKVL GGIGGR | Enterococcus faecalis (Streptococcus faecalis) | 109 | ATGAAAAAGA AATTAGTTAA AGGCTTAGTT ATTTGTGGCA TGATTGGGAT TGGTTTTACA GCATTAGGAA CAAATGTAGA AGCCGCCACG TATTACGGAA ATGGTGTCTA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TTGCAATAAG CAAAAATGTT GGGTAGATTG GAGTAGAGCA CGTTCTGAAA TTATAGACAG AGGCGTAAAA GCATACGTCA ATGGATTTAC GAAAGTGTTA GGTGGTATAG GTGGAAGATAA |
| 110 | Enterocin W alfa | Class IIb | MKKEELVG MAKEDPLNV ICENDNKLE NSGAKCPW WNLSCHLGN DGKICTYSH ECTAGCNA | Enterococcus faecalis (Streptococcus faecalis) | 111 | ATGAAAAAG AAGAATTAGT AGGAATGGCT AAGGAAGACT TTTTAAATGTT ATTTGTGAAA ATGACAACAA ACTAGAAAAT AGTGGAGCAA AATGTCCTTG GTGGAATCTT TCTTGTCATTT AGGCAATGAT GGTAAAATTT GCACTTATTCA CATGAATGTA CCGCAGGTTG TAATGCATAA |
| 112 | Enterocin W beta | Class IIb | MTELNKRLQ LKRDVSTEN SLKKISNTDE THGGVTTSIP CTVMVSAA VCPTLVCSN KCGGRG | Enterococcus faecalis (Streptococcus faecalis) | 113 | ATGACTGAAC TTAACAAAAG ATTACAATTA AAAAGAGATG TTTCAACAGA AAATAGTTTG AAAAAAATTT CTAATACTGA TGAAACACAT GGGGGAGTTA CTACATCAATT CCATGTACAG TAATGGTTAG TGCGGCAGTA TGTCCTACCCT TGTTTGCTCGA ATAAATGTGG CGGTAGAGGC TAG |
| 114 | Enterocin Xalpha | Class IIb | MQNVKEVS VKEMKQIIG GSNDSLWY GVGQFMGK QANCITNHP VKHMIIPGY CLSKILG | Enterococcus faecium (Streptococcus faecium) | 115 | ATGCAAAATG TAAAAGAAGT TTCTGTAAAA GAGATGAAAC AAATTATCGG TGGTTCTAAT GATAGTCTTT GGTATGGTGT AGGACAATTT ATGGGTAAAC AAGCAAACTG TATAACAAAC CATCCTGTTAA ACACATGATA ATTCCTGGAT ATTGTTTATCG AAAATTTTAG GGTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 116 | Enterocin Xbeta | Class IIb | MKKYNELSKKELLQIQGGIAPIIVAGLGYLVKDAWDHSDQIISGFKKGWNGGRRK | *Enterococcus faecium* (*Streptococcus faecium*) | 117 | ATGAAAAAATATAATGAGTTATCTAAAAAAGAACTTCTACAGATTCAAGGAGGAATAGCACCTATTATAGTTGCTGGCCTTGGCTATTTAGTAAAAGATGCATGGGATCACTCAGATCAAATAATCTCAGGATTTAAAAAAGGTTGGAATGGTGGACGTAGAAAATAA |
| 118 | Enterolysin A | class III | MKNILLSILGVLSIVVSLAFSSYSVNAASNEWSWPLGKPYAGRYEEGQQFGNTAFNRGGTYFHDGFDFGSAIYGNGSVYAVHDGKILYAGWDPVGGSLGAFIVLQAGNTNVIYQEFSRNVGDIKVSTGQTVKKGQLIGKFTSSHLHLGMTKKEWRSAHSSWNKDDGTWFNPIPILQGGSTPTPPNPGPKNFTTNVRYGLRVLGGSWLPEVTNFNNTNDGFAGYPNRQHDMLYIKVDKGQMKYRVHTAQSGWLPWVSKGDKSDTVNGAAGMPGQAIDGVQLNYITPKGEKLSQAYYRSQTTKRSGWLKVSADNGSIPGLDSYAGIFGEPLDRLQIGISQSNPF | *Enterococcus faecalis* (*Streptococcus faecalis*) | 119 | ATGAAAAATATTTTACTTTCTATTCTAGGGGTATTATCTATCGTTGTTTCTTTGGCGTTTTCTTCTTATTCTGTCAACGCAGCTTCTAATGAGTGGTCGTGGCCACTGGGCAAACCATATGCGGGAAGATATGAAGAAGGACAACAATTCGGAAACACTGCATTTAACCGAGGAGGTACTTATTTCCATGATGGGTTTGACTTTGGTTCTGCTATTTATGGAAATGGCAGTGTGTATGCTGTGCATGATGGTAAAATTTTATATGCTGGTTGGGATCCTGTAGGTGGAGGCTCATTAGGTGCATTTATTGTACTACAAGCGGGAAACACAAATGTGATTTATCAAGAATTTAGCCGAAATGTTGGAGATATTAAAGTTAGCACTGGACAAACTGTTAAAAAAGGACAGCTGATAGGAAAGTTTACTTCTAGTCATTTACATTTAGGAATGACAAAAAAAGAATGGCGTTCTGCTCATTCTTCTTGGAATAAAGATGATGGCACTTGGTTTAACCCAATTCCTATACTTCAAGGAGGATCTACGCC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TACGCCTCCA AATCCAGGAC CAAAAAATTT CACAACAAAT GTTCGTTACG GATTGCGGGT CCTCGGAGGT TCATGGTTAC CAGAAGTAAC CAACTTTAAC AATACCAATG ATGGTTTCGC AGGTTACCCT AATCGTCAAC ATGATATGCT TTATATAAAG GTAGATAAAG GGCAAATGAA ATATCGTGTTC ACACGGCTCA AAGTGGATGG TTGCCTTGGG TAAGTAAAGG GGATAAGAGC GATACAGTAA ATGGAGCGGC AGGTATGCCT GGACAAGCAA TTGATGGTGT TCAGCTAAAC TATATAACTCC TAAGGGAGAA AAATTATCAC AGGCTTACTA TCGTTCACAA ACTACGAAAC GATCAGGCTG GTTAAAAGTA AGTGCAGATA ATGGTTCTATT CCTGGACTAG ACAGTTATGC AGGAATCTTT GGAGAACCGT TGGATCGCTT GCAAATAGGT ATTTCACAGTC AAATCCATTTT AA |
| 120 | Epicidin 280 | Lantibiotic | MENKKDLFD LEIKKDNME NNNELEAQS LGPAIKATR QVCPKATRF VTVSCKKSD CQ | Staphylococcus epidermidis | 121 | ATGGAAAACA AAAAAGATTT ATTTGATTTAG AAATCAAAAA AGATAATATG GAAAATAATA ATGAATTAGA AGCTCAATCT CTTGGTCCTGC AATTAAGGCA ACTAGACAGG TATGTCCTAA AGCAACACGT TTTGTTACAGT TTCTTGTAAAA AAAGTGATTG TCAATAG |
| 122 | Epidermicin NI01 | Unclassified | MAAFMKLIQ FLATKGQKY VSLAWKHK GTILKWINA | Staphylococcus epidermidis | 123 | ATGGCAGCAT TTATGAAGTT AATTCAGTTCT TAGCAACTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | GQSFEWIYK QIKKLWA | | | AGGTCAAAAG TATGTTTCACT TGCATGGAAA CATAAAGGTA CTATTTTAAAA TGGATTAACG CCGGTCAAAG TTTTGAATGG ATTTATAAAC AAATCAAAAA ATTATGGGCA TAA |
| 124 | Epidermin | Lantibiotic | MEAVKEKN DLFNLDVKV NAKESNDSG AEPRIASKFI CTPGCAKTG SFNSYCC | Staphylococcus epidermidis | 125 | ATGGAAGCAG TAAAAGAAAA AAATGATCTTT TTAATCTTGAT GTTAAAGTTA ATGCAAAAGA ATCTAACGAT TCAGGAGCTG AACCAAGAAT TGCTAGTAAA TTTATATGTAC TCCTGGATGT GCAAAAACAG GTAGTTTTAA CAGTTATTGTT GTTAA |
| 126 | Epilancin K7 | Lantibiotic | MNNSLFDLN LNKGVETQK SDLSPQSAS VLKTSIKVSK KYCKGVTLT CGCNITGGK | Staphylococcus epidermidis | 127 | ATGAATAACT CATTATTCGAT TTAAACCTAA ACAAAGGTGT AGAAACTCAA AAGAGTGATT TAAGTCCGCA ATCTGCTAGT GTCTTGAAGA CTTCTATTAAA GTATCTAAAA AATATTGTAA AGGTGTTACT TTAACATGCG GTTGCAATAT TACTGGTGGT AAATAA |
| 128 | Gallidermin | Lantibiotic | MEAVKEKN ELFDLDVKV NAKESNDSG AEPRIASKFL CTPGCAKTG SFNSYCC | Staphylococcus gallinarum | 129 | ATGGAAGCAG TAAAAGAGAA AAATGAACTT TTTGATCTTGA CGTTAAAGTA AATGCAAAAG AGTCTAATGA TTCAGGCGCA GAACCACGAA TTGCTAGTAA ATTTTTATGTA CTCCTGGATG TGCCAAAACA GGTAGCTTCA ATAGCTACTG TTGTTAA |
| 130 | Garvicin A | IId | MENNNYTV LSDEELQKID GGIGGALGN ALNGLGTW ANMMNGGG FVNQWQVY | Lactococcus garvieae | 131 | ATGGAAACA ACAATTACAC AGTACTTTCA GATGAAGAAC TACAAAAAAT TGATGGTGGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | ANKGKINQY RPY | | | ATCGGCGGGG CTCTTGGTAAT GCTCTCAACG GATTAGGTAC CTGGGCAAAC ATGATGAACG GTGGAGGATT TGTTAATCAG TGGCAAGTTT ATGCTAATAA AGGAAAAATA AATCAATACC GTCCGTATTAA |
| 132 | Garvicin ML | Unclassified | MFDLVATG MAAGVAKTI VNAVSAGM DIATALSLFS GAFTAAGGI MALIKKYAQ KKLWKQLIAA | Lactococcus garvieae | 133 | ATGTTTGATTT AGTCGCGACT GGAATGGCTG CAGGTGTAGC AAAAACTATT GTTAATGCCG TTAGTGCTGG TATGGATATT GCCACTGCTTT ATCATTGTTCT CAGGAGCTTT TACTGCAGCT GGGGGAATTA TGGCACTCAT TAAAAAATAT GCTCAAAAGA AATTATGGAA ACAGCTTATT GCTGCATAA |
| 134 | Gassericin A | Unclassified | MVTKYGRN LGLNKVELF AIWAVLVVA LLLTTANIY WIADQFGIH LATGTARKL LDAMASGAS LGTAFAAIL GVTLPAWAL AAAGALGAT AA | Lactobacillus gasseri | 135 | ATGGTTACTA AGTACGGACG TAATTTAGGTT TGAACAAGGT AGAGTTGTTT GCAATTTGGG CGGTTTTAGT AGTTGCTCTTT TATTGACCAC AGCGAACATT TATTGGATTG CTGATCAATTC GGGATTCATT TAGCGACTGG AACAGCCCGT AAGTTATTAG ATGCAATGGC TTCTGGTGCCT CATTGGGAAC TGCCTTTGCTG CTATTTTGGGC GTGACATTAC CTGCATGGGC TTTGGCAGCT GCAGGAGCAT TGGGAGCGAC TGCAGCCTAG |
| 136 | Gassericin T (gassericin K7 B) | Unclassified | MKNFNTLSF ETLANIVGG RNNWAANIG GVGGATVA GWALGNAV CGPACGFVG AHYVPIAWA GVTAATGGF GKIRK | Lactobacillus gasseri | 137 | ATGAAAAATT TTAATACATTA TCATTTGAAA CATTGGCTAA CATAGTTGGT GGGAGAAATA ATTGGGCTGC TAATATAGGT GGAGTAGGTG GAGCGACAGT |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | | | | CGCTGGATGG GCTCTTGGAA ATGCAGTTTG CGGTCCTGCTT GTGGCTTTGTT GGAGCACACT ATGTTCCAAT AGCATGGGCT GGCGTAACGG CAGCTACTGG TGGATTCGGA AAGATAAGAA AGTAG |
| 138 | Glycocin F | Unclassified | MSKLVKTLT ISEISKAQNN GGKPAWCW YTLAMCGA GYDSGTCDY MYSHCFGIK HHSSGSSSY HC | Lactobacillus plantarum | 139 | ATGAGTAAAT TGGTTAAGAC ACTTACTATA AGTGAAATTT CTAAGGCTCA AAACAACGGT GGAAAACCTG CATGGTGTTG GTATACTTTA GCAATGTGTG GTGCTGGTTA TGATTCGGGA ACCTGTGATT ATATGTATTC GCATTGTTTTG GTATAAAGCA TCATAGTAGT GGTAGTAGCA GTTATCATTGT TAG |
| 140 | Halocin H4 | Unclassified | MSKDRDGR RTSRRGTLK KIGGFSLGAL SFGAVGRTQ AATGSSVTT ADIAPPGPN GDPKSVQID DKYTGAEM YGEGDFRVG LGTDLTMYP PVYRESLGN GSGGWEFDF TVCGSTACR FVDSNGDVK EDDKAKEM WWQEINFND INQDLYSRN DSDWVGSTP ADTQPEFDY TEFALARDG VTLALTALN PAMGSLALG ATYFLSDMV NWIASQHED DSSLRKWD YDGLSGPLY ADSSTYLLA RDEMTSNSY ESFTIDNIAV AFPEPVRTK YYVTFTAPD DPSTQSISTL EEEGIYRVP ATEVAAARP PGSRRSKSA ADEMVYVA DPKKFIEVEP | Haloferax mediterranei (strain ATCC 33500/DSM 1411/JCM 8866/ NBRC 14739/ NCIMB 2177/R-4) (Halobacterium mediterranei) | 141 | ATGTCGAAAG ACAGAGATGG GAGAAGGACA AGTCGGCGAG GCACGTTAAA GAAAATCGGC GGTTTCAGTCT CGGAGCGCTT AGTTTCGGGG CAGTCGGACG AACTCAAGCG GCGACCGGCT CATCGGTTAC GACCGCTGAT ATCGCACCTC CCGGACCGAA CGGAGACCCG AAGAGTGTTC AGATAGATGA TAAATACACC GGAGCCGAGA TGTACGGCGA GGGTGACTTC AGAGTCGGTC TCGGAACTGA CCTGACGATG TATCCGCCCG TGTACCGTGA GAGTCTTGGA AATGGAAGCG GGGGTTGGGA ATTCGACTTCA CCGTTTGTGG GTCCACTGCC TGTCGATTTGT GGACAGTAAC GGTGACGTCA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | VKNPSIPDRI YEEIEQKKK QRSRKQ | | | AAGAGGACGA CAAGGCGAAA GAAATGTGGT GGCAGGAAAT TAACTTCAAC GACATAAATC AGGATTTATA CAGTCGGAAC GATTCCGACT GGGTCGGGTC GACCCCTGCC GATACCCAAC CGGAGTTCGA TTACACCGAC TTTGCGCTCGC TCGGGACGGA GTGACGCTCG CTCTCACGGC ACTCAACCCC GCAATGGGGA GTCTTGCACTC GGTGCCACGT ACTTCCTCAGC GACATGGTGA ACTGGATTGC GAGCCAGCAC GAAGACGACA GTTCGCTCAA GAGAAAATGG GATTACGACG GGCTAAGTGG GCCGTTGTAC GCCGATTCGT CGACGTACCT ACTGGCACGC GACGAGATGA CTTCGAACTC GTACGAATCA TTCACGATCG ATAACATCGC CGTTGCCTTCC CAGAGTTCCC CGTCCGGACC AAGTACTACG TCACATTCACT GCGCCGGATG ACCCGTCAAC GCAGTCGATA TCTACGCTCG AAGAGGAGGG AATCTACCGA GTGCCCGCTA CGGAAGTGGC TGCGGCCAGA CCACCGGGGT CCCGACGTTC CAAATCGGCA GCCGACGAGA TGGTGTACGT TGCCGATCCG AAGAAGTTCA TAGAGGTCGA GCCGGTGAAG AACCCAAGTA TCCCGGACCG AATCTACGAG GAGATAGAGC AAAAAAAGAA ACAACGGAGT AGGAAACAGT AG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 142 | Halocin-S8 | Unclassified | MSDKDSINR RNVLRKIGGI GVASAVGFS GLASGESLS DDEKQDVID TIYKSQRVE QIKKKFGGV NIEPKKVQS VTTNQSGDL VTAKLSVSD GDLVYSSVK DTTVIVQFD RSASEIGES WPKNTEAFI KSTSSGVDL LRTATDEEIK DVTEGVNTS EIESADAVNI FIDPESQTYY MEKYDFNN KVLEMFELA TGGTSSGKIS PTREDQNHE YNVREHKVF NSEKQNIQL QSDCNINSN TAADVILCF NQVGSCALC SPTLVGGPV PTVACLLVV CFGTPNAVS AILEEVDNS CFNLIKDVIS CWDEWTSFW | Haloarchaeon S8a | 143 | ATGTCGGATA AAGACAGCAT TAACAGAAGA AATGTATTAA GAAAAATTGG CGGTATCGGT GTGGCTTCAG CTGTCGGATTT TCTGGTTTGG CAAGCGGGGA AAGTCTTAGC GATGATGAGA AACAAGATGT TATTGACACA ATTTACAAAT CACAAAGAGT TGAACAGATA AAGAAAAAGT TCGGAGGAGT GAATATTGAG CCGAAAAAGG TTCAATCTGTA ACGACCAATC AGAGCGGAGA TCTTGTTACGG CGAAGCTGTC GGTTAGTGAT GGGGATTTGG TATATTCGAG TGTCAAAGAT ACAACTGTAA TAGTTCAGTTC GATAGATCGG CTTCTGAAATT GGTGAAAGTT GGCCCAAGAA TACTGAGGCA TTCATCAAATC GACGTCCTCT GGGGTCGATC TTCTACGTACA GCAACTGATG AAGAAATAAA GGACGTTACT GAGGGAGTCA ACACATCTGA AATTGAATCT GCGGATGCTG TTAACATATTT ATTGATCCTG AATCACAGAC ATACTATATG GAGAAATATG ACTTTAATAAT AAGGTACTTG AGATGTTTGA ATTAGCGACA GGTGGGACAA GTAGTGGTAA AATCTCCCCC ACACGTGAAG ACCAGAATCA CGAATATAAT GTTAGGGAAC ATAAAGTATT TAACTCAGAA AAACAGAATA TACAACTTCA GAGTGACTGT AATATAAACA GTAACACCGC TGCTGATGTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ATTCTATGCTT CAACCAGGTT GGTTCTTGTG CACTCTGCTCC CCGACTTTAG TCGGAGGTCC AGTCCCTACA GTTGCATGTCT CTTAGTCGTCT GTTTCGGCAC TCCAAATGCT GTGTCCGCGA TACTTGAAGA AGTCGATAAT TCTTGCTTTAA CTTGATCAAG GATGTAATTT CGTGTTGGGA TGAATGGACT AGCTTCTGGT GA |
| 144 | Helveticin-J | Unclassified | MKHLNETTN VRILSQFDM DTGYQAVV QKGNVGSK YVYGLQLRK GATTILRGY RGSKINNPIL ELSGQAGGH TQTWEFAGD RKDINGEER AGQWFIGVK PSKIEGSKII WAKQIARVD LRNQMGPH YSNTDFPRL SYLNRAGSN PFAGNKMTH AEAAVSPDY TKFLIATVEN NCIGHFTIYN LDTINEKLD EKGNSEDVN LETVKYEDS FIIDNLYGDD NNSIVNSIQG YDLDNDGNI YISSQKAPDF DGSYYAHH KQIVKIPYYA RSKESEDQW RAVNLSEFG GLDIPGKHS EVESIQIIGE NHCYLTVAY HSKNKAGEN KTTLNEIYEL SWN | Lactobacillus helveticus (Lactobacillus suntoryeus) | 145 | ATGAAGCATT TAAATGAAAC AACTAATGTT AGAATTTTAA GTCAATTTGA TATGGATACT GGCTATCAAG CAGTAGTTCA AAAAGGCAAT GTAGGTTCAA AATATGTATA TGGATTACAA CTTCGCAAAG GTGCTACTAC TATCTTGCGTG GTTACCGTGG AAGTAAAATT AATAACCCTA TTCTTGAATTA TCTGGTCAAG CAGGTGGTCA CACACAGACA TGGGAATTTG CTGGTGATCG TAAAGACATT AATGGTGAAG AAAGAGCAGG TCAATGGTTT ATAGGTGTTA AACCATCGAA AATTGAAGGA AGCAAAATTA TTTGGGCAAA GCAAATTGCA AGAGTTGATC TTAGAAATCA AATGGGACCT CATTATTCAA ATACTGACTTT CCTCGATTATC CTACTTGAATC GCGCCGGTTC TAATCCATTTG CTGGTAATAA GATGACGCAT GCCGAAGCCG CAGTATCACC TGATTATACTA AGTTTTTAATT GCTACTGTTG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAAATAACTG TATTGGTCATT TTACTATATAC AATTTAGATA CAATTAATGA AAAACTTGAT GAAAAGGGAA ATAGTGAAGA TGTTAATCTCG AAACTGTTAA ATACGAAGAT AGTTTTATCAT TGATAATTTAT ATGGTGATGA TAATAATTCTA TTGTAAATTCA ATTCAAGGGT ATGATTTGGA TAATGATGGA AATATTTATAT TTCCAGTCAA AAAGCGCCAG ATTTTGATGG CTCTTATTATG CACATCATAA GCAGATTGTT AAGATTCCAT ATTATGCTCG GTCTAAAGAA AGCGAAGACC AATGGAGAGC TGTAAATTTA AGCGAATTCG GTGGCTTGGA TATTCCAGGT AAACATAGTG AAGTTGAAAG CATCCAAATT ATTGGTGAGA ATCATTGTTAC TTAACTGTTGC ATATCATTCTA AAAATAAAGC GGGTGAAAAT AAAACTACTT TGAATGAGAT TTATGAATTAT CTTGGAATTAG |
| 146 | Hiracin JM79 | Class II sec-dependent | MKKKVLKH CVILGILGTC LAGIGTGIKV DAATYYGN GLYCNKEKC WVDWNQAK GEIGKIIVNG WVNHGPWA PRR | Enterococcus hirae | 147 | ATGAAAAAGA AAGTATTAAA ACATTGTGTT ATTCTAGGAA TATTAGGAAC TTGTCTAGCTG GCATCGGTAC AGGAATAAAA GTTGATGCAG CTACTTACTAT GGAAATGGTC TTTATTGTAAC AAAGAAAAAT GTTGGGTAGA TTGGAATCAA GCTAAAGGAG AAATTGGAAA AATTATTGTTA ATGGTTGGGT TAATCATGGT CCATGGGCAC CTAGAAGGTAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 148 | Lactacin-F (lafA) | class IIB | MKQFNYLSHKDLAVVVGGRNNWQTNVGGAVGSAMIGATVGGTICGPACAVAGAHYLPILWTAVTAATGGFGKIRK | Lactobacillus johnsonii (strain CNCM I-12250/La1/ NCC 533) | 149 | ATGAAACAATTTAATTATTTATCACATAAAGATTTAGCAGTCGTTGTTGGTGGAAGAAATAATTGGCAAACAAATGTGGGAGGAGCAGTGGGATCAGCTATGATTGGGGCTACAGTTGGTGGTACAATTTGTGGACCTGCATGTGCTGTAGCTGGTGCCCATTATCTTCCTATTTTATGGACAGCGGTTACAGCTGCAACAGGTGGTTTTGGCAAGATAAGAAAGTAG |
| 150 | Lactacin-F (lafX) | class IIB | MKLNDKELSKIVGGNRWGDTVLSAASGAGTGIKACKSFGPWGMAICGVGGAAIGGYFGYTHN | Lactobacillus johnsonii (strain CNCM I-12250/La1/ NCC 533) | 151 | ATGAAATTAAATGACAAAGAATTATCAAAGATTGTTGGTGGAAATCGATGGGGAGATACTGTTTTATCAGCTGCTAGTGGCGCAGGAACTGGTATTAAAGCATGTAAAAGTTTTGGCCCATGGGGAATGGCAATTTGTGGTGTAGGAGGTGCAGCAATAGGAGGTTATTTTGGCTATACTCATAATTAA |
| 152 | Lacticin 3147 A1 | Lantibiotic | MNKNEIETQPVTWLEEVSDQNFDEDVFGACSTNTFSLSDYWGNNGAWCTLTHECMAWCK | Lactococcus lactis subsp. lactis (Streptococcus lactis) | 153 | ATGAACAAAAATGAAATTGAAACACAACCAGTTACATGGTTGGAAGAAGTATCTGATCAAAATTTTGATGAAGATGTATTTGGTGCGTGTAGTACTAACACATTCTCGCTCAGTGATTACTGGGGAAATAACGGGGCTTGGTGTACACTCACTCATGAATGTATGGCTTGGTGTAAATAA |
| 154 | Lacticin 3147 A2 | Lantibiotic | MKEKNMKKNDTIELQLGKYLEDDMIELAEGDESHGGTTPATPAISILSAYISTNTCPTTKCTRAC | Lactococcus lactis subsp. lactis (Streptococcus lactis) | 155 | ATGAAAGAAAAAAATATGAAAAAGAATGACACTATTGAATTACAATTGGGAAAATACCTTGAAGATGATATGATTGAATTAGCTGAAGGGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ATGAGTCTCA TGGAGGAACA ACACCAGCAA CTCCTGCAATC TCTATTCTCAG TGCATATATTA GTACCAATAC TTGTCCAACA ACAAAATGTA CACGTGCTTG TTAA |
| 156 | Lacticin 481 (Lactococcin DR) | Lantibiotic | MKEQNSFNL LQEVTESEL DLILGAKGG SGVIHTISHE CNMNSWQF VFTCCS | Lactococcus lactis subsp. lactis (Streptococcus lactis) | 157 | ATGAAAGAAC AAAACTCTTTT AATCTTCTTCA AGAAGTGACA GAAAGTGAAT TGGACCTTATT TTAGGTGCAA AAGGCGGCAG TGGAGTTATT CATACAATTTC TCATGAATGT AATATGAATA GCTGGCAATT TGTATTTACTT GCTGCTCTTAA |
| 158 | Lacticin Q | Unclassified | MAGFLKVV QLLAKYGSK AVQWAWAN KGKILDWLN AGQAIDWV VSKIKQILGIK | Lactococcus lactis | 159 | ATGGCAGGGT TTTTAAAAGT AGTTCAATTA CTAGCTAAAT ATGGTTCTAA AGCTGTACAA TGGGCTTGGG CAAACAAGGG TAAGATTTTA GATTGGCTTA ATGCAGGTCA GGCTATTGAT TGGGTAGTTT CGAAAATTAA GCAAATTTTA GGTATTAAGT AA |
| 160 | Lacticin Z | Unclassified | MAGFLKVV QILAKYGSK AVQWAWAN KGKILDWIN AGQAIDWV VEKIKQILGIK | Lactococcus lactis | 161 | ATGGCAGGGT TTTTAAAAGT AGTCCAAATT TTGGCTAAGT ATGGTTCTAA AGCCGTACAA TGGGCATGGG CAAATAAAGG AAAAATCTTA GATTGGATTA ATGCAGGTCA AGCTATTGAC TGGGTAGTTG AAAAGATTAA GCAAATTTTG GGTATTAAAT AA |
| 162 | Lactobin-A (Amylovorin-L471) | class IIB | MKQLNSEQL QNIIGGNRW TNAYSAALG CAVPGVKYG KKLGGVWG AVIGGVGGA AVCGLAGY VRKG | Lactobacillus amylovorus | 163 | ATGAAACAAT TGAATTCAGA ACAATTACAA AATATTATCG GTGGAAATAG ATGGACTAAT GCATACAGCG CAGCTTTGGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ATGCGCTGTC CCTGGAGTTA AATATGGAAA AAAACTTGGT GGCGTATGGG GTGCTGTAAT TGGTGGCGTA GGCGGTGCAG CAGTCTGTGG CTTGGCGGGT TATGTTCGTA AAGGCTAA |
| 164 | Lactocin-S | Lantibiotic | MKTEKKVL DELSLHASA KMGARDVE SSMNADSTP VLASVAVSM ELLPTASVL YSDVAGCFK YSAKHHC | Lactobacillus sakei L45 | 165 | ATGAAAACAG AAAAAAAGGT TTTAGATGAA CTGAGCTTAC ACGCTTCTGC AAAAAATGGGA GCACGTGATG TTGAATCCAG CATGAATGCA GACTCAACAC CAGTTTTAGC ATCAGTCGCT GTATCCATGG AATTATTGCC AACTGCGTCT GTTCTTTATTC GGATGTTGCA GGTTGCTTCA AATATTCTGC AAAACATCAT TGTTAG |
| 166 | Lactococcin 972 | Unclassified | MKTKSLVLA LSAVTLFSA GGIVAQAEG TWQHGYGV SSAYSNYHH GSKTHSATV VNNNTGRQ GKDTQRAG VWAKATVG RNLTEKASF YYNFW | Lactococcus lactis subsp. lactis (Streptococcus lactis) | 167 | ATGAAACCA AGTCTCTCGT ATTGGCATTA TCTGCGGTTA CGTTATTCTCT GCCGGAGGAA TTGTAGCTCA AGCTGAAGGA ACATGGCAAC ATGGATATGG TGTTAGTTCG GCATATTCAA ATTATCATCAT GGTAGCAAAA CTCATTCAGCC ACAGTTGTAA ATAATAATAC TGGCCGACAA GGTAAGGATA CACAACGTGC CGGTGTTTGG GCAAAAGCTA CTGTTGGACG TAACTTAACT GAAAAAGCTT CATTTTATTAT AACTTTTGGT AA |
| 168 | Lactococcin-A | Unclassified | MKNQLNFNI VSDEELSEA NGGKLTFIQ STAAGDLYY NTNTHKYV YQQTQNAFG AAANTIVNG | Lactococcus lactis subsp. cremoris (Streptococcus cremoris) | 169 | ATGAAAAATC AATTAAATTTT AATATTGTTTC AGATGAAGAA CTTTCAGAAG CTAACGGAGG AAAATTAACA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | WMGGAAGG FGLHH | | | TTTATTCAATC GACAGCGGCT GGAGATTTAT ATTACAATAC TAATACACAC AAATATGTTT ACCAACAAAC TCAAAACGCT TTTGGGGCTG CTGCTAATAC CATTGTTAAT GGATGGATGG GTGGCGCTGC TGGAGGTTTC GGGTTGCACC ATTGA |
| 170 | Lactococcin-B | Unclassified | MKNQLNFNI VSDEELAEV NGGSLQYV MSAGPYTW YKDTRTGKT ICKQTIDTAS YTFGVMAE GWGKTFH | Lactococcus lactis subsp. cremoris (Streptococcus cremoris) | 171 | ATGAAAAATC AATTAAATTTT AATATTGTTTC TGATGAAGAA CTTGCAGAAG TTAATGGAGG AAGCTTGCAG TATGTTATGA GTGCTGGACC ATATACTTGG TATAAAGATA CTAGAACAGG AAAAACAATA TGTAAACAGA CAATTGACAC AGCAAGTTAT ACATTTGGTG TAATGGCAGA AGGATGGGGA AAAACATTCC ACTAA |
| 172 | Lactocyclicin Q | Unclassified | MKLIDHLGA PRWAVDTIL GAIAVGNLA SWVLALVPG PGWAVKAG LATAAAIVK HQGKAAAA AW | Lactococcus sp. QU 12 | 173 | ATGAAATTAA TTGATCATTTA GGTGCTCCAA GATGGGCCGT TGATACTATT TAGGTGCAAT CGCAGTTGGG AACTTAGCAA GTTGGGTTCT AGCGCTTGTC CCTGGTCCAG GGTGGGCAGT AAAAGCTGGT TTAGCAACTG CTGCTGCCAT CGTTAAACAT CAAGGTAAAG CTGCCGCTGC TGCTTGGTAA |
| 174 | Laterosporulin | Unclassified | MACQCPDAI SGWTHTDY QCHGLENK MYRHVYAIC MNGTQVYC RTEWGSSC | Brevibacillus sp. GI-9 | 175 | ATGGCTTGCC AATGTCCAGA TGCGATCTCA GGTTGGACGC ATACAGATTA CCAGTGTCAC GGTTTGGAGA ATAAAATGTA TAGACATGTT TATGCAATTT GCATGAACGG TACTCAAGTA TATTGCAGAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CAGAGTGGGG TAGCAGCTGC TAG |
| 176 | Leucocin N | Class IId | MNKEYNSIS NFKKITNKD LQNINGGFIG RAIGDFVYF GAKGLRESG KLLNYYYKH KH | Leuconostoc pseudomesenteroides | 177 | ATGAATAAAG AATATAATAG CATTAGCAAT TTTAAAAAAA TTACTAATAA AGACTTGCAA AACATAAATG GTGGATTTATT GGTAGGGCAA TAGGTGACTT TGTGTACTTTG GAGCGAAGGG ACTAAGAGAA TCTGGTAAAC TACTTAATTAT TACTATAAGC ATAAGCATTGA |
| 178 | Leucocin Q | Class IId | MKNQLMSFE VISEKELSTV QGGKGLGKL IGIDWLLGQ AKDAVKQY KKDYKRWH | Leuconostoc pseudomesenteroides | 179 | ATGAAAAATC AGTTAATGTC TTTCGAAGTG ATATCAGAAA AAGAATTGTC CACGGTACAA GGTGGCAAAG GCTTAGGTAA ACTCATAGGA ATTGATTGGC TTTTGGGTCA AGCTAAGGAC GCTGTTAAAC AGTACAAGAA GGATTACAAA CGTTGGCACT AA |
| 180 | Leucocin-A (Leucocin A-UAL 187) | class IIA/YG NGV | MMNMKPTE SYEQLDNSA LEQVVGGK YYGNGVHC TKSGCSVNW GEAFSAGVH RLANGGNGFW | Leuconostoc gelidum | 181 | ATGATGAACA TGAAACCTAC GGAAAGCTAT GAGCAATTGG ATAATAGTGC TCTCGAACAA GTCGTAGGAG GTAAGTATTA TGGTAACGGA GTTCATTGCA CAAAAAGTGG TTGTTCTGTAA ACTGGGAGA AGCCTTTTCA GCTGGAGTAC ATCGTTTAGC AAATGGTGGA AATGGTTTCT GGTAA |
| 182 | Leucocin-B (Leucocin B-Ta11a) | class IIA/YG NGV | MNNMKSAD NYQQLDNN ALEQVVGGK YYGNGVHC TKSGCSVNW GEAFSAGVH RLANGGNGFW | Leuconostoc carnosum | 183 | ATGAATAACA TGAAATCTGC GGATAATTAT CAGCAATTGG ATAATAATGC TCTCGAACAA GTCGTAGGAG GTAAGTATTA TGGTAACGGA GTTCATTGCA CAAAAAGTGG TTGTTCTGTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ACTGGGAGA AGCCTTTTCA GCTGGAGTAC ATCGTTTAGC AAATGGTGGA AATGGTTTCT GGTAA |
| 184 | Leucocyclicin Q | Unclassified | MFLVNQLGI SKSLANTILG AIAVGNLAS WLLALVPGP GWATKAAL ATAETIVKH EGKAAAIAW | Leuconostoc mesenteroides | 185 | ATGTTCTTGGT AAATCAGTTA GGGATTTCAA AATCGTTAGC TAATACTATTC TTGGTGCAAT TGCTGTTGGT AATTTGGCCA GTTGGTTATTA GCTTTGGTTCC TGGTCCGGGT TGGGCAACAA AAGCAGCACT TGCGACAGCT GAAACAATTG TGAAGCATGA AGGAAAAGCA GCTGCTATTG CGTGGTAA |
| 186 | Lichenicidin A1 | Lantibiotic (two-peptide) | MSKKEMILS WKNPMYRT ESSYHPAGNI LKELQEEEQ HSIAGGTITL STCAILSKPL GNNGYLCTV TKECMPSCN | Bacillus licheniformis (strain DSM 13/ATCC 14580) | 187 | ATGTCAAAAA AGGAAATGAT TCTTTCATGGA AAAATCCTAT GTATCGCACT GAATCTTCTTA TCATCCAGCA GGGAACATCC TTAAAGAACT CCAGGAAGAG GAACAGCACA GCATCGCCGG AGGCACAATC ACGCTCAGCA CTTGTGCCATC TTGAGCAAGC CGTTAGGAAA TAACGGATAC CTGTGTACAG TGACAAAAGA ATGCATGCCA AGCTGTAACT AA |
| 188 | Linocin M18 | Unclassified | MNNLYRELA PIPGPAWAEI EEEARRTFK RNIAGRRIV DVAGPTGFE TSAVTTGHI RDVQSETSG LQVKQRIVQ EYIELRTPFT VTRQAIDDV ARGSGDSD WQPVKDAA TTIAMAEDR AILHGLDAA GIGGIVPGSS NAAVAIPDA VEDFADAVA QALSVLRTV GVDGPYSLL LSSAEYTKV | Brevibacterium linens | 189 | GTAATAACC TCTATCGCGA GCTTGCCCCC ATCCCCGGCC CGGCCTGGGC GGAGATCGAG GAGGAGGCTC GACGGACATT CAAACGCAAT ATCGCCGGCC GCCGGATCGT CGATGTCGCA GGGCCCACGG GCTTCGAGAC CTCCGCGGTG ACCACTGGCC ACATCCGAGA CGTCCAGTCG GAGACGAGCG GACTGCAGGT |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | SESTDHGYPI REHLSRQLG AGEIIWAPAL EGALLVSTR GGDYELHLG QDLSIGYYS HDSETVELY LQETFGFLA LTDESSVPLSL | | | TAAGCAGCGC ATCGTGCAGG AATACATCGA GCTGCGGACC CCATTCACCGT GACTCGGCAG GCCATCGATG ACGTGGCCCG CGGGTCCGGT GACTCGGACT GGCAGCCCGT CAAGGATGCG GCCACGACGA TCGCGATGGC TGAAGATCGG GCCATTCTCCA CGGGCTCGAT GCGGCCGGGA TCGGCGGAAT CGTTCCCGGC AGCTCGAATG CCGCAGTGGC CATCCCCGAC GCCGTCGAGG ACTTCGCGGA CGCCGTCGCC CAGGCGCTGA GTGTGCTGCG CACGGTGGGA GTCGACGGGC CCTACAGCCT GTTGCTCTCCT CCGCGGAGTA CACCAAGGTC TCCGAGTCCA CCGACCACGG CTACCCGATC CGCGAGCACC TCTCCCGGCA GCTCGGCGCC GGAGAGATCA TCTGGGCGCC CGCGCTCGAA GGGGCGCTGC TCGTCTCCAC GCGCGGGGGT GACTACGAGC TCCACCTCGG CCAGGACCTG TCGATCGGTT ACTACAGCCA CGACAGCGAG ACCGTCGAAC TCTATCTGCA GGAGACCTTC GGATTCCTCG CGCTGACCGA CGAATCCAGT GTGCCTTTGA GCCTCTGA |
| 190 | Listeriocin 743A | Class IIa | MKKAALKFII VIAILGFSFSF FSIQSEAKSY GNGVQCNK KKCWVDWG SAISTIGNNS AANWATGG AAGWKS | Listeria innocua | 191 | TTGAAGAAGG CAGCGTTAAA ATTTATTATTG TTATTGCTATT CTAGGTTTCA GTTTTTCTTTC TTTAGCATAC AATCTGAAGC TAAATCTTATG GAAATGGAGT TCAGTGTAAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAGAAAAAAT GTTGGGTAGA TTGGGGTAGT GCTATAAGTA CTATTGGAAA TAATTCTGCA GCGAATTGGG CTACAGGTGG AGCAGCTGGT TGGAAAAGCT GA |
| 192 | Mersacidin | Lantibiotic, type B | MSQEAIIRS WKDPFSREN STQNPAGNP FSELKEAQM DKLVGAGD MEAACTFTL PGGGGVCTL TSECIC | Bacillus sp. (strain HIL-Y85/54728) | 193 | ATGAGTCAAG AAGCTATCAT TCGTTCATGG AAAGATCCTT TTTCCCGTGA AAATTCTACA CAAAATCCAG CTGGTAACCC ATTCAGTGAG CTGAAAGAAG CACAAATGGA TAAGTTAGTA GGTGCGGGAG ACATGGAAGC AGCATGTACT TTTACATTGCC TGGTGGCGGC GGTGTTTGTA CTCTAACTTCT GAATGTATTT GTTAA |
| 194 | Mesentericin Y105 | class IIA/YG NGV | MTNMKSVE AYQQLDNQ NLKKVVGG KYYGNGVH CTKSGCSVN WGEAASAGI HRLANGGN GFW | Leuconostoc mesenteroides | 195 | ATGACGAATA TGAAGTCTGT GGAAGCATAT CAGCAATTAG ATAACCAGAA TCTCAAGAAA GTTGTTGGTG GAAAGTATTA TGGGAATGGT GTTCACTGTA CAAAAAGTGG ATGCTCTGTTA ACTGGGGAGA AGCTGCCTCA GCTGGCATAC ATCGTTTGGC CAATGGTGGA AATGGATTTT GGTAA |
| 196 | Michiganin-A | Lantibiotic | MNDILETET PVMVSPRW DMLLDAGE DTSPSVQTQI DAEFRRVVS PYMSSSGWL CTLTIECGTII CACR | Clavibacter michiganensis subsp. michiganensis | 197 | ATGAACGACA TCCTCGAGAC GGAGACCCCC GTCATGGTCA GCCCCCGGTG GGACATGCTG CTCGACGCGG GCGAGGACAC CAGCCCGTCC GTCCAGACCC AGATCGACGC GGAGTTCCGT CGCGTCGTGA GCCCGTACAT GTCCAGCAGC GGCTGGCTCT GCACGCTCAC CATCGAATGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGCACCATCA TCTGCGCGTG TCGCTGA |
| 198 | Microcin B17 (MccB17) | Unclassified | MELKASEFG VVLSVDALK LSRQSPLGV GIGGGGGGG GGGSCGGQ GGGCGGCSN GCSGGNGGS GGSGSHI | Escherichia coli | 199 | ATGGAATTAA AAGCGAGTGA ATTTGGTGTA GTTTTGTCCGT TGATGCTCTTA AATTATCACG CCAGTCTCCAT TAGGTGTTGG CATTGGTGGT GGTGGCGGCG GCGGCGGCGG CGGTAGCTGC GGTGGTCAAG GTGGCGGTTG TGGTGGTTGC AGCAACGGTT GTAGTGGTGG AAACGGTGGC AGCGGCGGAA GTGGTTCACA TATC |
| 200 | Microcin C7 | Unclassified | MRTGNAN | Escherichia coli | 201 | ATGCGTACTG GTAATGCAAA CTAA |
| 202 | Microcin E492 | Unclassified | MREISQKDL NLAFGAGET DPNTQLLND LGNNMAWG AALGAPGGL GSAALGAAG GALQTVGQ GLIDHGPVN VPIPVLIGPS WNGSGSGY NSATSSSGS GS | Klebsiella pneumoniae | 203 | ATGAGAGAAA TTAGTCAAAA GGACTTAAAT CTTGCTTTTG TGCAGGAGAG ACCGATCCAA ATACTCAACTT CTAAACGACC TTGGAAATAA TATGGCATGG GGTGCTGCTC TTGGCGCTCCT GGCGGATTAG GATCAGCAGC TTTGGGGGCC GCGGGAGGTG CATTACAAAC TGTAGGGCAA GGATTAATTG ACCATGGTCC TGTAAATGTC CCCATCCCTGT ACTCATCGGG CCAAGCTGGA ATGGTAGCGG TAGTGGTTAT AACAGCGCAA CATCCAGTTCC GGTAGTGGTA GTTAA |
| 204 | Microcin H47 | Unclassified | MREITESQL RYISGAGGA PATSANAAG AAAIVGALA GIPGGPLGV VVGAVSAGL TTAIGSTVGS GSASSSAGG GS | Escherichia coli | 205 | ATGCGAGAAA TAACAGAATC ACAGTTAAGA TATATTTCCGG GGCGGGAGGT GCGCCAGCGA CTTCAGCTAAT GCCGCAGGTG CTGCAGCTAT TGTTGGAGCT CTCGCCGGAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TACCTGGTGG TCCACTTGGG GTTGTAGTTG GAGCCGTATC TGCCGGTTTG ACAACAGCAA TTGGCTCGAC CGTGGGAAGT GGTAGTGCCA GTTCTTCTGCT GGTGGCGGTA GCTAA |
| 206 | Microcin J25 | Unclassified | MIKHFHFNK LSSGKKNNV PSPAKGVIQI KKSASQLTK GGAGHVPEY FVGIGTPISF YG | Escherichia coli | 207 | ATGATTAAGC ATTTTCATTTT AATAAACTGT CTTCTGGTAA AAAAAATAAT GTTCCATCTCC TGCAAAGGGG GTTATACAAA TAAAAAAATC AGCATCGCAA CTCACAAAAG GTGGTGCAGG ACATGTGCCT GAGTATTTTGT GGGGATTGGT ACACCTATAT CTTTCTATGGC TGA |
| 208 | Microcin-24 | Unclassified | MYMRELDR EELNCVGGA GDPLADPNS QIVRQIMSN AAWGPPLVP ERFRGMAVG AAGGVTQT VLQGAAAH MPVNVPIPK VPMGPSWN GSKG | Escherichia coli | 209 | ATGTATATGA GAGAGTTAGA TAGAGAGGAA TTAAATTGCG TTGGTGGGGC TGGAGATCCG CTTGCAGATC CTAATTCCCA AATTGTAAGA CAGATAATGT CTAATGCGGC ATGGGGCCCG CCTTTGGTGCC AGAGCGGTTT AGGGGAATGG CTGTTGGAGC CGCAGGTGGG GTTACGCAGA CAGTTCTTCAA GGAGCAGCAG CTCATATGCC GGTTAATGTC CCTATACCTA AAGTTCCGAT GGGACCCTCA TGGAACGGAA GTAAAGGATAA |
| 210 | Mundticin KS | Unclassified | MSQVVGGK YYGNGVSC NKKGCSVD WGKAIGIIGN NSAANLATG GAAGWKS | Enterococcus mundtii | 211 | ATGTCACAGG TAGTAGGTGG AAAATACTAC GGTAATGGAG TCTCATGTAAT AAAAAAGGGT GCAGTGTTGA TTGGGGAAAA GCGATTGGCA TTATTGGAAA TAATTCTGCTG CGAATTTAGC |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | | | | TACTGGTGGA GCAGCTGGTT GGAAAAGTTAA |
| 212 | Mundticin L | class IIA/YG NGV | MKKLTSKE MAQVVGGK YYGNGLSCN KKGCSVDW GKAIGIIGNN SAANLATGG AAGWKS | Enterococcus mundtii | 213 | TTGAAGAAAT TAACATCAAA AGAAATGGCA CAAGTAGTAG GTGGGAAATA CTACGGTAAT GGATTATCAT GTAATAAAAA AGGGTGCAGT GTTGATTGGG GAAAAGCTAT TGGCATTATT GGAAATAATT CTGCTGCGAA TTTAGCTACTG GTGGAGCAGC TGGTTGGAAA AGTTAA |
| 214 | Mutacin 1140 (Mutacin III) | Lantibiotic | MSNTQLLEV LGTETFDVQ EDLFAFDTT DTTIVASND DPDTRFKSW SLCTPGCAR TGSFNSYCC | Streptococcus mutans | 215 | ATGTCAAACA CACAATTATT AGAAGTCCTT GGTACTGAAA CTTTTGATGTT CAAGAAGATC TCTTTGCTTTT GATACAACAG ATACTACTATT GTGGCAAGCA ACGACGATCC AGATACTCGT TTCAAAAGTT GGAGCCTTTG TACGCCTGGT TGTGCAAGGA CAGGTAGTTT CAATAGTTAC TGTTGCTGA |
| 216 | Mutacin-2 | Lantibiotic | MNKLNSNA VVSLNEVSD SELDTILGGN RWWQGVVP TVSYECRMN SWQHVFTCC | Streptococcus mutans | 217 | ATGAACAAGT TAAACAGTAA CGCAGTAGTT CTTTGAATG AAGTTTCAGA TTCTGAATTG GATACTATTTT GGGTGGTAAT CGTTGGTGGC AAGGTGTTGT GCCAACGGTC TCATATGAGT GTCGCATGAA TTCATGGCAA CATGTTTTCAC TTGCTGTTAA |
| 218 | Nisin A | Lantibiotic | MSTKDFNLD LVSVSKKDS GASPRITSISL CTPGCKTGA LMGCNMKT ATCHCSIHV SK | Lactococcus lactis subsp. lactis (Streptococcus lactis) | 219 | ATGAGTACAA AAGATTTTAA CTTGGATTTG GTATCTGTTTC GAAGAAAGAT TCAGGTGCAT CACCACGCAT TACAAGTATTT CGCTATGTAC ACCCGGTTGT AAAACAGGAG CTCTGATGGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TTGTAACATG AAAACAGCAA CTTGTCATTGT AGTATTCACG TAAGCAAATAA |
| 220 | Nisin F | Lantibiotic | MSTKDFNLD LVSVSKKDS GASPRITSISL CTPGCKTGA LMGCNMKT ATCNCSVHV SK | Lactococcus lactis | 221 | ATGAGTACAA AAGATTTCAA CTTGGATTTG GTATCTGTTTC GAAGAAAGAT TCAGGTGCAT CACCACGCAT TACAAGTATTT CGCTATGTAC ACCCGGTTGT AAAACAGGAG CTCTGATGGG TTGTAACATG AAAACAGCAA CTTGTAATTGT AGCGTTCACG TAAGCAAA |
| 222 | Nisin Q | Lantibiotic | MSTKDFNLD LVSVSKTDS GASTRITSIS LCTPGCKTG VLMGCNLKT ATCNCSVHV SK | Lactococcus lactis | 223 | ATGAGTACAA AAGATTTCAA CTTAGATTTG GTATCTGTTTC AAAAACAGAT TCTGGCGCTTC AACACGTATT ACCAGCATTT CGCTTTGTAC ACCAGGTTGT AAAACAGGTG TTCTGATGGG ATGTAACCTG AAAACAGCAA CTTGTAATTGT AGCGTTCACG TAAGCAAATAA |
| 224 | Nisin U | Lantibiotic | MNNEDFNL DLIKISKENN SGASPRITSK SLCTPGCKT GILMTCPLK TATCGCHFG | Streptococcus uberis | 225 | ATGAACAATG AAGATTTTAA TTTGGATCTCA TCAAAATCTC AAAGGAAAAC AACTCAGGAG CTTCACCTCGA ATAACTAGTA AATCATTATGT ACTCCTGGAT GTAAGACGGG TATTTTGATGA CTTGTCCACTA AAAACTGCAA CCTGTGGTTG TCATTTTGGAT AA |
| 226 | Nisin Z | Lantibiotic | MSTKDFNLD LVSVSKKDS GASPRITSISL CTPGCKTGA LMGCNMKT ATCNCSIHV SK | Lactococcus lactis subsp. lactis (Streptococcus lactis) | 227 | ATGAGTACAA AAGATTTTAA CTTGGATTTG GTATCTGTTTC GAAGAAAGAT TCAGGTGCAT CACCACGCAT TACAAGTATTT CGCTATGTAC ACCCGGTTGT AAAACAGGAG CTCTGATGGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TTGTAACATG AAAACAGCAA CTTGTAATTGT AGTATTCACG TAAGCAAATAA |
| 228 | Nukacin ISK-1 | Lantibiotic | MENSKVMK DIEVANLLE EVQEDELNE VLGAKKKSG VIPTVSHDC HMNSFQFVF TCCS | Staphylococcus warneri | 229 | ATGGAAAATT CTAAAGTTAT GAAGGACATT GAAGTAGCAA ATTTATTAGA AGAGGTTCAA GAAGATGAAT TGAATGAAGT CTTAGGAGCT AAGAAAAAGT CAGGAGTAAT CCCAACTGTG TCACACGATT GCCATATGAA TTCTTTCCAAT TTGTATTTACT TGTTGTTCATAA |
| 230 | Paenicidin A | Lantibiotic | MAENLFDLD IQVNKSQGS VEPQVLSIV ACSSGCGSG KTAASCVET CGNRCFTNV GSLC | Paenibacillus polymyxa (Bacillus polymyxa) | 231 | ATGGCTGAAA ACTTATTTGAT CTGGACATTC AAGTAAACAA ATCTCAAGGT TCTGTAGAGC CTCAGGTTCT GAGCATTGTT GCATGTTCTA GCGGATGTGG TAGCGGTAAA ACAGCTGCCA GTTGTGTTGA AACTTGTGGC AACCGGTGCT TTACTAACGTT GGTTCACTCT GCTAA |
| 232 | Pediocin PA-1 (Pediocin ACH) | class IIA/YG NGV | MKKIEKLTE KEMANIIGG KYYGNGVT CGKHSCSVD WGKATTCII NNGAMAWA TGGHQGNH KC | Pediococcus acidilactici | 233 | ATGAAAAAAA TTGAAAAATT AACTGAAAAA GAAATGGCCA ATATCATTGG TGGTAAATAC TACGGTAATG GGGTTACTTG TGGCAAACAT TCCTGCTCTGT TGACTGGGGT AAGGCTACCA CTTGCATAATC AATAATGGAG CTATGGCATG GGCTACTGGT GGACATCAAG GTAATCATAA ATGCTAG |
| 234 | Penocin A | class IIA/YG NGV | MTEIKVLND KELKNVVGG KYYGNGVH CGKKTCYVD WGQATASIG KIIVNGWTQ HGPWAHR | Pediococcus pentosaceus (strain ATCC 25745/183-1w) | 235 | ATGACTGAAA TTAAAGTACT AAACGATAAG GAACTAAAAA ATGTCGTAGG AGGAAAGTAT TACGGTAACG GAGTGCATTG TGGTAAAAAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ACTTGCTATGT GGACTGGGGA CAAGCTACAG CTAGCATTGG AAAAATTATA GTGAACGGAT GGACACAACA CGGGCCTTGG GCACATAGAT AA |
| 236 | Pep5 | Lantibiotic | MKNNKNLF DLEIKKETSQ NTDELEPQT AGPAIRASV KQCQKTLKA TRLFTVSCK GKNGCK | Staphylococcus epidermidis | 237 | ATGAAAAATA ACAAAAATTT ATTTGATTTAG AAATTAAAAA AGAAACAAGT CAAAACACTG ATGAACTTGA ACCTCAAACT GCTGGACCAG CGATTAGAGC TTCTGTGAAA CAATGTCAGA AAACTTTGAA AGCTACGCGT TTATTTACAGT GTCTTGCAAA GGAAAAAACG GATGTAAATAG |
| 238 | Piscicolin 126 | class IIA/YG NGV | MKTVKELSV KEMQLTTGG KYYGNGVS CNKNGCTV DWSKAIGIIG NNAAANLTT GGAAGWNKG | Carnobacterium maltaromaticum (Carnobacterium piscicola) | 239 | ATGAAAACTG TTAAAGAACT TAGCGTTAAA GAAATGCAAC TAACTACAGG AGGTAAGTAT TACGGAAATG GCGTTTCCTGT AATAAAAATG GTTGTACTGT AGATTGGAGC AAAGCTATTG GGATTATAGG AAACAATGCA GCAGCAAATT TGACTACAGG TGGAGCCGCT GGTTGGAACA AAGGATAA |
| 240 | Plantaricin 1.25 β | Unclassified | MYKELTVDE LALIDGGKK KKKKVACT WGNAATAA ASGAVXGIL GGPTGALAG AIWGVSQCA SNNLHGMH | Lactobacillus plantarum | 241 | ATGTATAAAG AATTAACAGT TGATGAATTA GCATTGATTG ATGGAGGAAA AAAGAAGAAG AAAAAAGTAG CTTGTACTTGG GGAAATGCAG CAACAGCCGC TGCTTCTGGT GCAGTTANGG GTATTCTTGGT GGGCCTACTG GTGCACTGGC TGGAGCTATC TGGGGCGTTT CACAATGCGC GTCTAACAAC TTACACGGCA TGCACTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 242 | Plantaricin 423 | class IIa | MMKKIEKLT EKEMANIIG GKYYGNGV TCGKHSCSV NWGQAFSCS VSHLANFGH GKC | Lactobacillus plantarum | 243 | ATGATGAAAA AAATTGAAAA ATTAACTGAA AAAGAAATGG CCAATATCATT GGTGGTAAAT ACTATGGTAA TGGGGTTACT TGTGGTAAAC ATTCCTGCTCT GTTAACTGGG GCCAAGCATT TTCTTGTAGTG TGTCACATTTA GCTACTTCG GTCATGGAAA GTGCTAA |
| 244 | Plantaricin ASM1 | Unclassified | MSKLVKTLT VDEISKIQTN GGKPAWCW YTLAMCGA GYDSGTCDY MYSHCFGVK HSSGGGGSY HC | Lactobacillus plantarum | 245 | ATGAGTAAAC TAGTTAAAAC ATTAACTGTC GATGAAATCT CTAAGATTCA AACCAATGGT GGAAAACCTG CATGGTGTTG GTACACATTG GCAATGTGCG GTGCTGGTTA TGATTCAGGC ACTTGTGATT ATATGTATTCA CACTGCTTTG GTGTAAAACA CTCTAGCGGT GGTGGCGGTA GCTACCATTG TTAG |
| 246 | Plantaricin E | Unclassified | MLQFEKLQY SRLPQKKLA KISGGFNRG GYNFGKSVR HVVDAIGSV AGIRGILKSIR | Lactobacillus plantarum | 247 | ATGCTACAGT TTGAGAAATT ACAATATTCC AGGTTGCCGC AAAAAAAGCT TGCCAAAATA TCTGGTGGTTT TAATCGGGGC GGTTATAACT TTGGTAAAAG TGTTCGACAT GTTGTTGATG CAATTGGTTC AGTTGCAGGC ATTCGTGGTA TTTTGAAAAG TATTCGTTAA |
| 248 | Plantaricin F | Class IIb | MKKFLVLRD RELNAISGG VFHAYSARG VRNNYKSAV GPADWVISA VRGFIHG | Lactobacillus plantarum | 249 | ATGAAAAAT TTCTAGTTTTG CGTGACCGTG AATTAAATGC TATTTCAGGT GGCGTTTTCC ATGCCTATAG CGCGCGTGGC GTTCGGAATA ATTATAAAAG TGCTGTTGGG CCTGCCGATT GGGTCATTAG CGCTGTCCGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGATTCATCC ACGGATAG |
| 250 | Plantaricin J | Class IIb | MTVNKMIK DLDVVDAFA PISNNKLNG VVGGGAWK NFWSSLRKG FYDGEAGRA IRR | Lactobacillus plantarum | 251 | ATGACTGTGA ACAAAATGAT TAAGGATTTG GATGTAGTAG ATGCATTTGC ACCTATTTCTA ATAATAAGTT GAACGGGGTT GTTGGGGGAG GCGCTTGGAA AAATTTCTGG TCTAGTTTAA GAAAAGGATT TTATGATGGC GAAGCTGGCA GAGCAATCCG TCGTTAA |
| 252 | Plantaricin K | Unclassified | MKIKLTVLN EFEELTADA EKNISGGRR SRKNGIGYAI GYAFGAVER AVLGGSRDY NK | Lactobacillus plantarum | 253 | ATGAAAATTA AATTAACTGTT TTAAATGAAT TTGAAGAATT AACTGCTGAC GCTGAAAAGA ATATTTCTGGT GGCCGTCGGA GTCGTAAAAA TGGAATTGGA TACGCTATTG GTTATGCGTTT GGCGCGGTTG AACGGGCCGT GCTTGGTGGT TCAAGGGATT ATAATAAGTGA |
| 254 | Plantaricin NC8α | Unclassified | MDKFEKIST SNLEKISGG DLTTKLWSS WGYYLGKK ARWNLKHP YVQF | Lactobacillus plantarum | 255 | ATGGATAAAT TTGAAAAAAT TAGTACATCT AACCTAGAAA AGATCTCTGG CGGTGATTTA ACAACCAAGT TATGGAGCTC TTGGGGATAT TATCTTGGCA AGAAAGCACG TTGGAATTTA AAGCACCCAT ATGTTCAATTT |
| 256 | Plantaricin NC8β | Unclassified | MNNLNKFST LGKSSLSQIE GGSVPTSVY TLGIKILWSA YKHRKTIEK SFNKGFYH | Lactobacillus plantarum | 257 | ATGAATAACT TGAATAAATT TTCTACTCTAG GCAAGAGTAG CTTGTCTCAA TTGAGGGCGG ATCAGTCCCA ACTTCAGTAT ATACGCTTGG AATTAAAATT CTATGGTCTG CGTATAAGCA TCGCAAAACG ATTGAAAAAA GTTTTAATAA AGGCTTTTATC ATTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 258 | Plantaricin Sα | Unclassified | MNNALSFEQ QFTDFSTLSD SELESVEGG RNKLAYNM GHYAGKATI FGLAAWALLA | Lactobacillus plantarum | 259 | ATGAATAACG CATTAAGTTTT GAACAACAAT TTACAGACTTC AGCACCTTAT CGGACTCTGA ATTAGAATCC GTTGAGGGTG GCCGAAATAA GCTTGCATAT AATATGGGGC ATTACGCTGG TAAGGCAACC ATTTTTGGACT TGCAGCATGG GCACTCCTTG CATGA |
| 260 | Plantaricin Sβ | Unclassified | MDKIIKFQGI SDDQLNAVI GGKKKKQS WYAAAGDAI VSFGEGFLN AW | Lactobacillus plantarum | 261 | ATGGATAAGA TTATTAAGTTT CAAGGGATTT CTGATGATCA ATTAAATGCT GTTATCGGTG GGAAAAAGAA AAAACAATCT TGGTACGCAG CAGCTGGTGA TGCAATCGTT AGTTTTGGTG AAGGATTTTT AAATGCTTGG TAA |
| 262 | Plantaricin Wα | Lantibiotic (two-peptide) | MKISKIEAQ ARKDFFKKI DTNSNLLNV NGAKCKWW NISCDLGNN GHVCTLSHE CQVSCN | Lactobacillus plantarum | 263 | ATGAAAATTT CTAAGATTGA AGCTCAGGCT CGTAAAGATT TTTTTAAAAA AATCGATACT AACTCGAACT TATTAAATGT AAATGGTGCC AAATGCAAGT GGTGGAATAT TTCGTGTGATT TAGGAAATAA TGGCCATGTTT GTACCTTGTC ACATGAATGC CAAGTATCTT GTAACTAA |
| 264 | Plantaricin Wβ | Lantibiotic (two-peptide) | MTKTSRRKN AIANYLEPV DEKSINESFG AGDPEARSG IPCTIGAAVA ASIAVCPTTK CSKRCGKRKK | Lactobacillus plantarum | 265 | ATGACTAAAA CTAGTCGTCG TAAGAATGCT ATTGCTAATTA TTTAGAACCA GTCGACGAAA AAAGTATTAA TGAATCTTTTG GGGCTGGGGA TCCGGAAGCA AGATCCGGAA TTCCATGTACA ATCGGCGCAG CTGTCGCAGC ATCAATTGCA GTTTGTCCAA CTACTAAGTG TAGTAAACGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGTGGCAAGC GTAAGAAATAA |
| 266 | Plantaricin-A | Unclassified | MKIQIKGMK QLSNKEMQK IVGGKSSAY SLQMGATAI KQVKKLFKK WGW | Lactobacillus plantarum (strain ATCC BAA-793/ NCIMB 8826/ WCFS1) | 267 | ATGAAAATTC AAATTAAAGG TATGAAGCAA CTTAGTAATA AGGAAATGCA AAAAATAGTA GGTGGAAAGA GTAGTGCGTA TTCTTTGCAGA TGGGGGCAAC TGCAATTAAA CAGGTAAAGA AACTGTTTAA AAAATGGGGA TGGTAA |
| 268 | Propionicin SM1 | Unclassified | MNKTHKMA TLVIAAILAA GMTAPTAYA DSPGNTRITA SEQSVLTQIL GHKPTQTEY NRYVETYGS VPTEADINA YIEASESEGS SSQTAAHDD STSPGTSTEI YTQAAPARF SMFFLSGTW ITRSGVVSLS LKPRKGGIG NEGDERTW KTVYDKFHN AGQWTRYK NNGVDASM KKQYMCHF KYGMVKTP WNLEPHKK AADVSPVKCN | Propionibacterium jensenii | 269 | ATGAACAAAA CACACAAAAT GGCGACGCTG GTAATTGCCG CGATCTTGGC CGCCGGAATG ACCGCACCAA CTGCCTATGC AGATTCTCCT GGAAACACCA GAATTACAGC CAGCGAGCAA AGCGTCCTTA CCCAGATACT CGGCCACAAA CCTACACAAA CTGAATATAA CCGATACGTT GAGACTTACG GAAGCGTACC GACCGAAGCA GACATCAACG CATATATAGA AGCGTCTGAA TCTGAGGGAT CATCAAGTCA AACGGCTGCT CACGATGACT CGACATCACC CGGCACGAGT ACCGAAATCT ACACGCAGGC AGCCCCTGCC AGGTTCTCAA TGTTTTTCCTG TCCGGAACTT GGATCACTAG GAGTGGTGTA GTATCGCTCTC CTTGAAGCCA AGGAAGGGTG GTATTGGCAA CGAGGGGAC GAGCGTACCT GGAAGACTGT ATACGACAAA TTCCATAACG CTGGGCAATG GACACGATAC AAGAACAACG GCGTAGACGC CAGCATGAAA AAGCAGTACA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGTGCCACTTC AAGTACGGGA TGGTGAAGAC GCCATGGAAT CTGGAGCCCC ACAAGAAGGC TGCAGACGTC AGTCCAGTCA AGTGCAACTAG |
| 270 | Propionicin T1 | Unclassified | MKKTLLRSG TIALATAAAF GASLAAAPS AMAVPGGC TYTRSNRDV IGTCKTGSG QFRIRLDCN NAPDKTSVW AKPKVMVS VHCLVGQPR SISFETK | Propionibacterium thoenii | 271 | ATGAAGAAGA CCCTCCTGCG AAGTGGAACG ATCGCACTGG CGACCGCGGC TGCATTTGGC GCATCATTGG CAGCCGCCCC ATCTGCCATG GCCGTTCCTG GTGGTTGCAC GTACACAAGA AGCAATCGCG ACGTCATCGG TACCTGCAAG ACTGGAAGCG GCCAGTTCCG AATCCGACTT GACTGCAACA ACGCTCCAGA CAAAACTTCA GTCTGGGCCA AGCCCAAGGT AATGGTGTCG GTTCACTGTCT TGTTGGTCAA CCGAGGTCCA TCTCGTTCGA GACCAAGTGA |
| 272 | Propionicin-F | Unclassified | MNTKAVNL KSENTTKLV SYLTENQLD EFIRRIRIDG ALVEEVSQN AKQALDNTG LNGWINTDC DEGLLSDFIS KIASARWIPL AESIRPAVTD RDKYRVSC WFYQGMNI AIYANIGGV ANIIGYTEAA VATLLGAVV AVAPVVPGT PTPPKDKSS QYKEVPLAV RLSETYHEE GVRGLFDEL NYSESRMIS TLRRASTDG VLINSWNDG QDTILLKKY NFQDLQLTV RSRIVGNQTI IEECKITDGR KTLSDETV | Propionibacterium freudenreichii subsp. freudenreichii | 273 | ATGAATACCA AAGCTGTAAA TCTGAAGTCA GAAAACACGA CTAAGTTGGT GAGCTACCTT ACGGAAAATC AATTGGATGA GTTTATTAGA AGGATTCGCA TTGATGGCGC TCTTGTGGAA GAGGTCAGTC AAAATGCTAA GCAGGCCTTA GATAATACTG GGCTCAATGG CTGGATAAAT ACTGATTGCG ATGAAGGCCT TCTCTCTGATT TCATTTCAAA GATAGCAAGT GCTAGATGGA TTCCATTAGCT GAGTCAATTC GACCTGCGGT GACTGACAGG GATAAGTATC GAGTAAGTTG CTGGTTCTACC AGGGGATGAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TATAGCAATTT ACGCAAATAT CGGTGGCGTG GCCAATATTA TCGGCTATAC GGAGGCCGCA GTCGCAACAC TCCTTGGTGC AGTTGTGGCG GTAGCTCCTG TGGTCCCTGG AACTCCAACC CCTCCAAAGG ACAAGAGTTC GCAATATAAG GAGGTTCCCC TTGCCGTTCGT CTTTCCGAAA CATACCACGA AGAGGGAGTA CGAGGTCTAT TCGACGAGCT GAACTACTCC GAGAGCCGTA TGATCTCTACT CTAAGGCGAG CATCAACCGA TGGAGTCCTA ATTAATTCTTG GAACGATGGG CAGGATACAA TTCTGCTTAAG AAGTACAATT TCCAAGACTT GCAACTGACT GTCAGGAGCC GCATTGTTGG GAATCAAACA ATAATTGAAG AATGCAAAAT CACTGATGGT AGAAAAACTC TTTCAGACGA GACTGTGTAG |
| 274 | Pyocin S1 | Unclassified | MARPIADLIH FNSTTVTAS GDVYYGPG GGTGIGPIAR PIEHGLDSST ENGWQEFES YADVGVDP RRYVPLQVK EKRREIELQF RDAEKKLEA SVQAELDKA DAALGPAKN LAPLDVINRS LTIVGNALQ QKNQKLLLN QKKITSLGA KNFLTRTAE EIGEQAVRE GNINGPEAY MRFLDREME GLTAAYNVK LFTEAISSLQI RMNTLTAAK ASIEAAAAN KAREQAAAE AKRKAEEQA RQQAAIRAA | Pseudomonas aeruginosa | 275 | ATGGCACGAC CCATTGCTGA CCTTATCCACT TCAACTCTAC AACTGTCACG GCAAGCGGAG ACGTTATTAC GGCCCTGGGG GAGGTACCGG CATTGGCCCC ATTGCCAGAC CTATAGAGCA CGGCTTGGAT TCGTCCACTG AAAATGGCTG GCAAGAGTTT GAAAGTTATG CTGATGTGGG CGTTGACCCC AGACGCTATG TTCCTCTTCAG GTTAAAGAAA AACGCAGGGA GATCGAGCTT CAGTTCCGAG ATGCCGAGAA AAAACTTGAG |

TABLE 1.2-continued

Exemplary Bacteriocins

| Poly-peptide SEQ ID NO: | Name | Class | Polypeptide Sequence | Organism of origin | Poly-nucleotide SEQ ID NO: | Polynucleotide Sequence |
|---|---|---|---|---|---|---|
| | | | NTYAMPAN | | | GCGTCGGTAC |
| | | | GSVVATAAG | | | AAGCCGAGCT |
| | | | RGLIQVAQG | | | GGATAAGGCT |
| | | | AASLAQAIS | | | GATGCCGCTC |
| | | | DAIAVLGRV | | | TTGGTCCGGC |
| | | | LASAPSVMA | | | AAAGAATCTT |
| | | | VGFASLTYS | | | GCACCATTGG |
| | | | SRTAEQWQ | | | ACGTCATCAA |
| | | | DQTPDSVRY | | | CCGCAGTCTG |
| | | | ALGMDAAK | | | ACCATCGTTG |
| | | | LGLPPSVNL | | | GAAACGCCCT |
| | | | NAVAKASGT | | | CCAGCAAAAG |
| | | | VDLPMRLTN | | | AATCAAAAAC |
| | | | EARGNTTTL | | | TACTGCTGAA |
| | | | SVVSTDGVS | | | TCAGAAGAAG |
| | | | VPKAVPVRM | | | ATTACCAGCC |
| | | | AAYNATTGL | | | TGGGTGCAAA |
| | | | YEVTVPSTT | | | GAATTTCCTTA |
| | | | AEAPPLILTW | | | CCCGTACGGC |
| | | | TPASPPGNQ | | | GGAAGAGATC |
| | | | NPSSTTPVVP | | | GGTGAACAAG |
| | | | KPVPVYEGA | | | CGGTGCGAGA |
| | | | TLTPVKATP | | | AGGCAATATT |
| | | | ETYPGVITLP | | | AACGGGCCTG |
| | | | EDLIIGFPAD | | | AAGCCTATAT |
| | | | SGIKPIYVMF | | | GCGCTTCCTC |
| | | | RDPRDVPGA | | | GACAGGGAAA |
| | | | ATGKGQPVS | | | TGGAAGGTCT |
| | | | GNWLGAAS | | | CACGGCAGCT |
| | | | QGEGAPIPSQ | | | TATAACGTAA |
| | | | IADKLRGKT | | | AACTCTTCACC |
| | | | FKNWRDFRE | | | GAAGCGATCA |
| | | | QFWIAVAND | | | GTAGTCTCCA |
| | | | PELSKQFNP | | | GATCCGCATG |
| | | | GSLAVMRD | | | AATACGTTGA |
| | | | GGAPYVRES | | | CCGCCGCCAA |
| | | | EQAGGRIKIE | | | AGCAAGTATT |
| | | | IHHKVRVAD | | | GAGGCGGCCG |
| | | | GGGVYNMG | | | CAGCAAACAA |
| | | | NLVAVTPKR | | | GGCGCGTGAA |
| | | | HIEIHKGGK | | | CAAGCAGCGG |
| | | | | | | CTGAGGCCAA |
| | | | | | | ACGCAAAGCC |
| | | | | | | GAAGAGCAGG |
| | | | | | | CCCGCCAGCA |
| | | | | | | AGCGGCGATA |
| | | | | | | AGAGCTGCCA |
| | | | | | | ATACCTATGC |
| | | | | | | CATGCCGGCC |
| | | | | | | AATGGCAGCG |
| | | | | | | TTGTCGCCAC |
| | | | | | | CGCCGCAGGC |
| | | | | | | CGGGGTCTGA |
| | | | | | | TCCAGGTCGC |
| | | | | | | ACAAGGCGCC |
| | | | | | | GCATCCCTTG |
| | | | | | | CTCAAGCGAT |
| | | | | | | CTCCGATGCG |
| | | | | | | ATTGCCGTCCT |
| | | | | | | GGGCCGGGTC |
| | | | | | | CTGGCTTCAG |
| | | | | | | CACCCTCGGT |
| | | | | | | GATGGCCGTG |
| | | | | | | GGCTTTGCCA |
| | | | | | | GTCTGACCTA |
| | | | | | | CTCCTCCCGG |
| | | | | | | ACTGCCGAGC |
| | | | | | | AATGGCAGGA |
| | | | | | | CCAAACGCCC |
| | | | | | | GATAGCGTTC |
| | | | | | | GTTACGCCCT |
| | | | | | | GGGCATGGAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCCGCTAAAT TGGGGCTTCC CCCAAGCGTA AACCTGAACG CGGTTGCAAA AGCCAGCGGT ACCGTCGATC TGCCGATGCG CCTGACCAAC GAGGCACGAG GCAACACGAC GACCCTTTCG GTGGTCAGCA CCGATGGTGT GAGCGTTCCG AAAGCCGTTC CGGTCCGGAT GGCGGCCTAC AATGCCACGA CAGGCCTGTA CGAGGTTACG GTTCCCTCTAC GACCGCAGAA GCGCCGCCAC TGATCCTGAC CTGGACGCCG GCGAGTCCTC CAGGAAACCA GAACCCTTCG AGTACCACTC CGGTCGTACC GAAGCCGGTG CCGGTATATG AGGGAGCGAC CCTTACACCG GTGAAGGCTA CCCCGGAAAC CTATCCTGGG GTGATTACAC TACCGGAAGA CCTGATCATC GGCTTCCCGG CCGACTCGGG GATCAAGCCG ATCTATGTGA TGTTCAGGGA TCCGCGGGAT GTACCTGGTG CTGCGACTGG CAAGGGACAG CCCGTCAGCG GTAATTGGCT CGGCGCCGCC TCTCAAGGTG AGGGGGCTCC AATTCCAAGC CAGATTGCGG ATAAACTACG TGGTAAGACA TTCAAAAACT GGCGGGACTT TCGGGAACAA TTCTGGATAG CTGTGGCTAA TGATCCTGAG TTAAGTAAAC AGTTTAATCCT GGTAGTTTAG CTGTAATGAG AGATGGAGGG GCTCCTTATGT CAGAGAGTCA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GAACAGGCTG GCGGGAGAAT AAAGATCGAA ATCCACCACA AGGTTCGAGT AGCAGATGGA GGCGGCGTTT ACAATATGGG GAACCTTGTT GCAGTAACGC CAAAACGTCA TATAGAAATC CACAAGGGAG GGAAGTGA |
| 276 | Pyocin S2 | colicin/pyosin nuclease family | MAVNDYEP GSMVITHVQ GGGRDIIQYI PARSSYGTPP FVPPGPSPYV GTGMQEYR KLRSTLDKS HSELKKNLK NETLKEVDE LKSEAGLPG KAVSANDIR DEKSIVDAL MDAKAKSL KAIEDRPAN LYTASDFPQ KSESMYQSQ LLASRKFYG EFLDRHMSE LAKAYSADI YKAQIAILK QTSQELENK ARSLEAEAQ RAAAEVEAD YKARKANV EKKVQSELD QAGNALPQL TNPTPEQWL ERATQLVTQ AIANKKKLQ TANNALIAK APNALEKQK ATYNADLLV DEIASLQARL DKLNAETAR RKEIARQAAI RAANTYAM PANGSVVAT AAGRGLIQV AQGAASLAQ AISDAIAVLG RVLASAPSV MAVGFASLT YSSRTAEQW QDQTPDSVR YALGMDAA KLGLPPSVN LNAVAKASG TVDLPMRLT NEARGNTTT LSVVSTDGV SVPKAVPVR MAAYNATT GLYEVTVPS TTAEAPPLIL TWTPASPPG NQNPSSTTP VVPKPVPVY | Pseudomonas aeruginosa (strain ATCC 15692/ PAO1/1C/ PRS 101/ LMG 12228) | 277 | ATGGCTGTCA ATGATTACGA ACCTGGTTCG ATGGTTATTA CACATGTGCA GGGTGGTGGG CGTGACATAA TCCAGTATATT CCTGCTCGAT CAAGCTACGG TACTCCACCAT TTGTCCCACCA GGACCAAGTC CGTATGTCGG TACTGGAATG CAGGAGTACA GGAAGCTAAG AAGTACGCTT GATAAGTCCC ATTCAGAACT CAAGAAAAAC CTGAAAAATG AAACCCTGAA GGAGGTTGAT GAACTCAAGA GTGAAGCGGG GTTGCCAGGT AAAGCGGTCA GTGCCAATGA CATCCGCGAT GAAAAGAGTA TCGTTGATGC ACTCATGGAT GCCAAAGCAA AATCGCTAAA GGCCATTGAG GATCGCCCGG CCAATCTTTAT ACGGCTTCAG ACTTTCCTCAG AAGTCAGAGT CGATGTACCA GAGTCAGTTG CTGGCCAGCC GAAAATTCTA TGGAGAGTTC CTGGATCGCC ATATGAGTGA GCTGGCCAAA GCGTACAGCG CCGATATCTAT AAGGCGCAAA TCGCTATCTTG AAACAAACGT CTCAAGAGCT GGAGAATAAA GCCCGGTCAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | EGATLTPVK | | | TGGAAGCAGA |
| | | | ATPETYPGVI | | | AGCCCAGCGA |
| | | | TLPEDLIIGFP | | | GCCGCTGCTG |
| | | | ADSGIKPIYV | | | AGGTGGAGGC |
| | | | MFRDPRDVP | | | GGACTACAAG |
| | | | GAATGKGQP | | | GCCAGGAAGG |
| | | | VSGNWLGA | | | CAAATGTCGA |
| | | | ASQGEGAPIP | | | GAAAAAGTG |
| | | | SQIADKLRG | | | CAGTCCGAGC |
| | | | KTFKNWRDF | | | TTGACCAGGC |
| | | | REQFWIAVA | | | TGGGAATGCT |
| | | | NDPELSKQF | | | TTGCCTCAACT |
| | | | NPGSLAVMR | | | GACCAATCCA |
| | | | DGGAPYVRE | | | ACGCCAGAGC |
| | | | SEQAGGRIKI | | | AGTGGCTTGA |
| | | | EIHHKVRIA | | | ACGCGCTACT |
| | | | DGGGVYNM | | | CAACTGGTTA |
| | | | GNLVAVTPK | | | CGCAGGCGAT |
| | | | RHIEIHKGGK | | | CGCCAATAAG |
| | | | | | | AAGAAATTGC |
| | | | | | | AGACTGCAAA |
| | | | | | | CAATGCCTTG |
| | | | | | | ATTGCCAAGG |
| | | | | | | CACCCAATGC |
| | | | | | | ACTGGAGAAA |
| | | | | | | CAAAAGGCAA |
| | | | | | | CCTACAACGC |
| | | | | | | CGATCTCCTA |
| | | | | | | GTGGATGAAA |
| | | | | | | TCGCCAGCCT |
| | | | | | | GCAAGCACGG |
| | | | | | | CTGGACAAGC |
| | | | | | | TGAACGCCGA |
| | | | | | | AACGGCAAGG |
| | | | | | | CGCAAGGAAA |
| | | | | | | TCGCTCGTCA |
| | | | | | | AGCGGCGATC |
| | | | | | | AGGGCTGCCA |
| | | | | | | ATACTTATGCC |
| | | | | | | ATGCCAGCCA |
| | | | | | | ATGGCAGCGT |
| | | | | | | TGTCGCCACC |
| | | | | | | GCCGCAGGCC |
| | | | | | | GGGGTCTGAT |
| | | | | | | CCAGGTCGCA |
| | | | | | | CAAGGCGCCG |
| | | | | | | CATCCCTTGCT |
| | | | | | | CAAGCGATCT |
| | | | | | | CCGATGCGAT |
| | | | | | | TGCCGTCCTG |
| | | | | | | GGCCGGGTCC |
| | | | | | | TGGCTTCAGC |
| | | | | | | ACCCTCGGTG |
| | | | | | | ATGGCCGTGG |
| | | | | | | GCTTTGCCAG |
| | | | | | | TCTGACCTACT |
| | | | | | | CCTCCCGGAC |
| | | | | | | TGCCGAGCAA |
| | | | | | | TGGCAGGACC |
| | | | | | | AAACGCCCGA |
| | | | | | | TAGCGTTCGTT |
| | | | | | | ACGCCCTGGG |
| | | | | | | CATGGATGCC |
| | | | | | | GCTAAATTGG |
| | | | | | | GGCTTCCCCC |
| | | | | | | AAGCGTAAAC |
| | | | | | | CTGAACGCGG |
| | | | | | | TTGCAAAAGC |
| | | | | | | CAGCGGTACC |
| | | | | | | GTCGATCTGC |
| | | | | | | CGATGCGCCT |
| | | | | | | GACCAACGAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCACGAGGCA ACACGACGAC CCTTTCGGTG GTCAGCACCG ATGGTGTGAG CGTTCCGAAA GCCGTTCCGG TCCGGATGGC GGCCTACAAT GCCACGACAG GCCTGTACGA GGTTACGGTT CCCTCTACGA CCGCAGAAGC GCCGCCACTG ATCCTGACCT GGACGCCGGC GAGTCCTCCA GGAAACCAGA ACCCTTCGAG TACCACTCCG GTCGTACCGA AGCCGGTGCC GGTATATGAG GGAGCGACCC TTACACCGGT GAAGGCTACC CCGGAAACCT ATCCTGGGGT GATTACACTA CCGGAAGACC TGATCATCGG CTTCCCGGCC GACTCGGGGA TCAAGCCGAT CTATGTGATG TTCAGGGATC CGCGGGATGT ACCTGGTGCT GCGACTGGCA AGGGACAGCC CGTCAGCGGT AATTGGCTCG GCGCCGCCTC TCAAGGTGAG GGGGCTCCAA TTCCAAGCCA GATTGCGGAT AAACTACGTG GTAAGACATT CAAAAACTGG CGGGACTTTC GGGAACAATT CTGGATAGCT GTGGCTAATG ATCCTGAGTT AAGTAAACAG TTTAATCCTGG TAGTTTAGCT GTAATGAGAG ATGGAGGGGC TCCTTATGTCA GAGAGTCAGA ACAGGCTGGC GGGAGAATAA AGATCGAAAT CCACCACAAG GTTCGAATAG CAGATGGAGG CGGCGTTTAC AATATGGGGA ACCTTGTTGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AGTAACGCCA AAACGTCATA TAGAAATCCA CAAGGGAGGG AAGTGA |
| 278 | Ruminococcin-A | Lantibiotic | MRNDVLTLT NPMEEKELE QILGGGNGV LKTISHECN MNTWQFLFT CC | Ruminococcus gnavus | 279 | ATGAGAAATG ACGTATTAAC ATTAACAAAC CCAATGGAAG AGAACGAACT GGAGCAGATC TTAGGTGGTG GCAATGGTGT GTTAAAAACG ATTAGCCACG AATGCAATAT GAACACATGG CAGTTCCTGTT TACTTGTTGCT AA |
| 280 | Sakacin G | Class IIa | MKNAKSLTI QEMKSITGG KYYGNGVS CNSHGCSVN WGQAWTCG VNHLANGG HGVC | Lactobacillus sakei | 281 | ATGAAAAACG CAAAAAGCCT AACAATTCAA GAAATGAAAT CTATTACAGG TGGTAAATAC TATGGTAATG GCGTTAGCTG TAACTCTCAC GGCTGTTCAG TAAATTGGGG GCAAGCATGG ACTTGTGGAG TAAACCATCT AGCTAATGGC GGTCATGGAG TTTGTTAA |
| 282 | Sakacin-A | class IIA/YG NGV | MNNVKELS MTELQTITG GARSYGNG VYCNNKKC WVNRGEAT QSIIGGMISG WASGLAGM | Lactobacillus sakei | 283 | ATGAATAATG TAAAAGAATT AAGTATGACA GAATTACAAA CAATTACCGG CGGTGCTAGA TCATATGGCA ACGGTGTTTA CTGTAATAAT AAAAAAATGTT GGGTAAATCG GGGTGAAGCA ACGCAAAGTA TTATTGGTGG TATGATTAGC GGCTGGGCTA GTGGTTTAGC TGGAATGTAA |
| 284 | Sakacin-P (Sakacin 674) | class IIA/YG NGV | MEKFIELSLK EVTAITGGK YYGNGVHC GKHSCTVD WGTAIGNIG NNAAANWA TGGNAGWNK | Lactobacillus sakei | 285 | ATGGAAAAGT TTATTGAATTA TCTTTAAAAG AAGTAACAGC AATTACAGGT GGAAAATATT ATGGTAACGG TGTACACTGT GGAAAACATT CATGTACCGT AGACTGGGGA ACAGCTATTG GAAATATCGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAATAATGCA GCTGCAAACT GGGCCACAGG CGGAAACGCT GGCTGGAATA AATAA |
| 286 | Salivaricin 9 | lantibiotic | MKSTNNQSI AEIAAVNSL QEVSMEELD QIIGAGNGV VLTLTHECN LATWTKKLK CC | Streptococcus salivarius | 287 | ATGAAATCAA CAAATAATCA AAGTATCGCA GAAATTGCAG CAGTAAACTC ACTACAAGAA GTAAGTATGG AGGAACTAGA CCAAATTATT GGTGCCGGAA ACGGAGTGGT TCTTACTCTTA CTCATGAATG TAACCTAGCA ACTTGGACAA AAAAACTAAA ATGTTGCTAA |
| 288 | Salivaricin A | Lantibiotic | MSFMKNSK DILTNAIEEV SEKELMEVA GGKKGSGW FATITDDCPN SVFVCC | Streptococcus pyogenes serotype M28 (strain MGAS6180) | 289 | ATGAGTTTTAT GAAAAATTCA AAGGATATTT TGACTAATGC TATCGAAGAA GTTTCTGAAA AAGAACTTAT GGAAGTAGCT GGTGGTAAAA AAGGTTCCGG TTGGTTTGCA ACTATTACTG ATGACTGTCC GAACTCAGTA TTCGTTTGTTG TTAA |
| 290 | Salivaricin A3 | Lantibiotic | MKNSKDVL NNAIEEVSE KELMEVAG GKKGPGWIA TITDDCPNSI FVCC | Streptococcus salivarius | 291 | ATGAAAAACT CAAAAGATGT TTTGAACAAT GCTATCGAAG AGGTTTCTGA AAAAGAACTT ATGGAAGTAG CTGGTGGTAA AAAAGGTCCA GGTTGGATTG CAACTATTACT GATGACTGTC CAAACTCAAT ATTCGTTTGTT GTTAA |
| 292 | Salivaricin-A sa | Lantibiotic | MKNSKDILN NAIEEVSEKE LMEVAGGK RGSGWIATIT DDCPNSVFV CC | Streptococcus salivarius | 293 | ATGAAAAACT CAAAAGATAT TTTGAACAAT GCTATCGAAG AAGTTTCTGA AAAAGAACTT ATGGAAGTAG CTGGTGGTAA AAGAGGTTCA GGTTGGATTG CAACTATTACT GATGACTGTC CAAACTCAGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ATTCGTTTGTT GTTAA |
| 294 | Staphylococcin C55 alpha | Lantibiotic (two-peptide) | MKSSFLEKDI EEQVTWFEE VSEQEFDDD IFGACSTNTF SLSDYWGNK GNWCTATH ECMSWCK | Staphylococcus aureus | 295 | ATGAAAAGTT CTTTTTTAGAA AAAGATATAG AAGAACAAGT GACATGGTTC GAGGAAGTTT CAGAACAAGA ATTTGACGAT GATATTTTTGG AGCTTGTAGT ACAAACACTT TTTCTTTGAGT GACTATTGGG GTAATAAAGG AAATTGGTGT ACTGCTACTC ACGAATGTAT GTCTTGGTGT AAATAA |
| 296 | Staphylococcin C55 beta | Lantibiotic (two-peptide) | MKNELGKFL EENELELGK FSESDMLEIT DDEVYAAG TPLALLGGA ATGVIGYISN QTCPTTACT RAC | Staphylococcus aureus | 297 | ATGAAAAATG AATTAGGTAA GTTTTTAGAA GAAAACGAAT TAGAGTTAGG TAAATTTTCAG AATCAGACAT GCTAGAAATT ACTGATGATG AAGTATATGC AGCTGGAACA CCTTTAGCCTT ATTGGGTGGA GCTGCCACCG GGGTGATAGG TTATATTTCTA ACCAAACATG TCCAACAACT GCTTGTACAC GCGCTTGCTAG |
| 298 | Streptin | lantibiotic | MNNTIKDFD LDLKTNKKD TATPYVGSR YLCTPGSCW KLVCFTTTVK | Streptococcus pyogenes | 299 | ATGAATAACA CAATTAAAGA CTTTGATCTCG ATTTGAAAAC AAATAAAAAA GACACTGCTA CACCTTATGTT GGTAGCCGTT ACCTATGTAC CCCTGGTTCTT GTTGGAAATT AGTTTGCTTTA CAACAACTGT TAAATAA |
| 300 | Streptococcin A-FF22 | Lantibiotic | MEKNNEVIN SIQEVSLEEL DQIIGAGKN GVFKTISHEC HLNTWAFLA TCCS | Streptococcus pyogenes | 301 | ATGGAAAAAA ATAATGAAGT AATCAACTCT ATTCAAGAAG TTAGTCTTGA AGAACTCGAT CAAATTATCG GTGCTGGAAA AAATGGTGTG TTTAAAACAA TTTCTCATGAG TGTCATTTGA ATACATGGGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ATTCCTTGCTACTTGTTGTTCATAA |
| 302 | Streptococcin A-M49 | Lantibiotic | MTKEHEIINSIQEVSLEELDQIIGAGKNGVFKTISHECHLNTWAFLATCCS | Streptococcus pyogenes serotype M49 | 303 | ATGGAAAAAATAATGAAGTAATCAACTCTATTCAAGAAGTTAGTCTTGAAGAACTCGATCAAATTATCGGTGCTGGAAAAAATGGTGTGTTTAAAACAATTTCTCATGAGTGTCATTTGAATACATGGGCATTCCTTGCTACTTGTTGCTCATAA |
| 304 | Sublancin 168 | Lantibiotic | MEKLFKEVKLEELENQKGSGLGKAQCAALWLQCASGGTIGCGGGAVACQNYRQFCR | Bacillus subtilis (strain 168) | 305 | ATGGAAAAGCTATTTAAAGAAGTTAAACTAGAGGAACTCGAAAACCAAAAAGGTAGTGGATTAGGAAAAGCTCAGTGTGCTGCGTTGTGGCTACAATGTGCTAGTGGCGGTACAATTGGTTGTGGTGGCGGAGCTGTTGCTTGTCAAAACTATCGTCAATTCTGCAGATAA |
| 306 | Subtilin | Lantibiotic | MSKFDDFDLDVVKVSKQDSKITPQWKSESLCTPGCVTGALQTCFLQTLTCNCKISK | Bacillus subtilis | 307 | ATGTCAAAGTTCGATGATTTCGATTTGGATGTTGTGAAAGTCTCTAAACAAGACTCAAAAATCACTCCGCAATGGAAAAGTGAATCACTTTGTACACCAGGATGTGTAACTGGTGCATTGCAAACTTGCTTCCTTCAAACACTAACTTGTAACTGCAAAATCTCTAAATAA |
| 308 | Subtilosin | Unclassified | MKLPVQQVYSVYGGKDLPKGHSHSTMPFLSKLQFLTKIYLLDIHTQPFFI | Bacillus subtilis (strain 168) | 309 | TTGAAATTGCCGGTGCAACAGGTCTATTCGGTCTATGGGGGTAAGGATCTCCCAAAAGGGCATAGTCATTCTACTATGCCCTTTTTAAGTAAATTACAATTTTTAACTAAAATCTACCTCTTGGATATACATACACAACCGTTTTTCATTTGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 310 | Subtilosin-A | Unclassified | MKKAVIVEN KGCATCSIG AACLVDGPI PDFEIAGAT GLFGLWG | *Bacillus subtilis* (strain 168) | 311 | ATGAAAAAG CTGTCATTGTA GAAAACAAAG GTTGTGCAAC ATGCTCGATC GGAGCCGCTT GTCTAGTGGA CGGTCCTATC CCTGATTTTGA AATTGCCGGT GCAACAGGTC TATTCGGTCTA TGGGGGTAA |
| 312 | Thermophilin 1277 | Lantibiotic | MMNATENQI FVETVSDQE LEMLIGGAD RGWIKTLTK DCPNVISSIC AGTIITACKN CA | *Streptococcus thermophilus* | 313 | ATGATGAATG CTACTGAAAA CCAAATTTTTG TTGAGACTGT GAGTGACCAA GAATTAGAAA TGTTAATTGGT GGTGCAGATC GTGGATGGAT TAAGACTTTA ACAAAAGATT GTCCAAATGT AATTTCTTCAA TTTGTGCAGG TACAATTATTA CAGCCTGTAA AAATTGTGCT TAA |
| 314 | Thermophilin 13 | Unclassified | MKQYNGFE VLHELDLAN VTGGQINWG SVVGHCIGG AIIGGAFSGG AAAGVGCL VGSGKAIIN GL | *Streptococcus thermophilus* | 315 | ATGAAGCAGT ATAATGGTTTT GAGGTTCTAC ATGAACTTGA CTTAGCAAAT GTAACTGGCG GTCAAATTAA TTGGGGATCA GTTGTAGGAC ACTGTATAGG TGGAGCTATT ATCGGAGGTG CATTTTCAGG AGGTGCAGCG GCTGGAGTAG GATGCCTTGTT GGGAGCGGAA AGGCAATCAT AAATGGATTA TAA |
| 316 | Thermophilin A | Unclassified | MNTITICKFD VLDAELLST VEGGYSGKD CLKDMGGY ALAGAGSGA LWGAPAGG VGALPGAFV GAHVGAIAG GFACMGGMI GNKFN | *Streptococcus thermophilus* | 317 | ATGAATACAA TAACTATTTGT AAATTTGATG TTTTAGATGCT GAACTTCTTTC GACAGTTGAG GGTGGATACT CTGGTAAGGA TTGTTTAAAA GACATGGGAG GATATGCATT GGCAGGAGCT GGAAGTGGAG CTCTGTGGGG AGCTCCAGCA GGAGGTGTTG GAGCACTTCC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AGGTGCATTT GTCGGAGCTC ATGTTGGGGC AATTGCAGGA GGCTTTGCAT GTATGGGTGG AATGATTGGT AATAAGTTTA ACTAA |
| 318 | Thiocillin (Micrococcin P1) (Micrococcin P2) (Thiocillin I) (Thiocillin II) (Thiocillin III) (Thiocillin IV) (Antibiotic YM-266183) (Antibiotic YM-266184) | Unclassified | MSEIKKALN TLEIEDFDAI EMVDVDAM PENEALEIM GASCTTCVC TCSCCTT | Bacillus cereus (strain ATCC 14579/ DSM 31) | 319 | ATGAGTGAAA TTAAAAAGC ATTAAATACG CTTGAAATTG AAGATTTTGA TGCAATTGAA ATGGTTGATG TTGATGCTAT GCCAGAAAAC GAAGCGCTTG AAATTATGGG AGCGTCATGT ACGACATGCG TATGTACATG CAGTTGTTGT ACAACTTGA |
| 320 | Thuricin CD alpha | two-peptide lantibiotic | MEVMNNALI TKVDEEIGG NAACVIGCI GSCVISEGIG SLVGTAFTLG | Bacillus cereus 95/8201 | 321 | ATGGAAGTTA TGAACAATGC TTTAATTACAA AAGTAGATGA GGAGATTGGA GGAAACGCTG CTTGTGTAATT GGTTGTATTG GCAGTTGCGT AATTAGTGAA GGAATTGGTT CACTTGTAGG AACAGCATTT ACTTTAGGTT AA |
| 322 | Thuricin CD beta | two-peptide lantibiotic | MEVLNKQN VNIIPESEEV GGWVACVG ACGTVCLAS GGVGTEFAA ASYFL | Bacillus cereus 95/8201 | 323 | ATGGAAGTTT TAAACAAACA AAATGTAAAT ATTATTCCAG AATCTGAAGA AGTAGGTGGA TGGGTAGCAT GTGTTGGAGC ATGTGGTACA GTATGTCTTGC TAGTGGTGGT GTTGGAACAG AGTTTGCAGC TGCATCTTATT TCCTATAA |
| 324 | Thuricin-17 | Class IId | METPVVQPR DWTCWSCL VCAACSVEL LNLVTAATG ASTAS | Bacillus thuringiensis | 325 | ATGGAAACAC CAGTAGTACA ACCAAGGGAT TGGACTTGTT GGAGTTGCTT AGTATGTGCA GCATGTTCTGT GGAATTATTA AATTTAGTTAC TGCGGCAACA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGGGCTAGTA CTGCAAGCTAA |
| 326 | Trifolitoxin | Unclassified | MDNKVAKN VEVKKGSIK ATFKAAVLK SKTKVDIGG SRQGCVA | Rhizobium leguminosarum bv. trifolii | 327 | ATGGATAACA AGGTTGCGAA GAATGTCGAA GTGAAGAAGG GCTCCATCAA GGCGACCTTC AAGGCTGCTG TTCTGAAGTC GAAGACGAAG GTCGACATCG GAGGTAGCCG TCAGGGCTGC GTCGCTTAA |
| 328 | Ubericin A | Class IIa | MNTIEKFENI KLFSLKKIIG GKTVNYGN GLYCNQKKC WVNWSETA TTIVNNSIM NGLTGGNA GWHSGGRA | Streptococcus uberis | 329 | ATGAATACAA TTGAAAAATT TGAAAATATT AAACTTTTTC ACTAAAGAAA ATTATCGGTG GCAAAACTGT AAATTATGGT AATGGCCTTT ATTGTAACCA AAAAAAATGC TGGGTAAACT GGTCAGAAAC TGCTACAACA ATAGTAAATA ATTCCATCATG AACGGGCTCA CAGGTGGTAA TGCGGGTTGG CACTCAGGCG GGAGAGCATAA |
| 330 | Uberolysin | Unclassified | MDILLELAG YTGIASGTA KKVVDAIDK GAAAFVIISII STVISAGAL GAVSASADF IILTVKNYIS RNLKAQAVIW | Streptococcus uberis | 331 | ATGGACATTT TATTAGAACT CGCAGGATAT ACTGGGATAG CCTCAGGTAC TGCAAAAAAA GTTGTTGATG CCATTGATAA AGGAGCTGCA GCCTTTGTTAT TATTTCAATTA TCTCAACAGT AATTAGTGCG GGAGCATTGG GAGCAGTTTC AGCCTCAGCT GATTTTATTAT TTTAACTGTAA AAAATTACAT TAGTAGAAAT TTAAAAGCAC AAGCTGTCAT TTGGTAA |
| 332 | UviB | Unclassified | MDSELFKLM ATQGAFAILF SYLLFYVLK ENSKREDKY QNIIEELTEL LPKIKEDVE DIKEKLNK | Clostridium perfringens | 333 | ATGGATAGTG AATTATTTAA GTTAATGGCA ACACAAGGAG CCTTTGCAATA TTATTTTCGTA TTTATTGTTTT ATGTTTTAAA AGAGAATAGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAAAGAGAAG ATAAGTATCA AAATATAATA GAGGAGCTTA CAGAATTATT GCCAAAAATA AAAGAAGATG TAGAAGATAT AAAAGAAAAA CTTAATAAAT AG |
| 334 | Variacin | Lantibiotic, Type A | MTNAFQALD EVTDAELDA ILGGGSGVIP TISHECHMN SFQFVFTCCS | *Micrococcus varians* | 335 | ATGACGAACG CATTTCAGGC ACTGGACGAA GTCACGGACG CCGAGCTCGA CGCCATCCTT GGCGGGGGCA GTGGTGTTAT TCCCACGATC AGCCACGAGT GCCACATGAA CTCCTTCCAGT TCGTGTTCACC TGCTGCTCCTGA |
| 336 | Zoocin A | Unclassified | MKRIFFAFLS LCLFIFGTQT VSAATYTRP LDTGNITTGF NGYPGHVG VDYAVPVGT PVRAVANGT VKFAGNGA NHPWMLWM AGNCVLIQH ADGMHTGY AHLSKISVST DSTVKQGQII GYTGATGQ VTGPHLHFE MLPANPNW QNGFSGRID PTGYIANAP VFNGTTPTE PTTPTTNLKI YKVDDLQKI NGIWQVRN NILVPTDFT WVDNGIAA DDVIEVTSN GTRTSDQVL QKGGYFVIN PNNVKSVGT PMKGSGGLS WAQVNFTT GGNVWLNT TSKDNLLYGK | *Streptococcus equi* subsp. *zooepidemicus* | 337 | ATGAAACGTA TATTTTTTGCT TTCTTAAGTTT ATGCTTATTTA TATTCGGAAC ACAAACGGTA TCTGCAGCTA CTTATACTCG GCCATTAGAT ACGGGAAATA TCACTACAGG GTTTAACGGA TACCCTGGTC ATGTTGGAGT CGATTATGCA GTACCCGTTG GAACTCCGGT TAGAGCAGTT GCAAATGGTA CAGTCAAATT TGCAGGTAAT GGGGCTAATC ACCCATGGAT GCTTTGGATG GCTGGAAACT GTGTTCTAATT CAACATGCTG ACGGGATGCA TACTGGATAT GCACACTTAT CAAAAATTTC AGTTAGCACA GATAGTACAG TTAAACAAGG ACAAATCATA GGTTATACTG GTGCCACCGG CCAAGTTACC GGTCCACATT TGCATTTTGA AATGTTGCCA GCAAATCCTA ACTGGCAAAA TGGTTTTTCTG GAAGAATAGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TCCAACCGGA TACATCGCTA ATGCCCCTGT ATTTAATGGA ACAACACCTA CAGAACCTAC TACTCCTACA ACAAATTTAA AAATCTATAA AGTTGATGAT TTACAAAAAA TTAATGGTATT TGGCAAGTAA GAAATAACAT ACTTGTACCA ACTGATTTCAC ATGGGTTGAT AATGGAATTG CAGCAGATGA TGTAATTGAA GTAACTAGCA ATGGAACAAG AACCTCTGAC CAAGTTCTTCA AAAAGGTGGT TATTTTGTCAT CAATCCTAAT AATGTTAAAA GTGTTGGAAC TCCGATGAAA GGTAGTGGTG GTCTATCTTGG GCTCAAGTAA ACTTTACAAC AGGTGGAAAT GTCTGGTTAA ATACTACTAG CAAAGACAAC TTACTTTACGG AAAATAA |
| 338 | Fulvocin-C | Unclassified | ANCSCSTAS DYCPILTFCT TGTACSYTP TGCGTGWV YCACNGNFY | *Myxococcus fulvus* | 339 | GCGAACTGCA GCTGCAGCAC CGCGAGCGAT TATTGCCCGA TTCTGACCTTT TGCACCACCG GCACCGCGTG CAGCTATACC CCGACCGGCT GCGGCACCGG CTGGGTGTAT TGCGCGTGCA ACGGCAACTT TTAT |
| 340 | Duramycin-C | Lantibiotic | CANSCSYGP LTWSCDGNTK | *Streptomyces griseoluteus* | 341 | TGCGCGAACA GCTGCAGCTA TGGCCCGCTG ACCTGGAGCT GCGATGGCAA CACCAAA |
| 342 | Duramycin (duramycin-B) (Leucopeptin) | Lantibiotic B | CKQSCSFGPF TFVCDGNTK | *Streptoverticillium griseoverticillatum* | 343 | TGCAAACAGA GCTGCAGCTT TGGCCCGTTT ACCTTTGTGTG CGATGGCAAC ACCAAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 344 | Carnocin UI49 | lantibiotic | GSEIQPR | Carnobacterium sp. (strain UI49) | 345 | GGCAGCGAAA TTCAGCCGCGC |
| 346 | Lactococcin-Gα | Unclassified | GTWDDIGQG IGRVAYWVG KAMGNMSD VNQASRINR KKKH | Lactococcus lactis subsp. lactis (Streptococcus lactis) | 347 | GGCACCTGGG ATGATATTGG CCAGGGCATT GGCCGCGTGG CGTATTGGGT GGGCAAAGCG ATGGGCAACA TGAGCGATGT GAACCAGGCG AGCCGCATTA ACCGCAAAAA AAAACAT |
| 348 | Lactococcin-Gβ | Unclassified | KKWGWLAW VDPAYEFIK GFGKGAIKE GNKDKWKNI | Lactococcus lactis subsp. lactis (Streptococcus lactis) | 349 | AAAAAATGGG GCTGGCTGGC GTGGGTGGAT CCGGCGTATG AATTTATTAA AGGCTTTGGC AAAGGCGCGA TTAAAGAAGG CAACAAAGAT AAATGGAAAA ACATT |
| 350 | Ancovenin | Lantibiotic | CVQSCSFGP LTWSCDGNTK | Streptomyces sp. (strain A647P-2) | 351 | TGCGTGCAGA GCTGCAGCTT TGGCCCGCTG ACCTGGAGCT GCGATGGCAA CACCAAA |
| 352 | Actagardine (Gardimycin) | Lantibiotic | SSGWVCTLT IECGTVICAC | Actinoplanes liguriae | 353 | AGCAGCGGCT GGGTGTGCAC CCTGACCATT GAATGCGGCA CCGTGATTTG CGCGTGC |
| 354 | Curvaticin FS47 | Unclassified | YTAKQCLQA IGSCGIAGTG AGAAGGPA GAFVGAXV VXI | Lactobacillus curvatus | 355 | TATACCGCGA AACAGTGCCT GCAGGCGATT GGCAGCTGCG GCATTGCGGG CACCGGCGCG GGCGCGGCGG GCGGCCCGGC GGGCGCGTTT GTGGGCGCGN NNGTGGTGNN NATT [IN WHICH NNN = ANY AMINO-ACID CODING TRIPLET] |
| 356 | Bavaricin-MN | class IIA/YG NGV | TKYYGNGV YCNSKKCW VDWGQAAG GIGQTVVXG WLGGAIPGK | Lactobacillus sakei | 357 | ACCAAATATT ATGGCAACGG CGTGTATTGC AACAGCAAAA AATGCTGGGT GGATTGGGGC CAGGCGGCGG GCGGCATTGG CCAGACCGTG GTGNNNGGCT GGCTGGGCGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CGCGATTCCG GGCAAA[IN WHICH NNN = ANY AMINO-ACID CODING TRIPLET] |
| 358 | Mutacin B-Ny266 | Lantibiotic | FKSWSFCTP GCAKTGSFN SYCC | Streptococcus mutans | 359 | TTTAAAAGCT GGAGCTTTTG CACCCCGGGC TGCGCGAAAA CCGGCAGCTT TAACAGCTAT TGCTGCTTTAA AAGCTGGAGC TTTTGCACCCC GGGCTGCGCG AAAACCGGCA GCTTTAACAG CTATTGCTGC |
| 360 | Mundticin | class IIA/YG NGV | KYYGNGVS CNKKGCSVD WGKAIGIIGN NSAANLATG GAAGWSK | Enterococcus mundtii | 361 | AAATATTATG GCAACGGCGT GAGCTGCAAC AAAAAAGGCT GCAGCGTGGA TTGGGGCAAA GCGATTGGCA TTATTGGCAA CAACAGCGCG GCGAACCTGG CGACCGGCGG CGCGGCGGGC TGGAGCAAA |
| 362 | Bavaricin-A | class IIA/YG NGV | KYYGNGVH XGKHSXTVD WGTAIGNIG NNAAANXA TGXNAGG | Lactobacillus sakei | 363 | AAATATTATG GCAACGGCGT GCATNNNGGC AAACATAGCN NNACCGTGGA TTGGGGCACC GCGATTGGCA ACATTGGCAA CAACGCGGCG GCGAACNNNG CGACCGGCNN NAACGCGGGC GGC [IN WHICH NNN = ANY AMINO-ACID CODING TRIPLET] |
| 364 | Lactocin-705 | Class IIb | GMSGYIQGI PDFLKGYLH GISAANKHK KGRL | Lactobacillus paracasei | 365 | GGCATGAGCG GCTATATTCA GGGCATTCCG GATTTTCTGA AAGGCTATCT GCATGGCATT AGCGCGGCGA ACAAACATAA AAAAGGCCGC CTG |
| 366 | Leucocin-B | Unclassified | KGKGFWSW ASKATSWLT GPQQPGSPL LKKHR | Leuconostoc mesenteroides | 367 | AAAGGCAAAG GCTTTTGGAG CTGGGCGAGC AAAGCGACCA GCTGGCTGAC CGGCCCGCAG CAGCCGGGCA GCCCGCTGCT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GAAAAAACAT CGC |
| 368 | Leucocin C | class IIA/YG NGV | KNYGNGVH CTKKGCSVD WGYAWTNI ANNSVMNG LTGGNAGW HN | Leuconostoc mesenteroides | 369 | AAAAACTATG GCAACGGCGT GCATTGCACC AAAAAAGGCT GCAGCGTGGA TTGGGGCTAT GCGTGGACCA ACATTGCGAA CAACAGCGTG ATGAACGGCC TGACCGGCGG CAACGCGGGC TGGCATAAC |
| 370 | LCI | Unclassified | AIKLVQSPN GNFAASFVL DGTKWIFKS KYYDSSKGY WVGIYEVW DRK | Bacillus subtilis | 371 | GCGATTAAAC TGGTGCAGAG CCCGAACGGC AACTTTGCGG CGAGCTTTGT GCTGGATGGC ACCAAATGGA TTTTTAAAAGC AAATATTATG ATAGCAGCAA AGGCTATTGG GTGGGCATTT ATGAAGTGTG GGATCGCAAA |
| 372 | Lichenin | Unclassified | ISLEICXIFHDN | Bacillus licheniformis | 373 | ATTAGCCTGG AAATTTGCNN NATTTTTCATG ATAAC [IN WHICH NNN = ANY AMINO-ACID CODING TRIPLET] |
| 374 | Lactococcin MMFII | class IIA/YG NGV | TSYGNGVHC NKSKCWIDV SELETYKAG TVSNPKDILW | Lactococcus lactis subsp. lactis (Streptococcus lactis) | 375 | ACCAGCTATG GCAACGGCGT GCATTGCAAC AAAAGCAAAT GCTGGATTGA TGTGAGCGAA CTGGAAACCT ATAAAGCGGG CACCGTGAGC AACCCGAAAG ATATTCTGTGG |
| 376 | Serracin-P | Phage-Tail-Like | DYHHGVRVL | Serratia plymuthica | 377 | GATTATCATC ATGGCGTGCG CGTGCTG |
| 378 | Halocin-C8 | Unclassified | DIDITGCSAC KYAAG | Halobacterium sp. (strain AS7092) | 379 | GATATTGATA TTACCGGCTG CAGCGCGTGC AAATATGCGG CGGGC |
| 380 | Subpeptin JM4-B | Unclassified | XXKEIXHIFH DN | Bacillus subtilis | 381 | NNNNNNAAAG AAATTNNNCA TATTTTTCATG ATAAC [IN WHICH NNN = ANY AMINO-ACID CODING TRIPLET] |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 382 | Curvalicin-28a | Unclassified | TPVVNPPFLQQT | Lactobacillus curvatus | 383 | ACCCCGGTGGTGAACCCGCCGTTTCTGCAGCAGACC |
| 384 | Curvalicin-28b | Unclassified | VAPFPEQFLX | Lactobacillus curvatus | 385 | GTGGCGCCGTTTCCGGAACAGTTTCTGNNN [IN WHICH NNN = ANY AMINO-ACID CODING TRIPLET] |
| 386 | Curvalicin-28c | Unclassified | NIPQLTPTP | Lactobacillus curvatus | 387 | AACATTCCGCAGCTGACCCCGACCCCG |
| 388 | Thuricin-S | Unclassified | DWTXWSXLVXAACSVELL | Bacillus thuringiensis subsp. entomocidus | 389 | GATTGGACCNNNTGGAGCNNNCTGGTGNNNG TABLE 1.2-continued Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 396 | Bacteriocin E50-52 | Unclassified | TTKNYGNG VCNSVNWC QCGNVWAS CNLATGCAA WLCKLA | Enterococcus faecium (Streptococcus faecium) | 397 | ACCACCAAAA ACTATGGCAA CGGCGTGTGC AACAGCGTGA ACTGGTGCCA GTGCGGCAAC GTGTGGGCGA GCTGCAACCT GGCGACCGGC TGCGCGGCGT GGCTGTGCAA ACTGGCG |
| 398 | Paenibacillin | Unclassified | ASIIKTTIKVS KAVCKTLTC ICTGSCSNCK | Paenibacillus polymyxa (Bacillus polymyxa) | 399 | GCGAGCATTA TTAAAACCAC CATTAAAGTG AGCAAAGCGG TGTGCAAAAC CCTGACCTGC ATTTGCACCG GCAGCTGCAG CAACTGCAAA |
| 400 | Epilancin 15x | Unclassified | SASIVKTTIK ASKKLCRGF TLTCGCHFT GKK | Staphylococcus epidermidis | 401 | AGCGCGAGCA TTGTGAAAAC CACCATTAAA GCGAGCAAAA AACTGTGCCG CGGCTTTACC CTGACCTGCG GCTGCCATTTT ACCGGCAAAA AA |
| 402 | Enterocin-HF | class IIa | KYYGNGVS CNKKGCSVD WGKAIGIIGN NAAANLTTG GKAAWAC | Enterococcus faecium (Streptococcus faecium) | 403 | AAATATTATG GCAACGGCGT GAGCTGCAAC AAAAAAGGCT GCAGCGTGGA TTGGGGCAAA GCGATTGGCA TTATTGGCAA CAACGCGGCG GCGAACCTGA CCACCGGCGG CAAAGCGGCG TGGGCGTGC |
| 404 | Bacillocin 602 | Class IIa | ATYYGNGL YCNKQKHY TWVDWNKA SREIGKITVN GWVQH | Paenibacillus polymyxa (Bacillus polymyxa) | 405 | GCGACCTATT ATGGCAACGG CCTGTATTGC AACAAACAGA AACATTATAC CTGGGTGGAT TGGAACAAAG CGAGCCGCGA AATTGGCAAA ATTACCGTGA ACGGCTGGGT GCAGCAT |
| 406 | Bacillocin 1580 | Class IIa | VNYGNGVS CSKTKCSVN WGIITHQAF RVTSGVASG | Bacillus circulans | 407 | GTGAACTATG GCAACGGCGT GAGCTGCAGC AAAACCAAAT GCAGCGTGAA CTGGGGCATT ATTACCCATC AGGCGTTTCG CGTGACCAGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGCGTGGCGA GCGGC |
| 408 | Bacillocin B37 | Unclassified | FVYGNGVTS ILVQAQFLV NGQRRFFYT PDK | Paenibacillus polymyxa (Bacillus polymyxa) | 409 | TTTGTGTATG GCAACGGCGT GACCAGCATT CTGGTGCAGG CGCAGTTTCT GGTGAACGGC CAGCGCCGCT TTTTTTATACC CCGGATAAA |
| 410 | Rhamnosin A | Unclassified | AVPAVRKTN ETLD | Lactobacillus rhamnosus | 411 | GCGGTGCCGG CGGTGCGCAA AACCAACGAA ACCCTGGAT |
| 412 | Lichenicidin A2 | Lantibiotic (two-peptide) | MKNSAARE AFKGANHPA GMVSEEELK ALVGGNDV NPETTPATTS SWTCITAGV TVSASLCPTT KCTSRC | Bacillus licheniformis (strain DSM 13/ATCC 14580) | 413 | ATGAAAAACA GCGCGGCGCG CGAAGCGTTT AAAGGCGCGA ACCATCCGGC GGGCATGGTG AGCGAAGAAG AACTGAAAGC GCTGGTGGGC GGCAACGATG TGAACCCGGA AACCACCCCG GCGACCACCA GCAGCTGGAC CTGCATTACC GCGGGCGTGA CCGTGAGCGC GAGCCTGTGC CCGACCACCA AATGCACCAG CCGCTGC |
| 414 | Plantaricin C19 | Class IIa | KYYGNGLSC SKKGCTVN WGQAFSCG VNRVATAG HGK | Lactobacillus plantarum | 415 | AAATATTATG GCAACGGCCT GAGCTGCAGC AAAAAAGGCT GCACCGTGAA CTGGGGCCAG GCGTTTAGCT GCGGCGTGAA CCGCGTGGCG ACCGCGGGCC ATGGCAAA |
| 416 | Acidocin J1132 β | Class IIb | GNPKVAHCA SQIGRSTAW GAVSGA | Lactobacillus acidophilus | 417 | GGCAACCCGA AAGTGGCGCA TTGCGCGAGC CAGATTGGCC GCAGCACCGC GTGGGGCGCG GTGAGCGGCG CG |
| 418 | factor with anti-Candida activity | Unclassified | WLPPAGLLG RCGRWFRP WLLWLQSG AQYKWLGN LFGLGPK | Enterococcus faecalis | 419 | TGGCTGCCGC CGGCGGGCCT GCTGGGCCGC TGCGGCCGCT GGTTTCGCCC GTGGCTGCTG TGGCTGCAGA GCGGCGCGCA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GTATAAATGG CTGGGCAACC TGTTTGGCCT GGGCCCGAAA |
| 420 | Ava_1098 (putative heterocyst differentiation protein) | Unclassified | NLDQWLTE QVHEFQDM YLEPQAISN QDITFKLSDL DFIHN | *Anabaena variabilis* ATCC 29413 | 421 | TAATTTAGATC AGTGGTTAAC AGAACAAGTT CATGAGTTTC AAGATATGTA CTTGGAACCA CAAGCAATAT CCAATCAAGA CATTACCTTCA AACTATCTGA CCTAGATTTTA TTCATAATTGA |
| 422 | alr2818 (putative heterocyst differentiation protein) | Unclassified | NLDQWLTE QVHEFQDM YLEPQAISN QDITFKLSDL DFIHN | *Nostoc* sp 7120 | 423 | AATTTAGATC AATGGTTAAC AGAACAAGTT CATGAGTTTC AAGATATGTA CTTGGAACCA CAAGCAATAT CCAATCAAGA CATTACCTTCA AACTGTCAGA CCTAGATTTTA TTCATAATTGA |
| 424 | Aazo_0724 (putative heterocyst differentiation protein) | Unclassified | HREKKSA | *Nostoc azollae* 0708 | 425 | CACAGAGAGA AAAAATCAGC ATAG |
| 426 | AM1_4010 (putative heterocyst differentiation protein) | Unclassified | TSNNWLAK NYLSMWNK KSSNPNL | *Acaryochloris marina* MBIC11017 | 427 | ACAAGCAATA ACTGGCTAGC CAAAAACTAT CTTTCTATGTG GAATAAAAAG AGCAGTAATC CAAACCTTTAG |
| 428 | PCC8801_3266 (putative heterocyst differentiation protein) | Unclassified | FRYFWW | *Cyanothece* PCC 8801 | 429 | TTTAGATATTT TTGGTGGTAA |
| 430 | Cyan8802_2855 (putative heterocyst differentiation protein) | Unclassified | FRYFWW | *Cyanothece* PCC 8802 | 431 | TTTAGATATTT TTGGTGGTAA |
| 432 | PCC7424_3517 | Unclassified | CGEKWRIFS | *Cyanothece* PCC 7424 | 433 | TGTGGAGAAA AATGGAGAAT TTTTAGC |
| 434 | cce_2677 (putative HetP protein) | Unclassified | FRLQLWQF | *Cyanothece* ATCC 51142 | 435 | TTTCGCTTACA ACTGTGGCAA TTT |
| 436 | CY0110_11572 (putative heterocyst differentiation protein) | Unclassified | LGCNQSSIW SIFFWNH | *Cyanothece* CCY0110 | 437 | CTAGGATGTA ACCAGAGCAG TATCTGGTCA ATTTTTTTCTG GAATCATTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 438 | MC7420_4637 | Unclassified | YNLQGLPAI ESEDCIPDSV APSDDWFSG VSSLFNRLT GLG | *Microcoleus chthonoplastes* PCC 7420 | 439 | TATAACCTAC AGGGGTTGCC AGCAATTGAG TCAGAAGACT GTATCCCAGA TTCTGTAGCG CCTTCGGATG ATTGGTTTTCA GGCGTATCGT CTCTGTTTAAC CGCTTGACTG GGTTGGGTTAG |
| 440 | asr1611 (putative DUF37 family protein) | Unclassified | WMAIRRILR CHPFHPGGY DPVPELGEH CCHHDSGNKG | *Nostoc* sp 7120 | 441 | TGGATGGCGA TTCGCCGCATT TTGCGTTGTCA TCCATTCCACC CAGGGGGTTA TGATCCTGTA CCAGAGTTGG GTGAGCATTG TTGTCATCATG ATAGCGGGAA TAAGGGGTGA |
| 442 | Ava_4222 (putative DUF37 family protein) | Unclassified | WMGIRRILR CHPFHPGGY DPVPEVGEH CCHHDSGK | *Anabaena variabilis* ATCC 29413 | 443 | TGGATGGGGA TTCGCCGCATT TTGCGTTGTCA TCCATTCCACC CAGGCGGTTA TGATCCTGTA CCAGAGGTGG GTGAGCATTG TTGTCATCATG ATAGCGGGAA GTAG |
| 444 | N9414_07129 (putative DUF37 family protein) | Unclassified | WMATRRILR CHPFHPGGY DPVPEVKHN CCDQHLSDS GKQTTEDHH KGS | *Nodularia spumigena* CCY9414 | 445 | TGGATGGCGA CTCGGCGGAT TTTGCGTTGTC ATCCCTTCCAT CCTGGTGGAT ATGATCCAGT TCCAGAGGTA AAACACAATT GCTGCGATCA GCATCTGTCC GATTCTGGGA AACAGACCAC AGAAGACCAT CACAAAGGCT CGTAG |
| 446 | Aazo_0083 (putative DUF37 family protein) | Unclassified | WMATLRILC HPFHPGGYD PVPGLAEKS CCDHHD | *Nostoc azollae* 0708 | 447 | TGGATGGCAA CTTTGCGGATT TTACGCTGTC ATCCTTTCCAT CCTGGTGGTT ATGATCCTGT ACCAGGACTA GCGGAAAAAT CCTGTTGTGA CCATCATGATT GA |
| 448 | S7335_3409 (putative DUF37 family protein) | Unclassified | WLTAKRFCR CHPLHPGGY DPVPEKKSVL | *Synechococcus* PCC 7335 | 449 | TGGCTAACAG CCAAGCGCTT TTGTCGCTGTC ATCCGCTTCAT CCTGGCGGGT ATGATCCGGT ACCGGAGAAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 450 | P9303_21151 (putative DUF37 family protein) | Unclassified | WLTLRRLSR CHPFTPCGC DPVPD | *Prochlorococcus marinus* MIT 9303 | 451 | AAATCGGTAC TCTAA TGGCTCACCC TGCGGCGCCT GTCTCGTTGCC ATCCTTTTACC CCCTGTGGTT GCGACCCGGT GCCTGATTAA |

As used herein "bacteriocin polynucleotide" refers to a polynucleotide encoding a bacteriocin. In some embodiments, the host cell comprises at least one bacteriocin.

Bacteriocin Immunity Modulators

Exemplary bacteriocin immunity modulators are shown in Table 2. While the immunity modulators in Table 2 are naturally-occurring, the skilled artisan will appreciate that variants of the immunity modulators of Table 2, naturally-occurring immunity modulators other than the immunity modulators of Table 2, or synthetic immunity modulators can be used according to some embodiments herein.

In some embodiments, a particular immunity modulator or particular combination of immunity modulators confers immunity to a particular bacteriocin, particular class or category of bacteriocins, or particular combination of bacteriocins. Exemplary bacteriocins to which immunity modulators can confer immunity are identified in Table 2. While Table 2 identifies an "organism of origin" for exemplary immunity modulators, these immunity modulators can readily be expressed in other naturally-occurring, genetically modified, or synthetic microorganisms to provide a desired bacteriocin immunity activity in accordance with some embodiments herein. As such, as used herein "immunity modulator" refers not only to structures expressly provided herein, but also to structure that have substantially the same effect as the "immunity modulator" structures described herein, including fully synthetic immunity modulators, and immunity modulators that provide immunity to bacteriocins that are functionally equivalent to the bacteriocins disclosed herein.

Exemplary polynucleotide sequences encoding the polypeptides of Table 2 are indicated in Table 2. The skilled artisan will readily understand that the genetic code is degenerate, and moreover, codon usage can vary based on the particular organism in which the gene product is being expressed, and as such, a particular polypeptide can be encoded by more than one polynucleotide. In some embodiments, a polynucleotide encoding a bacteriocin immunity modulator is selected based on the codon usage of the organism expressing the bacteriocin immunity modulator. In some embodiments, a polynucleotide encoding a bacteriocin immunity modulator is codon optimized based on the particular organism expressing the bacteriocin immunity modulator. A vast range of functional immunity modulators can incorporate features of immunity modulators disclosed herein, thus providing for a vast degree of identity to the immunity modulators in Table 2. In some embodiments, an immunity modulator has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 2.

TABLE 2

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 452 | Microcin H47 immunity modulator MchI | MSYKKLY QLTAIFSLP LTILLVSLS SLRIVGEG NSYVDVFL SFIIFLGFIE LIHGIRKIL VWSGWKN GS | *Escherichia coli* | 453 | ATGAGTTATAAAAAAC TGTACCAATTGACGGCT ATATTTAGTTTACCTCT TACTATCTTATTGGTTT CACTTTCATCCCTTCGG ATTGTTGGCGAAGGGA ATTCTTATGTTGACGTT TTTCTAAGCTTTATAAT ATTTCTTGGTTTTATTG AGCTGATTCATGGGATT CGAAAGATTTTGGTCTG GTCAGGCTGGAAAAAC GGAAGTTAA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 454 | Colicin-E3 immunity modulator (Colicin-E3 chain B) (ImmE3) (Microcin-E3 immunity modulator) | MGLKLDLT WFDKSTED FKGEEYSK DFGDDGSV MESLGVPF KDNVNNG CFDVIAEW VPLLQPYF NHQIDISD NEYFVSFD YRDGDW | Escherichia coli | 455 | ATGGGACTTAAATTGG ATTTAACTTGGTTTGAT AAAAGTACAGAAGATT TTAAGGGTGAGGAGTA TTCAAAAGATTTTGGAG ATGACGGTTCAGTTATG GAAAGTCTAGGTGTGC CTTTTAAGGATAATGTT AATAACGGTTGCTTTGA TGTTATAGCTGAATGG GTACCTTTGCTACAACC ATACTTTAATCATCAAA TTGATATTTCCGATAAT GAGTATTTTGTTTCGTT TGATTATCGTGATGGTG ATTGGTGA |
| 456 | Colicin-E1 immunity modulator (ImmE1) (Microcin-E1 immunity modulator) | MSLRYYIK NILFGLYC TLIYIYLIT KNSEGYYF LVSDKML YAIVISTIL CPYSKYAI EYIAFNPIK KDFFERRK NLNNAPVA KLNLFMLY NLLCLVLA IPFGLLGLF ISIKNN | Escherichia coli | 457 | ATGAGCTTAAGATACTA CATAAAAAATATTTTAT TTGGCCTGTACTGCACA CTTATATATATATACCT TATAACAAAAAACAGC GAAGGGTATTATTTCCT TGTGTCAGATAAGATG CTATATGCAATAGTGAT AAGCACTATTCTATGTC CATATTCAAAATATGCT ATTGAATACATAGCTTT TAACTTCATAAAGAAA GATTTTTTCGAAAGAAG AAAAAACCTAAATAAC GCCCCCGTAGCAAAATT AAACCTATTTATGCTAT ATAATCTACTTTGTTTG GTCCTAGCAATCCCATT TGGATTGCTAGGACTTT TTATATCAATAAAGAAT AATTAA |
| 458 | Cloacin immunity modulator | MGLKLHIH WFDKKTEE FKGGEYSK DFGDDGSV IESLGMPL KDNINNG WFDVEKP WVSILQPH FKNVIDISK FDYFVSFV YRDGNW | Escherichia coli | 459 | ATGGGGCTTAAATTAC ATATTCATTGGTTTGAT AAGAAAACCGAAGAGT TTAAAGGCGGTGAATA CTCAAAAGACTTCGGT GATGATGGTTCTGTCAT TGAAAGTCTGGGGATG CCTTTTAAAGGATAATAT TAATAATGGTTGGTTTG ATGTTGAAAAACCATG GGTTTCGATATTACAGC CACACTTTAAAAATGTA ATCGATATTAGTAAATT TGATTACTTTGTATCCT TTGTTTACCGGGATGGT AACTGGTAA |
| 460 | Colicin-E2 immunity modulator (ImmE2) (Microcin-E2 immunity modulator) | MELKHSIS DYTEAEFL EFVKKICR AEGATEED DNKLVREF ERLTEHPD GSDLIYYP RDDREDSP EGIVKEIKE WRAANGK SGFKQG | Escherichia coli | 461 | ATGGAACTGAAACATA GTATTAGTGATTATACC GAGGCTGAATTTCTGG AGTTTGTAAAAAAAT ATGTAGAGCTGAAGGT GCTACTGAAGAGGATG ACAATAAATTAGTGAG AGAGTTTGAGCGATTA ACTGAGCACCCAGATG GTTCAGATCTGATTTAT TATCCTCGCGATGACAG GGAAGATAGTCCTGAA GGGATTGTCAAGGAAA TTAAGAATGGCGAGC TGCTAACGGTAAGTCA GGATTTAAACAGGGCT GA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 462 | Colicin-A immunity modulator (Microcin-A immunity modulator) | MMNEHSID TDNRKAN NALYLFIII GLIPLLCIF VVYYKTPD ALLLRKIA TSTENLPSI TSSYNPLM TKVMDIYC KTAPFLALI LYILTFKIR KLINNTDR NTVLRSCL LSPLVYAA IVYLFCFR NFELTTAG RPVRLMAT NDATLLLF YIGLYSIIFF TTYITLFTP VTAFKLLK KRQ | *Citrobacter freundii* | 463 | ATGATGAATGAACACT CAATAGATACGGACAA CAGAAAGGCCAATAAC GCATTGTATTTATTTAT AATAATCGGATTAATAC CATTATTGTGCATTTTT GTTGTTACTACAAAAC GCCAGACGCTTTACTTT TACGTAAAATTGCTACA AGCACTGAGAATCTCCC GTCAATAACATCCTCCT ACAACCCATTAATGACA AAGGTTATGGATATTTA TTGTAAAACAGCGCCTT TCCTTGCCTTAATACTA TACATCCTAACCTTTAA AATCAGAAAATTAATC AACAACACCGACAGGA ACACTGTACTTAGATCT TGTTTATTAAGTCCATT GGTCTATGCAGCAATTG TTTATCTATTCTGCTTC CGAAATTTTGAGTTAAC AACAGCCGGAAGGCCT GTCAGATTAATGGCCA CCAATGACGCAACACT ATTGTTATTTTATATTG GTCTGTACTCAATAATT TTCTTTACAACCTATAT CACGCTATTCACACCAG TCACTGCATTTAAATTA TTAAAAAAAAGGCAGT AA |
| 464 | Colicin-Ia immunity modulator | MNRKYYF NNMWWG WVTGGYM LYMSWDY EFKYRLLF WCISLCGM VLYPVAK WYIEDTAL KFTRPDFW NSGFFADT PGKMGLLA VYTGTVFI LSLPLSMIY ILSVIIKRLS VR | *Escherichia coli* | 465 | ATGAACGAAAAATATT ATTTTAATAATATGTGG TGGGGATGGGTGACGG GGGGATATATGCTGTA TATGTCATGGGATTATG AGTTTAAATACAGATTA CTGTTCTGGTGTATTTC TCTCTGCGGAATGGTTT TGTATCCGGTTGCAAAA TGGTATATTGAAGATAC AGCTCTAAAATTTACCC GGCCTGATTTCTGGAAC AGCGGTTTTTTTGCTGA TACACCTGGAAAAATG GGGTTGCTTGCGGTTTA TACGGGTACTGTTTTCA TATTATCTCTTCCGTTA AGTATGATATATATTCT TTCTGTTATTATAAAAA GGCTGTCTGTAAGATAG |
| 466 | Colicin-Ib immunity modulator | MKLDISVK YLLKSLIPI LIILTVFYL GWKDNQE NARMFYAF IGCIISAITF PFSMRIIQK MVIRFTGK EFWQKDFF TNPVGGSL TAIFELFCF VISVPVVAI YLIFILCKA LSGK | *Escherichia coli* | 467 | ATGAAACTGGATATATC TGTAAAGTATTTACTGA AAAGCCTGATACCAAT CCTCATTATTCTTACAG TTTTTTATCTGGGATGG AAAGATAACCAGGAAA ATGCAAGAATGTTTTAT GCGTTCATCGGATGCAT TATCAGTGCCATTACTT TTCCTTTTTCAATGAGG ATAATACAGAAAATGG TAATAAGGTTTACAGG GAAAGAATTCTGGCAA AAAGACTTCTTTACAAA TCCAGTTGGCGGAAGC TTAACTGCAATATTTGA ATTATTCTGTTTCGTTA |

TABLE 2-continued

Exemplary bacteriocin immunity modulators

| Poly-peptide SEQ ID NO: | Name | Polypeptide Sequence | Organism of origin | Poly-nucleotide SEQ ID NO: | Polynucleotide Sequence |
|---|---|---|---|---|---|
| | | | | | TATCAGTTCCTGTGGTT GCCATTTACTTAATTTT TATACTCTGCAAAGCCC TTTCAGGAAAATGA |
| 468 | Colicin-N immunity modulator (Microcin-N immunity modulator) | MHNTLLEK IIAYLSLPG FHSLNNPP LSEAFNLY VHTAPLAA TSLFIFTHK ELELKPKS SPLRALKIL TPFTILYIS MIYCFLLT DTELTLSS KTFVLIVK KRSVFVFF LYNTIYWD IYIHIFVLL VPYRNI | Escherichia coli | 469 | ATGCACAATACACTCCT CGAAAAAATCATCGCA TACCTATCCCTACCAGG ATTTCATTCATTAAACA ACCCGCCCCTAAGCGA AGCATTCAATCTCTATG TTCATACAGCCCCTTTA GCTGCAACCAGCTTATT CATATTCACACACAAAG AATTAGAGTTAAAACC AAAGTCGTCACCTCTGC GGGCACTAAAGATATT AACTCCTTTCACTATTC TTTATATATCCATGATA TACTGTTTCTTGCTAAC TGACACAGAACTAACC TTGTCATCAAAAACATT TGTATTAATAGTCAAAA AACGATCTGTTTTTGTC TTTTTTCTATATAACAC TATATATTGGGATATAT ATATTCACATATTTGTA CTTTTGGTTCCTTATAG GAACATATAA |
| 470 | Colicin-E8 immunity modulator (ImmE8) (Microcin-E8 immunity modulator) | MELKNSIS DYTETEFK KIIEDIINCE GDEKKQD DNLEHFIS VTEHPSGS DLIYYPEG NNDGSPEA VIKEIKEW RAANGKSG FKQG | Escherichia coli | 471 | ATGGAACTGAAAAACA GCATTAGTGATTACACT GAAACTGAATTCAAAA AAATTATTGAAGACATC ATCAATTGTGAAGGTG ATGAAAAAAACAGGA TGATAACCTCGAGCATT TTATAAGTGTTACTGAG CATCCTAGTGGTTCTGA TCTGATTTATTACCCAG AAGGTAATAATGATGG TAGCCCTGAAGCTGTTA TTAAAGAGATTAAAGA ATGGCGAGCTGCTAAC GGTAAGTCAGGATTTA AACAGGGCTGA |
| 472 | Lactococcin-A immunity modulator | MKKKQIEF ENELRSML ATALEKDI SQEERNAL NIAEKALD NSEYLPKII LNLRKALT PLAINRTL NHDLSELY KFITSSKAS NKNLGGG LIMSWGRLF | Lactococcus lactis subsp. lactis (Streptococcus lactis) | 473 | ATGAAAAAAAACAAA TAGAATTTGAAAACGA GCTAAGAAGTATGTTG GCTACCGCCCTTGAAAA AGACATTAGTCAAGAG GAAAGAAATGCTCTGA ATATTGCAGAAAAGGC GCTTGACAATTCTGAAT ATTTACCAAAAATTATT TTAAACCTCAGAAAAG CCCTAACTCCATTAGCT ATAAATCGAACACTTAA CCATGATTTATCTGAAC TGTATAAATTCATTACA AGTTCCAAAGCATCAA ACAAAAATTTAGGTGG TGGTTTAATTATGTCGT GGGGACGACTATTCTAA |
| 474 | Lactococcin-A immunity modulator | MKKKQIEF ENELRSML ATALEKDI SQEERNAL NIAEKALD NSEYLPKII LNLRKALT | Lactococcus lactis subsp. cremoris (Streptococcus cremoris) | 475 | ATGAAAAAAAACAAA TAGAATTTGAAAACGA GCTAAGAAGTATGTTG GCTACCGCCCTTGAAAA AGACATTAGTCAAGAG GAAAGAAATGCTCTGA ATATTGCAGAAAAGGC |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | PLAINRTL NHDLSELY KFITSSKAS NKNLGGG LIMSWGRLF | | | GCTTGACAATTCTGAAT ATTTACCAAAAATTATT TTAAACCTCAGAAAAG CCCTAACTCCATTAGCT ATAAATCGAACACTTAA CCATGATTTATCTGAAC TGTATAAATTCATTACA AGTTCCAAAGCATCAA ACAAAAATTTAGGTGG TGGTTTAATTATGTCGT GGGGACGACTATTCTAA |
| 476 | Colicin-D immunity modulator (Microcin-D immunity modulator) | MNKMAMI DLAKLFLA SKITAIEFS ERICVERR RLYGVKDL SPNILNCG EELFMAAE RFEPDADR ANYEIDDN GLKVEVRS ILEKFKL | Escherichia coli | 477 | ATGATCGATTTGGCGA AATTATTTTTAGCTTCG AAAATTACAGTGATTG AGTTTTCAGAGCGAATT TGTGTTGAACGGAGAA GATTGTATGGTGTTAAG GATTTGTCTCCGAATAT ATTAAATTGTGGGGAA GAGTTGTCTATGGCTGC TGAGCGATTTGAGCCT GATGCAGATAGGGCTA ATTATGAAATTGATGAT AATGGACTTAAGGTCG AGGTCCGATCTATCTTG GAAAAACTTAAATCAT AA |
| 478 | Colicin-E5 immunity modulator (ImmE5) (Microcin-E5 immunity modulator) | MKLSPKAA IEVCNEAA KKGLWILG IDGGHWLN PGFRIDSSA SWTYDMP EEYKSKIPE NNRLAIENI KDDIENGY TAFIITLKM | Escherichia coli | 479 | ATGAAGTTATCACCAA AAGCTGCAATAGAAGT TTGTAATGAAGCAGCG AAAAAAGGCTTATGGA TTTTGGGCATTGATGGT GGGCATTGGCTGAATC CTGGATTCAGGATAGA TAGTTCAGCATCATGGA CATATGATATGCCGGA GAATACAAATCAAAAA TCCCTGAAAATAATAG ATTGGCTATTGAAAATA TTAAAGATGATATTGA GAATGGATACACTGCTT TCATTATCACGTTAA |
| 480 | Colicin-E6 immunity modulator (ImmE6) (Microcin-E6 immunity modulator) | MGLKLHIN WFDKRTEE FKGGEYSK DFGDDGSV IERLGMPF KDNINNG WFDVIAEW VPLLQPYF NHQIDISD NEYFVSFD YRDGDW | Escherichia coli | 481 | ATGGGGCTTAAATTAC ATATTAATTGGTTTGAT AAGACGACCGAGGAAT TTAAAGGTGGTGAGTA TTCAAAAGATTTGGAG ATGATGGCTCGGTCATT GAACGTCTTGGAATGC CTTTAAAAGATAATATC AATAATGGTTGGTTTGA TGTTATAGCTGAATGG GTACCTTTGCTACAACC ATACTTTAATCATCAAA TTGATATTTCCGATAAT GAGTATTTTGTTTCGTT TGATTATCGTGATGGTG ATTGGTGA |
| 482 | Colicin-E8 immunity modulator in ColE6 (E8Imm[E6]) | MELKKSIG DYTETEFK KIIENIINCE GDEKKQD DNLEHFIS VTEHPSGS DLIYYPEG NNDGSPEA VIKEIKEW RAANGKSG FKQG | Escherichia coli | 483 | GTGGAGCTAAAGAAAA GTATTGGTGATTACACT GAAACCGAATTCAAAA AAATTATTGAAAACATC ATCAATTGTGAAGGTG ATGAAAAAAACAGGA TGATAACCTCGAGCATT TTATAAGTGTTACTGAG CATCCTAGTGGTTCTGA TCTGATTTATTACCCAG AAGGTAATAATGATGG |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | TAGCCCTGAAGCTGTTA TTAAAGAGATTAAAGA ATGGCGAGCTGCTAAC GGTAAGTCAGGATTTA AACAGGGCTGA |
| 484 | Colicin-E9 immunity modulator (ImmE9) (Microcin-E9 immunity modulator) | MELKHSIS DYTEAEFL QLVTTICN ADTSSEEE LVKLVTHF EEMTEHPS GSDLIYYP KEGDDDSP SGIVNTVK QWRAANG KSGFKQG | Escherichia coli | 485 | ATGGAACTGAAGCATA GCATTAGTGATTATACA GAAGCTGAATTTTTACA ACTTGTAACAACAATTT GTAATGCGAACACTTCC AGTGAAGAAGAACTGG TTAAATTGGTTACACAC TTTGAGGAAATGACTG AGCACCCTAGTGGTAG TGATTTAATATATTACC CAAAAGAAGGTGATGA TGACTCACCTTCAGGTA TTGTAAACACAGTAAA ACAATGGCGAGCCGCT AACGGTAAGTCAGGAT TTAAACAGGGCTAA |
| 486 | Colicin-M immunity modulator (Microcin-M immunity modulator) | MLTLYGYI RNVFLYR MNDRSCG DFMKVISM KFIPILTIIA LAAVFFWS EDKGPACY QVSDEQAR TFVKNDYL QRMKRWD NDVQLLGT EIPKITWEK IERSLTDVE DEKTLLVP FKAEGPDG KRMYYGM YHCEEGY VEYAND | Escherichia coli | 487 | ATGAAAGTAATTAGCA TGAAATTTATTTTTATT TTAACGATTATTGCTCT TGCTGCTGTTTTTTTCT GGTCTGAAGATAAAGG TCCGGCATGCTATCAGG TCAGCGATGAACAGGC CAGAACGTTTGTAAAA AATGATTACCTGCAAA GAATGAAACGCTGGGA CAACGATGTACAACTTC TTGGTACAGAAATCCC GAAAATTACATGGGAA AAGATTGAGAGAAGTT TAACAGATGTTGAAGA TGAAAAAACACTTCTTG TCCCATTTAAAGCTGAA GGCCCGGACGGTAAGA GAATGTATTATGGCATG TACCATTGTGAGGAGG GATATGTTGAATATGCG AATGACTAA |
| 488 | Colicin-B immunity modulator (Microcin-B immunity modulator) | MTSNKDK NKKANEIL YAFSIIGIIP LMAILILRI NDPYSQVL YYLYNKV AFLPSITSL HDPVMTTL MSNYNKT APVMGILV FLCTYKTR EIIKPVTRK LVVQSCFW GPVFYAILI YITLFYNLE LTTAGGFF KLLSHNVI TLFILYCSI YFTVLTMT YAILLMPL LVIKYFKG RQ | Escherichia coli | 489 | ATGACCAGCAATAAAG ATAAGAACAAGAAAGC AAACGAAATATTATAT GCATTTTCCATAATCGG GATTATTCATTAATGG CTATATTAATACTTCGA ATAAATGATCCATATTC TCAAGTGCTGTACTACT TATATAATAAGGTGGC ATTTCTCCCTTCTATTA CATCATTGCATGATCCC GTCATGACAACACTTAT GTCAAACTACAACAAG ACAGCGCCAGTTATGG GTATTCTCGTTTTTCTT TGCACATATAAGACAA GAGAAATCATAAAGCC AGTAACAAGAAACTT GTTGTGCAATCCTGTTT CTGGGGGCCCGTTTTTT ATGCCATTCTGATTTAT ATCACACTGTTCTATAA TCTGGAACTAACAACA GCAGGTGTTTTTTTAA ATTATTATCTCATAATG TCATCACTCTGTTTATT TTATATTGCTCCATTTA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | CTTTACTGTTTTAACCA TGACATATGCGATTTTA CTGATGCCATTACTTGT CATTAAATATTTTAAAG GGAGGCAGTAA |
| 490 | Colicin-V immunity modulator (Microcin-V immunity modulator) | MDRKRTK LELLFAFII NATAIYIAL AIYDCVFR GKDFLSMH TFCFSALM SAICYFVG DNYYSISD KIKRRSYE NSDSK | Escherichia coli | 491 | ATGGATAGAAAAGAA CAAAATTAGAGTTGTTA TTTGCATTTATAATAAA TGCCACCGCAATATATA TTGCATTAGCTATATAT GATTGTGTTTTTAGAGG AAAGGACTTTTTATCCA TGCATACATTTTGCTTC TCTGCATTAATGTCTGC AATATGTTACTTTGTTG GTGATAATTATTATTCA ATATCCGATAAGATAA AAAGGAGATCATATGA GAACTCTGACTCTAAAT GA |
| 492 | Colicin-E1* immunity modulator (ImmE1) (Microcin-E1* immunity modulator) | MSLRYYIK NILFGLYC ALIYIYLIT KNNEGYYF LASDKMLY AIVISTILCP YSKYAIEHI FFKFIKKDF FRKRKNLN KCPRGKIK PYLCVYNL LCLVLAIPF GLLGLVYI NKE | Shigella sonnei | 493 | ATGAGTTTAAGATACTA CATAAAAAATATTTTGT TTGGCCTATACTGCGCA CTTATATATATATACCT TATAACAAAAAACAAC GAAGGGTATTATTTCCT AGCGTCAGATAAGATG CTATACGCAATAGTGAT AAGCACTATTCTATGCC CATATTCAAAATATGCT ATTGAACACATATTTTT TAAGTTCATAAAGAAA GATTTTTTCAGAAAAAG AAAAAACCTAAATAAA TGCCCCCGTGGCAAAA TTAAACCGTATTTATGC GTATACAATCTACTTTG TTTGGTCCTAGCAATCC CATTTGGATTGCTAGGA CTTGTTTATATCAATAA AGAATAA |
| 494 | Colicin-E1 immunity modulator (ImmE1) (Microcin-E1 immunity modulator) | MSLRYYIK NILFGLYC TLIYIYLIT KNSEEYYF LVTDKML YAIVISTIL CPYSKYAI EHIAFNFIK KHFFERRK NLNNAPVA KLNLFMLY NLLCLVLA IPFGLLGLF ISIKNN | Escherichia coli | 495 | ATGAGCTTAAGATACTA CATAAAAAATATTTTAT TTGGCCTATCTGCACA CTTATATATATATACCT TATAACAAAAACAGC GAAGAGTATTATTTCCT TGTGACAGATAAGATG CTATATGCAATAGTGAT AAGCACTATTCTATGTC CATATTCAAAATATGCT ATTGAACACATAGCTTT TAACTTCATAAAGAAAC ATTTTTTCGAAAGAAGA AAAAACCTAAATAACG CCCCCGTAGCAAAATTA AACCTATTTATGCTATA TAATCTACTTTGTTTGG TCCTAGCAATCCCATTT GGATTGCTAGGACTTTT TATATCAATAAAGAATA ATTAA |
| 496 | Probable leucocin-A immunity modulator | MRKNNILL DDAKIYTN KLYLLLID RKDDAGY GDICDVLF QVSKKLDS TKNVEALI | Leuconostoc gelidum | 497 | TTGAGAAAAAATAACA TTTTATTGGACGATGCT AAAATATACACGAACA AACTCTATTTGCTATTA ATCGATAGAAAGATG ACGCTGGGTATGGAGA TATTTGTGATGTTTTGT |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | NRLVNYIRI TASTNRIKF SKDEEAVII ELGVIGQK AGLNGQY MADFSDKS QFYSIFER | | | TTCAGGTATCCAAAAA ATTAGATAGCACAAAA AATGTAGAAGCATTGA TTAACCGATTGGTCAAT TATATACGAATTACCGC TTCAACAAACAGAATTA AGTTTTCAAAAGATGA AGAGGCTGTAATTATA GAACTTGGTGTAATTG GTCAGAAGGCTGGATT AAACGGCCAATACATG GCTGATTTTTCTGACAA ATCTCAGTTTTATAGTA TCTTTGAAAGATAA |
| 498 | Lactococcin-B immunity modulator | MKKKVDT EKQITSWA SDLASKNE TKVQEKLI LSSYIQDIE NHVYFPKA MISLEKKL RDQNNICA LSKEVNQF YFKVVEVN QRKSWMV GLIV | Lactococcus lactis subsp. cremoris (Streptococcus cremoris) | 499 | ATGAAAAAAAAGTTG ATACAGAAAAACAAAT TACTTCTTGGGCATCTG ACTTAGCTTCCAAAAAT GAAACAAAGGTTCAAG AAAAATTAATACTGTCT TCTTATATTCAGGACAT CGAAAACCATGTTTACT TTCCAAAAGCAATGATT TCTTTAGAAAAAAATT ACGAGACCAAAATAAT ATTTGCGCTTTATCAAA AGAAGTCAATCAGTTTT ATTTTAAAGTTGTTGAA GTAAATCAAGAAAAT CCTGGATGGTAGGTTTG ATAGTTTAA |
| 500 | Pediocin PA-1 immunity modulator (Pediocin ACH immunity modulator) | MNKTKSE HIKQQALD LFTRLQFLL QKHDTIEP YQYVLDIL ETGISKTK HNQQTPER QARVVYN KIASQALV DKLHFTAE ENKVLAAI NELAHSQK GWGEFNM LDTTNTWP SQ | Pediococcus acidilactici | 501 | ATGAATAAGACTAAGT CGGAACATATTAAACA ACAAGCTTTGGACTTAT TTACTAGGCTACAGTTT TTACTACAGAAGCACG ATACTATCGAACCTTAC CAGTACGTTTTAGATAT TCTGGAGACTGGTATCA GTAAAACTAAACATAA CCAGCAAACGCCTGAA CGACAAGCTCGTGTAG TCTACAACAAGATTGCC AGCCAAGCGTTAGTAG ATAAGTTACATTTTACT GCCGAAGAAAACAAAG TTCTAGCAGCCATCAAT GAATTGGCGCATTCTCA AAAAGGGTGGGGCGAG TTTAACATGCTAGATAC TACCAATACGTGGCCTA GCCAATAG |
| 502 | Putative carnobacteriocin-BM1 immunity modulator | MIKDEKIN KIYALVKS ALDNTDV KNDKKLSL LLMRIQET SINGELFY DYKKELQP AISMYSIQ HNFRVPDD LVKLLALV QTPKAWS GF | Carnobacterium maltaromaticum (Carnobacterium piscicola) | 503 | ATGATAAAGATGAAA AAATAAATAAATCTAT GCTTTAGTTAAGAGCGC ACTTGATAATACGGAT GTTAAGAATGATAAAA AACTTTCTTTACTTCTT ATGAGAATACAAGAAA CATCAATTAATGGAGA ACTATTTTACGATTATA AAAAAGAATTACAGCC AGCTATTAGTATGTACT CTATTCAACATAACTTT CGGGTTCCTGACGATCT AGTAAAACTGTTAGCAT TAGTTCAAACACCTAAA GCTTGGTCAGGGTTTTAA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 504 | Putative carnobacteriocin-B2 immunity modulator (Carnocin-CP52 immunity modulator) | MDIKSQTL YLNLSEAY KDPEVKAN EFLSKLVV QCAGKLTA SNSENSYIE VISLLSRGI SSYYLSHK RIIPSSMLTI YTQIQKDI KNGNIDTE KLRKYEIA KGLMSVPY IYF | Carnobacterium maltaromaticum (Carnobacterium piscicola) | 505 | ATGGATATAAAGTCTCA AACATTATATTTGAATC TAAGCGAGGCATATAA AGACCCTGAAGTAAAA GCTAATGAATTCTTATC AAAATTAGTTGTACAAT GTGCTGGGAAATTAAC AGCTTCAAACAGTGAG AACAGTTATATTGAAGT AATATCATTGCTATCTA GGGGTATTTCTAGTTAT TATTTATCCCATAAACG TATAATTCCTTCAAGTA TGTTAACTATATATACT CAAATACAAAAGGATA TAAAAAACGGGAATAT TGACACCGAAAAATTA AGGAAATATGAGATAG CAAAAGGATTAATGTC CGTTCCTTATATATATT TCTAA |
| 506 | Nisin immunity modulator | MRRYLILI VALIGITGL SGCYQTSH KKVRFDEG SYTNFIYD NKSYFVTD KEIPQENV NNSKVKFY KLLIVDMK SEKLLSSSN KNSVTLVL NNIYEASD KSLCMGIN DRYYKILP ESDKGAVK ALRLQNFD VTSDISDD NFVIDKND SRKIDYMG NIYSISDTT VSDEELGE YQDVLAE VRVFDSVS GKSIPRSE WGRIDKD GSNSKQSR TEWDYGEI HSIRGKSLT EAFAVEIN DDFKLATK VGN | Lactococcus lactis subsp. lactis (Streptococcus lactis) | 507 | ATGAGAAGATATTTAAT ACTTATTGTGGCCTTAA TAGGGATAACAGGTTT ATCAGGGTGTTATCAA ACAAGTCATAAAAAGG TGAGGTTTGACGAAGG AAGTTATACTAATTTTA TTTATGATAATAAATCG TATTTCGTAACTGATAA GGAGATTCCTCAGGAG AACGTTAACAATTCCAA AGTAAAATTTTATAAGC TGTTGATTGTTGACATG AAAAGTGAGAAACTTT TATCAAGTAGCAACAA AAATAGTGTGACTTTGG TCTTAAATAATATTTAT GAGGCTTCTGACAAGT CGCTATGTATGGGTATT AACGACAGATACTATA AGATACTTCCAGAAAG TGATAAGGGGCGGTC AAAGCTTTGAGATTACA AAACTTTGATGTGACAA GCGATATTTCTGATGAT AATTTTGTTATTGATAA AAATGATTCACGAAAA ATTGACTATATGGGAA ATATTTACAGTATATCG GACACCACCGTATCTGA TGAAGAATTGGGAGAA TATCAGGATGTTTTAGC TGAAGTACGTGTGTTTG ATTCAGTTAGTGGCAA AAGTATCCCGAGGTCT GAATGGGGAGAATTG ATAAGGATGGTTCAAA TTCCAAACAGAGTAGG ACGGAATGGGATTATG GCGAAATCCATTCTATT AGAGGAAATCTCTTA CTGAAGCATTTGCCGTT GAGATAAATGATGATT TTAAGCTTGCAACGAA GGTAGGAAACTAG |
| 508 | Trifolitoxin immunity modulator | MNDEICLT GGGRTTVT RRGGVVY REGGPWSS | Rhizobium leguminosarum bv. trifolii | 509 | ATGAATGATGAGATTT GCCTGACAGGTGGCGG ACGAACGACTGTCACG CGGCGCGGCGGAGTCG |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | TVISLLRHL | | | TGTATCGCGAAGGCGG |
| | | EASGFAEA | | | CCCGTGGTCATCAACCG |
| | | PSVVGTGF | | | TCATTTCGCTCCTGCGG |
| | | DERGRETL | | | CATCTGGAAGCCTCTGG |
| | | SFIEGEFVH | | | CTTCGCTGAAGCTCCTT |
| | | PGPWSEEA | | | CCGTTGTCGGCACCGGT |
| | | FPQFGMML | | | TTCGATGAGCGCGGCC |
| | | RRLHDATA | | | GGGAGACATTATCGTTT |
| | | SFKPPENS | | | ATCGAGGGTGAGTTTG |
| | | MWRDWFG | | | TTCACCCAGGCCCTTGG |
| | | RNLGEGQH | | | TCGGAGGAGGCTTTTCC |
| | | VIGHCDTG | | | GCAATTTGGAATGATGT |
| | | PWNIVCRS | | | TGCGGCGACTGCACGA |
| | | GLPVGLID | | | TGCCACCGCCTCGTTCA |
| | | WEVAGPV | | | AACCTCCCGAAAACTC |
| | | RADIELAQ | | | GATGTGGCGCGATTGG |
| | | ACWLNAQ | | | TTCGGGCGTAACCTCG |
| | | LYDDDIAE | | | GTGAGGGTCAACACGT |
| | | RVGLGSVT | | | AATAGGACACTGCGAC |
| | | MRAHQVR | | | ACAGGCCCATGGAACA |
| | | LLLDGYGL | | | TTGTTTGCCGGTCAGGA |
| | | SRKQRGGF | | | TTGCCTGTCGGGTTGAT |
| | | VDKLITFA | | | AGATTGGGAGGTGGCT |
| | | VHDAAEQ | | | GGGCCTGTCAGGGCGG |
| | | AKEAAVTP | | | ATATCGAATTGGCCCA |
| | | ESNDAEPL | | | GGCTTGTTGGCTGAATG |
| | | WAIAWRT | | | CCCAGCTCTACGATGAC |
| | | RSASWML | | | GACATTGCGGAGAGGG |
| | | HHRQTLEA | | | TCGGATTAGGCTCTGTG |
| | | ALA | | | ACCATGAGAGCGCATC |
| | | | | | AAGTTCGCCTGCTGCTT |
| | | | | | GACGGCTATGGTCTGTC |
| | | | | | TCGGAAGCAACGCGGC |
| | | | | | GGCTTCGTCGACAAGCT |
| | | | | | AATCACGTTCGCAGTTC |
| | | | | | ACGATGCGGCCGAGCA |
| | | | | | GGCGAAAGAGGCGGCT |
| | | | | | GTCACGCCAGAGTCGA |
| | | | | | ACGATGCGGAACCGCT |
| | | | | | ATGGGCAATTGCCTGG |
| | | | | | CGCACTAGAAGTGCCT |
| | | | | | CCTGGATGCTCCATCAT |
| | | | | | CGGCAAACACTGGAAG |
| | | | | | CAGCGCTGGCATAG |
| 510 | Antilisterial bacteriocin subtilosin biosynthesis protein AlbD | MNNIIPIMS LLFKQLYS RQGKKDAI RIAAGLVIL AVFEIGLIR QAGIDESV LRKTYIILA LLLMNTY MVFLSVTS QWKESYM KLSCLLPIS SRSFWLAQ SVVLFVDT CLRRTLFFF ILPLFLFGN GTLSGAQT LFWLGRFS FFTVYSIIF GVVLSNHF VKKKNLM FLLHAAIFA CVCISAAL MPAATIPL CAVHILWA VVIDFPVFL QAPPQQGK MHSPMRRS EFSFYKRE | Bacillus subtilis (strain 168) | 511 | ATGAATAACATAATCCC TATCATGTCTTTGCTGT TCAAACAGCTTTACAGC CGGCAAGGGAAAAAGG ACGCCATCCGCATTGCC GCAGGCCTTGTCATTCT GGCCGTGTTTGAAATC GGGCTGATCCGCCAGG CCGGCATTGATGAATC GGTGTTGCGCAAAACG TATATCATACTCGCGCT TCTTTTGATGAACACAT ATATGGTGTTTCTTTCC GTGACATCACAATGGA AGGAATCTTATATGAA GCTGAGCTGCCTGCTGC CGATTTCTTCACGGAGC TTTTGGCTCGCCCAGAG TGTCGTTTTGTTTGTCG ATACCTGTTTGAGAAG AACTTTATTCTTTTTTA TTTTACCGCTGTTCTTA TTTGGAAACGGAACGC TGTCAGGGGCGCAAAC ATTGTTTGGCTCGGCA GGTTTTCGTTTTTTACC GTTTACTCCATTATTTT CGGAGTTGTGCTAAGC |

TABLE 2-continued

Exemplary bacteriocin immunity modulators

| Poly-peptide SEQ ID NO: | Name | Polypeptide Sequence | Organism of origin | Poly-nucleotide SEQ ID NO: | Polynucleotide Sequence |
|---|---|---|---|---|---|
| | | WNRFISSK | | | AACCACTTCGTCAAAAA |
| | | AMLLNYA | | | GAAGAACTTGATGTTTC |
| | | VMAVFSGF | | | TGCTGCATGCGGCGAT |
| | | FSFQMMNT | | | ATTCGCCTGTGTATGTA |
| | | GIFNQQVI | | | TCAGCGCCGCTTTGATG |
| | | YIVISALLL | | | CCGGCCGCCACGATTCC |
| | | ICSPIALLY | | | GCTTTGCGCGGTTCATA |
| | | SIEKNDRM | | | TCCTGTGGGCGGTGGT |
| | | LLITLPIKR | | | CATTGACTTTCCTGTCT |
| | | KTMFWAK | | | TTCTGCAGGCGCCTCCG |
| | | YRFYSGLL | | | CAGCAGGGCAAGATGC |
| | | AGGFLLVV | | | ATTCATTTATGCGGCGA |
| | | MIVGFISGR | | | TCTGAATTTTCGTTTTA |
| | | SISVLTFLQ | | | CAAAAGAGAATGGAAC |
| | | CIELLLAG | | | CGATTTATCTCTTCTAA |
| | | AYIRLTAD | | | AGCGATGCTGTTAAATT |
| | | EKRPSFSW | | | ACGCGGTAATGGCGGT |
| | | QTEQQLWS | | | ATTCAGCGGCTTCTTTT |
| | | GFSKYRSY | | | CGTTCCAGATGATGAA |
| | | LFCLPLFLA | | | CACCGGCATCTTCAATC |
| | | ILAGTAVS | | | AGCAAGTGATTTATATC |
| | | LAVIPIAGL | | | GTGATTTCCGCGCTTTT |
| | | VIVYYLQK | | | GCTCATCTGCTCGCCGA |
| | | QDGGFFDT | | | TCGCCCTTTTGTATTCG |
| | | SKRERLGS | | | ATTGAAAAAAATGACC |
| | | | | | GGATGCTGCTCATCACG |
| | | | | | CTTCCGATCAAGCGAA |
| | | | | | AAACGATGTTTTGGGC |
| | | | | | GAAATATCGCTTTTATT |
| | | | | | CAGGCCTATTGGCAGG |
| | | | | | CGGATTTCTCCTTGTCG |
| | | | | | TGATGATTGTGGGTTTCA |
| 512 | Putative ABC transporter ATP-binding protein AlbC (Antilisterial bacteriocin subtilosin biosynthesis protein AlbC) | MSILDIHD VSVWYER DNVILEQV DLHLEKGA VYGLLGV NGAGKTTL INTLTGVN RNFSGRFT LCGIEAEA GMPQKTSD QLKTHRYF AADYPLLF TEITAKDY VSFVHSLY QKDFSEQQ FASLAEAF HFSKYINR RISELSLGN RQKVVLM TGLLLRAP LFILDEPLV GLDVESIE VFYQKMR EYCEAGGT ILFSSHLLD VVQRFCDY AAILHNKQ IQKVIPIGE ETDLRREF FEVIGHE | Bacillus subtilis (strain 168) | 513 | GCATTTTGGATATACAC GATGTATCCGTTTGGTA TGAACGGGACAACGTC ATCTTAGAGCACGTGG ACTTACACTTAGAAAAA GGCGCCGTTTACGGATT GCTTGGGGTAAACGGT GCCGGCAAAACAACAC TGATCAATACGCTGACA GGAGTGAACCGCAATT ACAGCGGGGGCTTTAC GCTGTGCGGCATTGAA GCTGAGGCCGGCATGC CGCAGAAAACATCAGA TCAACTGAAGATTCACC GTTACTTCGCCGCTGAT TATCCGCTGCTGTTTAC AGAAATTACGGCGAAG GACTATGTGTCTTTCGT CCATTCGCTTTATCAAA AGGATTTTTCAGAGCG ACAGTTTGCCAGTTTGG CTGAGGCCTTTCATTTT TCAAAATACATCAACA GGAGAATCTCGGAGCT GTCCTTGGGGAACAGG CAAAAGGTTGTGTTGAT GACAGGATTATTGCTGC GGGCTCCCCTGTTTATT TTGGATGAGCCGCTCGT CGGTTTGGATGTGGAA TCAATAGAGGTCTTTTA TCAGAAAATGCGGGAG TACTGTGAGGAAGGCG GAACCATTTTGTTTTCT TCCCATCTGCTCGATGT CGTGCAGAGATTTTGTG ATTTTGCGGCCATTCTG CACAACAAACAGATCC AAAAGGTCATTCCGATT |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | GGGGAGGAGACCGATC TGCGGCGGGAATTTTTT GAGGTTATCGGCCATG AATAA |
| 514 | Antilisterial bacteriocin subtilosin biosynthesis protein AlbB | MSPAQRRI LLYILSFIF VIGAVVYF VKSDYLFT LIFIAIAILF GMRARKA DSR | Bacillus subtilis (strain 168) | 515 | TTGTCACCAGCACAAA GAAGAATTTTACTGTAT ATCCTTTCATTTATCTT TGTCATCGGCGCAGTC GTCTATTTTGTCAAAAG CGATTATCTGTTTACGC TGATTTTCATTGCCATT GCCATTCTGTTCGGGAT GCGCGCGCGGAAGGCT GACTCGCGATGA |
| 516 | Colicin-E7 immunity modulator (ImmE7) (Microcin-E7 immunity modulator) | MELKNSIS DYTEAEFV QLLKEIEK ENVAATD DVLDVLLE HFVKITEH PDGTDLIY YPSDNRDD SPEGIVKEI KEWRAAN GKPGFKQG | Escherichia coli | 517 | ATGGAACTGAAAAATA GTATTAGTGATTACACA GAGGCTGAGTTTGTTCA ACTTCTTAAGGAAATTG AAAAAGAGAATGTTGC TGCACTCGATGATGTGT TAGATGTGTTACTCGAA CACTTTGTAAAAATTAC TGAGCATCCAGATGGA ACGGATCTGATTTATTA TCCTAGTGATAATAGA GACGATAGCCCCGAAG GGATTGTCAAGGAAAT TAAAGAATGGCGAGCT GCTAACGGTAAGCCAG GATTTAAACAGGGCTGA |
| 518 | Pyocin-S1 immunity modulator | MKSKISEY TEKEFLEF VEDIYTNN KKKFPTEE SHIQAVLE FKKLTEHP SGSDLLYY PNENREDS PAGVVKEV KEWRASK GLPGFKAG | Pseudomonas aeruginosa | 519 | ATGAAGTCCAAGATTTC CGAATATACGGAAAAA GAGTTTCTTGAGTTTGT TGAAGACATATACACA AACAATAAGAAAAAGT TCCCTACCGAGGAGTCT CATATTCAAGCCGTGCT TGAATTTAAAAAACTAA CGGAACACCCAAGCGG CTCAGACCTTCTTTACT ACCCCAACGAAAATAG AGAAGATAGCCCAGCT GGAGTTGTAAAGGAAG TTAAAGAATGGCGTGC TTCCAAGGGGCTTCCTG GCTTTAAGGCCGGTTAG |
| 520 | Pyocin-S2 immunity modulator | MKSKISEY TEKEFLEF VKDIYTNN KKKFPTEE SHIQAVLE FKKLTEHP SGSDLLYY PNENREDS PAGVVKEV KEWRASK GLPGFKAG | Pseudomonas aeruginosa (strain ATCC 15692/ PAO1/1C/ PRS 101/ LMG 12228) | 521 | ATGAAGTCCAAGATTTC CGAATATACGGAAAAA GAGTTTCTTGAGTTTGT TAAAGACATATACACA AACAATAAGAAAAAGT TCCCTACCGAGGAGTCT CATATTCAAGCCGTGCT TGAATTTAAAAAACTAA CGGAACACCCAAGCGG CTCAGACCTTCTTTACT ACCCCAACGAAAATAG AGAAGATAGCCCAGCT GGAGTTGTAAAGGAAG TTAAAGAATGGCGTGC TTCCAAGGGGCTTCCTG GCTTTAAGGCCGGTTAG |
| 522 | Hiracin-JM79 immunity factor | MDFTKEEK LLNAISKV YNEATIDD YPDLKEKL FLYSKEISE GKSVGEVS | Enterococcus hirae | 523 | ATGGATTTTACTAAAGA AGAAAAACTTTTAAAT GCAATTAGTAAAGTAT ACAATGAAGCAACTAT AGATGACTATCCTGACT TAAAAGAAAAGCTCTTT |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | MKLSSFLG RYILKHKF GLPKSLIEL QEIVSKES QVYRGWA SIGIWS | | | CTTTATTCTAAAGAAAT CAGTGAGGGAAAAAGT GTTGGTGAAGTTAGTAT GAAATTAAGTAGTTTTC TTGGAAGATATATTTTA AAACATAAATTTGGATT ACCTAAATCTTTAATAG AATTACAAGAAATTGTT AGTAAGGAATCTCAAG TATATAGAGGATGGGC TTCTATTGGTATTTGGA GTTAA |
| 524 | Probable mesentericin-Y105 immunity modulator | MKKKYRY LEDSKNYT STLYSLLV DNVDKPG YSDICDVL LQVSKKLD NTQSVEAL INRLVNYIR ITASTYKIIF SKKEEELII KLGVIGQK AGLNGQY MADFSDKS QFYSVFDQ | Leuconostoc mesenteroides | 525 | TTGAAAAAAAGTATC GGTATTTAGAAGATAG CAAAAATTACACTAGTA CACTCTATTCTCTGTTA GTTGATAATGTTGACAA ACCTGGATACTCAGATA TTTGCGATGTTTTGCTT CAAGTTTCTAAGAAGTT GGATAATACTCAAAGT GTTGAAGCGCTAATTA ATCGATTGGTTAATTAT ATTCGTATTACTGCTTC AACATACAAAATTATTT TTTCAAAAAAGAAGA GGAATTGATTATAAAA CTTGGTGTTATTGGACA AAAAGCTGGACTTAAT GGTCAGTATATGGCTG ATTTTTCAGACAAGTCT CAGTTTTACAGCGTTTT CGATCAGTAA |
| 526 | Microcin-24 immunity modulator | MSFLNFAF SPVFFSIMA CYFIVWRN KRNEFVCN RLLSIIIISFL ICFIYPWLN YKIEVKYY IFEQFYLFC FLSSLVAV VINLIVYFI LYRRCI | Escherichia coli | 527 | ATGAGTTTTCTTAATTT TGCATTTTCTCCTGTAT TCTTCTCCATTATGGCG TGTTATTTCATTGTATG GAGAAATAAACGAAAC GAATTTGTCTGCAATAG ATTGCTATCAATTATAA TAATATCTTTTTTGATA TGCTTCATATATCCATG GCTAAATTACAAAATC GAAGTTAAATATTATAT ATTTGAACAGTTTTATC TTTTTTGTTTTTTATCGT CACTCGTGGCTGTTGTA ATAAACCTAATTGTATA CTTTATATTATACAGGA GATGTATATGA |
| 528 | Colicin-K immunity modulator | MHLKYYL HNLPESLIP WILILIFND NDNTPLLFI FISSIHVLL YPYSKLTIS RYIKENTK LKKEPWYL CKLSALFY LLMAIPVG LPSFIYYTL KRN | Escherichia coli | 529 | ATGCATTTAAAATACTA CCTACATAATTTACCTG AATCACTTATACCATGG ATTCTTATTTTAATATT TAACGACAATGATAAC ACTCCTTTGTTATTTAT ATTTATATCATCAATAC ATGTATTGCTATATCCA TACTCTAAATTAACCAT ATCTAGATATATCAAAG AAAATACAAAGTTAAA AAAAGAACCCTGGTAC TTATGCAAGTTATCTGC ATTGTTTATTTATTAA TGGCAATCCCAGTAGG ATTGCCAAGTTTCATAT ATTACACTCTAAAGAG AAATTAA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 530 | Microcin C7 self-immunity modulator MccF | MMIQSHPL LAAPLAVG DTIGFFSSS APATVTAK NRFFRGVE FLQRKGFK LVSGKLTG KTDFYRSG TIKERAQE FNELVYNP DITCIMSTI GGDNSNSL LPFLDYDA IIANPKIIIG YSDTTALL AGIYAKTG LITFYGPAL IPSFGEHPP LVDITYESF IKILTRKQS GIYTYTLP EKWSDESI NWNENKIL RPKKLYKN NCAFYGSG KVEGRVIG GNLNTLTG IWGSEWM PEILNGDIL FIEDSRKSI ATIERLFS MLKLNRVF DKVSAIILG KHELFDCA GSKRRPYE VLTEVLDG KQIPVLDG FDCSHTHP MLTLPLGV KLAIDFDN KNISITEQY LSTEK | *Escherichia coli* | 531 | ATGATGATACAATCTCA TCCACTACTGGCCGCTC CCCTGGCAGTAGGAGA TACAATTGGTTTCTTTT CATCATCTGCTCCGGCA ACAGTTACTGCAAAAA ATCGTTTTTTTCGGGGA GTTGAGTTTCTTCAGAG AAAGGGATTTAAGCTG GTATCAGGGAAGCTTA CCGGTAAAACAGATTTT TATCGTTCAGGTACTAT TAAAGAAAGAGCTCAA GAATTTAATGAGTTAGT CTACAATCCTGATATTA CCTGTATAATGTCAACG ATCGGTGGAGATAACA GTAATTCACTACTACCG TTTCTGGACTATGATGC TATCATTGCAAACCCCA AAATTATCATAGGTTAC TCAGATACAACTGCTTT ATTAGCAGGAATATAT GCAAAAACAGGGTTAA TAACATTCTATGGACCA GCTCTTATTCCTTCGTT TGGTGAACATCCACCTC TTGTGGATATAACATAT GAATCATTTATTAAAAT ACTAACAAGAAAACAA TCAGGAATATATACCTA CACATTACCTGAAAAGT GGAGTGATGAGAGCAT AAACTGGAATGAAAAC AAGATATTAAGGCCTA AGAAGCTATATAAAAA CAACTGTGCCTTTTATG GTTCCGGAAAAGTTGA GGGGCGTGTAATTGGA GGAAATCTAAATACTTT GACAGGTATATGGGGG AGTGAATGGATGCCTG AAATTCTTAATGGAGAT ATATTGTTTATTGAGGA CAGTCGGAAAAGCATT GCAACAATTGAACGAT TATTCTCTATGCTAAAG CTTAATCGCGTGTTTGA TAAAGTTAGTGCAATA ATACTCGGGAAACATG AGCTTTTTGATTGTGCA GGAAGTAAACGCAGAC CATATGAAGTATTAACA GAGGTATTAGATGGGA AACAGATTCCTGTACTG GATGGATTTGATTGTTC ACATACACATCCAATGC TAACTCTTCCACTTGGT GTAAAATTAGCTATTGA CTTTGACAACAAAATA TAT |
| 532 | Sakacin-A immunity factor | MKADYKKI NSILTYTST ALKNPKIIK DKDLVVLL TIIQEEAKQ NRIFYDYK RKFRPAVT RFTIDNNFE IPDCLVKL | *Lactobacillus sakei* | 533 | GGCAGATTATAAAAAA ATAAATTCAATACTAAC TTACACATCTACTGCTT TAAAAAACCCTAAAATT ATAAAAGATAAAGATT TAGTAGTCCTTCTAACT ATTATTCAAGAAGAAG CCAAACAAATAGAAT CTTTTATGATTATAAAA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | LSAVETPK AWSGFS | | | GAAAATTTCGTCCAGC GGTTACTCGCTTTACAA TTGATAATAATTTTGAG ATTCCTGATTGTTTGGT TAAACTACTGTCAGCTG TTGAAACACCTAAGGC GTGGTCTGGATTTAGTT AG |
| 534 | Colicin-E5 immunity modulator in ColE9 (E5Imm[E9]) | MKLSPKAA IEVCNEAA KKGLWILG IDGGHWLN PGFRIDSSA SWTYDMP EEYKSKTP ENNRLAIE NIKDDIEN GYTAFIITL KM | Escherichia coli | 535 | TGAAGTTATCACCAAA AGCTGCAATAGAAGTT TGTAATGAAGCAGCGA AAAAAGGCTTATGGAT TTTGGGCATTGATGGTG GGCATTGGCTGAATCCT GGATTCAGGATAGATA GTTCAGCATCATGGAC ATATGATATGCCGGAG GAATACAAATCAAAAA CCCCTGAAAATAATAG ATTGGCTATTGAAAATA TTAAAGATGATATTGA GAATGGATACACTGCTT TCATTATCACGTTAAAG ATGTAA |
| 536 | Antilisterial bacteriocin subtilosin biosynthesis protein AlbD | MNNIFPIM SLLFKQLY SRQGKKDA IRIAAGLVI LAVFEIGLI RQAGIDES VLGKTYIIL ALLLMNTY MVFLSVTS QWKESYM KLSCLLPIS SRSFWLAQ SVVLFVDT CLRRTLFFF ILPLFLFGN GTLSGAQT LFWLGRFS FFTVYSILF GVMLSNHF VKKKNSM FLLHAAVF AFVCLSAA FMPAVTIP LCAVHML WAVIIDFP VFLQAPPH QSKMHFF MRRSEFSF YKREWNR FISSKAMLL NYVVMAA FSGFFSFQ MMNTGIFN QQVIYIVIS ALLLICSPI ALLYSIEK NDRMLLIT LPIKRRTM FWAKYRF YSGLLAGG FLLVAIIVG FISGRPISA LTFVQCME LLLAGAFIR LTADEKRP SFGWQTEQ QLWSGFSK | Bacillus subtilis | 537 | TTGGGGAGGAGACCGA TCTGCGGCGGGAATTTT TTGAGGTTATCGGCCAT GAATAACATATTCCCA TCATGTCGTTGCTGTTC AAACAGCTGTACAGCC GGCAAGGGAAAAAGGA CGCTATCCGCATTGCTG CAGGGCTTGTGATTCTC GCCGTGTTTGAAATCG GGCTGATCCGACAAGC CGGCATTGACGAATCG GTGTTGGGAAAAACGT ATATCATATTGGCGCTT CTCTTAATGAACACGTA TATGGTGTTTCTTTCCG TGACATCACAATGGAA GGAATCTTATATGAAG CTGAGCTGTCTGCTGCC GATTTCATCACGGAGCT TTTGGCTCGCCCAGAGT GTCGTTCTGTTTGTCGA TACCTGTTTGAGAAGA ACGTTATTCTTTTTTAT TTTACCGCTGTTCTTAT TTGGAAACGGAACGCT GTCAGGGGCGCAAACA TTGTTTTGGCTTGGCAG ATTTTCGTTTTTTACCG TTTACTCGATTCTATTC GGAGTTATGCTAAGCA ACCATTTCGTCAAAAAG AAGAACTCGATGTTTCT GCTGCATGCGGCGGTA TTCGCCTTTGTATGCCT CAGTGCCGCTTTTATGC CGGCCGTCACGATCCC GCTATGCGCGGTTCACA TGCTATGGGCGGTGAT CATTGACTTTCCGGTCT TTCTGCAGGCGCCTCCG CATCAGAGCAAGATGC ATTTTTTATGCGGCGA TCTGAATTTTCGTTTTA CAAAAGAGAATGGAAC CGATTTATTTCTTCTAA AGCGATGCTGTTAAATT |

TABLE 2-continued

Exemplary bacteriocin immunity modulators

| Poly-peptide SEQ ID NO: | Name | Polypeptide Sequence | Organism of origin | Poly-nucleotide SEQ ID NO: | Polynucleotide Sequence |
|---|---|---|---|---|---|
| | | YRSYLFCL PLFLATLA GTAVSLAV IPIAALIIVY YLQKQDG GFFDTSKR ERIGS | | | ACGTGGTGATGGCGGC GTTCAGCGGATTCTTTT CGTTCCAGATGATGAA CACTGGCATCTTCAATC AGCAAGTGATTTATATT GTGATTTCCGCTCTATT GCTGATTTGCTCGCCGA TCGCCCTTTTGTACTCT ATTGAAAAAAACGATC GCATGCTGCTCATCACG CTTCCAATTAAAAGAA GAACGATGTTTTGGGC GAAATATCGCTTTTATT CAG |
| 538 | Microcin-J25 export ATP-binding/permease protein McjD (Microcin-J25 immunity modulator) (Microcin-J25 secretion ATP-binding protein McjD) | MERKQKN SLFNYIYSL MDVRGKF LFFSMLFIT SLSSIIISISP LILAKITDL LSGSLSNFS YEYLVLLA CLYMFCVI SNKASVFL FMILQSSLR INMQKKM SLKYLREL YNENITNL SKNNAGYT TQSLNQAS NDIYILVR NVSQNILS PVIQLISTI VVVLSTKD WFSAGVFF LYILVFVIF NTRLTGSL ASLRKHSM DITLNSYSL LSDTVDN MIAAKKNN ALRLISERY EDALTQEN NAQKKYW LLSSKVLL LNSLLAVIL FGSVFIYNI LGVLNGV VSIGHFIMI TSYIILLST PVENIGAL LSEIRQSM SSLAGFIQR HAENKATS PSIPFLNME RKLNLSIRE LSFSYSDD KKILNSVS LDLFTGKM YSLTGPSG SGKSTLVK IISGYYKN YFGDIYLN DISLRNISD EDLNDAIY YLTQDDYI FMDTLRFN LRLANYDA SENEIFKVL KLANLSVV NNEPVSLD THLINRGN | Escherichia coli | 539 | ATGGAAAGAAAACAGA AAAACTCATTATTTAAT TATATTTATTCATTAAT GGATGTAAGAGGTAAA TTTTTATTCTTTTCCAT GTTATTCATTACATCAT TATCATCGATAATCATA TCTATTTCACCATTGAT TCTTGCAAAGATTACAG ATTTACTGTCTGGCTCA TTGTCAAATTTTAGTTA TGAATATCTGGTTTTAC TTGCCTGTTTATACATG TTTTGCGTTATATCTAA TAAAGCAAGTGTTTTTT TATTTATGATACTGCAA AGTAGTCTACGTATTAA CATGCAGAAAAAAATG TCGCTAAAGTATTTGAG AGAATTGTATAACGAA AATATAACTAACTTGAG TAAAAATAATGCTGGA TATACAACGCAAAGTCT TAACCAGGCTTCAAATG ACATTTATATTCTTGTG AGAAATGTTTCCAGA ATATCCTGTCACCTGTT ATACAACTTATTTCCAC TATTGTTGTTGTTTTAT CTACGAAGGACTGGTTT TCTGCCGGTGTGTTTTT TCTCTATATTCTGGTAT TTGTAATTTTTAATACC AGACTGACTGGCAGTTT AGCGTCTCTCAGAAAA CACAGCATGGATATCA CTCTTAACTCTTATAGT CTGTTATCTGATACTGT TGATAACATGATAGCA GCTAAAAAGAATAATG CATTAAGACTTATTTCT GAACGTTATGAAGATG CTCTCACTCAGGAAAAC AATGCTCAGAAAAAAT ACTGGTTACTCAGTTCT AAAGTTCTTTTATTGAA CTCTTTACTTGCTGTAA TATTATTTGGTTCTGTA TTCATATATAATATTTT AGGTGTGCTGAATGGT GTAGTTAGTATCGGCCA CTTCATTATGATTACAT CATATATCATTCTTCTT TCAACGCCAGTGGAAA ATATAGGGGCATTGCT AAGTGAGATCAGGCAG TCAATGTCTAGCCTGGC AGGTTTTATTCAACGTC |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | NYSGGQK QRISLARLF LRKPAIIID EATSALDY INESEILSSI RTHFPDALI INISHRINL LECSDCVY VLNEGNIV ASGHFRDL MVSNEYIS GLASVTE | | | ATGCCGAGAATAAAGC CACATCTCCTTCAA |
| 540 | Microcin E492 immunity modulator | MTLLSFGF SPVFFSVM AFCIISRSK FYPQRTRN KVIVLILLT FFICFLYPL TKVYLVGS YGIFDKFY LFCFISTLI AIAINVVIL TINGAKNE RN | *Klebsiella pneumoniae* | 541 | ATGACATTACTTTCATT TGGATTTTCTCCTGTTT TCTTTTCAGTCATGGCG TTCTGTATCATTTCACG TAGTAAATTCTATCCGC AGAGAACGCGAAACAA AGTTATTGTTCTGATTT TACTAACTTTTTTATT TGTTTTTTATATCCATT AACAAAAGTGTATCTG GTGGGAAGTTACGGTA TATTTGACAAATTCTAC CTCTTTTGCTTTATTTC TACGTTAATTGCAATAG CAATTAACGTAGTGATA CTTACAATAAATGGAG CTAAGAATGAGAGAAA TTAG |

Poison-Antidote Systems

It can be desirable to contain a particular microbial cell within a desired environment, for example by killing or arresting the growth of the microbial cell if it is no longer in the desired environment. Poison-antidote systems, which are distinct from bacteriocins, can be useful for accomplishing such containment, or for other selective growth of microbial cells. Exemplary poison antidote systems are described in U.S. Pat. Nos. 5,910,438, 6,180,407, 7,176,029, and 7,183,097, each of which is hereby incorporated by reference in its entirety. In some embodiments, a poison-antidote system comprises a cytotoxic (poison) polypeptide, and a corresponding antitoxin (antidote) polypeptide in a single cell. As used herein, a "poison polynucleotide" refers to a polynucleotide encoding a poison polypeptide, and an "antidote polynucleotide" refers to a polynucleotide encoding an antidote polypeptide.

In some embodiments, the poison polypeptide is expressed constitutively, while the antidote polypeptide is only expressed under desired conditions. In some embodiments, the poison polypeptide is only expressed under undesired conditions, while the antidote polypeptide is only expressed under desired conditions. For example, in some embodiments, a poison/antidote system is configured so that the microbial cell survives under desired environmental conditions, but dies under undesired environmental conditions. For example, in some embodiments, a poison antidote system is configured so that the microbial cell is killed if it escapes from the environment in which it is being used in an industrial process. In other embodiments, a poison antidote system is configured so that the microbial cell survives when a vector (e.g. a plasmid) encoding an antidote polypeptide is present, but dies when the vector is absent. In some embodiments, the poison polypeptide is encoded by a poison polynucleotide in the host genome, while the antidote polypeptide is encoded by an antidote polynucleotide on a vector (such as a plasmid or extrachromosomal array or episome or minichromosome), and as such is only expressed when the vector is present in the host cell. In some embodiments, the poison polypeptide is encoded by a poison polynucleotide on a first vector, while the antidote polypeptide is encoded by an antidote polynucleotide on a second vector, and as such is only expressed when the second vector is present. In some embodiments, the presence of the antidote polynucleotide (and thus the presence of the antidote polypeptide) depends on the presence or absence of a recombination event, for example the integration of a polynucleotide sequence encoding the antidote polynucleotide into the host genome. It should be appreciated that in some embodiments in which expression of the antidote polypeptide depends on the presence or absence of a vector or recombination event, the poison and antidote polypeptide can each be expressed constitutively. Optionally, in some embodiments in which expression of the antidote polypeptide depends on the presence or absence of a vector or a recombination event, expression of the poison polypeptide and/or antidote polypeptide is conditional, for example so that the poison is only expressed in conditions in which the microbial cell is not desired, and/or the antidote polypeptide is only expressed in conditions in which the microbial cell is desired.

Exemplary microbial toxin polypeptide/antitoxin polypeptide pairs (also referred to as "poison/antidote" pairs) that can used in poison antidote systems in conjunction with some embodiments herein include, but are not limited to RelE/RelB, CcdB/CcdA, Kis/Kid, SoK/HoK, PasB (or PasC)/PasA, PemK/PemI, Doc/Phd, MazE/MazF and ParE/ParD. Without being limited by any particular theory, many poison polypeptides, for example RelE, are highly conserved across Gram-positive and Gram-negative bacteria and Archae, and as such, can have cytotoxic activity in a broad range of naturally occurring, genetically modified, and fully synthetic microbial cells. Further, without being limited by any particular theory, it is contemplated that an antidote polypeptide can generally inhibit the activity of its poison polypeptide partner in a variety of host environments, and as such, poison/antidote pairs such as those described herein can readily be used in a broad range of naturally occurring, genetically modified, and fully synthetic microbial cells.

It is noted that a poison-antidote system is distinct from a bacteriocin system at least in that a poison-antidote system provides an endogenous system by which a microbial cell can kill or arrest itself, while a bacteriocin system provides an exogenous system by which a microbial cell can kill or arrest other cells. It is further noted, however, that, while a poison-antidote system cannot be used to kill or arrest cells other than the individual cell in which the poison is produced, in some embodiments, a poison-antidote system may be used along with a bacteriocin system as described herein. For example, in some embodiments a bacteriocin system as described herein may be used to kill or arrest the growth of cells other than the bacteriocin producing cell in a culture while the poison-antidote system may be used to kill or arrest the growth of the bacteriocin producing cell should it escape from its desired environment. A poison-antidote system may also be used to select for bacteriocin producing cells which have been genetically engineered to express a molecule useful in an industrial process (an "industrially useful molecule"). For example, in some embodiments, expression of an antidote can be tied to expression of an industrially useful molecule or bacteriocin by placing polynucleotides encoding the bacteriocin and the industrially useful molecule, or polynucleotides encoding the bacteriocin and antidote under the control of a single promoter. Accordingly, in some embodiments, a microbial cell encoding a bacteriocin or bacteriocin immunity modulator further comprises a poison antidote system. In some embodiments, the bacteriocin system is useful for regulating growth of the microbial cell or other microbial cells within a particular environment, while the poison-antidote system is useful for containing the microbial cell within a particular environment.

Promoters

Promoters are well known in the art. A promoter can be used to drive the transcription of one or more genes. In some embodiments, a promoter drives expression of polynucleotide encoding a desired gene product as described herein. In some embodiments, a promoter drives expression of a bacteriocin polynucleotide as described herein. In some embodiments, a promoter drives expression of an immunity modulator polynucleotide as described herein. In some embodiments, a promoter drives expression of a bacteriocin nucleotide and an immunity modulator polynucleotide. In some embodiments, a promoter drives expression of polynucleotide encoding at least one of a bacteriocin, immunity modulator, industrially useful molecule, poison molecule, or antidote molecule. Some promoters can drive transcription at all times ("constitutive promoters"). Some promoters can drive transcription under only select circumstances ("conditional promoters"), for example depending on the presence or absence of an environmental condition, chemical compound, gene product, stage of the cell cycle, or the like.

The skilled artisan will appreciate that depending on the desired expression activity, an appropriate promoter can be selected, and placed in cis with a sequence to be expressed. Exemplary promoters with exemplary activities are provided in Table 3.1-3.11 herein. The skilled artisan will appreciate that some promoters are compatible with particular transcriptional machinery (e.g. RNA polymerases, general transcription factors, and the like). As such, while compatible "species" are identified for some promoters described herein, it is contemplated that according to some embodiments herein, these promoters can readily function in microorganisms other than the identified species, for example in species with compatible endogenous transcriptional machinery, genetically modified species comprising compatible transcriptional machinery, or fully synthetic microbial organisms comprising compatible transcriptional machinery.

The promoters of Tables 3.1-3.11 herein are publicly available from the Biobricks foundation. Per the Biobricks foundation, use of these promoters in accordance with BioBrick™ Public Agreement (BPA) is encouraged.

It should be appreciated that any of the "coding" polynucleotides described herein (for example a bacteriocin polynucleotide, immunity polynucleotide, poison polynucleotide, antidote polynucleotide, or product polynucleotide) is generally amenable to being expressed under the control of a desired promoter. In some embodiments, a single "coding" polynucleotide is under the control of a single promoter. In some embodiments, two or more "coding" polynucleotides are under the control of a single promoter, for example two, three, four, five, six, seven, eight, nine, or ten polynucleotides. As such, in some embodiments, a "cocktail" of different bacteriocins can be produced by a single microbial organism. In some embodiments, a bacteriocin polynucleotide is under the control of a promoter. In some embodiments, an immunity modulator is under the control of a promoter. In some embodiments, a polynucleotide encoding a desired gene product is under the control of a promoter. In some embodiments, the bacteriocin polynucleotide and the polynucleotide encoding a desired gene product are under the control of the same promoter. In some embodiments, a bacteriocin polynucleotide and the polynucleotide encoding a desired gene product are under the control of different promoters. In some embodiments, the immunity modulator polynucleotide and the polynucleotide encoding a desired gene product are under the control of the same promoter. In some embodiments, the bacteriocin polynucleotide and the immunity modulator polynucleotide are under the control of different promoters.

Generally, translation initiation for a particular transcript is regulated by particular sequences at or 5' of the 5' end of the coding sequence of a transcript. For example, a coding sequence can begin with a start codon configured to pair with an initiator tRNA. While naturally-occurring translation systems typically use Met (AUG) as a start codon, it will be readily appreciated that an initiator tRNA can be engineered to bind to any desired triplet or triplets, and accordingly, triplets other than AUG can also function as start codons in certain embodiments. Additionally, sequences near the start codon can facilitate ribosomal assembly, for example a Kozak sequence ((gcc)gccRccAUGG, SEQ ID NO: 542, in which R represents "A" or "G") or Internal Ribosome Entry Site (IRES) in typical eukaryotic translational systems, or a Shine-Delgarno sequence (GGAGGU, SEQ ID NO: 543) in typical prokaryotic translation systems.

As such in some embodiments, a transcript comprising a "coding" polynucleotide sequence, for example a bacteriocin polynucleotide or immunity modulator polynucleotide, or polynucleotide encoding a desired industrial product, comprises an appropriate start codon and translational initiation sequence. In some embodiments, for example if two or more "coding" polynucleotide sequences are positioned in cis on a transcript, each polynucleotide sequence comprises an appropriate start codon and translational initiation sequence(s). In some embodiments, for example if two or more "coding" polynucleotide sequences are positioned in cis on a transcript, the two sequences are under control of a single translation initiation sequence, and either provide a single polypeptide that can function with both encoded polypeptides in cis, or provide a means for separating two polypeptides encoded in cis, for example a 2A sequence or the like. In some embodiments, a translational intiator tRNA is regulatable, so as to regulate initiation of translation of a bacteriocin, immunity modulator, poison molecule, antidote molecule, or industrially useful molecule.

TABLE 3.1

Exemplary Metal-Sensitive Promoters

| SEQ ID NO: | Name | Description | Sequence |
|---|---|---|---|
| 544 | BBa_I721001 | Lead Promoter | gaaaaccttgtcaatgaagagcgatctatg |
| 545 | BBa_I731004 | FecA promoter | ttctcgttcgactcatagctgaacacaaca |
| 546 | BBa_I760005 | Cu-sensitive promoter | atgacaaaattgtcat |
| 547 | BBa_I765000 | Fe promoter | accaatgctgggaacggccagggcacctaa |
| 548 | BBa_I765007 | Fe and UV promoters | ctgaaagcgcataccgctatggagggggtt |
| 549 | BBa_J3902 | PrFe (PI + PII rus operon) | tagatatgcctgaaagcgcataccgctatg |

TABLE 3.2

Exemplary Cell Signaling-Responsive Promoters

| SEQ ID NO: | Name | Description | Sequence |
|---|---|---|---|
| 550 | BBa_I1051 | Lux cassette right promoter | tgttatagtcgaatacctctggcggtgata |
| 551 | BBa_I14015 | P(Las) TetO | ttttggtacactccctatcagtgatagaga |
| 552 | BBa_I14016 | P(Las) CIO | cttttggtacactacctctggcggtgata |
| 553 | BBa_I14017 | P(Rhl) | tacgcaagaaaatggtttgttatagtcgaa |
| 554 | BBa_I739105 | Double Promoter (LuxR/HSL, positive/cI, negative) | cgtgcgtgttgataacaccgtgcgtgttga |
| 555 | BBa_I746104 | P2 promoter in agr operon from S. aureus | agattgtactaaatcgtataatgacagtga |
| 556 | BBa_I751501 | plux-cI hybrid promoter | gtgttgatgcttttatcaccgccagtggta |
| 557 | BBa_I751502 | plux-lac hybrid promoter | agtgtgtggaattgtgagcggataacaatt |
| 558 | BBa_I761011 | CinR, CinL and glucose controlled promotor | acatcttaaaagttttagtatcatattcgt |
| 559 | BBa_J06403 | RhIR promoter repressible by CI | tacgcaagaaaatggtttgttatagtcgaa |
| 560 | BBa_J102001 | Reverse Lux Promoter | tcttgcgtaaacctgtacgatcctacaggt |
| 561 | BBa_J64000 | rhlI promoter | atcctcctttagtcttccccctcatgtgtg |
| 562 | BBa_J64010 | lasI promoter | taaaattatgaaatttgcataaattcttca |
| 563 | BBa_J64067 | LuxR + 3OC6HSL independent R0065 | gtgttgactattttacctctggcggtgata |
| 564 | BBa_J64712 | LasR/LasI Inducible & RHLR/RHLI repressible Promoter | gaaatctggcagttttggtacacgaaagc |

TABLE 3.2-continued

Exemplary Cell Signaling-Responsive Promoters

| SEQ ID NO: | Name | Description | Sequence |
|---|---|---|---|
| 565 | BBa_K091107 | pLux/cI Hybrid Promoter | acaccgtgcgtgttgatatagtcgaataaa |
| 566 | BBa_K091117 | pLas promoter | aaaattatgaaatttgtataaattcttcag |
| 567 | BBa_K091143 | pLas/cI Hybrid Promoter | ggttcttttggtacctctggcggtgataa |
| 568 | BBa_K091146 | pLas/Lux Hybrid Promoter | tgtaggatcgtacaggtataaattcttcag |
| 569 | BBa_K091156 | pLux | caagaaaatggtttgttatagtcgaataaa |
| 570 | BBa_K091157 | pLux/Las Hybrid Promoter | ctatctcatttgctagtatagtcgaataaa |
| 571 | BBa_K145150 | Hybrid promoter: HSL-LuxR activated, P22 C2 repressed | tagtttataatttaagtgttctttaatttc |
| 572 | BBa_K266000 | PAI + LasR -> LuxI (AI) | caccttcgggtgggcctttctgcgtttata |
| 573 | BBa_K266005 | PAI + LasR -> LasI & AI + LuxR --\|LasI | aataactctgatagtgctagtgtagatctc |
| 574 | BBa_K266006 | PAI + LasR -> LasI + GFP & AI + LuxR --\|LasI + GFP | caccttcgggtgggcctttctgcgtttata |
| 575 | BBa_K266007 | Complex QS -> LuxI & LasI circuit | caccttcgggtgggcctttctgcgtttata |
| 576 | BBa_K658006 | position 3 mutated promoter lux pR-3 (luxR & HSL regulated) | caagaaaatggtttgttatagtcgaataaa |
| 577 | BBa_K658007 | position 5 mutated promoter lux pR-5 (luxR & HSL regulated) | caagaaaatggtttgttatagtcgaataaa |
| 578 | BBa_K658008 | position 3&5 mutated promoter lux pR-3/5 (luxR & HSL regulated) | caagaaaatggtttgttatagtcgaataaa |
| 579 | BBa_R0061 | Promoter (HSL-mediated luxR repressor) | ttgacacctgtaggatcgtacaggtataat |
| 580 | BBa_R0062 | Promoter (luxR & HSL regulated -- lux pR) | caagaaaatggtttgttatagtcgaataaa |
| 581 | BBa_R0063 | Promoter (luxR & HSL regulated - lux pL) | cacgcaaaacttgcgacaaacaataggtaa |
| 582 | BBa_R0071 | Promoter (Rh1R & C4-HSL regulated) | gttagctttcgaattggctaaaaagtgttc |
| 583 | BBa_R0078 | Promoter (cinR and HSL regulated) | ccattctgctttccacgaacttgaaaacgc |
| 584 | BBa_R0079 | Promoter (LasR & PAI regulated) | ggccgcgggttcttttggtacacgaaagc |
| 585 | BBa_R1062 | Promoter, Standard (luxR and HSL regulated -- lux pR) | aagaaaatggtttgttgatactcgaataaa |

TABLE 3.3

Exemplary Constitutive E. coli $\sigma^{70}$ Promoters

| SEQ ID NO: | Name | Description | Sequence |
|---|---|---|---|
| 586 | BBa_I14018 | P(Bla) | gtttatacataggcgagtactctgttatgg |
| 587 | BBa_I14033 | P(Cat) | agaggttccaactttcaccataatgaaaca |

TABLE 3.3-continued

Exemplary Constitutive *E. coli* σ[70] Promoters

| SEQ ID NO: | Name | Description | Sequence |
|---|---|---|---|
| 588 | BBa_I14034 | P(Kat) | taaacaactaacggacaattctacctaaca |
| 589 | BBa_I732021 | Template for Building Primer Family Member | acatcaagccaaattaaacaggattaacac |
| 590 | BBa_I742126 | Reverse lambda cI-regulated promoter | gaggtaaaatagtcaacacgcacggtgtta |
| 591 | BBa_J01006 | Key Promoter absorbs 3 | caggccggaataactccctataatgcgcca |
| 592 | BBa_J23100 | constitutive promoter family member | ggctagctcagtcctaggtacagtgctagc |
| 593 | BBa_J23101 | constitutive promoter family member | agctagctcagtcctaggtattatgctagc |
| 594 | BBa_J23102 | constitutive promoter family member | agctagctcagtcctaggtactgtgctagc |
| 595 | BBa_J23103 | constitutive promoter family member | agctagctcagtcctagggattatgctagc |
| 596 | BBa_J23104 | constitutive promoter family member | agctagctcagtcctaggtattgtgctagc |
| 597 | BBa_J23105 | constitutive promoter family member | ggctagctcagtcctaggtactatgctagc |
| 598 | BBa_J23106 | constitutive promoter family member | ggctagctcagtcctaggtatagtgctagc |
| 599 | BBa_J23107 | constitutive promoter family member | ggctagctcagccctaggtattatgctagc |
| 600 | BBa_J23108 | constitutive promoter family member | agctagctcagtcctaggtataatgctagc |
| 601 | BBa_J23109 | constitutive promoter family member | agctagctcagtcctagggactgtgctagc |
| 602 | BBa_J23110 | constitutive promoter family member | ggctagctcagtcctaggtacaatgctagc |
| 603 | BBa_J23111 | constitutive promoter family member | ggctagctcagtcctaggtatagtgctagc |
| 604 | BBa_J23112 | constitutive promoter family member | agctagctcagtcctagggattatgctagc |
| 605 | BBa_J23113 | constitutive promoter family member | ggctagctcagtcctagggattatgctagc |
| 606 | BBa_J23114 | constitutive promoter family member | ggctagctcagtcctaggtacaatgctagc |
| 607 | BBa_J23115 | constitutive promoter family member | agctagctcagcccttggtacaatgctagc |
| 608 | BBa_J23116 | constitutive promoter family member | agctagctcagtcctagggactatgctagc |
| 609 | BBa_J23117 | constitutive promoter family member | agctagctcagtcctagggattgtgctagc |
| 610 | BBa_J23118 | constitutive promoter family member | ggctagctcagtcctaggtattgtgctagc |
| 611 | BBa_J23119 | constitutive promoter family member | agctagctcagtcctaggtataatgctagc |
| 612 | BBa_J23150 | 1bp mutant from J23107 | ggctagctcagtcctaggtattatgctagc |
| 613 | BBa_J23151 | 1bp mutant from J23114 | ggctagctcagtcctaggtacaatgctagc |

TABLE 3.3-continued

Exemplary Constitutive *E. coli* σ⁷⁰ Promoters

| SEQ ID NO:Name | Description | Sequence |
|---|---|---|
| 614 BBa_J44002 | pBAD reverse | aaagtgtgacgccgtgcaaataatcaatgt |
| 615 BBa_J48104 | NikR promoter, a protein of the ribbon helix-helix family of trancription factors that repress expre | gacgaatacttaaaatcgtcatacttattt |
| 616 BBa_J54200 | lacq_Promoter | aaacctttcgcggtatggcatgatagcgcc |
| 617 BBa_J56015 | lacIQ - promoter sequence | tgatagcgcccggaagagagtcaattcagg |
| 618 BBa_J64951 | *E. Coli* CreABCD phosphate sensing operon promoter | ttatttaccgtgacgaactaattgctcgtg |
| 619 BBa_K088007 | GlnRS promoter | catacgccgttatacgttgtttacgctttg |
| 620 BBa_K119000 | Constitutive weak promoter of lacZ | ttatgcttccggctcgtatgttgtgtggac |
| 621 BBa_K119001 | Mutated LacZ promoter | ttatgcttccggctcgtatggtgtgtggac |
| 622 BBa_K137029 | constitutive promoter with (TA)10 between -10 and -35 elements | atatatatatatatataatggaagcgtttt |
| 623 BBa_K137030 | constitutive promoter with (TA)9 between -10 and -35 elements | atatatatatatataatggaagcgtttt |
| 624 BBa_K137031 | constitutive promoter with (C)10 between -10 and -35 elements | ccccgaaagcttaagaatataattgtaagc |
| 625 BBa_K137032 | constitutive promoter with (C)12 between -10 and -35 elements | ccccgaaagcttaagaatataattgtaagc |
| 626 BBa_K137085 | optimized (TA) repeat constitutive promoter with 13 bp between -10 and -35 elements | tgacaatatatatatatataatgctagc |
| 627 BBa_K137086 | optimized (TA) repeat constitutive promoter with 15 bp between -10 and -35 elements | acaatatatatatatatataatgctagc |
| 628 BBa_K137087 | optimized (TA) repeat constitutive promoter with 17 bp between -10 and -35 elements | aatatatatatatatatataatgctagc |
| 629 BBa_K137088 | optimized (TA) repeat constitutive promoter with 19 bp between -10 and -35 elements | tatatatatatatatatataatgctagc |
| 630 BBa_K137089 | optimized (TA) repeat constitutive promoter with 21 bp between -10 and -35 elements | tatatatatatatatatataatgctagc |
| 631 BBa_K137090 | optimized (A) repeat constitutive promoter with 17 bp between -10 and -35 elements | aaaaaaaaaaaaaaaaatataatgctagc |
| 632 BBa_K137091 | optimized (A) repeat constitutive promoter with 18 bp between -10 and -35 elements | aaaaaaaaaaaaaaaaatataatgctagc |
| 633 BBa_K256002 | J23101:GFP | caccttcgggtgggcctttctgcgtttata |

TABLE 3.3-continued

Exemplary Constitutive *E. coli* σ⁷⁰ Promoters

| SEQ ID NO: | Name | Description | Sequence |
|---|---|---|---|
| 634 | BBa_K256018 | J23119:IFP | caccttcgggtgggcctttctgcgtttata |
| 635 | BBa_K256020 | J23119:HO1 | caccttcgggtgggcctttctgcgtttata |
| 636 | BBa_K256033 | Infrared signal reporter (J23119:IFP:J23119:HO1) | caccttcgggtgggcctttctgcgtttata |
| 637 | BBa_K292000 | Double terminator + constitutive promoter | ggctagctcagtcctaggtacagtgctagc |
| 638 | BBa_K292001 | Double terminator + Constitutive promoter + Strong RBS | tgctagctactagagattaaagaggagaaa |
| 639 | BBa_K418000 | IPTG inducible Lac promoter cassette | ttgtgagcggataacaagatactgagcaca |
| 640 | BBa_K418002 | IPTG inducible Lac promoter cassette | ttgtgagcggataacaagatactgagcaca |
| 641 | BBa_K418003 | IPTG inducible Lac promoter cassette | ttgtgagcggataacaagatactgagcaca |
| 642 | BBa_M13101 | M13K07 gene I promoter | cctgtttttatgttattctctctgtaaagg |
| 643 | BBa_M13102 | M13K07 gene II promoter | aaatatttgcttatacaatcttcctgttttt |
| 644 | BBa_M13103 | M13K07 gene III promoter | gctgataaaccgatacaattaaaggctcct |
| 645 | BBa_M13104 | M13K07 gene IV promoter | ctcttctcagcgtcttaatctaagctatcg |
| 646 | BBa_M13105 | M13K07 gene V promoter | atgagccagttcttaaaatcgcataaggta |
| 647 | BBa_M13106 | M13K07 gene VI promoter | ctattgattgtgacaaaataaacttattcc |
| 648 | BBa_M13108 | M13K07 gene VIII promoter | gtttcgcgcttggtataatcgctgggggtc |
| 649 | BBa_M13110 | M13110 | ctttgcttctgactataatagtcagggtaa |
| 650 | BBa_M31519 | Modified promoter sequence of g3. | aaaccgatacaattaaaggctcctgctagc |
| 651 | BBa_R1074 | Constitutive Promoter I | caccacactgatagtgctagtgtagatcac |
| 652 | BBa_R1075 | Constitutive Promoter II | gccggaataactccctataatgcgccacca |
| 653 | BBa_S03331 | --Specify Parts List-- | ttgacaagcttttcctcagctccgtaaact |

TABLE 3.4

Exemplary Constitutive *E. coli* σˢ Promoters

| SEQ ID NO: | Name | Description | Sequence |
|---|---|---|---|
| 654 | BBa_J45992 | Full-length stationary phase osmY promoter | ggtttcaaaattgtgatctatatttaacaa |
| 655 | BBa_J45993 | Minimal stationary phase osmY promoter | ggtttcaaaattgtgatctatatttaacaa |

TABLE 3.5

Exemplary Constitutive *E. coli* σ³² Promoters

| SEQ ID NO: | Name | Description | Sequence |
|---|---|---|---|
| 656 | BBa_J45504 | htpG Heat Shock Promoter | tctattccaataaagaaatcttcctgcgtg |

TABLE 3.6

Exemplary Constitutive *B. subtilis* σ^A Promoters

| SEQ ID NO: | Name | Description | Sequence |
|---|---|---|---|
| 657 | BBa_K143012 | Promoter veg a constitutive promoter for *B. subtilis* | aaaaatgggctcgtgttgtacaataaatgt |
| 658 | BBa_K143013 | Promoter 43 a constitutive promoter for *B. subtilis* | aaaaaaagcgcgcgattatgtaaaatataa |
| 659 | BBa_K780003 | Strong constitutive promoter for *Bacillus subtilis* | aattgcagtaggcatgacaaaatggactca |
| 660 | BBa_K823000 | PliaG | caagcttttcctttataatagaatgaatga |
| 661 | BBa_K823002 | PlepA | tctaagctagtgtattttgcgtttaatagt |
| 662 | BBa_K823003 | Pveg | aatgggctcgtgttgtacaataaatgtagt |

TABLE 3.7

Exemplary Constitutive *B. subtilis* σ^B Promoters

| SEQ ID NO: | Name | Description | Sequence |
|---|---|---|---|
| 663 | BBa_K143010 | Promoter ctc for *B. subtilis* | atccttatcgttatgggtattgtttgtaat |
| 664 | BBa_K143011 | Promoter gsiB for *B. subtilis* | taaaagaattgtgagcgggaatacaacaac |
| 665 | BBa_K143013 | Promoter 43 a constitutive promoter for *B. subtilis* | aaaaaaagcgcgcgattatgtaaaatataa |

TABLE 3.8

Exemplary Constitutive Promoters from miscellaneous prokaryotes

| SEQ ID NO: | Name | Description | Sequence |
|---|---|---|---|
| 666 | a_K112706 | Pspv2 from *Salmonella* | tacaaaataattcccctgcaaacattatca |
| 667 | BBa_K112707 | Pspv from *Salmonella* | tacaaaataattcccctgcaaacattatcg |

TABLE 3.9

Exemplary Constitutive Promoters from bacteriophage T7

| SEQ ID NO: | Name | Description | Sequence |
|---|---|---|---|
| 668 | BBa_I712074 | T7 promoter (strong promoter from T7 bacteriophage) | agggaatacaagctacttgttcttttgca |

TABLE 3.9-continued

Exemplary Constitutive Promoters from bacteriophage T7

| SEQ ID NO | Name | Description | Sequence |
|---|---|---|---|
| 669 | BBa_I719005 | T7 Promoter | taatacgactcactatagggaga |
| 670 | BBa_J34814 | T7 Promoter | gaatttaatacgactcactatagggaga |
| 671 | BBa_J64997 | T7 consensus -10 and rest | taatacgactcactatagg |
| 672 | BBa_K113010 | overlapping T7 promoter | gagtcgtattaatacgactcactatagggg |
| 673 | BBa_K113011 | more overlapping T7 promoter | agtgagtcgtactacgactcactatagggg |
| 674 | BBa_K113012 | weaken overlapping T7 promoter | gagtcgtattaatacgactctctatagggg |
| 675 | BBa_R0085 | T7 Consensus Promoter Sequence | taatacgactcactatagggaga |
| 676 | BBa_R0180 | T7 RNAP promoter | ttatacgactcactatagggaga |
| 677 | BBa_R0181 | T7 RNAP promoter | gaatacgactcactatagggaga |
| 678 | BBa_R0182 | T7 RNAP promoter | taatacgtctcactatagggaga |
| 679 | BBa_R0183 | T7 RNAP promoter | tcatacgactcactatagggaga |
| 680 | BBa_Z0251 | T7 strong promoter | taatacgactcactatagggagaccacaac |
| 681 | BBa_Z0252 | T7 weak binding and processivity | taattgaactcactaaagggagaccacagc |
| 682 | BBa_Z0253 | T7 weak binding promoter | cgaagtaatacgactcactattagggaaga |

TABLE 3.10

Exemplary Constitutive Promoters from yeast

| SEQ ID NO | Name | Description | Sequence |
|---|---|---|---|
| 683 | BBa_I766555 | pCyc (Medium) Promoter | acaaacacaaatacacacactaaattaata |
| 684 | BBa_I766556 | pAdh (Strong) Promoter | ccaagcatacaatcaactatctcatataca |
| 685 | BBa_I766557 | pSte5 (Weak) Promoter | gatacaggatacagcggaaacaacttttaa |
| 686 | BBa_J63005 | yeast ADH1 promoter | tttcaagctataccaagcatacaatcaact |
| 687 | BBa_K105027 | cyc100 minimal promoter | cctttgcagcataaattactatacttctat |
| 688 | BBa_K105028 | cyc70 minimal promoter | cctttgcagcataaattactatacttctat |
| 689 | BBa_K105029 | cyc43 minimal promoter | cctttgcagcataaattactatacttctat |
| 690 | BBa_K105030 | cyc28 minimal promoter | cctttgcagcataaattactatacttctat |
| 691 | BBa_K105031 | cyc16 minimal promoter | cctttgcagcataaattactatacttctat |
| 692 | BBa_K122000 | pPGK1 | ttatctacttttacaacaaatataaaaca |
| 693 | BBa_K124000 | pCYC Yeast Promoter | acaaacacaaatacacacactaaattaata |
| 694 | BBa_K124002 | Yeast GPD (TDH3) Promoter | gtttcgaataaacacacataaacaaacaaa |
| 695 | BBa_K319005 | yeast mid-length ADH1 promoter | ccaagcatacaatcaactatctcatataca |

TABLE 3.10-continued

Exemplary Constitutive Promoters from yeast

| SEQ ID NO: | Name | Description | Sequence |
|---|---|---|---|
| 696 | BBa_M31201 | Yeast CLB1 promoter region, G2/M cell cycle specific | accatcaaaggaagctttaatcttctcata |

TABLE 3.11

Exemplary Constitutive Promoters from miscellaneous eukaryotes

| SEQ ID NO: | Name | Description | Sequence |
|---|---|---|---|
| 697 | BBa_I712004 | CMV promoter | agaacccactgcttactggcttatcgaaat |
| 698 | BBa_K076017 | Ubc Promoter | ggccgttttggcttttttgttagacgaag |

The above-referenced promoters are provided by way of non-limiting example only. The skilled artisan will readily recognize that many variants of the above-referenced promoters, and many other promoters (including promoters isolated from naturally existing organisms, variations thereof, and fully synthetic promoters) can readily be used in accordance with some embodiments herein.

Regulation of Gene Activity

Gene activity can be regulated to either increase or decrease activity of the gene product. In some embodiments, the gene product for which activity is regulated comprises a bacteriocin, immunity modulator, industrially useful molecule, poison molecule, or antidote molecule. In some embodiments, two or more of such gene products are regulated under a single gene regulation system. In some embodiments, gene activity is regulated at the level of gene expression. In some embodiments, gene activity is regulated at the transcriptional level, for example by activating or repressing a promoter. In some embodiments, gene activity is regulated at the post-transcriptional level, for example through regulation of RNA stability. In some embodiments, gene activity is regulated at the translational level, for example through regulation of initiation of translation. In some embodiments, gene activity is regulated at the post-translational level, for example through regulation of polypeptide stability, post-translational modifications to the polypeptide, or binding of an inhibitor to the polypeptide.

In some embodiments, gene activity is increased. In some embodiments, activity of at least one of a bacteriocin, immunity modulator, industrially useful molecule, poison molecule, or antidote molecule is increased. Conceptually, gene activity can be increased by directly activating gene activity, or by decreasing the activity of an inhibitor of gene activity. In some embodiments, gene activity is activated by at least one of: inducing promoter activity, inhibiting a transcriptional repressor, increasing RNA stability, inhibiting a post-transcriptional inhibitor (for example, inhibiting a ribozyme or antisense oligonucleotide), inducing translation (for example, via a regulatable tRNA), making a desired post-translational modification, or inhibiting a post-translational inhibitor (for example a protease directed to a polypeptide encoded by the gene). In some embodiments, a compound present in a desired environment induces a promoter. For example, the presence of iron in culture medium can induce transcription by an iron-sensitive promoter as described herein. In some embodiments, a compound present in a desired culture medium inhibits a transcriptional repressor. For example, the presence of tetracycline in an environment can inhibit the tet repressor, and thus allow activity from the tetO promoter. In some embodiments, a compound found only outside of a desired culture medium induces transcription.

In some embodiments, gene activity is decreased. Conceptually, gene activity can be decreased by directly inhibiting gene activity, or by decreasing the activity of an activator of gene activity. In some embodiments, gene activity is reduced, but some level of activity remains. In some embodiments, gene activity is fully inhibited. In some embodiments, gene activity is decreased by at least one of inhibiting promoter activity, activating a transcriptional repressor, decreasing RNA stability, activating a post-transcriptional inhibitor (for example, expressing a ribozyme or antisense oligonucleotide), inhibiting translation (for example, via a regulatable tRNA), failing to make a required post-translational modification, inactivating a polypeptide (for example by binding an inhibitor or via a polypeptide-specific protease), or failing to properly localize a polypeptide (e.g. failing to secrete a bacteriocin). In some embodiments, gene activity is decreased by removing a gene from a desired location, for example by excising a gene using a FLP-FRT or cre-lox cassette, or through loss or degradation of a plasmid. In some embodiments, a gene product (e.g. a polypeptide) or a product produced by a gene product (e.g. the product of an enzymatic reaction) inhibits further gene activity (e.g. a negative feedback loop).

Genetic Modification of Microbial Organisms

Techniques of genetically modifying microorganisms are well known in the art. In some embodiments, a microorganism is genetically modified to comprise nucleic acid sequence regulating the expression of, and encoding, at least one of bacteriocins, immunity modulators, industrially useful molecules, poison molecules, or antidote molecules.

Polynucleotides can be delivered to microorganisms, and can be stably integrated into the chromosomes of these microorganisms, or can exist free of the genome, for example in a plasmid, extrachromosomal array, episome, minichromosome, or the like.

Exemplary vectors for genetic modification of microbial cells include, but are not limited to, plasmids, viruses (including bacteriophage), and transposable elements. Additionally, it will be appreciated that entire microbial genomes comprising desired sequences can be synthesized and assembled in a cell (see, e.g. Gibson et al. (2010), Science 329: 52-56). As such, in some embodiments, a microbial genome (or portion thereof) is synthesized with desired features such as bacteriocin polynucleotide(s), and introduced into a microbial cell.

It can be useful to flexibly genetically modify a microbial cell, for example to engineer or reengineer a microbial cell to have a desired type and/or spectrum of bacteriocin or immunity modulator activity. In some embodiments, a cassette for inserting one or more desired bacteriocin and/or immunity modulator polynucleotides into a polynucleotide sequence is provided. Exemplary cassettes include, but are not limited to, a Cre/lox cassette or FLP/FRT cassette. In some embodiments, the cassette is positioned on a plasmid, so that a plasmid with the desired bacteriocin and/or immunity modulator combination can readily be introduced to the microbial cell. In some embodiments, the cassette is positioned in the genome of the microbial cell, so that a cassette with the desired bacteriocin and/or immunity modulator combination can be introduced to the desired location.

In some embodiments, plasmid conjugation can be used to introduce a desired plasmid from a "donor" microbial cell to a recipient microbial cell. Goñi-Moreno, et al. (2013) Multicellular Computing Using Conjugation for Wiring. PLoS ONE 8(6): e65986, hereby incorporated by reference in its entirety. In some embodiments, plasmid conjugation can genetically modify a recipient microbial cell by introducing a conjugation plasmid from a donor microbial cell to a recipient microbial cell. Without being limited by any particular theory, conjugation plasmids that comprise the same or functionally same set of replication genes typically cannot coexist in the same microbial cell. As such, in some embodiments, plasmid conjugation "reprograms" a recipient microbial cell by introducing a new conjugation plasmid to supplant another conjugation plasmid that was present in the recipient cell. In some embodiments, plasmid conjugation is used to engineer (or reengineer) a microbial cell with a particular combination of one or more bacteriocins and/or immunity modulators. According to some embodiments, a variety of conjugation plasmids comprising different combinations of bacteriocins and/or immunity modulators is provided. The plasmids can comprise additional genetic elements as described herein, for example promoters, translational initiation sites, and the like. In some embodiments the variety of conjugation plasmids is provided in a collection of donor cells, so that a donor cell comprising the desired plasmid can be selected for plasmid conjugation. In some embodiments, a particular combination of bacteriocins and/or immunity modulators is selected, and an appropriate donor cell is conjugated with a microbial cell of interest to introduce a conjugation plasmid comprising that combination into a recipient cell. In some embodiments, the recipient cell is a "newly engineered" cell, for example to be introduced into or for initiating a culture. In some embodiments, the recipient cell is a "reengineered cell," for example to introduce a new bacteriocin (and optionally immunity modulator) activity to an existing culture that has encountered a new type of invader cell, and/or to remove a bacteriocin activity that is no longer desired in the culture.

Culture Media

Microbial culture environments can comprise a wide variety of culture media, for example feedstocks. The selection of a particular culture medium can depend upon the desired application. Conditions of a culture medium include not only chemical composition, but also temperature, amounts of light, pH, $CO_2$ levels, and the like.

In some embodiments, a genetically engineered microorganism as described herein is added to a culture medium that comprises other microorganisms and at least one feedstock. In some embodiments, the culture medium comprises a compound that induces the activity or expression of a bacteriocin and/or immunity modulator. In some embodiments, the culture medium comprises a compound that represses the activity or expression of a bacteriocin and/or immunity modulator. In some embodiments, a compound that induces the activity of the bacteriocin is present outside of the feedstock, but not in the feedstock. In some embodiments, a compound that represses the activity of the immunity modulator is present outside the feedstock, but not in the feedstock.

The term "feedstock" is used herein in a broad sense to encompass material that can be consumed, fermented, purified, modified, or otherwise processed by microbial organisms, for example in the context of industrial processes. As such, "feedstock" is not limited to food or food products. As used herein a "feedstock" is a category of culture medium. Accordingly, as used herein "culture medium" includes, but it is not limited to feedstock. As such, whenever a "culture medium" is referred to herein, feedstocks are also expressly contemplated.

Genetically Engineered Microbial Cells

In some embodiments, genetically modified microbial cells are provided. Genetically modified microbial cells can be configured for a wide variety of purposes. In some embodiments, microbial cells comprise genetic modifications to regulate the expression of at least one of bacteriocins, immunity modulators, industrially useful molecules, poison molecules, or antidote molecules. In some embodiments, microbial cells comprise genetic modifications to regulate the expression of bacteriocins. In some embodiments, microbial cells comprise genetic modifications to regulate the expression of immunity modulators.

In some embodiments, the genetically modified microbial cells are modified to produce a product. In some embodiments, the product is a gene product, for example a polypeptide or RNA. As such, polynucleotide "coding" sequence as referred to herein can refer to sequence encoding either a polypeptide or an RNA. In some embodiments, microbial cells can be configured to produce one or more gene products that contribute to synthesis of a desired product, for example a carbohydrate, biofuel, lipid, small molecule, or metal. In some embodiments, the product is synthesized via the activity of one or more gene products of the microbial cell. Optionally, synthesis of the product can also involve the activity of one or more gene products of one or more other microbial cells. In some embodiments, microbial cells can be configured to decontaminate or decompose one or more substances in a culture media, for example a feedstock. The decontamination can be mediated wholly, or partially by one or more gene products of the microbial cells. In some embodiments, microbial cells can be configured to scavenge for a material, for example a metal such as iron or a rare earth metal.

Controlling the Growth of Microbial Cells

In some embodiments, genetically modified microbial cells are modified to regulate the growth of other microbial cells. In some embodiments, the microbial cells regulate the growth of other microbial cells of the same species or strain, for example their own clones. In some embodiments, the microbial cells regulated the growth of microbial cells of a different species or strain, for example invaders. In some embodiments, a microbial cell secretes a bacteriocin to regulate other microbial cells. The regulation of each of the other microbial cells can depend on its expression (or lack thereof) of an immunity modulator having protective effects against the particular the secreted bacteriocin.

As used herein "desired cell" and the like refer to a microbial cell with at least one characteristic for which survival, growth, and/or proliferation of the microbial cell is desired, or at least an absence of negative control of the cell's growth is desired. In some embodiments, a desired cell is in an appropriate environment, for example its industrially-applicable feedstock. In some embodiments, a desired cell is a cell that is positively selected for, for example a cell that has undergone a particular recombination even, or is expressing high levels of a useful gene product. In some embodiments, a desired cell is a cell configured to neutralize contaminating cells, for example pathogenic cells. In some embodiments a desired cell is positively selected for by its expression of an immunity modulator corresponding to at least one bacteriocin that can be present in the environment. Without being bound by any particular theory, it is contemplated that a microbial cell capable of neutralizing other microbial cells which lack a similar neutralizing function will have a competitive advantage. As such, in some embodiments, a desired cell is selected for through its ability to neutralize other cells. In some embodiments a desired cell is positively selected for by expressing both a bacteriocin and a corresponding immunity modulator.

As used herein "undesired cell" and the like refer to a microbial cell with at least one characteristic making survival, growth, or proliferation undesirable. In some embodiments, the undesired cell is an invading microbial cell, for example a contaminating cell that has entered a culture environment. In some embodiments, an undesired cell has escaped from an appropriate culture medium, for example its industrially-applicable feedstock. In some embodiments, an undesired cell has lost a particular plasmid, or has failed to undergo a particular recombination event. In some embodiments, an undesired cell has failed to produce, or produces low levels of desired gene product. In some embodiments, an undesired cell is selected against. In some embodiments, an undesired cell is selected against through by reducing the cell's expression or activity of an immunity modulator that protects against a bacteriocin in the environment. In some embodiments, an undesired cell is selected against through by reducing the cell's expression or activity of an immunity modulator that protects against a bacteriocin secreted by the cell and clones thereof. In some embodiments, an undesired cell is selected against by reducing the cell's expression of a bacteriocin, thereby putting the cell at a competitive disadvantage against other microbial cells.

FIG. 1 is a flow diagram depicting options for configuring a microbial cell to control the growth of a second microbial cell according to some embodiments herein. In some embodiments, a first microbial cell is provided. In some embodiments, the first microbial cell secretes an active bacteriocin 100. In some embodiments, the first microbial cell is not desired 102. For example, in some embodiments, one or more of the first microbial cell being outside its industrial environment, a desired environmental conditional for the first microbial cell being absent, the first microbial cell having made sufficient product, or the first microbial cell lacking a recombination event or vector can make the first microbial cell undesirable in a particular environment at a particular time 112. As such, when the first microbial cell is not desired, its immunity modulator (corresponding to the bacteriocin) can be inactive 122. For example, one or more of an immunity modulator promoter can be inactive, an immunity modulator transcriptional repressor can be active, post-transcriptional silencing (e.g. by a ribozyme or antisense) can occur, a regulatable tRNA can not be induced, post-transcriptional silencing can occur (e.g. by a site-specific protease, or a silencing post-translational modification), or a vector encoding an immunity modulator can be absent 132. In some embodiments, when the first cell does not have an active immunity modulator, the first cell is neutralized by the bacteriocin 142 produced by other cells in the culture. In some embodiments, a second microbial cell proceeds with growth 192 as a result of the first cell being neutralized.

In some embodiments, the first microbial cell is desired 106. For example, one or more of the first microbial cell being inside of its industrial environment, a desired environmental condition for the first microbial cell being present, the first microbial cell having not yet made sufficient product yet, or the first microbial cell having undergone a recombination event or comprising a particular vector can make the microbial cell desirable in a particular environment at a particular time 116. As such, when the first microbial cell is desired, it can produce an active immunity modulator 126. For example, in some embodiments, the first microbial cell can be configured to have one or more of a constitutive promoter for the immunity modulator polynucleotide, an activated (but not necessarily constitutive) promoter for the immunity modulator polynucleotide, an inactive repressor of immunity modulator transcription, a regulatable tRNA that is induced to facilitate production of the immunity modulator, an absence of post-translational and post-transcriptional silencing of the immunity modulator, or a vector encoding the immunity modulator can be present 136. As such, the first microbial cell can survive 146 in the presence of bacteriocin secreted by the first microbial cell. As a result of the bacteriocin secreted by the first microbial cell, a second microbial cell can grow 192 or be neutralized 196, depending on whether the second microbial cell has 172 or does not have 176 immunity modulator activity.

In some embodiments, the second microbial cell is desired 152. For example, one or more of a desired recombination event having occurred in the second microbial cell, a desired vector present in the second microbial cell, the second microbial cell producing a product of which more is desired (e.g. a positive feedback loop), or the immunity locus and the desired product being under the same transcriptional control when appropriate levels of desired product are being transcribed can a make the second microbial cell desirable 162. When the second microbial cell is desired, it can provide immunity modulator activity to protect against the particular bacteriocin (or bacterocins) produced by the first microbial cell 172. For example, in some embodiments, the second microbial cell can be configured such that an immunity modulator promoter is active (for example, a constitutive promoter), an immunity modulator transcriptional repressor is inactive, there is a lack of post-transcriptional silencing, a regulatable tRNA being induced to facilitate the expression of the immunity modulator, a lack of post-translational silencing (e.g. by a site-specific protease) of the immunity modulator, or a vector encoding an immunity modulator can be present 182. As such, in some embodiments, when immunity modulator activity is provided, the second microbial cell can survive 192.

In some embodiments, a second microbial cell is not desired 156. For example, one or more of the second microbial cell being an invader (e.g. a contaminating cell), an undesired environmental condition for the second microbial cell (e.g. the presence of an undesired compound or condition, or the absence of a desired compound or condition), the second microbial cell having produced product, but no more product being desired (e.g. a negative feedback loop), or an immunity modulator locus and desired product locus being under the same transcriptional control and transcript levels being undesirably low (e.g. indicating an inability to produce a desired product) can make the second microbial cell undesirable 166. As such, in some embodiments, there can be no immunity modulator activity or an insufficient amount of an immunity modulator to protect against the action of the bacteriocin in the second microbial cell 176. For example, one or more of an immunity modulator promoter can be inactive, an immunity modulator transcriptional repressor can be active, post-transcriptional silencing of the immunity modulator (e.g. by a ribozyme or antisense oligonucleotide) can occur, a regulatable tRNA can not be induced (so that expression of the immunity modulator is not facilitated), post-transcriptional silencing of the immunity modulator can occur (e.g. by a site-specific protease, or a silencing post-translational modification), or a vector encoding an immunity modulator can be absent 186. In some embodiments, the first microbial cell provides secreted bacteriocin activity 100. As such, in some embodiments, the second microbial cell can be killed by the bacteriocin 196.

One skilled in the art will appreciate that, for this and other functions, structures, and processes, disclosed herein, the functions, structures and steps may be implemented or performed in differing order or sequence. Furthermore, the outlined functions and structures are only provided as examples, and some of these functions and structures may be optional, combined into fewer functions and structures, or expanded into additional functions and structures without detracting from the essence of the disclosed embodiments.

For a large variety of genetically modified microbial cells, it can be useful to control the growth of other microbial cells in the culture. In some embodiments, a microbial cell controls the growth of other microbial cells in the culture. Exemplary functions and configurations by which a first microbial cell can control the growth of one or more other microbial cells according to some embodiments herein are described in Table 4.

TABLE 4

Exemplary uses of bacteriocin systems in genetically modified microbial cells according to some embodiments herein

| Exemplary Function | Exemplary configurations (according to some embodiments) |
|---|---|
| Biological containment: | Immunity modulator activity only in the desired culture medium, but not outside and bacteriocin activity at least outside of the desired culture medium; escape of the bacteriocin producing cell outside the desired culture environment results in cytotoxicity or growth inhibition of the bacteriocin producing cell |
| Genetic guard | Bacteriocin constitutively produced; genetic guard microbial organism does not produce gene products for modulating industrial process of interest; immunity modulator constitutively produced (e.g under control of constitutive promoter) and/or genetic guard microbial organism is insensitive to the bacteriocin (e.g. a *S. cerevisiae* genetic guard producing bacteriocins that target *E. coli*) |
| Selection of recombinants: | Desired recombination event causes an immunity modulator to be restored in a bacteriocin-expressing host. Alternatively the immunity modulator can be restored only after the desired recombination event. |
| Vector stability: | Immunity modulator (or at least one gene essential for immunity is encoded on a plasmid, and a corresponding bacteriocin locus is encoded on chromosome); clones that lose the desired plasmid lack immunity and are neutralized by the bacteriocin |
| Minimization of genetic drift | Immunity modulator activity dependent on production of industrial product (e.g. immunity modulator expression controlled by an operon, in which a repressor is active in the absence of industrial product, and inactive in the presence of industrial product); if a mutation causes the microbial organism's production of industrial product to fall below a desired level or cease, the microbial organism ceases to produce immunity modulator, and is neutralized by the bacteriocin. |
| Selection for microbes presenting a high yield of expression expression (and/or expressing clones) | Immunity modulator is co-expressed with the gene of interest; microbial organisms producing high levels of gene product of interest can be selected by increasing bacteriocin concentration; microbial organisms producing low levels of gene product of interest (e.g. having a low "industrial fitness") are neutralized |
| Destruction during fermentation of contaminating microbes. | Desired microbial cells constitutively express at least one type of bacteriocin; secreted bacteriocins neutralize invading microbial cells Desired microbial cells express at least one type of bacteriocin when in the desired environment (e.g. bacteriocin is under the control of an inducible promoter that is activated by an intermediate of the fermentation |

TABLE 4-continued

Exemplary uses of bacteriocin systems in genetically modified
microbial cells according to some embodiments herein

| Exemplary Function | Exemplary configurations (according to some embodiments) |
|---|---|
|  | process); secreted bacteriocins neutralize contaminating cells |
| Control of the ratio of a microbial flora, | Immunity modulator activity is repressed by accumulated product made by a microbial cell; bacteriocins secreted by the microbial cell (or other cells) neutralize the microbial cell |

Figure 2B:
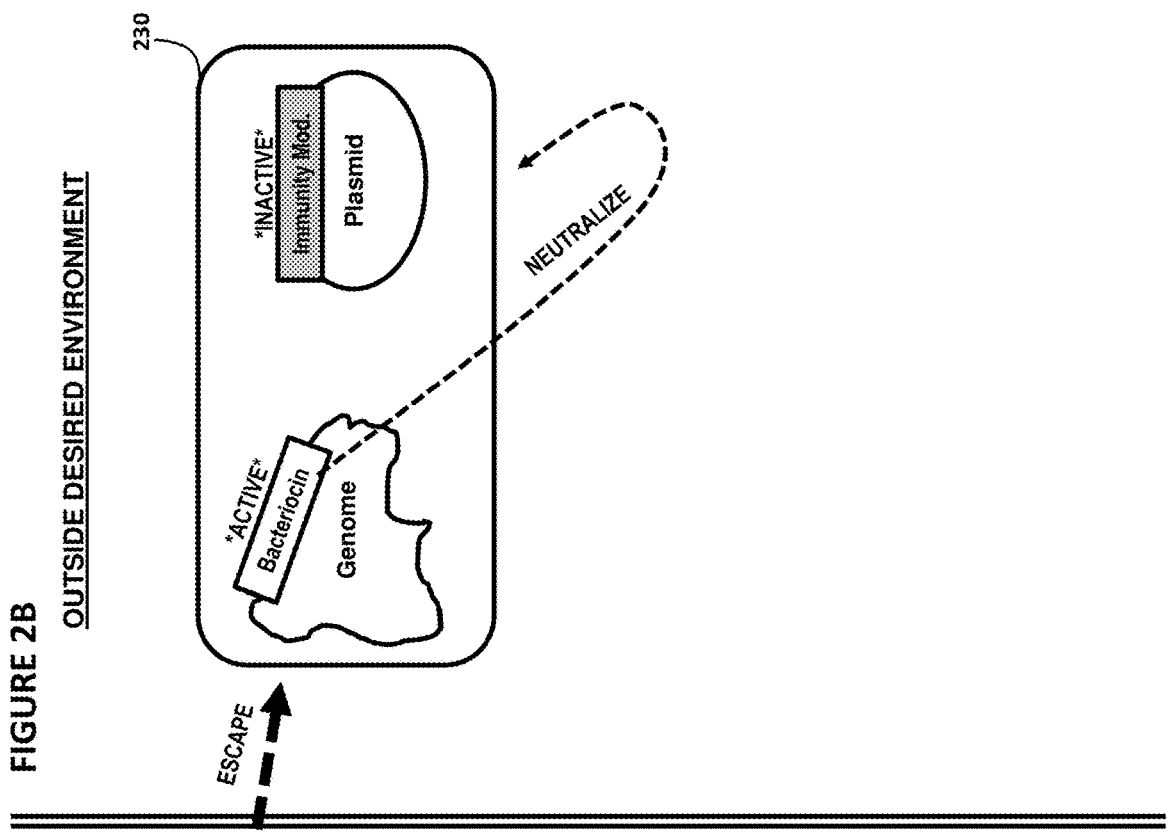
FIG. 2B is a schematic diagram illustrating control of the growth of a first microbial cell when the first microbial cell is no longer in a desired growth environment according to some of the embodiments herein.
Figure 2A:
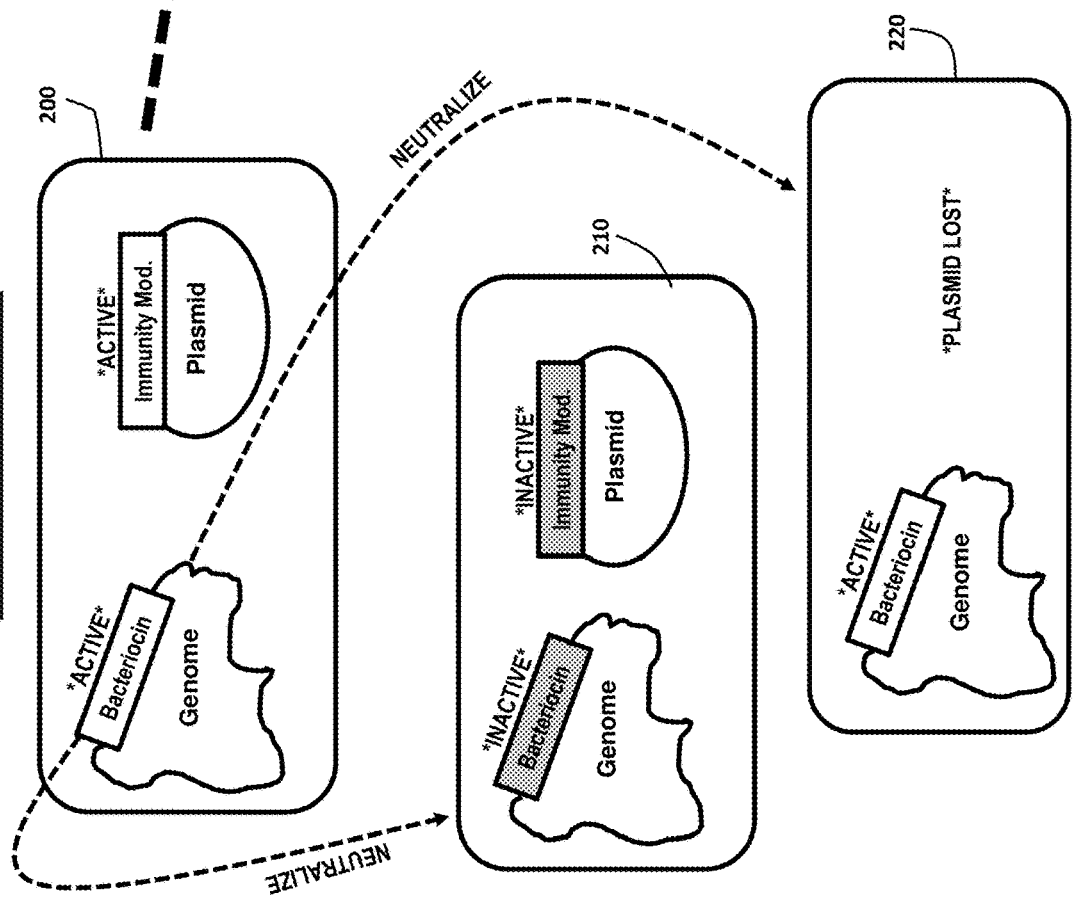
FIG. 2A is a schematic diagram illustrating a first microbial cell controlling the growth of other microbial cells according to some of the embodiments herein.

FIG. 2 is a schematic diagram depicting a genetically engineered microbial cell controlling the growth of at least one other microbial cell according to some embodiments herein. A first microbial cell 200 can comprise a bacteriocin polynucleotide and a corresponding immunity modulator polynucleotide. The bacteriocin polynucleotide can optionally be integrated into the cell's genome, while the immunity modulator polynucleotide can optionally be integrated into a plasmid present in the cell. In some embodiments an undesired clone of the cell 210 (a "non-expressing clone") can lack immunity modulator activity, and optionally can lack bacteriocin activity. The bacteriocin activity of the first microbial cell 200 can neutralize the non-expressing clone 210. In some embodiments, an undesired clone of the cell 220 can lose a plasmid comprising the immunity modulator polynucleotide. The bacteriocin activity of the first microbial cell 200 can neutralize the undesired clone 220. In some embodiments, the microbial cell 230 can escape from the desired environment, causing the clone to lack immunity modulator activity. Bacteriocin activity from the escaped cell 230 and/or clones of the escaped cell can neutralize the escaped cell 230. In some embodiments, the escaped cell 230 further comprises a poison-antidote system to facilitate killing of the escaped cell upon its escape.

Figure 3:
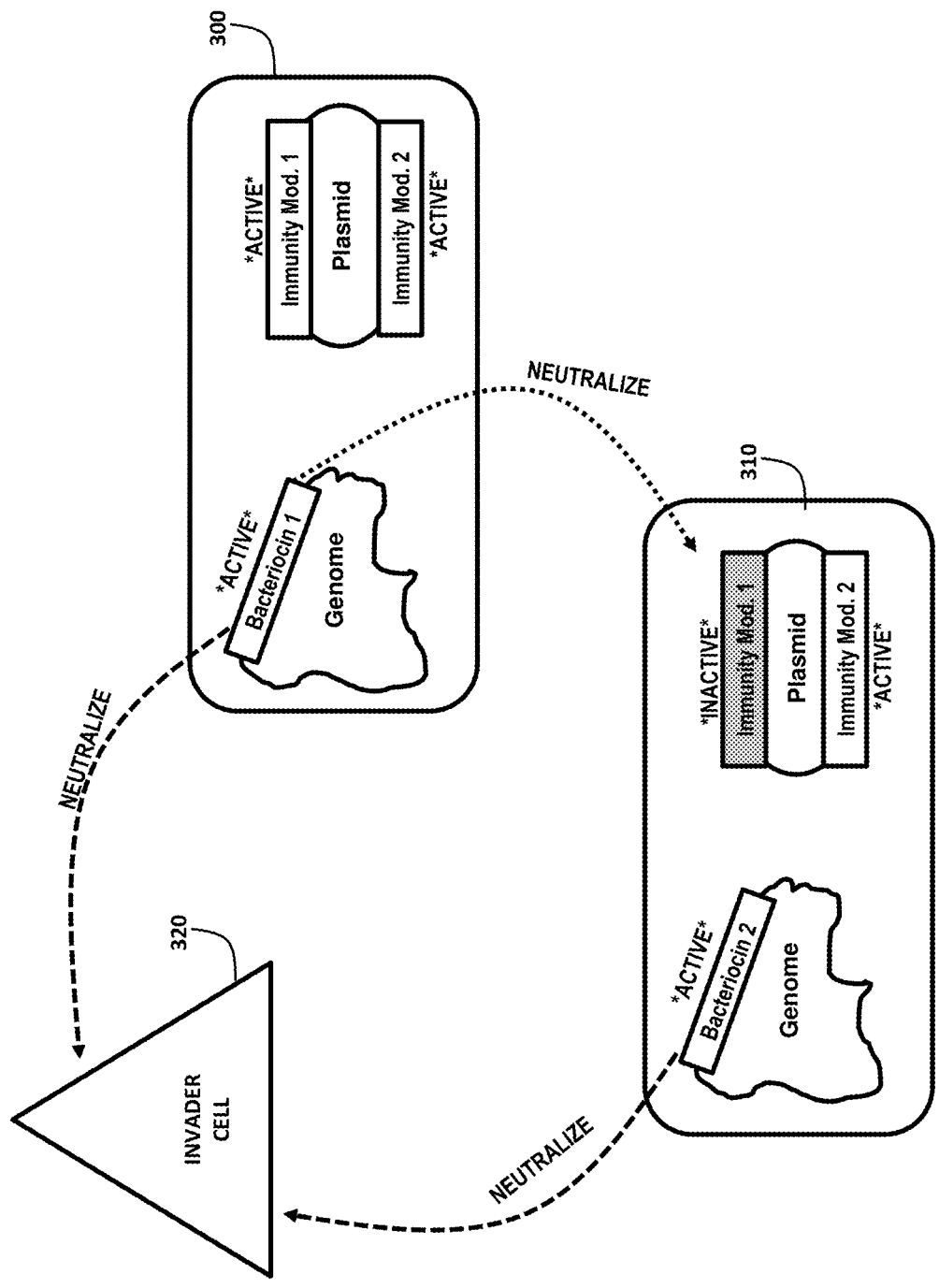
FIG. 3 is a schematic diagram illustrating a first microbial cell controlling growth of a second microbial cell and neutralizing an invading cell in a desired environment according to some of the embodiments herein.

FIG. 3 is a schematic diagram of a first genetically engineered microbial cell 300 controlling the growth of a second genetically engineered microbial cell 310 and an invader cell 320 in a desired environment according to some embodiments herein. The first genetically engineered microbial cell 300 can comprise a first bacteriocin polynucleotide. The second genetically engineered microbial cell 310 can comprise a second bacteriocin polynucleotide. Each of the first and second genetically engineered microbial cells (300 and 310) can comprise a first immunity modulator polynucleotide encoding resistance to the first bacteriocin, and a second immunity modulator polynucleotide encoding resistance to the second bacteriocin. If the second genetically engineered microbial cell 310 becomes undesired, it can lose first immunity modulator activity via any of the mechanisms discussed herein, and thus be controlled by the first bacteriocin activity from the first genetically engineered microbial cell 300. If an invader cell 320 enters the desired environment, the first bacteriocin from the first genetically engineered microbial cell 300 and the second bacteriocin from the second genetically engineered microbial cell 310 can neutralize the invader cell.

Figure 4:
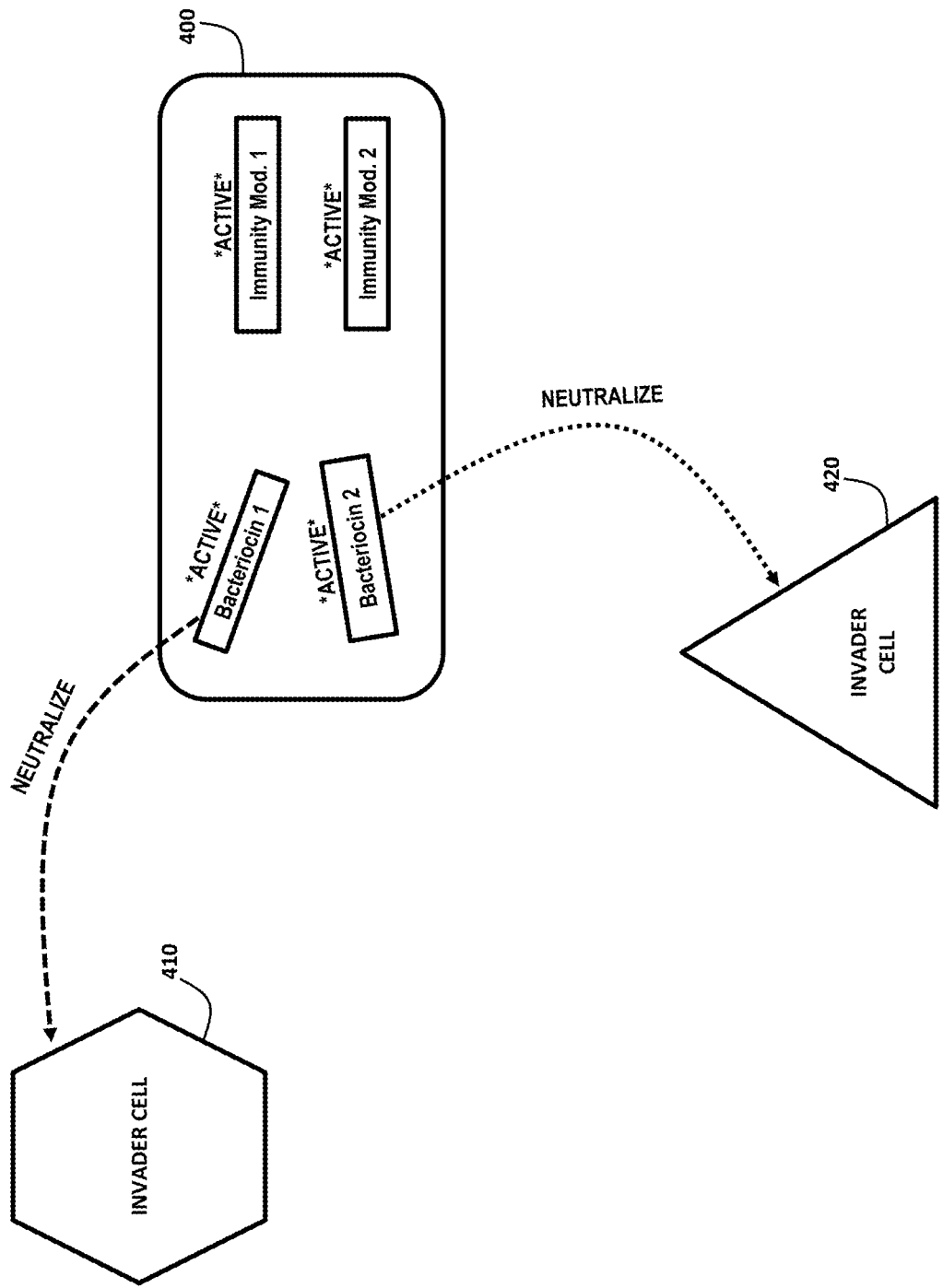
FIG. 4 is a schematic diagram illustrating a first microbial cell neutralizing a first invading cell with a first bacteriocin and second invading cells with a second bacteriocin in a desired environment according to some of the embodiments herein.

FIG. 4 is a schematic diagram of a first genetically engineered microbial cell 400 controlling the growth of a first invader cell 410 and a second invader cell 420 in a desired environment according to some embodiments herein. The first genetically engineered cell 400 can comprise at least a first bacteriocin polynucleotide encoding a first bacteriocin, and at least a second bacteriocin polynucleotide encoding a second bacteriocin. The first genetically engineered cell 400 can produce the first bacteriocin to neutralize a first invader cell 410. The first genetically engineered cell 410 can produce the second bacteriocin to neutralize a second invader cell 420. In some embodiments, the first invader cell is of a different strain or species from the second invader cell. In some embodiments, the first invader cell responds to a different spectrum of bacteriocin activity than the second invader cell. In some embodiments, the first invader cell typically occupies a different ecological niche than the second invader cell.

Figure 5:
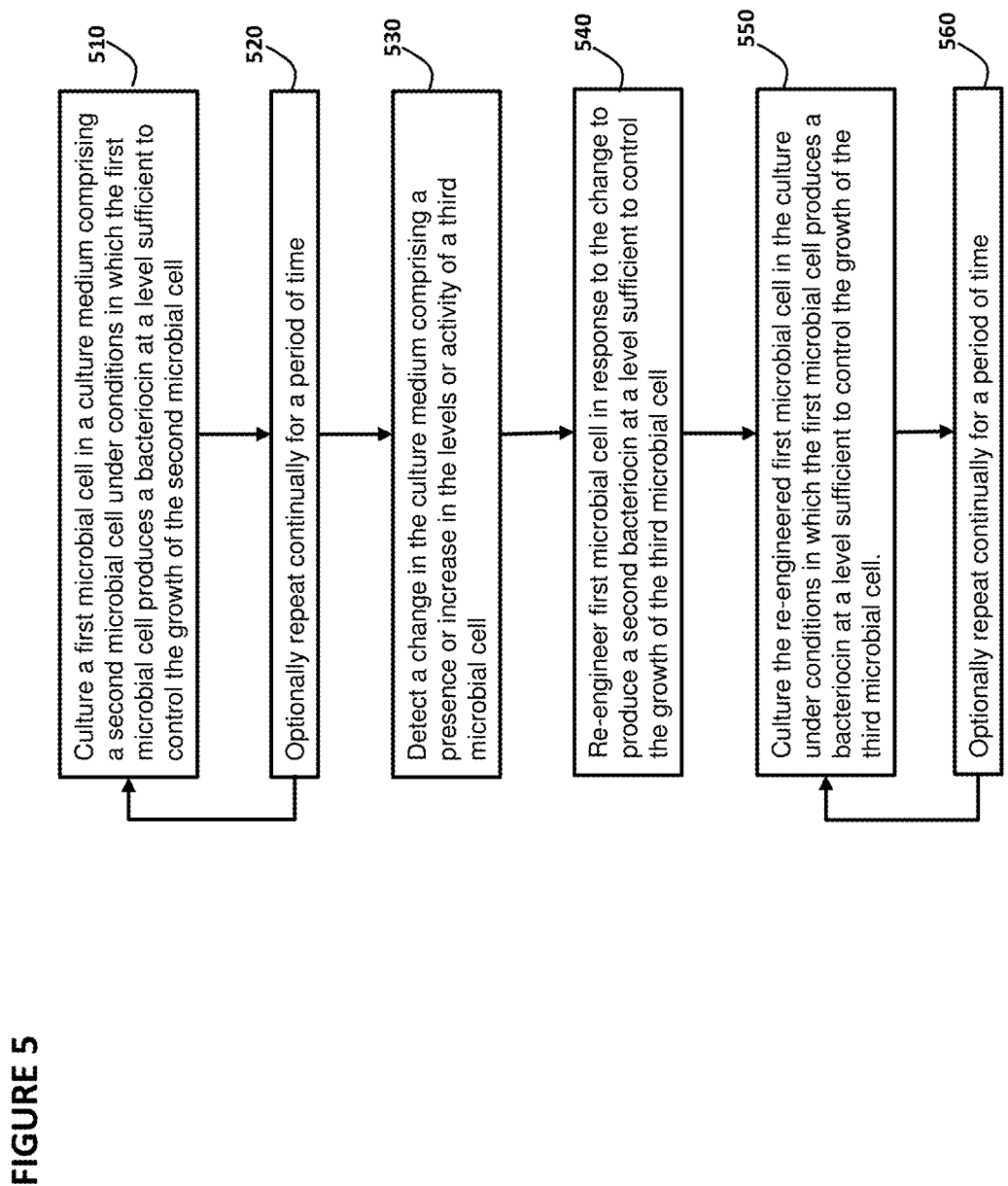
FIG. 5 is a flow diagram illustrating methods of controlling the growth of at least a second microbial cell in culture according to some embodiments herein.

FIG. 5 is a flow diagram illustrating methods of controlling the growth of at least a second microbial cell in culture according to some embodiments herein. The method can comprise culturing a first microbial cell in a culture medium comprising a second microbial cell under conditions in which the first microbial cell produces a bacteriocin at a level sufficient to control the growth of the second microbial cell 510. The culturing of the first microbial cell can optionally be continually maintained for a period of time 520. In some embodiments, the culturing of the first microbial cell is maintained continually for at least 3 days, for example at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, or 500 days, including ranges between any two of the listed values. A change in the culture medium comprising a presence or increase in the levels or activity of a third microbial cell can be detected 530. The first microbial cell can be re-engineered in response to the change to produce a second bacteriocin at a level sufficient to control the growth of the third microbial cell 540. The re-engineered first microbial cell can be cultured in the culture under conditions in which the first microbial cell produces a bacteriocin at a level sufficient to control the growth of the third microbial cell 550. The culture of the re-engineered microbial cell can be repeated continually for a period of time 560. In some embodiments, the culturing of the re-engineered microbial cell is maintained continually for at least 3 days, for example at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, or 500 days, including ranges between any two of the listed values.

In some embodiments, a first microbial cell can control the growth of a second microbial cell. In some embodiments, a first microbial cell can control the growth of a second microbial cell of the same strain as the first microbial cell. Each cell of the strain can comprise a bacteriocin polynucleotide and an immunity modulator polynucleotide, such that the immunity modulator, if expressed, protects against the bacteriocin. As such, if a clone of the strain loses expression of the immunity modulator, it will be neutralized by bacteriocin activity from the same strain. In some embodiments, the immunity modulator polynucleotide is in cis to the bacteriocin polynucleotide. As such, even if the bacteriocin polynucleotide and immunity modulator polynucleotide are both eliminated (e.g. if a plasmid is lost or a FLP-FRT cassette is excised), bacteriocin activity from other cells can still neutralize the cell. In some embodiments, the immunity modulator polynucleotide is in trans to the bacteriocin polynucleotide. The immunity modulator activity can be lost when the microbial cell is undesired (for example, if a plasmid is lost, or if a particular environmental condition induces a loss of immunity modulator activity).

Accordingly, bacteriocin activity from both the microbial cell and also other cells of the strain can induce the neutralizing of the microbial cell.

In some embodiments, a ratio of two or more microbial species or strains is controlled. An exemplary control of ratios is illustrated in FIG. 3 (see cells 300 and 310). In some embodiments, a first microbial strain or species loses an immunity modulator activity via any of the mechanisms discussed herein when it is less desired than a bacteriocin-producing second strain or species, increasing the ratio of second strain or species to the first strain or species. In some embodiments in which the ratio of a first and second strain or species is controlled, a bacteriostatic bacteriocin or bacteriocins are selected (as opposed to bacteriocitic bacteriocins) so that the control of growth can be readily reversible, and/or to minimize the risk of eliminating either of the strains or species. In some embodiments, a first microbial strain or species produces a first bacteriocin under the control of a promoter that is activated in the presence of a compound or substance of interest, for example an intermediate or a product such as an industrially useful molecule. As such, levels of the bacteriocin increase as the levels of the compound of interest increase. In some embodiments, a second microbial strain or species produces (or catalyzes the production of) the compound or substance of interest, but does not have immunity modulator activity for the bacteriocin. As levels of the compound or substance of interest increase, levels of the bacteriocin increase, thus neutralizing the second strain (which lacks an appropriate immunity modulator or which has an insufficient amount of an appropriate immunity modulator to protect against the action of the bacteriocin). As such, relative levels of the first strain compared to the second strain increase. In some embodiments, a first microbial strain produces a first product and first bacteriocin activity, and a second microbial strain produces a second product and second bacteriocin activity. In some embodiments, the first product and the second product are intermediates in the same biosynthetic pathway. The first microbial strain can provide a first and second immunity modulator activity, in which the second immunity modulator activity can protect against the second bacteriocin and is negatively regulated by accumulation of the first product (e.g. expression of the second immunity modulator is repressed by the presence of the first product), and the first immunity modulator activity can protect against the first bacteriocin. The second microbial strain can also provide a first and second immunity modulator activity, except that the first immunity modulator activity is negatively regulated by accumulation of the second product (e.g. expression of the first immunity modulator is repressed by the presence of the second product). As such, when a relatively high amount of the first product has accumulated, the second immunity modulator in the first microbial strain is inactivated, and the microbial cells of the first strain are neutralized by the second bacteriocin, thus increasing the ratio of the second strain to the first strain, and increasing the relative amount of second product to first product. When a relatively high amount of the second product has accumulated, the first immunity modulator in the second microbial strain is inactivated, and the microbial cells of the second strain are neutralized by the first bacteriocin, the increasing the ratio of the first strain to the second strain and increasing the relative amount of first product to second product. As such, the ratio of the first stain to the second strain can be adjusted, depending on relative levels of product. In some embodiments, an equilibrium of ratios of the first strain to the second strain is maintained. In some embodiments, an equilibrium of ratios of the first product to the second product is maintained. In some embodiments, the first microbial strain's second immunity modulator responds to a first environmental condition or compound, and the ratio between the first and second microbial strain is otherwise controlled as above. In some embodiments, the second microbial strain's first immunity modulator responds to a second environmental condition or compound, and the ratio between the first and second microbial strain is otherwise controlled as above.

In some embodiments, it is desired that a microbial cell be contained within a particular environment, for example so that the first microbial cell can only survive in a particular culture medium such as industrial feedstock. In some embodiments, a microbial cell comprises a bacteriocin polynucleotide and an immunity modulator polynucleotide, such that the immunity modulator corresponds to the bacteriocin. In some embodiments, when the microbial cell is in a desired environment, the microbial cell produces an active bacteriocin and corresponding immunity modulator, but when the microbial cell escapes the desired environment, the microbial cell produces the active bacteriocin but no active immunity modulator. As a result, the microbial cell can grow in the desired environment, but is neutralized by its own bacteriocin when it escapes. For example, in some embodiments, the bacteriocin encoded by the bacteriocin polynucleotide is constitutively expressed, while the immunity modulator is expressed only when the microbial cell is in a desired environment. For example, in some embodiments, the bacteriocin encoded by the bacteriocin polynucleotide is constitutively expressed, while the immunity modulator is expressed only when the microbial cell is in an environment. For example, in some embodiments, a transcriptional activator of the immunity modulator is only present in the desired environment. For example, in some embodiments, the bacteriocin encoded by the bacteriocin polynucleotide and the immunity modulator is constitutively expressed, but if the microbial cell escapes, the immunity modulator is deleted (for example via the FLP-FRT system). Without being limited to any particular theory, if a genetic system for neutralizing an escaped microbial cell is not used within the culture itself, there may be little or no selective pressure to maintain the system within the culture, so that mutations can accumulate which reduce or eliminate the functioning of that genetic system. As such, if the microbial cell escapes from the culture, there is a possibility that the genetic system will no longer function. In contrast, it is appreciated herein that if a bacteriocin/immunity modulator system is useful both within a culture (for example, to control the growth of other genetically engineered cells in the culture, and/or to neutralize invading microbial cells), and also outside of a culture (for example, to neutralize a microbial cell that has escaped from culture), the use within the culture can provide selective pressure for the bacteriocin system to continue to function. Such selective pressure in accordance with some embodiments herein can minimize genetic drift. Such selective pressure in accordance with some embodiments herein can help to ensure that if the microbial cell escapes from the desired culture environment, the bacteriocin/immunity modulator system will be functioning to appropriately neutralize the escaped cell. As such, in some embodiments a single genetically engineered circuit, for example a bacteriocin/immunity modulator system is useful both to neutralize other microbial cells within a desired culture environment, and further to neutralize a microbial cell and/or its clones upon escape from a desired culture environment. It is contemplated in accordance with some embodiments herein, any or all of the configuration of bacteriocins disclosed herein can be tuned so that upon escape from the desired culture environment, the escaping microbial organism will be neutralized by its own bacteriocins (and/or bacteriocins of its direct or indirect progeny, and/or bacteriocins of another escaped cell and/or its direct or indirect progeny).

In some embodiments, a microbial cell can control growth in two or more ways. In some embodiments, a microbial cell can perform two or more of the functions described in Table 4. In some embodiments, the microbial cell uses the same bacteriocin/immunity modulator pair for two or more different functions. In some embodiments, the microbial cell uses a first bacteriocin/immunity modulator pair for a first function, and a second bacteriocin/immunity modulator pair for a second function. For example, in some embodiments, a microbial cell can express a bacteriocin which limits the growth of "non-expressing" clones that have lost immunity modulator activity in a desired environment, and can also provide containment within the desired environment by failing to express its own immunity modulator (while still expressing bacteriocin) if the microbial cell is outside of a desired environment. A schematic illustration of such two forms of growth regulation is illustrated in FIG. 2. For example, in some embodiments, a first microbial cell can express a bacteriocin which limits the growth of a second microbial cell, and can also neutralize the invading cell. A schematic illustration of such two forms of growth regulation is illustrated in FIG. 3. In some embodiments, two or more forms of growth control are provided using the same bacteriocin-immunity modulator pair. In some embodiments, each form of growth control is provided using a different bacteriocin immunity modulator pair. For example, a first immunity locus can be present on a plasmid that also includes a polynucleotide encoding a desired product. A clone that loses the plasmid will be neutralized by a corresponding first bacteriocin. A second immunity modulator polynucleotide (corresponding to a second immunity modulator) can be integrated into the genome of the microbial cell and can be silenced when the microbial cell escapes from its desired environment (for example, the second immunity modulator polypeptide can be in a FLP-FRT cassette that is excised upon escape). As such, upon escape, the microbial cell can be neutralized by the second bacteriocin.

It is noted that some embodiments described herein are compatible with poison-antidote systems. As such, in some embodiments a microbial cell, in addition to a bacteriocin and immunity modulator further comprises a poison-antidote system configured to kill or arrest the cell when it is not in a desired environment.

It can be useful to control the growth of two or more different types of microbial cells. For example, an environment can comprise, or can potentially comprise, two or more different types of undesired microbial organisms. As different microbial organisms can have different susceptibility to bacteriocins (for example, by possessing different profiles of immunity modulators), a combination of two or more bacteriocins (e.g. a "cocktail" of bacteriocins) can be useful for controlling the growth of two or more microbial organisms. In some embodiments, a single microbial cell produces two or more different bacteriocins for example, at least 2, 3, 4, 5, 6, 7, 8, 9, 10, 11, 12, 13, 14, 15, 16, 17, 18, 19, 20, 25, 30, 35, 40, 45, or 50 different bacteriocins, including ranges between any two of the listed values. In some embodiments, a mixture of two or more different bacteriocin-producing microbial cells are provided, for example, 2, 3, 4, 5, 6, 7, 8, 9, 10, 11, 12, 13, 14, 15, 16, 17, 18, 19, 20, 25, 30, 35, 40, 45, or 50 different bacteriocin-producing microbial cells, including ranges between any two of the listed values. Optionally, one or more of the bacteriocin-producing microbial cells can produce two or more different bacteriocins.

It can be useful for a single microbial cell to regulate the growth of two or more different types of microbial cells. For example, it can be possible for a first type of invading cell to possess immunity to a first type of bacteriocin but not a second type of bacteriocin. As such, in some embodiments, a microbial cell comprises two or more bacteriocin polynucleotides, each of which encodes a different bacteriocin (see, e.g. FIG. 4). In some embodiments, the microbial cell comprises polynucleotides encoding at least three different bacteriocins, for example at least three, four five, six, seven, eight, nine, ten, eleven, twelve, thirteen, fourteen, fifteen, sixteen, seventeen, eighteen, nineteen, twenty, or more different bacteriocins, including ranges between any two of the listed values. In some embodiments, two or more bacteriocin polynucleotides are under control of a single promoter. In some embodiments, each bacteriocin polynucleotide under the control of a single promoter comprises its own translational initiation site. In some embodiments, each bacteriocin polynucleotide is under the control of a different promoter. In some embodiments, two different bacteriocins are under the control of two different but structurally or functionally identical promoters.

It can be useful for a microbial cell to control the growth of other microbial cells in its industrial environment, so as to help ensure the consistent production of an industrial product, regardless of the geographical location of the culture environment. Without being limited by any particular theory, certain industrial products manufactured via microbial culture may have certain characteristics that result from local microbial flora associated with a certain region (for example, Camembert cheese can have particular characteristics that result from local microbial flora in Camembert, France, or sourdough bread can have particular characteristics that result from local microbial flora in San Francisco, Calif.). As such, it can be desirable to control the microbial flora in a particular feedstock, so that a consistent industrial product can be produced in a variety of geographical locations. In some embodiments, a microbial cell is engineered to produce bacteriocins to neutralize invading microbial cells found in a variety of geographical locations, which can ensure more consistent industrial product characteristics for product produced in a variety of locations. For example, a microbial cell designed to be used in a particular industrial process and to be grown in a first geographic location may be engineered to express one or more bacteriocins effective against one or more invading organisms commonly encountered in the first geographic location. A microbial cell designed to be used in the same industrial process and to be grown in a second geographic location may be engineered to express one or more bacteriocins effective against one or more invading organisms commonly encountered in the second geographic location. Alternatively, a microbial cell designed to be used in a particular industrial process and to be grown in two different geographical locations may be engineered to express on or more bacteriocins effective against one or more invading organisms commonly encountered in each of the two geographical locations.

Frequently in industrial biotechnology, the goal is to work in continuous process, and it is contemplated that the longer the process continues, the higher the probability of contamination. Accordingly, the capacity to fight against contaminants can be useful for a continuous industrial process. Synthetic microorganisms designed in laboratories are frequently used in industrial processes. As such, it can be useful for these lab-engineered "champions" to fight against undesired invading microbial strains (for example wild-type strains from the environment and/or cross-contaminants from another industrial process) and also control their potential genetic drift and escape in the environment. In accordance with some embodiments herein, invading microbial strains can be fought, genetic drift can be minimized, and escape can be minimized by inducing suicidal bacteriocins based genetic circuits.

It can be useful for a microbial culture to remain stable for a continuous period of time, for example to ensure consistent industrial product characteristics over a continuous period of time. In some embodiments, a culture is stably maintained, at least in part, by bacteriocin-mediated neutralization of invading microbial cells. In some embodiments, a culture is stably maintained, at least in part, by bacteriocin-mediated control of ratios of two or more types of genetically engineered microbial cell in the culture. In some embodiments, a culture is stably maintained, at least in part, by reengineering a microbial cell already present in the culture. In some embodiments, the microbial cell is reengineered to add at least one additional bacteriocin activity (for example by adding a new bacteriocin, or expanding the expression of a bacteriocin already present) to neutralize a new type of invading microbial organism. In some embodiments, the microbial cell is reengineered to remove at least one bacteriocin activity that is no longer needed. Exemplary methods of maintaining a stable culture according to some embodiments herein are illustrated in FIG. 5. In some embodiments, a stable culture is maintained for at least about 3 days, for example about 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, or 500 days, including ranges between any two of the listed values.

Method for Detection of Ratios of Microbial Organisms

According to some embodiments herein, the ratios of two or more microbial strains or species can be controlled, depending on relative quantities of product, and/or compounds in the environment. Accordingly, in some embodiments, the ratios of the two or more microbial strains or species can be indicative of relative quantities of the product and/or compounds in the environment. In some embodiments, relative quantities of microbes of a first strain or species and second strain or species as described herein are detected, thereby indicating relative ratios or quantities of a first product or compound to a second product or compound. Relative quantities of each microbial strain or species can be detected in a variety of ways. In some embodiments, each strain or species comprises a unique oligonucleotide or polypeptide "bar code" sequence to facilitate specific detection. In some embodiments, each strain or species comprises a different bacteriocin (and thus a different bacteriocin polynucleotide), which can serve as a bar code. In some embodiments, at least one of quantitative PCR, oligonucleotide array analysis, flow cytometry, immunocytochemistry, in situ hybridization, ELISA, immunoblotting, oligonucleotide spot blotting, or the like is performed to determine relative quantities of the two different microbial strains or species.

Method for Determining Modulation of Growth of Microbial Organisms in Industrial Medium In some embodiments, growth of microbial organisms in industrial medium is modulated. Before adding a particular genetically engineered microbial cell or combination of genetically engineered cells to an existing industrial culture of microbial cells, it can be useful to determine the effects, if any, of the bacteriocins on the growth of the microbial cells in the existing industrial culture. In some embodiments, the effect of a particular bacteriocin or combination of bacteriocins produced by genetically engineered cells on microbial organisms is assessed. A medium or other composition comprising one or more bacteriocins produced by genetically engineered microbial cells as described herein can be provided. In some embodiments, the medium comprises a supernatant comprising one or more bacteriocins. In some embodiments, the composition comprises one or more enriched or purified bacteriocins. In some embodiments, the supernatant or composition is thermally stable, for example to facilitate elimination of any microbes therein through high-temperature incubation, while retaining the function of any bacteriocins therein. In some embodiments, the medium or composition comprises a lyophilized material comprising bacteriocins. In some embodiments, the medium or composition comprises a substrate bound to bacteriocins, for example a gel, a matrix, or beads. The medium or compositions comprising bacteriocins can be added to the existing culture. In some embodiments, the medium or composition is added to a culture in an industrial culture environment. In some embodiments, the medium or composition is contacted with a sample of a culture from an industrial culture environment. The growth or absence of growth of microbial organisms in the industrial culture can be assessed for example to determine whether the one or more bacteriocins are effective against a new invading organism which has appeared in the culture or to determine the effects of the one or more bacteriocins on the existing organisms in the culture.

Before a genetically engineered microbial cell is produced, it can be useful to simulate the effects of one or more bacteriocins on a particular culture environment. In some embodiments, a particular bacteriocin or combination of bacteriocins with desired activity in a known culture environment is identified, and a microbial cell is constructed to produce the desired bacteriocin combination of bacteriocins. In some embodiments, a candidate bacteriocin or combination of bacteriocins is contacted with a portion of an industrial culture of interest, and effects of the bacteriocin or bacteriocins on microbial organisms in the culture are identified. In some embodiments, a variety of bacteriocins is provided. In some embodiments, the variety of bacteriocins is provided in a kit. In some embodiments, the bacteriocins were produced by microbial cells. In some embodiments, the bacteriocins are in supernatant from one or more microbial cells as described herein. In some embodiments, the bacteriocins were chemically synthesized. One or more candidate bacteriocins or mixtures of bacteriocins can be prepared, and can be contacted with a portion of the industrial culture environment. In some embodiments, one or more bacteriocins are added to the supernatant of a bacteriocin-producing genetically engineered cell that is already present in culture, for example to ascertain the effects of engineering the cell to produce at least one additional bacteriocin. In some embodiments, a sample from the industrial culture environment is contacted with each candidate bacteriocin or mixture of bacteriocins. In some embodiments, each candidate bacteriocin or mixture of bacteriocins is added to the culture environment. In some embodiments, effects of each candidate bacteriocin or mixture of bacteriocins are observed, for example as effects on the growth of at least one desired microbial cell in the culture, and/or the growth of at least one undesired microbial cell in the culture.

Upon identification of a desired combination of bacteriocins, a microbial cell can be constructed to produce the desired combination of bacteriocins. In some embodiments, an existing microbial cell, for example a microbial cell that is producing a desired product or intermediate in industrial culture is reengineered to produce the desired combination of bacteriocins. In some embodiments, the microbial cell is reengineered via plasmid conjugation. In some embodiments, a new cell is engineered to produce the desired combination of bacteriocins and added to the industrial culture.

Genetic Guard Microbial Organisms and Systems

It can be useful for a bacteriocin-producing microbial organism to protect other microbial organisms from undesired microbial organisms. Accordingly, in some embodiments, a "genetic guard microbial organism" is provided (which, as a shorthand, may also be referred to herein as a "genetic guard"). As used herein, a "genetic guard" refers to a microbial organism or collection of microbial organisms that produces one or more bacteriocins so as to protect a "protected" microbial organism that is immune to neutralizing effects of the bacteriocins, but does not itself produce the bacteriocins. The "protected" microbial organism can perform a desired industrial process (for example, fermentation), while, as used herein, the "genetic guard" itself does not perform the desired industrial process. The genetic guard microbial organisms can express and secrete one or more bacteriocins. Optionally, the genetic guard microbial organisms can constititvely express and secrete one or more of the bacteriocins. The genetic guard microbial organism can be non-susceptible to the bacteriocins produced by the genetic guard, for example by producing immunity modulator(s) to the bacteriocin(s) secreted by the genetic guard, and/or by being a type of microbial organism that is not susceptible to the to the bacteriocin(s) produced by the genetic guard (e.g. if the genetic guard comprises a yeast and secretes bacteriocins that specifically neutralize particular bacteria such as lactic acid bacteria). In some embodiments, the protected microbial organism produces immunity modulator(s) to the bacteriocin(s) produced by the genetic guard. In some embodiments, the protected microbial organism is not susceptible to the bacteriocins produced by the genetic guard (e.g. if the protected microbial organism comprises a yeast, and the genetic guard microbial organism produces bacteriocins that specifically neutralize particular bacteria). In some embodiments, the protected microbial organism is not genetically modified ("non-GMO"). In some embodiments, the protected microbial organism is non-GMO, but is from a strain selected to have desired properties, for example via selective pressure, and/or classical mutagenesis. It is contemplated that even if the protected microbial organism has desirable industrial properties, the protected microbial organism may be insufficient at fighting-off one or more undesired microbial organisms, for example invading local flora. Accordingly, in some embodiments herein, a genetic guard protects a protected microbial organism from undesired microbial organisms. By way of example, non-GMO microbial organisms can be useful in a number of processes, for example food production, or purification such as water purification. In some embodiments, non-GMO "protected" microbial organisms are selected based on their ability to destroy one or more contaminants (for example, known water contaminants), and a genetic guard is provided to protect the protected microbial organisms from known or potential invading undesired microbial organisms. In some embodiments, systems comprising a genetic guard as described herein are provided.

It can be useful to maintain a culture medium that does not contain genetically modified organisms, for example to perform particular industrial processes, and/or to comply with certain production standards or specifications. It is contemplated that in accordance with some embodiments herein, genetic guards can be separated from the "protected" microbial organism by a membrane that is permeable to bacteriocins, but not to the genetic guard microbial organisms. As such, bacteriocins produced by the genetic guard can enter a culture medium occupied by the protected microbial organisms, thus protecting the protected organisms from one or more undesired microbial organisms while the genetic guard remains separated from the microbial organism.

It is contemplated herein that a particular culture medium can be invaded by and/or subject to a variety of undesired microbial organisms, which may susceptible to different bacteriocins or combinations of bacteriocins. Accordingly, in some embodiments, the genetic guard microbial organism produces two or more different bacteriocins, for example, 2, 3, 4, 5, 6, 7, 8, 9, 10, 11, 12, 13, 14, 15, 16, 17, 18, 19, 20, 2, 30, 35, 40, 45, 50, 55, 60, 65, 70, 75, 80, 85, 90, 95, or 100 different bacteriocins, including ranges between any two of the listed values, for example 2 to 100, 2 to 50, 2 to 20, 2 to 10, 5 to 100, 5 to 50, 5 to 20, 5 to 10, 10 to 100, 10 to 50, 10 to 20, 20 to 100, 20 to 50, or 50 to 100 different bacteriocins. By way of example, in some embodiments, the genetic guard comprises a single *E. coli* strains, which produces 20 different bacteriocins. In some embodiments, the genetic guard produces a cocktail of bacteriocins. In some embodiments, the genetic guard comprises a mixture of two or more different bacteriocin-producing microbial organisms, for example, 2, 3, 4, 5, 6, 7, 8, 9, 10, 11, 12, 13, 14, 15, 16, 17, 18, 19, 20, 2, 30, 35, 40, 45, or 50 different bacteriocin-producing microbial organisms, so as to provide a desired combination of bacteriocins. By way of example, in some embodiments, the genetic guard comprises a combination of 4 different *E. coli* strains, each of which produces 5 different bacteriocins (for a total of 20 different bacteriocins). In some embodiments, the genetic guard produces a cocktail of bacteriocins that target a particular category of microbial organism, for example lactic acid bacteria.

It can be useful for the genetic guard to be separated from a particular environment or culture medium, for example to maintain an industrial culture environment or feedstock free of genetically modified organisms (GMOs). In some embodiments, the genetic guard is physically separated from the protected microbial organism. Optionally, the protected microbial organism is non-GMO. In some embodiments, the genetic guard is temporally separated from the protected microbial organism. Optionally, the protected microbial organism is non-GMO. For example, temporal separation in accordance with some embodiments can comprise adding the genetic guard to a culture medium to neutralize invading organisms, and subsequently adding the protected microbial organism to the culture medium. Optionally, the genetic guard can be neutralized prior to adding the protected microbial organism, for example via bacteriocins or a poison-antidote system as described herein. Optionally, the genetic guard can be neutralized by their own bacteriocins, for example by repressing expression of the corresponding immunity modulator or immunity modulators in the genetic guard. For example, temporal separation in accordance with some embodiments can comprise culturing the protected microbial organism in a culture medium, and subsequently adding the genetic guard to the culture medium.

In some embodiments, the genetic guard is positioned in a first environment, and the protected microbial organism or organisms are positioned in a second environment. The first environment can be separated from a second environment by a membrane permeable to bacteriocins produced by the genetic guard but not the genetic guard itself. In some embodiments, the membrane is not permeable to the protected microbial organism. In some embodiments, the first environment is in fluid communication with the second environment. Without being limited by any theory it is contemplated that as bacteriocins typically comprise diffusible stable peptide molecules, the bacteriocins can readily move in aqueous solution from the first environment to the second environment. In some embodiments, the first environment comprises a first chamber, tank, or pond and the second environment comprises a second chamber, tank, or pond. In some embodiments, the second environment comprises an open-air environment. Optionally, an industrial process, for example fermentation, is taking place in the second environment. In some embodiments, the first environment comprises a capsule positioned inside of the second environment. A variety of membranes are suitable for arrangements and systems in accordance with embodiments herein, so long as the membranes are permeable to bacteriocins, but not to genetic guards. In some embodiments, the membrane comprises at least one of a mesh, strainer, filter, selective valve, unidirectional valve, or porous membrane. In some embodiments, the membrane comprises one or more pores having a diameter smaller than the diameter of the genetic guard. In some embodiments, the bacteriocins diffuse through the membrane. In some embodiments, fluidic motion from the first environment to the second environment drives the movement of the bacteriocins. In some embodiments, the genetic guard is selected based on known or likely undesired microbial organisms in the culture medium. In some embodiments, the genetic guard is changed after a period of time. For example, in response to changes in the invading undesired microbial organisms, the genetic guard can be adjusted so that additional bacteriocins are added, and/or some bacteriocins are removed.

In some embodiments, an existing microbially-mediated industrial process is performed in a new location, which is characterized by one or more potential undesired microbial organisms. As the microbial organisms of the existing industrial process may not produce bacteriocins against some or all of the undesired microbial organisms of the new location, a genetic guard producing bacteriocins targeting the undesired microbial organisms can be added to the culture medium in the new location. As such, the bacteriocins of the genetic guard can neutralize one or more undesired microbial organisms, if present in the culture medium.

In some embodiments, the genetic guard produces a cocktail of bacteriocins. The cocktail of bacteriocins can be collected while the genetic guard is not, and the cocktail of bacteriocins can be contacted with a culture medium of interest. As such, separation can be maintained between the culture medium and the genetic guard. The skilled artisan will appreciate that a number of methods are suitable for separating the bacteriocins from the genetic guard, so long as the methods do not substantially damage, denature, or destroy the bacteriocins. In some embodiments, the cocktail of bacteriocins is collected by filtering out the genetic guard. In some embodiments, the cocktail of bacteriocins is collected by centrifuging to separate the genetic guard from the bacteriocins. In some embodiments, the cocktail of bacteriocins is collected by neutralizing the genetic guard. In some embodiments, the cocktail is stored prior to contact with the culture medium.

Figure 6:
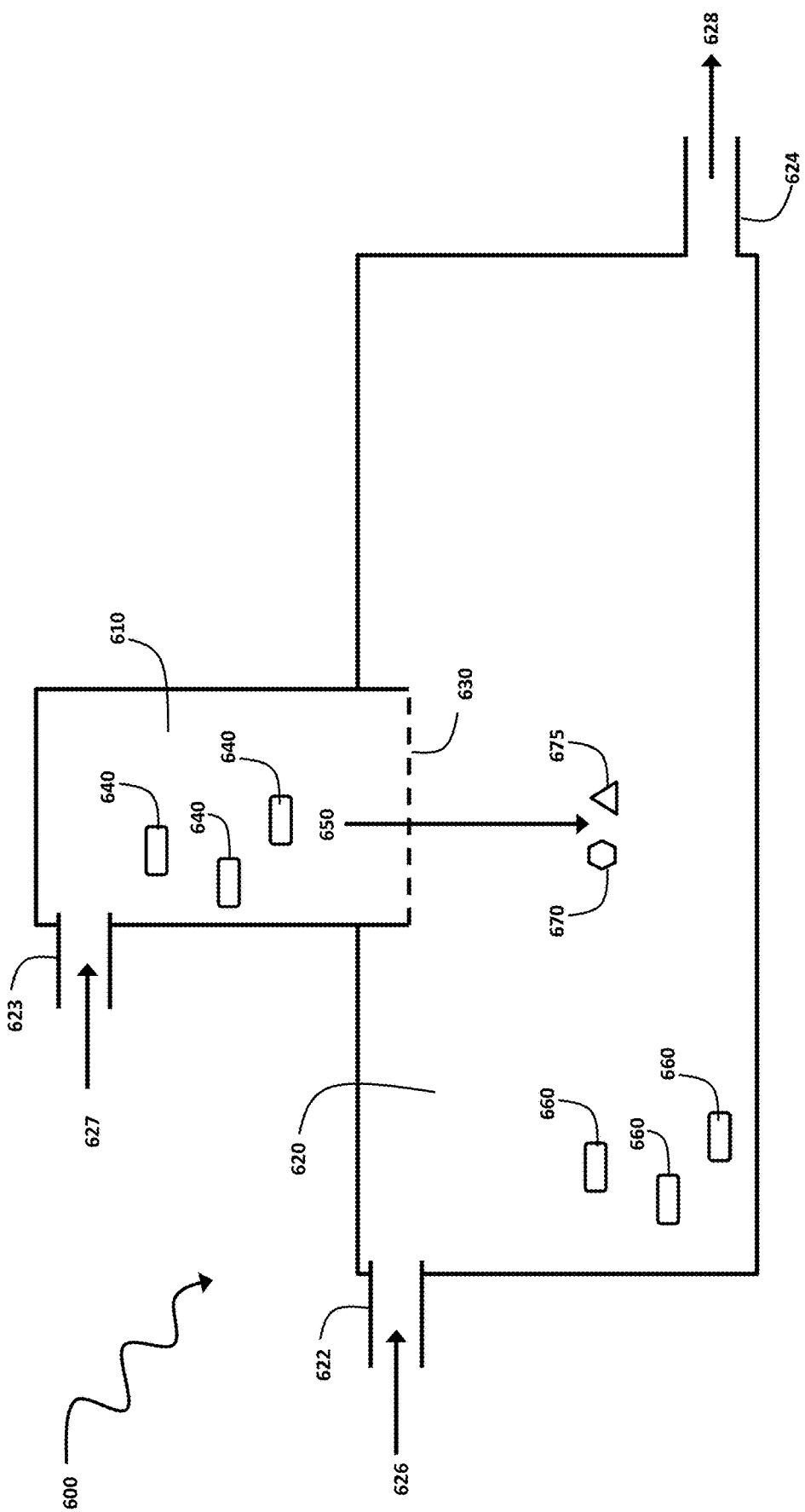
FIG. 6 is a schematic diagram illustrating a system comprising a genetic guard in accordance with some embodiments herein.

FIG. 6 is a schematic diagram illustrating a system 600 comprising a genetic guard in accordance with some embodiments herein. The system 600 can comprise a first environment 610 and a second environment 620. Optionally, the second environment 620 can comprise an inlet 622 and/or an outlet 624. A fluid or culture medium to be treated, for example polluted water or feedstock can enter 626 via the inlet 622, and exit 628 via the outlet. The first environment 610 can be separated from the second environment 620 by a membrane 630 that is permeable to bacteriocins, but is not permeable to genetic guard microbial organisms 640. The first environment 610 can comprise genetic guard microbial organisms 640, which produce bacteriocins that can move 650 between the first environment 610 and the second environment 620. The second environment 620 can comprise protected microbial organisms 660, which are not susceptible to the neutralizing effects of the bacteriocins produced by the genetic guard 640. Optionally, the protected microbial organisms 660 can be non-GMO. However, if undesired microbial organisms 670, 675 are present, the undesired microbial organisms 670, 675 can be neutralized by the bacteriocins. In some embodiments, the system 600 comprises a treatment system for polluted water. In some embodiments, the system comprises a second inlet 623 so that fluid to be treated enters 627 the first environment 610 before entering the second environment 620. Optionally, the system can comprise the second inlet 623 but not the first inlet 622. Optionally, the system can comprise the second inlet 623 and the first inlet 622. As such, the genetic guard microbial organisms 640 can secrete bacteriocins to neutralize invading undesired organisms 670, 675, while maintaining physical separation between the genetic guard microbial organisms 640 and protected microbial organisms 660.

Figure 7:
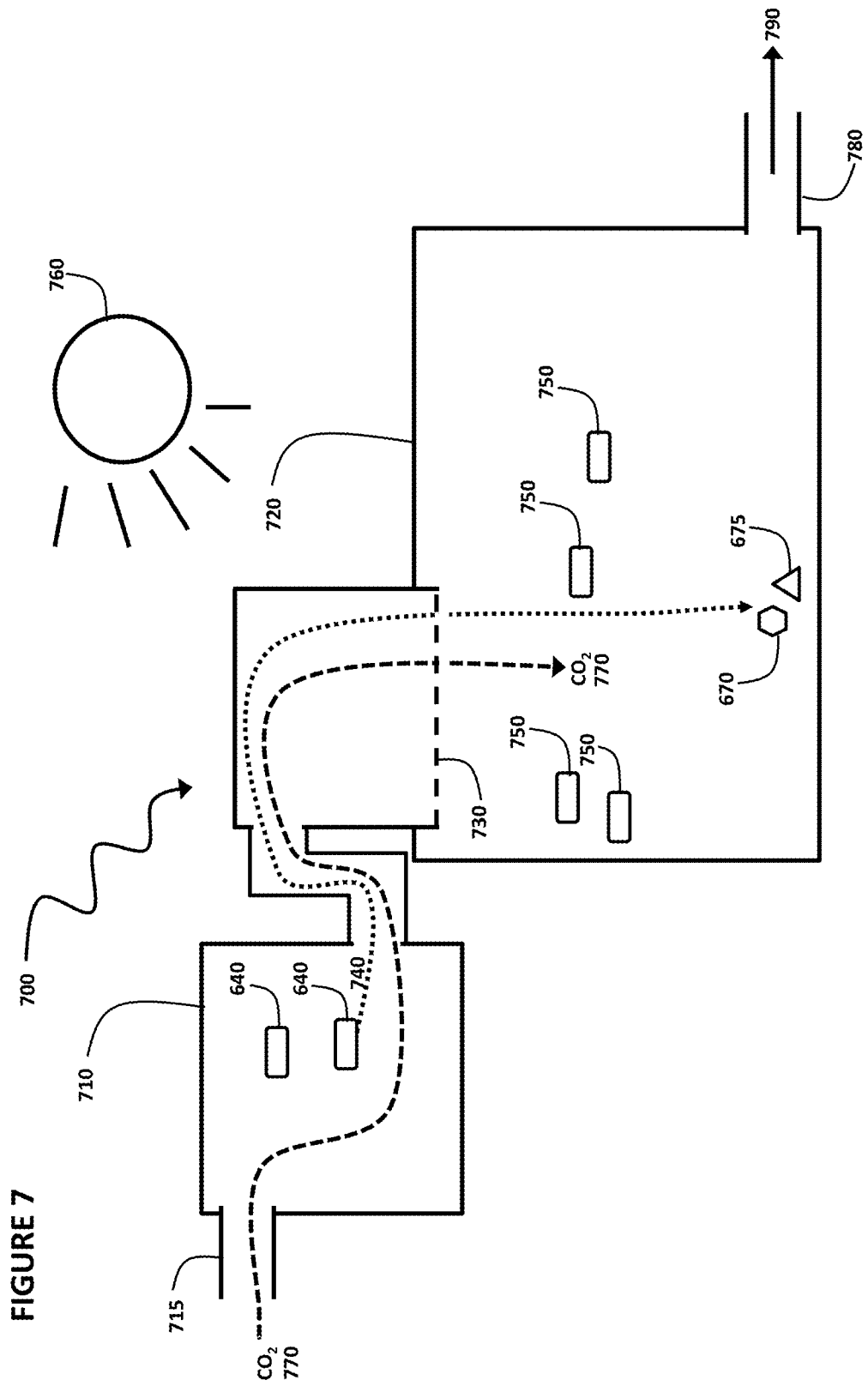
FIG. 7 is a schematic diagram illustrating a genetic guard system that can be useful for photosynthetic production in accordance with some embodiments herein.

FIG. 7 is a schematic diagram illustrating a genetic guard system 700 that can be useful for photosynthetic production in accordance with some embodiments herein. The system 700 can comprise a first environment 710. Optionally, the first environment 710 can comprise an inlet 715. The first environment 710 and optional inlet 715 can be in fluid and gas communication with a second environment 720. The first environment 710 can be separated from the second environment 720 by a membrane 730 that is permeable to bacteriocins and gas, but is not permeable to genetic guard microbial organisms 640. The first environment 710 can comprise genetic guard microbial organisms 640, which produce bacteriocins 740 that can move between the first environment 710 and the second environment 720. The second environment can comprise photosynthetic microbial organisms 750, for example photosynthetic microalgae. Optionally, the photosynthetic microbial organisms 750 are non-GMO. A source of light 760 can be in optical communication with the second environment 720. It is contemplated that the source of light 760 can comprise sunlight and/or artificial light. $CO_2$ 770 can enter the second environment 720, and can be used in combination with light from the light source 760 for photosynthetic production by the photosynthetic microbial organisms 750. Optionally the $CO_2$ 770 can enter the inlet 715 of the first environment 710, and enter the second environment 720 through the membrane 730. Bacteriocins 740 produced by the genetic guard microbial organisms 740 can enter the second environment 720 through the membrane 730, and can neutralize undesired microbial organisms 780, 785 in the second environment. Optionally, the second environment can comprise an outlet 780, and biomass 790 produced by the photosynthetic microbial organism 760 can exit the second environment 720 via the outlet 790. As such, the genetic guard microbial organisms 640 can secrete bacteriocins to neutralize invading undesired organisms 670, 675, while maintaining physical separation between the genetic guard microbial organisms 640 and photosynthetic microbial organisms 750 and biomass 790.

Preservation and/or Storage of Feedstock

It can be useful to store a feedstock without performing an industrial process in the feedstock, for example to build up a reserve in case additional output is needed later on, to decrease output for the time being, and/or to transport the feedstock to a different location. For example, a feedstock for feeding animals can be harvested in the summer, and stored until winter, when it is used to feed animals. For example, a feedstock may undergo an initial round of fermentation to produce a desired component in the feedstock, or to destroy or remove a desired component in the feedstock, and/or to stabilize the feedstock for storage, and the feedstock may then be preserved until it is to be consumed.

It is contemplated herein that undesired microbial organisms can contaminate a feedstock during storage, and/or consume or destroy one or more components of the feedstock. For example, microbial organisms can be selected or engineered to produce glucose from cellulose in a feedstock. However, in a feedstock comprising glucose, undesired microbial organisms can catabolize the glucose. Accordingly, in some embodiments, a genetic guard is added to a feedstock so as to protect the feedstock from one or more undesired microbial organisms during storage. In some embodiments, the feedstock undergoes an initial round of processing (e.g. fermentation) to produce, remove, or destroy at least one component (for example to stabilize the feedstock for storage and/or to provide a desired component in the feedstock such as glucose from cellulose), and the genetic guard then protects the feedstock from subsequent undesired microbial organisms. In some embodiments, the genetic guard is physically separated from the feedstock by a bacteriocin-permeable membrane during fermentation and/or during storage. It is contemplated that bacteriocin-mediated neutralization of undesired microbial organisms in a feedstock in accordance with some embodiments herein can permit a feedstock to be stored stably for long periods of time. In some embodiments, the feedstock is stably stored for at least one month, for example, at least one month, 2, 3, 4, 5, 6, 7, 8, 9, 10, 11, 12, 13, 14, 15, 16, 17, 18, 19, 20, 21, 22, 23, or 24 months.

In some embodiments, the genetic guard is contacted with the feedstock. In some embodiments, the genetic guard is already present in the feedstock, and proliferation of the genetic guard is induced prior to or during storage so that the genetic guard produces bacteriocins to neutralize undesired microbial organisms in the feedstock.

Methods of Preparing and Using Bacteriocin-Producing Microbial Organisms:

In accordance with some embodiments herein, bacteriocin-producing microbial organisms can be prepared for use in an industrial process which is subject to, or at risk of contamination or interference by undesired microbial organisms. In some embodiments, a circuit for desired production of bacteriocins is designed, nucleic acid sequences are engineered, and the circuit is assembled and introduced to a host microbial organism.

Figure 8:
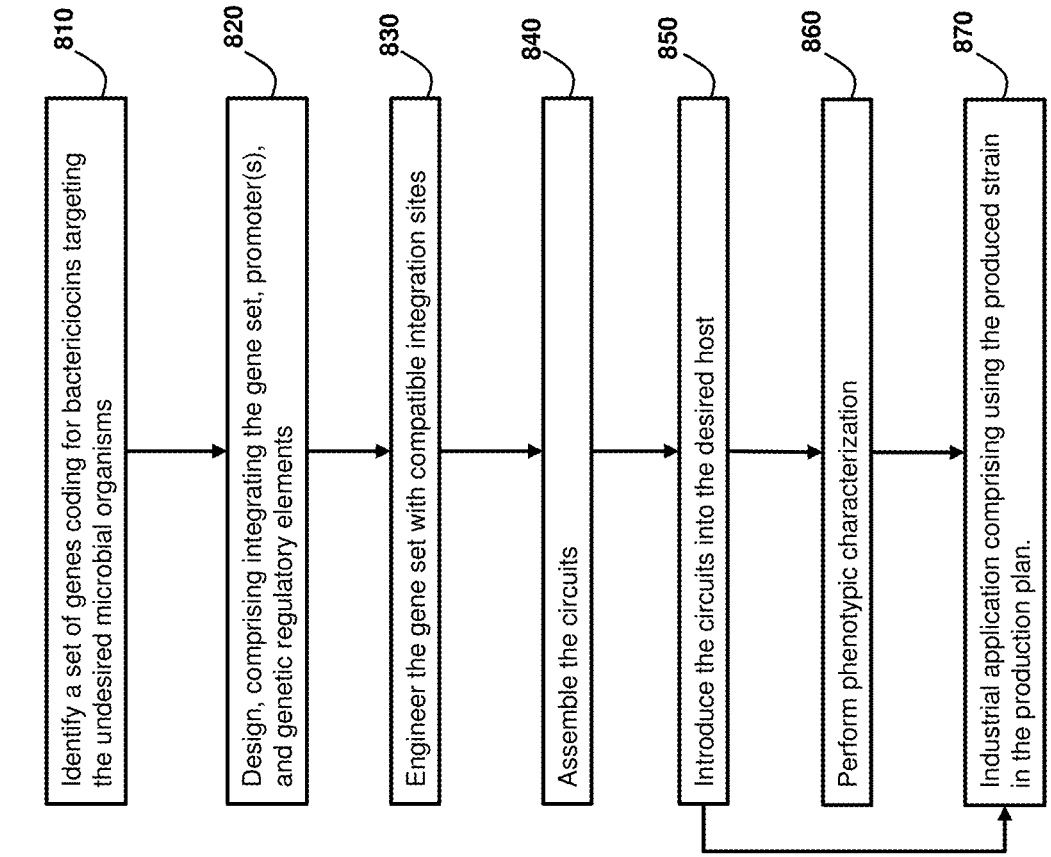
FIG. 8 is a flow diagram illustrating methods of producing and using bacteriocins in accordance with some embodiments herein.

FIG. 8 is a flow diagram illustrating methods of preparing and using bacteriocin. The method can comprise identifying a set of genes coding for bacteriocins targeting the undesired microbial organisms 810. An approach for identifying genes in accordance with some embodiments herein comprises identifying bacteriocin genes using an electronic database, for example bactibase, accessible on the world wide web at bactibase.pfba-lab-tun.org/main.php. The method can comprise designing a construct for expressing a bacteriocin, comprising integrating the gene set, promoter(s), and genetic regulatory elements 820. As such, a construct can be designed. Approaches for designing an appropriate construct in accordance with some embodiments herein can comprise using parts databases, for example electronic databases such as the Biobricks foundation parts database. It is contemplated herein that in accordance with some embodiments, the skilled artisan can selected desired components (including, but not limited to bacteriocin nucleotides, promoters, and genetic regulatory elements) based on their identified functions, and engineer a construct with a desired functionality based upon the identified functionality of these components. By way of example, functionalities of different possible components can be found in one or more databases, such as the Biobricks catalog. A catalog of Biobricks components is accessible on the world wide web at parts.igem.org. The method can comprise engineering the gene set with compatible integration sites 830, which can allow the genes to be assembled in a desired manner and/or appropriately introduced to a desired host. A variety of suitable integration sites can be used, for example restriction sites, substrates for an enzymatic recombination reaction, or sequences for homologous recombination. In some embodiments, the gene set is synthesized. In some embodiments, a nucleic acid comprising the gene set is synthesized. In some embodiments, the gene set is provided in one or more vectors such as plasmids. The method can comprise assembling the circuits 840. The circuits can include one or more bacteriocin nucleic acids, and a suitable promoter(s) and regulatory element(s). A variety of configurations of circuits can be suitable. In some embodiments, a single promoter drives expression of multiple bacteriocins and optional gene products of interest. In some embodiments, different bacteriocin nucleic acids are under the control of different promoters. In some embodiments, a circuit is comprised in a single construct such as a plasmid. In some embodiments, a circuit is comprised in two or more constructs such as plasmids. In some embodiments, a nucleic acid comprising the complete circuit is synthesized. In some embodiments, the circuit is assembled using conventional molecular cloning techniques, or a combination of nucleic acid synthesis and molecular cloning. Molecular cloning techniques are well known to the skilled artisan. Many suitable molecular cloning techniques are described in Green and Sambrook "Molecular Cloning: A Laboratory Manual" (2012) Cold Spring Harbor Laboratory Press; 4th edition, which is hereby incorporated by reference in its entirety. The method can comprise introducing the circuits into the desired host 850. Suitable hosts include, but are not limited to, naturally occurring, genetically engineered, and fully synthetic microbial organisms, including, but not limited to the exemplary microbial organisms described herein. Optionally, the method includes performing phenotypic characterization 860, for example strain behavior. For example, it can be useful to select for desired transformants or recombinants, confirm that a strain is producing the desired bacteriocins, and/or confirm that a regulatory circuit is responsive to an appropriate stimulus such as industrial precursor or product. The method can comprise industrial application comprising using the produced strain in the production plan 870. For example, a bacteriocin-producing strain can be introduced to an existing culture medium, or can be used as a starter culture for a new culture medium.

Kits

Kits are provided according to some embodiments herein. In some embodiments, the kits contain at least one of bacteriocins, bacteriocin polynucleotides, immunity modulators, immunity modulator polynucleotides, other genetic elements (such as promoters, expression vectors, conjugation plasmids, and the like), genetically engineered microbial cells, and/or culture medium as described herein. In some embodiments, the kits further contain packaging, and/or instructions for use of the contents therein. In some embodiments, the kits comprise a variety of bacteriocins, for example for use in ascertaining the effects of a candidate bacteriocin or combination thereof on a culture environment. In some embodiments, the kits comprise a variety of bacteriocin polynucleotides and immunity modulator polynucleotides, for example for constructing a microbial cell with desired characteristics. In some embodiments, the kits comprise a variety of donor microbial cells that comprise donor plasmids encoding a variety of combinations of at least one bacteriocin and/or at least one immunity modulator.

Example 1: Protection of Cyanobacteria and Neutralization Upon Escape

A cyanobacterium comprising a biosynthetic pathway for a lipid is provided. The cyanobacterium has been genetically engineered to comprise a bacteriocin polynucleotide under the control of a first promoter that is constitutively active. The cyanobacterium comprises an immunity modulator polynucleotide for an immunity modulator that protects against the bacteriocin, and that is under the control of a second promoter that is only active in the presence of a precursor found in an industrially useful feedstock. The cyanobacterium is placed in the feedstock. While it is producing lipids in the feedstock, the cyanobacterium also secretes active bacteriocin, thus neutralizing invading microorganisms. Upon escape from the feedstock, the cyanobacterium no longer possesses immunity modulator activity, but still produces bacteriocin, and thus is neutralized by the bacteriocin.

Example 2: Protection of Bacillus, Maintenance of a Plasmid, and Neutralization Upon Escape A genetically engineered *Bacillus* cell is provided, comprising a bacteriocin polynucleotide integrated into its chromosomal genome, and a plasmid comprising an immunity modulator polynucleotide for an immunity modulator that protects against the bacteriocin as well as a polynucleotide encoding a polypeptide to be manufactured. The bacteriocin is under the control of a constitutive promoter. The immunity modulator polynucleotide is under the control of a promoter that is only active in the presence of a precursor found in the industrially useful feedstock. As such, when the *Bacillus* is in the feedstock, it produces the bacteriocin to kill invading microbial cells. Moreover, when *Bacillus* clones lose the plasmid, they become undesirable (as they no longer can produce the polypeptide to be manufactured), and as a result of also losing the immunity modulator, are killed by the bacteriocin. Upon escape from the feedstock, the *Bacillus* cell no longer possesses immunity modulator activity, but still produces bacteriocin, and thus is neutralized by the bacteriocin produced by the other genetically engineered *Bacillus* cells in its environment.

Example 3: Regulation of Levels of Two Partner Strains of *S. cerevisiae*

A first *S. cerevisiae* strain is provided. The first strain comprises a bacteriocin polynucleotide under the control of a first promoter that is induced by the presence of a metabolite. As such, the bacteriocin is expressed more strongly as levels of the metabolite increase. The encoded bacteriocin arrests the *S. cerevisiae* cell cycle, but is bacteriostatic, not bacteriolytic. The first strain also comprises an immunity modulator polynucleotide for conferring immunity to the first bacteriocin under control of a promoter that is activated by a compound present only in the industrial feedstock. A second, partner strain of *S. cerevisiae* comprises a polynucleotide encoding an enzyme that produces the metabolite, but does not comprise a corresponding immunity modulator activity. As levels of the metabolite increase through activity of the second strain, the first strain produces more and more bacteriocin, thus arresting the cell cycle of the second strain, and reducing the relative amount of cells of the second strain available. Meanwhile, the first strain continues to proliferate. Accordingly, the relative ratio of the first strain to the second strain is increased, and buildup of the metabolite is reduced.

Example 4: Regulation of *A. Ferrooxidans* by *E. coli*

An *Acidithiobacillus ferrooxidans* strain is engineered to produce stored energy from the oxidation of Fe(II) to Fe(III) in a feedstock comprising an iron source that diffuses Fe(II) into the feedstock. An *E. coli* strain is engineered to control the growth of the first strain of *A. ferrooxidans*. The *A. ferroxidans* strain comprises a nucleic acid encoding Colicin-Ia (SEQ ID NO: 56) under the control of a rus operon promoter (SEQ ID NO: 549), and a nucleic acid encoding a Colicin-Ia immunity modulator (SEQ ID NO: 464) under the control of a constitutive promoter (*B. subtilis* ctc promoter, SEQ ID NO: 663). However, the ferroxidans strain does not produce any Colicin-E1 immunity modulator. The *E. coli* strain comprises a nucleic acid encoding Colicin-E1 (SEQ ID NO: 54) and Colicin-E1 immunity modulator (SEQ ID NO: 465) under the control of a constitutive promoter (SEQ ID NO: 651) integrated into its genome. However, the *E. coli* strain does not produce Colicin-Ia immunity modulator (SEQ ID NO: 464). As the *A. ferroxidans* oxidizes Fe(II) to Fe(III), levels of Fe(II) decrease. As such, activity of the rus promoter decreases, and the *A. ferroxidans* produces lower levels of Colicin-Ia (SEQ ID NO: 54). Accordingly, any neutralization of the *E. coli* strain is minimized. The second strain of *E. coli* proliferates, producing higher levels of Colicin-E1 (SEQ ID NO: 54). The Colicin-E1 neutralizes the *A. ferroxidans*, so that less *A. ferroxidans* is present to oxidize Fe(II) into Fe(III). Accordingly levels of Fe(II) increase again. As Fe(II) accumulates, the *A. ferroxidans* produce higher levels of Colicin-Ia (SEQ ID NO: 56), neutralizing organisms the second strain of *E. coli*. Accordingly, there in minimal *E. coli* producing Colicin-E1, and neutralization of *A. ferroxidans* is minimal as well. The *A. ferroxidans* proliferates, oxidizing the Fe(II) into Fe(III) and storing energy.

Example 5: Genetic Guard for Ethanol Synthesis by Non-GMO Microbial Organism A genetic guard in accordance with some embodiments herein is used to protect a non-GMO microbial organism that produces ethanol from glucose in a feedstock. The genetic guard comprises an E. coli strain comprising and expressing 20 different bacteriocin nucleic acids under the control of a single constitutive promoter, and as such, produces 20 different bacteriocins in approximately stoichiometric ratios. It is also contemplated that in accordance with some embodiments herein, another suitable option is to provide a genetic guard comprising five different E. coli strains, each of which comprise and express five different bacteriocins. The genetic guard is disposed in the first environment 610 of a system as illustrated in FIG. 6. The bacteriocins diffuse through a porous membrane to enter the second environment. The porous membrane is made of porous polytetrafluoroethylene that is permeable to bacteriocins and liquid, but is not permeable to the genetic guard. Non-GMO fermenting S. cerevisiae are cultured in the second environment. The non-GMO fermenting S. cerevisiae produce ethanol from glucose in the feedstock. The bacteriocins from the genetic guard neutralize invading microbial organisms, preventing contamination of the feedstock and consumption of the ethanol by invading microbial organisms. The porous membrane maintains physical separation between the genetically-engineered genetic guard and non-GMO fermenting yeast. As such, the fermenting yeast is protected from undesired microbial organisms, while a portion of the feedstock is keep free of GMO's.

Example 6: Protection of Non-GMO Photosynthetic Microalgae by Genetic Guard

A genetic guard in accordance with some embodiments herein is used to protect a non-GMO photosynthetic microalgae that produces biomass. The biomass can be suitable for a variety of downstream applications, for example extracting compounds of interest, energy, or animal feed. The genetic guard comprises a mixture of 50 different B. subtilis strains, each of which produces a different bacteriocin. The genetic guard is disposed in an aqueous first environment 710 of a system as illustrated in FIG. 7. The system further comprises an aqueous second environment 720, which contains non-GMO photosynthetic microalgae, which yield biomass. The first environment is separated from the second environment by a 0.5 µm fiberglass filter, so as to allow gas, liquid, and bacteriocins to pass between the first environment and second environment, while blocking bacteriocins from passing between the first environment and second environment. $CO_2$ enters the system through an inlet in the first environment, and diffuses through the first environment and second environment. Sunlight enters the second environment, and drives the photosynthetic microalgae to produce biomass. As a result, a high-glucose biomass is produced in the second environment. The 50 different bacteriocins also diffuse from the first environment to the second environment. The bacteriocins neutralize invading undesired microbial organisms, thus preventing contamination the biomass and preventing undesired microbial organisms from interfering with biomass production and/or catabolizing the biomass. Biomass is harvested from the second environment via an outlet. As such, physical separation is maintained between genetically engineered genetic guard and non-GMO photosynthetic microalgae, while neutralizing invading microorganisms in the second environment.

Example 7: Protection of Saccharomyces cerevisiae Against Lactic Acid Bacteria Family (LAB)

A Saccharomyces cerevisiae is engineered to produce multiple bacteriocins active on Lactic Acid Bacteria (LAB). Leucococin C (SEQ ID NO: 368) and Diversin V41 (SEQ ID NO: 74) are shown to be active on LAB bacteria according to the bactibase database, which is accessible on the world wide web at bactibase.pfba-lab-tun.org/main.php. It is appreciated that as S. cerevisiae are not sensitive to Leucococin or Diversin V41, there is no need to integrate corresponding immunity loci into the S. cerevisiae. As such, Leucococin C (SEQ ID NO: 368) and Diversin V41 (SEQ ID NO: 74) are selected, and polynucleotides are encoding Leucococin C (SEQ ID NO: 369) and Diversin V41 (SEQ ID NO: 75) are provided. The polynucleotides encode Leucococin C (SEQ ID NO: 368) and Diversin V41 (SEQ ID NO: 74), each fused to signal peptide from yeast mating factor alpha to facilitate secretion by the S. cerevisiae. The polynucleotides are integrated into the genome of a single S. cerevisiae strain under the control of a strong constitutive promoter, PPGK1 (3-Phosphoglyceratekinase) (SEQ ID NO: 692). The transformation is performed using standard homologous recombination. It is contemplated herein that other suitable strong constitutive promoters include, but are not limited to PTEF1 (translation elongation factor) and PGAP (glycerinaldehyde-3-phosphate dehydrogenase) (a list of constitutive yeast promoters is accessible on the world wide web at parts.igem.org/Promoters/Catalog/Yeast/Constitutive). The bacteriocin activity expressed by the transformed S. cerevisiae is measured by inhibitory assays on LAB cultures invading the production plan. As the makeup of undesired microbial organisms invading the feedstock changes over time, S. cerevisiae strains producing additional, fewer, and/or different bacteriocins can be produced and introduced into the industrial feedstock.

What is claimed is:

1. A genetically engineered microbial cell comprising:
a first nucleic acid under the control of a first promoter, the first nucleic acid encoding a secreted bacteriocin capable of inhibiting or preventing reproduction of at least one of the genetically engineered microbial cell, or a second microbial cell; and
a second nucleic acid comprising a nucleic acid sequence which encodes an immunity modulator that protects against the secreted bacteriocin, wherein the genetically engineered microbial cell has been genetically engineered to decrease or eliminate at least one of transcription, post-transcriptional expression or post-transcriptional activity of the immunity modulator concurrent with expression of the secreted bacteriocin, thereby causing the secreted bacteriocin to inhibit or prevent reproduction of the genetically engineered microbial cell.

2. The genetically engineered microbial cell of claim 1, wherein the first promoter is constitutive.

3. The genetically engineered microbial cell of claim 1, wherein the first promoter is regulatable.

4. The genetically engineered microbial cell of claim 1, wherein the genetically engineered microbial cell comprises at least one of the following to decrease or eliminate at least one of transcription, post-transcriptional expression, or post-transcriptional activity of said immunity modulator:
   (a) a second promoter operably linked to the second nucleic acid which encodes the immunity modulator, the second promoter genetically engineered to be inactive concurrent with transcription of the first nucleic acid by the first promoter;
   (b) a second promoter operably linked to the second nucleic acid which encodes the immunity modulator; and
      a nucleic acid encoding a transcriptional repressor configured to repress the second promoter while the first promoter is active;
   (c) a ribozyme or antisense oligonucleotide complementary to the second nucleic acid which encodes the immunity modulator, the ribozyme or antisense oligonucleotide genetically engineered to be expressed while the first promoter is active;
   (d) a regulatable tRNA specific for a transcript of the second nucleic acid which encodes the immunity modulator, and genetically engineered to not be induced while the first promoter is active;
   (e) a site-specific protease specific for a site on the immunity modulator;
   (f) a FLP-FRT or cre-lox cassette comprising the second nucleic acid which encodes the immunity modulator; or
   (g) a plasmid comprising the second nucleic acid which encodes the immunity modulator.

5. The genetically engineered microbial cell of claim 1, further comprising a third nucleic acid encoding a second secreted bacteriocin capable of inhibiting or preventing reproduction of a third microbial cell.

6. The genetically engineered microbial cell of claim 5, wherein the third microbial cell is of a different species than the genetically engineered microbial cell.

7. The genetically engineered microbial cell of claim 5, wherein the third microbial cell is pathogenic.

8. The genetically engineered microbial cell of claim 5, wherein the third nucleic acid is in cis with the first nucleic acid.

9. The genetically engineered microbial cell of claim 5, wherein the third nucleic acid is under the control of the first promoter.

10. The genetically engineered microbial cell of claim 5, further comprising a third promoter, wherein the third nucleic acid is under the control of the third promoter.

11. The genetically engineered microbial cell of claim 5, further comprising a fourth nucleic acid which encodes a second immunity modulator that protects the genetically engineered microbial cell against said second secreted bacteriocin.

12. The genetically engineered microbial cell of claim 11, wherein the fourth nucleic acid is in cis to the second nucleic acid.

13. The genetically engineered microbial cell of claim 1, wherein the engineered microbial cell is selected from the group consisting of: *Bacillus* species, *Paenibacillus* species, *Streptomyces* species, *Micrococcus* species, *Corynebacterium* species, *Acetobacter* species, Cyanobacteria species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellus*, and *Escherichia coli*.

14. The genetically engineered microbial cell of claim 1, wherein the engineered microbial cell is of the genus *Enterococcus*.

15. The genetically engineered microbial cell of claim 1, wherein the engineered microbial cell is of the genus *Lactobacillus*.

16. The genetically engineered microbial cell of claim 1, wherein the engineered microbial cell is of the species *Escherichia coli*.

17. The genetically engineered microbial cell of claim 1, wherein the second microbial cell is of a different species or strain than the genetically engineered microbial cell.

18. The genetically engineered microbial cell of claim 1, wherein the second microbial cell is of the same species or strain as the genetically engineered microbial cell.

\* \* \* \* \*